US012289992B2

(12) United States Patent
Han et al.

(10) Patent No.: US 12,289,992 B2
(45) Date of Patent: Apr. 29, 2025

(54) DISPLAY APPARATUS AND LIGHT ABSORBER INCLUDED IN DISPLAY APPARATUS

(71) Applicant: Samsung Display Co., Ltd., Yongin-si (KR)

(72) Inventors: Sanghyun Han, Hwaseong-si (KR); Jongwoo Kim, Hwaseong-si (KR); Eunjae Jeong, Hwaseong-si (KR); Dongjun Kim, Suwon-si (KR); Wonmin Yun, Yongin-si (KR); Young Kook Kim, Suwon-si (KR); Eung Seok Park, Seoul (KR); Yongchan Ju, Yongin-si (KR); Yisu Kim, Seoul (KR); Byoungduk Lee, Seongnam-si (KR); Seokhwan Hwang, Suwon-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 824 days.

(21) Appl. No.: 17/250,808

(22) PCT Filed: Sep. 27, 2019

(86) PCT No.: PCT/KR2019/012652

§ 371 (c)(1),
(2) Date: Mar. 4, 2021

(87) PCT Pub. No.: WO2020/071695

PCT Pub. Date: Apr. 9, 2020

(65) Prior Publication Data

US 2022/0158099 A1 May 19, 2022

(30) Foreign Application Priority Data

Oct. 5, 2018 (KR) ........................ 10-2018-0118701
Oct. 5, 2018 (KR) ........................ 10-2018-0118704
(Continued)

(51) Int. Cl.
*H01L 51/00* (2006.01)
*C07D 239/34* (2006.01)
(Continued)

(52) U.S. Cl.
CPC ......... *H10K 85/654* (2023.02); *C07D 239/34* (2013.01); *C07D 251/22* (2013.01);
(Continued)

(58) Field of Classification Search
None
See application file for complete search history.

(56) References Cited

U.S. PATENT DOCUMENTS 3,442,898 A 5/1969 Luethi
5,096,489 A 3/1992 Laver
(Continued)

FOREIGN PATENT DOCUMENTS

CN 1571814 A 1/2005
CN 1795232 A 6/2006
(Continued)

OTHER PUBLICATIONS

International Search Report for corresponding Application No. PCT/KR2019/012652 dated Jan. 6, 2020, 4pp.
(Continued)

*Primary Examiner* — Anthony J Frost
(74) *Attorney, Agent, or Firm* — Womble Bond Dickinson (US) LLP

(57) ABSTRACT

A display apparatus according to an embodiment includes light-emitting devices and an encapsulation member, wherein the encapsulation member includes a light absorber including a hexagonal heterocycle containing two or more nitrogen atoms as ring-forming atoms, and first to third substituents substituted at the hexagonal heterocycle, the first to third substituents being different from one another,
(Continued)

and thus can effectively block external light, thereby exhibiting improved reliability.

31 Claims, 13 Drawing Sheets

(30) Foreign Application Priority Data

Oct. 5, 2018 (KR) ........................ 10-2018-0118707
Feb. 21, 2019 (KR) ........................ 10-2019-0020685

(51) Int. Cl.

| | |
|---|---|
| ***C07D 251/22*** | (2006.01) |
| ***C07D 405/04*** | (2006.01) |
| ***H10K 50/844*** | (2023.01) |
| ***H10K 50/86*** | (2023.01) |
| ***H10K 85/60*** | (2023.01) |
| *H10K 59/35* | (2023.01) |
| *H10K 59/38* | (2023.01) |

(52) U.S. Cl.

CPC ....... *C07D 405/04* (2013.01); *H10K 50/8445* (2023.02); *H10K 50/865* (2023.02); *H10K 85/615* (2023.02); *H10K 85/622* (2023.02); *H10K 85/623* (2023.02); *H10K 85/6574* (2023.02); *H10K 59/35* (2023.02); *H10K 59/38* (2023.02)

(56) References Cited

U.S. PATENT DOCUMENTS

| | | | | |
|---|---|---|---|---|
| 5,753,729 | A | 5/1998 | Valet et al. | |
| 6,111,103 | A | 8/2000 | Ehlis et al. | |
| 6,242,598 | B1 | 6/2001 | Stevenson et al. | |
| 6,310,071 | B1 | 10/2001 | Oberdorf et al. | |
| 7,087,753 | B2 | 8/2006 | Toan et al. | |
| 8,389,719 | B2 | 3/2013 | Vogel et al. | |
| 8,586,735 | B2 | 11/2013 | Vogel et al. | |
| 9,660,222 | B2 | 5/2017 | Ikeda et al. | |
| 10,707,445 | B2 | 7/2020 | Yun et al. | |
| 2001/0003363 | A1 | 6/2001 | Marien et al. | |
| 2002/0028937 | A1 | 3/2002 | Gupta et al. | |
| 2002/0171606 | A1 | 11/2002 | Yabuki | |
| 2003/0146412 | A1* | 8/2003 | Gupta | G03C 1/8155 544/211 |
| 2007/0184212 | A1 | 8/2007 | Nimura et al. | |
| 2009/0136768 | A1* | 5/2009 | Vogel | C09D 7/48 205/198 |
| 2014/0203257 | A1* | 7/2014 | Hwang | H10K 85/40 544/333 |
| 2017/0352837 | A1* | 12/2017 | Yun | H10K 50/844 |
| 2018/0203174 | A1 | 7/2018 | Lee et al. | |
| 2019/0131532 | A1 | 5/2019 | Han et al. | |
| 2019/0229290 | A1 | 7/2019 | Kim | |
| 2019/0280064 | A1 | 9/2019 | Kim et al. | |

FOREIGN PATENT DOCUMENTS

| | | | |
|---|---|---|---|
| CN | 101193870 | A | 6/2008 |
| CN | 106835693 | A | 6/2017 |
| CN | 107452752 | A | 12/2017 |
| CN | 109721482 | A | 5/2019 |
| CN | 110071095 | A | 7/2019 |
| CN | 110246980 | A | 9/2019 |
| EP | 3 477 722 | A1 | 5/2019 |
| EP | 3 517 533 | A2 | 7/2019 |
| JP | 61-024577 | A | 2/1986 |
| JP | 2005506384 | A | 3/2005 |
| JP | 2008545771 | A | 12/2008 |
| JP | 2019-81756 | A | 5/2019 |
| KR | 10-1999-008299 | | 1/1999 |
| KR | 10-0178403 | B1 | 4/1999 |
| KR | 10-1999-0072128 | A | 9/1999 |
| KR | 10-1999-0077522 | A | 10/1999 |
| KR | 10-2001-0053056 | A | 6/2001 |
| KR | 10-0361628 | B1 | 2/2003 |
| KR | 10-2005-0084912 | | 8/2005 |
| KR | 10-0555072 | B1 | 2/2006 |
| KR | 10-0589869 | B1 | 6/2006 |
| KR | 10-2008-0020677 | A | 3/2008 |
| KR | 10-2013-0043929 | A | 5/2013 |
| KR | 10-1355874 | B1 | 2/2014 |
| KR | 10-2017-0050742 | A | 5/2017 |
| KR | 10-1744876 | B1 | 6/2017 |
| KR | 10-2017-0136972 | A | 12/2017 |
| KR | 10-2018-0000913 | A | 1/2018 |
| KR | 10-2018-0035000 | A | 4/2018 |
| KR | 10-2018-0051313 | A | 5/2018 |
| KR | 10-1981294 | B1 | 5/2019 |
| KR | 10-2020-0043951 | A | 4/2020 |
| KR | 10-2103589 | B1 | 4/2020 |
| KR | 20200039856 | A | 4/2020 |
| KR | 20200039857 | A | 4/2020 |
| KR | 20200040166 | A | 4/2020 |
| WO | 03/035734 | A1 | 5/2003 |
| WO | WO 2014/141725 | A1 | 9/2014 |

OTHER PUBLICATIONS

Chinese Examination report issued on Jan. 26, 2024, from the Chinese Patent Office in corresponding Chinese Patent Application No. 201980065956.0 (12 pages).

Pater, Richard, "Photostable o-Hydroxyphenylquinazolines", Research and Development Division Publication No. 461, vol. 7, (Oct. 1970) JWilmington, Del.19899, pp. 1113-1124 (12 pages).

European Examination Report dated Sep. 3, 2024, in corresponding European Patent Application No. 19 868 585.1 (7 pages).

* cited by examiner

DISPLAY APPARATUS AND LIGHT ABSORBER INCLUDED IN DISPLAY APPARATUS

CROSS-REFERENCE TO RELATED APPLICATION

This application is a National Phase Application of International Application No. PCT/KR2019/012652 filed Sep. 27, 2019, which claims priority to Korean Patent Application No. 10-2018-0118701, filed on Oct. 5, 2018, Korean Patent Application No. 10-2018-0118707, filed on Oct. 5, 2018, Korean Patent Application No. 10-2018-0118704, filed on Oct. 5, 2018, and Korean Patent Application No. 10-2019-0020685, filed on Feb. 21, 2019, the entire content of each of which is hereby incorporated by reference.

DESCRIPTION

Technical Field

The present invention disclosed herein relates to a display apparatus and a light absorber used in the display apparatus, and more particularly, to a light absorber included in an encapsulation member and a display apparatus including the same.

Background Art

Recently, the development of an organic electroluminescence display as an image display apparatus is being actively conducted. Unlike liquid crystal display apparatuses and the like, the organic electroluminescence display is a so-called self-luminescent display apparatus, in which holes and electrons injected from a first electrode and a second electrode recombine in an emission layer, and thus a luminescent material including an organic compound in the emission layer emits light to implement display. In the application of a self-luminescent light emitting device to a display apparatus, there is a demand for a light-emitting device having a low driving voltage, high luminous efficiency, and a long service life, and ensuring stability of the light-emitting device is necessary so that such characteristics can be stably attained.

In particular, the light-emitting device has vulnerability in that it is easily degraded by exposure to ultraviolet rays during a manufacturing process, or exposure to sunlight due to outdoor use, and thus a technique for blocking ultraviolet rays and a portion of visible rays from entering the inside of the light-emitting device is being continuously required.

DISCLOSURE OF THE INVENTION

Technical Problem

An object of the present invention is to provide a display apparatus having improved reliability of a light-emitting device by including a light absorber in an encapsulation member.

Another object of the present invention is to provide a light absorber which efficiently absorbs a portion of visible rays and ultraviolet rays.

Technical Solution

An embodiment provides a display apparatus including: a light-emitting device including a first electrode, a second electrode facing the first electrode, and a plurality of organic layers disposed between the first electrode and the second electrode; and an encapsulation member which is disposed on the light-emitting device and includes a light absorber, wherein the light absorber includes a hexagonal heterocycle containing two or more nitrogen atoms as ring-forming atoms, and first to third substituents which are substituted at the hexagonal heterocycle, the first to third substituents being different from one another, where the first substituent is a substituted phenyl group containing at least one hydroxyl group, and the second substituent is a condensed ring group in which three or more rings are condensed.

The encapsulation member may include at least one organic film and at least one inorganic film, and the at least one organic film may include the light absorber.

The at least one organic film and the at least one inorganic film may be alternately laminated, and the at least one organic film may include: a first organic film configured to absorb light in a first wavelength region; and a second organic film configured to absorb light in a second wavelength region different from the light in the first wavelength region.

The encapsulation member may cover the light-emitting device.

A polarizing member disposed on the encapsulation member may be further included.

The encapsulation member may include: a first inorganic film disposed adjacent to the second electrode; a second inorganic film disposed on the first inorganic film; and an organic film which is disposed between the first inorganic film and the second inorganic film and includes the light absorber, wherein the organic film may have a transmittance of 10% or less in a wavelength of 405 nm, a transmittance of 70% or more in a wavelength of 430 nm, and a transmittance of 97% or more in a wavelength of 450 nm.

The plurality of organic layers may include: a hole transport region disposed on the first electrode; an emission layer disposed on the hole transport region; and an electron transport region disposed on the emission layer.

A light shield layer disposed on the encapsulation member may be further included.

The hexagonal heterocycle may be triazine or pyrimidine.

The first substituent may be represented by any one among H1 to H5 below, and R in H4 and H5 below is a substituted or unsubstituted alkoxy group having 1 to 20 carbon atoms.

H1

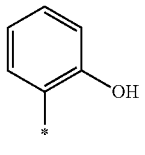

H2

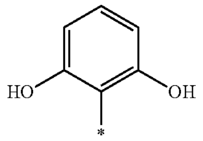

H3

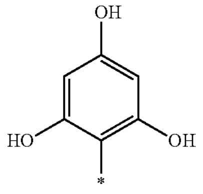

-continued

H4

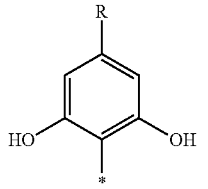

H5

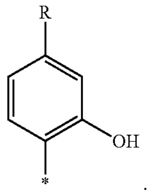

The second substituent may be a substituted or unsubstituted anthracene group, a substituted or unsubstituted pyrene group, a substituted or unsubstituted chrysene group, a substituted or unsubstituted dibenzofuran derivative, a substituted or unsubstituted carbazole derivative, or a substituted or unsubstituted fluorene derivative, a substituent of the substituted or unsubstituted dibenzofuran derivative, a substituent of the substituted or unsubstituted carbazole derivative, and a substituent of the substituted or unsubstituted fluorene derivative may be each independently a hydrogen atom, an alkyl group having 1 to 20 carbon atoms, an alkenyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or adjacent groups may be bonded to each other to form a ring.

The third substituent may be a substituted or unsubstituted alkoxy group having 1 to 20 carbon atoms, a substituted or unsubstituted aryloxy group having 6 to 30 ring-forming carbon atoms, a substituted or unsubstituted alkylthio group having 1 to 20 carbon atoms, a substituted or unsubstituted arylthio group having 6 to 30 ring-forming carbon atoms, or a substituted or unsubstituted phenyl group.

The light absorber may be represented by Formula 1 or Formula 2 below:

Formula 1

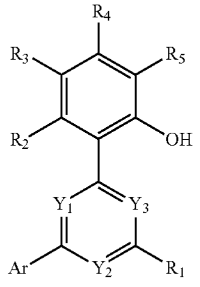

-continued

Formula 2

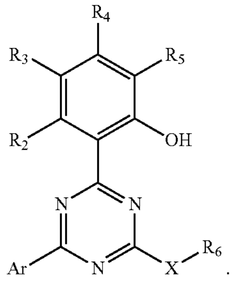

In Formula 1 and Formula 2 above, Ar is a substituted or unsubstituted aryl group having 13 to 60 ring-forming carbon atoms, or a substituted or unsubstituted heteroaryl group having 12 to 60 ring-forming carbon atoms, $R_2$ to $R_5$ are each independently a hydrogen atom, a deuterium atom, a halogen atom, a cyano group, a substituted or unsubstituted alkyl group having 1 to 30 carbon atoms, a substituted or unsubstituted alkoxy group having 1 to 20 carbon atoms, a substituted or unsubstituted aryloxy group having 6 to 30 ring-forming carbon atoms, a substituted or unsubstituted alkylamine group having 1 to 30 carbon atoms, a substituted or unsubstituted arylamine group having 6 to 30 ring-forming carbon atoms, a substituted or unsubstituted heterocyclic group having 2 to 30 ring-forming carbon atoms, or a substituted or unsubstituted aryl group having 6 to 30 ring-forming carbon atoms. In Formula 1 above, two among $Y_1$ to $Y_3$ are N and the rest is CH, $R_1$ is a hydrogen atom, a substituted or unsubstituted alkyl group having 1 to 30 carbon atoms, a substituted or unsubstituted alkoxy group having 1 to 20 carbon atoms, a substituted or unsubstituted aryloxy group having 6 to 30 ring-forming carbon atoms, a substituted or unsubstituted alkylthio group having 1 to 20 carbon atoms, a substituted or unsubstituted arylthio group having 6 to 30 ring-forming carbon atoms, a substituted or unsubstituted heterocyclic group having 2 to 30 ring-forming carbon atoms, or a substituted or unsubstituted aryl group having 6 to 30 ring-forming carbon atoms. In Formula 2 above, X is O or S, and $R_6$ is a substituted or unsubstituted alkyl group having 1 to 30 carbon atoms, a substituted or unsubstituted heterocyclic group having 2 to 30 ring-forming carbon atoms, or a substituted or unsubstituted aryl group having 6 to 30 ring-forming carbon atoms.

Formula 1 above may be represented by any one among Formula 1-1 to Formula 1-4 below. In Formula 1-1 to Formula 1-4 below, Ar, $Y_1$ to $Y_3$, $R_1$, and $R_4$ are the same as defined in Formula 1.

Formula 1-1

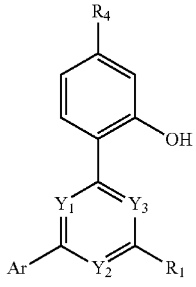

-continued
Formula 1-2
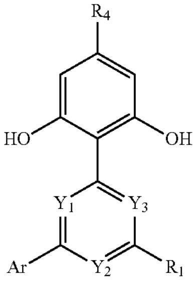
Formula 1-3
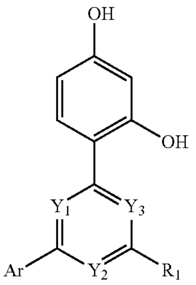
Formula 1-4
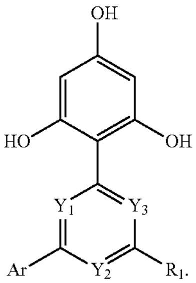
Formula 2 above may be represented by any one among Formula 2-1 to Formula 2-4 below. In Formula 2-1 to Formula 2-4 below, X, Ar, $R_4$, and $R_6$ are the same as defined in Formula 1 and Formula 2.
Formula 2-1
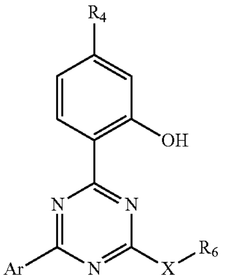
Formula 2-2
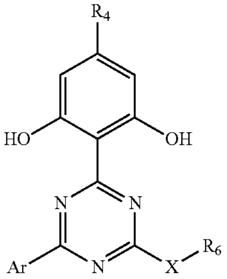
-continued
Formula 2-3
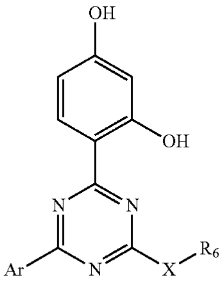
Formula 2-4
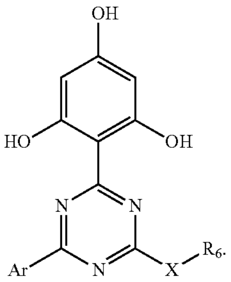
Ar above may be represented by any one among Ar-a to Ar-h below:
Ar-a
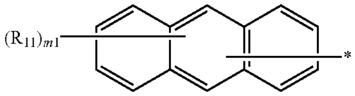
Ar-b
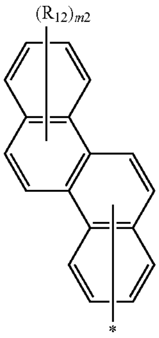
Ar-c
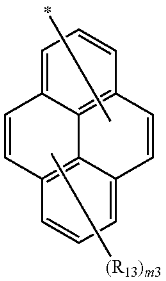
Ar-d
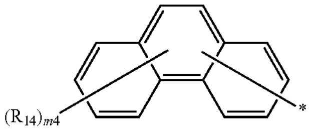

-continued

Ar-e

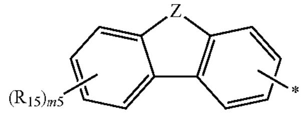

Ar-f

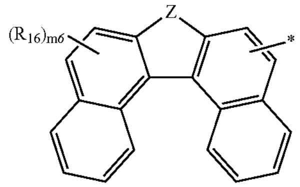

Ar-g

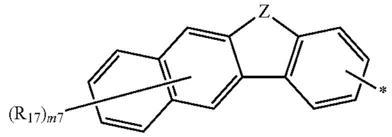

Ar-h

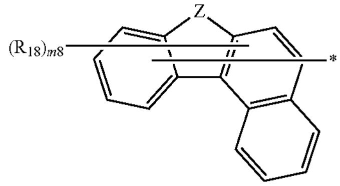

In Ar-e to Ar-h above, Z is O, S, $NR_a$, $CR_bR_c$, $R_a$ to $R_c$ are each independently a hydrogen atom, a deuterium atom, a halogen atom, an alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, in Ar-a to Ar-h above, $R_{11}$ to $R_{18}$ are each independently a hydrogen atom, a deuterium atom, a halogen atom, an alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and m1 to m8 are each independently an integer of 0 to 4.

Formula 1 above may be represented by any one among Formula 1-A to Formula 1-C below. In Formula 1-A to Formula 1-C below, $Y_1$ to $Y_3$, Ar, and $R_1$ to $R_5$ are the same as defined in Formula 1.

Formula 1-A

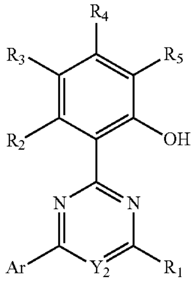

-continued

Formula 1-B

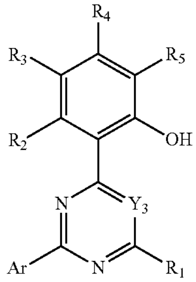

Formula 1-C

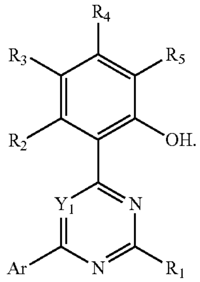

An embodiment provides a display apparatus including: a light-emitting device including a first electrode, a second electrode facing the first electrode, and a plurality of organic layers disposed between the first electrode and the second electrode; and an encapsulation member which is disposed on the light-emitting device and comprises an organic film including a light absorber, wherein the organic film has a transmittance of 10% or less in a wavelength of 405 nm, a transmittance of 70% or more in a wavelength of 430 nm, and a transmittance of 97% or more in a wavelength of 450 nm, and the light absorber includes a hexagonal heterocycle containing two or more N atoms as a ring-forming atom and first to third substituents which are substituted at the hexagonal heterocycle, the first to third being different from one another.

The hexagonal heterocycle may be triazine or pyrimidine.

The first substituent may be a substituted phenyl group containing at least one hydroxyl group, the second substituent may be a condensed ring group in which three or more rings are condensed, and the third substituent may be a substituted or unsubstituted oxy group, a substituted or unsubstituted thio group, or a substituted or unsubstituted phenyl group.

The first substituent may be represented by any one among H1 to H5 below. In H4 and H5 below, R is a substituted or unsubstituted alkoxy group having 1 to 20 carbon atoms.

H1

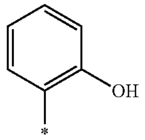

H2

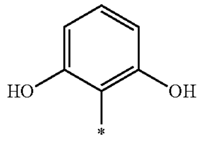

-continued

H3

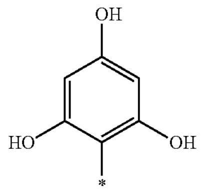

H4

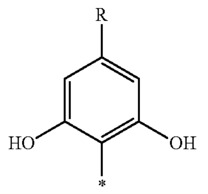

H5

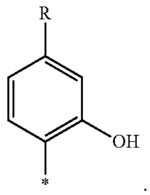

.

The second substituent may be represented by any one among Ar-a to Ar-h below:

Ar-a

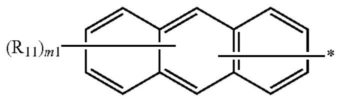

Ar-b

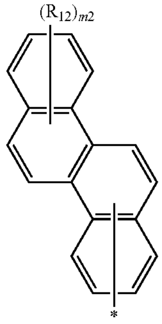

Ar-c

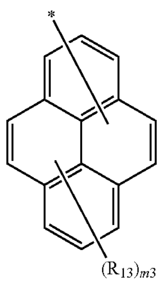

Ar-d

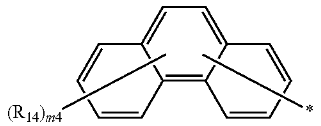

-continued

Ar-e

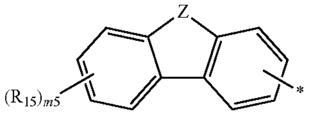

Ar-f

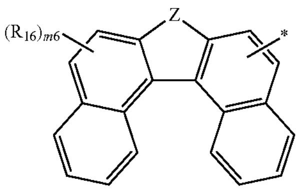

Ar-g

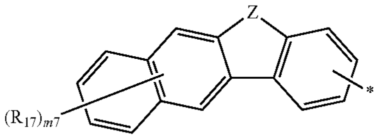

Ar-h

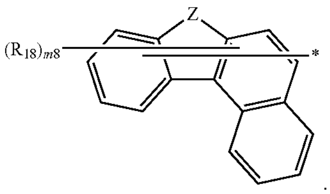

.

In Ar-e to Ar-h above, Z is O, S, $NR_a$, $CR_bR_c$, $R_a$ to $R_c$ are each independently a hydrogen atom, a deuterium atom, a halogen atom, an alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, in Ar-a to Ar-h above, $R_{11}$ to $R_{18}$ are each independently a hydrogen atom, a deuterium atom, a halogen atom, an alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and m1 to m8 are each independently an integer of 0 to 4.

The third substituent may be represented by any one among S1 to S15 below:

S1

S2

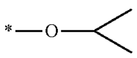

S3

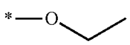

S4

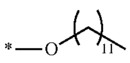

S5

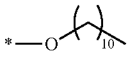

S6

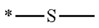

S7

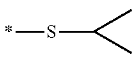

S8

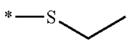

-continued

S9

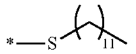

S10

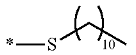

S11

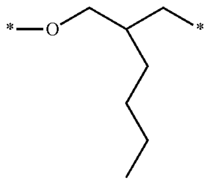

S12

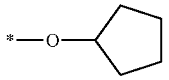

S13

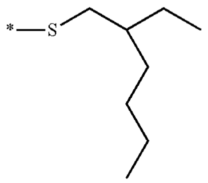

S14

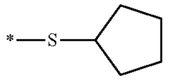

S15

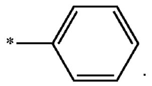

Another embodiment provides a light absorber represented by Formula 1 or Formula 2 below:

Formula 1

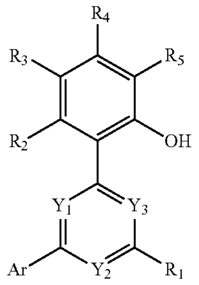

Formula 2

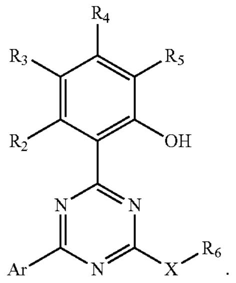

In Formula 1 and Formula 2 above, Ar is a substituted or unsubstituted aryl group having 13 to 60 ring-forming carbon atoms, or a substituted or unsubstituted heteroaryl group having 12 to 60 ring-forming carbon atoms, $R_2$ to $R_5$ are each independently a hydrogen atom, a deuterium atom, a halogen atom, a cyano group, a substituted or unsubstituted alkyl group having 1 to 30 carbon atoms, a substituted or unsubstituted alkoxy group having 1 to 20 carbon atoms, a substituted or unsubstituted aryloxy group having 6 to 30 ring-forming carbon atoms, a substituted or unsubstituted alkylamine group having 1 to 30 carbon atoms, a substituted or unsubstituted arylamine group having 6 to 30 ring-forming carbon atoms, a substituted or unsubstituted heterocyclic group having 2 to 30 ring-forming carbon atoms, or a substituted or unsubstituted aryl group having 6 to 30 ring-forming carbon atoms. In Formula 1 above, two among $Y_1$ to $Y_3$ are N and the rest is CH, $R_1$ is a hydrogen atom, a substituted or unsubstituted alkyl group having 1 to 30 carbon atoms, a substituted or unsubstituted alkoxy group having 1 to 20 carbon atoms, a substituted or unsubstituted aryloxy group having 6 to 30 ring-forming carbon atoms, a substituted or unsubstituted alkylthio group having 1 to 20 carbon atoms, a substituted or unsubstituted arylthio group having 6 to 30 ring-forming carbon atoms, a substituted or unsubstituted heterocyclic group having 2 to 30 ring-forming carbon atoms, or a substituted or unsubstituted aryl group having 6 to 30 ring-forming carbon atoms. In Formula 2 above, X is O or S, and $R_6$ is a substituted or unsubstituted alkyl group having 1 to 30 carbon atoms, a substituted or unsubstituted heterocyclic group having 2 to 30 ring-forming carbon atoms, or a substituted or unsubstituted aryl group having 6 to 30 ring-forming carbon atoms.

Advantageous Effects

The display apparatus of an embodiment may have improved reliability by absorbing external light in the encapsulation member.

The light absorber of an embodiment may be applied to the encapsulation member on the light-emitting device to mainly absorb light in an ultraviolet wavelength region, thereby preventing deterioration of the light-emitting device and improving reliability.

MODE FOR CARRYING OUT THE INVENTION

Figure 1:
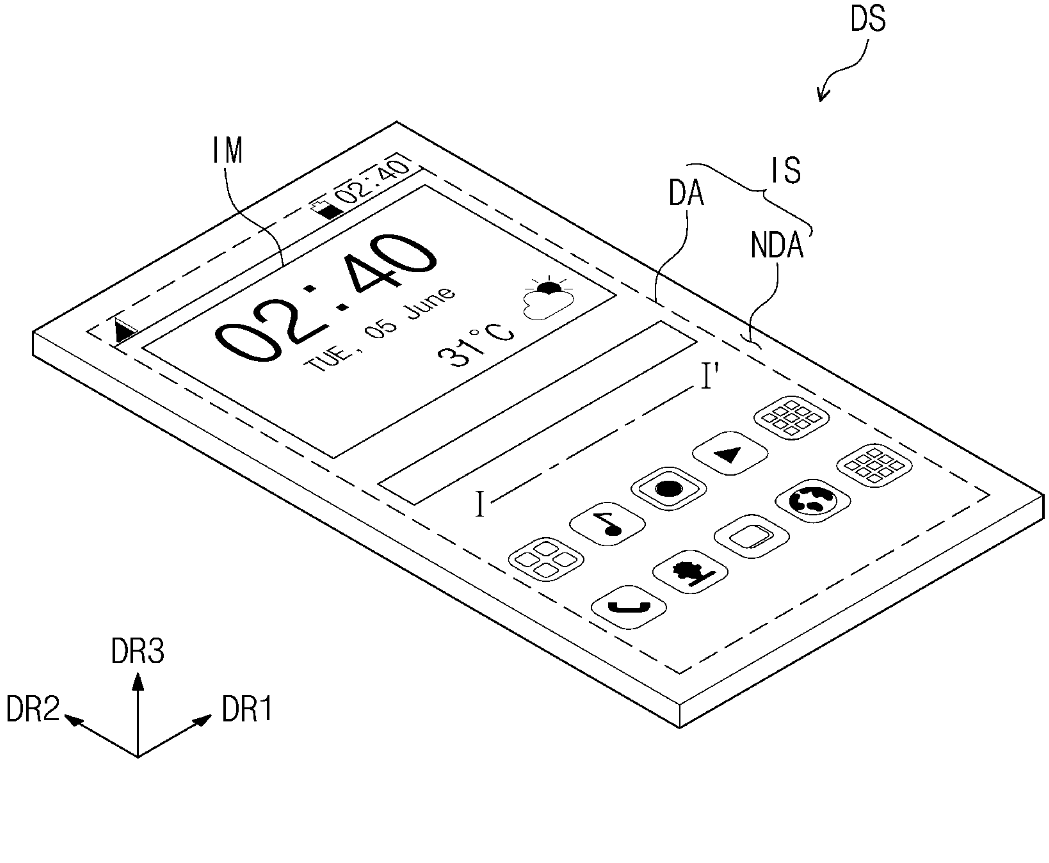
FIG. 1 is a perspective view of a display apparatus of an embodiment.

Since the present invention may make various modifications and have various shapes, particular embodiments are illustrated in the drawings and are described in the detailed description. It should be understood, however, that it is not intended to limit the present invention to the particular forms disclosed, but rather, is intended to cover all modifications, equivalents, and alternatives falling within the spirit and scope of the invention.

In the present description, when an element (or a region, a layer, a portion, etc.) is referred to as being "on," "connected to," or "coupled to" another element, it means that the element may be directly disposed on/connected to/coupled to the other element, or that a third element may be disposed therebetween.

Like reference numerals refer to like elements throughout. Also, in the drawings, the thickness, the ratio, and the dimensions of elements are exaggerated for an effective description of technical contents.

The term "and/or" includes all combinations of one or more of which associated configurations may define.

It will be understood that, although the terms "first," "second," etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the inventive concept. The terms of a singular form may include plural forms unless the context clearly indicates otherwise.

In addition, terms such as "below," "lower," "above," "upper," and the like are used to describe the relationship of the configurations shown in the drawings. The terms are used as a relative concept and are described with reference to the direction indicated in the drawings.

Unless otherwise defined, all terms (including technical and scientific terms) used herein have the same meaning as commonly understood by one of ordinary skill in the art to which the inventive concept pertains. In addition, terms defined in commonly used dictionaries should be interpreted as having meanings consistent with the meanings in the context of the related art, and are expressly defined herein unless they are interpreted in an ideal or overly formal sense.

It should be understood that the terms "comprise," or "have" are intended to specify the presence of stated features, integers, steps, operations, elements, components, or combinations thereof in the disclosure, but do not preclude the presence or addition of one or more other features, integers, steps, operations, elements, components, or combinations thereof.

Hereinafter, a display apparatus according to an embodiment of the preset invention and a light absorber of an embodiment included therein will be described with reference to the accompanying drawings.

Figure 2A:
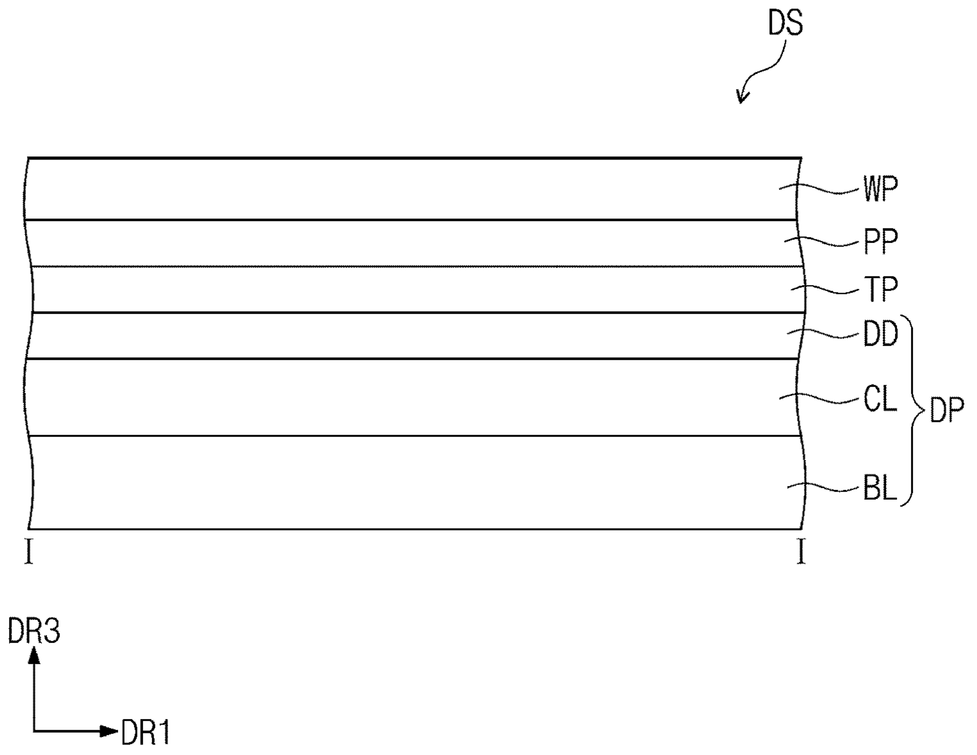
FIG. 2A is a cross-sectional view taken long line I-I' of FIG. 1.
Figure 2B:
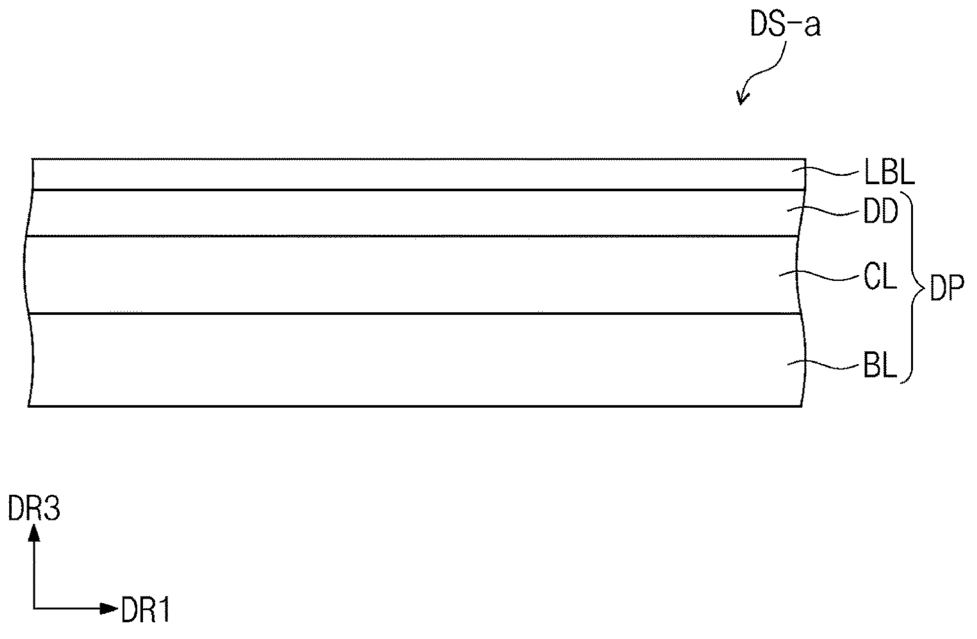
FIG. 2B is a cross-sectional view of a display apparatus of an embodiment.
Figure 3:
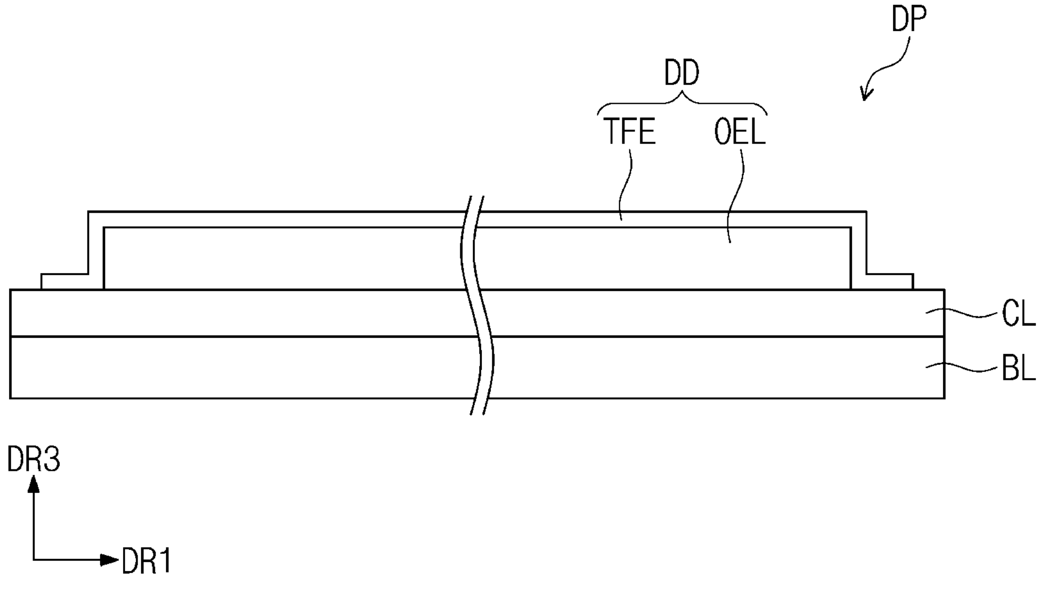
FIG. 3 is a cross-sectional view of a display panel according to an embodiment.
Figure 4:
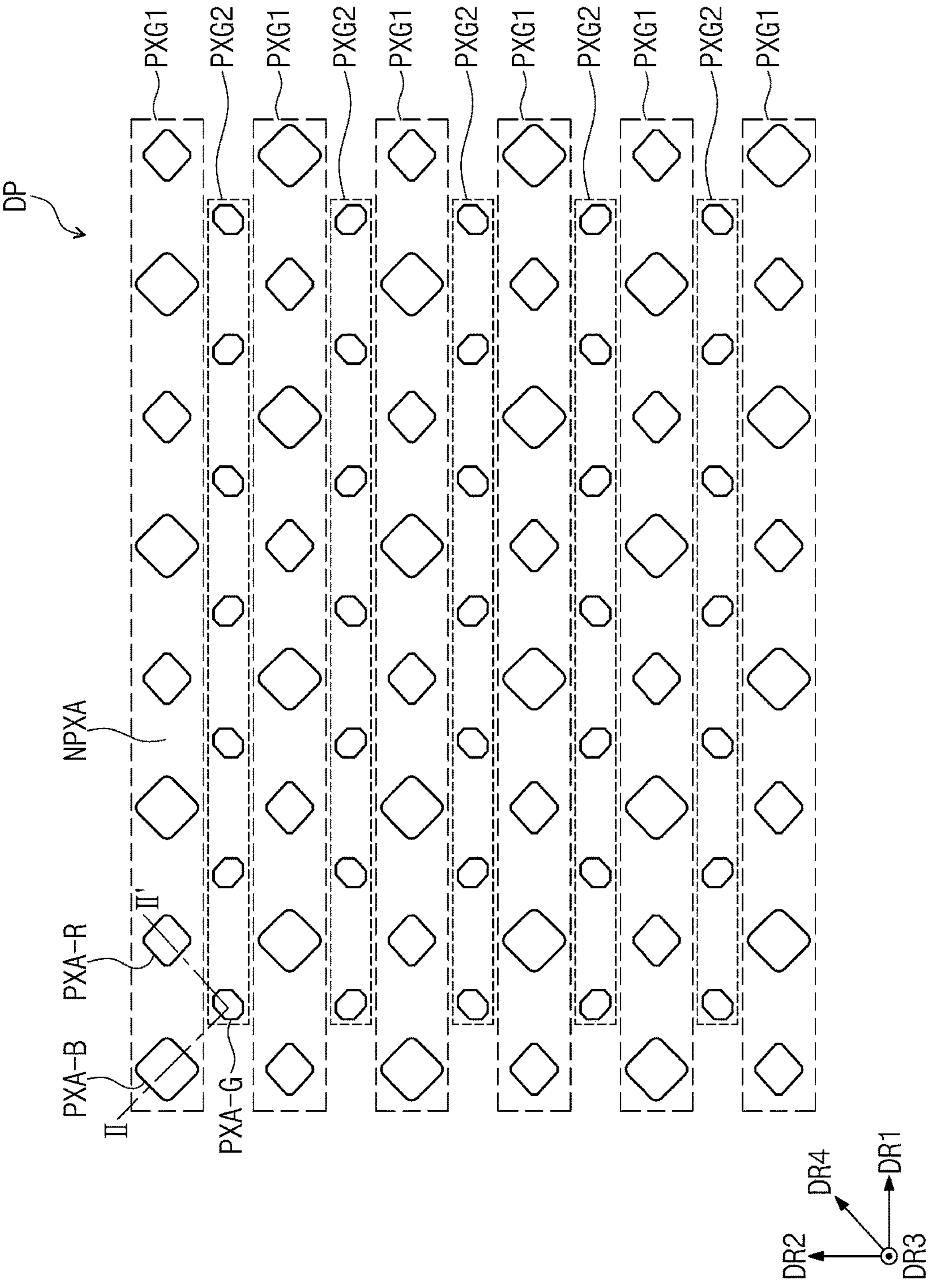
FIG. 4 is a plan view of a display panel according to an embodiment.
Figure 5:
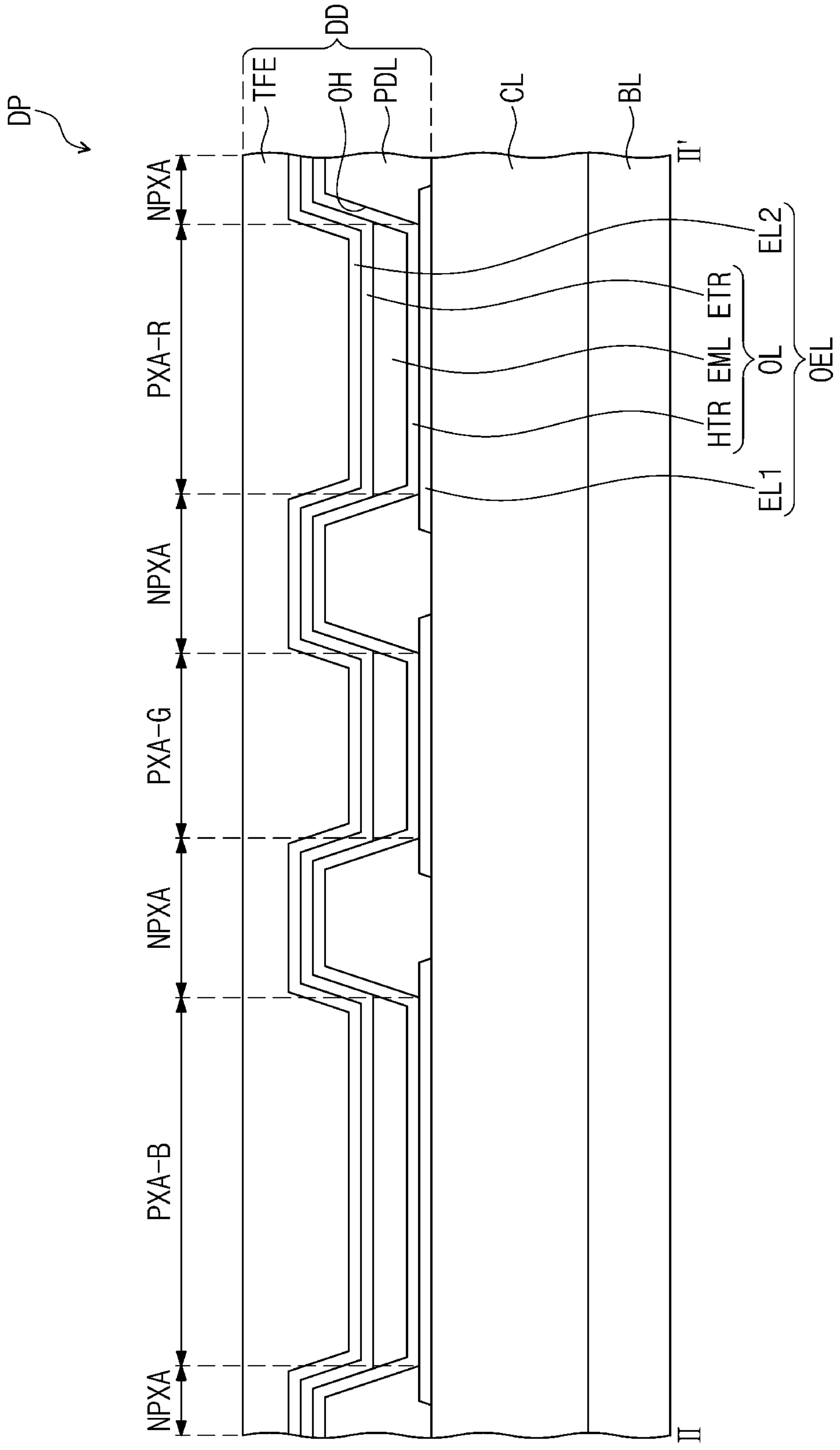
FIG. 5 is a cross-sectional view taken along line II-II' of FIG. 4.
Figure 6:
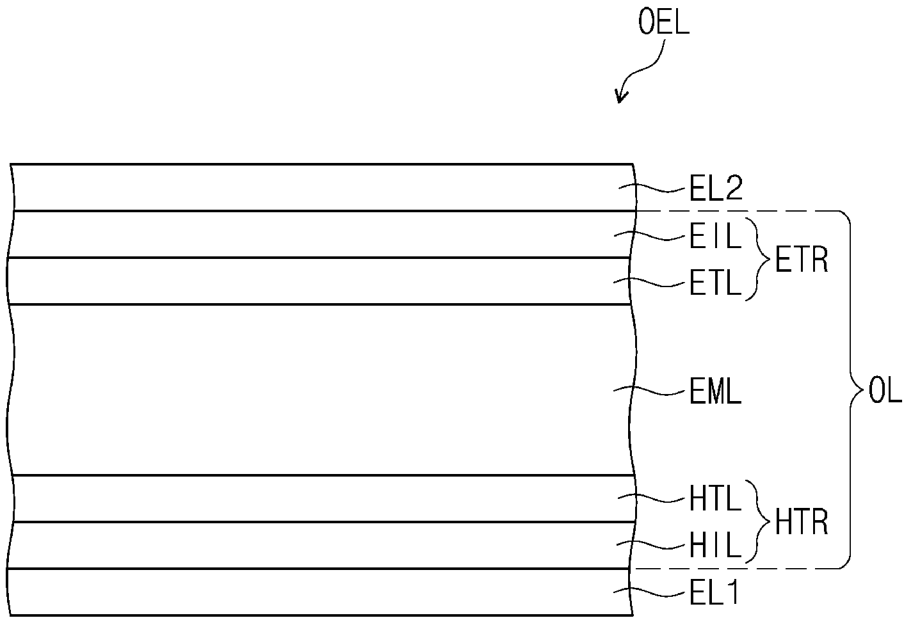
FIG. 6 is a cross-sectional view of a light-emitting device according to an embodiment.
Figure 7:
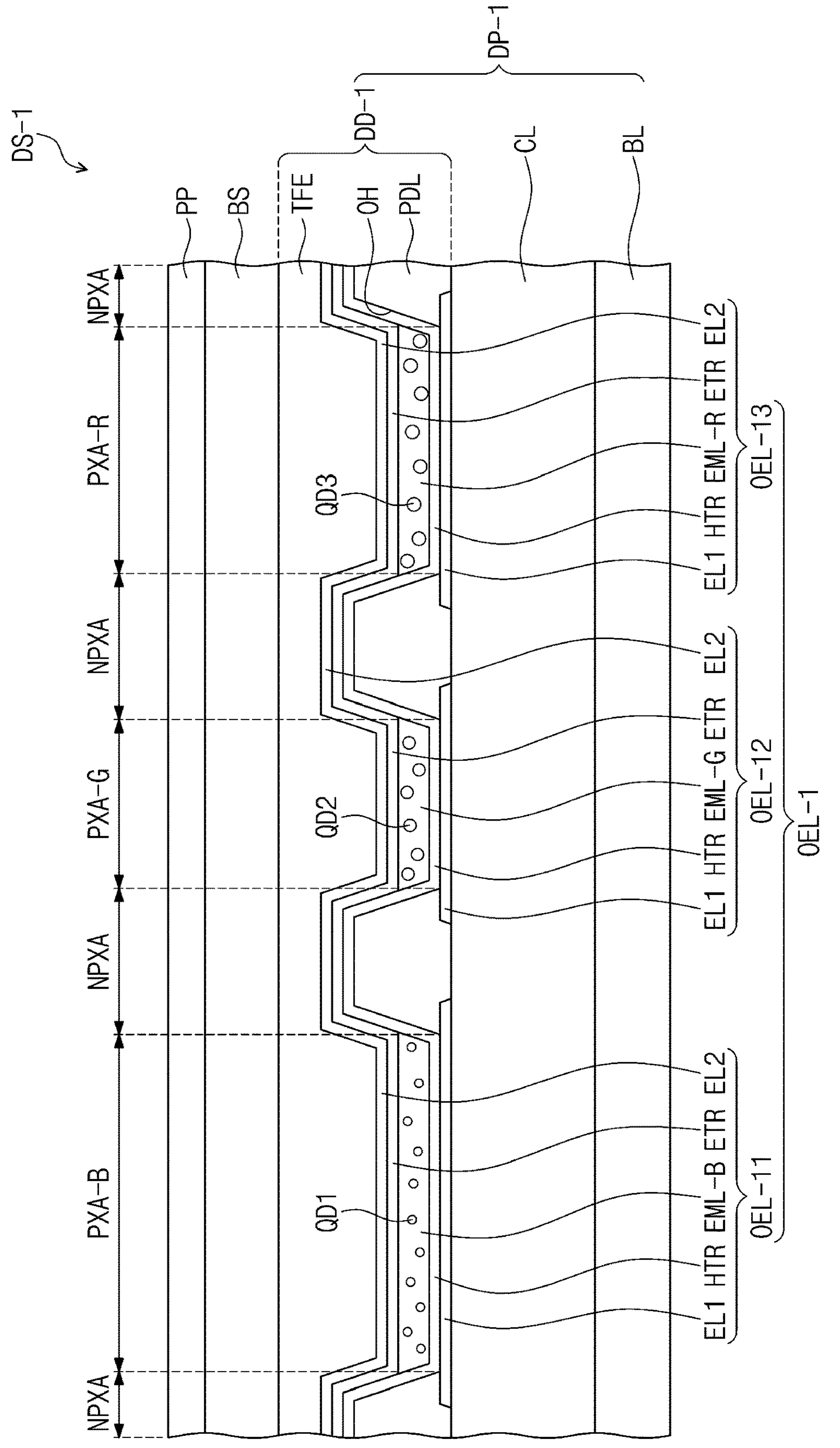
FIGS. 7 to 9 each are a cross-sectional view of a display apparatus according to an embodiment.
Figure 8:
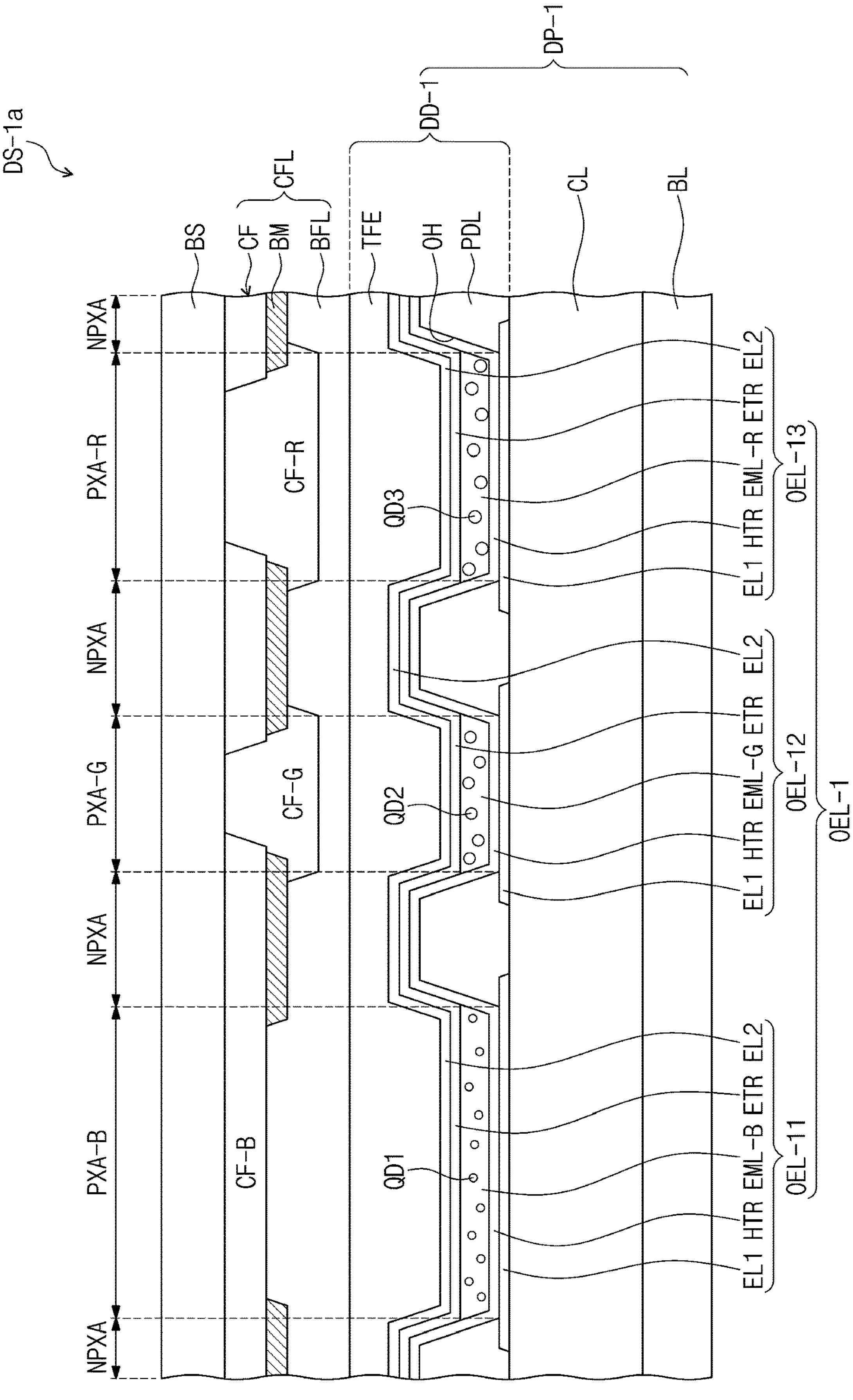
Figure 9:
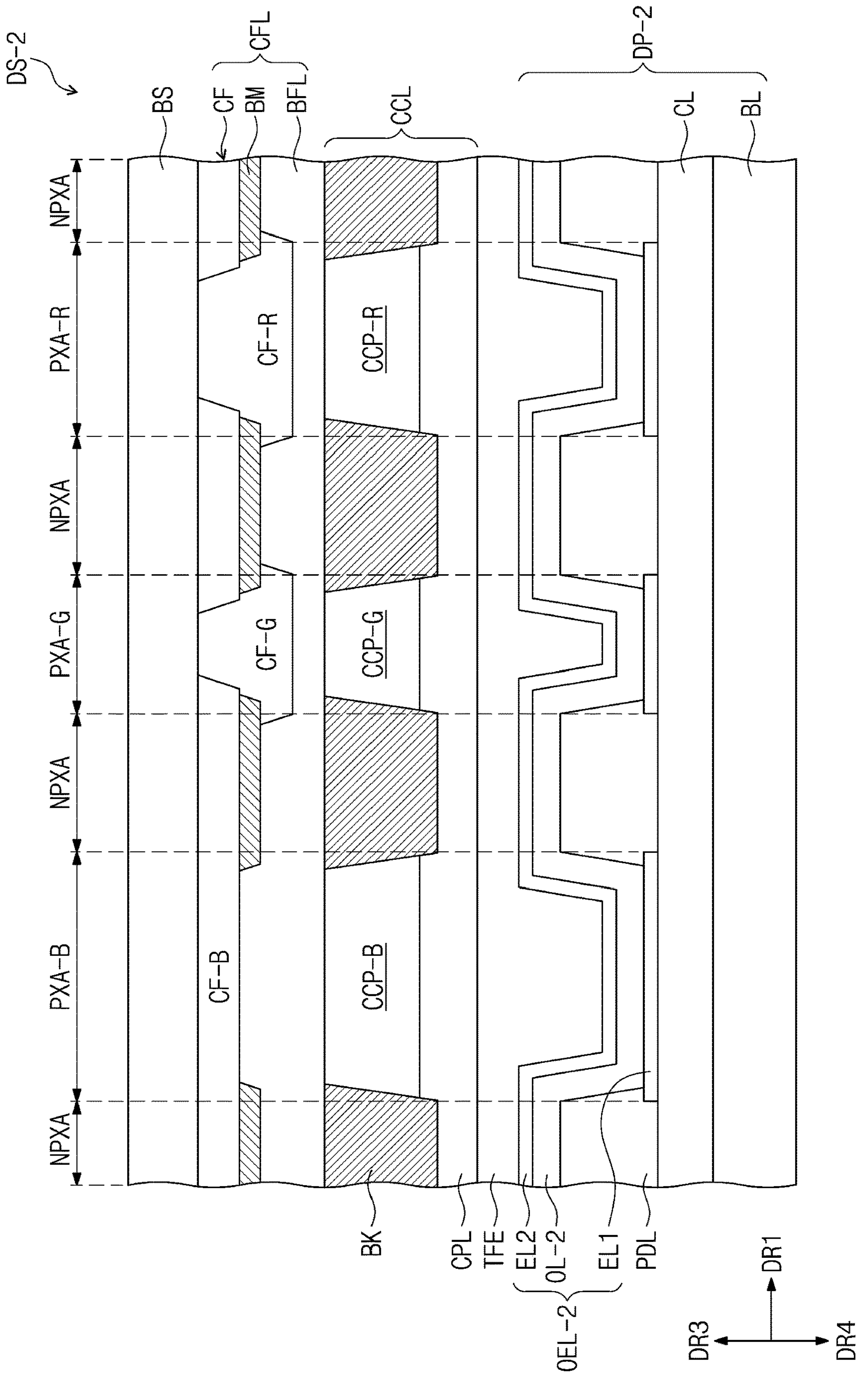
Figure 10:
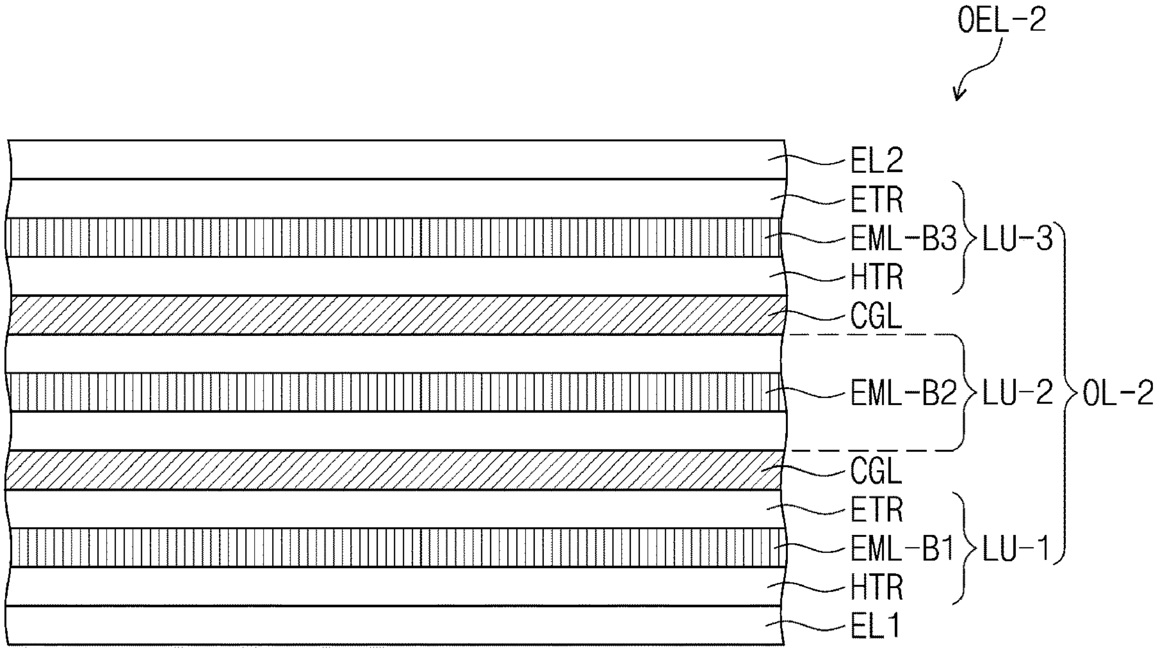
FIG. 10 is a cross-sectional view of a light-emitting device according to an embodiment.

FIG. 1 is a perspective view of the display apparatus of an embodiment, and FIGS. 2A and 2B each are a cross-sectional view of the display apparatus of an embodiment. FIG. 2A is a cross-sectional view illustrating a part taken along line I-I' of FIG. 1. FIG. 3 is a cross-sectional view of a display panel included in a display apparatus of an embodiment. FIG. 4 is a plan view of a display panel included in a display apparatus of an embodiment, and FIG. 5 is a cross-sectional view illustrating a part taken along line II-II' of FIG. 4. FIG. 6 is a cross-sectional view of a light-emitting device according to an embodiment. FIGS. 7 to 9 each are a cross-sectional view of a display apparatus of an embodiment. FIG. 10 is a cross-sectional view of a light-emitting device according to an embodiment.

Referring to FIG. 1, a display apparatus DS can display an image IM through a display surface IS. In FIG. 1, the display surface IS is illustrated parallel to a surface defined by a first directional axis DR1 and a second directional axis DR2 crossing the first directional axis DR1. However, this is merely an example, and in another embodiment, a display device (not shown) may have a curved shape.

The normal direction of the display surface IS, that is, the thickness direction of the display apparatus DS, is indicated by a third direction DR3. A front surface (or a top surface) and a rear surface (or a bottom surface) in each of the members are distinguished by the third directional axis DR3. However, the directions indicated by the first to third directional axes DR1, DR2, and DR3 are relative concepts, and may thus be changed to other directions.

In FIG. 1, a mobile electronic device is illustrated as an example of the display apparatus DS. However, the display apparatus DS may be used in large scale electronic devices such as a television, a monitor, or an outdoor advertising board, as well as, in small-to-medium scale electronic devices such as a personal computer, a laptop computer, a personal digital terminal, a vehicle navigation unit, a game console, a smart phone, a tablet, and a camera. These are merely provided as embodiments, and thus other electronic devices may be adopted as long as not departing from the inventive concept.

The display surface IS includes a display region DA on which the image IM is displayed and a non-display region NDA adjacent to the display region DA. The non-display region NDA is a region in which an image is not displayed. FIG. 1 illustrates watch windows and application icons as an example of the image IM.

The display region DA may have a tetragonal shape. The non-display region NDA may surround the display region DA. However, the embodiment is not limited thereto, and the shape of the display region DA and the shape of the non-display region NDA may be relatively designed. Also, the non-display region NDA may not be present on a front surface of the display apparatus DS.

Display panels DP, DP-1, and DP-2 may be luminous display panels included in the display apparatuses DS, DS-a, DS-1, DS-1*a*, and DS-2 of embodiments illustrated in FIGS. 1 to 9. For example, the display panels DP, DP-1, and DP-2 may be organic electroluminescence display panels or quantum dot light emitting display panels. However, the embodiment is not limited thereto.

The display panel DP according to an embodiment may include an encapsulation member TFE disposed on the light-emitting devices OEL, OEL-1, and OEL-2.

Hereinafter, in the description of the display apparatus and the display panel of an embodiment, the display apparatuses DS and DS-a and the display panel DP illustrated in FIGS. 1 to 5 will be mainly described, but the embodiment is not limited thereto, and the description of the configuration with the same or similar reference numerals may be equally applied to the description of the display apparatuses DS-1, DS-1*a*, and DS-2 illustrated in FIGS. 7 to 9.

The encapsulation member TFE in the display apparatuses DS and DS-a may include a light absorber. In an embodiment, the encapsulation member TFE may include the light absorber to absorb a portion of incident light from the outside of the display apparatuses DS and DS-a. The encapsulation member TFE including the light absorber may absorb external light to block at least a portion of external light transmitted to the light-emitting device OEL.

The encapsulation member TFE in the display apparatuses DS and DS-a of an embodiment may include the light absorber of an embodiment including a hexagonal heterocycle containing two or more nitrogen atoms as a ring-forming atom, and first to third substituents which are substituted at the hexagonal heterocycle.

The light absorber of an embodiment may include a hexagonal heterocycle containing two or more nitrogen atoms as a ring-forming atom, and first to third substituents which are substituted at the hexagonal heterocycle, the first to third substituents being different from each other. The first substituent in the light absorber of an embodiment may be a substituted phenyl group containing at least one hydroxyl group, and the second substituent may be a condensed ring group in which three or more rings are condensed.

The third substituent may be different from the first substituent and the second substituent. The third substituent may be an alkyl group, an oxy group, a thio group, an alkyl group, a heterocyclic group, etc. For example, the third substituent may be a substituted or unsubstituted oxy group or a substituted or unsubstituted thio group that is directly substituted at a core, which is a hexagonal heterocycle, or a substituted or unsubstituted phenyl group that is directly substituted at the hexagonal heterocycle.

In the light absorber of an embodiment, the hexagonal heterocycle may be triazine or pyrimidine.

In the light absorber of an embodiment, the first substituent may be a phenyl group substituted with 1 to 3 hydroxyl groups. The first substituent may be represented by any one among H1 to H5 below.

H1

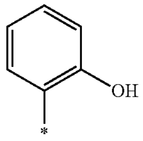

H2

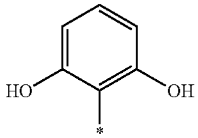

H3

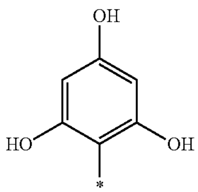

H4

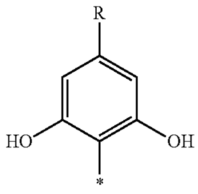

-continued

H5

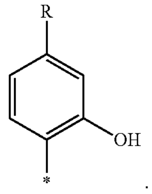

Meanwhile, in H4 and H5, R may be a substituted or unsubstituted alkoxy group. For example, in H4 and H5, R may be a methoxy group, an undecyloxy group, a dodecyloxy group, a cyclopentoxy group, or an ethyl pentyloxy group, but is not limited thereto.

The second substituent may be a substituted or unsubstituted anthracene group, a substituted or unsubstituted pyrene group, a substituted or unsubstituted chrysene group, a substituted or unsubstituted dibenzofuran derivative, a substituted or unsubstituted carbazole derivative, or a substituted or unsubstituted fluorene derivative. Meanwhile, a substituent of the substituted or unsubstituted dibenzofuran derivative, a substituent of the substituted or unsubstituted carbazole derivative, and a substituent of the substituted or unsubstituted fluorene derivative may be each independently a hydrogen atom, an alkyl group having 1 to 20 carbon atoms, an alkenyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or adjacent groups may be bonded to each other to form a ring.

The second substituent may be represented by any one among Ar-a to Ar-h.

Ar-a

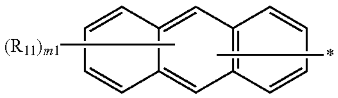

Ar-b

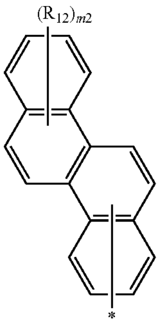

Ar-c

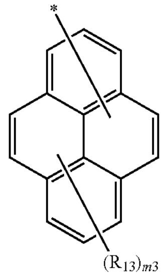

-continued

Ar-d

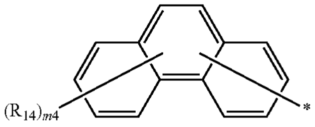

Ar-e

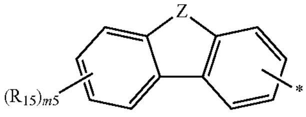

Ar-f

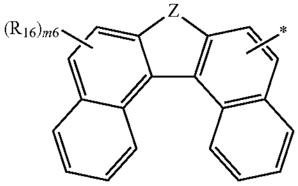

Ar-g

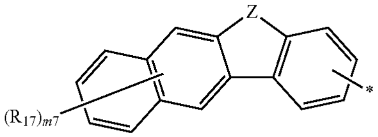

Ar-h

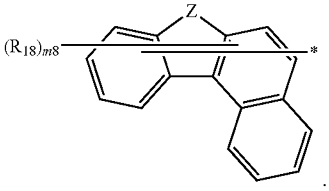

In Ar-e to Ar-h, Z may be O, S, $NR_a$, $CR_bR_c$, and $R_a$ to Re may be each independently a hydrogen atom, a deuterium atom, a halogen atom, an alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In addition, in Ar-a to Ar-h, $R_{11}$ to $R_{18}$ are each independently a hydrogen atom, a deuterium atom, a halogen atom, an alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and m1 to m8 may be each independently an integer of 0 to 4.

When m1 to m8 are an integer of 2 or more, a plurality of $R_{11}$'s to $R_{18}$'s may be the same as or different from each other.

In the light absorber of an embodiment, the third substituent may be a hydrogen atom, a substituted or unsubstituted alkyl group having 1 to 30 carbon atoms, a substituted or unsubstituted alkoxy group having 1 to 20 carbon atoms, a substituted or unsubstituted aryloxy group having 6 to 30 ring-forming carbon atoms, a substituted or unsubstituted alkylthio group having 1 to 20 carbon atoms, a substituted or unsubstituted arylthio group having 6 to 30 ring-forming carbon atoms, a substituted or unsubstituted heterocyclic group having 2 to 30 ring-forming carbon atoms, or a substituted or unsubstituted aryl group having 6 to 30 ring-forming carbon atoms. For example, the third substituent may be a substituted or unsubstituted alkoxy group having 1 to 20 carbon atoms, a substituted or unsubstituted aryloxy group having 6 to 30 ring-forming carbon atoms, a substituted or unsubstituted alkylthio group having 1 to 20 carbon atoms, a substituted or unsubstituted arylthio group having 6 to 30 ring-forming carbon atoms, or a substituted or unsubstituted phenyl group.

The third substituent may be represented by any one among S1 to S15.

S1

S2

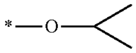

S3

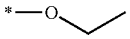

S4

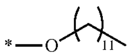

S5

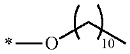

S6

S7

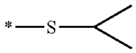

S8

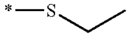

S9

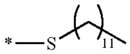

S10

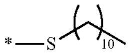

S11

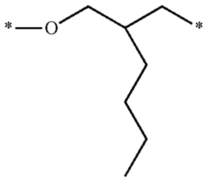

S12

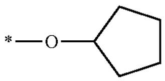

S13

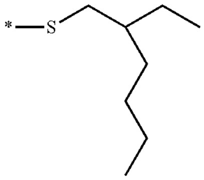

S14

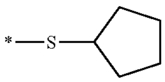

S15

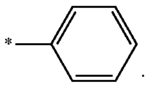

In the description, the term "substituted or unsubstituted" may indicate that a group is unsubstituted or is substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents exemplified above may be substituted or unsubstituted. For example, a biphenyl group may be interpreted as an aryl group or a phenyl group substituted with a phenyl group.

In the description, the phrase “bonded to an adjacent group to form a ring” may indicate that one is bonded to an adjacent group to form a substituted or unsubstituted hydrocarbon ring, or a substituted or unsubstituted heterocycle. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocyclic or polycyclic. In addition, the rings formed by being bonded to each other may be connected to another ring to form a spiro structure.

In the description, the term “an adjacent group” may mean a substituent substituted for an atom which is directly connected to an atom substituted with a corresponding substituent, another substituent substituted for an atom which is substituted with a corresponding substituent, or a substituent sterically positioned at the nearest position to a corresponding substituent. For example, two methyl groups in 1,2-dimethylbenzene may be interpreted as “adjacent groups” to each other, and two ethyl groups in 1,1-diethylcyclopentane may be interpreted as “adjacent groups” to each other.

In the description, examples of the halogen atom may include a fluorine atom, a chlorine atom, a bromine atom, and an iodine atom.

In the description, the alkyl group may be a linear, branched or cyclic type. The number of carbons in the alkyl group is 1 to 50, 1 to 30, 1 to 20, 1 to 10, or 1 to 6. Examples of the alkyl group may include a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc., but are not limited thereto.

In the description, an aliphatic hydrocarbon ring group means any functional group or substituent derived from an aliphatic hydrocarbon ring. The aliphatic hydrocarbon ring group may be a saturated hydrocarbon ring group having 5 to 20 ring-forming carbon atoms.

In the description, an aryl group means any functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, etc., but are not limited thereto.

In the description, the fluorenyl group may be substituted, and two substituents may be combined with each other to form a spiro structure. Examples of the substituted fluorenyl group are as follows. However, an embodiment of the present invention is not limited thereto.

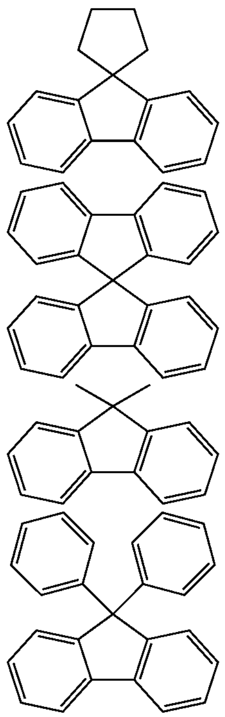

In the description, a heterocyclic group means any functional group or substituent derived from a ring containing at least one of B, O, N, P, Si, or S as a hetero atom. The heterocyclic group includes an aliphatic heterocyclic group and an aromatic heterocyclic group. The aromatic heterocyclic group may be a heteroaryl group. The aliphatic heterocycle and the aromatic heterocycle may be monocyclic or polycyclic.

In the description, the aliphatic heterocyclic group may include at least one of B, O, N, P, Si, or S as a hetero atom. When the aliphatic heterocyclic group includes two or more hetero atoms, the two or more hetero atoms may be the same as or different from each other. The number of ring-forming carbon atoms in the aliphatic heterocyclic group may be 2 to 30, 2 to 20, or 2 to 10. Examples of the aliphatic heterocyclic group include an oxirane group, a pyran group, a pyrrolidine group, a piperidine group, a tetrahydrofuran group, a tetrahydrothiophene group, a thiane group, a tetrahydropyran group, a 1,4-dioxane group, etc., but are not limited to thereto.

In the description, the heteroaryl group may include at least one of B, O, N, P, Si, or S as a hetero atom. When the heteroaryl group contains two or more heteroatoms, the two or more heteroatoms may be the same as or different from each other. The heteroaryl group may be a monocyclic heteroaryl group or a polycyclic heteroaryl group. The number of ring-forming carbon atoms in the heteroaryl group may be 2 to 30, 2 to 20, or 2 to 10. Examples of the heteroaryl group may include a thiophene group, a furan group, a pyrrole group, an imidazole group, a triazole group, a pyridine group, a bipyridine group, a pyrimidine group, a triazine group, a triazole group, an acridyl group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzoimidazole group, a benzothiazole group, a benzocarbazole group, a benzothiophene group, a dibenzothiophene group, a thienothiophene group, a benzofuran group, a phenanthroline group, a thiazole group, an isoxazole group, an oxazole group, an oxadiazolyl group, a thiadiazole group, a phenothiazine group, a dibenzosilole group, a dibenzofuran group, etc., but the embodiment of the inventive concept is not limited thereto.

In the description, the number of carbon atoms in an amino group is not specifically limited, but may be 1 to 30. The amino group may include an alkyl amino group, an aryl amino group, or a heteroaryl amino group. Examples of the amino group include a methylamino group, a dimethylamino group, a phenylamino group, a diphenylamino group, a naphthylamino group, a 9-methyl-anthracenylamino group, a triphenylamino group, etc., but are not limited thereto.

In the description, a thio group may include an alkylthio group and an arylthio group.

In the description, an oxy group may include an alkoxy group and an aryl oxy group. The alkoxy group may be a linear, branched or cyclic chain. The number of carbon atoms in the alkoxy group is not particularly limited, but for example, it may be 1 to 20 or 1 to 10. Examples of an oxy group include methoxy, ethoxy, n-propoxy, isopropoxy, butoxy, pentyloxy, hexyloxy, octyloxy, nonyloxy, decyloxy, benzyloxy, etc., but the embodiment of the inventive concept is not limited thereto.

In the description, the alkenyl group may be linear or branched. Although the number of carbon atoms is not specifically limited, it is 2 to 30, 2 to 20, or 2 to 10. Examples of the alkenyl group include a vinyl group, a 1-butenyl group, a 1-pentenyl group, a 1,3-butadienyl aryl group, a styrenyl group, a styryl vinyl group, etc., but the embodiment of the inventive concept is not limited thereto.

In the description, the number of carbon atoms in an amine group is not specifically limited, but may be 1 to 30. The amine group may include an alkyl amine group and an aryl amine group. Examples of the amine group may include a methylamine group, a dimethylamine group, a phenylamine group, a diphenylamine group, a naphthylamine group, a 9-methyl-anthracenylamine group, a triphenylamine group, etc., but are not limited thereto.

In the description, the alkyl group in an alkylthio group, an alkylsulfoxy group, an alkylaryl group, an alkylamino group, an alkyl boron group, an alkyl silyl group, and an alkyl amine group is the same as the examples of the alkyl group described above.

In the description, the aryl group in an aryloxy group, an arylthio group, an arylsulfoxy group, an arylamino group, an arylboron group, an arylsilyl group, an arylamine group is the same as the examples of the aryl group described above.

Meanwhile, in the description, "—*" refers to a position to be connected.

In the light absorber of an embodiment, the first substituent includes at least one hydroxyl group (—OH), and may be a part which absorbs light to be converted into thermal energy. In addition, the second substituent may be a part which adjusts a wavelength region of light absorbed by the light absorber. The third substituent may be a part which adjusts solubility of the light absorber of an embodiment.

The light absorber of an embodiment may absorb light in an ultraviolet wavelength region. For example, the light absorber of an embodiment may primarily absorb light in a wavelength region of 405 nm or less. The light absorber of an embodiment may primarily absorb light in a wavelength region of 380 nm to 405 nm.

The light absorber of an embodiment may be represented by Formula 1 or Formula 2 below:

Formula 1

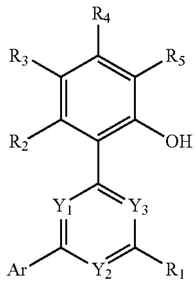

Formula 2

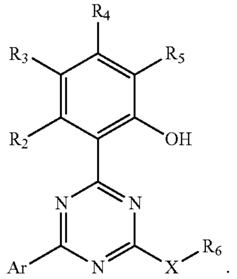

In Formula 1 above, two among $Y_1$ to $Y_3$ may be N, and the rest may be CH.

Formula 1 represents the case where a core is pyrimidine in the light absorber of an embodiment, and Formula 2 represents the case where a core is triazine in the light absorber of an embodiment.

In Formula 1 and Formula 2, Ar may be a substituted or unsubstituted aryl group having 13 to 60 ring-forming carbon atoms, or a substituted or unsubstituted heteroaryl group having 12 to 60 ring-forming carbon atoms. In addition, in Formula 1 and Formula 2, $R_2$ to $R_5$ may be each independently a hydrogen atom, a deuterium atom, a halogen atom, a cyano group, a substituted or unsubstituted alkyl group having 1 to 30 carbon atoms, a substituted or unsubstituted alkoxy group having 1 to 20 carbon atoms, a substituted or unsubstituted aryloxy group having 6 to 30 ring-forming carbon atoms, a substituted or unsubstituted alkylamine group having 1 to 30 carbon atoms, a substituted or unsubstituted arylamine group having 6 to 30 ring-forming carbon atoms, a substituted or unsubstituted heterocyclic group having 2 to 30 ring-forming carbon atoms, or a substituted or unsubstituted aryl group having 6 to 30 ring-forming carbon atoms.

Meanwhile, in Formula 1, $R_1$ may be a hydrogen atom, a substituted or unsubstituted alkyl group having 1 to 30 carbon atoms, a substituted or unsubstituted alkoxy group having 1 to 20 carbon atoms, a substituted or unsubstituted aryloxy group having 6 to 30 ring-forming carbon atoms, a substituted or unsubstituted alkylthio group having 1 to 20 carbon atoms, a substituted or unsubstituted arylthio group having 6 to 30 ring-forming carbon atoms, a substituted or unsubstituted heterocyclic group having 2 to 30 ring-forming carbon atoms, or a substituted or unsubstituted aryl group having 6 to 30 ring-forming carbon atoms. For example, in Formula 1, $R_1$ may be a substituted or unsubstituted alkoxy group having 1 to 20 carbon atoms, a substituted or unsubstituted alkylthio group having 1 to 20 carbon atoms, or an unsubstituted phenyl group.

The light absorber represented by Formula 1 includes three different substituents, and the three substituents each may be

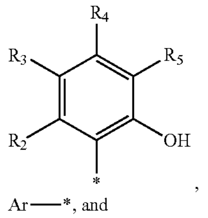
,

Ar—*, and

*—$R_1$.

In addition, the light absorber represented by Formula 2 may include each of three different substituents of

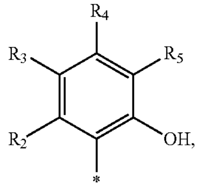
, Ar—*, and *—$XR_6$.

"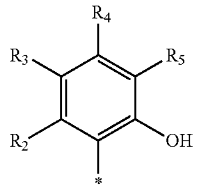"

among the three substituents may be a part which absorbs light to be converted into thermal energy. In addition, "Ar—*"

includes a condensed ring having three rings or more, and ma be a part which adjusts a wavelength region of light absorbed by the light absorber.

"*—$R_1$" or "*—$XR_6$"

may be a part which adjusts solubility of the light absorber of an embodiment. In particular, when $R_1$ is a substituted or unsubstituted alkoxy or $R_6$ is a substituted or unsubstituted alkyl group, solubility of the light absorber of an embodiment may be more improved.

In Formula 1 and Formula 2, Ar may be represented by any one among Ar-a to Ar-h below Ar-a

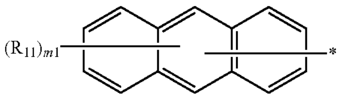

Ar-b

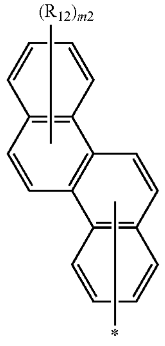

Ar-c

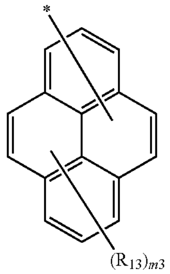

Ar-d

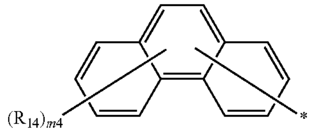

Ar-e

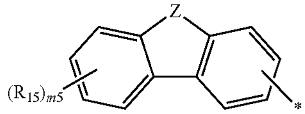

-continued

Ar-f

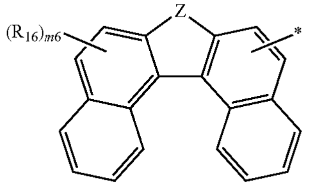

Ar-g

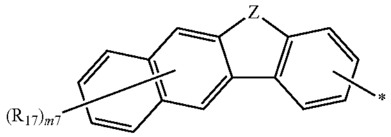

Ar-h

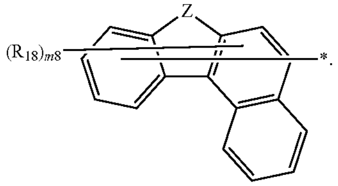

In Ar-a to Ar-h above, $R_{11}$ to $R_{18}$ are each independently a hydrogen atom, a deuterium atom, a halogen atom, an alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and m1 to m8 are each independently an integer of 0 to 4.

When m1 to m8 are 0, Ar-a to Ar-h each may be unsubstituted. For example, Ar may be unsubstituted anthracene, unsubstituted phenanthrene, unsubstituted pyrene, or unsubstituted chrysene.

Formula 1 may be represented by any one among Formula 1-1 to Formula 1-4.

Formula 1-1

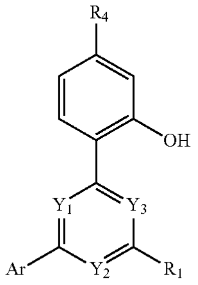

Formula 1-2

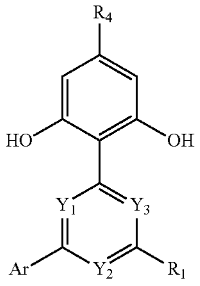

-continued

Formula 1-3

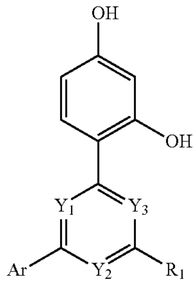

Formula 1-4

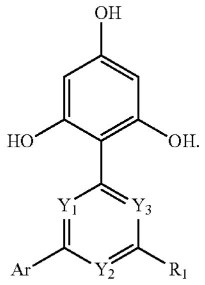

In addition, Formula 2 may be represented by any one among Formula 2-1 to Formula 2-4.

Formula 2-1

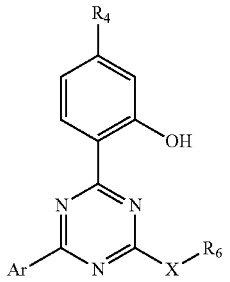

Formula 2-2

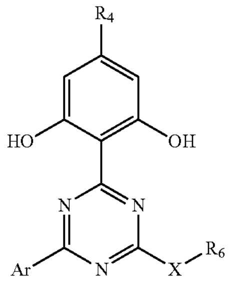

-continued

Formula 2-3

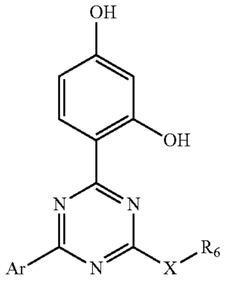

Formula 2-4

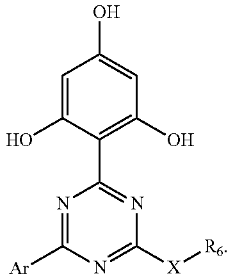

In Formula 1-1 and Formula 2-1, the phenyl group substituted at a hexagonal heterocycle, which is a core, includes one hydroxyl group; in Formula 1-2, Formula 2-2, Formula 1-3, and Formula 2-3, the phenyl group substituted at the hexagonal heterocycle includes two hydroxyl groups, and in Formula 1-4 and Formula 2-4, the phenyl group substituted at the hexagonal heterocycle includes three hydroxyl groups. Meanwhile, Formula 1-2 and Formula 2-2 represent the case where both of the two hydroxyl groups are substituted in the ortho-position relative to the attachment position of hexagonal heterocycle, which is a core, and Formula 1-3 and Formula 2-3 represent the case where one of the two hydroxyl groups is substituted in the ortho-position relative to the hexagonal heterocycle, and the other hydroxyl group is substituted in the para-position relative to the attachment position of hexagonal heterocycle.

In Formula 1-1 to Formula 1-4, the same descriptions as those in Formula 1 above may be applied to Ar, $Y_1$ to $Y_3$, $R_1$, and $R_4$. In addition, in Formula 2-1 to Formula 2-4 above, the same descriptions as those described in Formula 1 and Formula 2 above may be applied to X, Ar, $R_4$, and $R_6$.

Meanwhile, in the light absorber represented by Formula 1 of an embodiment, two selected from among $Y_1$ to $Y_3$ may be a nitrogen atom (N). That is, in Formula 1, two selected from among $Y_1$ to $Y_3$ may be a nitrogen atom (N), and the rest may be CH. For example, $Y_1$ and $Y_2$ may be nitrogen atoms and $Y_3$ may be CH, or $Y_1$ and $Y_3$ may be nitrogen atoms and $Y_2$ may be CH, or $Y_2$ and $Y_3$ may be nitrogen atoms and $Y_2$ may be CH.

The light absorber represented by Formula 1 of an embodiment may be represented by any one among Formula 1-A to Formula 1-C below. Formula 1-A to Formula 1-C represent the light absorber of an embodiment having pyrimidine as the core. Formula 1-A to Formula 1-C represent the case where the arrangement positions of the nitrogen atoms in the core that is pyrimidine are different from each other. Formula 1-A is the case where $Y_1$ and $Y_3$ are nitrogen atoms in Formula 1, Formula 1-B is the case where $Y_1$ and $Y_2$ are nitrogen atoms in Formula 1, and Formula 1-C is the case where $Y_2$ and $Y_3$ are nitrogen atoms in Formula 1.

Formula 1-A

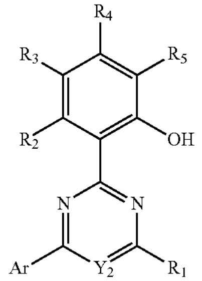

Formula 1-B

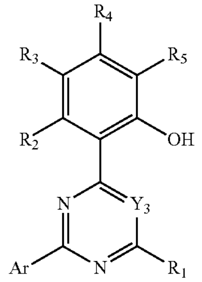

Formula 1-C

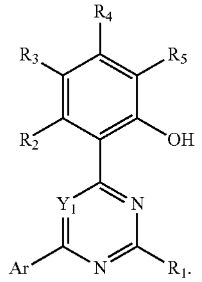

In Formula 1-A to Formula 1-C above, the same descriptions as those in Formula 1 above may be applied to $Y_1$ to $Y_3$, Ar, and $R_1$ to $R_5$.

The light absorber of an embodiment may be represented by any one among the compounds represented by Compound Group 1 below. The light absorber represented by Formula 1 may be represented by any one among the compounds represented by Compound Group 1 below:

Compound Group 1

1

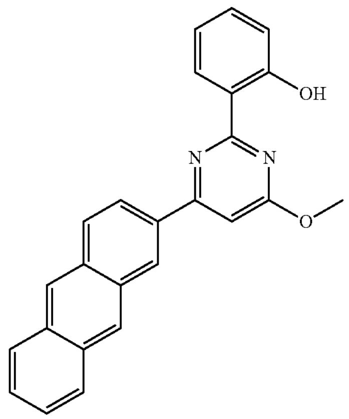

2
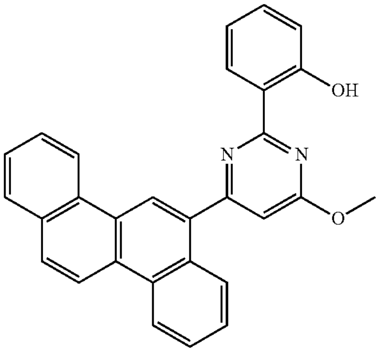 [SMILES: COc1cc(-c2cc3c4ccccc4ccc3c3ccccc23)nc(-c2ccccc2O)n1]
3
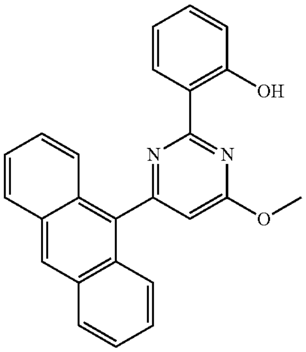
4
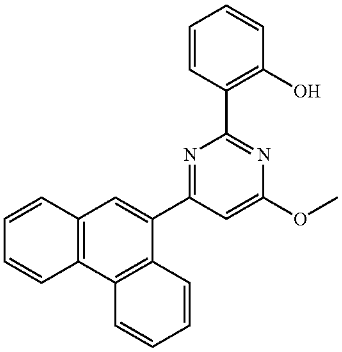
5
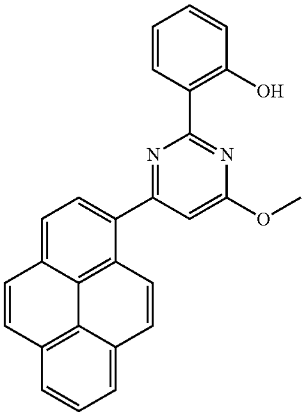
6
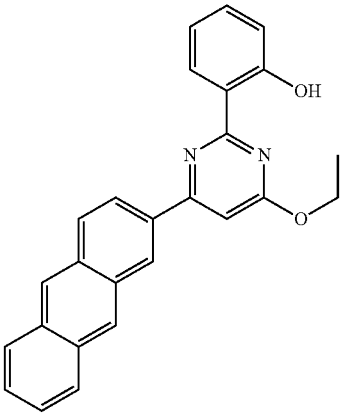
7
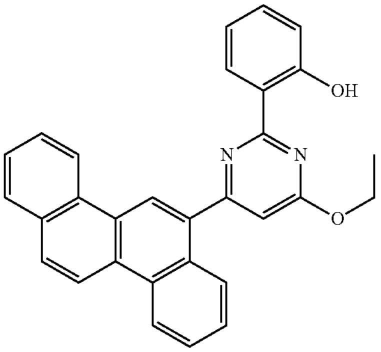
8
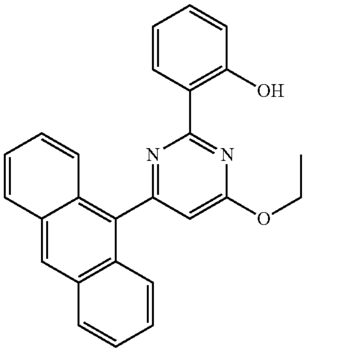
9
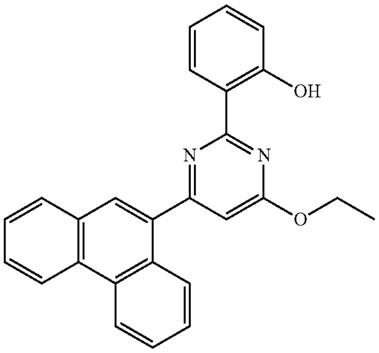

-continued
10
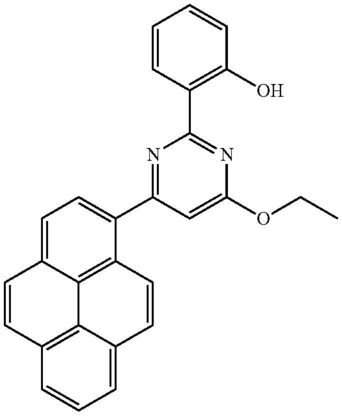
11
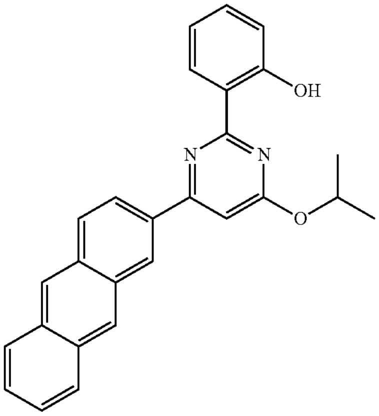
12
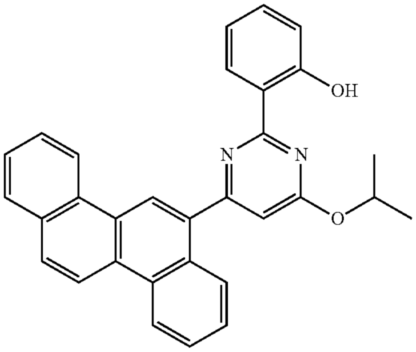
13
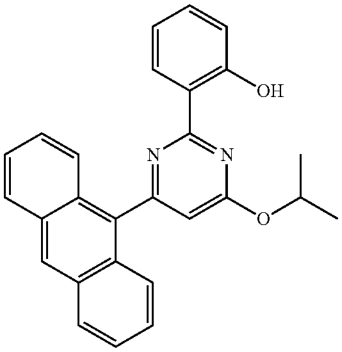
-continued
14
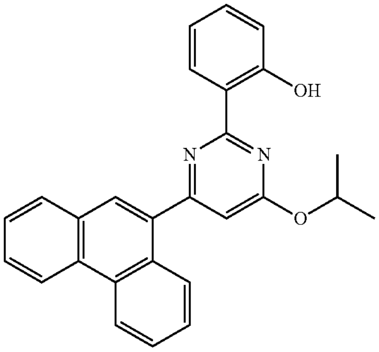
15
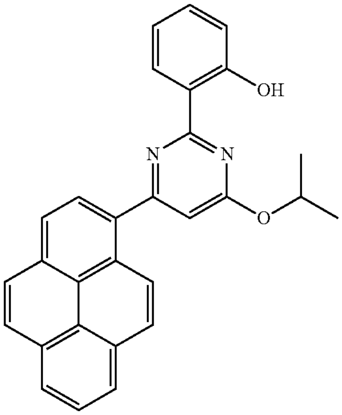 [SMILES: CC(C)Oc1cc(-c2ccc3ccc4cccc5ccc2c3c45)nc(-c2ccccc2O)n1]
16
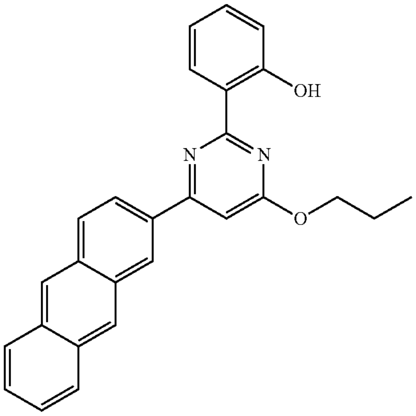
17
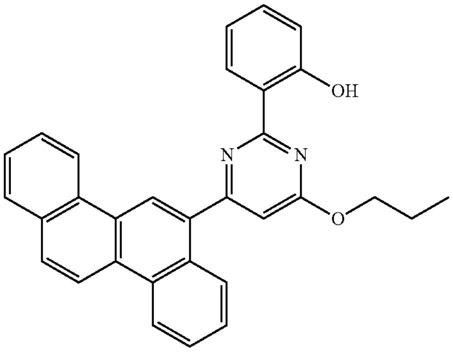

-continued
18
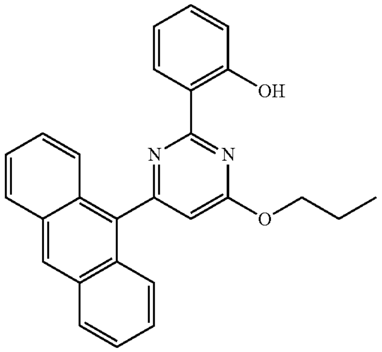
19
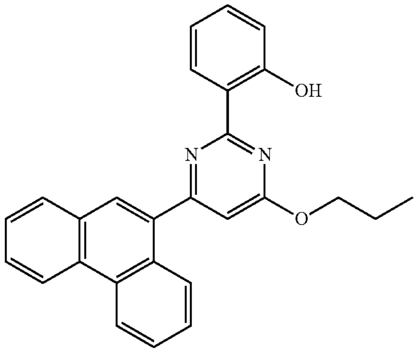
20
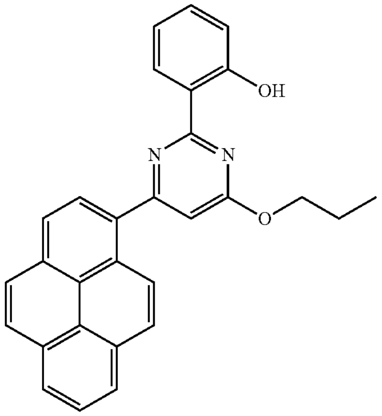
21
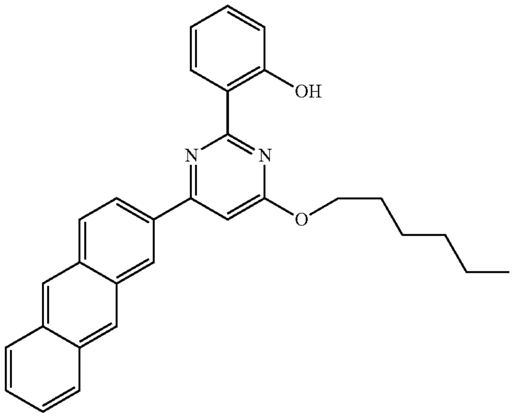
-continued
22
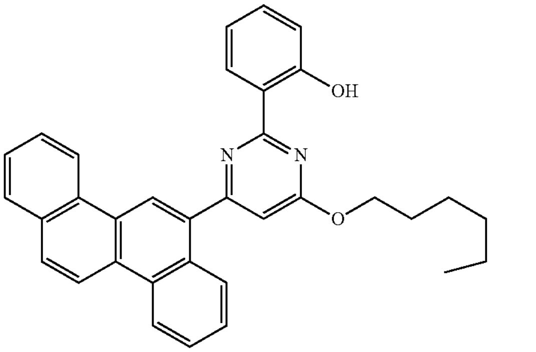
23
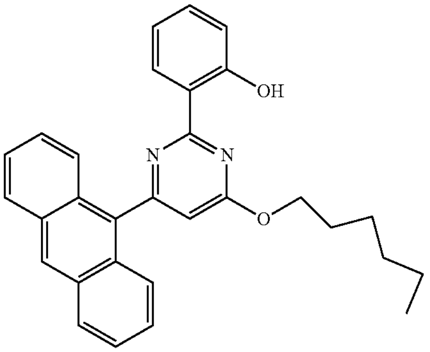
24
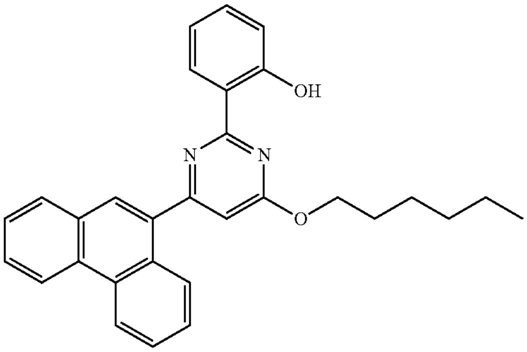
25
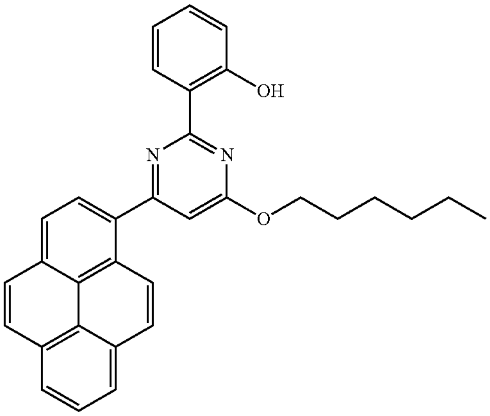 [SMILES: CCCCCCOc1cc(-c2ccc3ccc4cccc5ccc2c3c45)nc(-c2ccccc2O)n1]

-continued
26
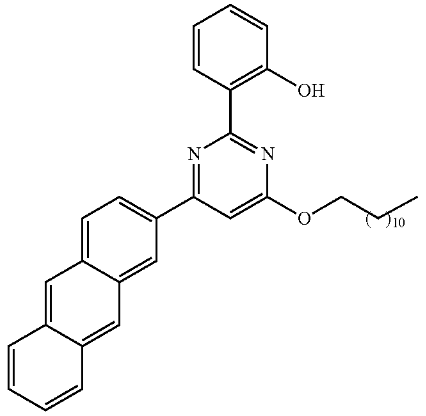
27
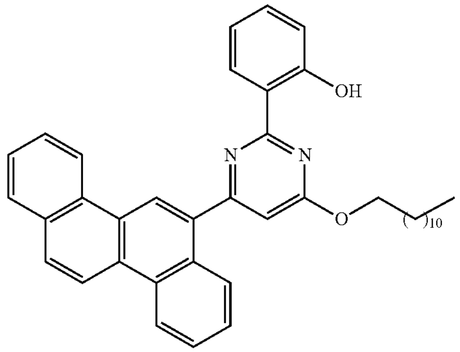
28
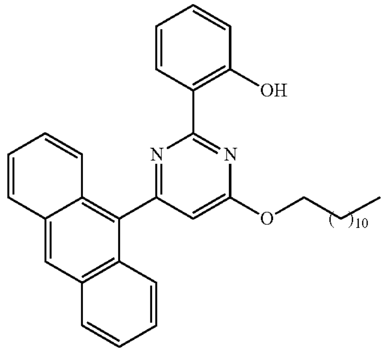
29
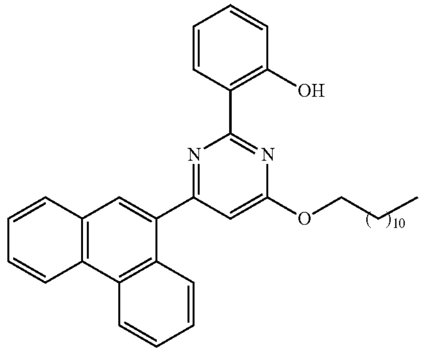
-continued
30
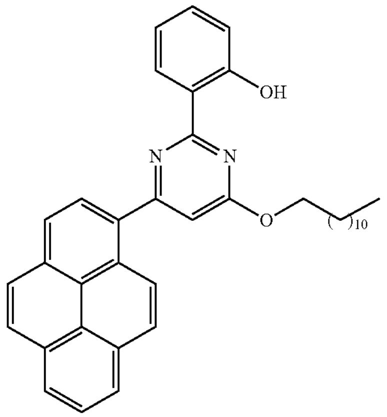
31
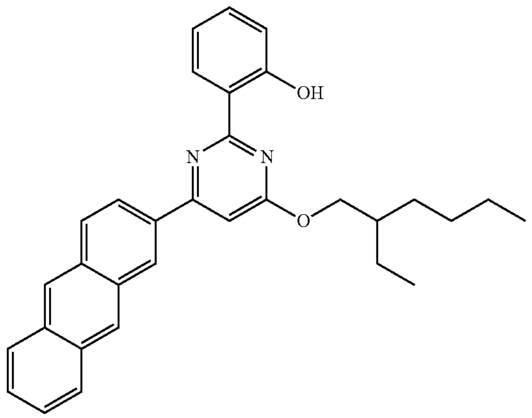
32
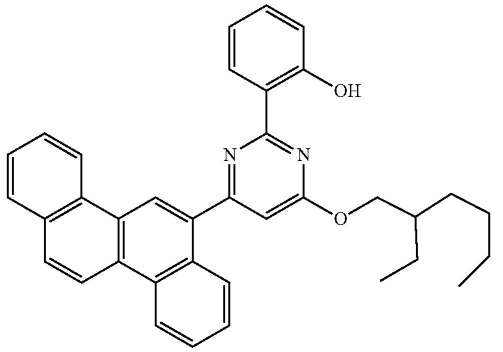
33
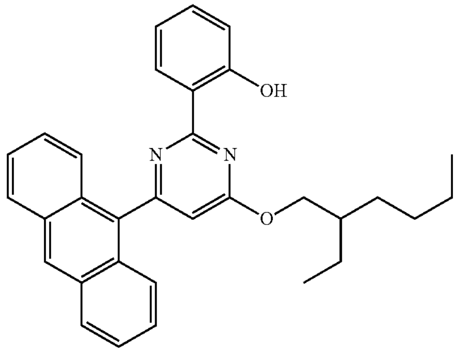

-continued
34
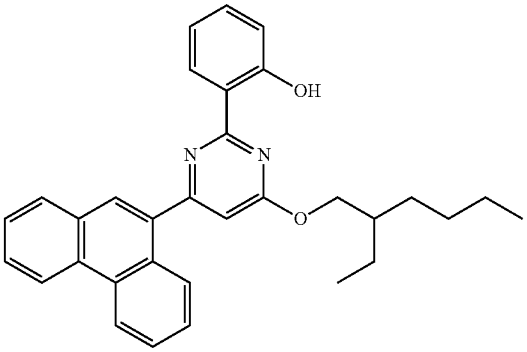
35
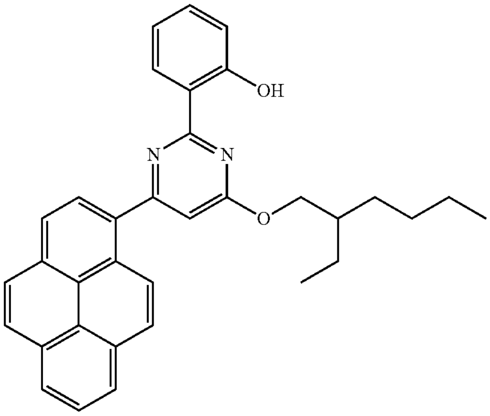
36
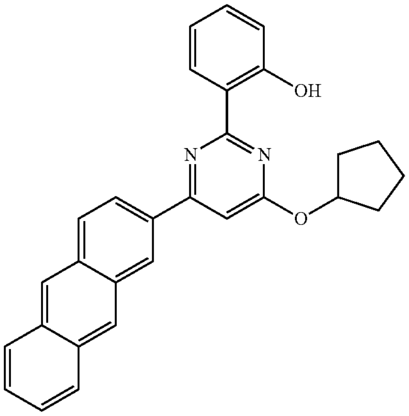 [SMILES: Oc1ccccc1-c1nc(OC2CCCC2)cc(-c2ccc3cc4ccccc4cc3c2)n1]
37
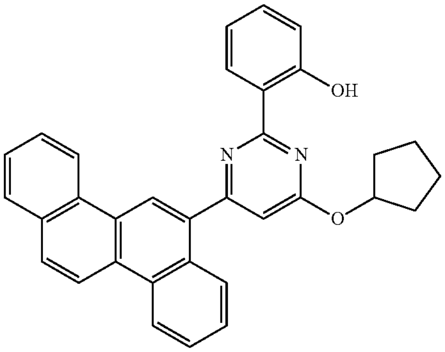
-continued
38
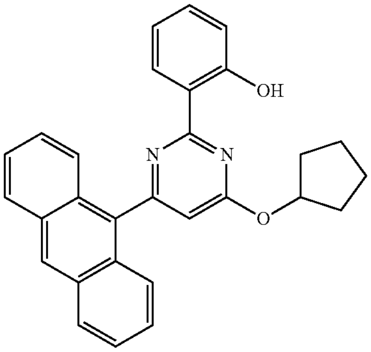
39
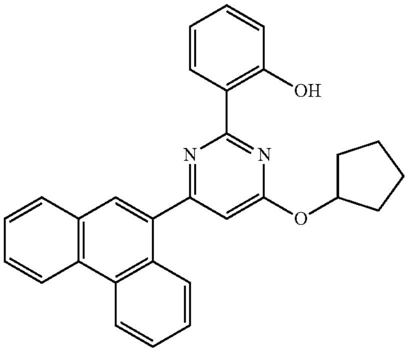
40
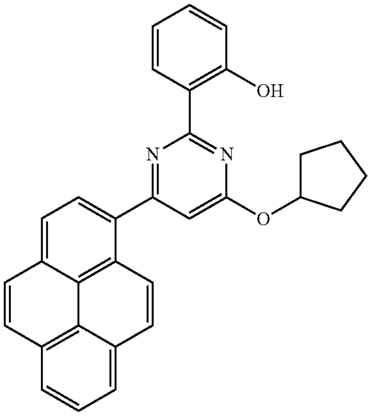
41
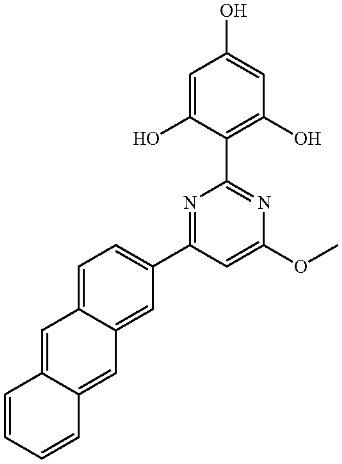

-continued
42
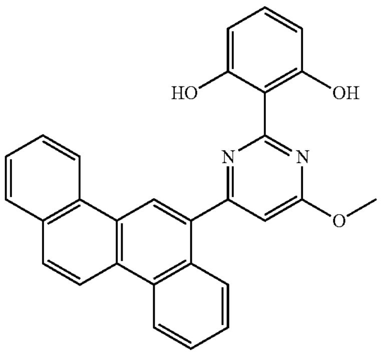
43
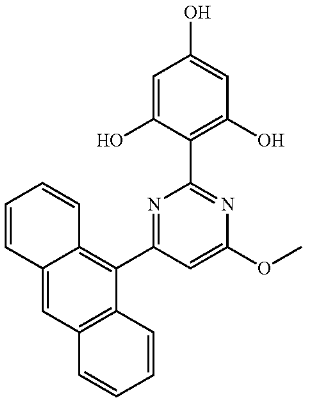
44
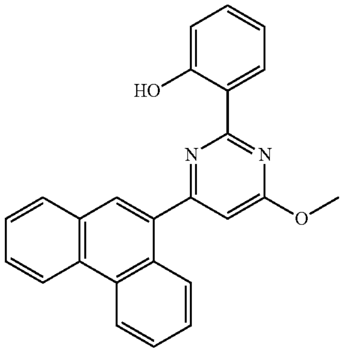
45
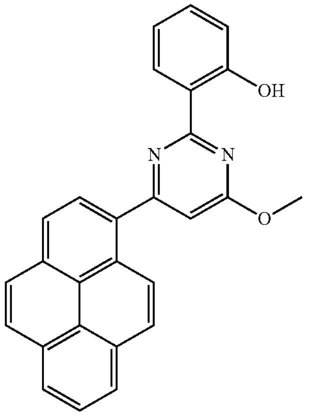
-continued
46
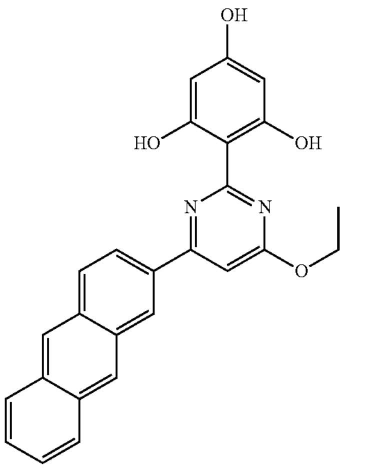
47
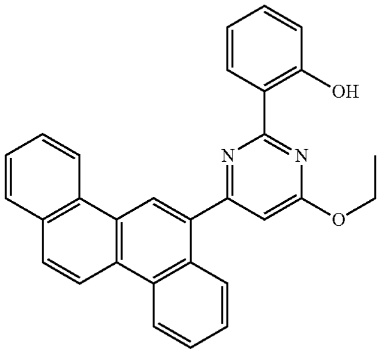
48
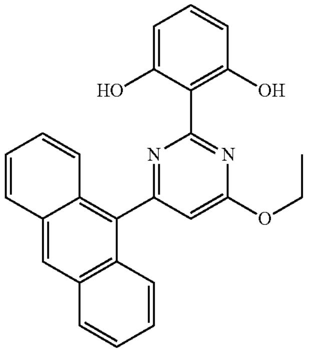
49
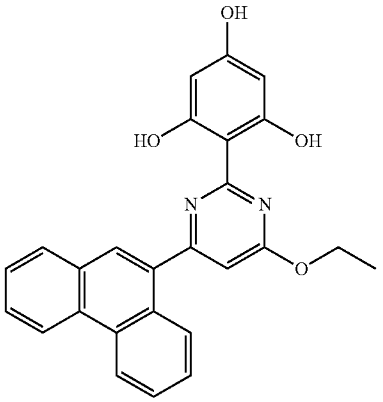

50
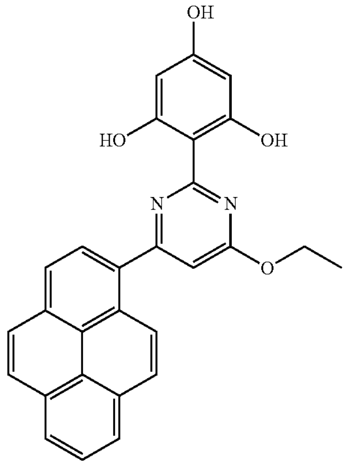
51
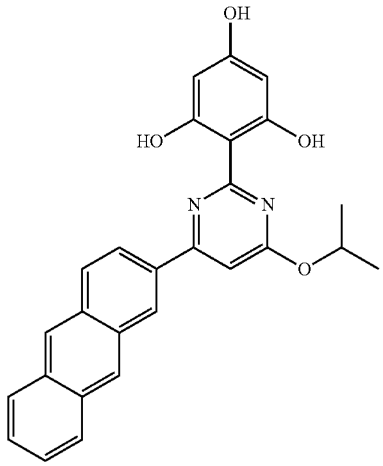
52
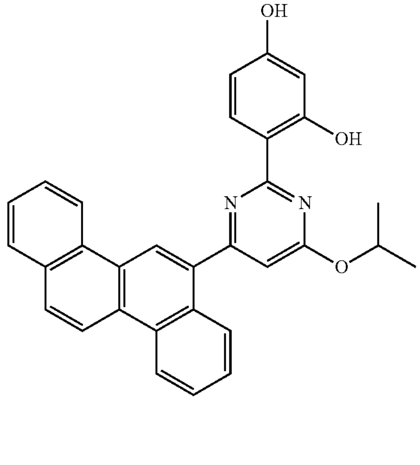
53
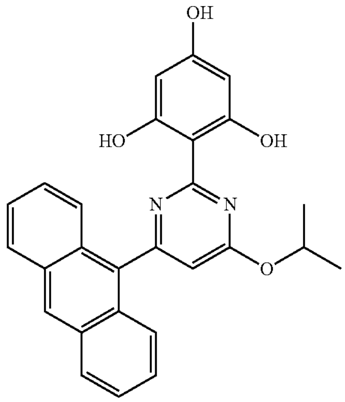
54
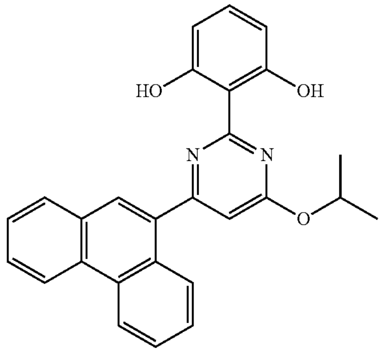
55
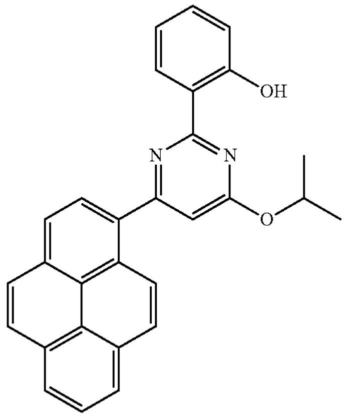
56
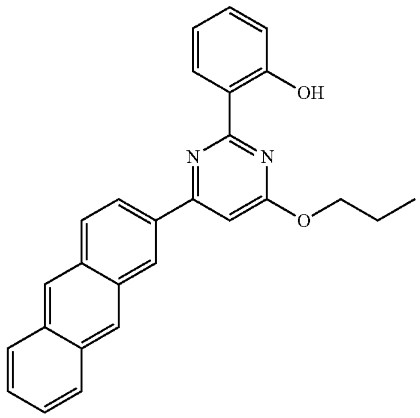 [SMILES: CCCOc1cc(-c2ccc3cc4ccccc4cc3c2)nc(-c2ccccc2O)n1]

-continued
57
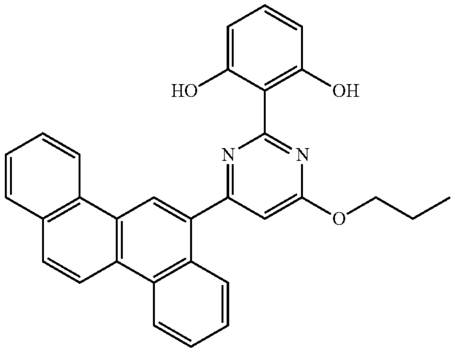
58
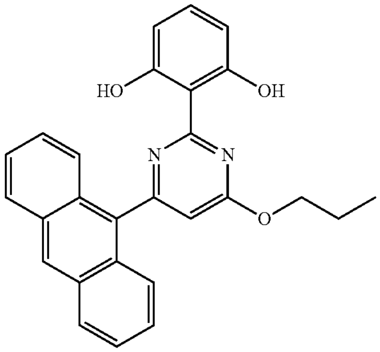
59
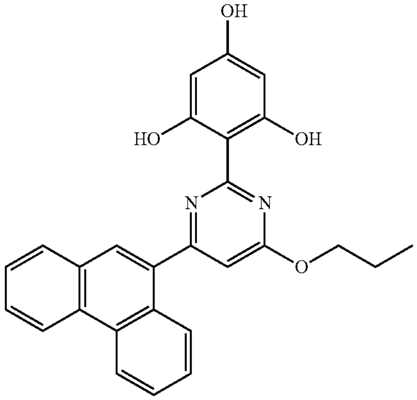
60
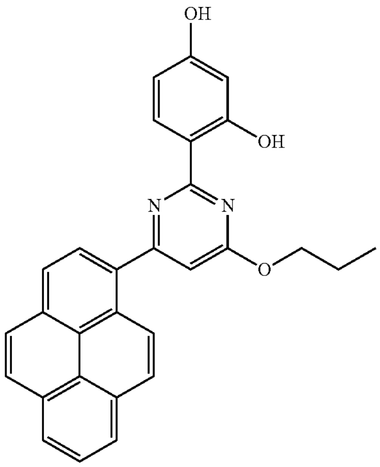
-continued
61
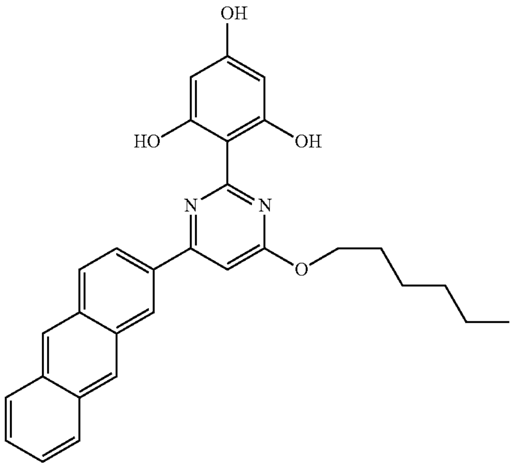
62
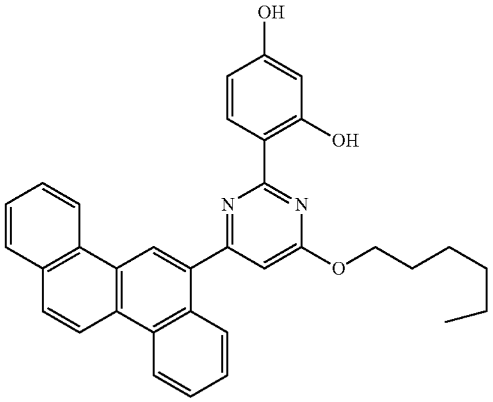
63
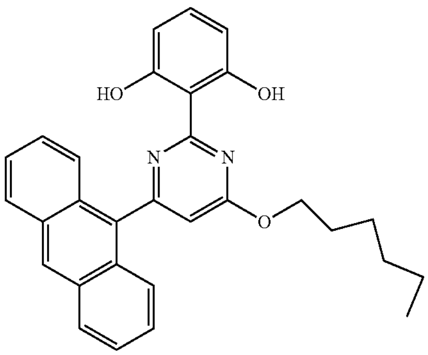

-continued
64
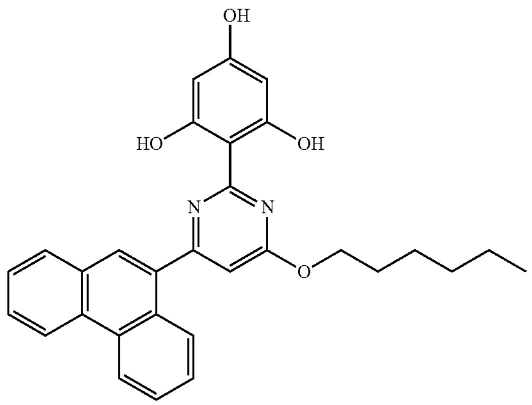
65
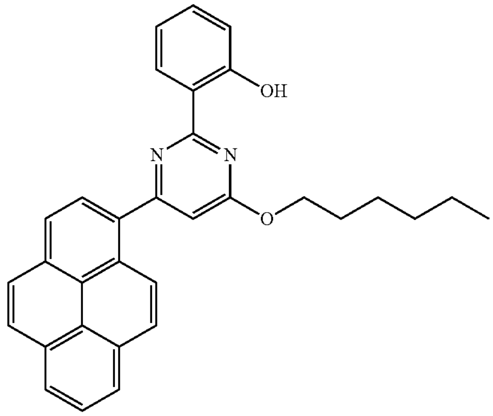
66
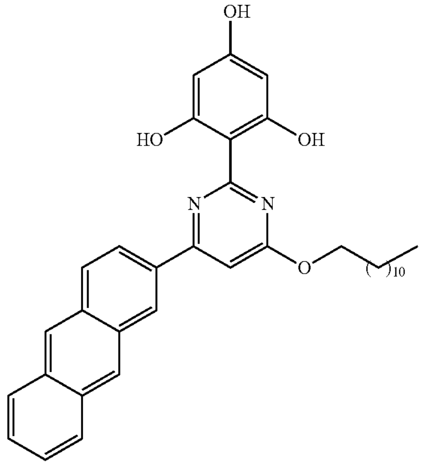
-continued
67
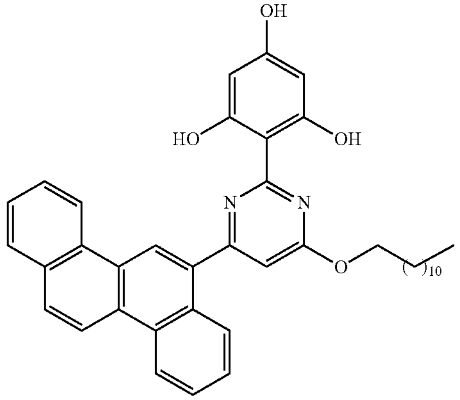
68
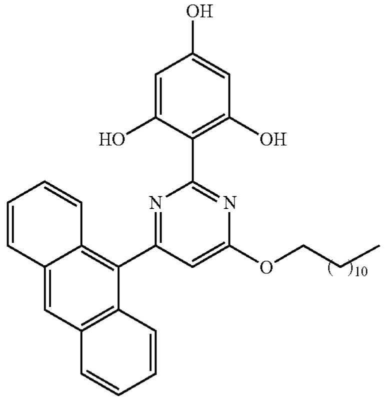
69
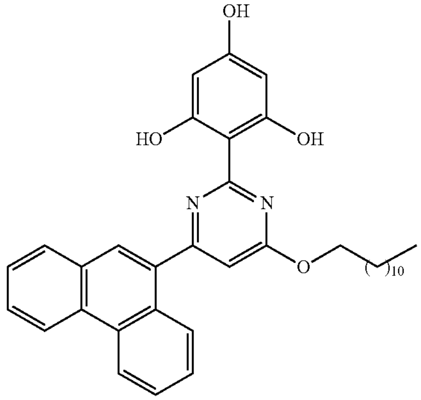
70
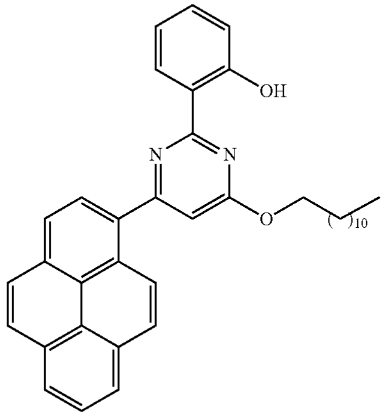

-continued
71
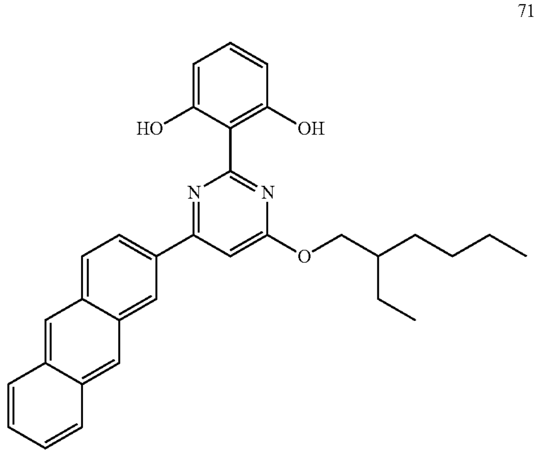
72
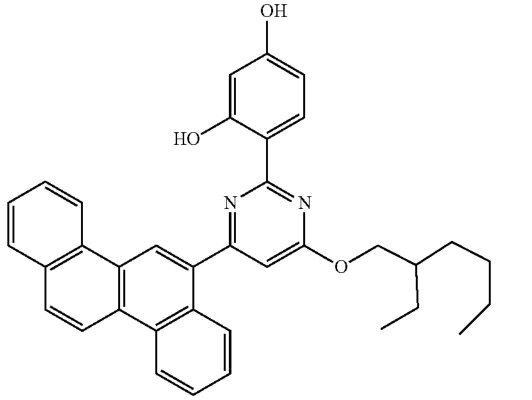
73
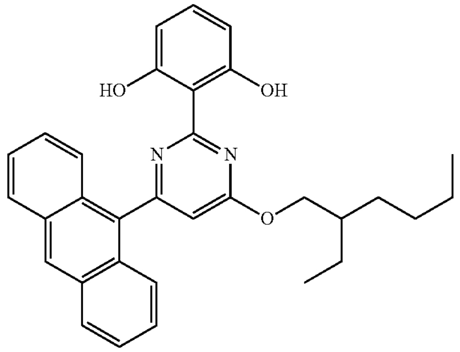
74
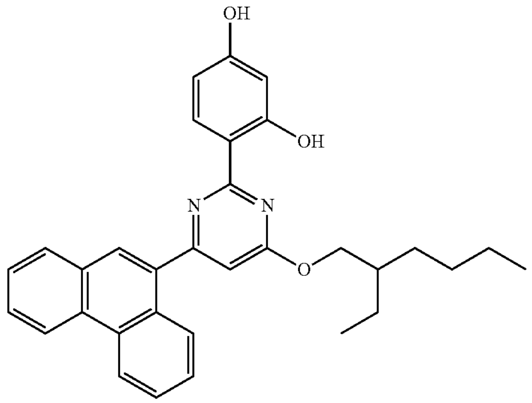
-continued
75
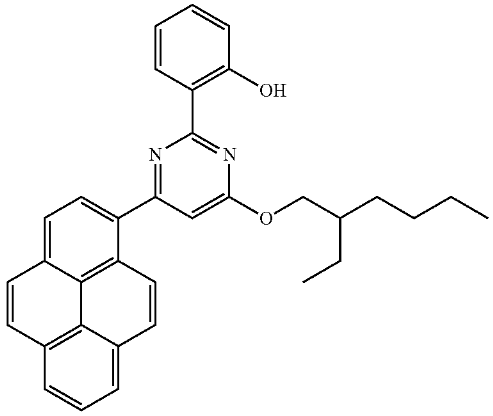
76
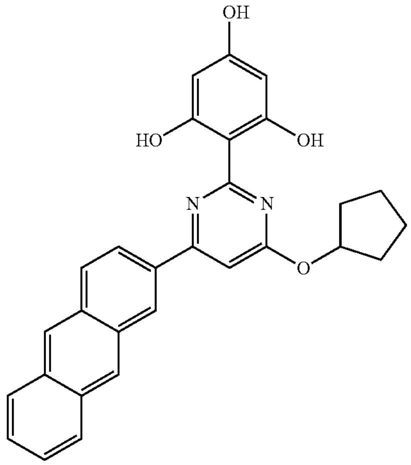
77
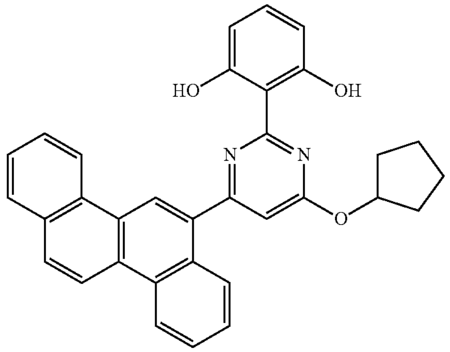
78
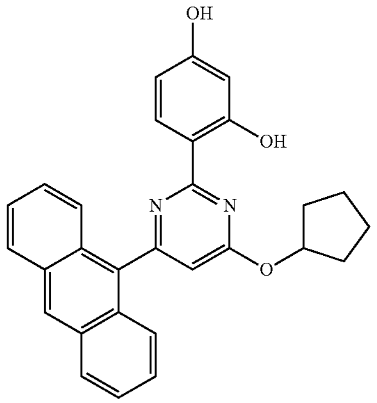 [SMILES: Oc1ccc(-c2nc(OC3CCCC3)cc(-c3c4ccccc4cc4ccccc34)n2)c(O)c1]

-continued
79
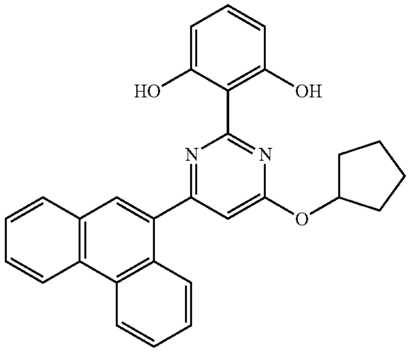
80
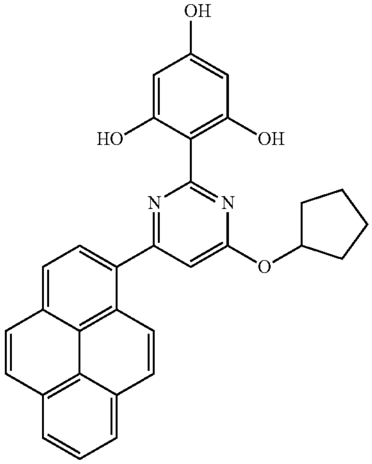
81
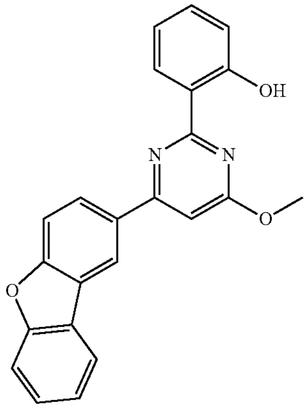
82
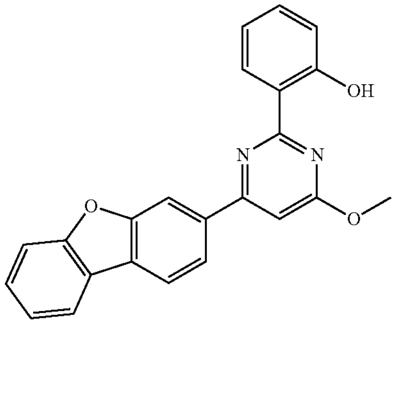
-continued
83
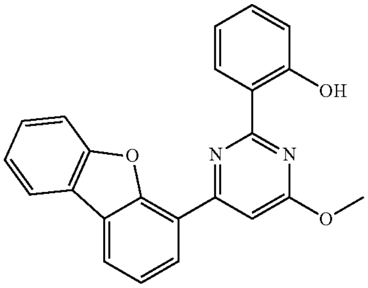
84
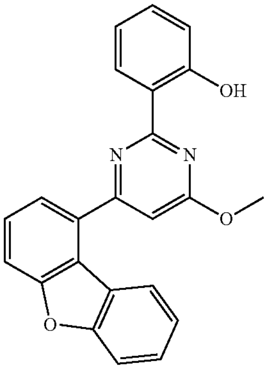
85
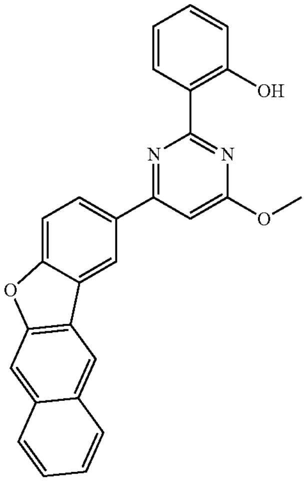
86
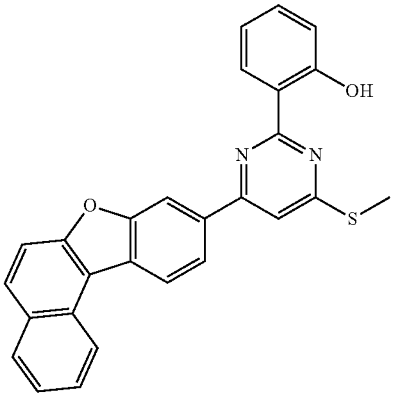

-continued
87
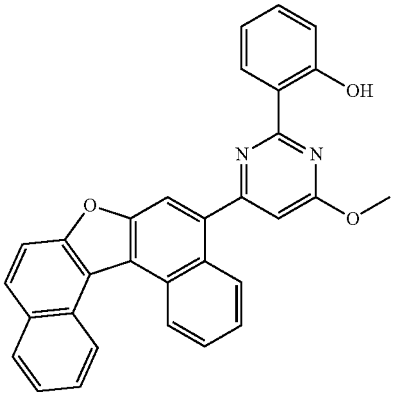
88
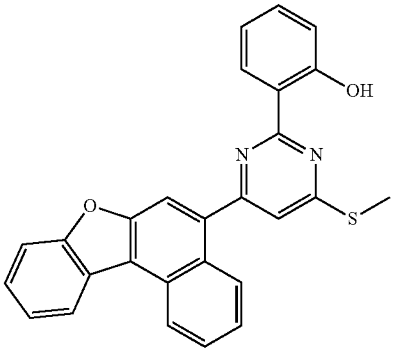
89
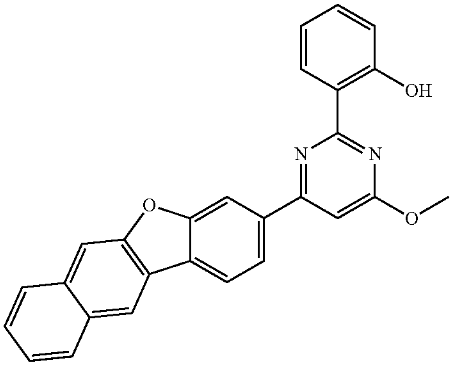
90
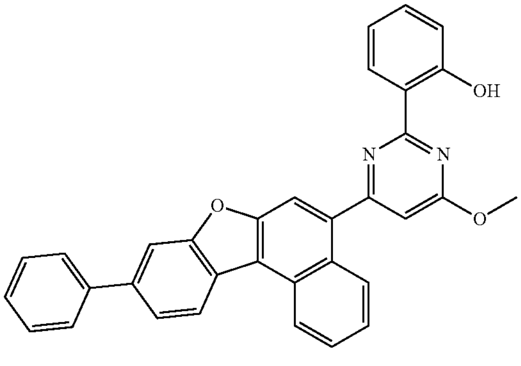
-continued
91
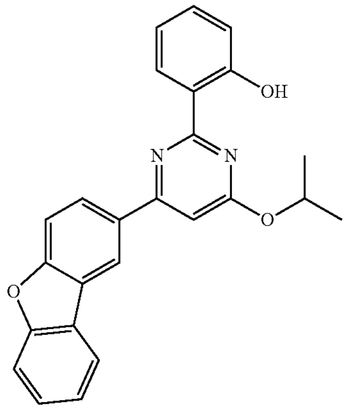
92
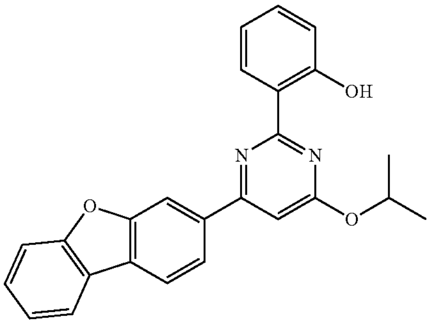
93
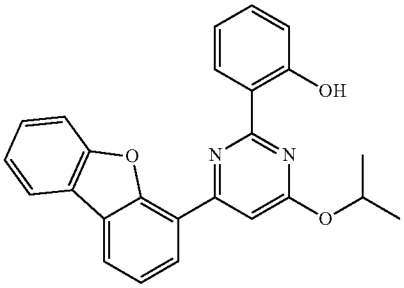
94
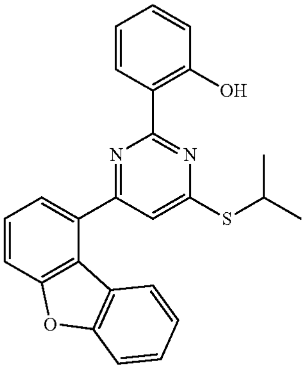

-continued
95
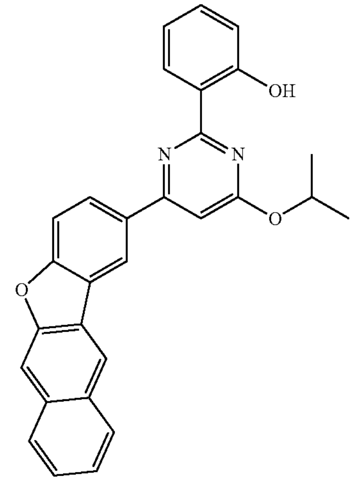
96
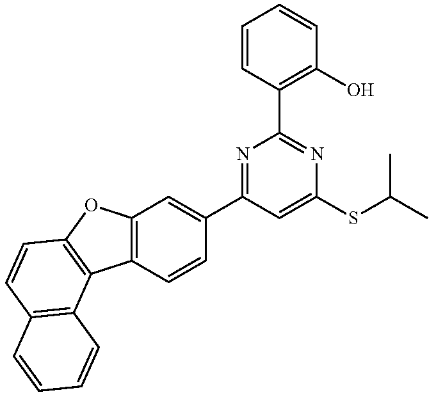
97
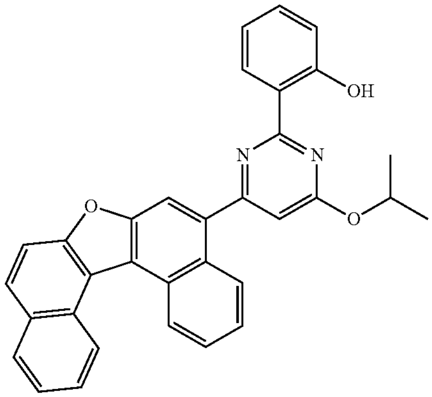
98
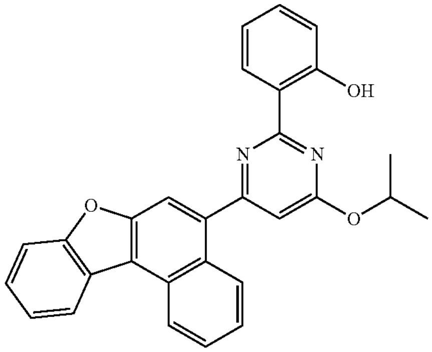
-continued
99
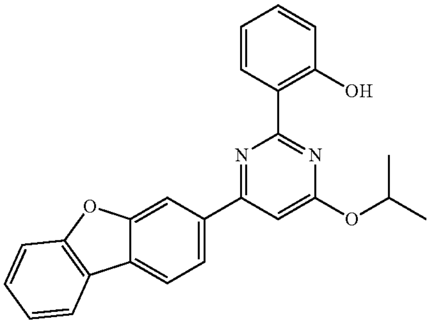
100
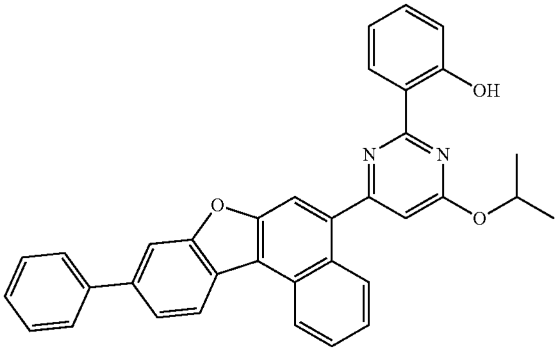
101
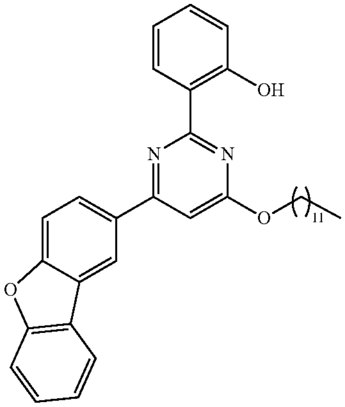
102
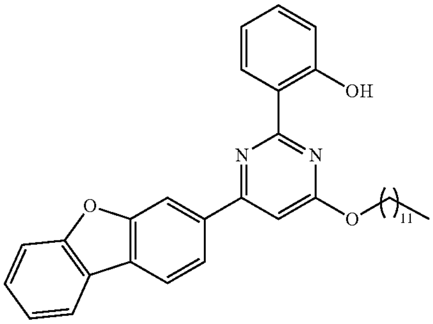

-continued
103
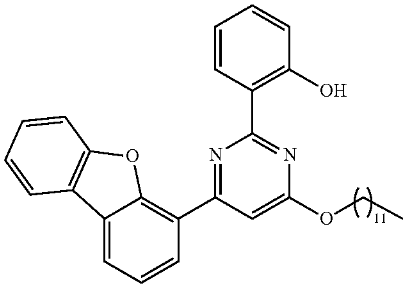
104
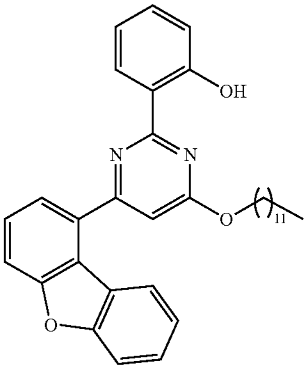
105
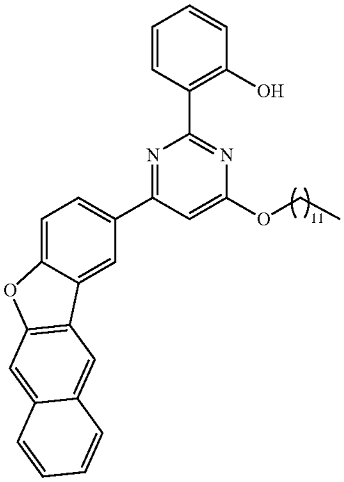
106
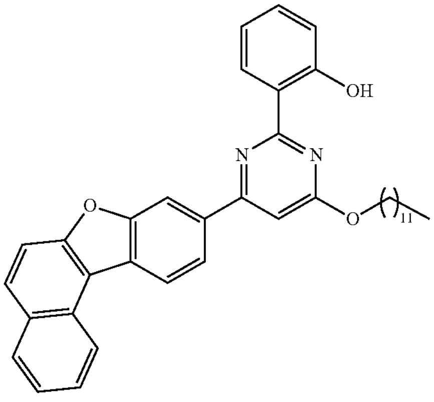
-continued
107
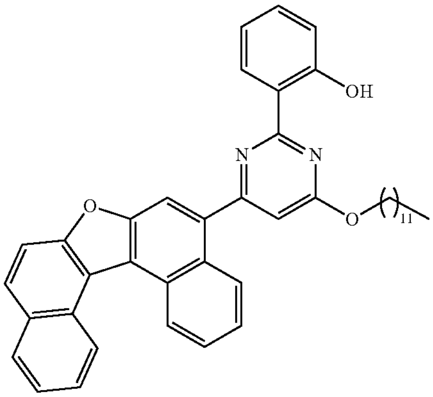
108
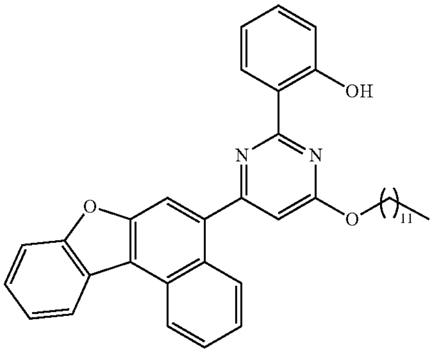
109
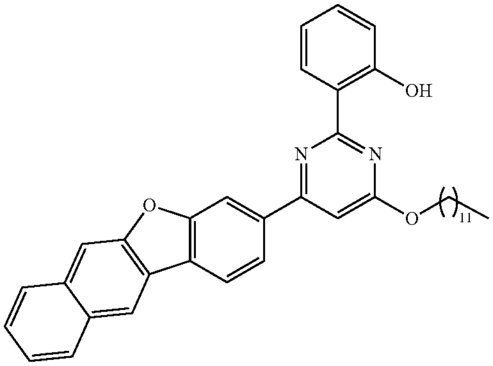
110
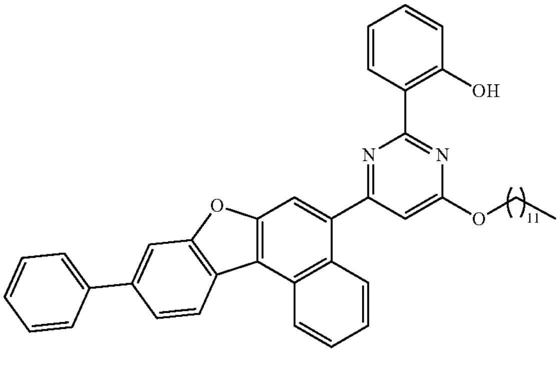

-continued
111
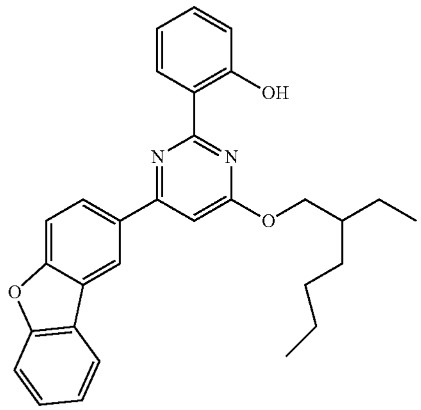
112
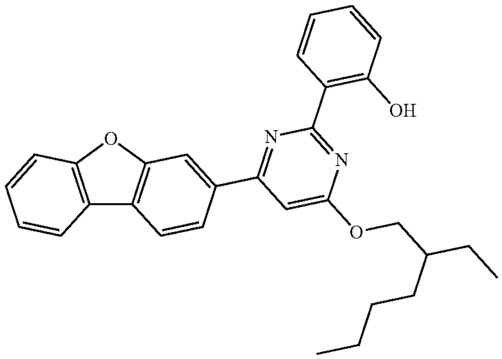
113
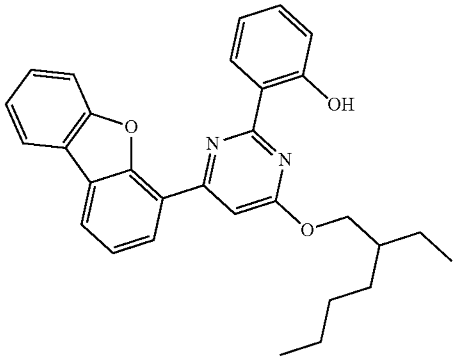
114
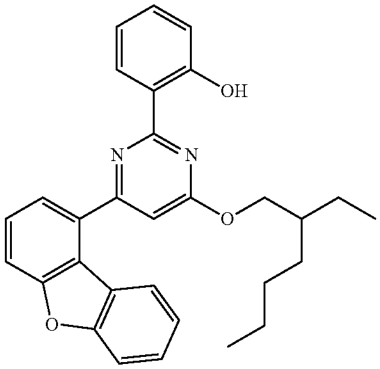
-continued
115
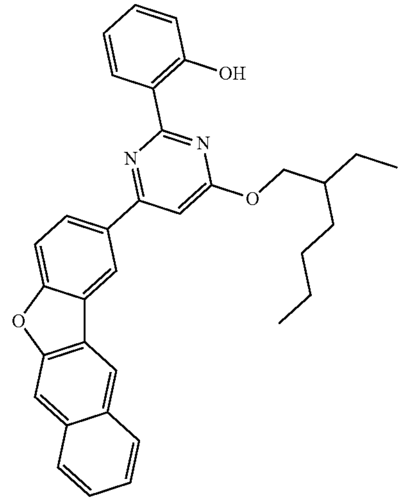
116
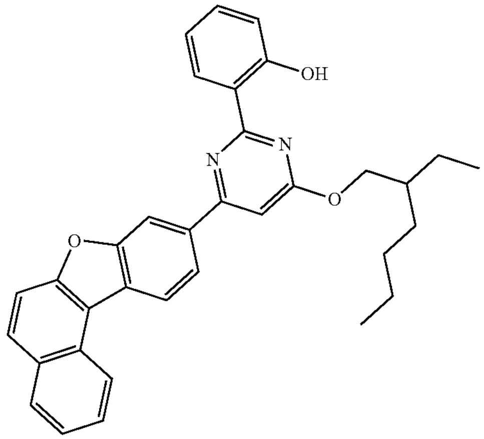
117
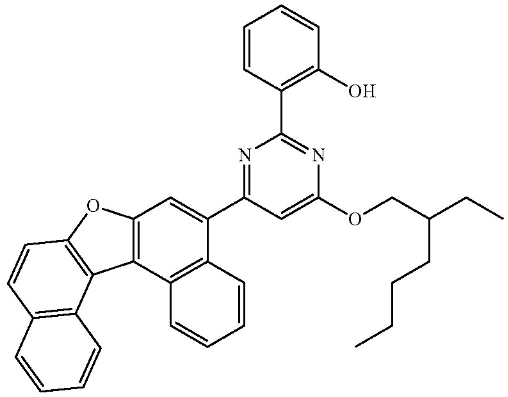

-continued
118
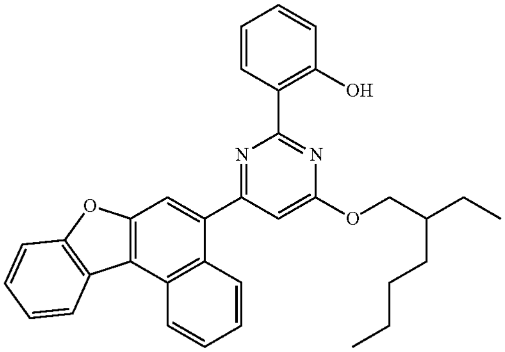
119
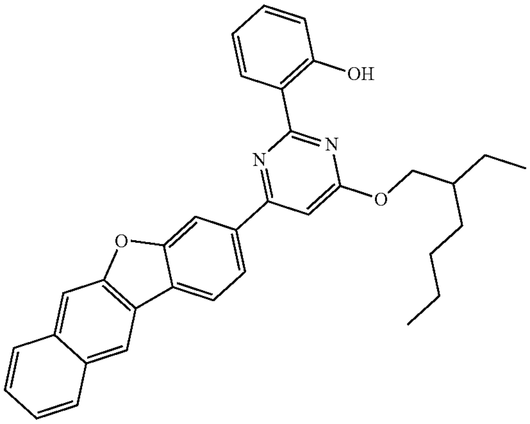
120
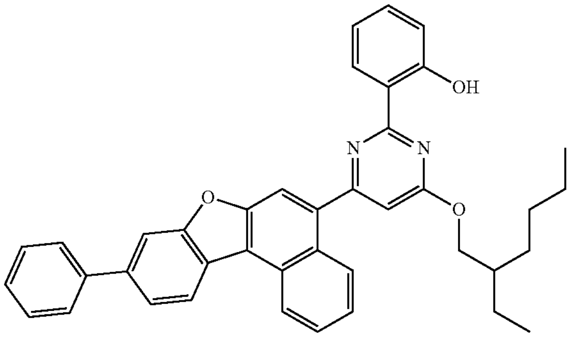
121
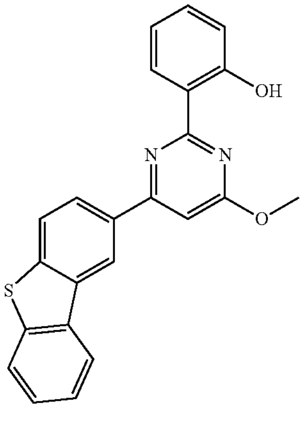
-continued
122
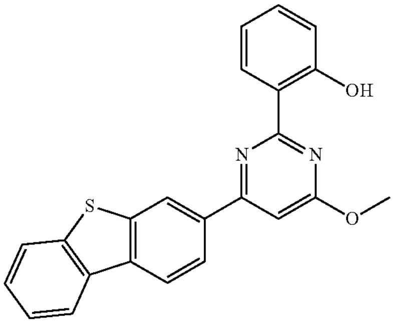
123
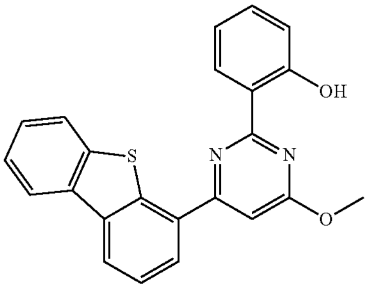
124
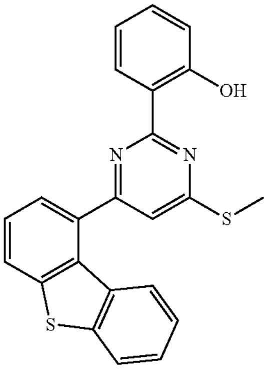
125
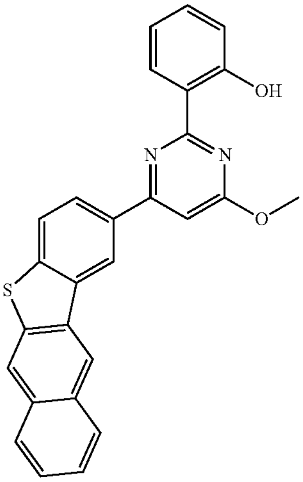

-continued
126
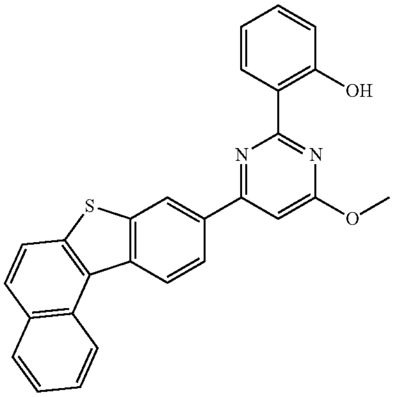
127
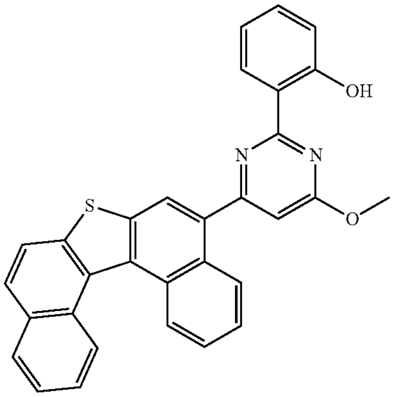
128
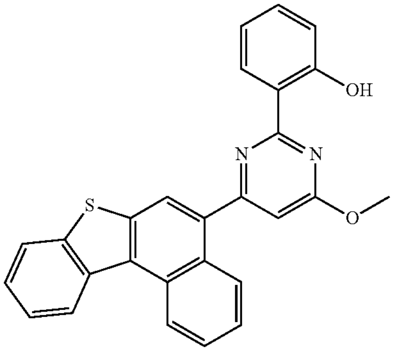
129
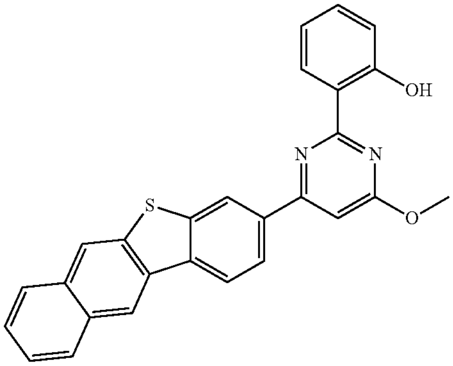
-continued
130
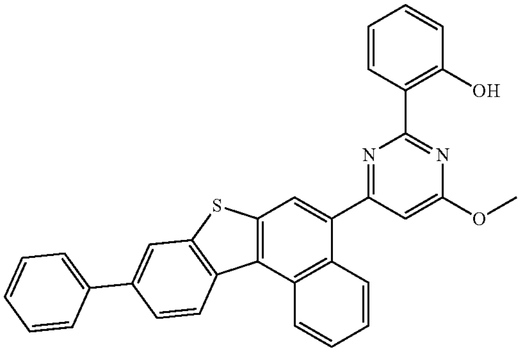
131
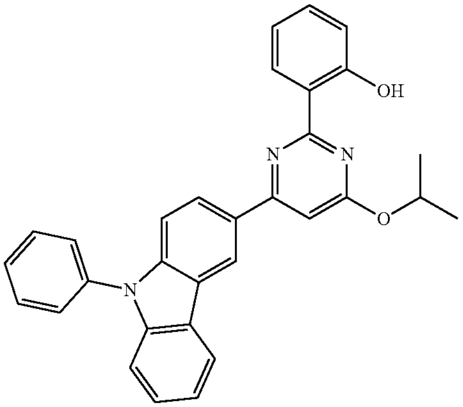
132
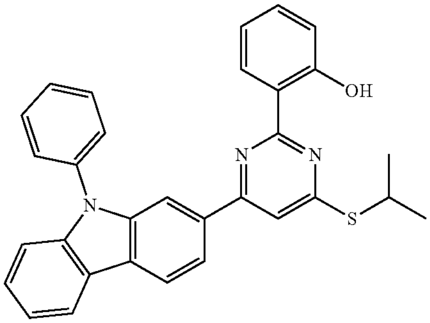
133
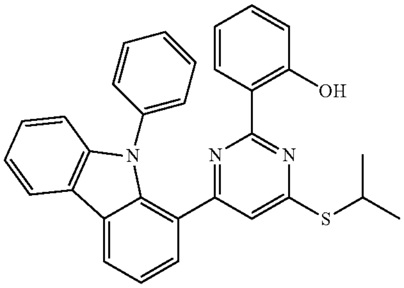

134
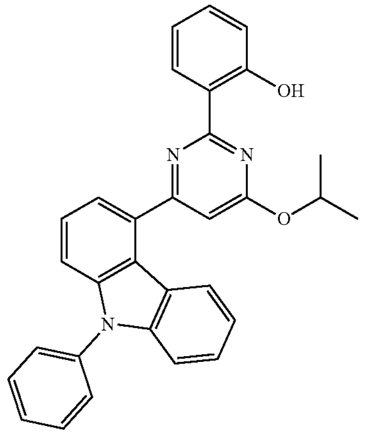
135
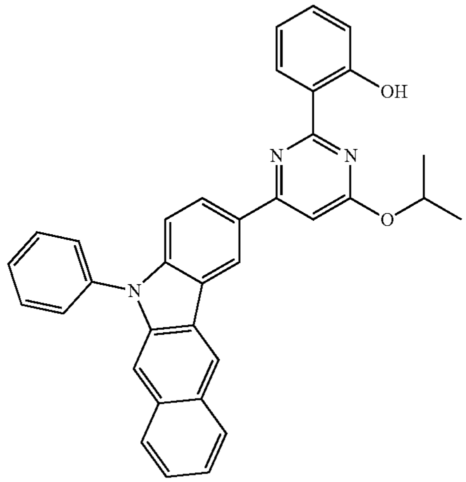
136
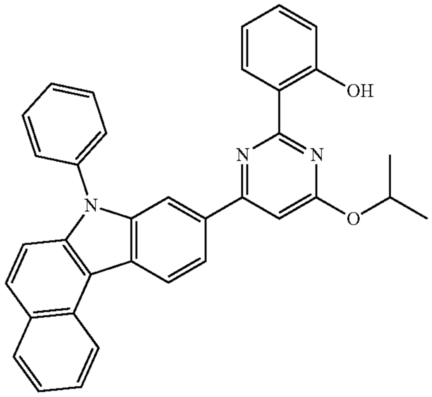
137
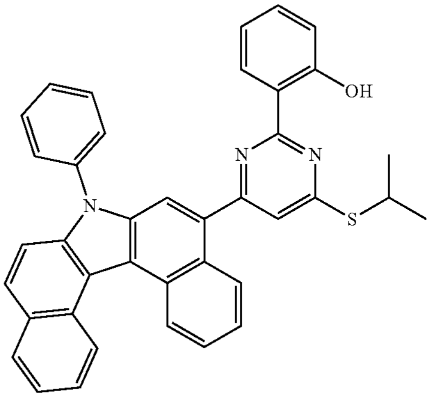
138
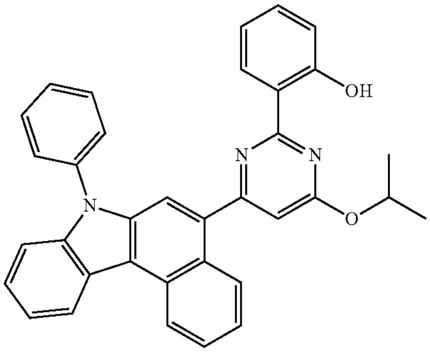
139
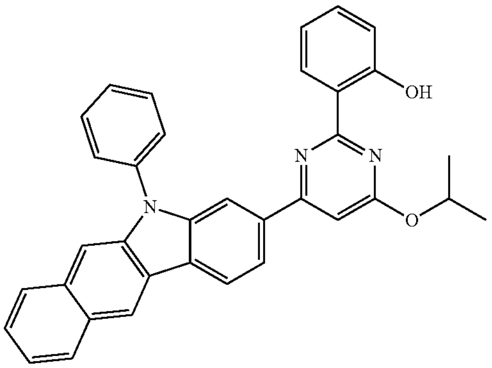
140
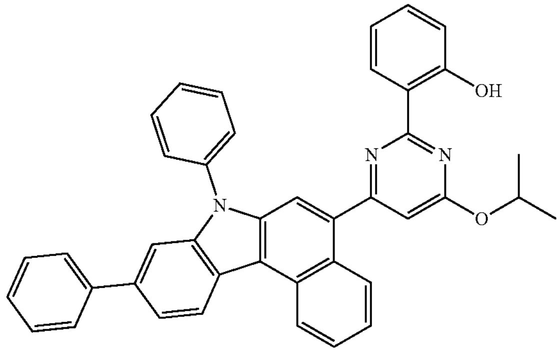

-continued
141
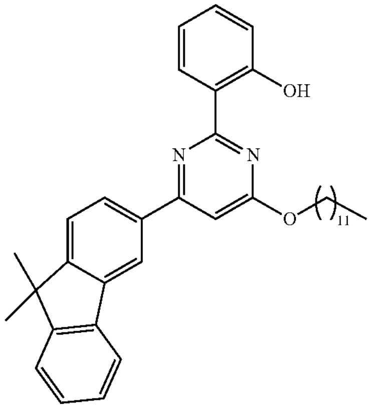
142
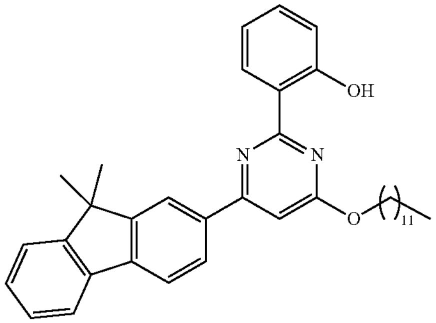
143
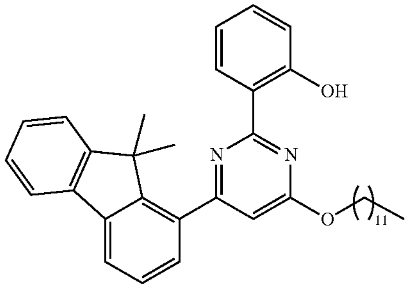
144
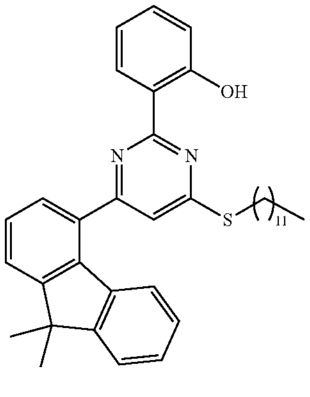
-continued
145
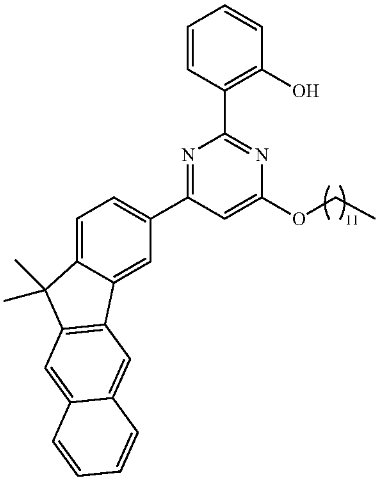
146
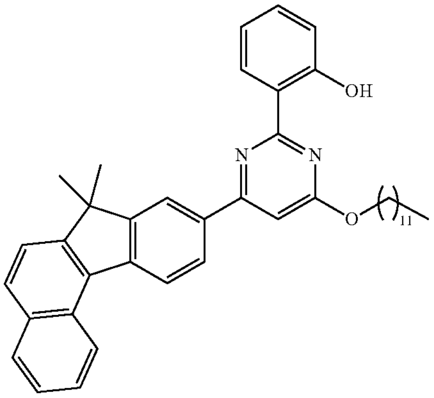
147
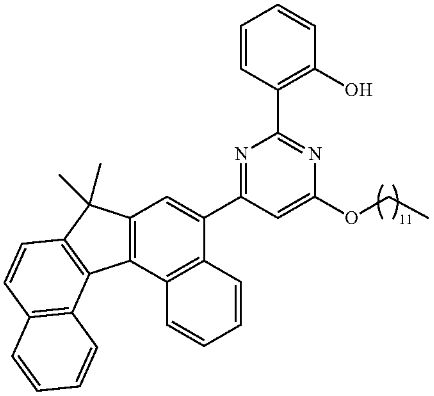
148
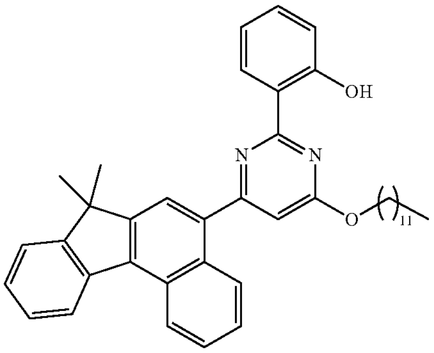

-continued
149
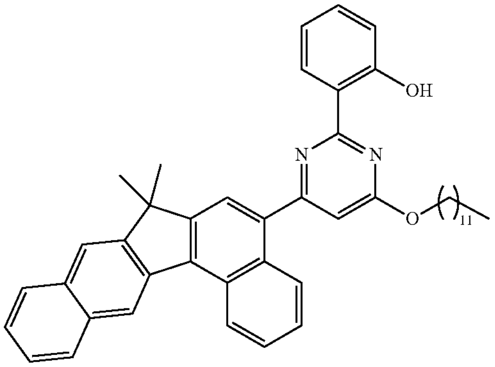
150
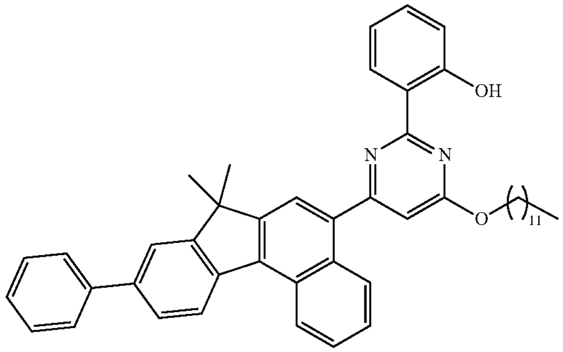
151
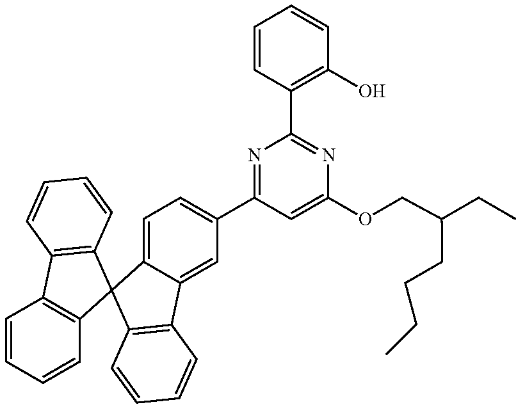
152
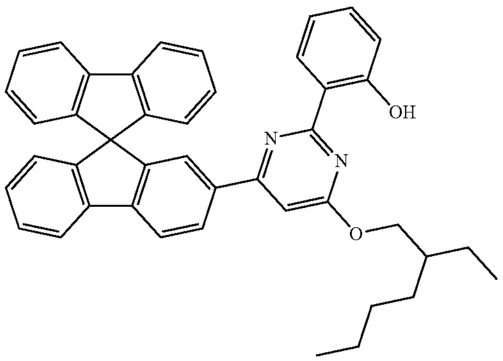
-continued
153
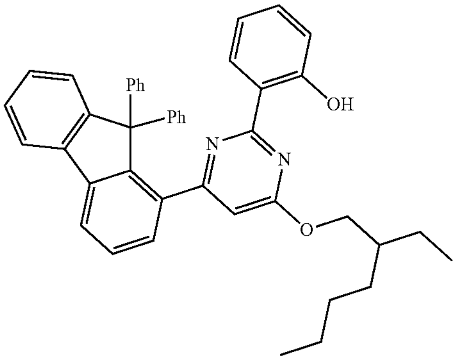
154
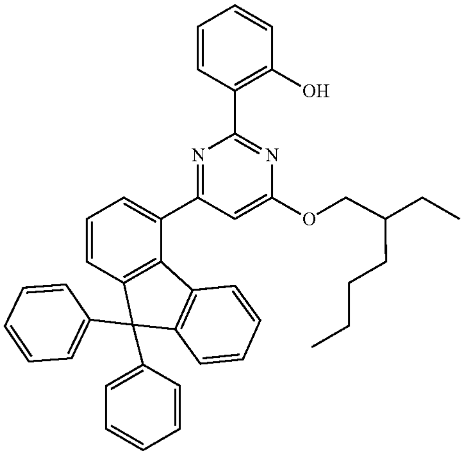
155
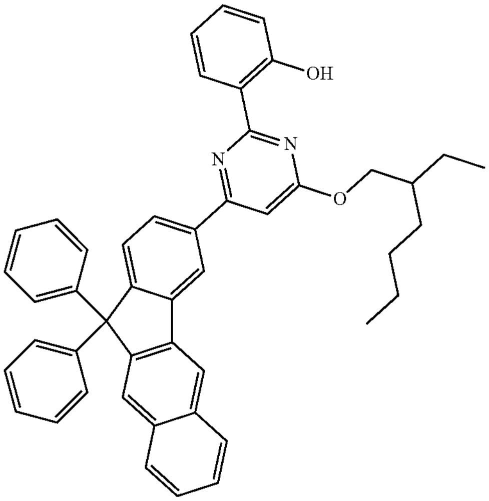

-continued
156
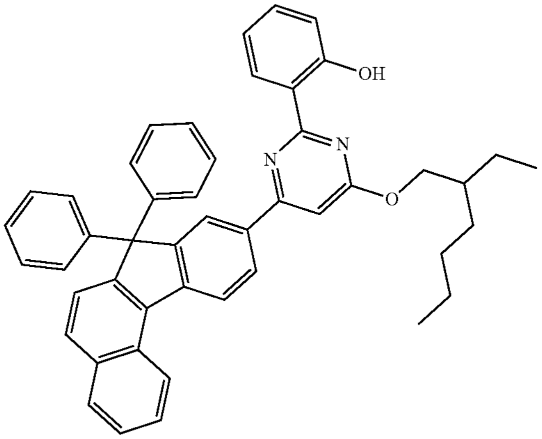
157
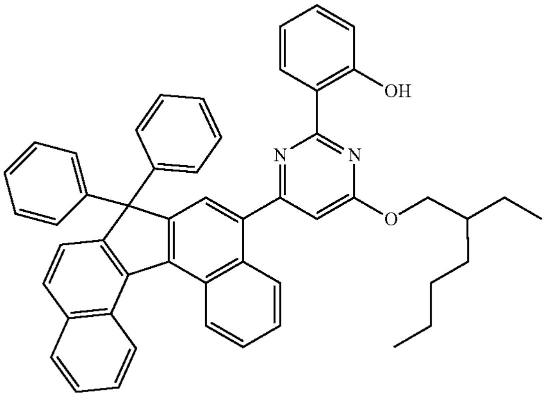
158
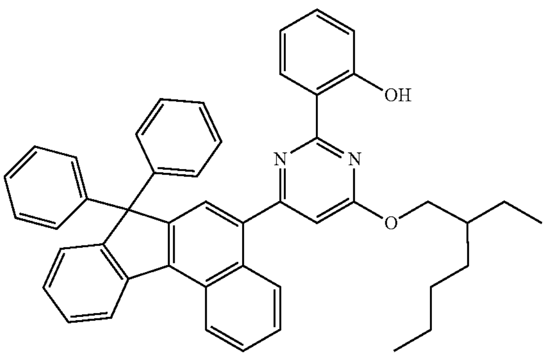
-continued
159
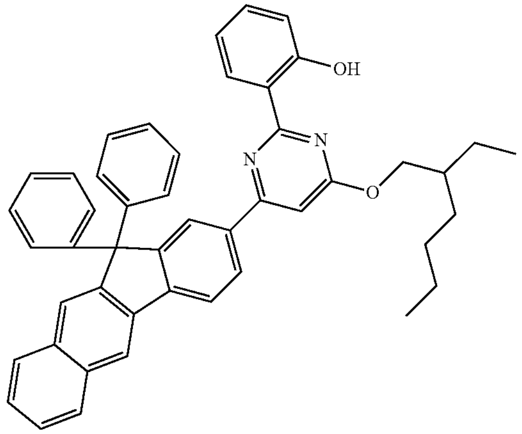
160
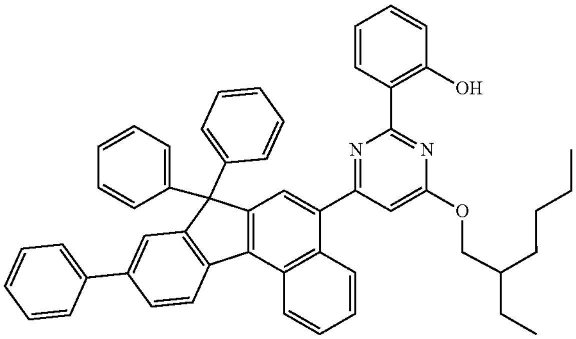
161
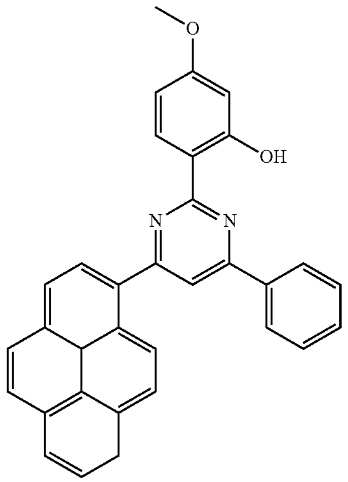

-continued
162
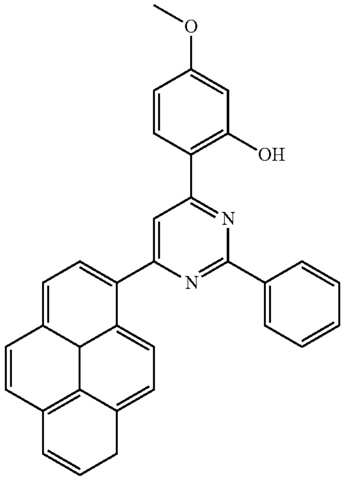
163
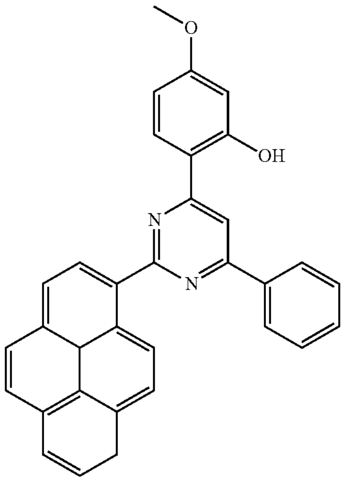
164
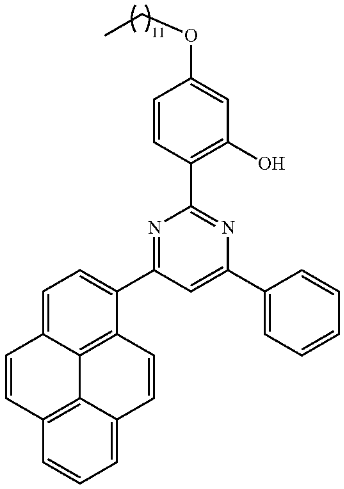
-continued
165
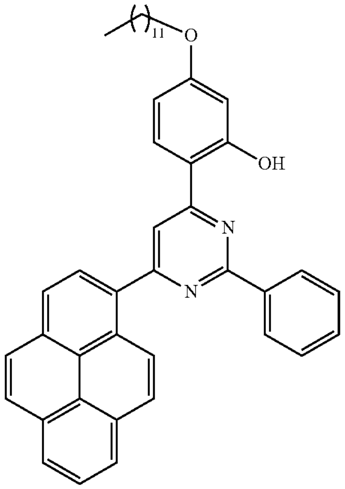
166
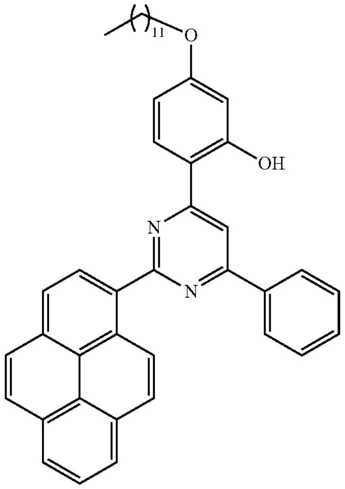
167
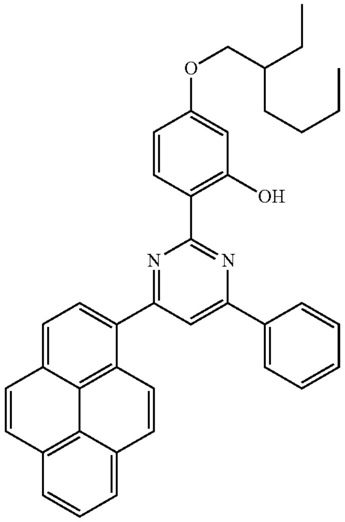

-continued
168
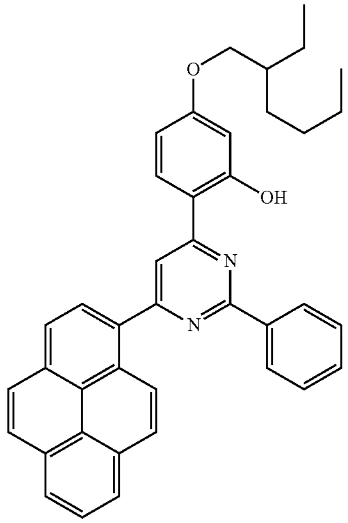
169
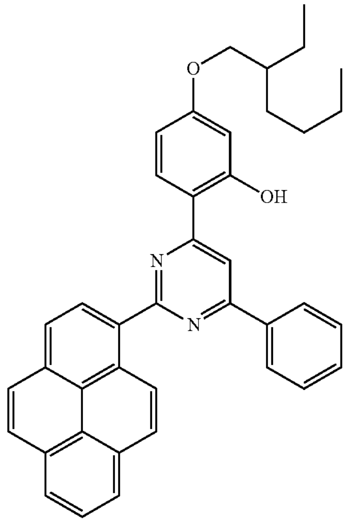
170
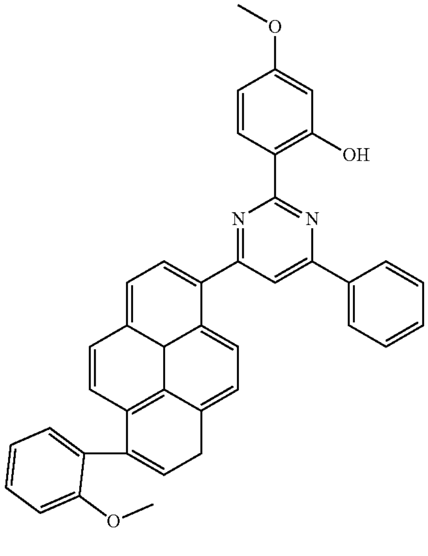
-continued
171
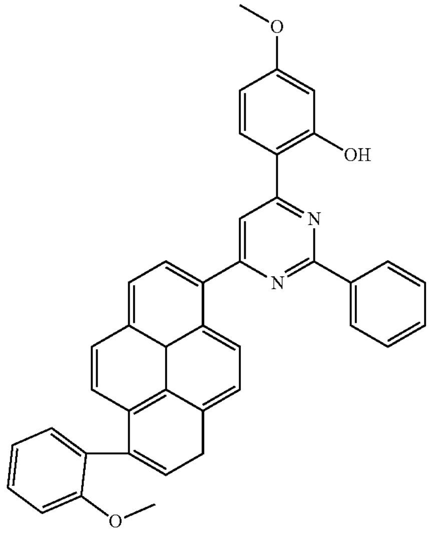
172
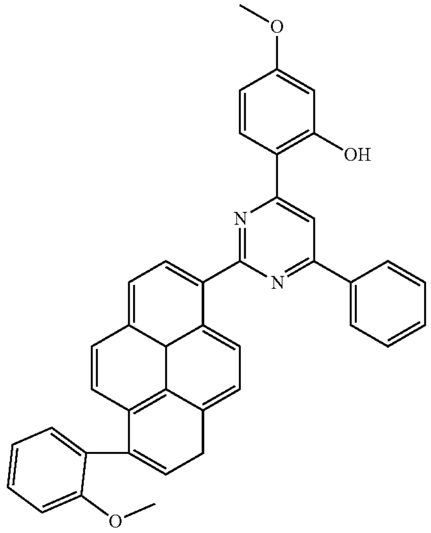
173
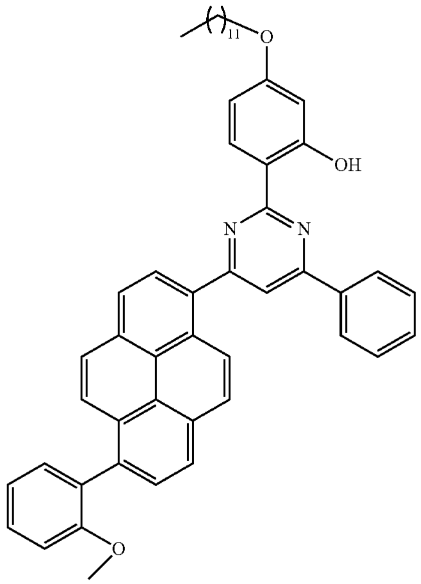

-continued
174
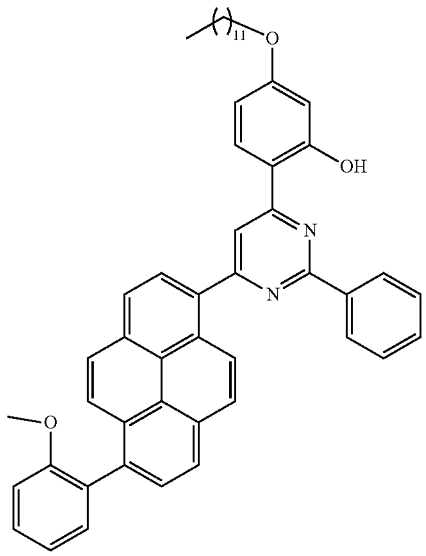
175
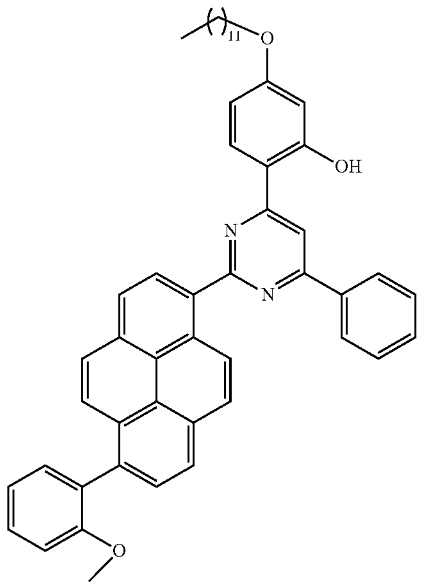
-continued
176
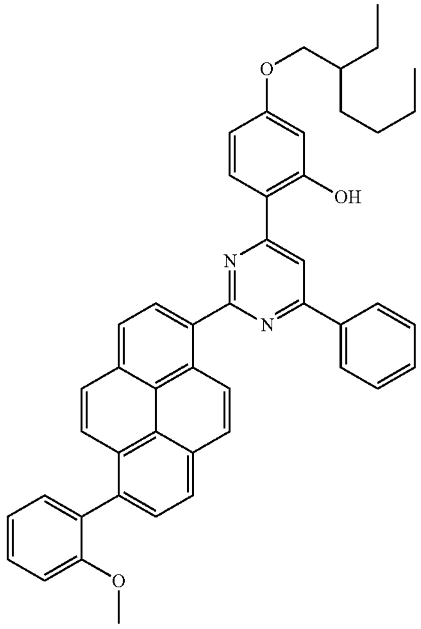
177
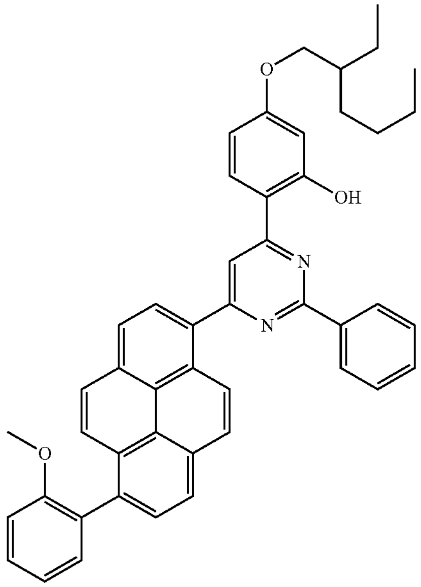

-continued
178
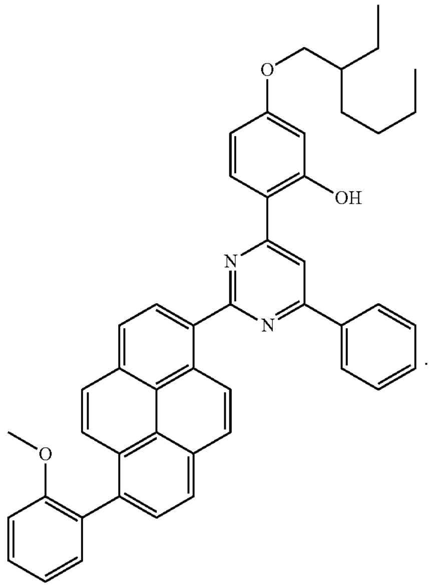
The light absorber of an embodiment may be represented by any one among the compounds represented by Compound Group 2 below. The light absorber represented by Formula 2 may be represented by any one among the compounds represented by Compound Group 2 below:
1
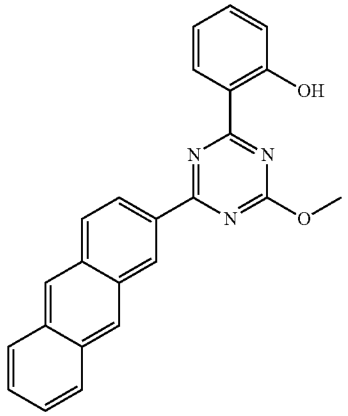
2
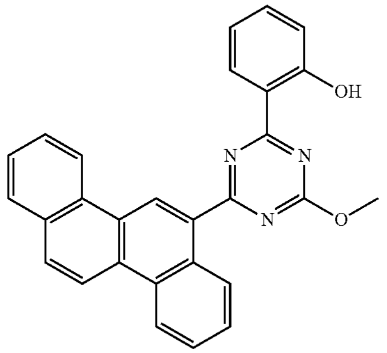
-continued
3
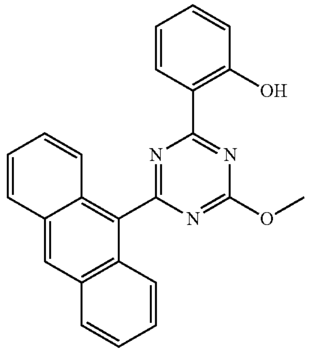
4
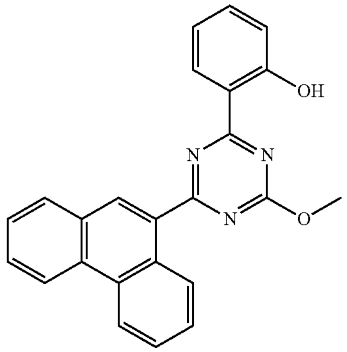
5
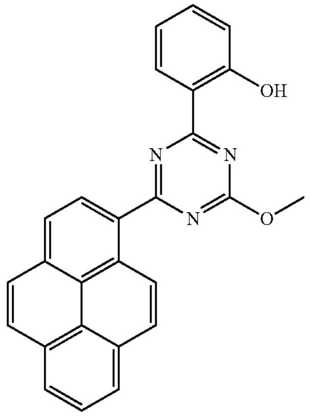
6
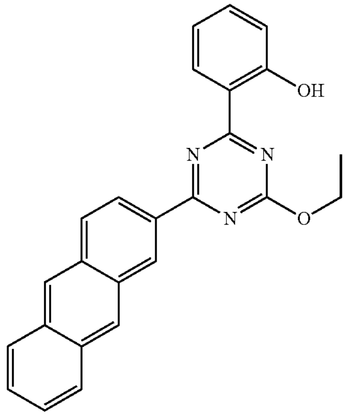

-continued
7
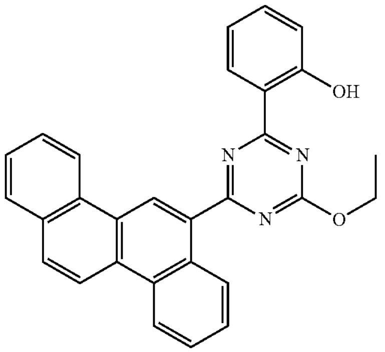
8
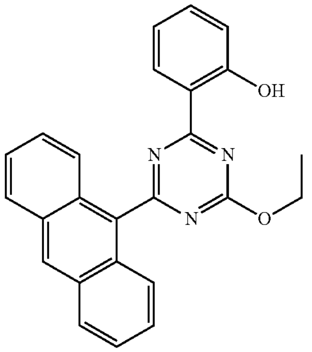
9
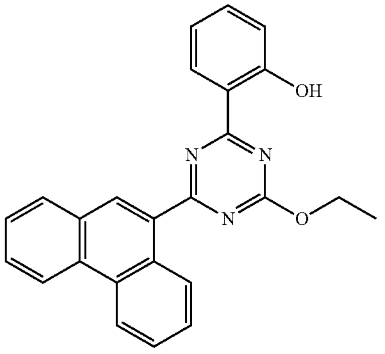
10
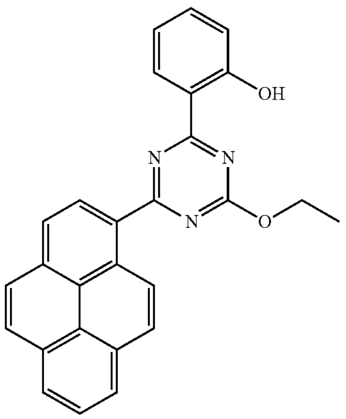
-continued
11
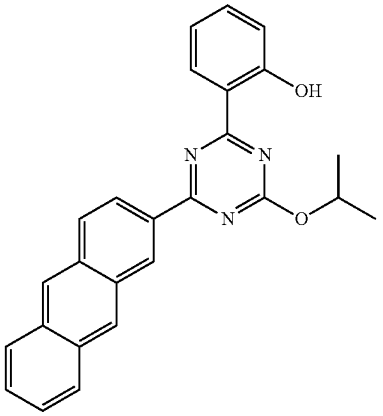
12
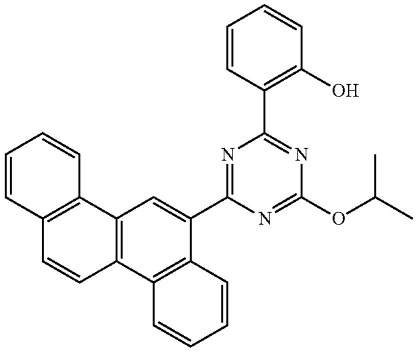
13
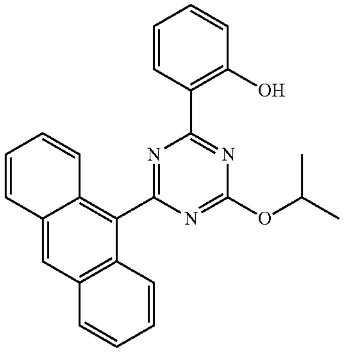
14
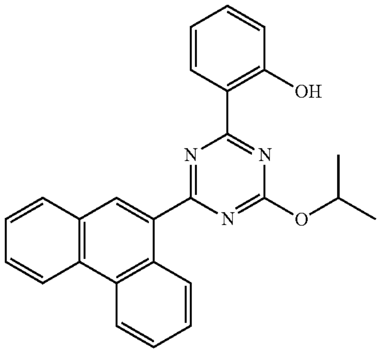

15
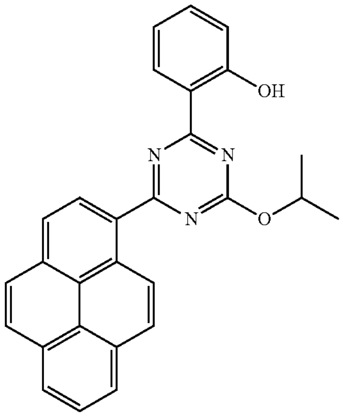
16
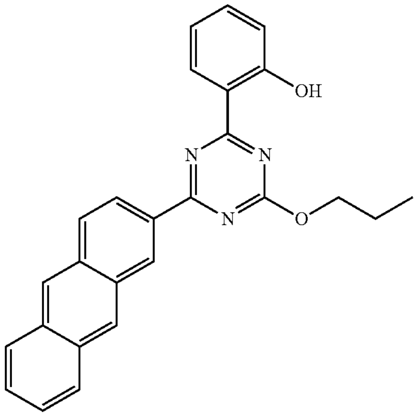
17
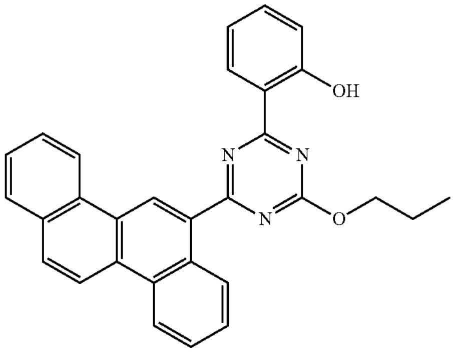
18
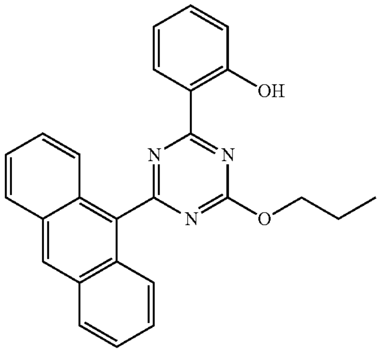
19
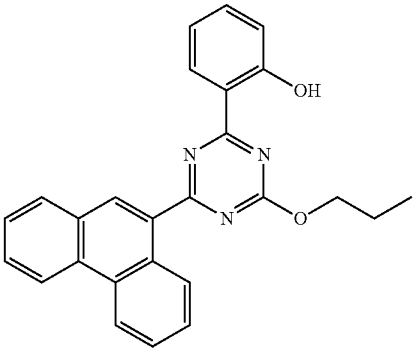
20
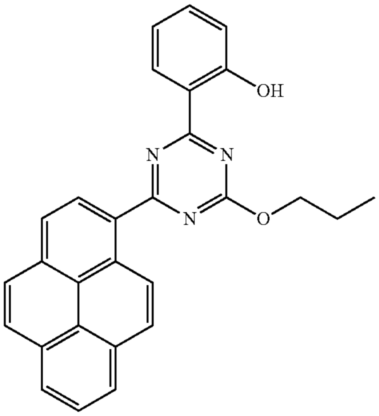
21
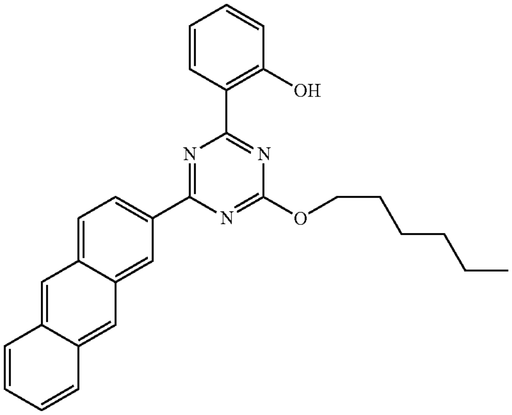
22
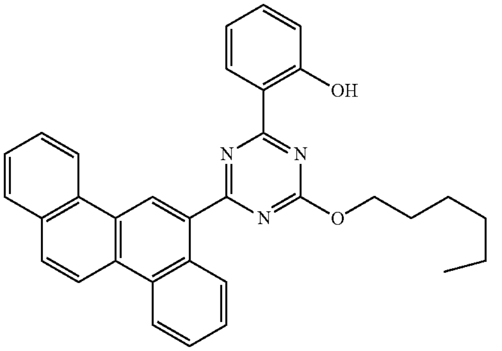

-continued
23
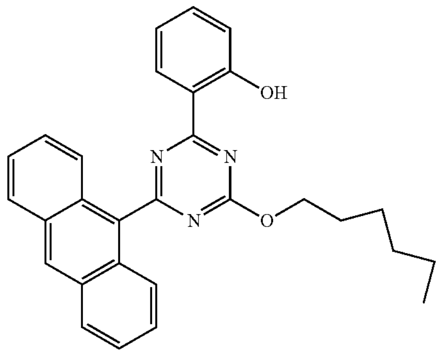
24
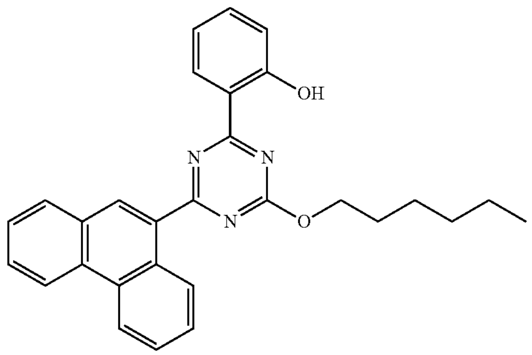
25
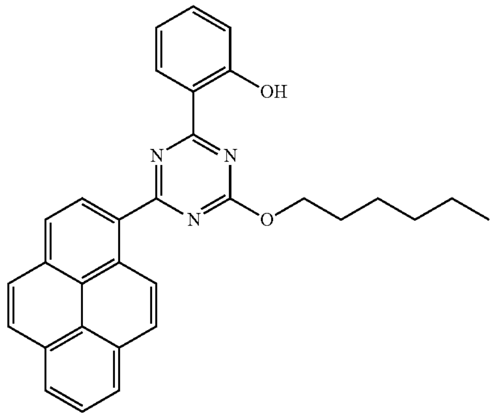
26
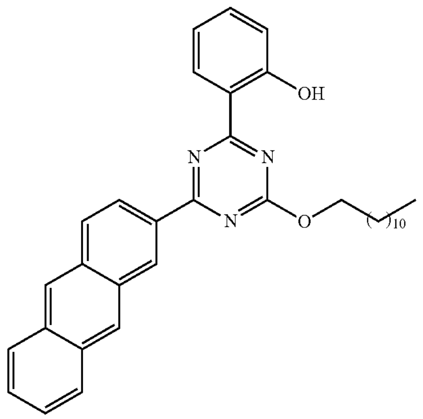
-continued
27
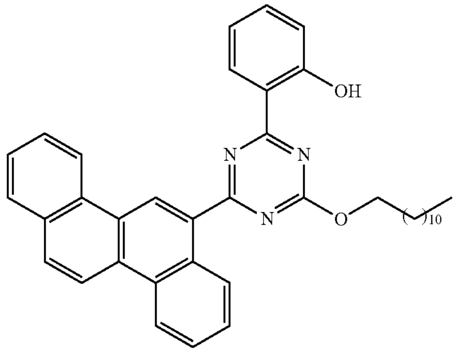
28
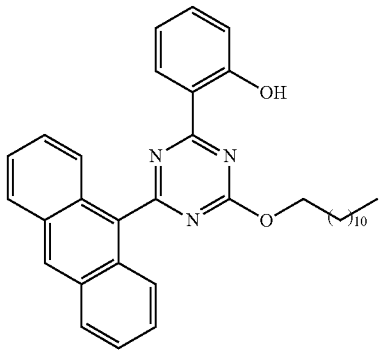
29
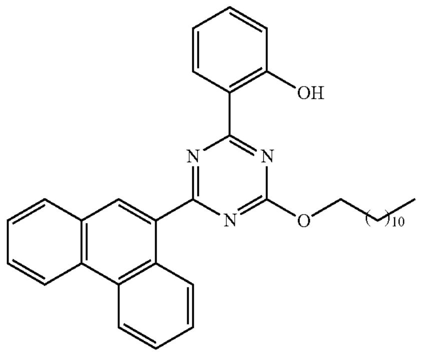
30
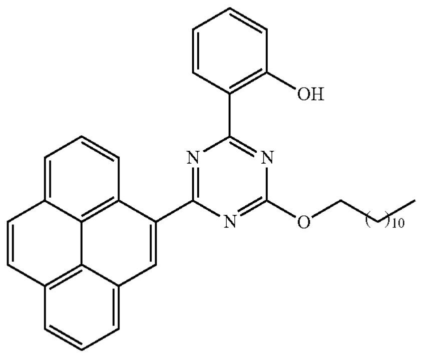

-continued
31
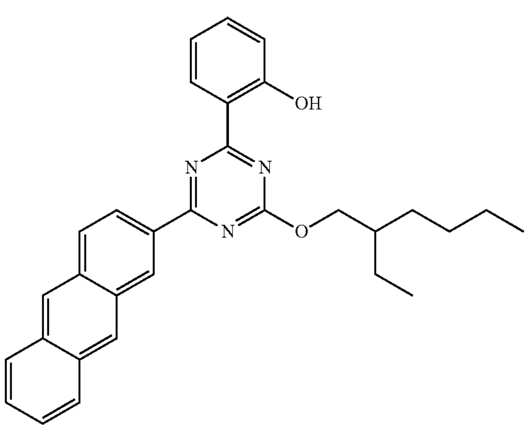
32
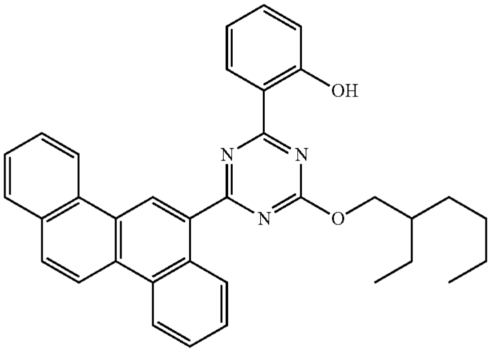
33
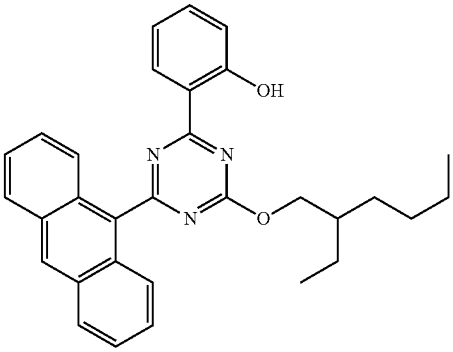
34
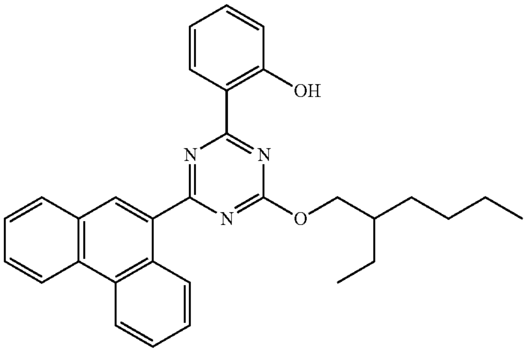
-continued
35
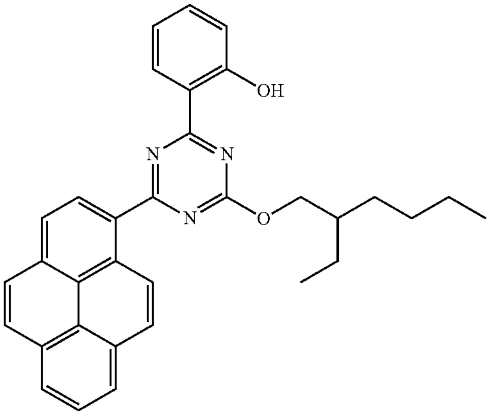
36
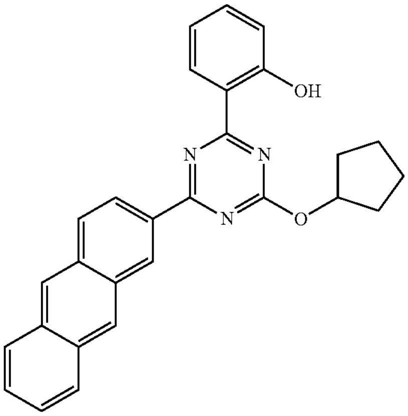
37
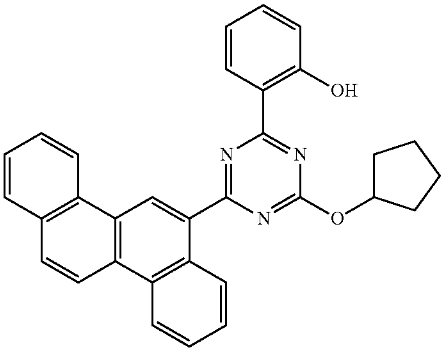
38
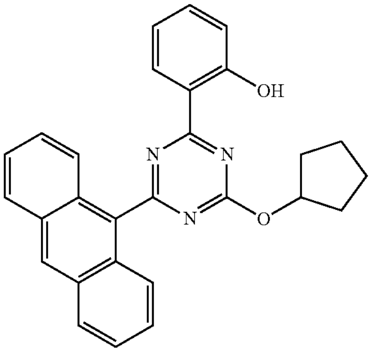

-continued
39
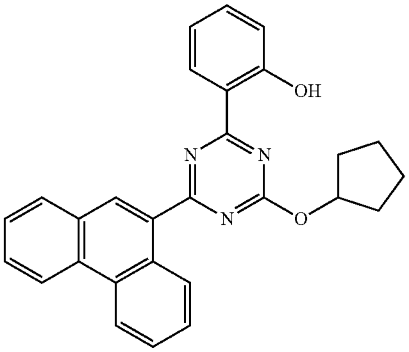
40
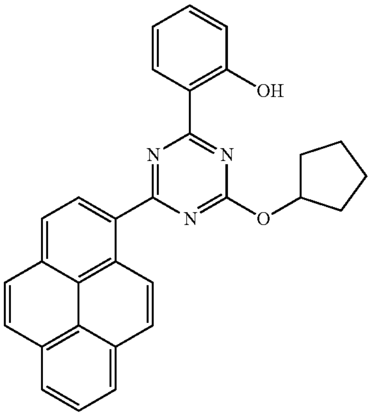
41
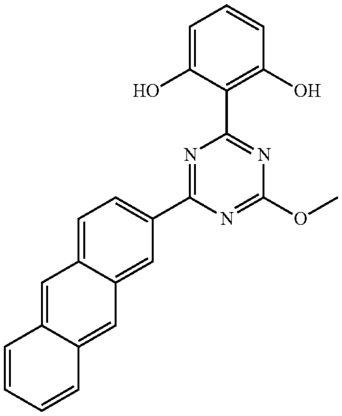
42
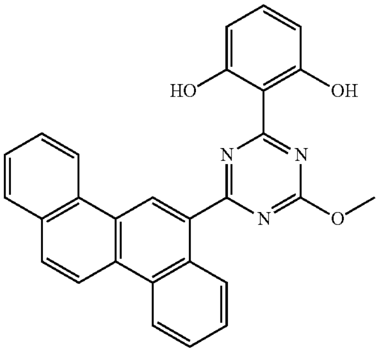
-continued
43
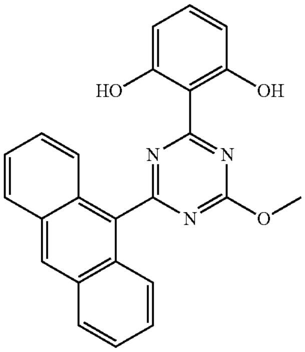
44
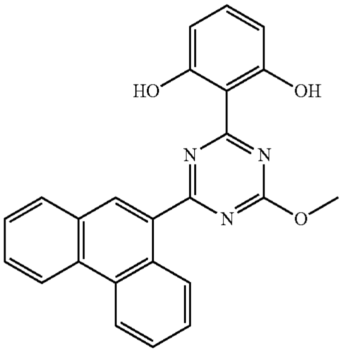
45
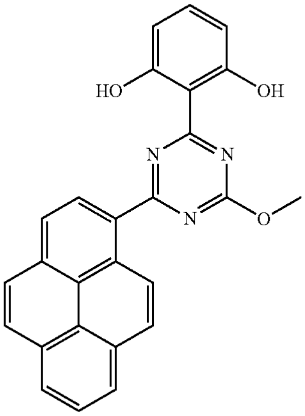
46
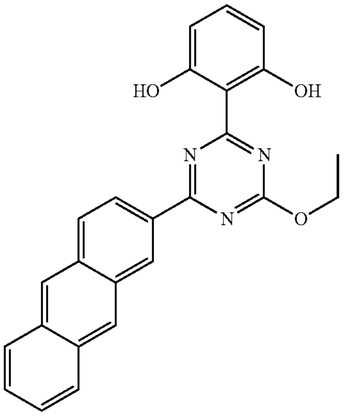

-continued
47
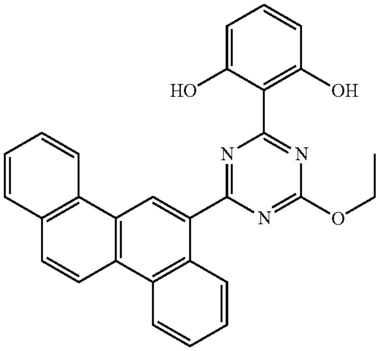
48
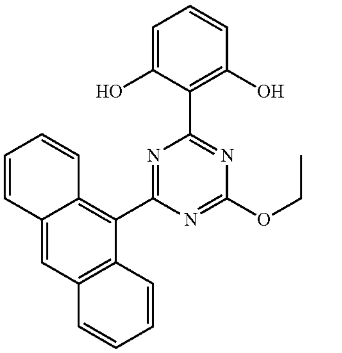
49
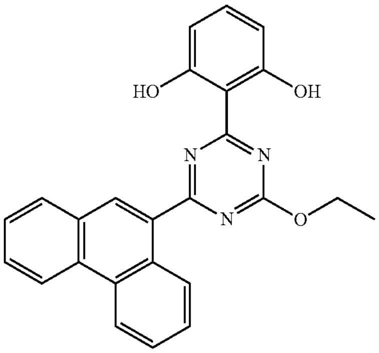
50
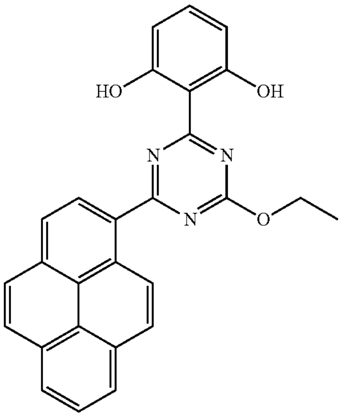
-continued
51
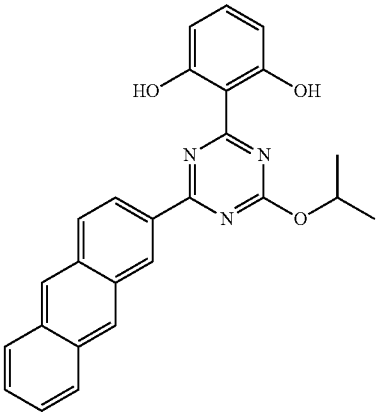
52
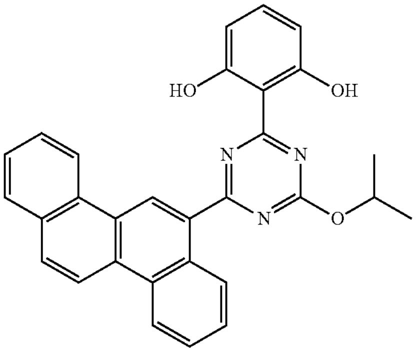
53
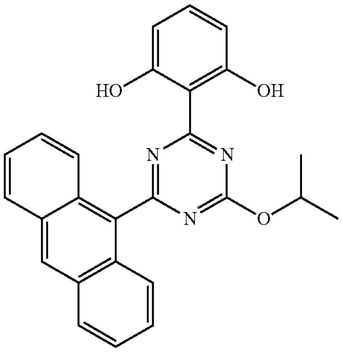
54
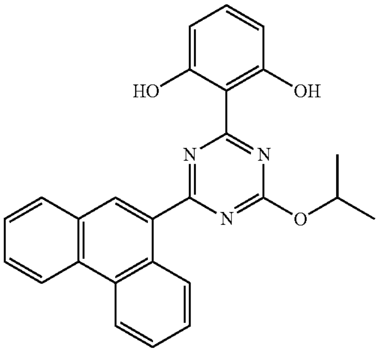

-continued
55
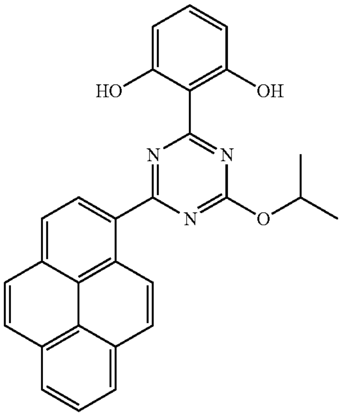
56
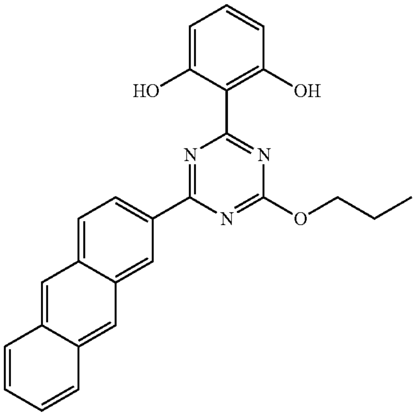
57
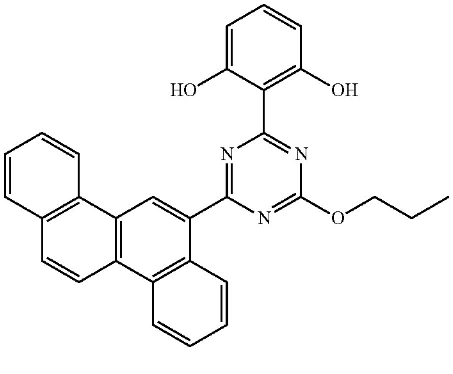
58
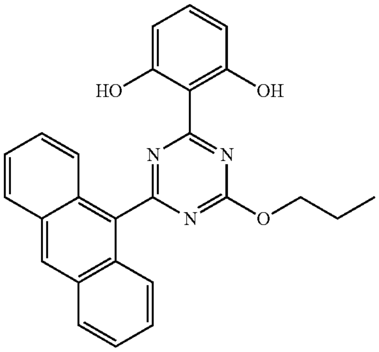
-continued
59
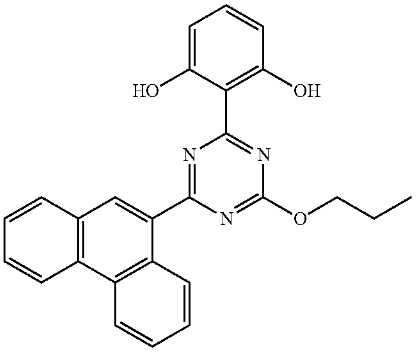
60
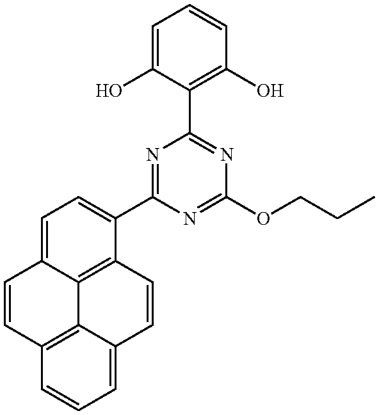
61
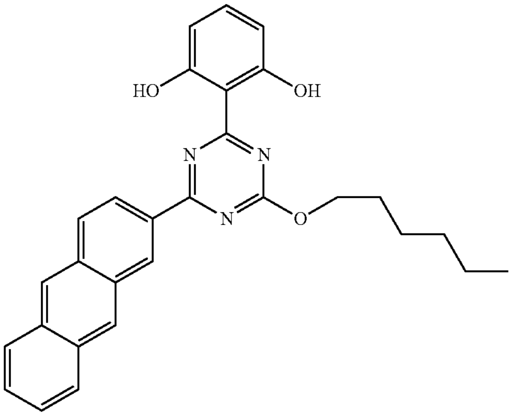
62
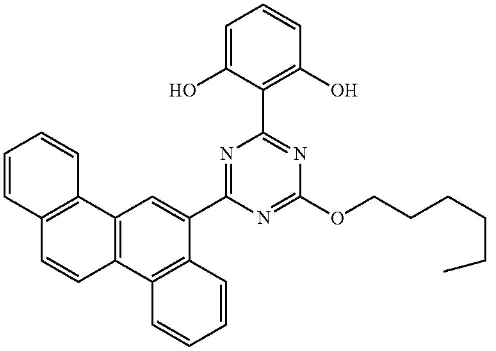

-continued
63
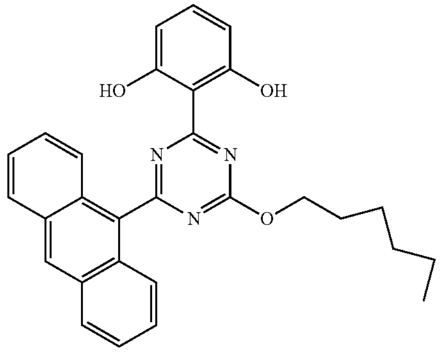
64
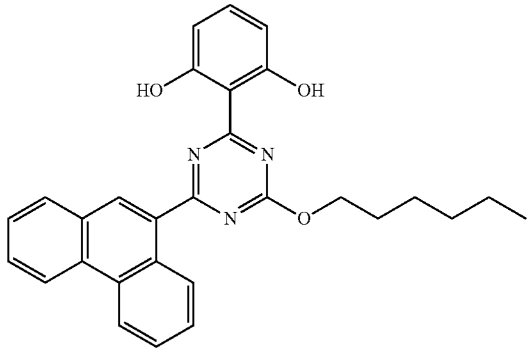
65
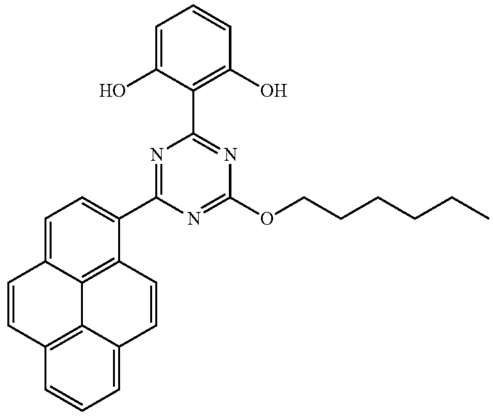
66
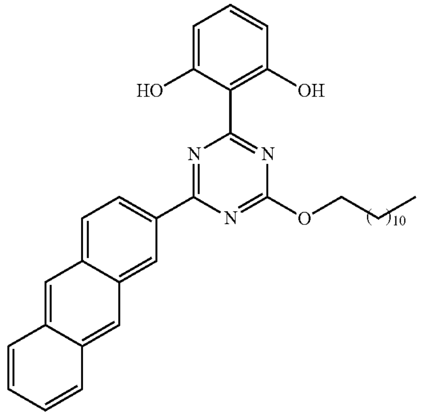
-continued
67
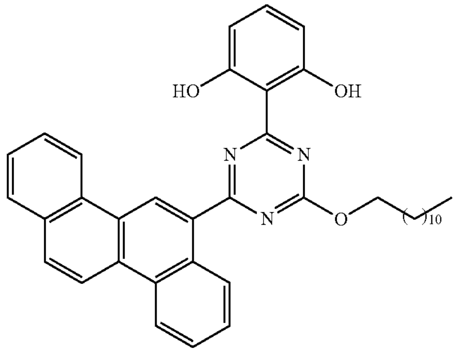
68
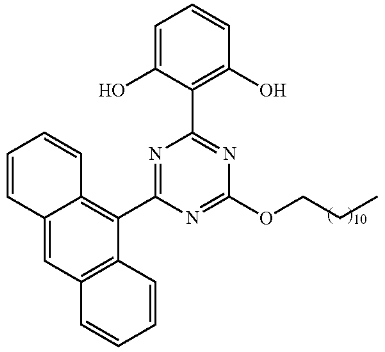
69
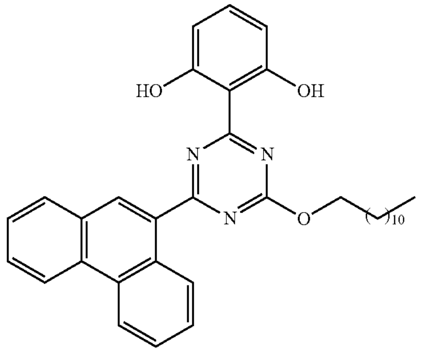
70
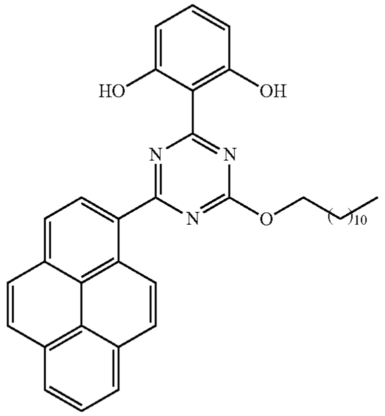

-continued
71
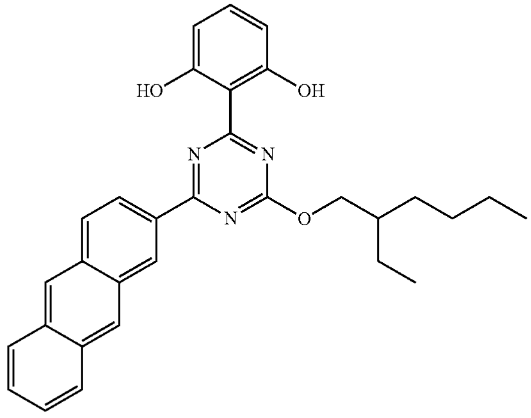
72
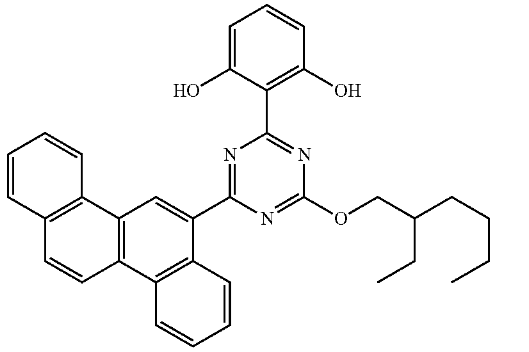
73
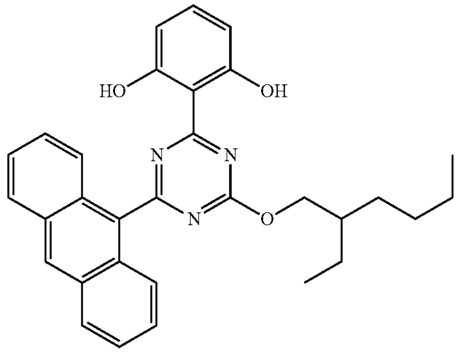
74
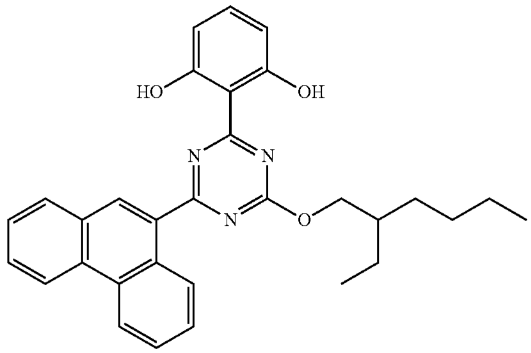
-continued
75
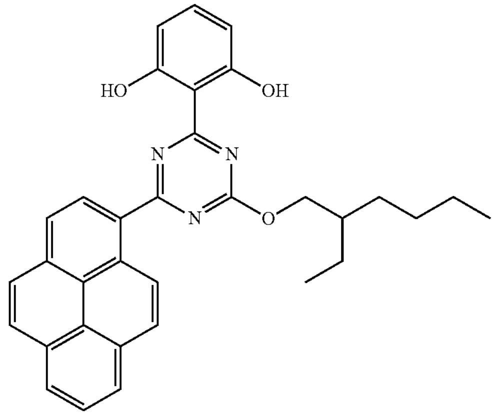
76
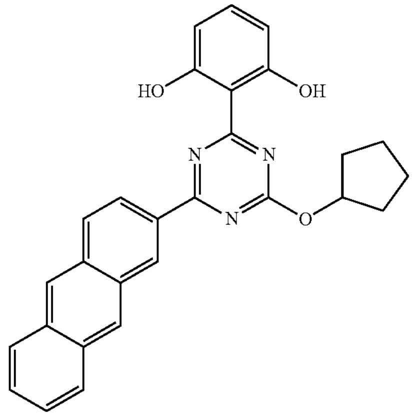
77
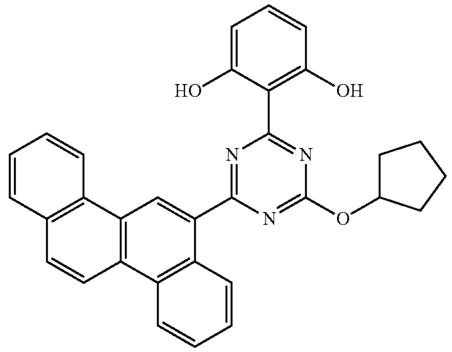
78
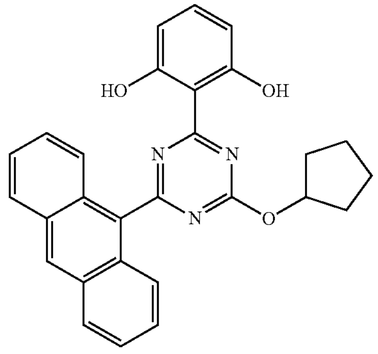

-continued
79
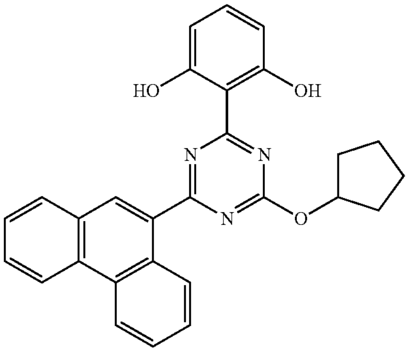
80
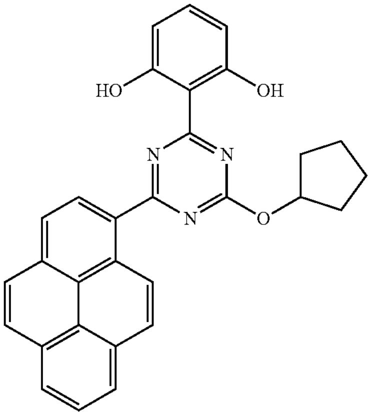
81
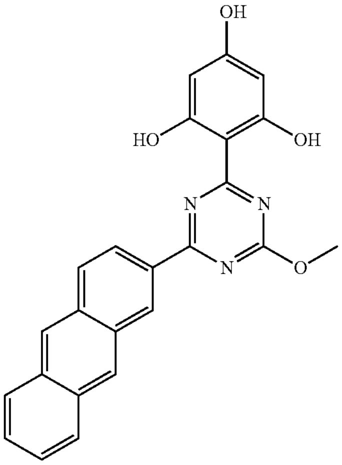
82
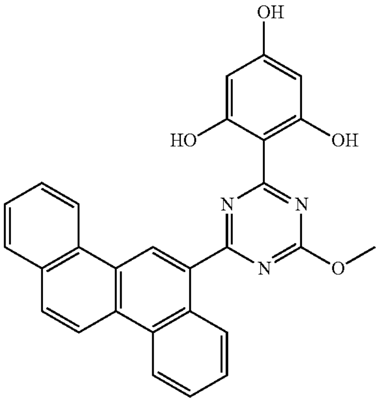
-continued
83
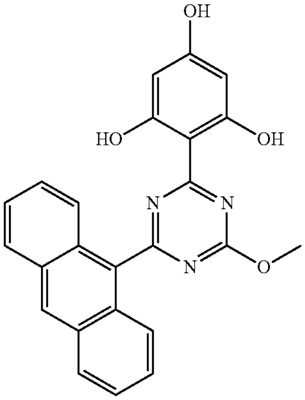
84
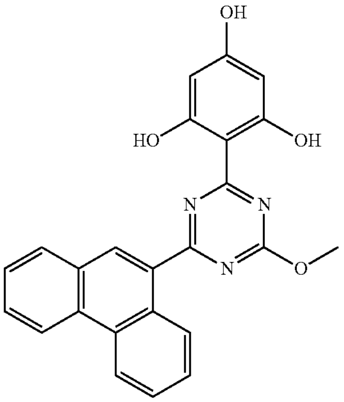
85
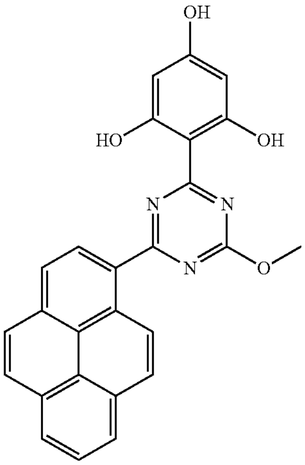

-continued
86
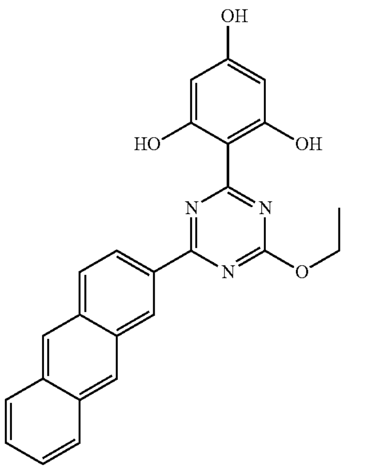
87
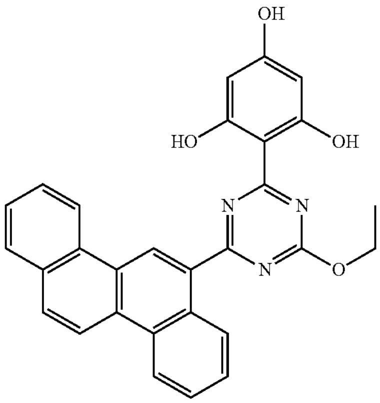
88
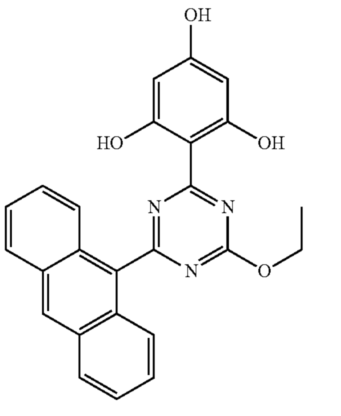
-continued
89
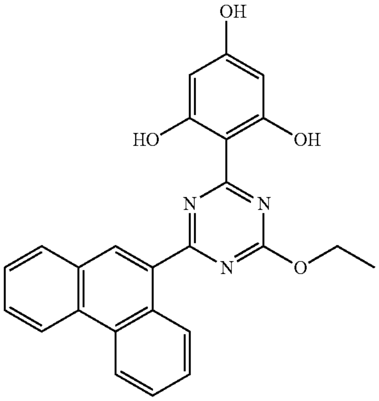
90
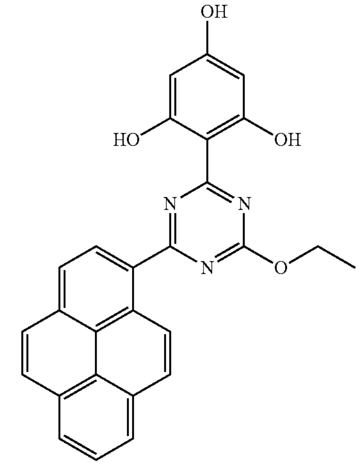
91
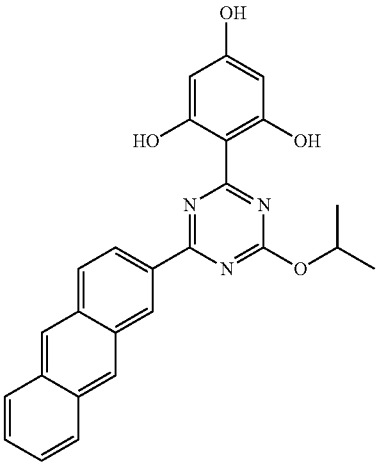

-continued
92
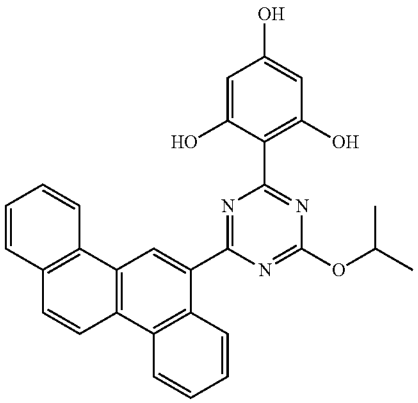
93
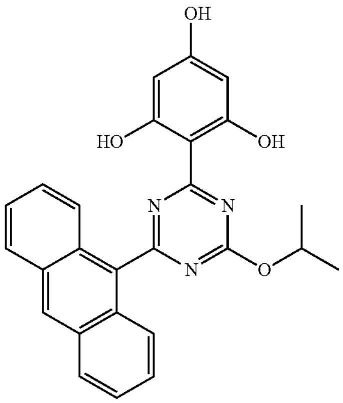
94
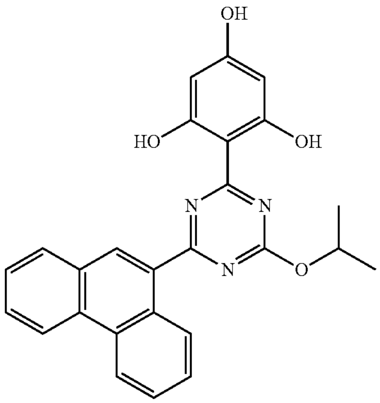
-continued
95
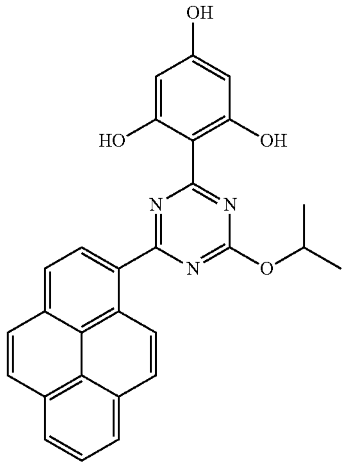
96
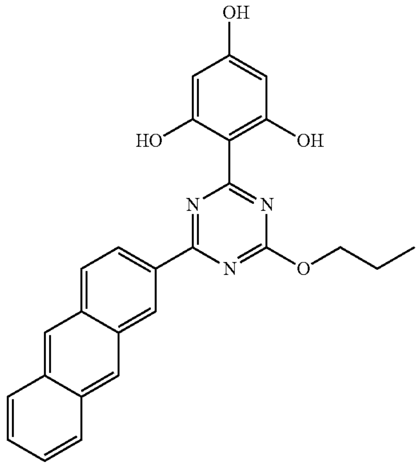
97
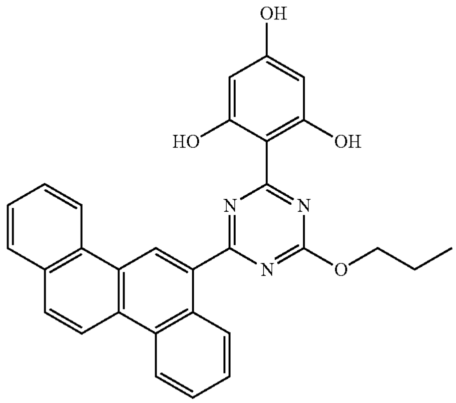

98
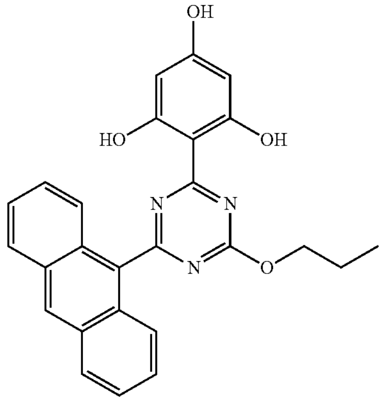
99
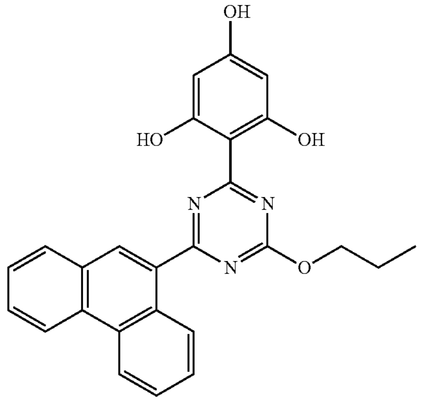
100
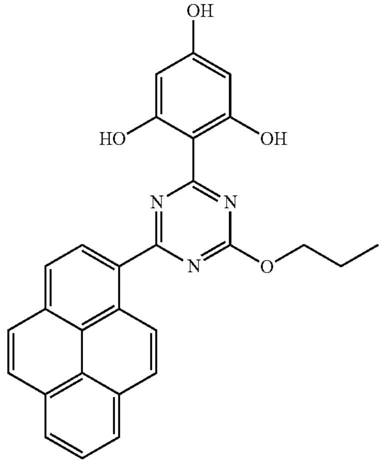
101
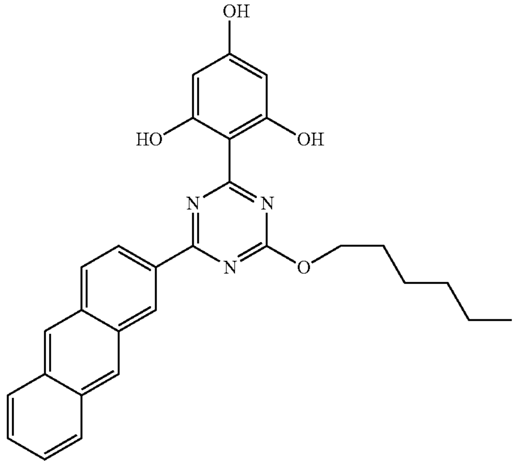
102
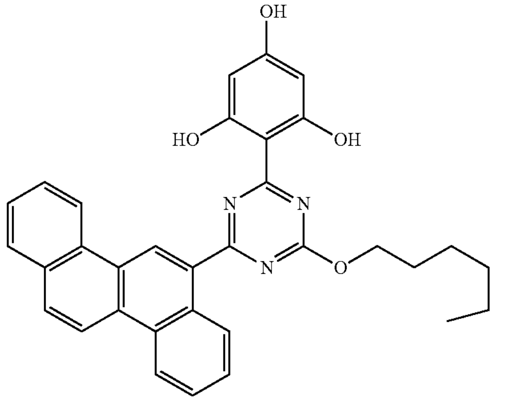
103
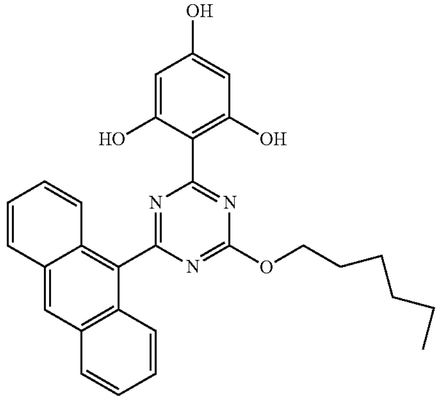

-continued
104
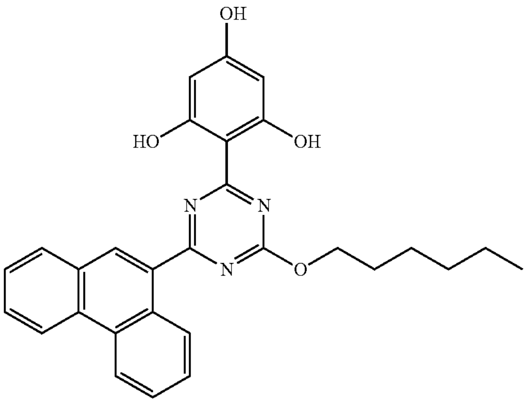
105
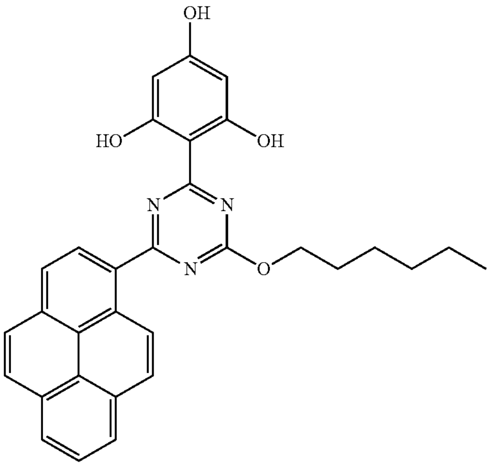
106
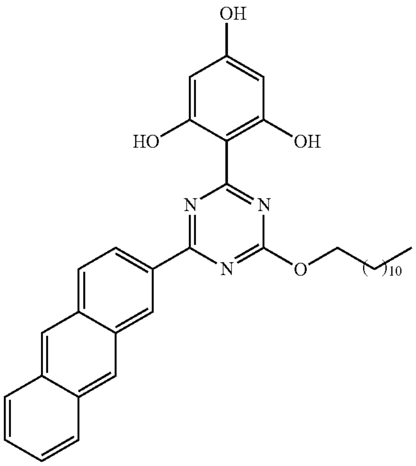
-continued
107
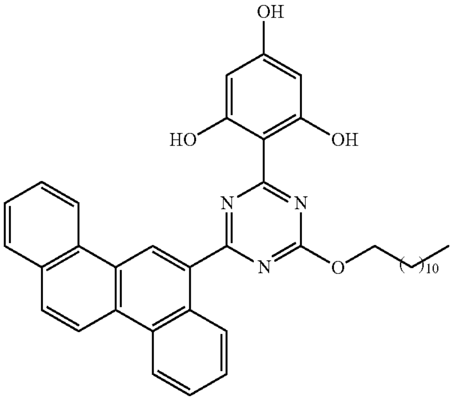
108
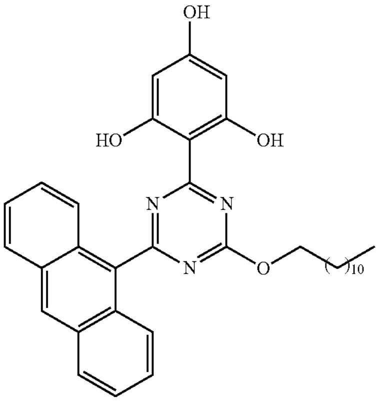
109
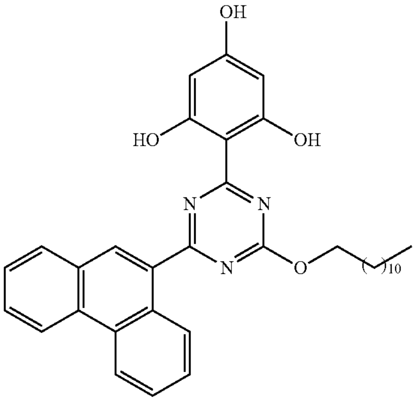
110
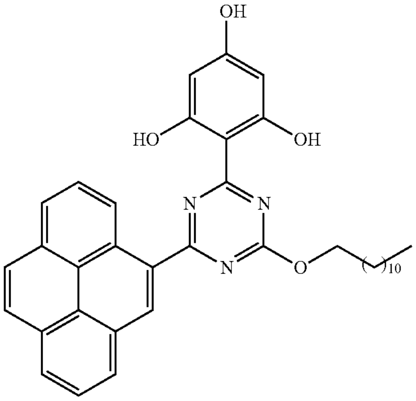

-continued
111
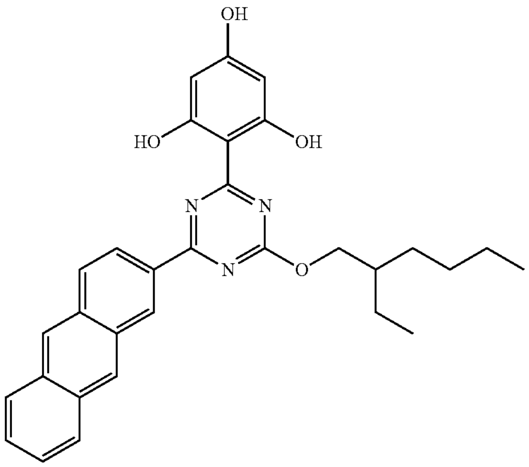
112
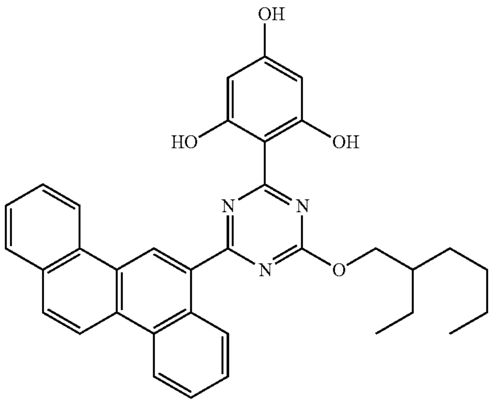
113
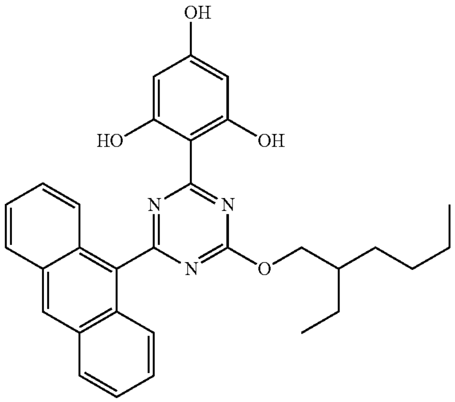
-continued
114
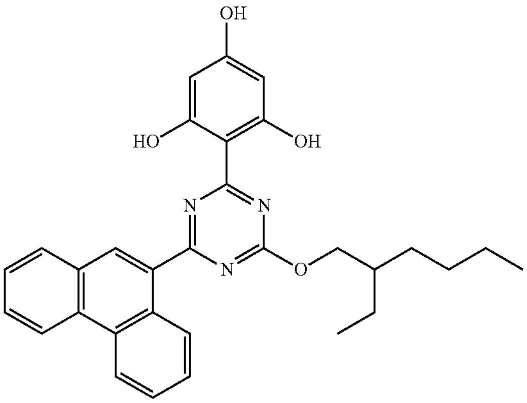
115
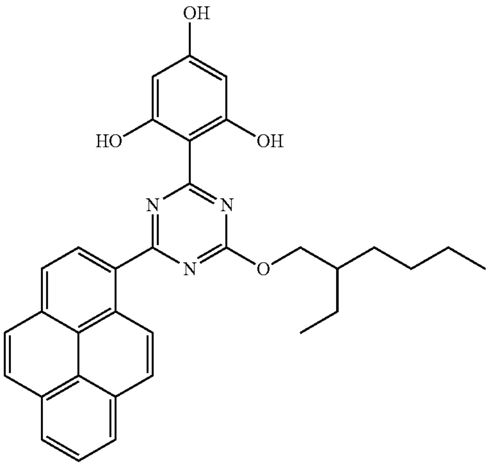
116
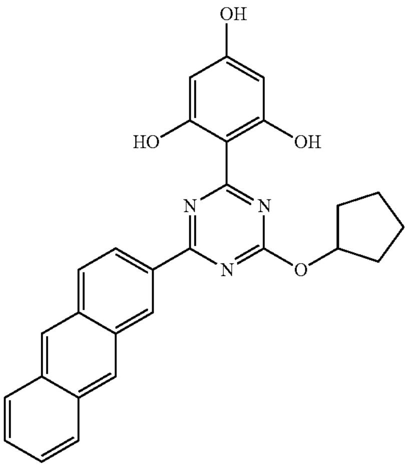

-continued
117
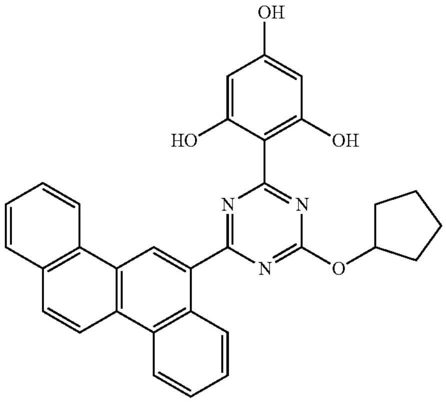
118
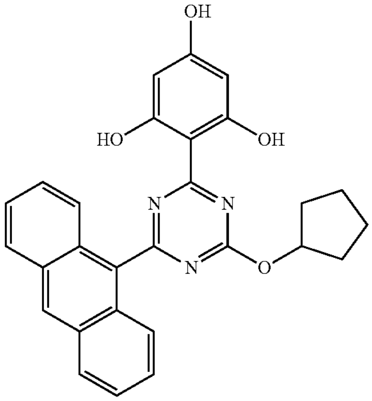
119
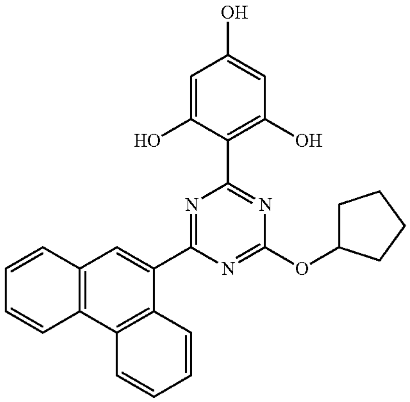
-continued
120
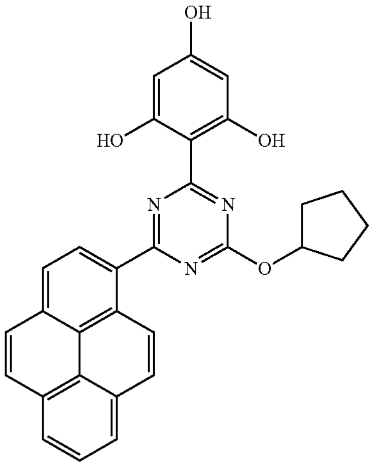
121
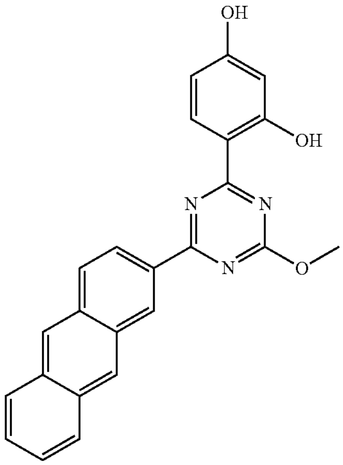
122
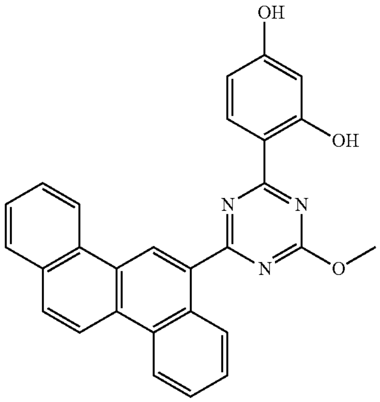

-continued
123
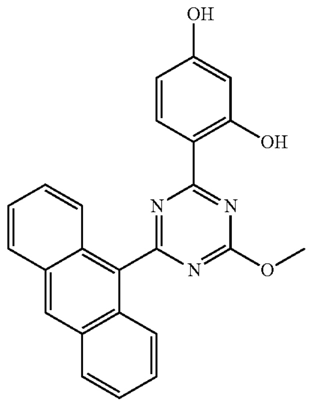
124
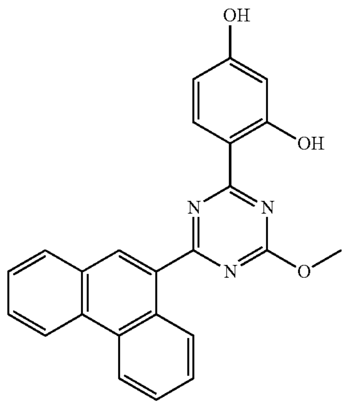
125
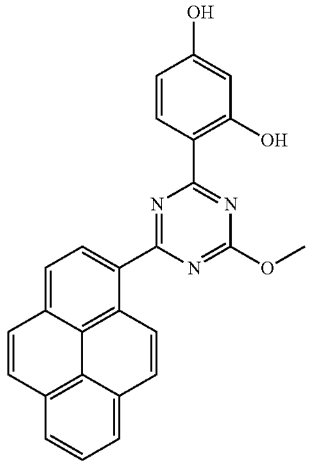
-continued
126
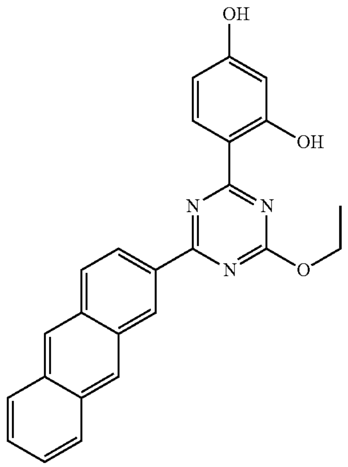
127
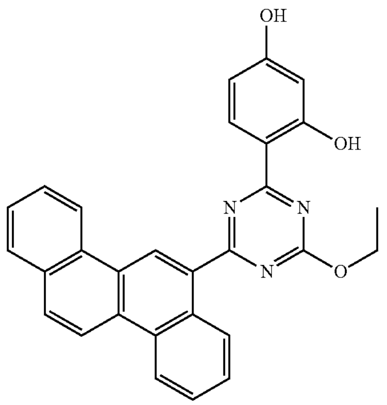
128
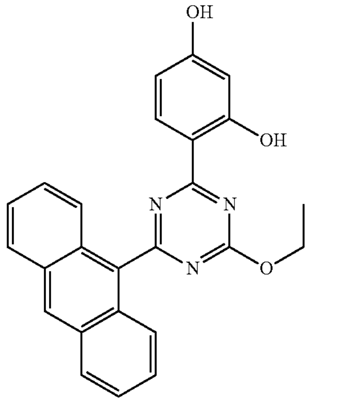

-continued
129
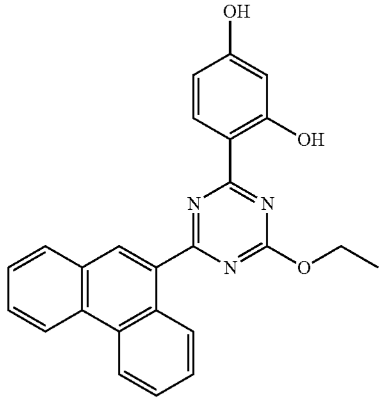
130
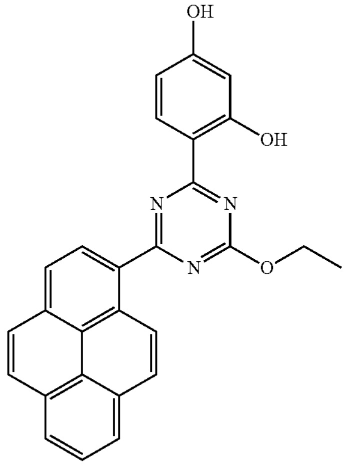
131
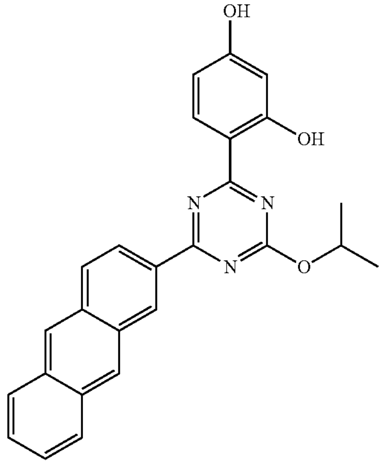
-continued
132
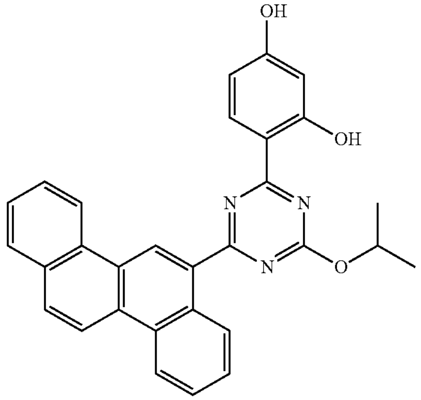
133
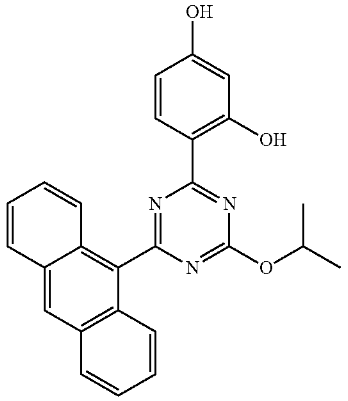
134
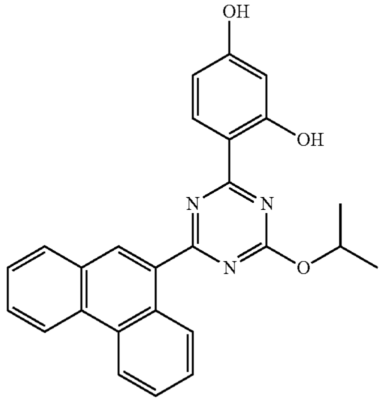

-continued
135
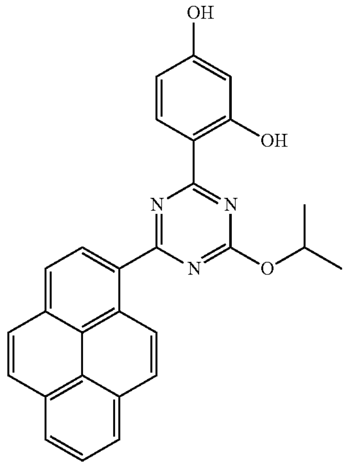
136
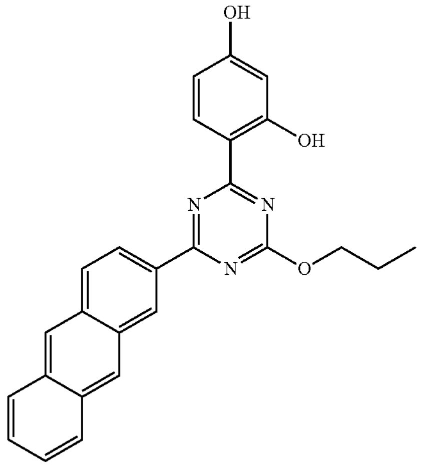
137
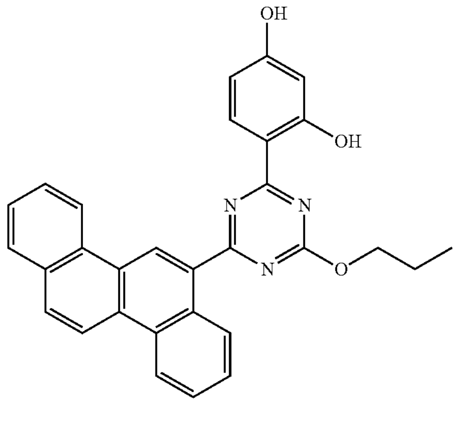
-continued
138
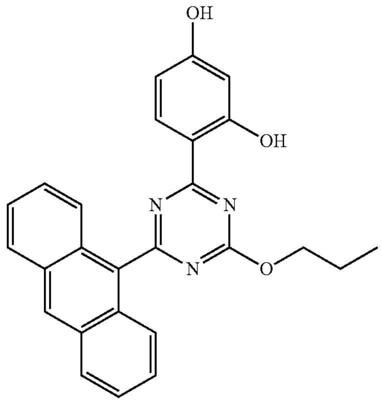
139
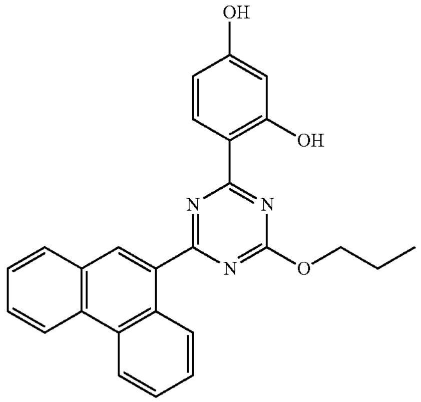
140
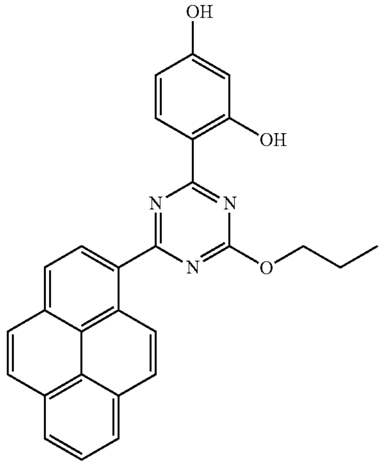

-continued
141
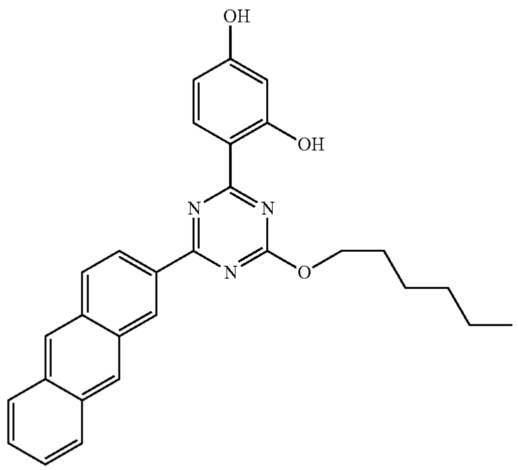
142
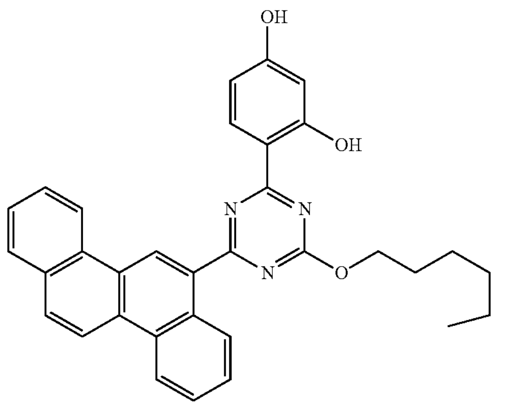
143
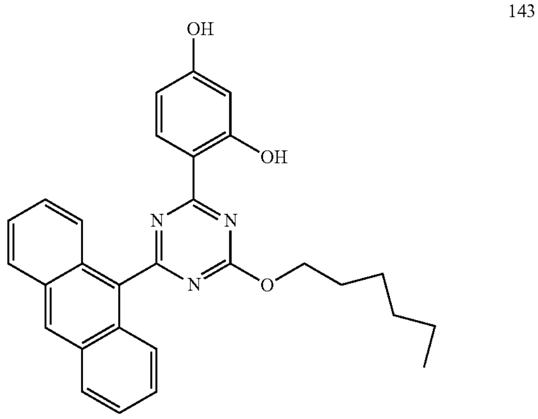
-continued
144
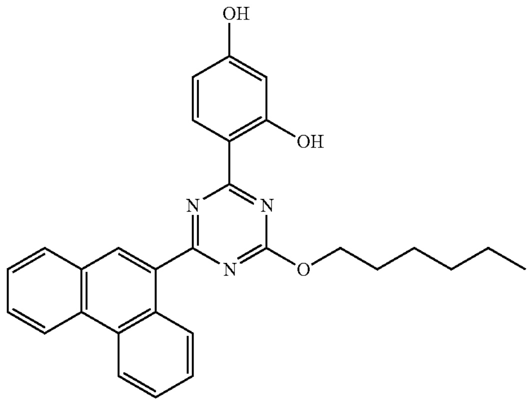
145
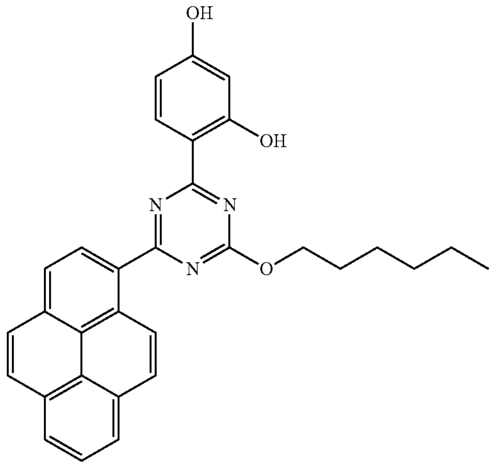
146
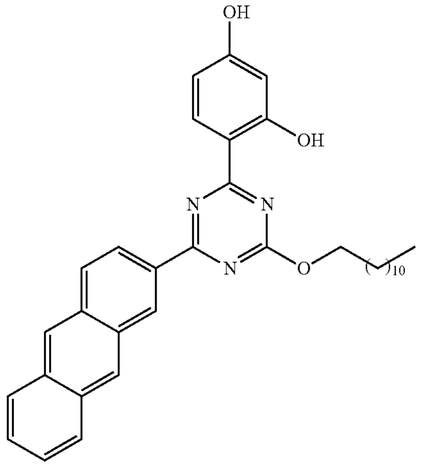

-continued
147
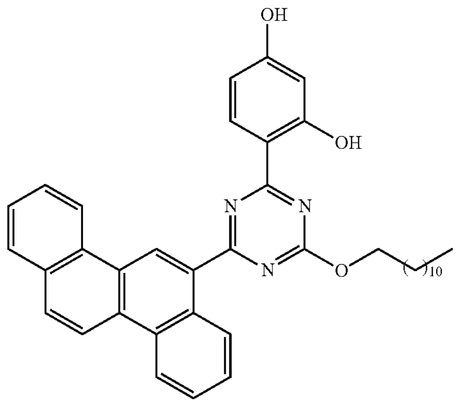
148
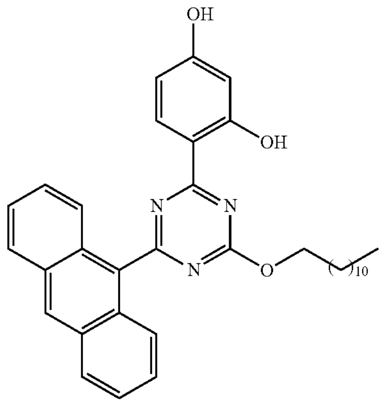
149
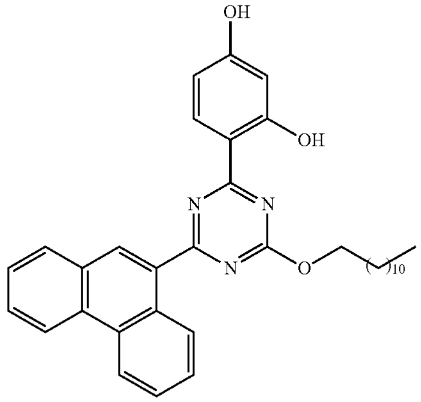
150
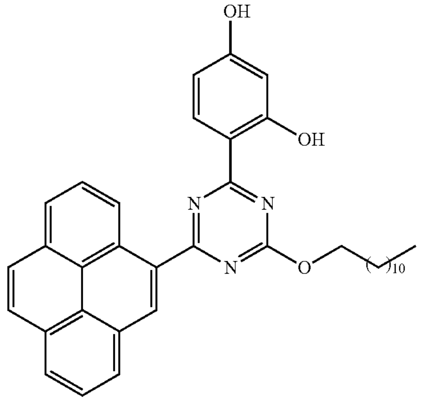
-continued
151
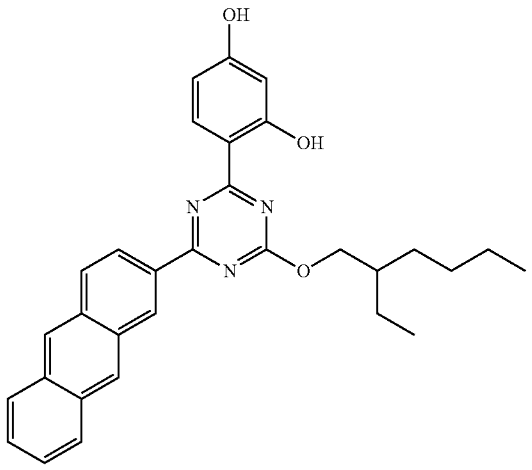
152
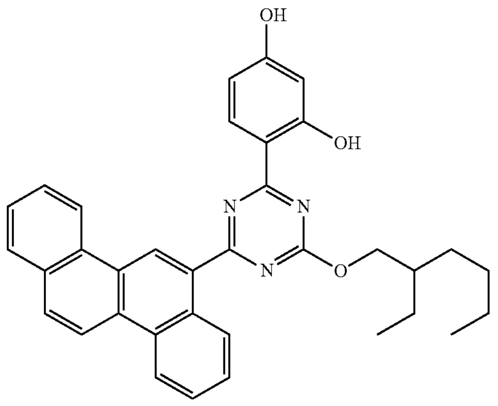
153
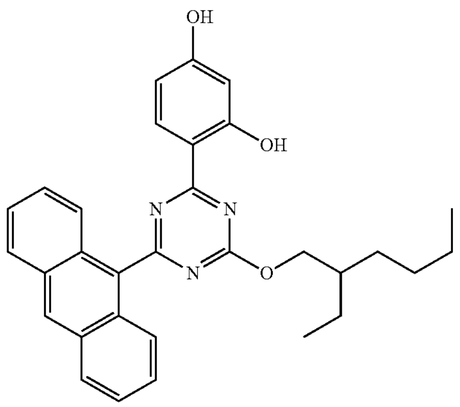

-continued
154
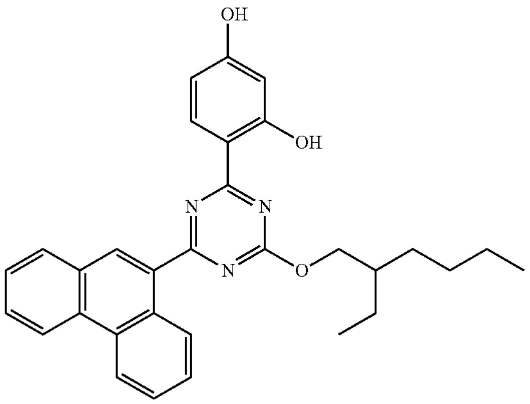
155
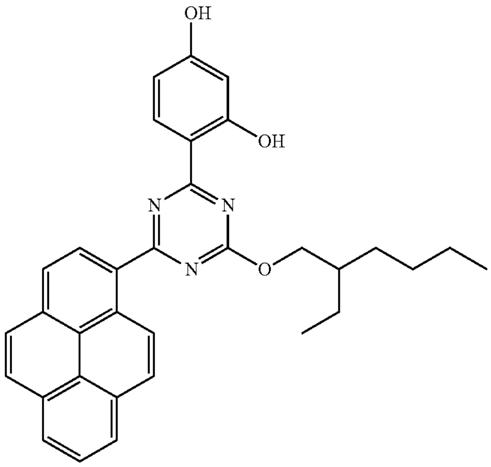
156
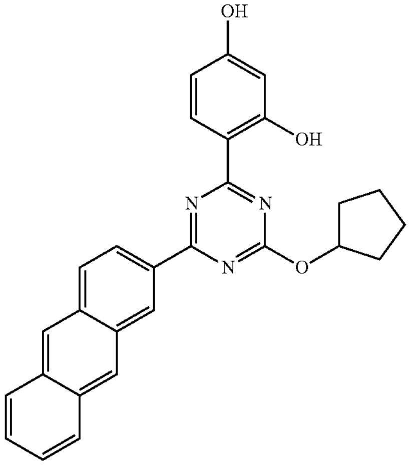
-continued
157
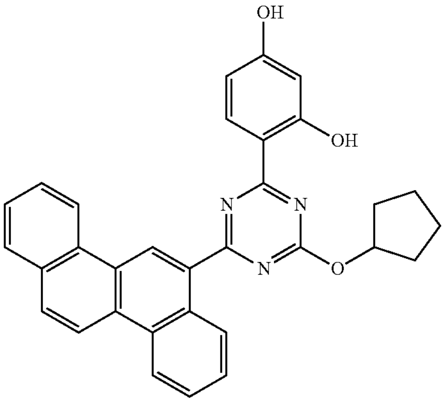
158
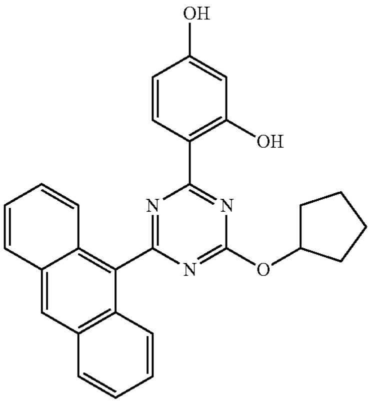
159
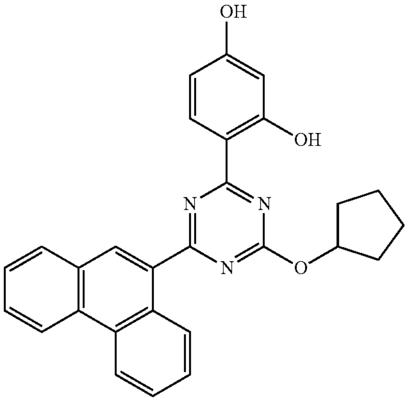

-continued
160
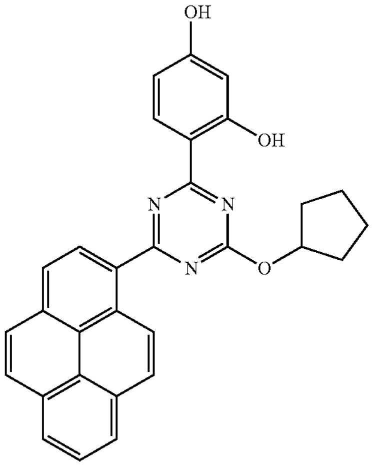
161
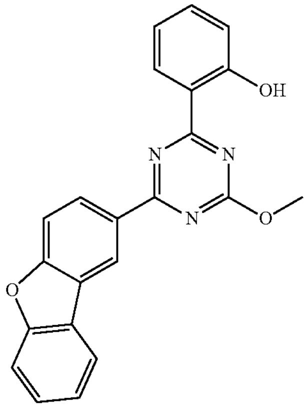
162
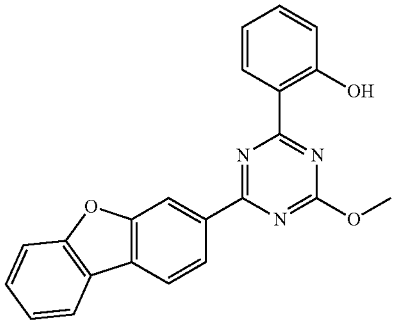
163
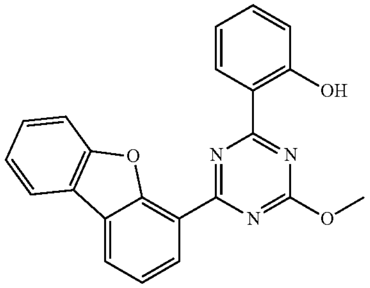
-continued
164
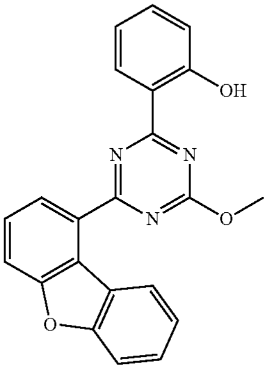
165
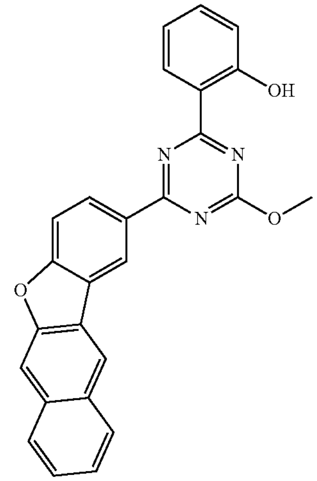
166
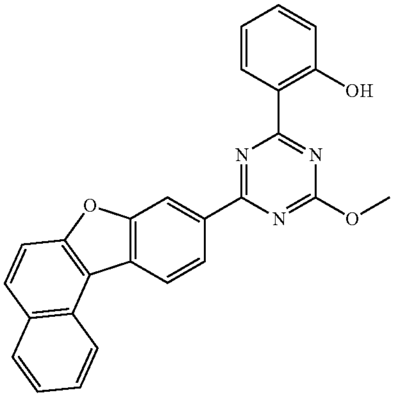
167
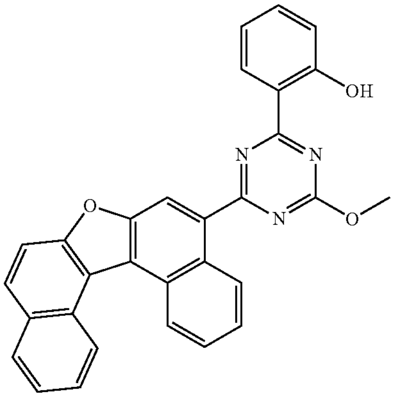

-continued
168
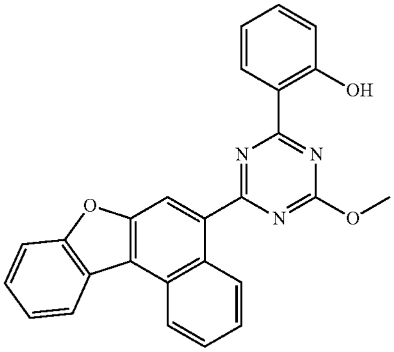
169
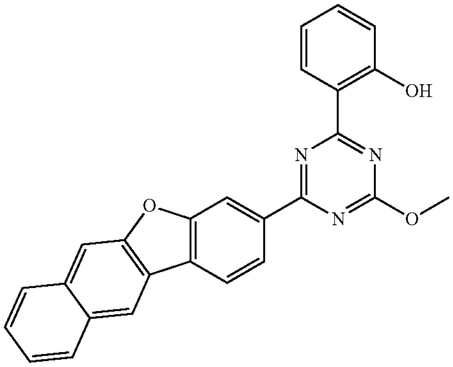
170
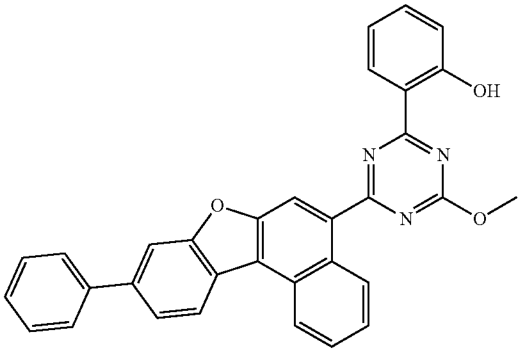
171
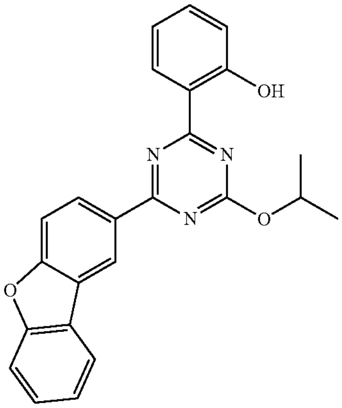
-continued
172
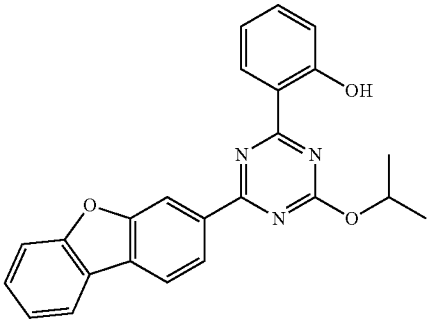
173
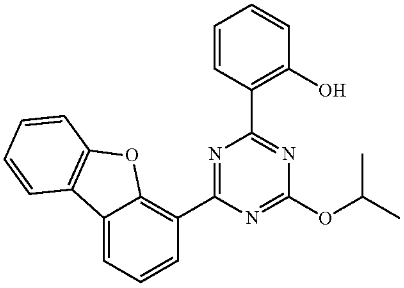
174
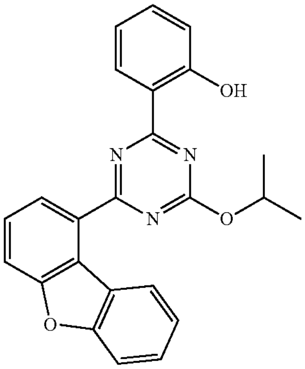
175
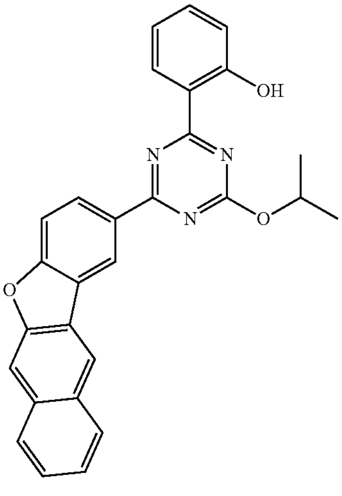 [SMILES: CC(C)Oc1cc(-c2ccc3oc4cc5ccccc5cc4c3c2)nc(-c2ccccc2O)n1]

-continued
176
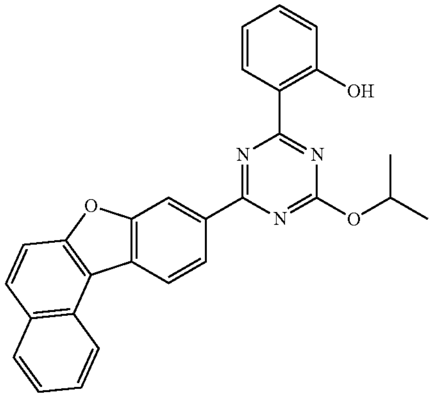
177
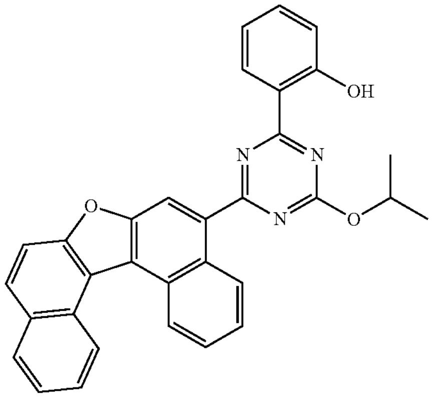
178
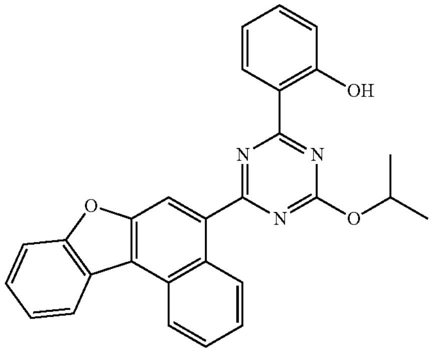
179
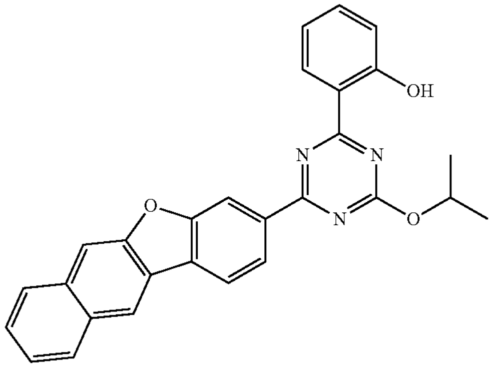
-continued
180
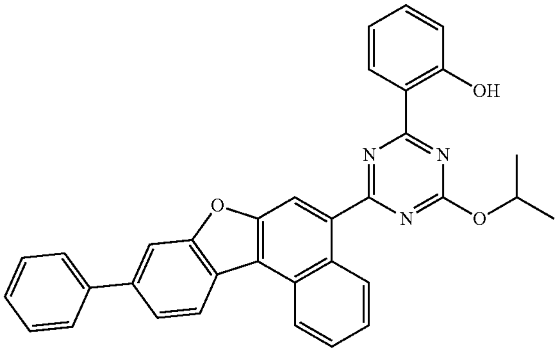
181
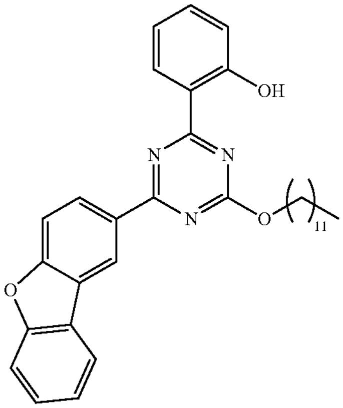
182
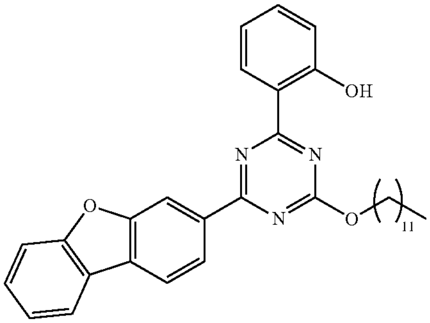
183
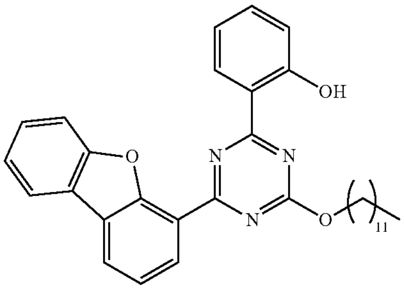

184
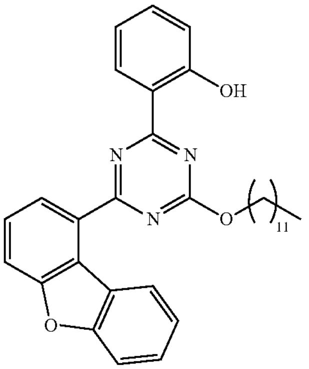
185
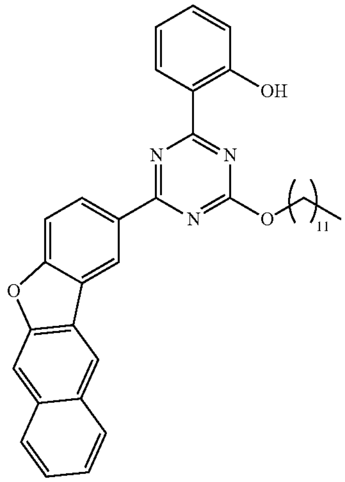
186
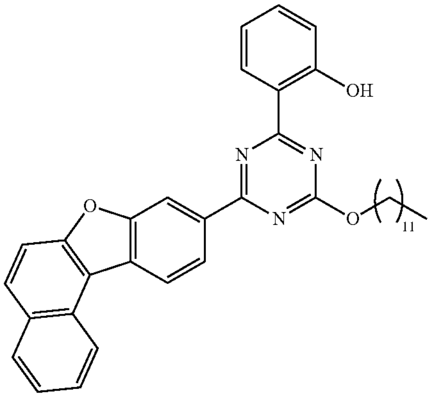
187
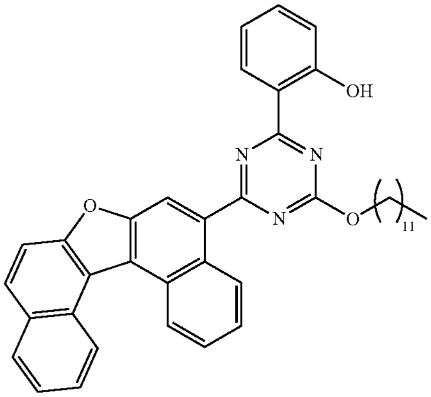
188
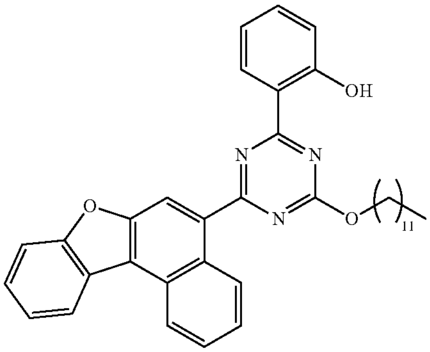
189
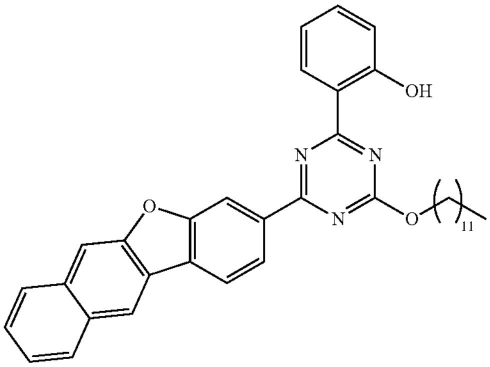
190
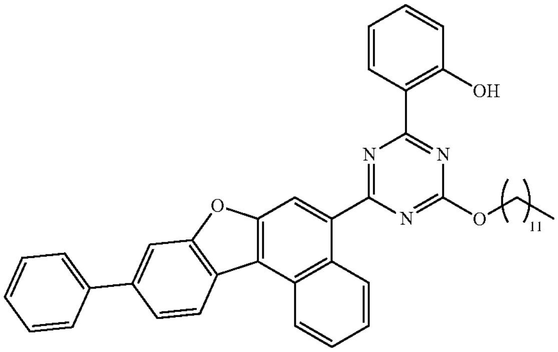
191
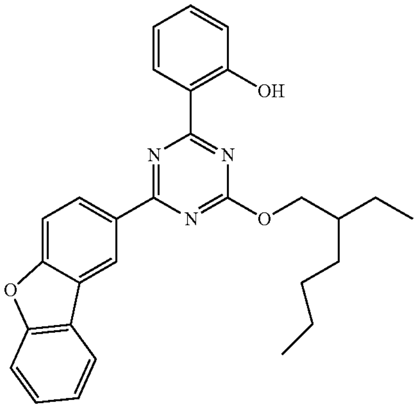

192
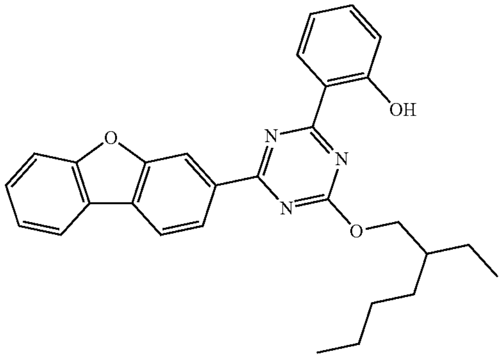
193
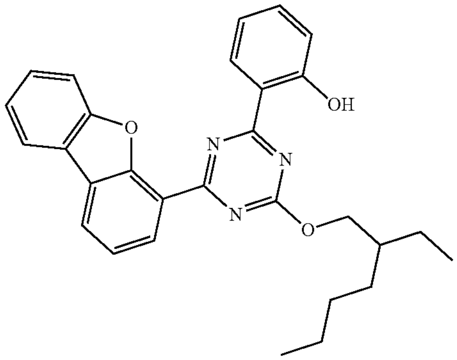
194
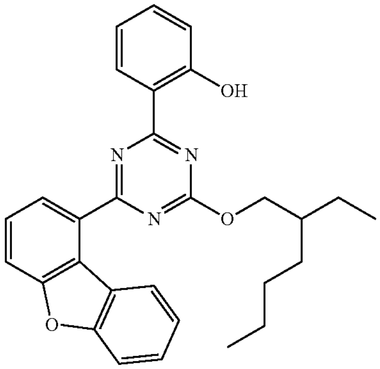
195
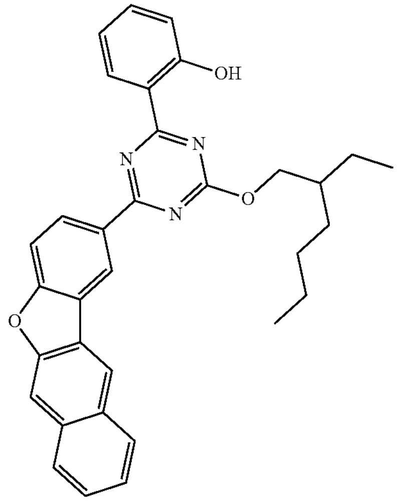
196
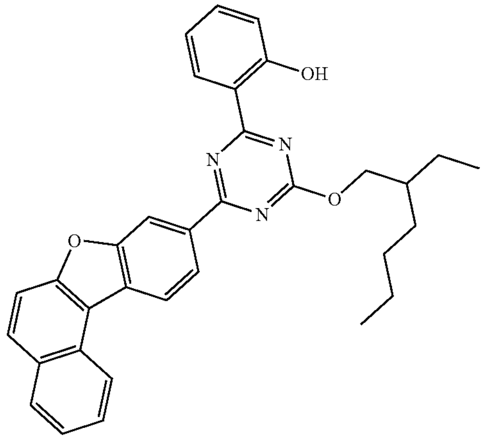
197
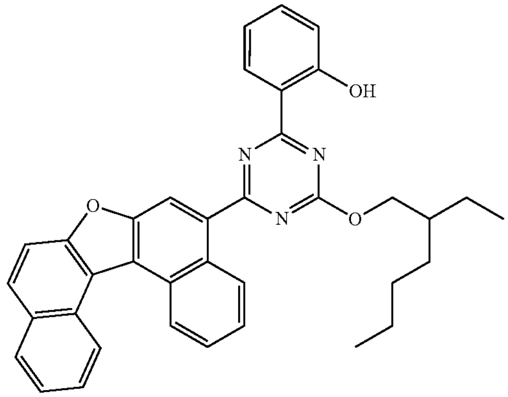
198
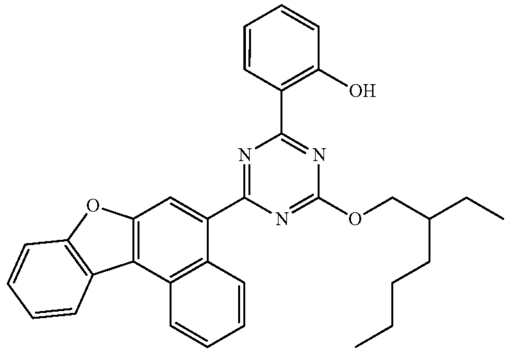

-continued
199
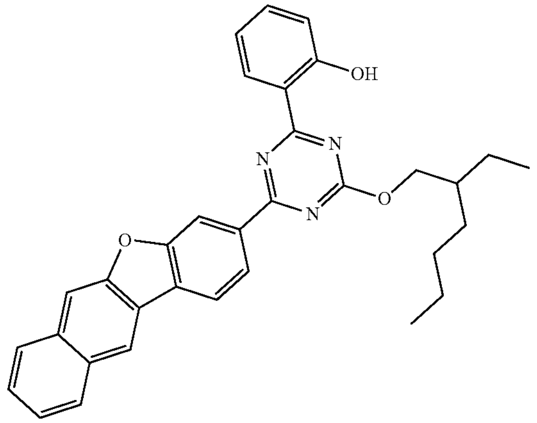
200
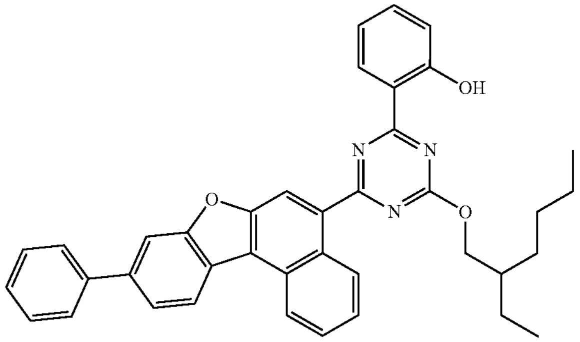
201
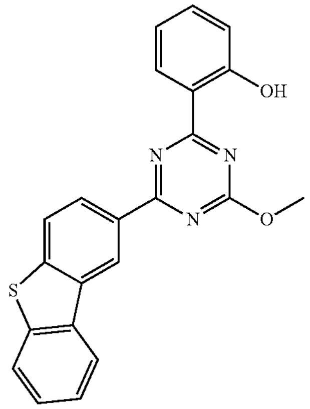
202
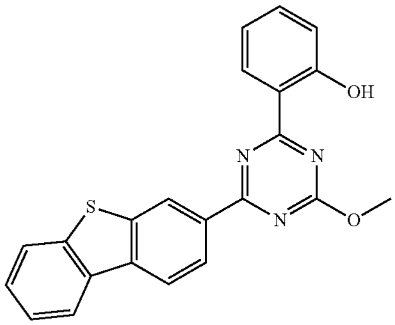
-continued
203
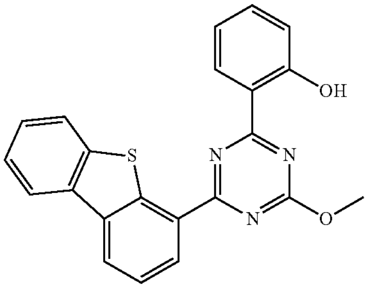
204
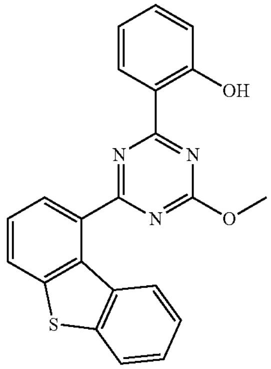
205
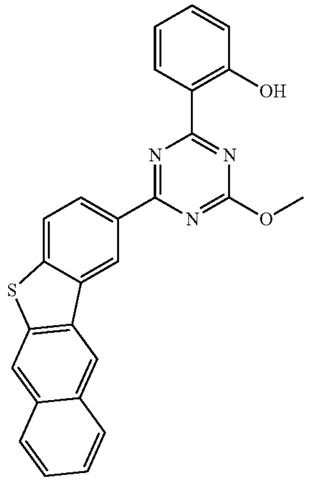
206
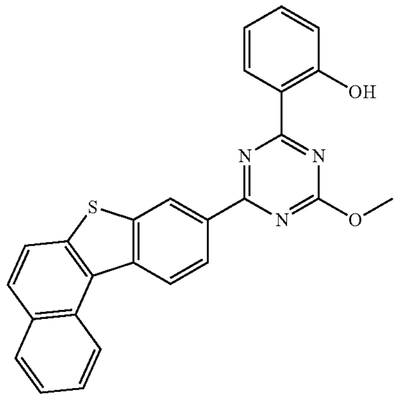

-continued
207
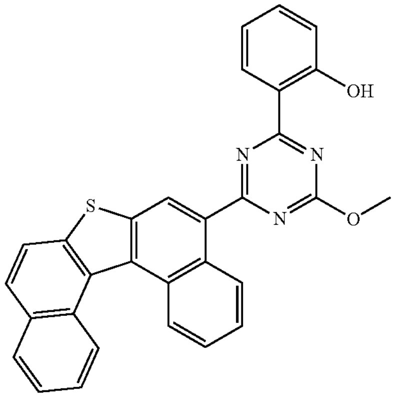
208
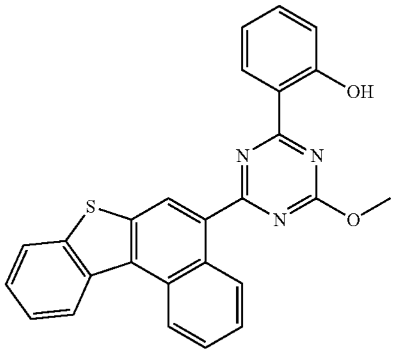
209
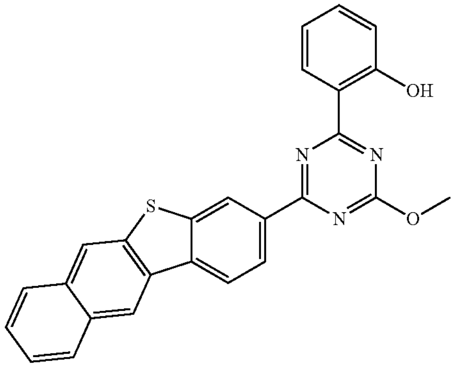
210
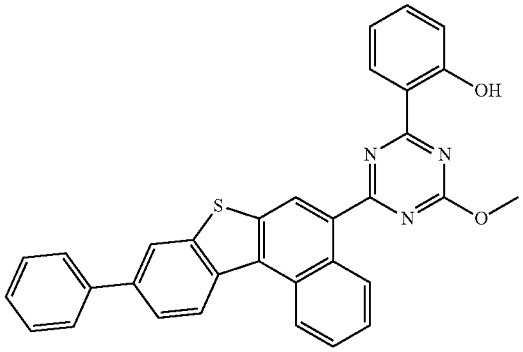
-continued
211
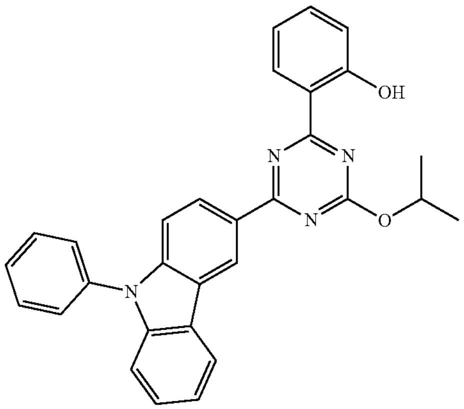
212
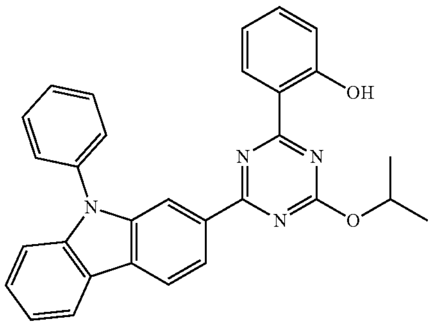
213
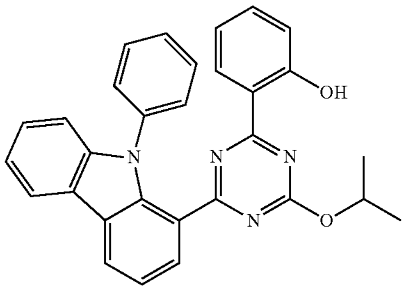
214
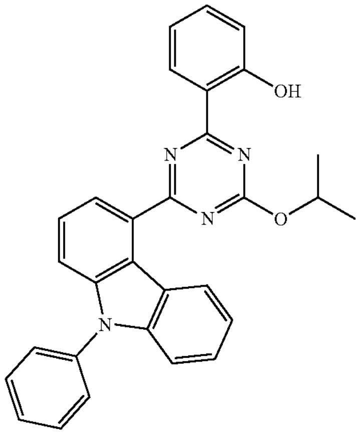

-continued
215
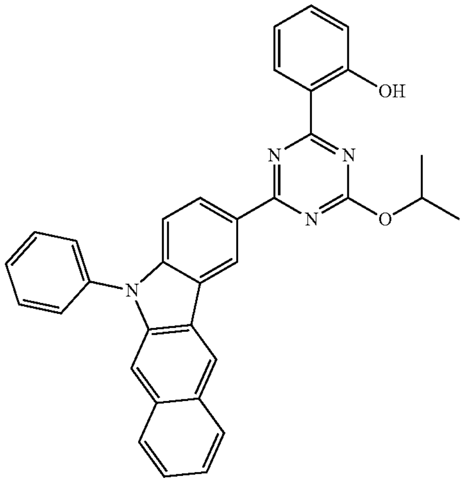
216
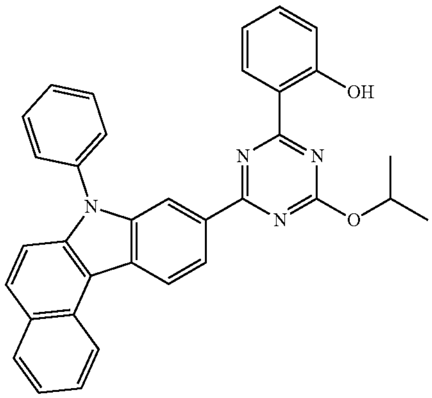
217
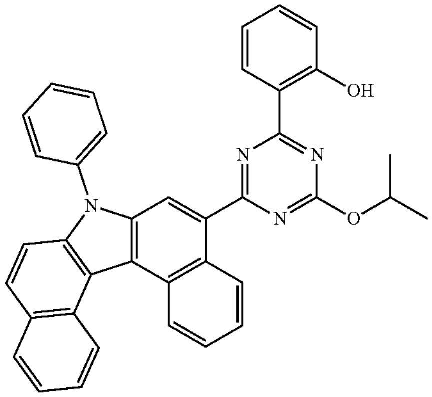
218
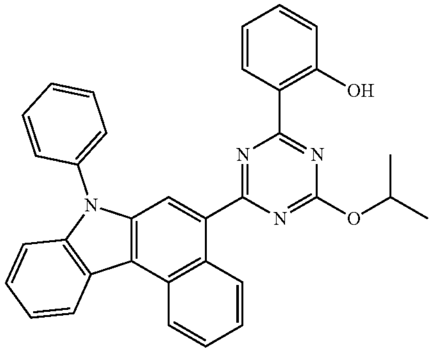
-continued
219
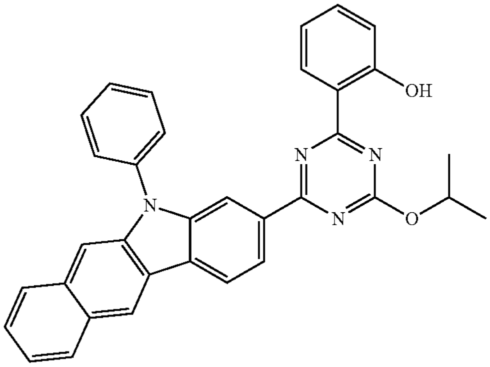
220
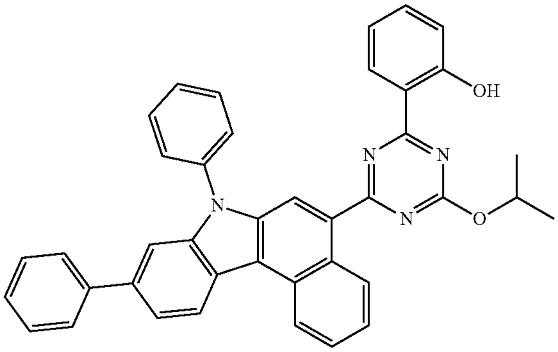
221
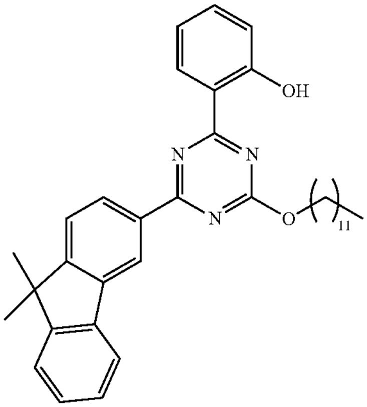
222
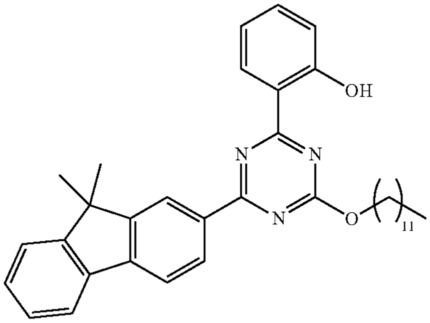

-continued
223
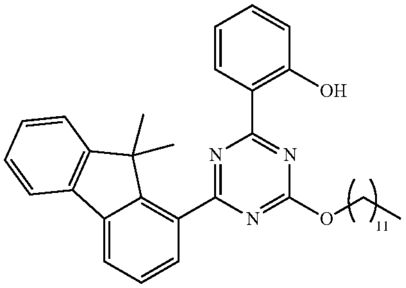
224
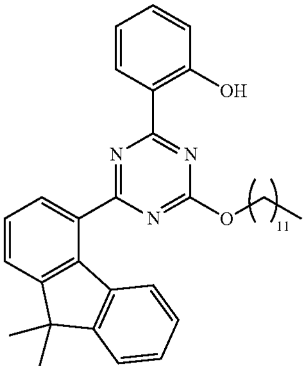
225
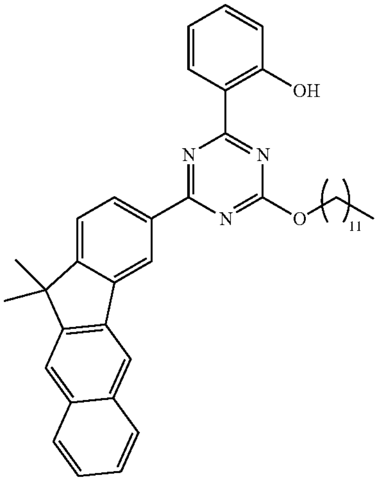
226
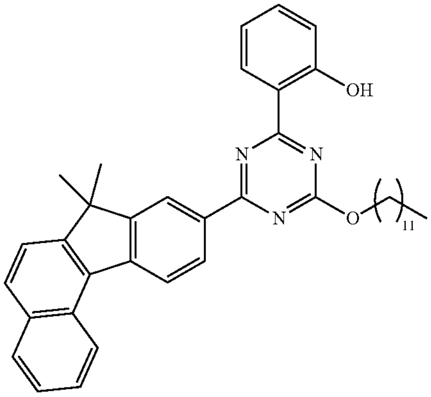
-continued
227
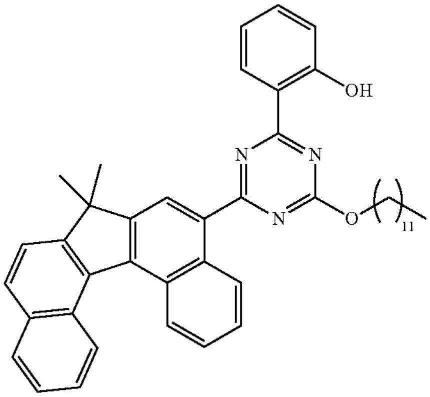
228
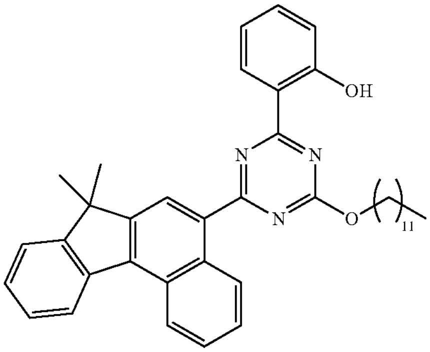
229
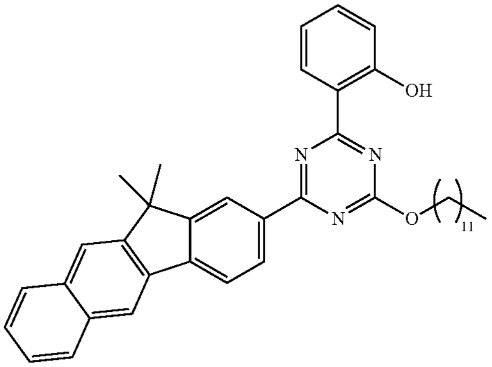
230
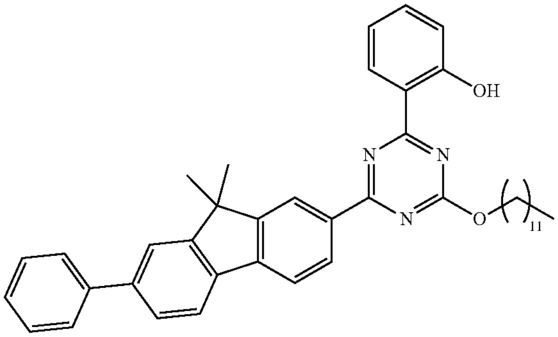

-continued
231
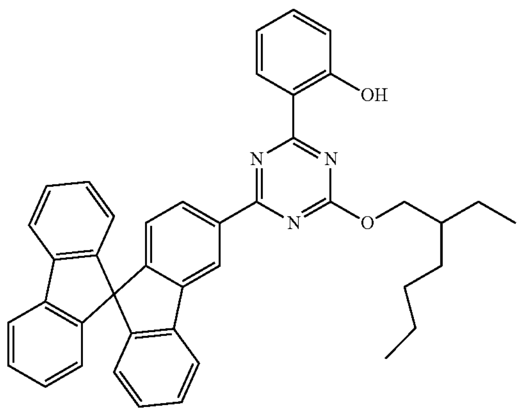
232
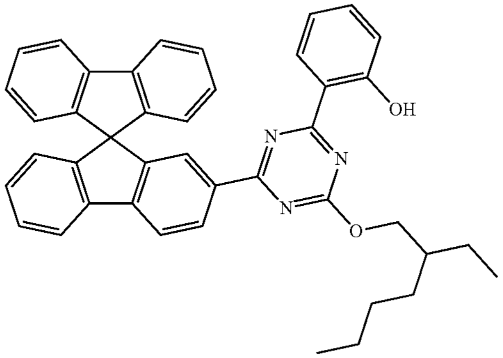
233
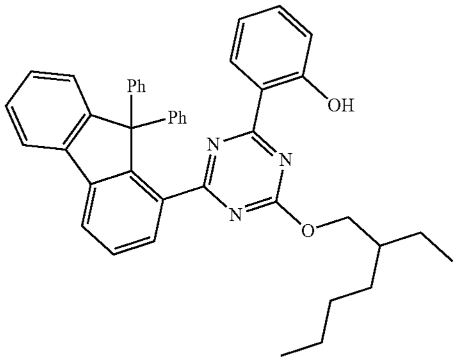
234
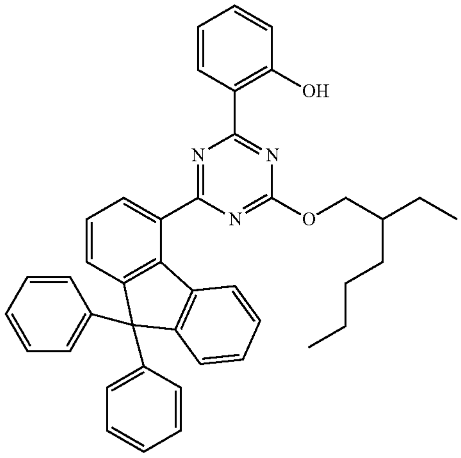
-continued
235
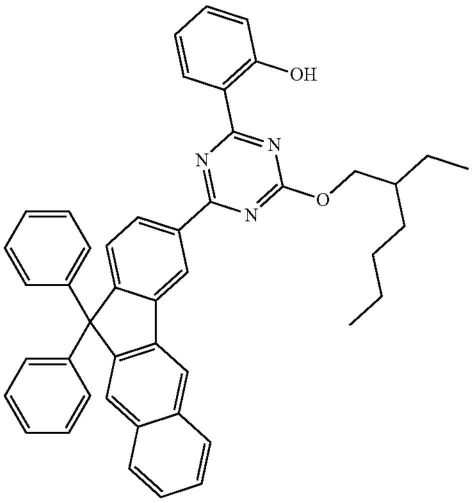
236
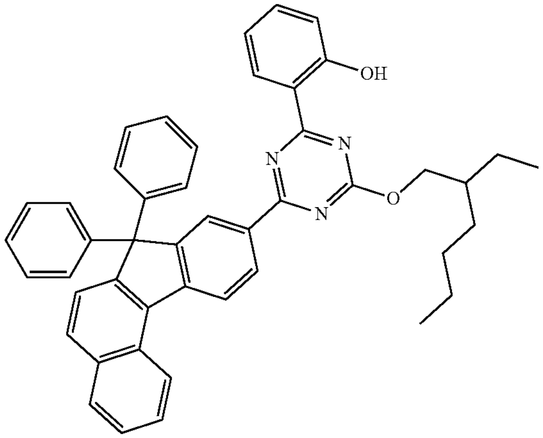
237
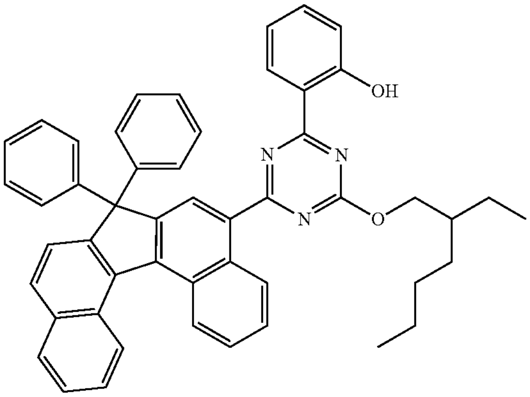

238
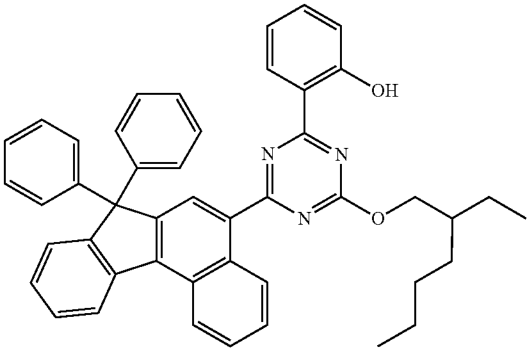
239
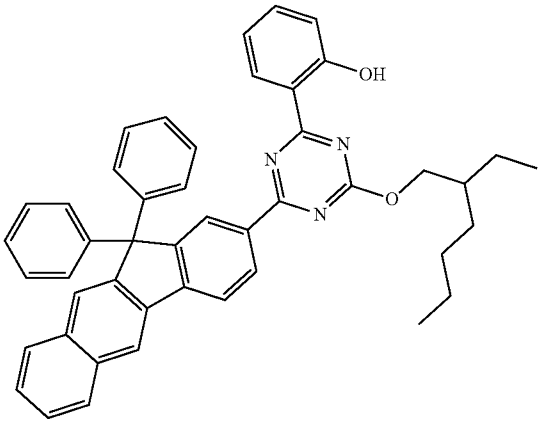
240
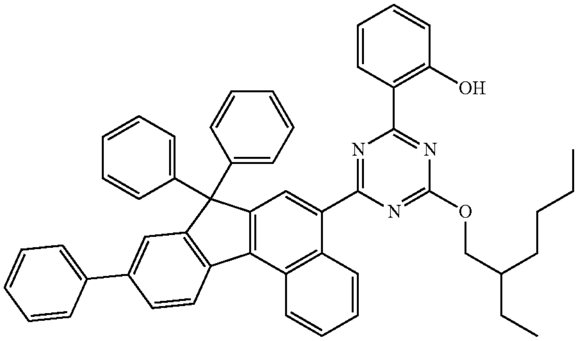
241
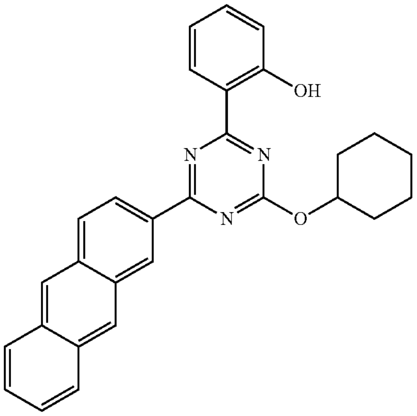
242
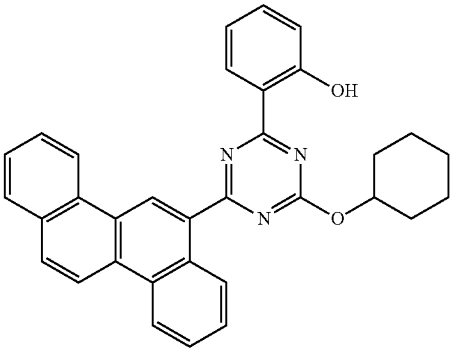
243
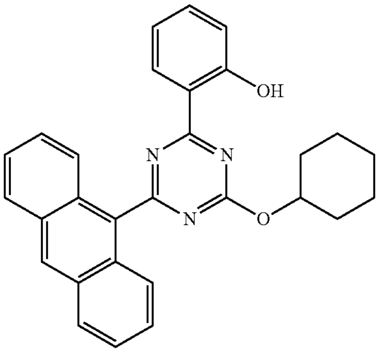
244
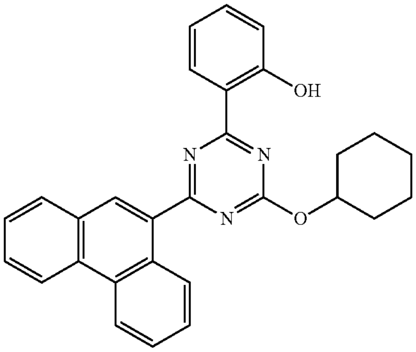
245
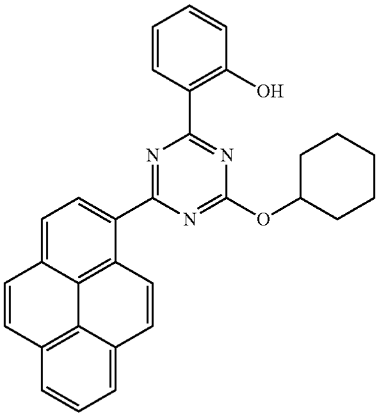

-continued
246
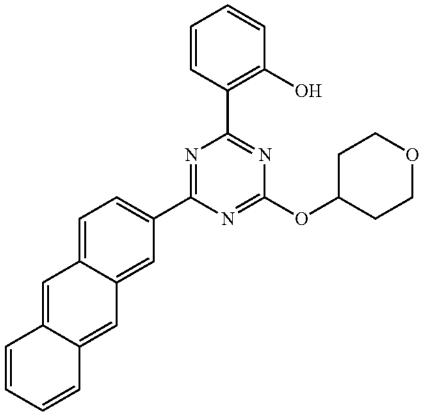
247
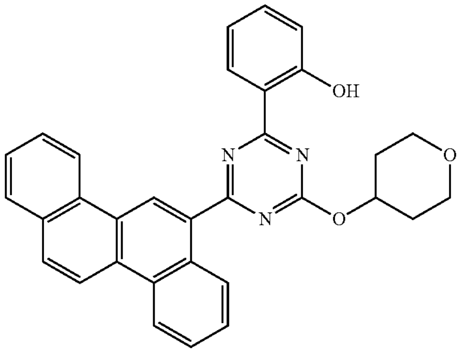
248
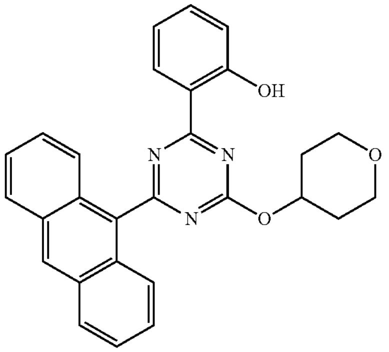
249
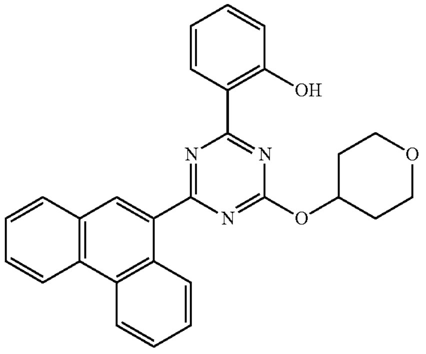
-continued
250
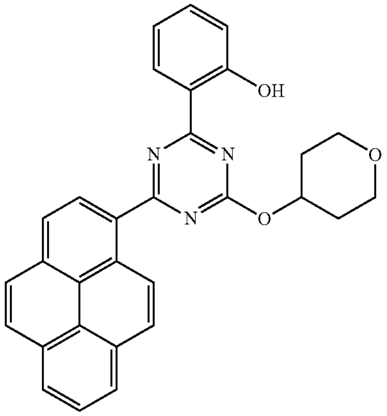
251
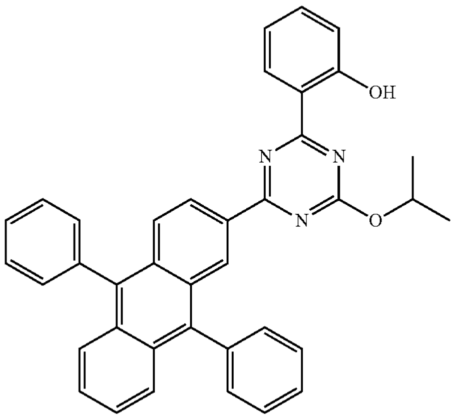
252
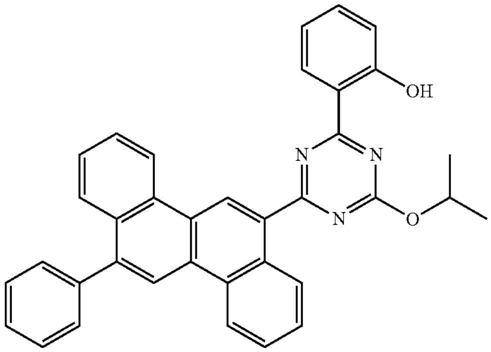
253
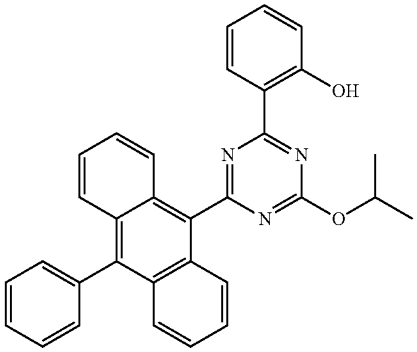

-continued
254
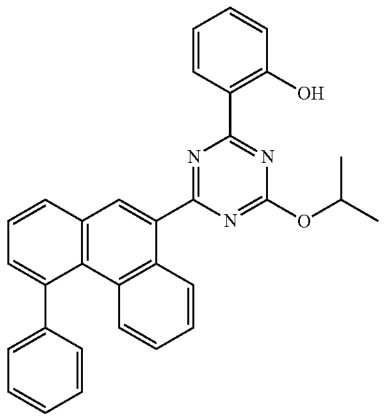
255
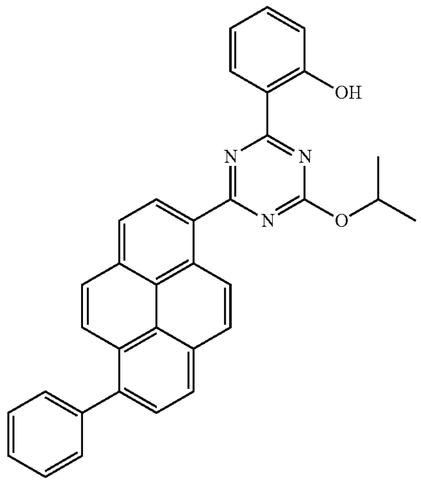
256
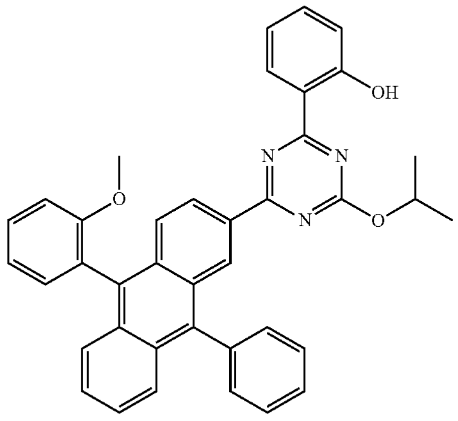
-continued
257
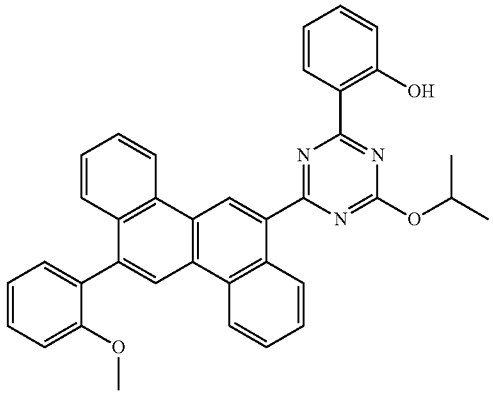
258
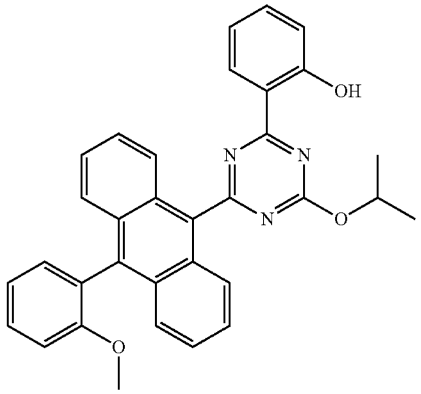
259
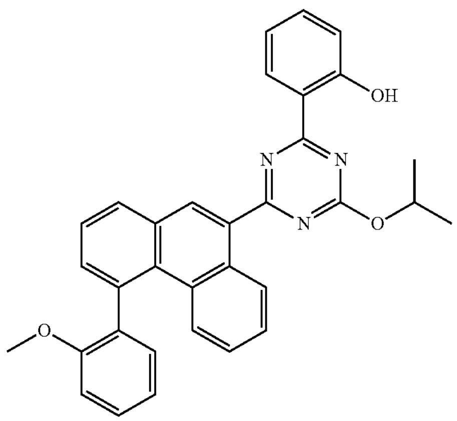

-continued
260
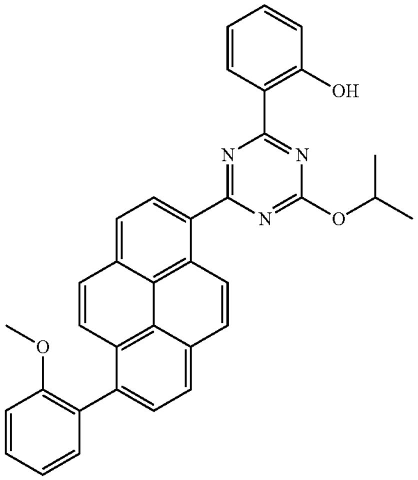
261
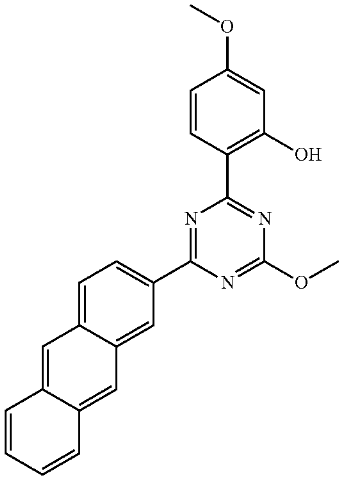
262
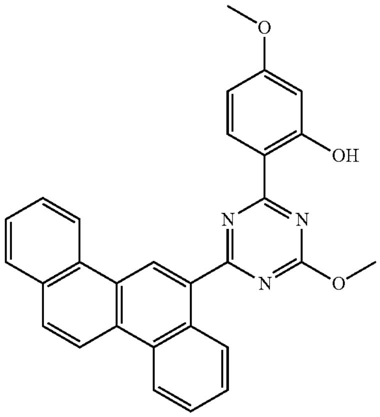
-continued
263
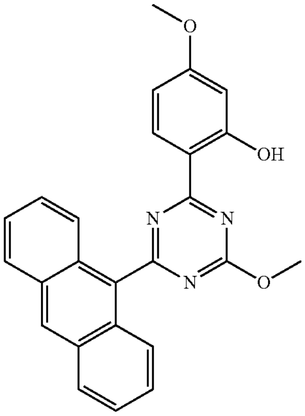
264
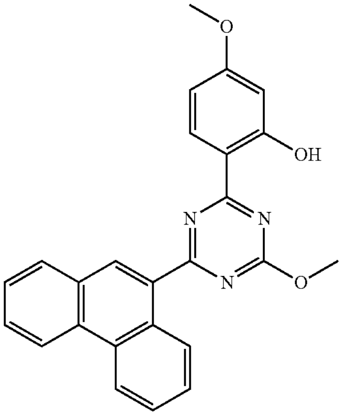
265
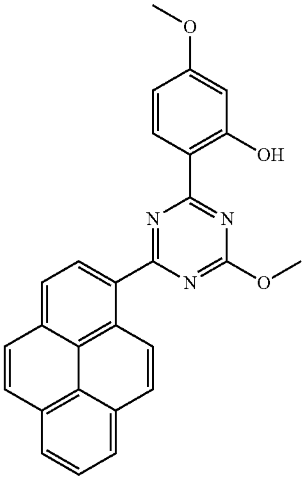

-continued
266
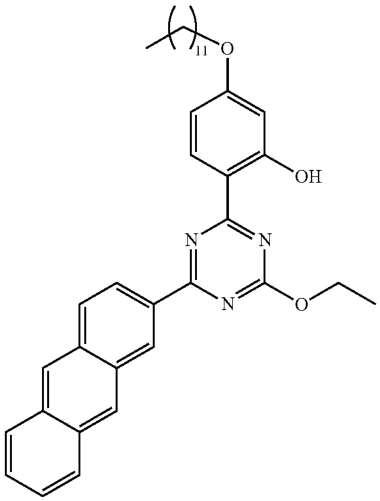
267
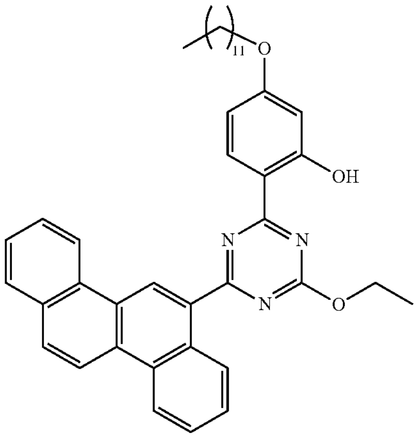
268
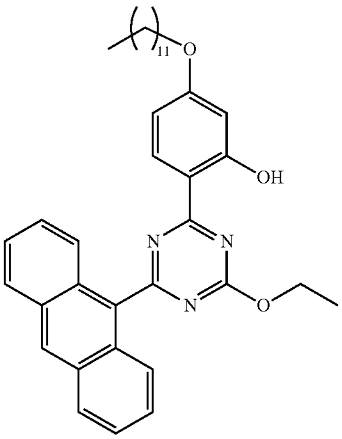
-continued
269
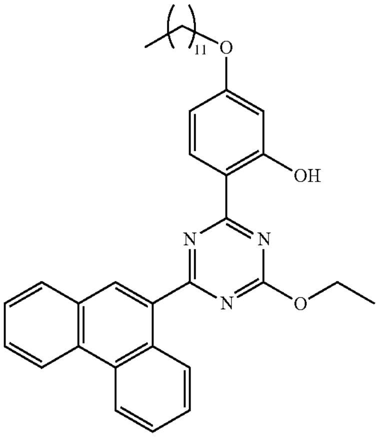
270
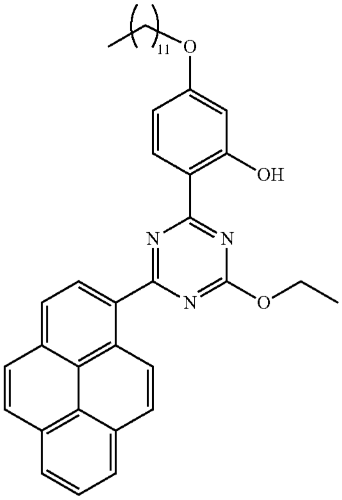
271
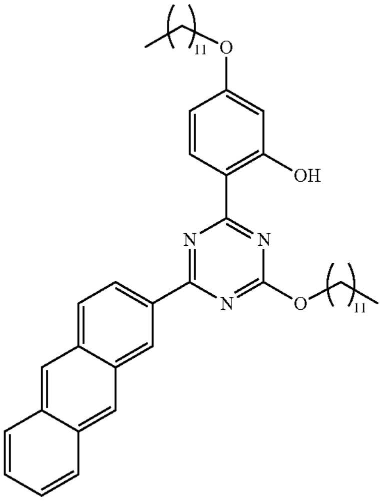

-continued
272
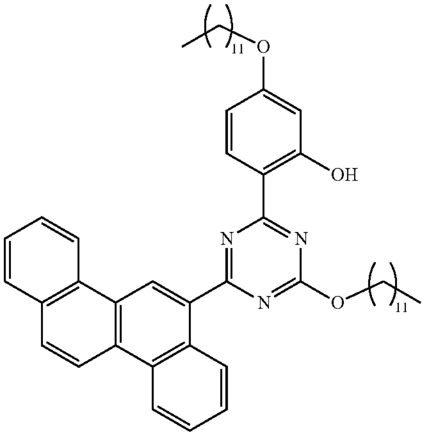
273
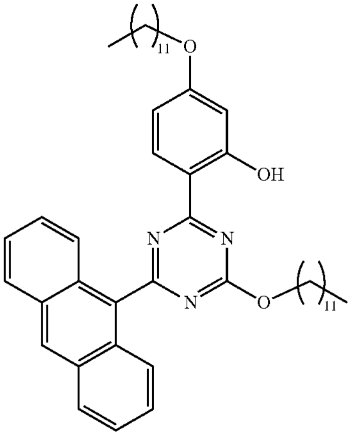
274
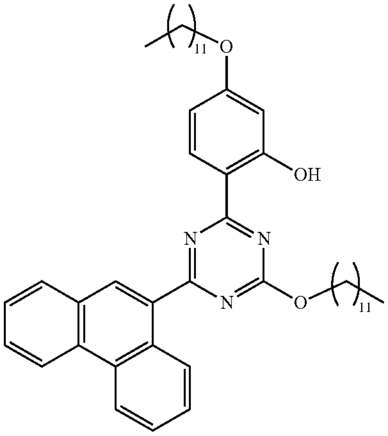
-continued
275
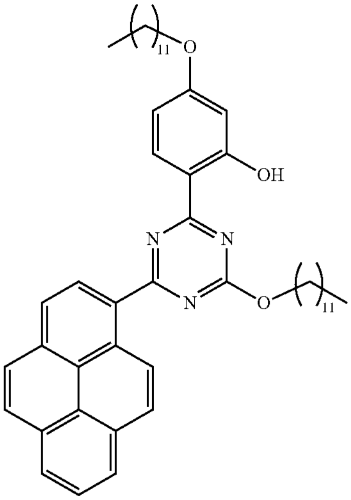
276
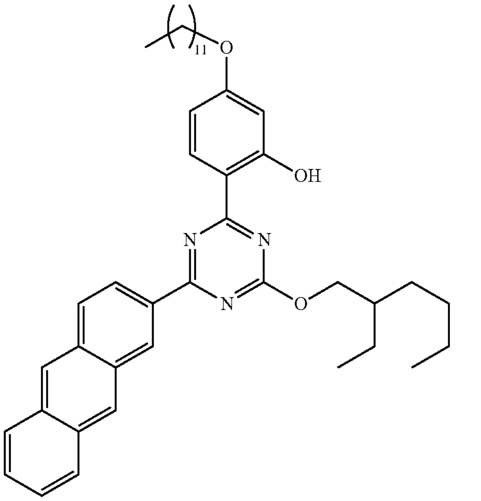
277
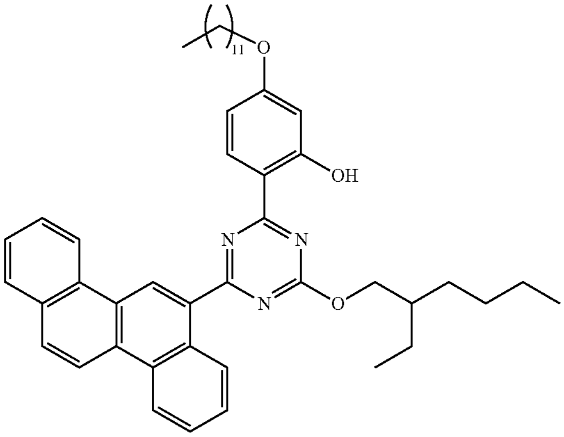

-continued
278
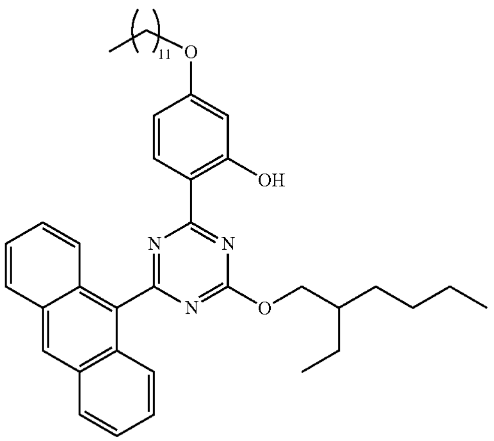
279
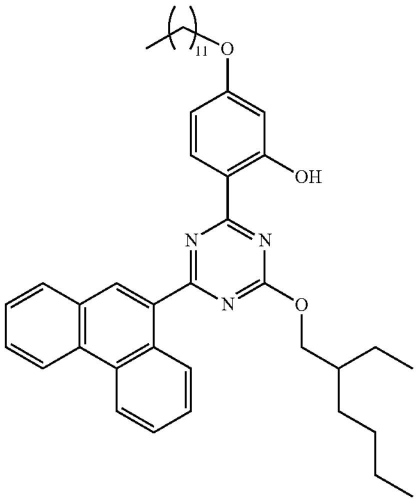
280
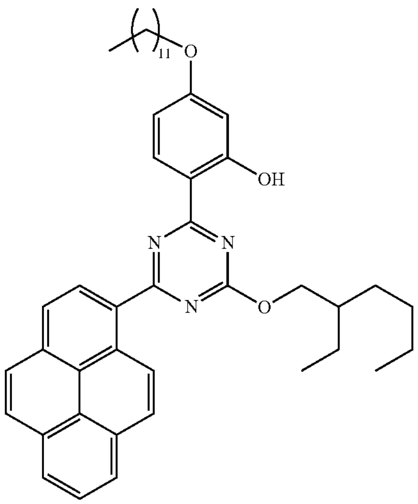
-continued
281
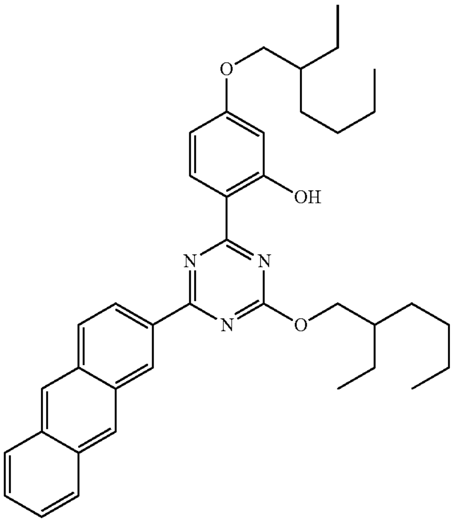
282
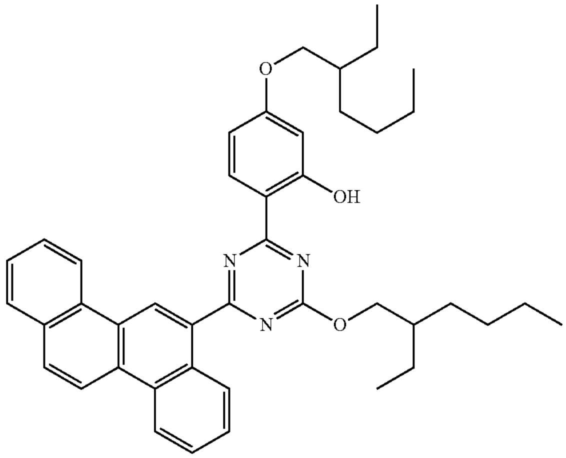
283
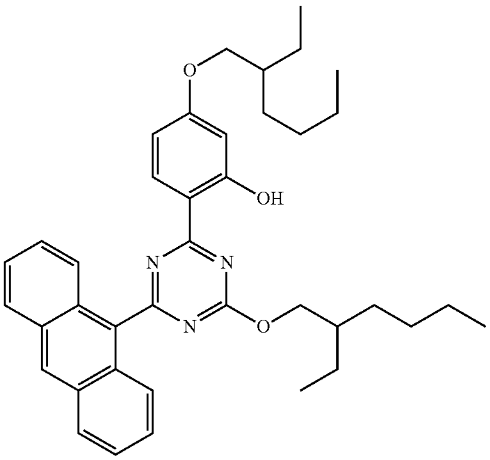

-continued
284
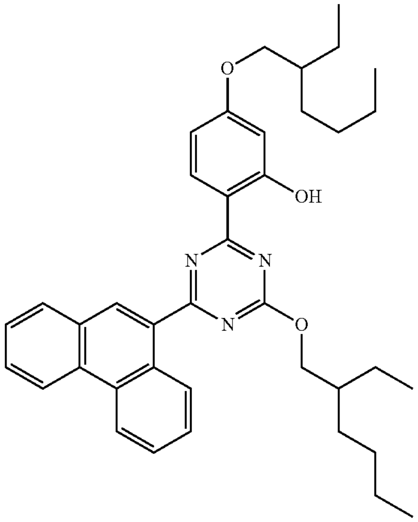
285
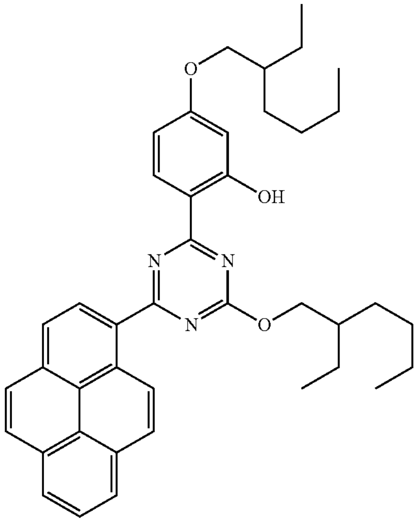
286
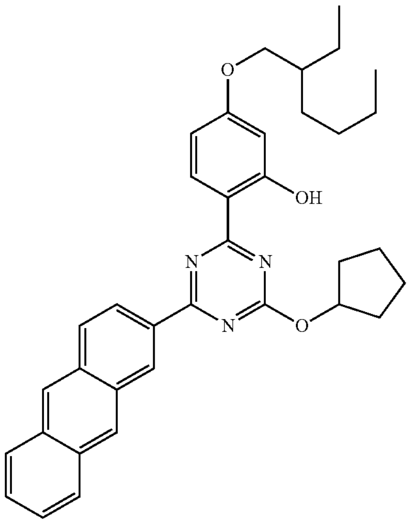
-continued
287
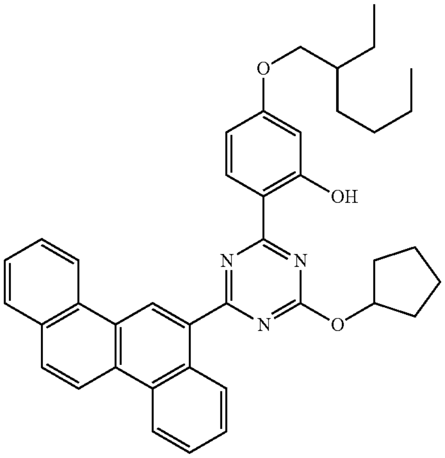
288
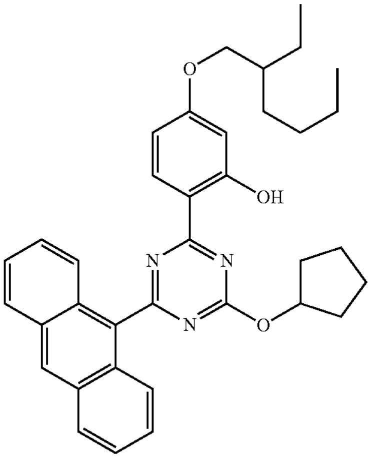
289
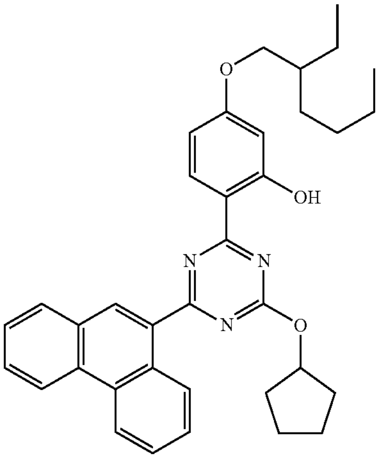

-continued
290
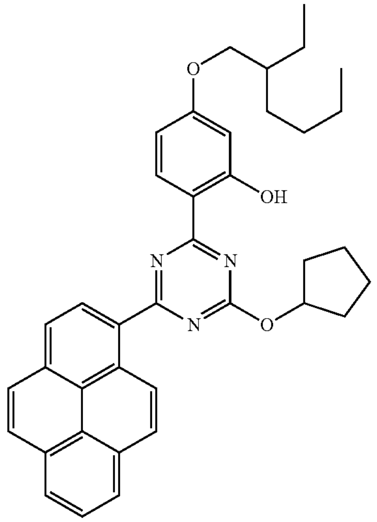
291
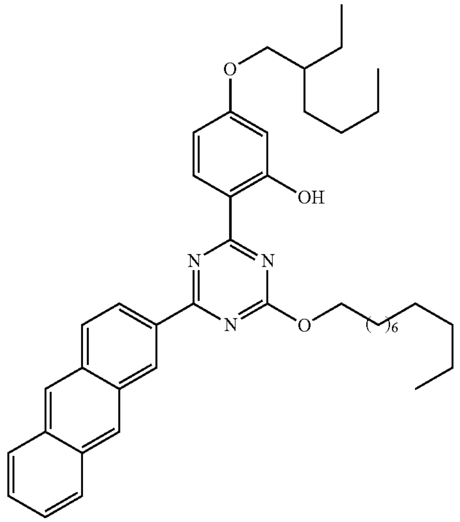
292
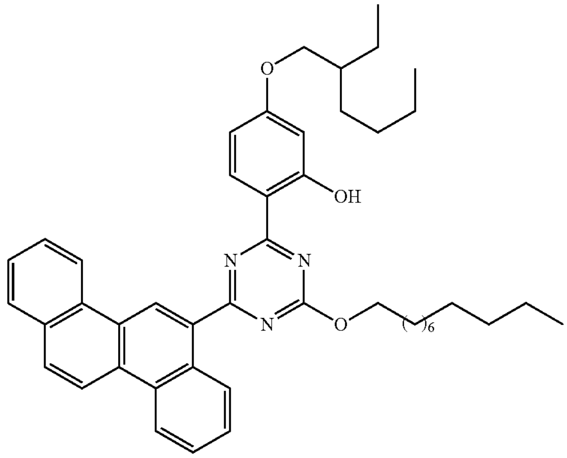
-continued
293
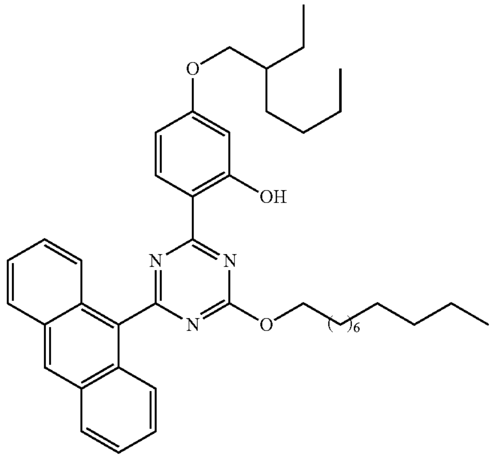
294
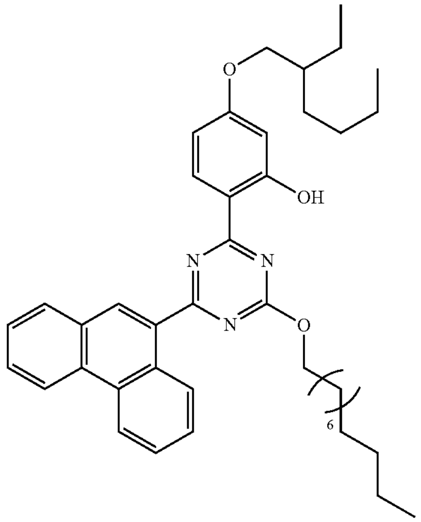
295
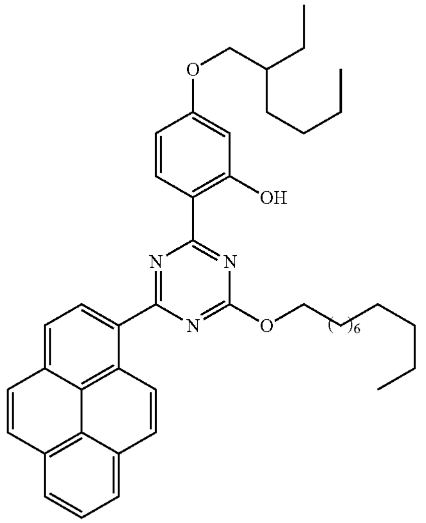

-continued
296
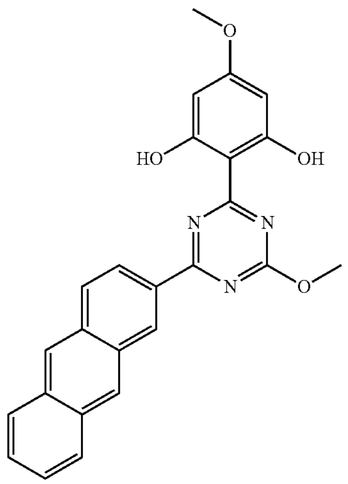
297
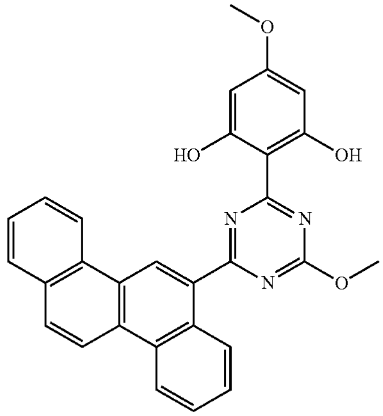
298
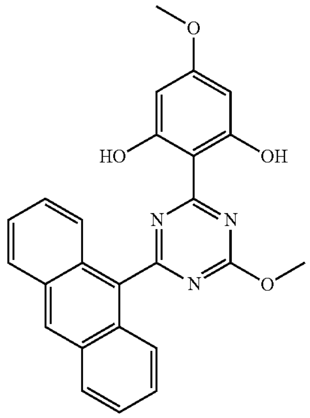
-continued
299
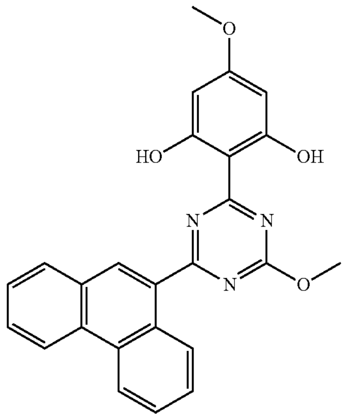
300
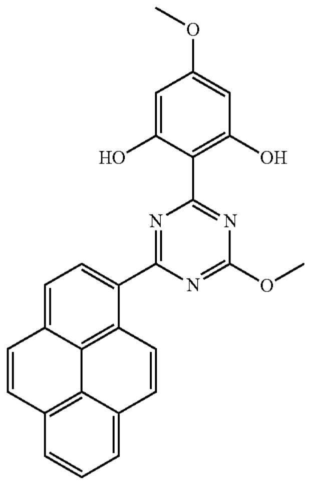
301
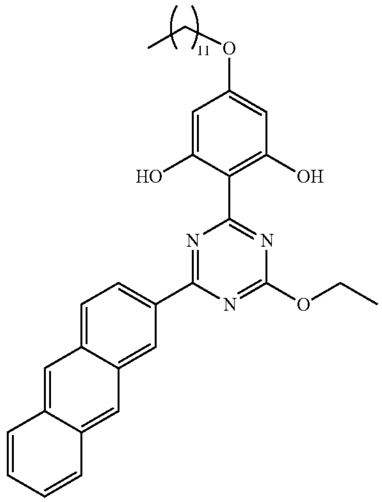

-continued
302
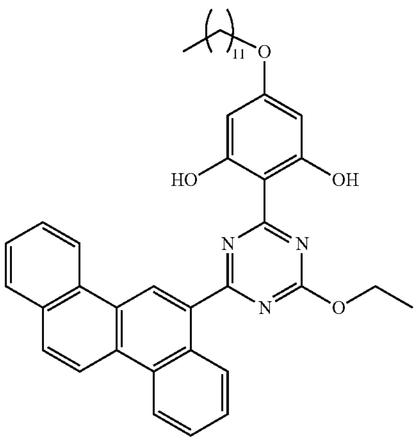
303
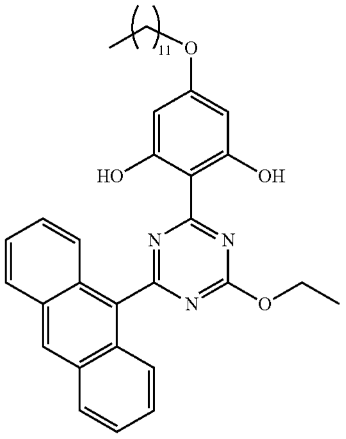
304
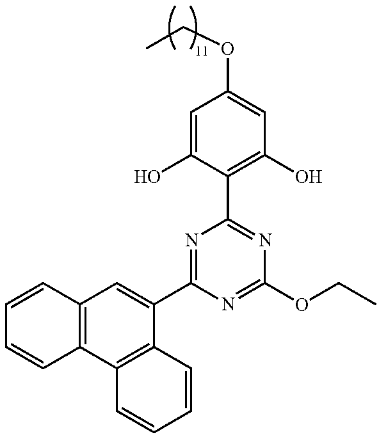
-continued
305
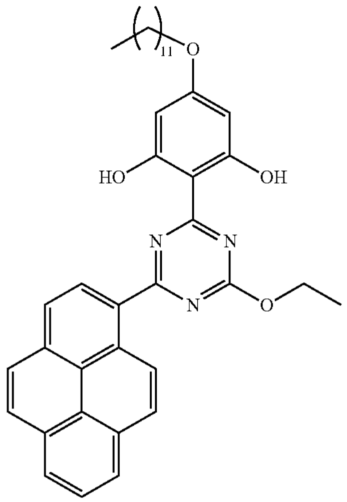
306
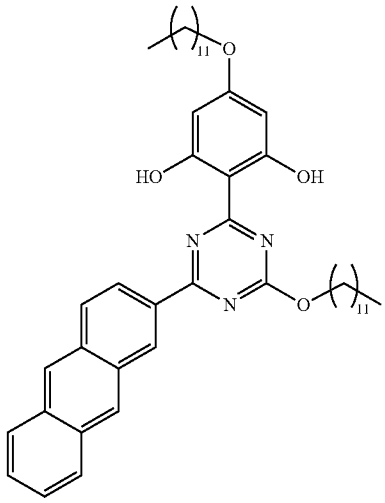
307
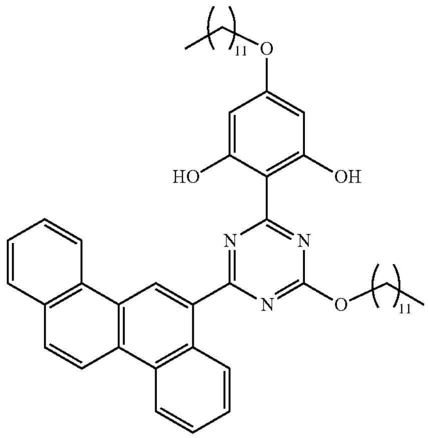

-continued
308
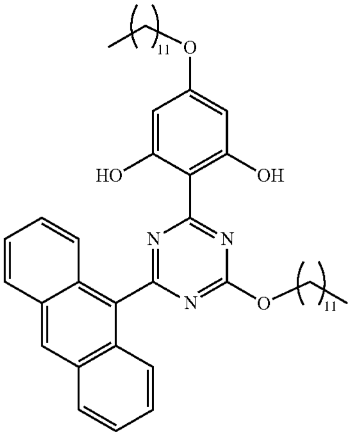
309
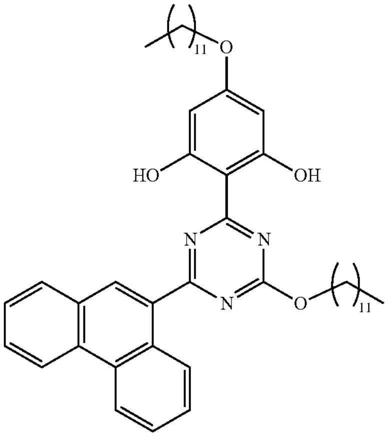
310
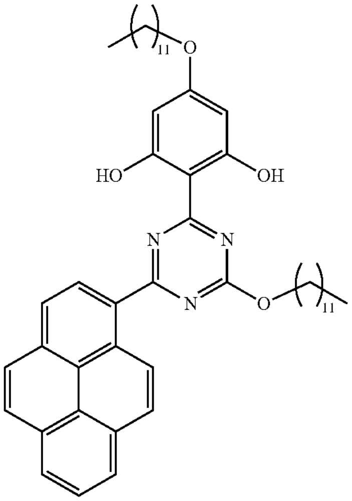
-continued
311
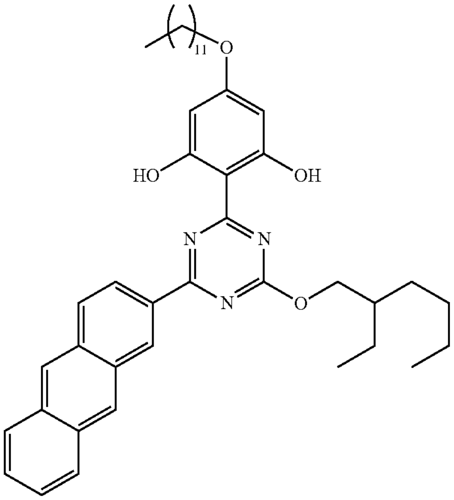
312
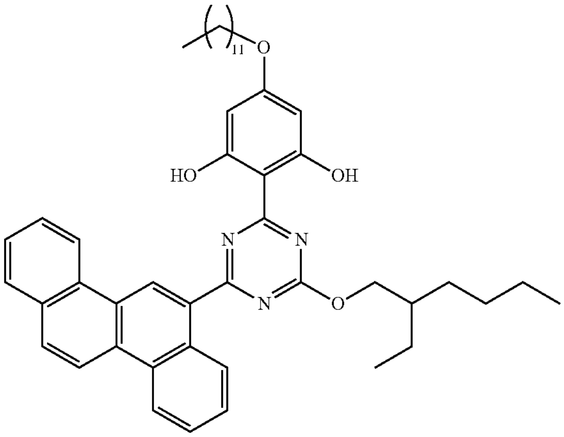
313
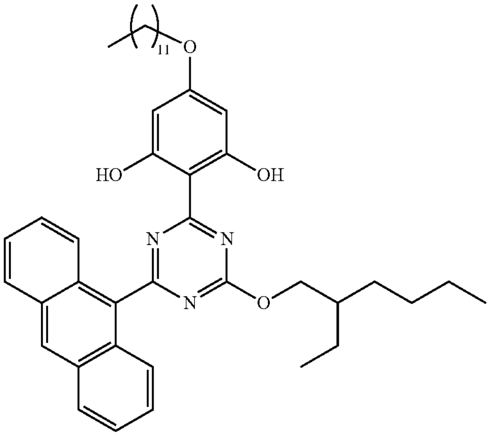

-continued
314
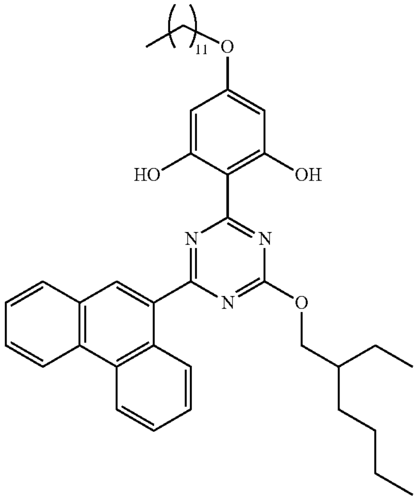
315
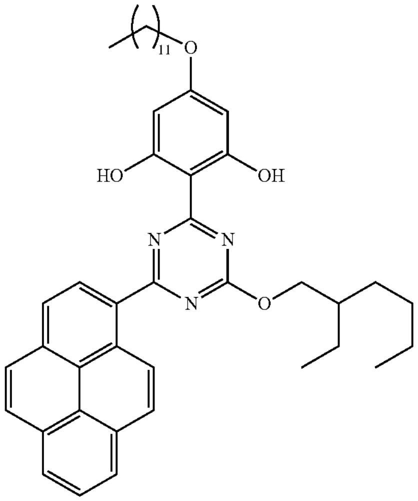
316
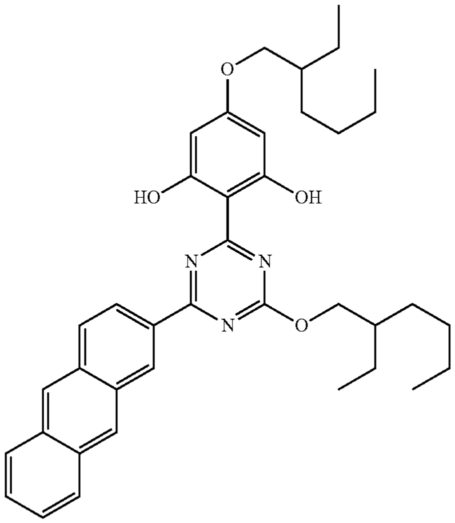
-continued
317
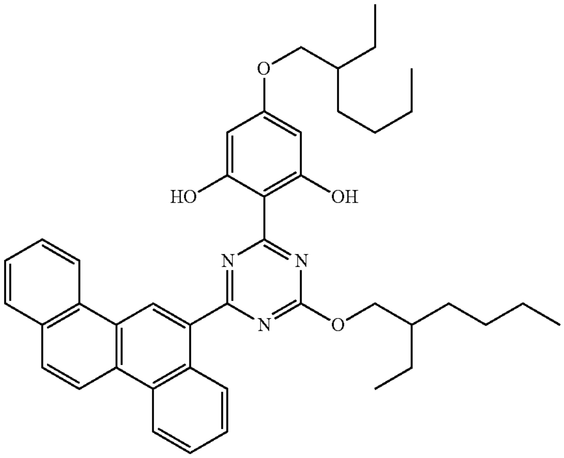
318
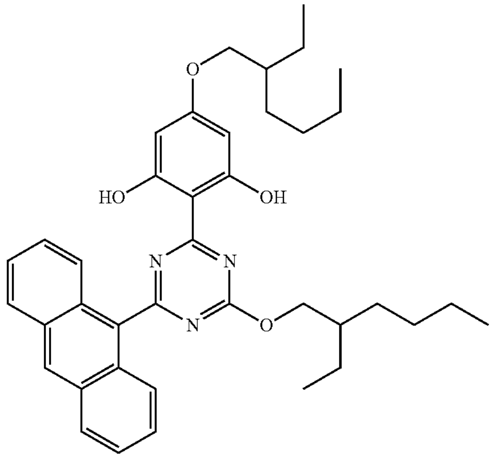
319
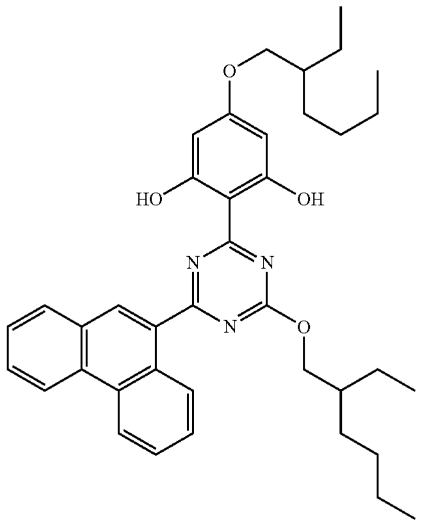

-continued
320
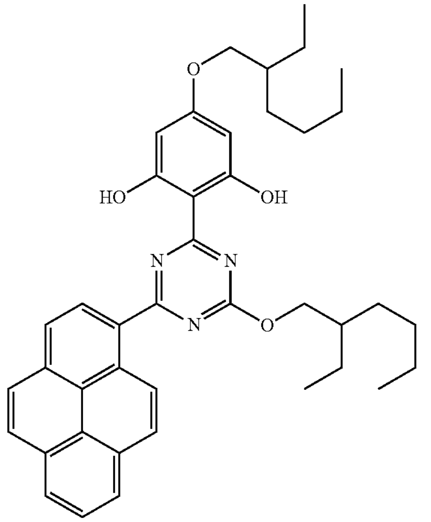
321
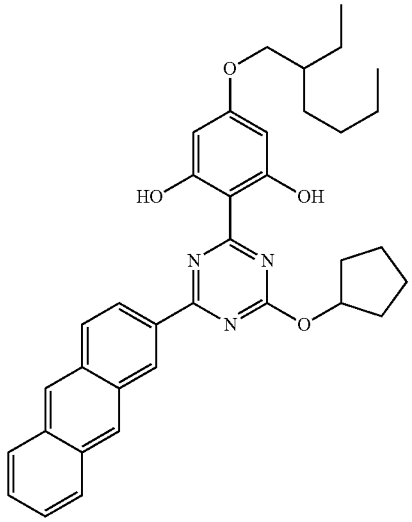
322
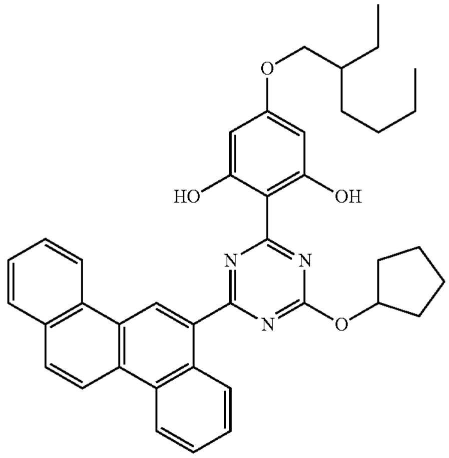
-continued
323
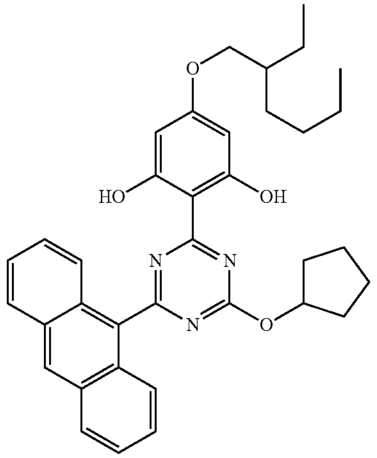
324
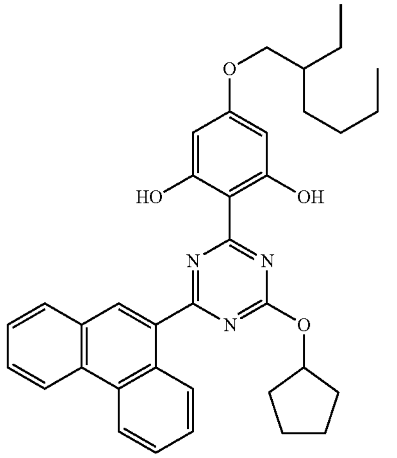
325
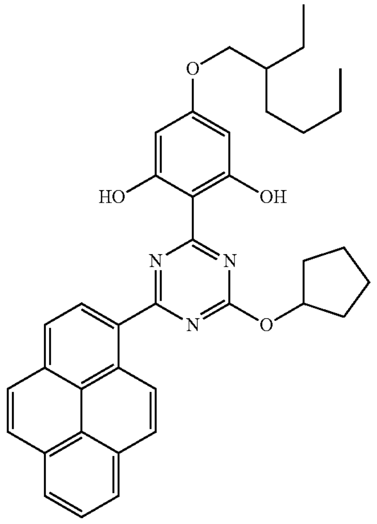

-continued
326
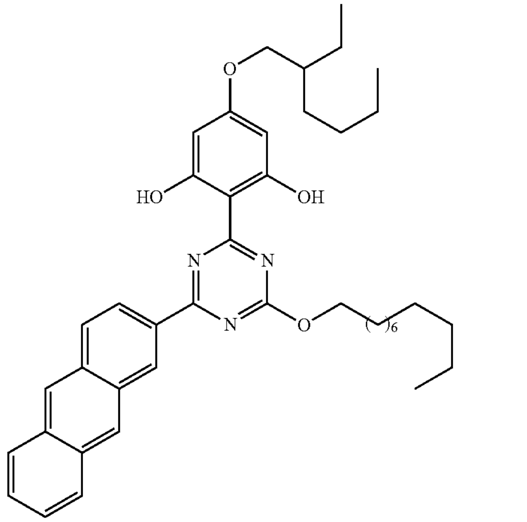
327
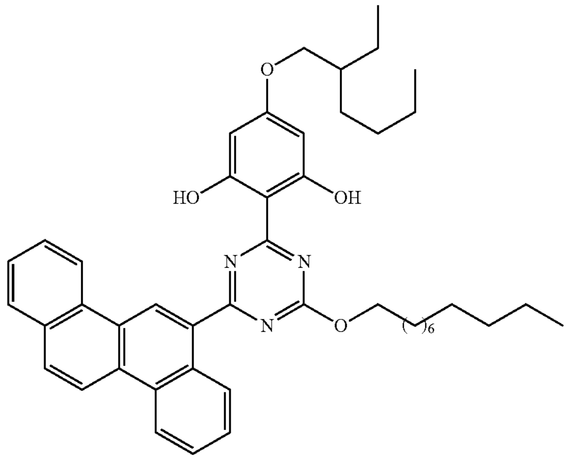
328
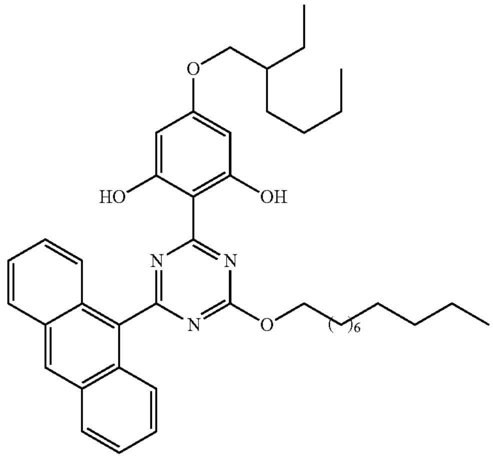
-continued
329
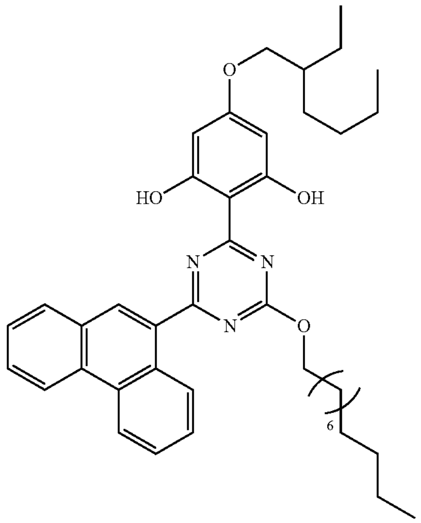
330
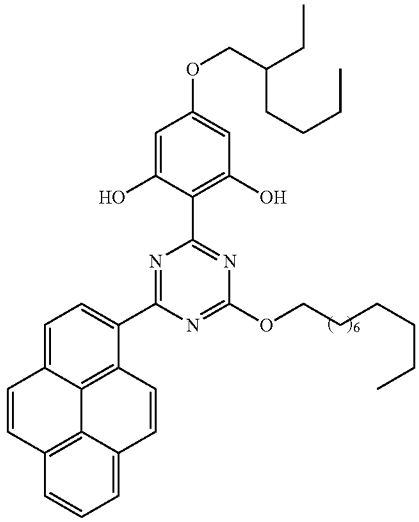
331
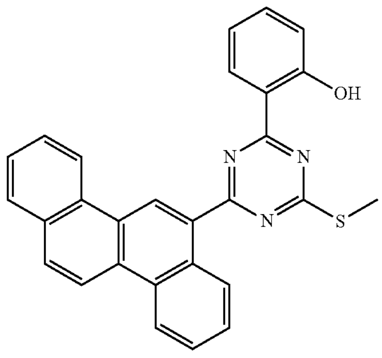

-continued
332
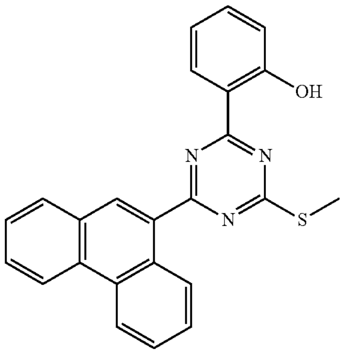
333
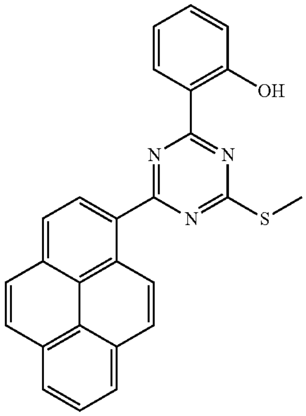
334
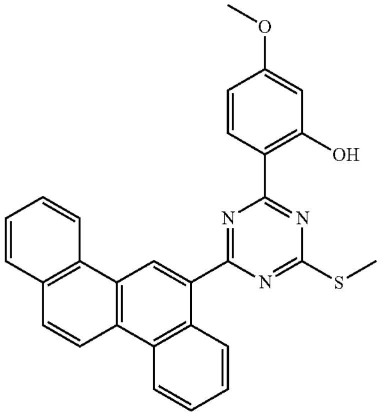
335
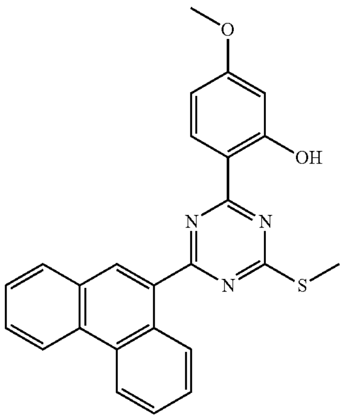
-continued
336
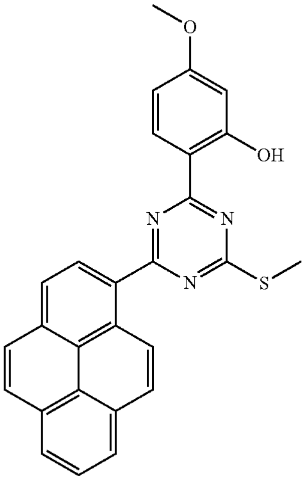
337
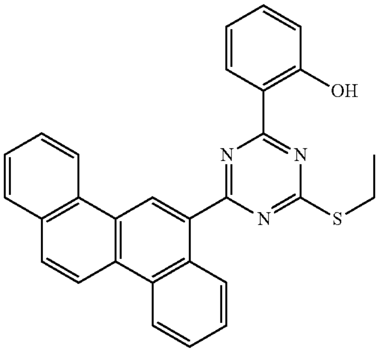
338
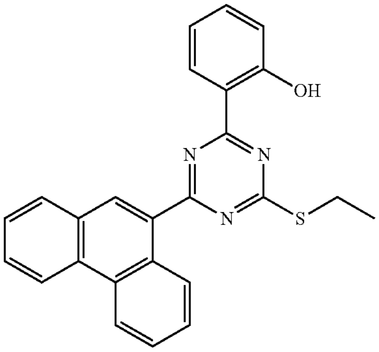
339
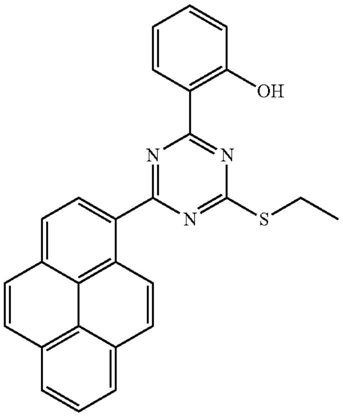

-continued
340
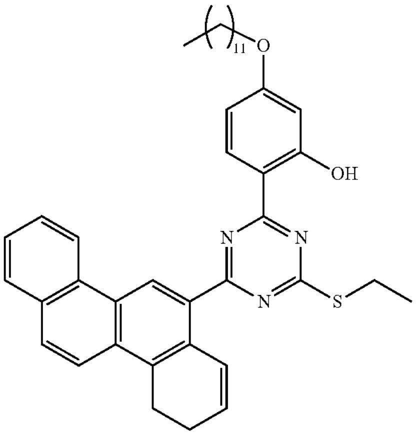
341
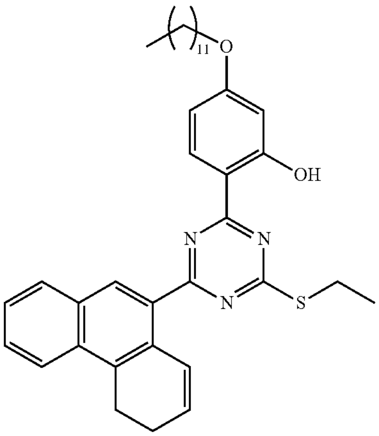
342
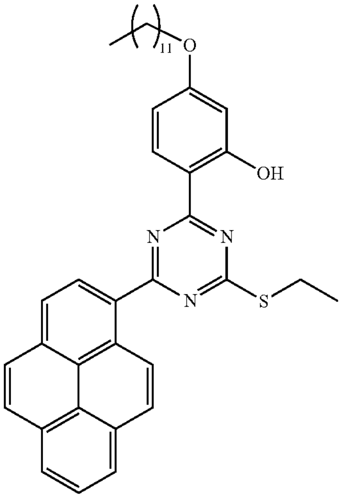
-continued
343
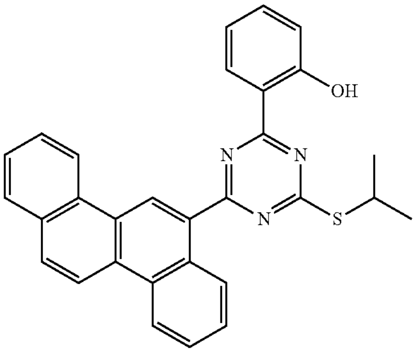
344
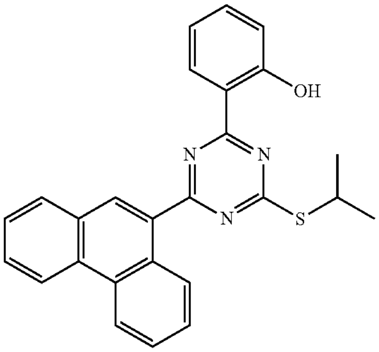
345
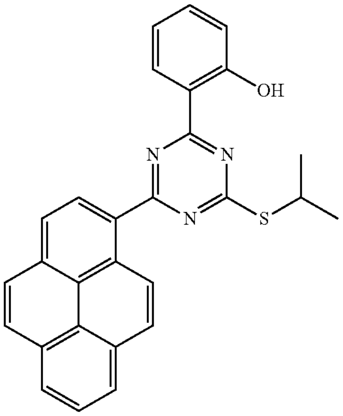
346
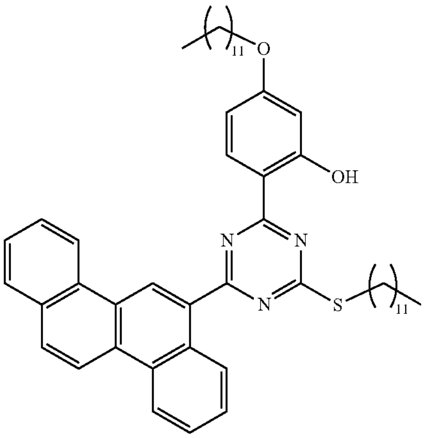

-continued
347
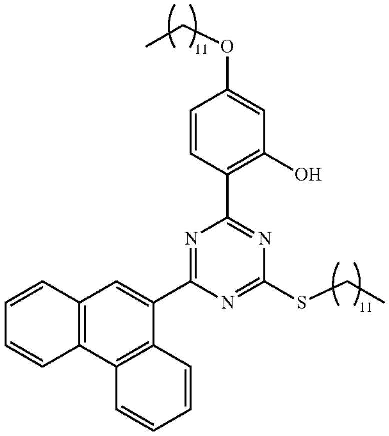
348
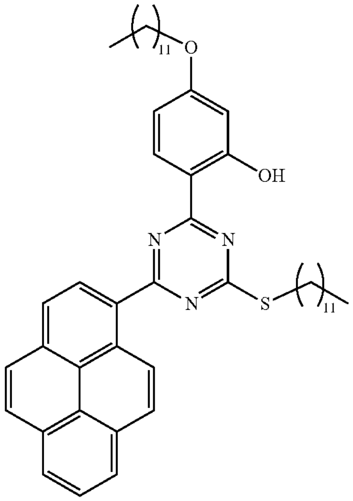
349
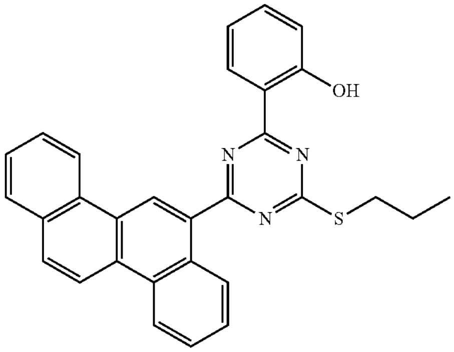
350
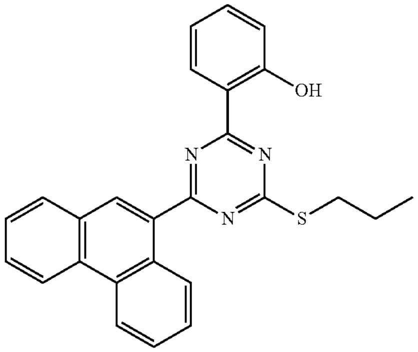
-continued
351
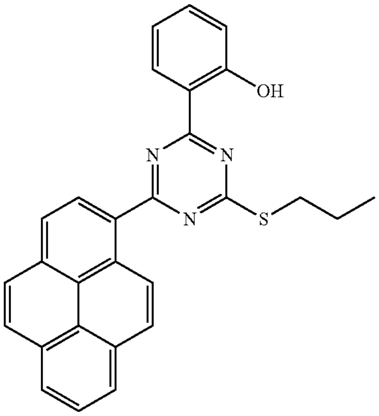
352
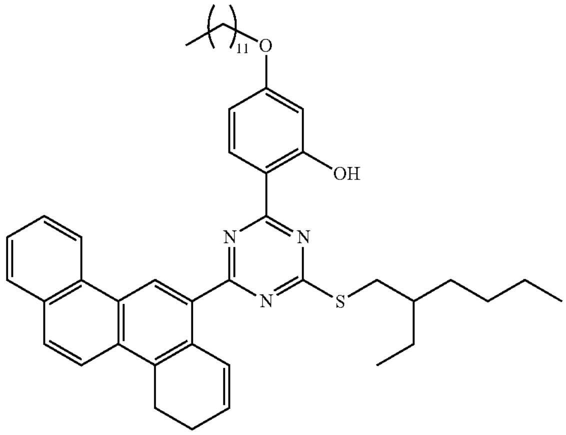
353
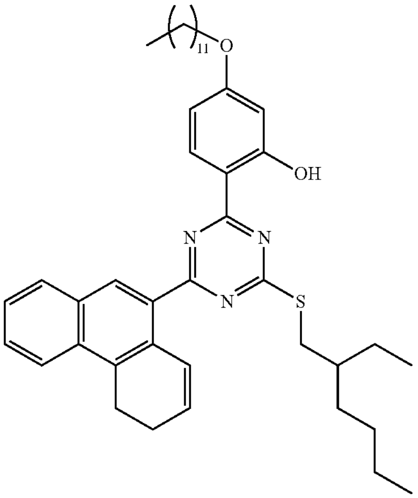

-continued
354
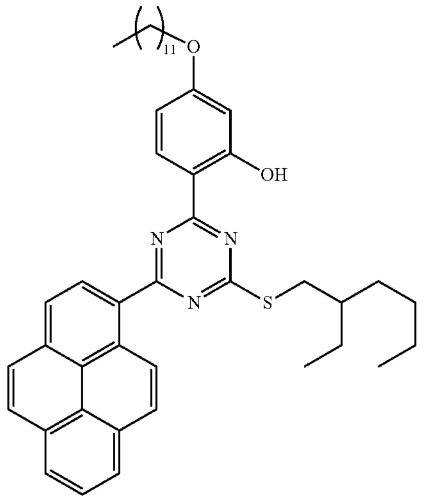
355
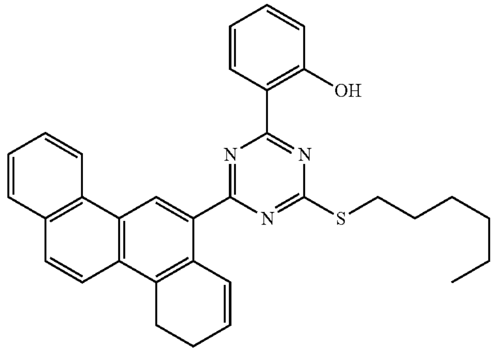
356
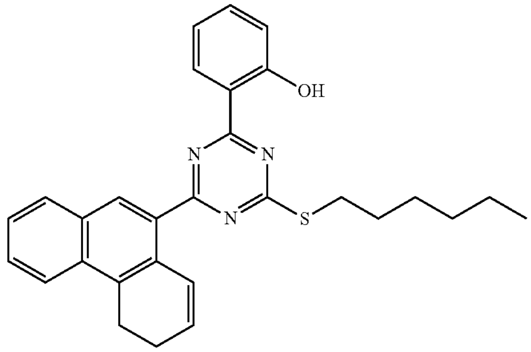
-continued
357
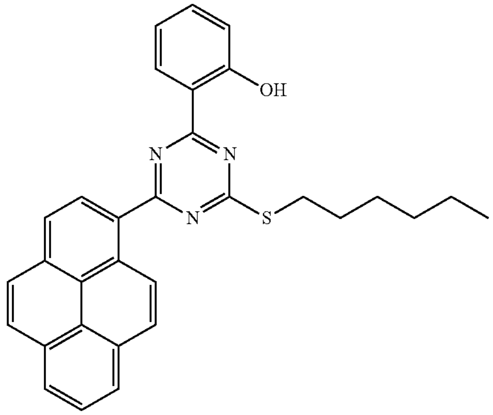
358
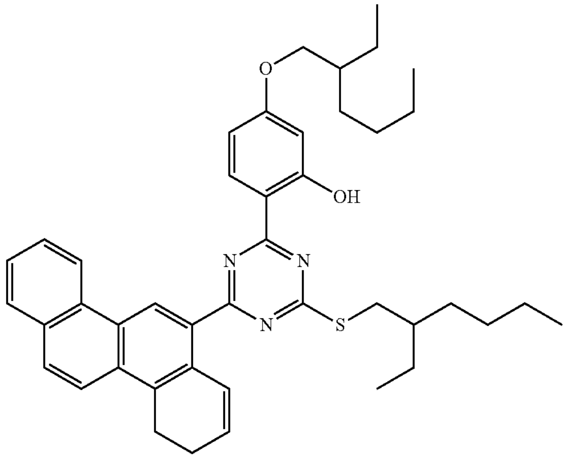
359
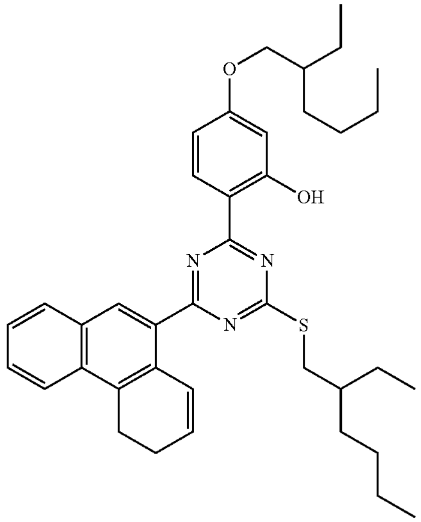

360
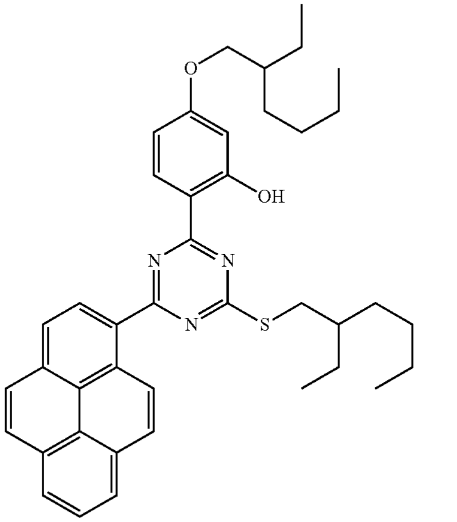
361
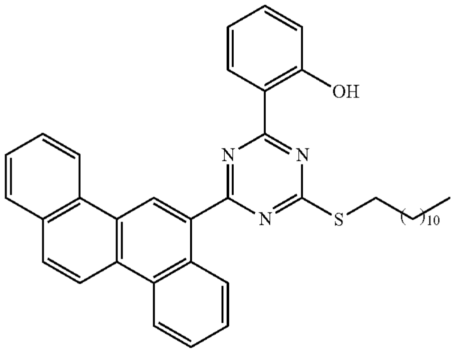
362
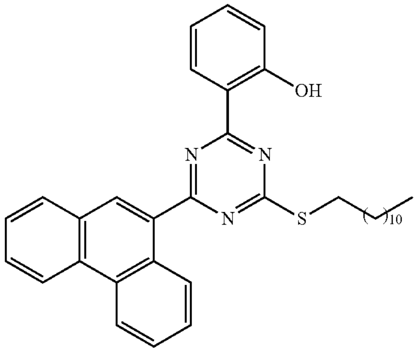
363
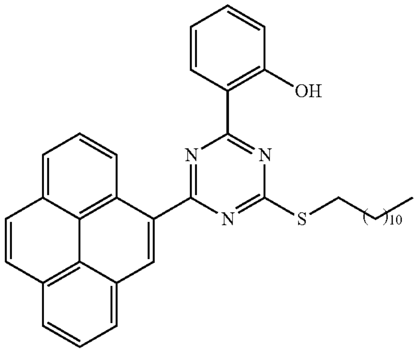
364
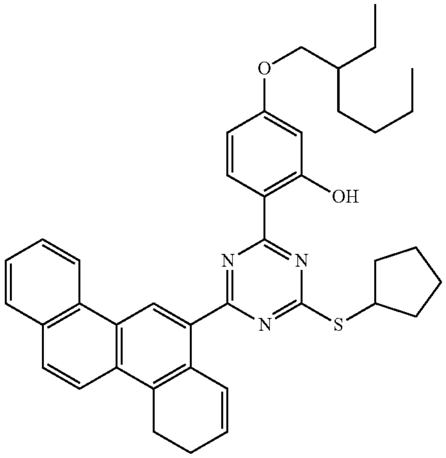
365
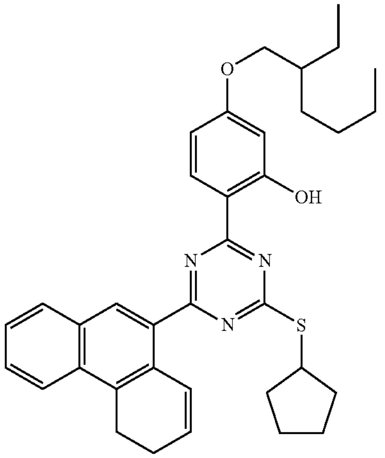
366
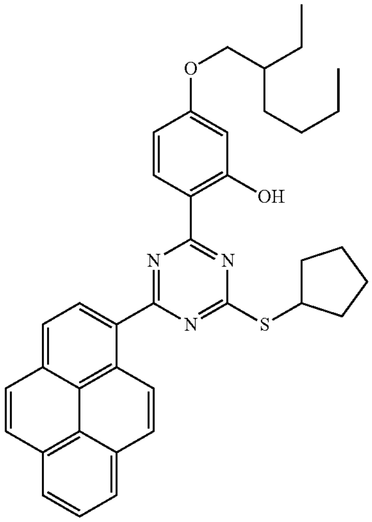

-continued

367

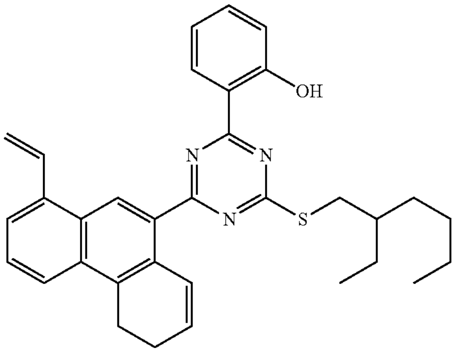

368

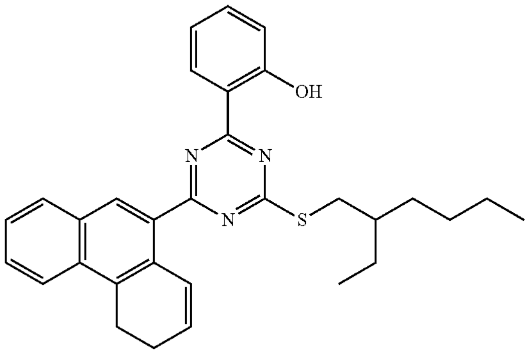

369

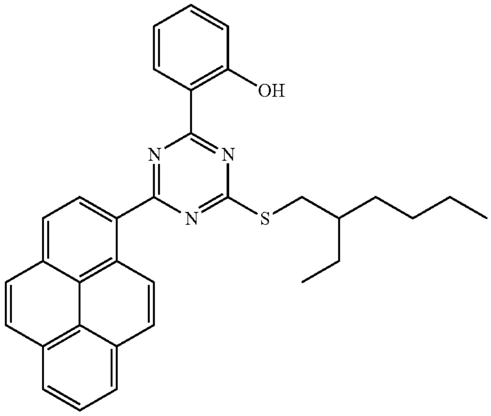

370

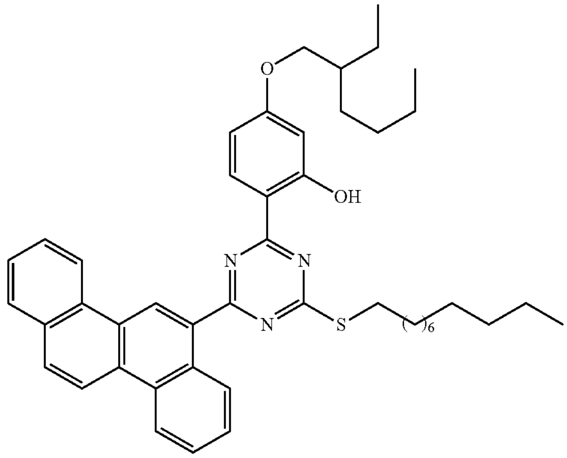

-continued

371

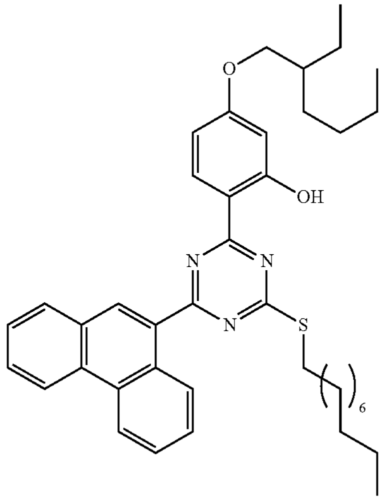

372

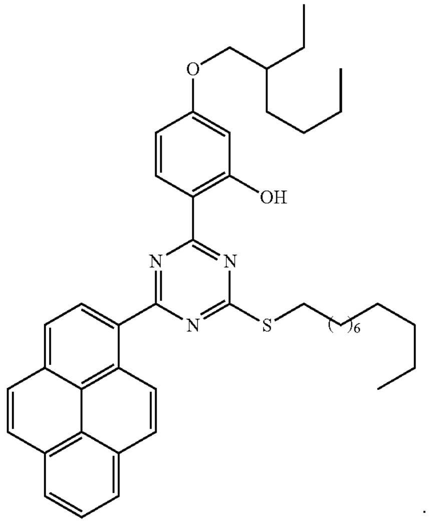

.

The display apparatuses DS and DS-a of an embodiment may include, as a light absorber, at least one among the compounds of Compound Group 1 or Compound Group 2 as described above. In an embodiment, the encapsulation member TFE may include, as a light absorber, at least one among the compounds of Compound Group 1 or Compound Group 2.

The light absorber of an embodiment as described above may be included in the display apparatus to absorb a portion of incident light into the display apparatus. For example, the light absorber of an embodiment may absorb light in an ultraviolet wavelength region. The light absorber of an embodiment may absorb a portion of external light of the display apparatus.

The light absorber of an embodiment may primarily absorb light in a wavelength region of 405 nm. The light absorber of an embodiment may primarily absorb light in a wavelength region of 380 nm to 410 nm.

In FIGS. 1 to 5, the display apparatuses DS and DS-a of an embodiment may include the light absorber of an embodiment as described above. The display panel DP of the display apparatuses DS and DS-a of an embodiment may include the encapsulation member TFE, and the encapsulation member TFE may include the light absorber of an embodiment as described above. The display apparatuses DS and DS-a of an embodiment may include the light absorber of an embodiment as described above in the encapsulation member TFE to prevent the external light from entering the light-emitting device OEL.

In addition, the display apparatuses DS-1, DS-1*a*, and DS-2 according to an embodiment illustrated in FIGS. 7 to 9 as described below may include the light absorber of an embodiment as described above. The display panels DP-1 and DP-2 of the display apparatuses DS-1, DS-1*a*, and DS-2 of an embodiment may include the encapsulation member TFE, and the encapsulation member TFE may include the light absorber of an embodiment as described above. The display apparatuses DS-1, DS-1*a*, and DS-2 of an embodiment may include the light absorber of an embodiment as described above in the encapsulation member TFE to prevent the external light from entering the light-emitting device OEL-1 and OEL-2.

Referring to FIG. 2A, a display apparatus DS of an embodiment may include a display panel DP, an input sensing unit TP disposed on the display panel DP, and a polarizing member PP disposed on the display panel DP. The polarizing member PP may be disposed on the input sensing unit TP.

In the display apparatus DS of an embodiment, the display panel DP may be an organic electroluminescence display panel. The display panel DP may include a base layer BL, a circuit layer CL disposed on the base layer BL, and a display device layer DD.

The base layer BL may be a member providing a base surface on which the display device layer DD is disposed. The base layer BL may be a glass substrate, a metal substrate, a plastic substrate, etc. However, the embodiment is not limited thereto, and the base layer BL may be an inorganic layer, an organic layer, or a composite material layer.

In an embodiment, the circuit layer CL is disposed on the base layer BL, and the circuit layer CL may include a plurality of transistors (not shown). Each of the transistors (not shown) may include a control electrode, an input electrode, and an output electrode. For example, the circuit layer CL may include a switching transistor and a driving transistor for driving the light-emitting device OEL.

The polarizing member PP may block the external light provided from the outside to the display panel DP. The polarizing member PP may block a portion of the external light, and the polarizing member PP may block, for example, light having a wavelength of 380 nm or less.

Alternatively, the polarizing member PP may reduce reflected light which is generated in the display panel DP by the external light. For example, the polarizing member PP may prevent reflected light in the case where the light provided from the outside of the display apparatus DS enters the display panel DP and emits back. The polarizing member PP may be a circular polarizer having an anti-reflective function, or the polarizing member PP may include a linear polarizer and a $\lambda/4$ phase retarder.

The input sensing unit TP may perceive a direct touch by a user, an indirect touch by a user, a direct touch by an object, or an indirect touch by an object. Meanwhile, the input sensing unit TP may detect at least one among the position and force (pressure) of the externally applied touch. The input sensing unit TP of an embodiment of the present invention may have various configurations or be configured using various materials, and is not limited to any one embodiment. For example, in the display apparatus DS of an embodiment, the input sensing unit TP may be a touch sensing unit configured to sense a touch.

In addition, the display apparatus DS of an embodiment may further include a window member WP. The window member WP may define the front surface of the display apparatus DS. The window member WP may stably protect internal components of the display apparatus DS from the external impacts. The window member WP may include a glass substrate or a plastic substrate.

Meanwhile, a cross-sectional view shown in FIG. 2A illustrates that the display apparatus DS includes all of the input sensing unit TP, the polarizing member PP, and the window member WP, but the embodiment is not limited thereto. In the display apparatus DS of an embodiment, at least one among the input sensing unit TP, the polarizing member PP, and the window member WP may be omitted. For example, in the display apparatus DS of an embodiment, the input sensing unit TP or the window member WP may be omitted. In addition, unlike this, in the display apparatus DS of an embodiment, the polarizing member PP or the window member WP may be omitted.

The display apparatus DS of an embodiment shown in FIG. 2A may further include an adhesive member (not shown) for coupling each of members. The adhesive member (not shown) may be an optical clear adhesive layer OCA or OCR. The adhesive member (not shown) may be disposed between the input sensing unit TP and the polarizing member PP, or between the polarizing member PP and the window member WP.

At least one member provided on the display panel DP in the display apparatus DS of an embodiment shown in FIG. 2A may include a light shielding material. For example, at least one among the input sensing unit TP, the polarizing member PP, the window member WP, and the adhesive member (not shown) may include an ultraviolet light absorber as the light blocking material. Meanwhile, at least one among the input sensing unit TP, the polarizing member PP, the window member WP, and the adhesive member (not shown) may include the light absorber of an embodiment as described above or the known ultraviolet light absorber as the light blocking material.

FIG. 2B illustrates a cross-sectional view of a display apparatus DS-a of an embodiment, and the display apparatus DS-a may include a display panel DP and a light blocking layer LBL provided on the display panel DP. The light blocking layer LBL may block light provided from the outside of the display panel DP, for example ultraviolet light. The light blocking layer LBL may be provided in a film shape. The light blocking layer LBL may be provided on the display panel DP in a film shape including a polymer. In the display apparatus DS-a of an embodiment, the display panel DP may be an organic electroluminescence display panel. In the display apparatus DS-a, the display panel DP may include a base layer BL, a circuit layer CL and a display device layer DD. FIG. 3 illustrates a cross-sectional view of a display panel DP of an embodiment, and the display panel DP may include a base layer BL, a circuit layer CL, and a display device layer DD which are sequentially stacked in a direction of a third directional axis DR3. The display device layer DD may include a light-emitting device OEL and an encapsulation member TFE. In an embodiment, the light-emitting device OEL may an organic electroluminescence device.

The encapsulation member TFE may be disposed on the light-emitting device OEL. The encapsulation member TFE may cover the light-emitting device OEL. The light-emitting device OEL may be sealed by the encapsulation member TFE.

FIG. 4 is an enlarged plan view of a portion of a display panel DP included in a display apparatus DS according to an embodiment. FIG. 5 is a cross-sectional view of a display panel DP according to an embodiment, and FIG. 5 is a cross-sectional view illustrating a part taken along line II-II' of FIG. 4.

Referring to FIGS. 4 and 5, the display panel DP may include non-light emitting regions NPXA and light emitting regions PXA-R, PXA-G, and PXA-B. The light emitting regions PXA-R, PXA-G, and PXA-B each may be a region in which light generated in the light-emitting device OEL is emitted. Each area of the light emitting regions PXA-R, PXA-G, and PXA-B may be different from each other, where the area means area when viewed on a plane.

The light emitting regions PXA-R, PXA-G, and PXA-B may be divided into a plurality of groups according to colors of light generated in the light-emitting device OEL. In the display panel DP of an embodiment shown in FIGS. 4 and 5, three light emitting regions PXA-R, PXA-G, and PXA-B which emit red light, green light, and blue light are illustrated as an example.

The light emitting regions PXA-R, PXA-G, and PXA-B may have different area according to colors of light emitted in an emission layer EML of the light-emitting device OEL. For example, referring to FIG. 4, in the display panel DP of an embodiment, the blue light emitting region PXA-B of the light-emitting device which emits blue light may have the largest area, and the green light emitting region PXA-G of the light-emitting device which generates green light may have the smallest area. However, the embodiment is not limited thereto, and the light emitting regions PXA-R, PXA-G, and PXA-B may emit different color light other than the blue light, green light, and red light, the light emitting regions PXA-R, PXA-G, and PXA-B may have the same area as each other, or the light emitting regions PXA-R, PXA-G, and PXA-B may be provided in a different area ratio from those illustrated in FIG. 4.

Each of the light emitting regions PXA-R, PXA-G, and PXA-B may be a region divided by a pixel defining layer PDL. The non-light emitting regions NPXA may be regions between the adjacent light emitting regions PXA-R, PXA-G, and PXA-B, which correspond to the pixel defining layer PDL. Meanwhile, in the description, each of the light emitting regions PXA-R, PXA-G, and PXA-B may correspond to a pixel.

The pixel defining layer PDL may be formed of a polymer resin. For example, the pixel defining layer PDL may include a polyacrylate-based resin or a polyimide-based resin. In addition, the pixel defining layer PDL may further include an inorganic material, in addition to the polymer resin. Meanwhile, the pixel defining layer PDL may include a light absorbing material or a black pigment or a black dye. The pixel defining layer PDL including the black pigment or the black dye may implement a black pixel defining layer. In forming the pixel defining layer PDL, carbon black, etc. may be used as the black pigment or the black dye, but the embodiment is not limited thereto.

Also, the pixel defining layer PDL may be formed of an inorganic material. For example, the pixel defining layer PDL may include silicon nitride (SiNx), silicon oxide (SiOx), silicon oxynitride (SiOxNy), etc. The pixel defining layer PDL may define the light emitting regions PXA-R, PXA-G, and PXA-B. The light emitting regions PXA-R, PXA-G, and PXA-B and the non-light emitting regions NPXA may be divided by the pixel defining layer PDL.

The blue light emitting regions PXA-B and the red light emitting regions PXA-R may be alternately arranged along the first directional axis DR1 to constitute a first group PXG1. The green light emitting regions PXA-G may be arranged along the first directional axis DR1 to constitute a second group PXG2.

The first group PXG1 may be disposed to be spaced apart from the second group PXG2 in the second direction DR2. Each of the first group PXG1 and the second group PXG2 may be provided in plurality. The first groups PXG1 and the second groups PXG2 may be alternately arranged with respect to each other along the second directional axis DR2.

One green light emitting region PXA-G may be disposed to be spaced apart from one blue light emitting region PXA-B or one red light emitting region PXA-R in a direction of a fourth directional axis DR4. The direction of the fourth directional axis DR4 may be a direction between the direction of the first directional axis DR1 and the direction of the second directional axis DR2.

The arrangement structure of the light emitting regions PXA-R, PXA-G, and PXA-B shown in FIG. 4 may be referred to as a PenTile®/PENTILE® structure. However, the arrangement structure of the light emitting regions PXA-R, PXA-G, and PXA-B in the display panel DP according to an embodiment is not limited to the arrangement structure shown in FIG. 4. For example, in an embodiment, the light emitting regions PXA-R, PXA-G, and PXA-B may have a stripe structure, in which a red light emitting region PXA-R, a green light emitting region PXA-G, and a blue light emitting region PXA-B are sequentially and alternately arranged along the first directional axis DR1.

In an embodiment, the light-emitting device OEL may include a first electrode EL1 and a second electrode EL2 which face each other, and a plurality of organic layers OL disposed between the first electrode EL1 and the second electrode EL2. The organic layers OL may include a hole transport region HTR, an emission layer EML, and an electron transport region ETR.

The light-emitting device OEL may include the first electrode EL1, the hole transport region HTR disposed on the first electrode EL1, the emission layer EML disposed on the hole transport region HTR, and the electron transport region ETR disposed on the emission layer EML, and the second electrode EL2 disposed on the electron transport region ETR.

The encapsulation member TFE may be disposed on the light-emitting device OEL, and the encapsulation member TFE may disposed on the second electrode EL2. The encapsulation member TFE may be directly disposed on the second electrode EL2. The encapsulation member TFE may be formed by stacking one layer or a plurality of layers. The encapsulation member TFE may be a thin film encapsulation layer. The encapsulation member TFE may protect the light-emitting device OEL. The encapsulation member TFE may cover an upper surface of the second electrode EL2 disposed in an opening OH, and may fill the opening OH. The encapsulation member TFE may include the light absorber of an embodiment as described above to absorb a portion of light provided in the light-emitting device OEL.

That is, referring to FIGS. 1 to 5, the display apparatuses DS and DS-a of an embodiment may include the encapsulation member TFE including the light absorber of an embodiment. In addition, the display apparatuses DS and DS-a of an embodiment may further include functional layers which absorb or block the external light, in addition to the encapsulation member TFE.

For example, in the display apparatus DS of an embodiment shown in FIG. 2A, at least one among the input sensing unit TP, the polarizing member PP, the window member WP, and the adhesive member (not shown) may serve as a functional layer configured to block a portion of the external light. Meanwhile, in the display apparatus DS-1 of an embodiment shown in FIG. 2B, the light blocking layer LBL disposed on the display panel DP may be a functional layer which blocks a portion of the external light.

FIG. 6 is a cross-sectional view representing an embodiment of the light-emitting device OEL included in the display panel DP of an embodiment. The light-emitting device OEL may include a first electrode EL1, a hole transport region HTR disposed on the first electrode EL1, an emission layer EML disposed on the hole transport region HTR, and an electron transport region ETR disposed on the emission layer EML, and a second electrode EL2 disposed on the electron transport region ETR, wherein the hole transport region HTR may include a hole injection layer HIL and a hole transport layer HTL, and the electron transport region ETR may include an electron injection layer EIL and an electron transport layer ETL.

In FIGS. 5 and 6, the first electrode constituting the light-emitting device OEL has conductivity. The first electrode EL1 may be formed of a metal alloy or a conductive compound. The first electrode EL1 may be an anode. The first electrode EL1 may be a pixel electrode.

In the display panel DP according to an embodiment, the first electrode EL1 may be a reflective electrode. However, the embodiment is not limited thereto. For example, the first electrode EL1 may be a transmissive electrode or a transflective electrode. When the first electrode EL1 is the transflective electrode or the reflective electrode, the first electrode EL1 may include Ag, Mg Cu, Al, Pt, Pd, Au, Ni, Nd, Ir, Cr, Li, Ca, LiF/Ca, LiF/Al, Mo, Ti, a compound thereof or a mixture thereof (e.g., a mixture of Ag and Mg). Alternatively, the first electrode EL1 may have a multilayer structure including a reflective layer or a transflective layer formed of the above-illustrated materials, and a transparent conductive layer formed of indium tin oxide (ITO), indium zinc oxide (IZO), zinc oxide (ZnO), indium tin zinc oxide (ITZO), etc. For example, the first electrode EL1 may be a multilayer metal film and have a structure in which a metal film of ITO/Ag/ITO is stacked.

The hole transport region HTR may have a single layer formed of a single material, a single layer formed of a plurality of different materials, or a multilayer structure including a plurality of layers formed of a plurality of different materials. For example, the hole transport region HTR may have a single layer structure formed of a plurality of different materials, or a structure of a hole injection layer HIL/hole transport layer HTL, a hole injection layer HIL/hole transport layer HTL/buffer layer (not shown), a hole injection layer HIL/buffer layer (not shown), a hole transport layer HTL/buffer layer (not shown), or a hole injection layer HIL/hole transport layer HTL/electron blocking layer (not shown), which are sequentially stacked from the first electrode EL1, but the embodiment is not limited thereto.

For example, the hole transport region HTR may include the hole injection layer HIL and the hole transport layer HTL, and a known hole injection material and a known hole transport material may be used in the hole injection layer HIL and the hole transport layer HTL, respectively.

Meanwhile, the hole transport region HTR may be disposed on the first electrode EL1 in the opening OH defined in the pixel defining layer PDL, and may be disposed extending to an upper portion of the pixel defining layer PDL. However, the embodiment is not limited thereto, and the hole transport region HTR may be patterned to be disposed inside the opening OH.

The emission layer EML is provided on the hole transport region HTR. The emission layer EML may have a single layer formed of a single material, a single layer formed of a plurality of different materials, or a multilayer structure having a plurality of layers formed of a plurality of different materials.

The emission layer EML is not specifically limited to a material if the material for forming the emission layer EML is usually used, but for example, the emission layer EML may be formed of materials that emit red, green, and blue colors, and may include a fluorescent material or a phosphorescent material. Also, the emission layer EML may include a host or dopant. For example, the emission layer EML may be disposed in the opening OH defined in the pixel defining layer PDL, but the embodiment is not limited thereto.

When the display panel DP is the organic electroluminescence display panel, the emission layer EML, for example, may include, as a host material, at least one of bis[2-(diphenylphosphino)phenyl]ether oxide (DPEPO), 4,4'-bis(carbazol-9-yl)biphenyl (CBP), 1,3-Bis(carbazol-9-yl)benzene (mCP), 2,8-bis(diphenylphosphoryl)dibenzo[b,d]furan (PPF), 4,4',4"-tris(carbazol-9-yl)-triphenylamine (TcTa), or 1,3,5-tris(N-phenylbenzimidazole-2-yl)benzene (TPBi). However, the embodiment is not limited thereto and, for example, tris(8-hydroxyquinolino)aluminum ($Alq_3$), 4,4'-bis(N-carbazolyl)-1,1'-biphenyl (CBP), poly(n-vinylcabazole (PVK), 9,10-di(naphthalene-2-yl)anthracene (ADN), 4,4',4"-Tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenylcyclotriphosphazene (CP1), 1,4-bis(triphenylsilyl)benzene (UGH2), hexaphenylcyclotrisiloxane (DPSiO3), octaphenylcyclotetra siloxane (DPSiO4), 2,8-bis(diphenylphosphoryl)dibenzofuran (PPF), etc. may be used as a host material.

In addition, the emission layer EML may include, as a dopant material, styryl derivatives (e.g., 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenz enamine (N-BDAVBi)), perylene and the derivatives thereof (e.g., 2,5,8,11-tetra-t-butylperylene (TBP)), pyrene and the derivatives thereof (e.g., 1-dipyrene, 1,4-dipyrenylbenzene, 1,4-bis(N,N-diphenylamino)pyrene), etc.

When the display panel DP according to an embodiment is a quantum dot light emitting display panel, the display panel DP may include a quantum dot material in the emission layer EML. The core of the quantum dot may be selected from among a Group II-VI compound, a Group III-V compound, a Group IV-VI compound, a Group IV element, a Group IV compound, and a combination thereof.

The Group II-VI compound may be selected from the group consisting of a binary compound selected from the group consisting of CdSe, CdTe, ZnS, ZnSe, ZnTe, ZnO, HgS, HgSe, HgTe, MgSe, MgS, and a mixture thereof; a ternary compound selected from the group consisting of AgInS, CuInS, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof; and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof; a ternary compound selected from the group consisting of GaNP, GaNAs, GaNSb, GaPAs, GaPSb, AlNP, AlNAs, AlNSb, AlPAs, AlPSb, InGaP, InNP, InNAs, InNSb, InPAs, InPSb, GaAlNP, and a mixture thereof; and a quaternary compound selected from the group consisting of GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof.

The Group IV-VI compound may be selected from the group consisting of a binary compound selected from the group consisting of SnS, SnSe, SnTe, PbS, PbSe, PbTe, and a mixture thereof; a ternary compound selected from the group consisting of SnSeS, SnSeTe, SnSTe, PbSeS, PbSeTe, PbSTe, SnPbS, SnPbSe, SnPbTe, and a mixture thereof; and a quaternary compound selected from the group consisting of SnPbSSe, SnPbSeTe, SnPbSTe, and a mixture thereof. The Group IV element may be selected from the group consisting of Si, Ge, and a mixture thereof. The Group IV compound may be a binary compound selected from the group consisting of SiC, SiGe, and a mixture thereof.

In this case, a binary compound, a ternary compound, or a quaternary compound may be present in a particle with a uniform concentration distribution, or may be present in the same particle with a partially different concentration. In addition, the quantum dot may have a core/shell structure in which one quantum dot surrounds another quantum dot. An interface between the core and the shell may have a concentration gradient in which the concentration of an element present in the shell becomes lower toward the center.

In some embodiments, a quantum dot may have the above-described core-shell structure including a core having nano-crystals and a shell surrounding the core. The shell of the quantum dot may serve as a protective layer to prevent the chemical deformation of the core so as to maintain semiconductor properties, and/or a charging layer to impart electrophoresis properties to the quantum dot. The shell may be a single layer or multiple layers. An interface between a core and a shell may have a concentration gradient in which the concentration of an element present in the shell becomes lower toward the center. An example of the quantum dot shell may be a metal or non-metal oxide, a semiconductor compound, or a combination thereof.

For example, the metal or non-metal oxide may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and NiO, or a ternary compound such as $MgAl_2O_4$, $CoFe_2O_4$, $NiFe_2O_4$, and $CoMn_2O_4$, but the present invention is not limited thereto.

Also, the semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but the present invention is not limited thereto.

The quantum dot may have a full width of half maximum (FWHM) of a light emission wavelength spectrum of about 45 nm or less, preferably about 40 nm or less, more preferably about 30 nm or less, and color purity or color reproducibility may be improved in the above range. In addition, light emitted through such a quantum dot is emitted in all directions, and thus a wide viewing angle may be improved.

In addition, although the form of a quantum dot is not particularly limited as long as it is a form commonly used in the art, more specifically, a quantum dot in the form of spherical, pyramidal, multi-arm, or cubic nanoparticles, nanotubes, nanowires, nanofibers, nanoparticles, etc. may be used.

The quantum dot may control the color of emitted light according to the particle size thereof. Accordingly, the quantum dot may have various light emission colors such as blue, red, and green.

The electron transport region ETR is disposed on the emission layer EML. The electron transport region ETR may include at least one of a hole blocking layer (not shown), the electron transport layer ETL, or the electron injection layer EIL, but is not limited thereto.

When the electron transport region ETR includes the electron injection layer EIL and the electron transport layer ETL, a known electron injection material and a known electron transport material may be used in the electron injection layer EIL and the electron transport layer ETL, respectively.

The second electrode EL2 is provided on the electron transport region ETR. The second electrode EL2 may be a common electrode or a cathode. The second electrode EL2 may be formed of a metal alloy or a conductive compound. The second electrode EL2 may be a transmissive electrode, a transflective electrode, or a reflective electrode. When the second electrode EL2 is the transmissive electrode, the second electrode EL2 may be formed of a transparent metal oxide, for example, indium tin oxide (ITO), indium zinc oxide (IZO), zinc oxide (ZnO), indium tin zinc oxide (ITZO), etc.

When the second electrode EL2 is the transflective electrode or the reflective electrode, the second electrode EL2 may include Ag, Mg Cu, Al, Pt, Pd, Au, Ni, Nd, Ir, Cr, Li, Ca, LiF/Ca, LiF/Al, Mo, Ti, a compound thereof or a mixture thereof (e.g., a mixture of Ag and Mg). Alternatively, the second electrode EL2 may have a multilayer structure including a reflective layer or a transflective layer formed of the above-illustrated materials, and a transparent conductive layer formed of indium tin oxide (ITO), indium zinc oxide (IZO), zinc oxide (ZnO), indium tin zinc oxide (ITZO), etc.

Referring to FIG. 5, the electron transport region ETR and the second electrode EL2 may be disposed in a region overlapping the first electrode EL1 as well as may be disposed further extending in the pixel defining layer PDL. Meanwhile, although not shown, the second electrode EL2 may be connected with an auxiliary electrode. If the second electrode EL2 is connected with the auxiliary electrode, the resistance of the second electrode EL2 may decrease.

In the display panel DP of an embodiment, the first electrode EL1, among the first electrode and the second electrode which face each other, may be a reflective electrode, and the second electrode may be a transmissive electrode. In an embodiment, the light-emitting device OEL may emit light through a front surface. However, the embodiment is not limited thereto.

FIGS. 7 to 9 are cross-sectional views of display apparatuses of an embodiment. The display apparatuses DS-1 and DS-1*a* of an embodiment shown in FIGS. 7 and 8 include the display panel DP-1 including a base layer BL, a circuit layer CL disposed on the base layer BL, and a display device layer DD-1. In the display apparatuses DS-1 and DS-1*a* of an embodiment shown in FIGS. 7 and 8, the display panel DP-1 may be a quantum dot light-emitting display panel. The display panel DP-1 may include a plurality of light-emitting devices OEL-11, OEL-12, and OEL-13, and the light-emitting devices OEL-11, OEL-12, and OEL-13 may include emission layers EML-B, EML-G, and EML-R containing quantum dots QD1, QD2, and QD3.

Those descriptions provided with respect to the quantum dot used in the emission layer EML may be equally applied to the quantum dots QD1, QD2, and QD3 included in the light-emitting device OEL-1 of an embodiment.

The display apparatuses DS-1 and DS-1*a* according to an embodiment shown in FIGS. 7 and 8 may include non-light emitting regions NPXA and light emitting regions PXA-B, PXA-G, and PXA-R. The light emitting regions PXA-B, PXA-G, and PXA-R each may be a region in which light generated from light-emitting devices OEL-11, OEL-12, and OEL-13 is emitted, respectively. The light emitting regions PXA-B, PXA-G, and PXA-R may be spaced apart from each other on a plane.

The plurality of light-emitting devices OEL-11, OEL-12, and OEL-13 may emit light in different wavelength regions. A first emission layer EML-B of a first light-emitting device OEL-11 may include a first quantum dot QD1. The first quantum dot QD1 may emit blue light that is first color light. A second emission layer EML-G of a second light-emitting device OEL-12 and a third emission layer EML-R of a third light-emitting device OEL-13 may include a second quantum dot QD2 and a third quantum dot QD3, respectively. The second quantum dot QD2 and the third quantum dot QD3 may emit green light that is second color light and red light that is third color light, respectively.

In an embodiment shown in FIGS. 7 and 8, the first to third quantum dots QD1, QD2, and QD3 may have different sizes. For example, the first quantum dot QD1 used in the first light-emitting device OEL-11, which emits light in a relatively short wavelength region, may have a relatively small average diameter compared to the second quantum dot QD2 of the second light-emitting device OEL-12 and the third quantum dot QD3 of the third light-emitting device OEL-13, which emit light in a relatively long wavelength region. However, the embodiment is not limited thereto, the first to third quantum dots QD1, QD2, and QD3 may have similar diameters.

FIG. 7 illustrates an embodiment of the display apparatus DS-1 including a polarizing member PP disposed on an upper portion of the display panel DP-1, and FIG. 8 illustrates an embodiment of the display apparatus DS-1*a* including a color filter layer CFL disposed on an upper portion of the display panel DP-1. The polarizing member PP and the color filter layer CFL may block external light provided from the outside of the display apparatuses DS-1 and DS-1*a* to the display panel DP. The polarizing member PP and the color filter layer CFL may function to prevent reflection for minimizing the reflection by the external light. Those descriptions provided in FIG. 2A as described above may be equally applied to the polarizing member PP.

In the display apparatus DS-1*a* of an embodiment shown in FIG. 8, the color filter layer CFL may include a light shielding unit BM and a color filter part CF. The color filter part CF may include a plurality of filters CF-B, CF-G, and CF-R. That is, the color filter layer CFL may include a first filter CF-B configured to transmit the first color light, a second filter CF-G configured to transmit the second color light, and a third filter CF-R configured to transmit the third color light. For example, the first filter CF-B may be a blue color filter, the second filter CF-G may be a green color filter, and the third filter CF-R may be a red color filter.

The filters CF-B, CF-G, and CF-R each may include a polymeric photosensitive resin and a pigment or dye. The first filter CF-B may include a blue pigment or dye, the second filter CF-G may include a green pigment or dye, and the third filter CF-R may include a red pigment or dye.

Meanwhile, the embodiment is not limited thereto, and the first filter CF-B may not include a pigment or dye. The first filter CF-B may include a polymeric photosensitive resin and may not include a pigment or dye. The first filter CF-B may be transparent. The first filter CF-B may be formed of a transparent photosensitive resin.

The light shielding unit BM may be a black matrix. The light shielding unit BM may include an organic light shielding material or an inorganic light shielding material containing a black pigment or dye. The light shielding unit BM may prevent light leakage, and may separate boundaries between the adjacent filters CF-B, CF-G, and CF-R.

The color filter layer CFL may further include a buffer layer BFL. For example, the buffer layer BFL may be a protective layer which protects the filters CF-B, CF-G, and CF-R. The buffer layer BFL may be an inorganic material layer containing at least one inorganic material from among silicon nitride, silicon oxide, and silicon oxynitride. The buffer layer BFL may be formed of a single layer or a plurality of layers.

In an embodiment shown in FIG. 8, the first filter CF-B of the color filter layer CFL is illustrated to overlap the second filter CF-G and the third filter CF-R, but the embodiment is not limited thereto. For example, the first to third filters CF-B, CF-G, and CF-R may be divided by the light shielding unit BM and not overlap one another. Meanwhile, in an embodiment, the first to third filters CF-B, CF-G, and CF-R may be disposed corresponding to the blue light emitting region PXA-B, the green light emitting region PXA-G, and the red light emitting region PXA-R, respectively.

Meanwhile, referring to FIG. 8, the display apparatus DS-1*a* of an embodiment may include a base substrate BS disposed on an upper portion of the color filter layer CFL. The base substrate BS may be a member configured to provide a base surface in which the color filter layer CFL or the like is disposed. The base substrate BS may be a glass substrate, a metal substrate, a plastic substrate, etc. However, the embodiment is not limited thereto, and the base substrate BS may be an inorganic layer, an organic layer, or a composite material layer.

The display apparatus DS-2 of an embodiment shown in FIG. 9 includes the display panel DP-2 including a base layer BL, a circuit layer CL disposed on the base layer BL, and a light-emitting device OEL-2. In the display apparatus DS-2 of an embodiment shown in FIG. 9, the display panel DP-2 may be an organic electroluminescence display panel. For example, the light-emitting device OEL-2 included in the display panel DP-2 may be a tandem type light-emitting device as shown in FIG. 10.

The light-emitting device OEL-2 according to an embodiment may include a first electrode EL1 and a second electrode EL2 which face each other, and a plurality of light emitting units LU-1, LU-2, and LU-3 disposed between the first electrode EL1 and the second electrode EL2. The light emitting units LU-1, LU-2, and LU-3 may be stacked in the thickness direction. A charge generation layer CGL may be disposed between two of the light emitting units LU-1, LU-2, and LU-3. The light emitting units LU-1, LU-2, and LU-3 each may include a hole transport region HTR, emission layers EML-B1, EML-B2, and EML-B3, and an electron transport region ETR. The emission layers EML-B1, EML-B2, and EML-B3 included in the light emitting units LU-1, LU-2, and LU-3, respectively, may emit light in the same wavelength region. For example, in the light-emitting device OEL according to an embodiment, the emission layers EML-B1, EML-B2, and EML-B3 may all emit blue light. However, the embodiment is not limited thereto, and the emission layers EML-B1, EML-B2, and EML-B3 may emit light in different wavelength regions.

Referring to FIG. 9, the display apparatus DS-2 of an embodiment may include a color conversion layer CCL disposed on the display panel DP-2. In addition, the display apparatus DS-2 according to an embodiment may further include a color filter layer CFL. The color filter layer CFL may be disposed between the base substrate BS and the color conversion layer CCL.

The color conversion layer CCL may include a plurality of partition walls BK, which are disposed to be spaced apart from each other, and color control units CCP-B, CCP-G, and CCP-R, which are disposed between the partition walls BK. The partition walls BK may include a polymer resin and a liquid-repellent additive. The partition walls BK may include a light absorbing material or a pigment or dye PG. For example, the partition walls BK may include a black pigment or black dye to implement black partition walls. In forming the black partition walls, carbon black, etc. may be used as the black pigment or the black dye, but the embodiment is not limited thereto.

The color conversion layer CCL may include a first color control unit CCP-B configured to transmit first color light, a second color control unit CCP-G containing a quantum dot which converts the first color light into second color light, and a third color control unit CCP-R containing a quantum dot which converts the first color light into third color light. The second color light may be light in a longer wavelength region than the first color light, and the third color light may be light in a longer wavelength region than the first color light and the second color light. For example, the first color light may be blue light, the second color light may be green light, and the third color light may be red light. Those descriptions provided with respect to the quantum dot used in the emission layer EML as described above may be equally applied to the quantum dot included in the color control units CCP-B, CCP-G, and CCP-R.

The color conversion layer CCL may further include a capping layer CPL. The capping layer CPL may be disposed on the color control units CCP-B, CCP-G, and CCP-R and the partition walls BK. The capping layer CPL may serve to prevent the penetration of moisture and/or oxygen (hereinafter, referred to as 'moisture/oxygen'). The capping layer CPL may be disposed on the color control units CCP-B, CCP-G, and CCP-R to block the color control units CCP-B, CCP-G, and CCP-R from being exposed to moisture/oxygen. The capping layer CPL may include at least one inorganic layer.

Figure 11:
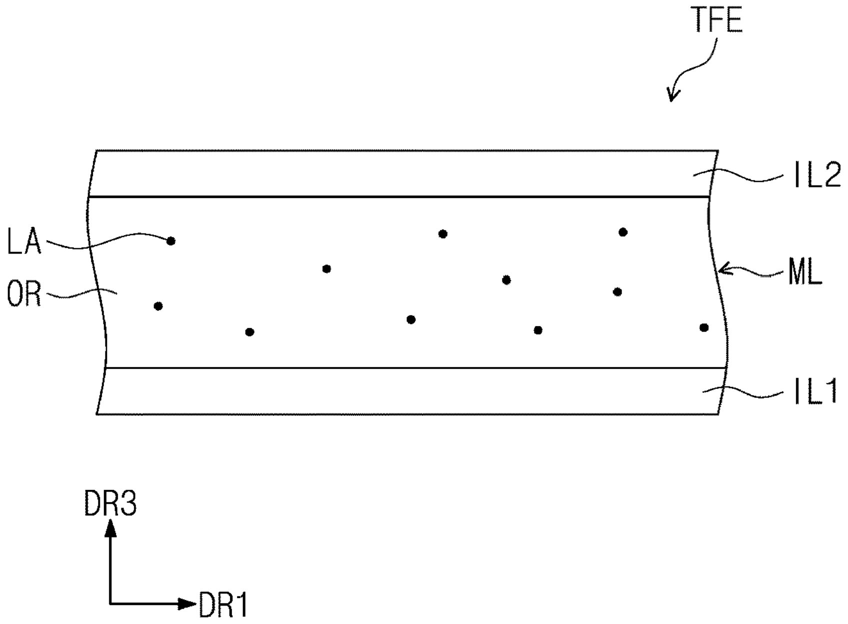
FIG. 11 is a cross-sectional view of an encapsulation member according to an embodiment.
Figure 12:
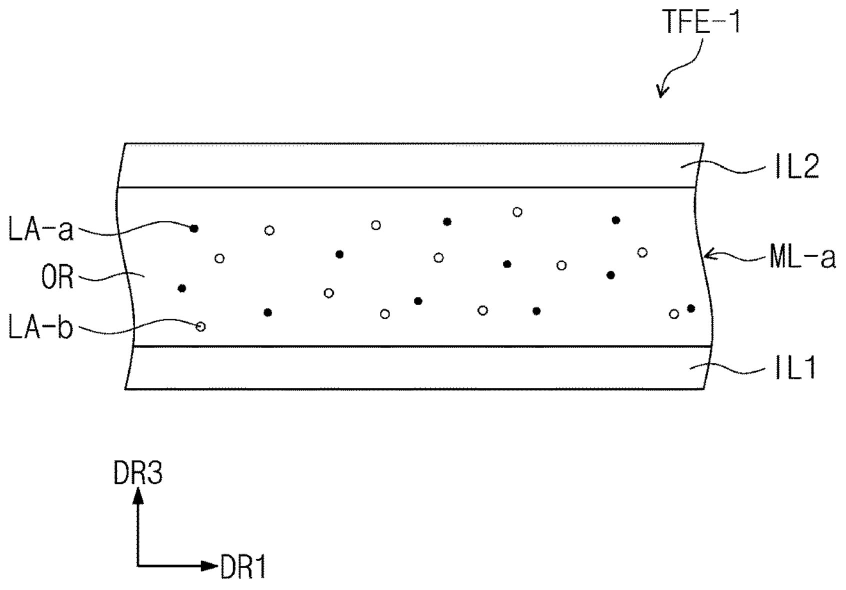
FIGS. 12 and 13 each are a cross-sectional view of an encapsulation member according to an embodiment.
Figure 13:
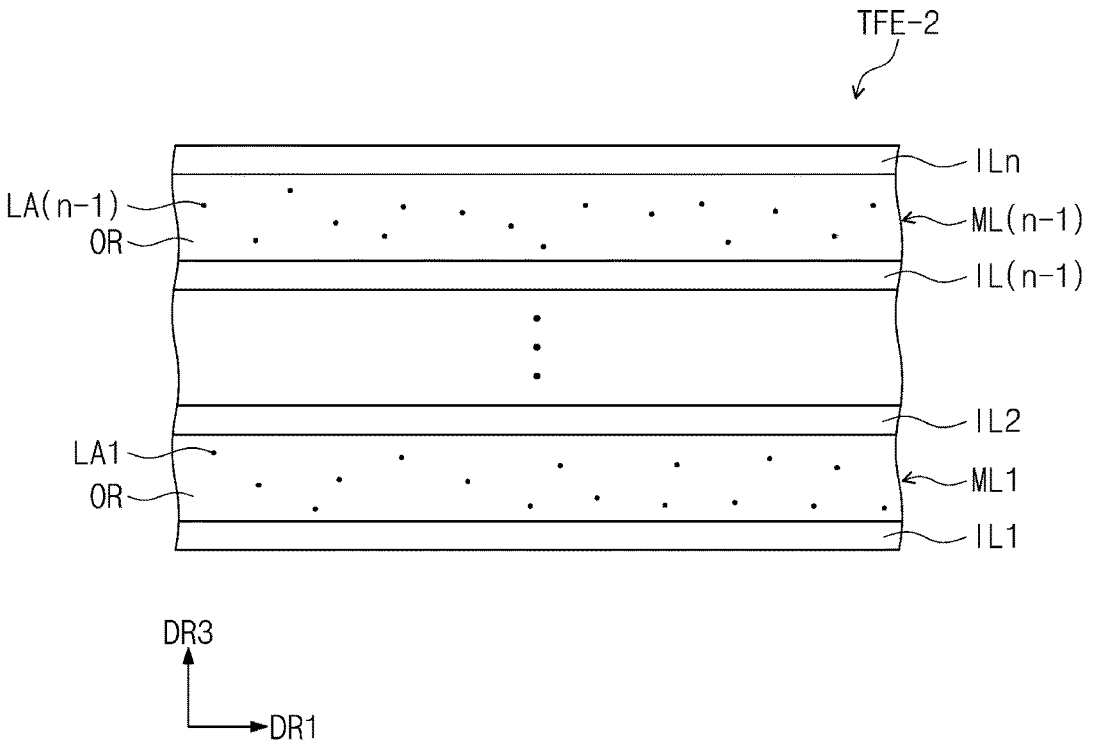

The display apparatus DS-2 of an embodiment may include the color filter layer CFL disposed on the color conversion layer CCL, and those descriptions provided in FIG. 8 may be equally applied to the color filter layer CFL and the base substrate BS. FIGS. 11 to 13 are cross-sectional views illustrating examples of encapsulation members according to an embodiment. Referring to FIGS. 11 to 13, the encapsulation members TFE, TFE-1, and TFE-2 according to an embodiment may include at least one organic film and at least one inorganic film.

The encapsulation member TFE of an embodiment shown in FIG. 11 may include one organic film ML and inorganic films IL1 and IL2 disposed on an upper surface and a lower surface of the organic film ML, respectively. That is, the encapsulation member TFE of an embodiment may be a structure in which the first inorganic film IL1, the organic film ML, and the second inorganic film IL2 are stacked in this order.

The organic film ML may include a light absorber LA of an embodiment. The organic film ML may include the light absorber LA and a base resin OR. The base resin OR may be formed from an acrylic monomer and a photoinitiator. The base resin OR may be formed through an ultraviolet-curing process from a plurality of different acrylic monomers and the photoinitiator, or one acrylic monomer and the photoinitiator. For example, the acrylic monomer may be a methacrylate monomer. The organic film ML may be formed to have a thickness of 3 μm to 30 μm.

In the organic film ML, the light absorber LA may be included in an amount of 1-5 wt % with respect to 100 of the weight of the monomer forming the base resin OR. When the light absorber LA is included in an amount of less than 1 wt % with respect to the weight of the monomer, the degree of the light absorption in the organic film ML may be reduced, thereby not exhibiting the effect of blocking the external light. In addition, when the light absorber LA is included in an amount of greater than 5 wt % with respect to the weight of the monomer, there may be limitations that the activation of the photoinitiator used to form the organic film ML may be reduced, and the phase-separation may occur after the step of forming the organic film ML by using ultraviolet rays.

For example, the monomer used to form the organic film ML may be at least one among M1 to M4 below:

M1

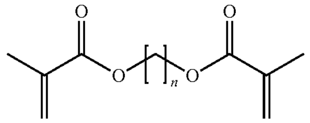

M2

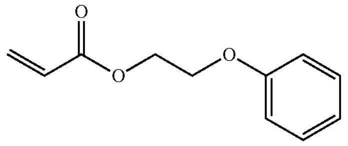

M3

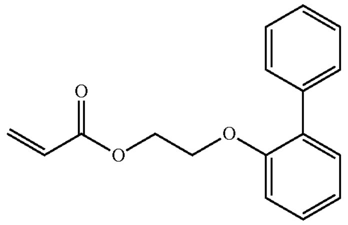

M4

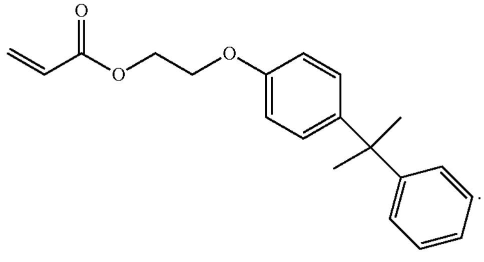

.

In addition, the photoinitiator used to form the organic film ML may be activated in a wavelength region of 360 nm to 400 nm. For example, the photoinitiator may be I1 or I2 below:

I1

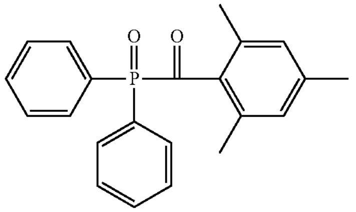

I2

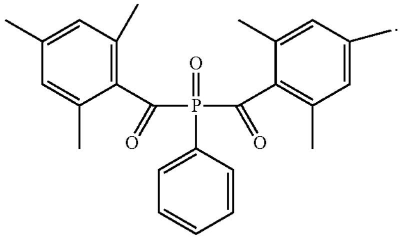

The organic film ML may include the light absorber of an embodiment as described above to absorb UV light. The organic film ML may have a transmittance of 10% or less at 405 nm wavelength, a transmittance of 70% or more at 430 nm wavelength, and a transmittance of 97% or more at 450 nm wavelength.

The inorganic films IL1 and IL2 may include at least one of SiON, $SiN_X$, $SiO_X$, SiC, $Al_2O_3$, or $ZrO_X$. The first inorganic film IL1 and the second inorganic film IL2 may be layers formed by including the same material. In addition, unlike this, the first inorganic film IL1 and the second inorganic film IL2 may be formed of different materials. The first inorganic film IL1 and the second inorganic film IL2 each may be formed to have a thickness of 0.5 μm to 2.0 μm. The inorganic films IL1 and IL2 may have a single layer including one material, or a plurality of layers each including a different material.

FIGS. 12 and 13 are views illustrating examples of encapsulation members according to an embodiment, and in the description with respect to examples of the encapsulation members shown in FIGS. 12 and 13, the duplicated features with respect to the encapsulation member TFE illustrated in FIG. 11 are not described again, but their differences will be mainly described.

FIG. 12 is a cross-sectional view illustrating another example of an encapsulation member according to an embodiment. Unlike the encapsulation member TFE shown in FIG. 11, the encapsulation member TFE-1 shown in FIG. 12 may include, in an organic film ML-a, a first light absorber LA-a and a second light absorber LA-b, which absorb light in a different wavelength region. At least one of the first light absorber LA-a or the second light absorber LA-b may have a structure of the light absorber of an embodiment as described above. However, the first light absorber LA-a or the second light absorber LA-b may have a partially different wavelength of the light absorbed. Meanwhile, FIG. 12 illustrates the case of including two different light absorbers, but the embodiment is not limited thereto, and the organic film ML-a in the encapsulation member TFE-1 of an embodiment may include at least three different light absorbers. Meanwhile, different light absorbers may all be light absorbers of an embodiment as described above. In addition, unlike this, the organic film ML-a may further include a known light absorber, in addition to the light absorber of an embodiment.

FIG. 13 is a cross-sectional view illustrating an example of an encapsulation member including a plurality of inorganic films and a plurality of organic films. Referring to FIG. 9, the encapsulation member TFE-2 may include n inorganic films IL1, . . . , ILn and (n−1) organic films ML1, . . . , ML(n−1). Meanwhile, n may be an integer of 2 or more.

The first inorganic film IL1 among the n inorganic films IL1, . . . , ILn of the encapsulation member TFE-2 may be disposed to be directly contacted with the second electrode EL2 (FIG. 5) of the light-emitting device OEL.

The (n−1) organic films ML1, . . . , ML(n−1) of the encapsulation member TFE-2 may be disposed alternately with the n inorganic films IL1, . . . , ILn. The (n−1) organic films ML1, . . . , ML(n−1) may have greater average thickness than the n inorganic films IL1, . . . , ILn.

The n inorganic films IL1, . . . , ILn may include the same or different inorganic material, and may have the same or different thickness. In addition, the (n−1) organic films ML1, . . . , ML(n−1) may include the same or different organic material, and may have the same or different thickness.

Meanwhile, at least one organic film among the (n−1) organic films ML1, . . . , ML (n−1) may include the light absorber of an embodiment as described above. In the encapsulation member TFE-2 of an embodiment, at any one organic film among the (n−1) organic films ML1, . . . , ML(n−1) may include the light absorber of an embodiment. In addition, in the encapsulation member TFE-2 of an embodiment, a plurality of organic films selected from among the (n−1) organic films ML1, . . . , ML(n−1) may include the light absorber of an embodiment. In addition, each of the (n−1) organic films ML1, . . . ML(n−1) may include the light absorber of an embodiment.

The light absorbers LA1, . . . , LA(n−1) of an embodiment included in the (n−1) organic films ML1, . . . , ML(n−1), respectively may be all the same or at least one may be different. Meanwhile, the (n−1) organic films ML1, . . . , ML(n−1) may further include a known light absorber, in addition to the light absorber of an embodiment as described above.

Figure 14:
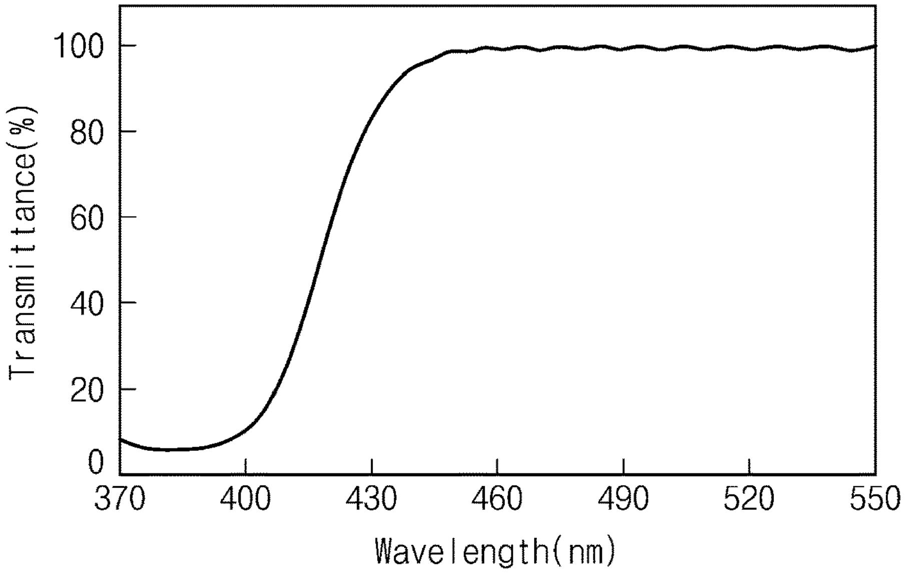
FIG. 14 is a graph illustrating a transmittance of an encapsulation member in an organic film according to an embodiment.

FIG. 14 is a graph in which light transmittance in the organic film of the encapsulation member including the light absorber of an embodiment is measured. FIG. 14 is that transmittance according to a wavelength is measured with respect to a single layer organic film manufactured to have a thickness of 10 μm, wherein the organic film includes 3 wt % of the light absorber of an embodiment with respect to the total content of the monomers. The light absorber used in an embodiment shown in FIG. 14 corresponds to Compound 35 of Compound Group 2, but when other compounds in Compound Group 1 or Compound Group 2 corresponding to the light absorber according to an embodiment are included as an organic film material, similar results may also be shown. Referring to the graph of FIG. 14, the organic film exhibits transmittance of 10% or less at 405 nm wavelength, and thus, it may be confirmed that the light absorber of an embodiment efficiently absorbs light in a wavelength region in the vicinity of 405 nm.

In addition, referring to FIG. 14, it may be confirmed that the organic film of the encapsulation member including the light absorber of an embodiment exhibits transmittance of 70% or more at 430 nm wavelength, and transmittance of 97% or more at 450 nm wavelength. That is, the organic film has transmittance of 70% or more at 430 nm and high transmittance of 97% or more in a visible light region of 450 nm or more, and thus since the wavelength region of the light emitted from the light-emitting device OEL (FIG. 5) is not overlapped, luminous efficiency of the light-emitting device OEL (FIG. 5) may not be reduced even when the organic film includes the light absorber.

Figure 15:
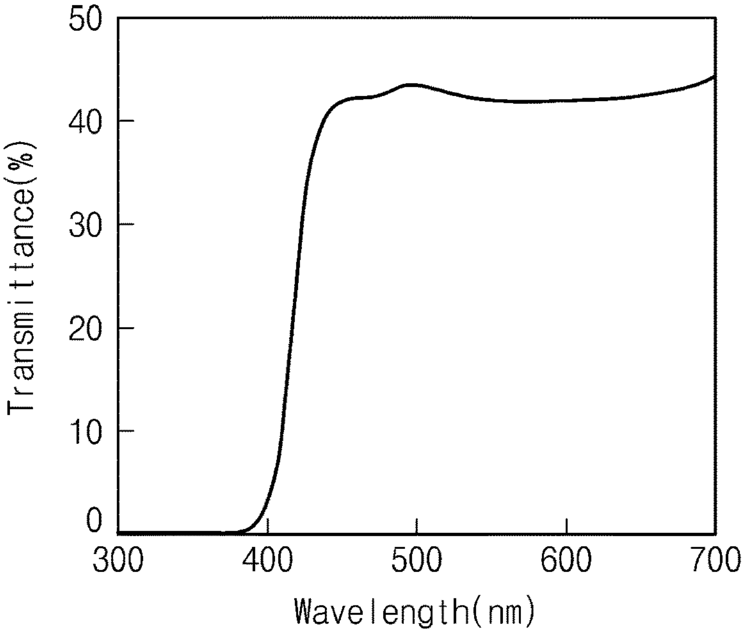
FIG. 15 is a graph illustrating a transmittance in a display apparatus of an embodiment.

FIG. 15 is a graph in which light transmittance is measured in the case of the encapsulation member including the light absorber of an embodiment and the polarizing member disposed on the encapsulation member. FIG. 15 is that transmittance according to a wavelength is measured after the polarizing member is provided on the organic film manufactured in the same conditions as those used in the evaluation of transmittance of FIG. 14. Referring to the graph of FIG. 15, when the polarizing member is included in the organic film, transmittance of 5% or less at 405 nm wavelength is exhibited, and thus, it may be confirmed that the light absorber of an embodiment efficiently absorbs light in a wavelength region in the vicinity of 405 nm.

In addition, referring to FIG. 15, it may be seen that when the organic film of the encapsulation member including the light absorber of an embodiment and the polarizing member are stacked, transmittance of 30% or more at 430 nm wavelength is exhibited.

Meanwhile, compared to FIG. 14, it may be seen that the transmittance graph of FIG. 15 shows a low transmittance even in a wavelength region of 400 nm or less. That is, compared to FIG. 14, it may be seen that when the polarizing member is further included on the encapsulation member, transmittance in a short wavelength region of 400 nm or less may be more decreased, and thus when the polarizing member is further included on the encapsulation member, light in an ultraviolet wavelength region is more effectively blocked.

Figure 16:
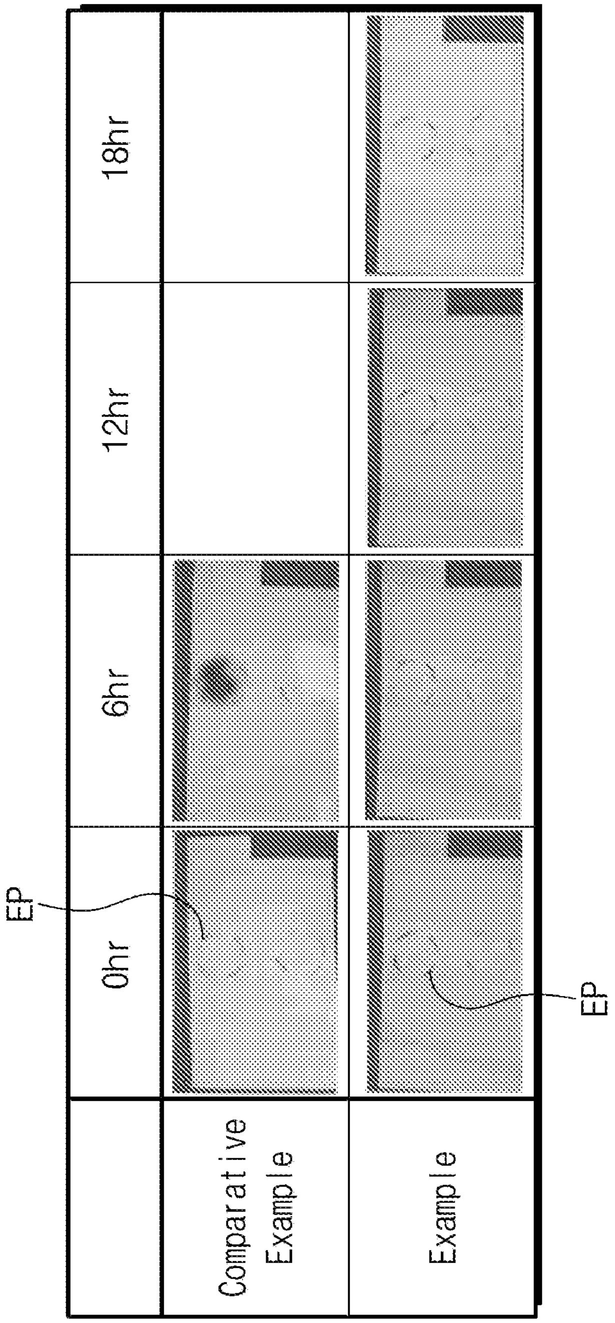
FIG. 16 is an image illustrating the presence/absence of damage depending on the exposure time of ultraviolet rays in Example and Comparative Example.

FIG. 16 is an image confirming reliability of the display panel during exposure to UV light. In FIG. 16, Comparative Example is the case where the organic film of the encapsulation member does not include the light absorber, and Example is the case where the organic film of the encapsulation member includes the light absorber of an embodiment. The light absorber used in Example shown in FIG. 16 may be the same as the light absorber used in Example in FIG. 14.

Samples of Comparative Example and Example was exposed to light having a short wavelength of 405 nm, and it was observed whether the display panel was damaged over time. In FIG. 16, EP represents a part which is exposed to the light having a short wavelength of 405 nm.

When comparing Comparative Example and Example of FIG. 16, Comparative Example already showed damaged surface characteristics 6 hours after the exposure, and Example did not show changes in surface characteristics even until 18 hours after the exposure. Referring to FIG. 16, it may be confirmed that the light absorber of an embodiment effectively absorbs light in a wavelength region of 405 nm, and thus the encapsulation member according to an embodiment may effectively block the external light in a wavelength region of 405 nm.

The display apparatus according to an embodiment includes, in the encapsulation member, the light absorber including the hexagonal heterocycle containing two or more nitrogen atoms as a ring-forming atom and three different substituents which are substituted at the hexagonal heterocycle, and thus can effectively block the external light which enters the light-emitting device, thereby exhibiting improved reliability. In the display apparatus according to an embodiment, at least one organic film of the encapsulation member includes the light absorber including the hexagonal heterocycle containing two or more nitrogen atoms as a ring-forming atom and three different substituents which are substituted at the hexagonal heterocycle, and thus blocks the external light which enters the light-emitting device, thereby exhibiting improved display quality.

Hereinafter, with reference to Examples and Comparative Examples, the light absorber according to an embodiment of the present invention will be described in detail. In addition, Examples shown below are illustrated only for the understanding of the present invention, and the scope of the invention is not limited thereto.

Examples

1. Synthesis of Light Absorber 1-1. Synthesis of Light Absorber Represented by Formula 1

A synthesis method of a light absorber represented by Formula 1 of an embodiment as described above will be described in detail by illustrating a synthesis method of Compounds 2, 15, 25, 36, 56, 78, 95, 115, 148, and 177 of Compound Group 1. In addition, in the following descriptions, a synthesis method of the light absorber is provided as an example, but the synthesis method according to an embodiment of the present invention is not limited to the following examples.

(1) Synthesis of Compound 2 of Compound Group 1

Compound 1 of Compound Group 1 of the light absorber according to an embodiment may be synthesized, for example, by Reaction Scheme 1-1 below:

Reaction Scheme 1-1

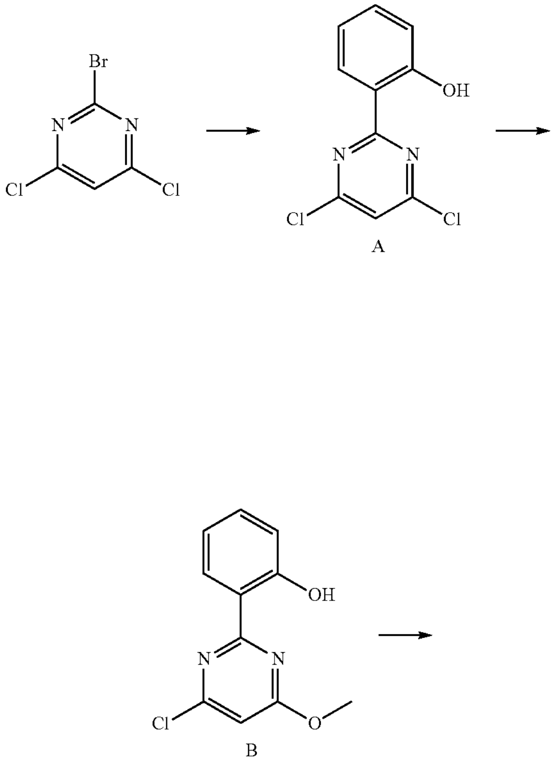

A

B

-continued

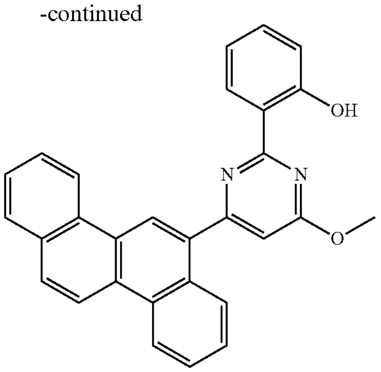

2

Synthesis of Intermediate A 2-bromo-4,6,-dichloro-pyrimidine (2.25 g), 2-hydroxyphenylboronic acid (1.38 g), $Pd(PPh_3)_4$ (0.5 g), and $K_2CO_3$ (2.72 g) were added to a solution of THF/water (50 mL/25 mL), and then the mixture was stirred at 80° C. for 5 hours. After the reaction was completed, the temperature was decreased to room temperature and the reaction solution was extracted with ethyl acetate three times. The product was dried with anhydrous magnesium sulfate, filtered, and concentrated at reduced pressure to obtain residues. The obtained residues were cleansed with methylene chloride (MC) to obtain Intermediate 2-3 (1.97 g, yield: 80%). The produced compound was identified by using LC-MS. (Calculated value: 239.99, measured value: 240.52).

Synthesis of Intermediate B

Intermediate A (1.97 g) was mixed in 50 mL of dimethylformamide (DMF), and then NaOMe (1 g) was added thereto. Then, the mixture was stirred at 100° C. for 1 hour. After the reaction, the temperature was decreased to room temperature, the reaction was quenched with water to obtain residues, and the obtained residues were cleansed with MC to obtain Intermediate 2-4 (1.69 g, yield: 90%). The produced compound was identified by using LC-MS. (Calculated value: 236.04, measured value: 236.9852).

Synthesis of Compound 2

Compound 2 (2.56 g, yield: 83%) was obtained in the same manner as the synthesis of Intermediate A except that Intermediate B instead of 2-bromo-4,6,-dichloro-pyrimidine, and 6-chryseneboronic acid instead of 2-hydroxyphenylboronic acid, were used. The produced compound was identified by using LC-MS. (Calculated value: 428.15, measured value: 429.06).

(2) Synthesis of Compound 15 of Compound Group 1

Compound 15 of Compound Group 1 of the light absorber according to an example may be synthesized by Reaction Scheme 1-2 below, for example.

Reaction Scheme 1-2

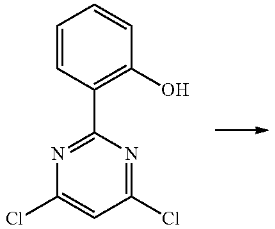

A

-continued

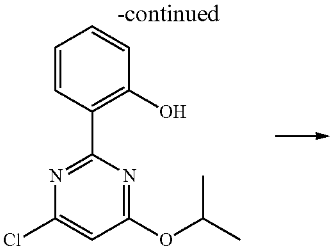

C

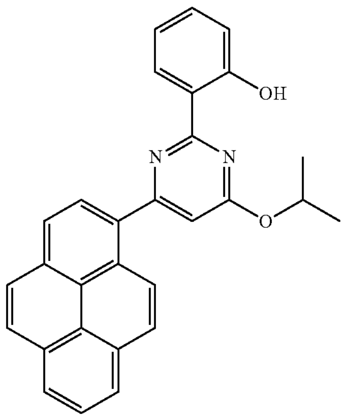

15

Synthesis of Intermediate C

Isopropyl alcohol (0.6 g) was mixed in 50 mL of DMF, and then the reaction temperature was decreased to 0° C. NaH (60% mineral oil, 400 mg) was slowly added thereto, the temperature was then increased to room temperature, and the mixture was stirred for 1 hour. The reaction temperature was decreased again to 0° C., and then Intermediate A (2.41 g) mixed in 50 mL of DMF was slowly added dropwise to the reaction container. The reaction temperature was maintained for 30 minutes, the temperature was then slowly increased to room temperature, and the mixture was stirred for 6 hours. After the reaction was quenched with water, the reaction solution was extracted with ethyl acetate and cleansed with water four times. After performing distillation under reduced pressure, the obtained residues were cleansed with MC to obtain Intermediate C (2.112 g, yield: 80%) The produced compound was identified to be Intermediate C by using LC-MS. (Calculated value: 264.07, measured value: 265.10).

Synthesis of Compound 15

Compound 15 (2.75 g, yield: 80%) was obtained in the same manner as the synthesis of Intermediate A except that Intermediate C instead of 2-bromo-4,6,-dichloro-pyrimidine, and 1-pyreneboronic acid instead of 2-hydroxyphenylboronic acid, were used. The produced compound was identified by using LC-MS. (Calculated value: 430.17, measured value: 431.22).

(3) Synthesis of Compound 25 of Compound Group 1

Compound 25 of Compound Group 1 of the light absorber according to an example may be synthesized by Reaction Scheme 1-3 below, for example.

Reaction Scheme 1-3

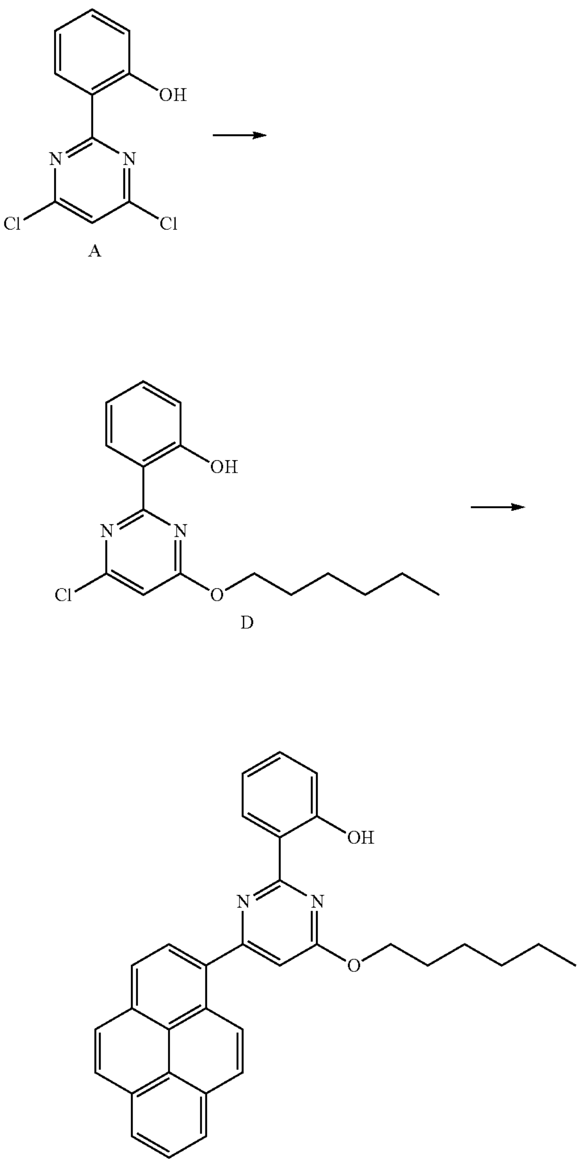

25

Synthesis of Intermediate D

Intermediate D (2.45 g, yield: 80%) was obtained in the same manner as the synthesis of Intermediate C except that 1-hexanol instead of isopropyl alcohol was used. The produced compound was identified by using LC-MS. (Calculated value: 306.11, measured value: 307.04).

Synthesis of Compound 25

Compound 25 (3.02 g, yield: 80%) was obtained in the same manner as the synthesis of Intermediate A except that Intermediate C instead of 2-bromo-4,6,-dichloro-pyrimidine, and 1-pyreneboronic acid instead of 2-hydroxyphenylboronic acid, were used. The produced compound was identified by using LC-MS. (Calculated value: 472.22, measured value: 473.10).

(4) Synthesis of Compound 36 of Compound Group 1

Compound 36 of Compound Group 1 of the light absorber according to an example may be synthesized by Reaction Scheme 1-4 below, for example.

Reaction Scheme 1-4

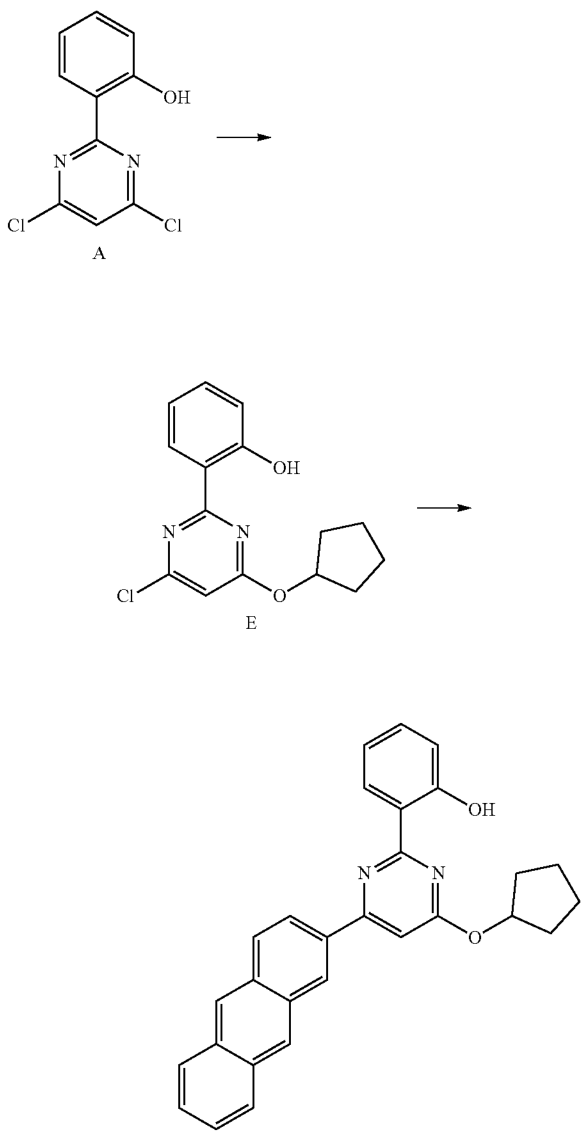

36

Synthesis of Intermediate E

Intermediate E (2.32 g, yield: 80%) was obtained in the same manner as the synthesis of Intermediate C except that cyclopentanol instead of isopropyl alcohol was used. The produced compound was identified by using LC-MS. (Calculated value: 290.08, measured value: 290.98).

Synthesis of Compound 36

Compound 36 (2.76 g, yield: 80%) was obtained in the same manner as the synthesis of Intermediate A except that Intermediate E instead of 2-bromo-4,6,-dichloro-pyrimidine, and 2-anthraceneboronic acid instead of 2-hydroxyphenylboronic acid, were used. The produced compound was identified by using LC-MS. (Calculated value: 432.18, measured value: 433.10).

(5) Synthesis of Compound 56 of Compound Group 1

Compound 56 of Compound Group 1 of the light absorber according to an example may be synthesized by Reaction Scheme 1-5 below, for example.

Reaction Scheme 1-5

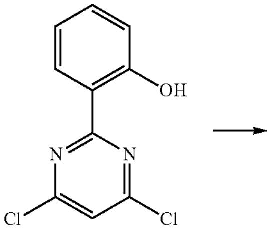

A

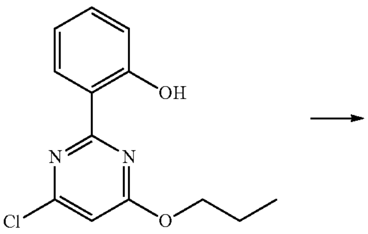

F

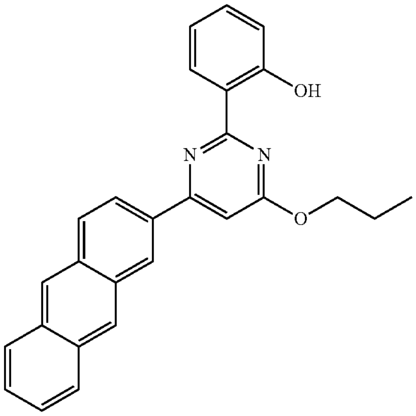

56

Synthesis of Intermediate F

Intermediate F (2.11 g, yield: 80%) was obtained in the same manner as the synthesis of Intermediate C except that propanol instead of isopropyl alcohol was used. The produced compound was identified by using LC-MS. (Calculated value: 264.07, measured value: 264.90).

<Synthesis of Compound 56

Compound 56 (2.59 g, yield: 80%) was obtained in the same manner as the synthesis of Intermediate A except that Intermediate F instead of 2-bromo-4,6,-dichloro-pyrimidine, and 2-anthraceneboronic acid instead of 2-hydroxyphenylboronic acid, were used. The produced compound was identified by using LC-MS. (Calculated value: 406.17, measured value: 407.96).

(6) Synthesis of Compound 78 of Compound Group 1

Compound 78 of Compound Group 1 of the light absorber according to an example may be synthesized by Reaction Scheme 1-6 below, for example.

Reaction Scheme 1-6

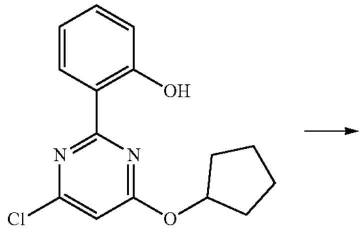

E

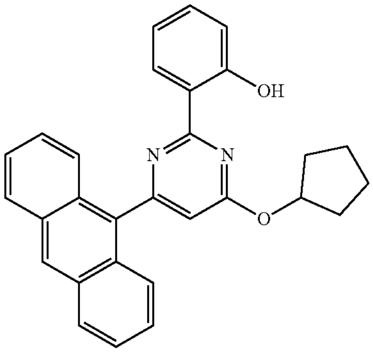

78

Compound 78 (2.76 g, yield: 80%) was obtained in the same manner as the synthesis of Compound 36 except that 9-anthraceneboronic acid instead of 2-anthraceneboronic acid was used. The produced compound was identified by using LC-MS. (Calculated value: 432.18, measured value: 433.12).

(7) Synthesis of Compound 95 of Compound Group 1

Compound 95 of Compound Group 1 of the light absorber according to an example may be synthesized by Reaction Scheme 1-7 below, for example.

Reaction Scheme 1-7

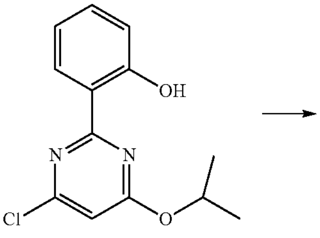

C

-continued

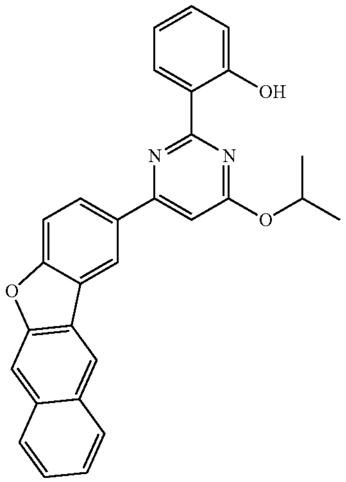

95

Compound 95 (2.85 g, yield: 80%) was obtained in the same manner as the synthesis of Compound 15 except that naphtho[2,3-b]benzofuran-2-ylboronic acid instead of 1-pyreneboronic acid was used. The produced compound was identified by using LC-MS. (Calculated value: 446.16, measured value: 447.08).

(8) Synthesis of Compound 115 of Compound Group 1

Compound 115 of Compound Group 1 of the light absorber according to an example may be synthesized by Reaction Scheme 1-8 below, for example.

Reaction Scheme 1-8

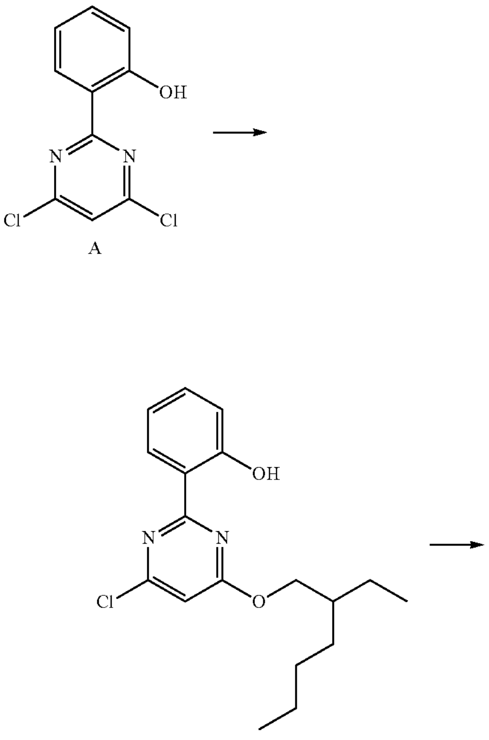

A

G

-continued

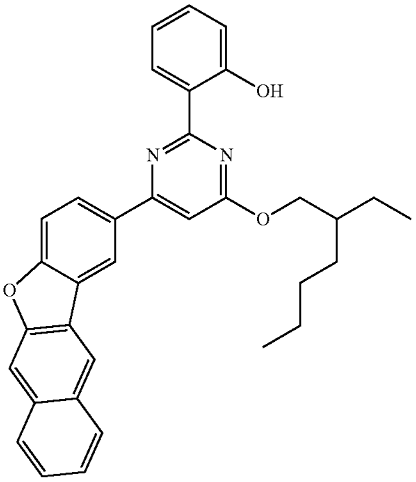

115

Synthesis of Intermediate G

Intermediate G (2.67 g, yield: 80%) was obtained in the same manner as the synthesis of Intermediate C except that 2-ethyl-hexanol instead of isopropyl alcohol was used. The produced compound was identified by using LC-MS. (Calculated value: 334.14, measured value: 264.90).

Synthesis of Compound 115

Compound 115 (3.30 g, yield: 80%) was obtained in the same manner as the synthesis of Intermediate A except that Intermediate G instead of 2-bromo-4,6,-dichloro-pyrimidine, and naphtho[2,3-b]benzofuran-2-ylboronic acid instead of 2-hydroxyphenylboronic acid, were used. The produced compound was identified by using LC-MS. (Calculated value: 516.24, measured value: 517.10).

(9) Synthesis of Compound 148 of Compound Group 1

Compound 148 of Compound Group 1 of the light absorber according to an example may be synthesized by Reaction Scheme 1-9 below, for example.

Reaction Scheme 1-9

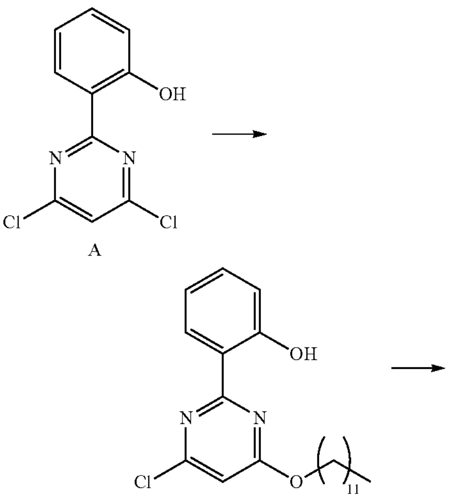

A

H

-continued

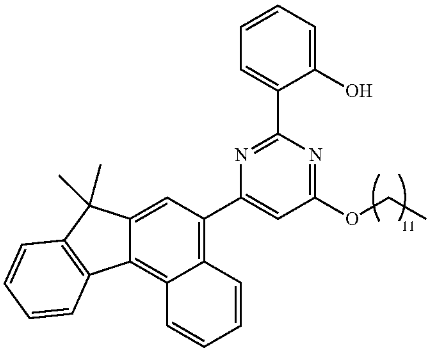

148

Synthesis of Intermediate H

Intermediate H (3.12 g, yield: 80%) was obtained in the same manner as the synthesis of Intermediate C except that dodecanol instead of isopropyl alcohol was used. The produced compound was identified by using LC-MS. (Calculated value: 390.21, measured value: 391.10).

Synthesis of Compound 148

Compound 148 (3.82 g, yield: 80%) was obtained in the same manner as the synthesis of Intermediate A except that Intermediate H instead of 2-bromo-4,6,-dichloro-pyrimidine, and (7,7-dimethyl-7H-benzo[c]fluoren-5-yl)boronic acid instead of 2-hydroxyphenylboronic acid, were used. The produced compound was identified by using LC-MS. (Calculated value: 598.36, measured value: 599.20).

(10) Synthesis of Compound 177 of Compound Group 1

Compound 177 of Compound Group 1 of the light absorber according to an example may be synthesized by Reaction Scheme 1-10 below, for example.

Reaction Scheme 1-10

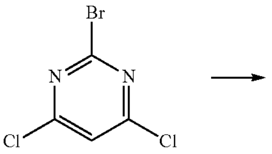

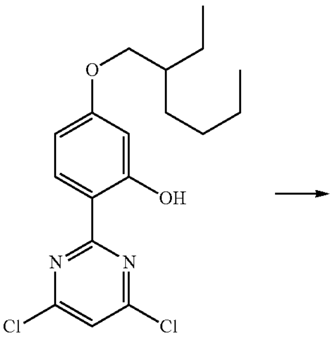

I

-continued

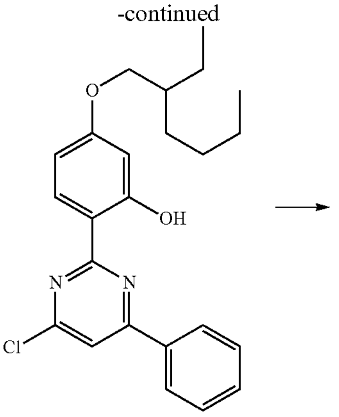

J

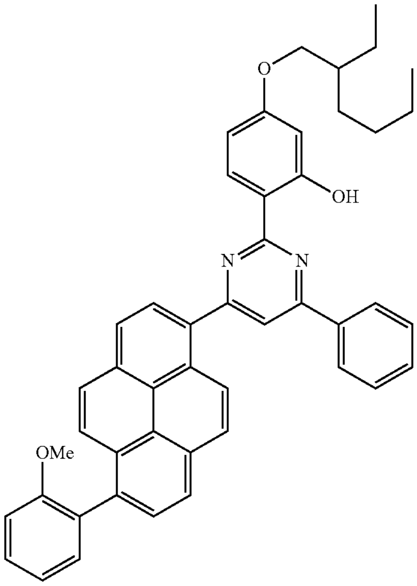

177

Synthesis of Intermediate I

Intermediate I (2.94 g, yield: 80%) was obtained in the same manner as the synthesis of Intermediate A except that (4-((2-ethylhexyl)oxy)-2-hydroxyphenyl)boronic acid instead of 2-hydroxyphenylboronic acid was used. The produced compound was identified by using LC-MS. (Calculated value: 368.11, measured value: 369.90).

Synthesis of Intermediate J

Intermediate J (3.48 g, yield: 80%) was obtained in the same manner as the synthesis of Compound 2 except that Intermediate I instead of Intermediate B, and (6-(2-methoxyphenyl)pyren-1-yl)boronic acid instead of 6-chryseneboronic acid, was used. The produced compound was identified by using LC-MS. (Calculated value: 680.34, measured value: 681.22), Synthesis of Compound 177

Compound 177 (3.30 g, yield: 80%) was obtained in the same manner as the synthesis of Intermediate A except that Intermediate J instead of 2-bromo-4,6,-dichloro-pyrimidine, and naphtho[2,3-b]benzofuran-2-ylboronic acid instead of 2-hydroxyphenylboronic acid, were used. The produced compound was identified by using LC-MS. (Calculated value: 516.24, measured value: 517.10).

(11) NMR Data

NMR data on the Example Compounds of Compound Group 1 synthesized by the above-described synthesis method are listed in Table 1 below:

TABLE 1

| Example Compounds | NMR (400 hz) |
|---|---|
| Compound 2 of Compound Group 1 | 9.61(brs, 1H), 9.27(s, 1H), 9.08(d, 1H), 8.84(d, 1H), 8.17(d, 1H), 7.92(m, 2H), 7.81-7.54(m, 6H), 7.32(t, 1H), 7.06(d, 1H), 7.02-7.00(m, 2H), 3.85(s, 3H) |
| Compound 15 of Compound Group 1 | 9.61(brs, 1H), 8.52(d, 1H), 8.31(d, 1H), 8.16(d, 1H), 8.08-8.04(m, 4H), 7.92(m, 1H), 7.7-7.55(m, 2H), 7.32(t, 1H), 7.06-7.00(m, 2H), 5.24(m, 1H), 1.35(d, 2H) |
| Compound 25 of Compound Group 1 | 15.30(s, 1H), 8.73(d, 1H), 8.31(d, 1H), 8.21-7.88(m, 7H), 7.86(d, 1H), 7.40(m, 1H), 7.08-7.00(m, 2H) 4.64(t, 2H), 2.06(m, 2H), 1.16(t, 3H) |
| Compound 36 of Compound Group 1 | 15.30(s, 1H), 9.01(s, 1H), 8.81(d, 1H), 8.46(d, 1H), 7.97-7.95(m, 2H), 7.79-7.36(m, 5H), 7.07-7.00(m, 2H), 4.67(t, 2H), 1.94-1.85(m, 2H), 1.68-1.58(m, 2H), 1.29-1.23(m, 4H) 0.97-0.98(m, 3H) |
| Compound 56 of Compound Group 1 | 15.30(s, 1H), 8.74(d, 1H), 8.31(d, 1H), 8.19-7.86(m, 8H), 7.40(m, 1H), 7.08-7.00(m, 2H), 4.29(d, 1H), 4.17(d, 1H), 2.00-1.74(m, H), 1.68-1.59(m, H), 1.43-1.18(m, H), 0.89(q, 3H) |
| Compound 78 of Compound Group 1 | 15.30(s, 1H), 8.73(d, 1H), 8.31(d, 1H), 8.22-7.94(m, 6H), 7.88(d, 1H), 7.40-7.34(m, 1H), 7.10-7.00(m, 2H), 5.86(m, 1 H), 2.26-2.16(m, 2H), 1.93-1.74(m, 4H), 1.72-1.62(m, 2H) |
| Compound 95 of Compound Group 1 | 15.30(s, 2H), 8.75(d, 1H), 8.31(d, 1H), 8.16-8.02(m, 6H), 7.86(d, 1H), 7.16(t, 1H), 6.17(d, 2H), 4.28(ab, 2H), 2.00-1.80(m, 2H), 1.71-1.60(m, 1H), 1.48-1.19(m, 6H), 0.91(t, 3H), 0.84(t, 3H) |
| Compound 115 of Compound Group 1 | 12.81(s, 3H), 9.01(m, 1H), 8.85-8.76(m, 2H), 8.46-8.44(m, 1H), 7.98-7.95(m, 1H), 7.82-7.77(m, 1H), 7.69-7.60(m, 2H), 7.56(dt, 1H), 5.88(s, 2H), 5.50(m, 1H), 1.37(d, 3H) |
| Compound 148 of Compound Group 1 | 15.30(s, 1H), 9.46(s, 1H), 8.76-8.65(m, 3H), 8.02-7.96(m, 2H), 7.81(t, 1H), 7.65-7.56(m, 3H), 7.40(m, 1H), 7.08-7.00(m, 2H), 4.67(t, 2H), 1.95-1.91(m, 2H), 1.66-1.58(m, 2H), 1.32-1.24(m, 4H), 0.96-0.87(m, 3H) |
| Compound 177 of Compound Group 1 | 10.90(s, 2H), 9.01(s, 1H), 8.81(d, 2H), 8.46(m, 1H), 8.22(d, 1H), 7.98(d, 1H), 7.78(t, 1H). 7.66-7.53(m, 3H), 6.53(s, 1H), 6.31 (d, 1H), 4.36(ab, 2H), 2.20(m, 1H), 1.43-1.20(m, 6H), 0.96-0.87(m, 6H) |

1-2. Synthesis of Light Absorber Represented by Formula 2A

Synthesis method of a light absorber represented by Formula 2 of an embodiment as described above will be described in detail by illustrating a synthesis method of Compounds 2, 15, 20, 24, 35, 40, 75, 94, 102, 154, 169, 227, 280, 295, 299, and 320 of Compound Group 2. In addition, in the following descriptions, a synthesis method of the light absorber is provided as an example, but the synthesis method according to an embodiment of the present invention is not limited to the following examples.

(1) Synthesis of Compound 2 of Compound Group 2

Compound 2 of Compound Group 2 of the light absorber according to an example may be synthesized by Reaction Scheme 2-1 below, for example.

Reaction Scheme 2-1

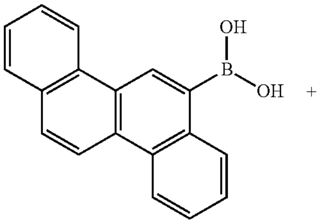

2-1

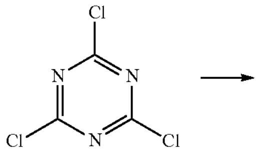

2-2

-continued

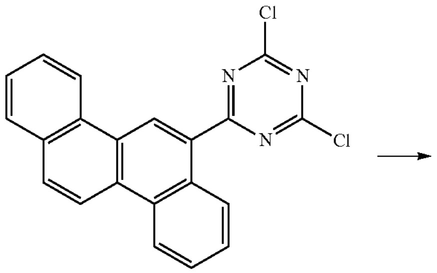

2-3

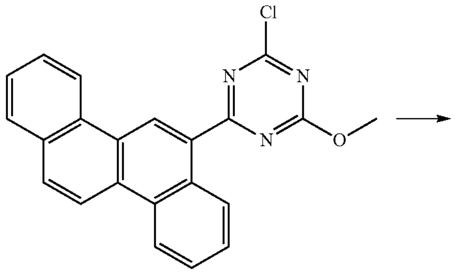

2-4

-continued

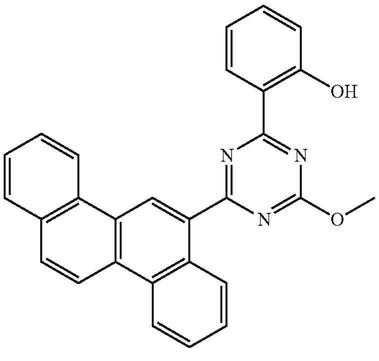

2

Synthesis of Intermediate 2-3

Compound 2-1 (chrysen-6-ylboronic acid, 5.4 g), Compound 2-2 (cyanuric chloride, 3.6 g), $Pd(PPh_3)_4$ (0.8 g), and $K_2CO_3$ (7.2 g) were added to a solution of THF/water (80 mL/20 mL), and then the mixture was stirred at 70° C. for 5 hours. After the reaction was completed, the temperature was decreased to room temperature and extracted with ethyl acetate three times. The product was dried with anhydrous magnesium sulfate, filtered, and concentrated at reduced pressure to obtain residues. The obtained residues were cleansed with methylene chloride (MC) to obtain Intermediate 2-3 (6.2 g, yield: 84%). The produced compound was identified to be Intermediate 2-3 by using LC-MS. ($C_{21}H_{11}Cl_2N_3$, calculated value: 375.03, measured value: 375.05).

Synthesis of Intermediate 2-4

Intermediate 2-3 (6 g) was mixed in 300 mL of dimethylformamide (DMF) and then NaOMe (860 mg) was added thereto. Then, the mixture was stirred at 100° C. for 1 hour. After the reaction, the temperature was decreased to room temperature, the reaction was quenched with water to obtain residues, and the obtained residues were cleansed with MC to obtain Intermediate 2-4 (4.8 g, yield: 81%). The produced compound was identified to be Intermediate 2-4 by using LC-MS. ($C_{22}H_{14}ClN_3O$, calculated value: 371.08, measured value: 371.09).

Synthesis of Compound 2

Compound 2 (4.5 g, yield: 82%) was obtained in the same manner as the synthesis of Intermediate 2-3 except that Intermediate 2-4 (4.8 g) and (2-hydroxyphenyl)boronic acid (1.9 g) were used. The produced compound was identified to be Compound 2 by using LC-MS. ($C_{28}H_{19}N_3O_2$, calculated value: 429.15, measured value: 429.17).

(2) Synthesis of Compound 15 of Compound Group 2

Compound 15 of Compound Group 2 of the light absorber according to an example may be synthesized by Reaction Scheme 2-2 below, for example.

Reaction Scheme 2-2

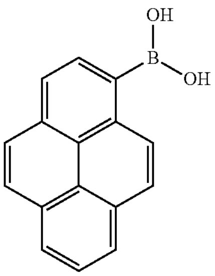

15-1

+

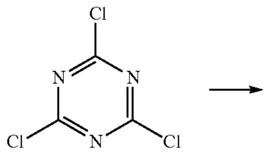

2-2

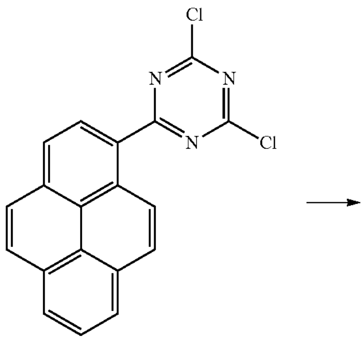

15-2

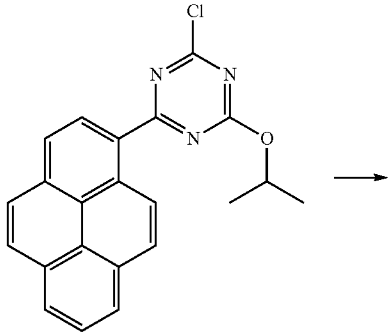

15-3

-continued

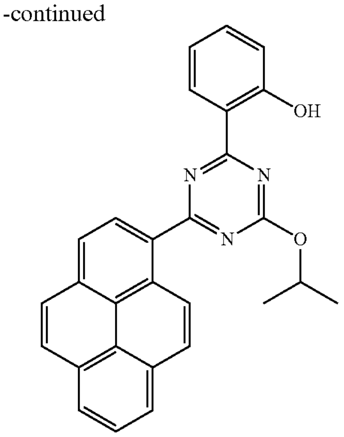

15

Synthesis of Intermediate 15-2

Intermediate 15-2 (5.7 g, yield: 80%) was obtained in the same manner as the synthesis of Intermediate 2-3 except that Intermediate 15-1 (5 g) was used. The produced compound was identified to be Intermediate 15-2 by using LC-MS. ($C_{19}H_9Cl_2N_3$, calculated value: 349.02, measured value: 349.01).

Synthesis of Intermediate 15-3

Isopropyl alcohol (1 g) was mixed in 40 mL of DMF, and then the reaction temperature was decreased to 0° C. NaH (60% mineral oil, 400 mg) was slowly added thereto, the temperature was then increased to room temperature, and the mixture was stirred for 1 hour. The reaction temperature was decreased again to 0° C., and then Intermediate 15-2 (5.7 g) mixed in 50 mL of DMF was slowly added dropwise to the reaction container. The reaction temperature was maintained for 30 minutes, the temperature was then slowly increased to room temperature, and the mixture was stirred for 6 hours. After the reaction was quenched with water, the reaction solution was extracted with ethyl acetate and cleansed with water four times. After performing distillation under reduced pressure, the obtained residues were cleansed with MC to obtain Intermediate 15-3 (5.2 g, yield: 86%) The produced compound was identified to be Intermediate 15-3 by using LC-MS. ($C_{22}H_{16}ClN_3O$, calculated value: 373.10, measured value: 373.14).

Synthesis of Compound 15

Compound 15 (4.7 g, yield: 78%) was obtained in the same manner as the synthesis of Intermediate 2-3 except that Intermediate 2-4 (5.2 g) and (2-hydroxyphenyl)boronic acid (2.1 g) were used. The produced compound was identified to be Compound 15 by using LC-MS. ($C_{28}H_{21}N_3O_2$, calculated value: 431.16, measured value: 431.19).

(3) Synthesis of Compound 20 of Compound Group 2

Compound 20 of Compound Group 2 of the light absorber according to an example may be synthesized by Reaction Scheme 2-3 below, for example.

Reaction Scheme 2-3

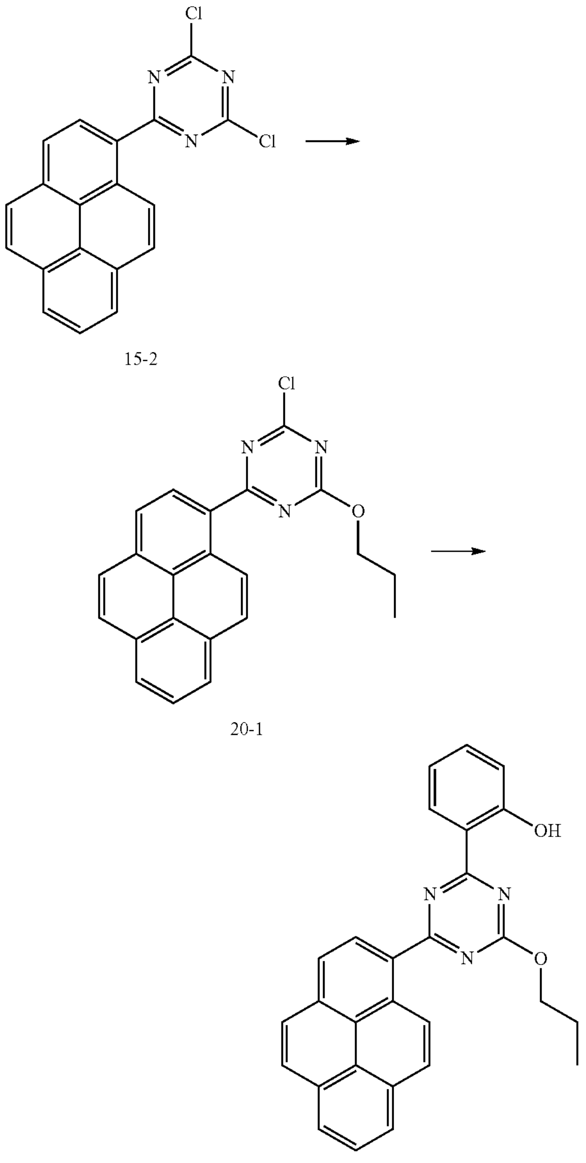

15-2

20-1

20

Synthesis of Intermediate 20-1

Intermediate 20-1 (4.6 g, yield: 87%) was obtained in the same manner as the synthesis of Intermediate 15-3 except that Intermediate 15-2 (5 g) and n-propanol (1 g) were used. The produced compound was identified to be Intermediate 20-1 by using LC-MS. ($C_{22}H_{16}ClN_3O$, calculated value: 373.10, measured value: 373.12).

Synthesis of Compound 20

Compound 20 (4.8 g, yield: 91%) was obtained in the same manner as the synthesis of Compound 2 except that Intermediate 20-1 (4.6 g) was used. The produced compound was identified to be Compound 20 by using LC-MS. ($C_{28}H_{21}N_3O_2$, calculated value: 431.16, measured value: 431.18).

(4) Synthesis of Compound 24 of Compound Group 2

Compound 24 of Compound Group 2 of the light absorber according to an example may be synthesized by Reaction Scheme 2-4 below, for example.

Reaction Scheme 2-4

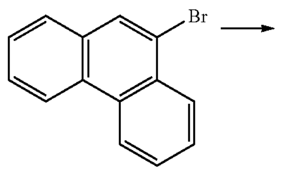

24-1

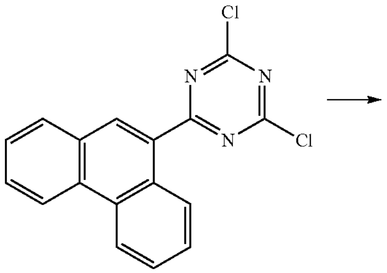

24-2

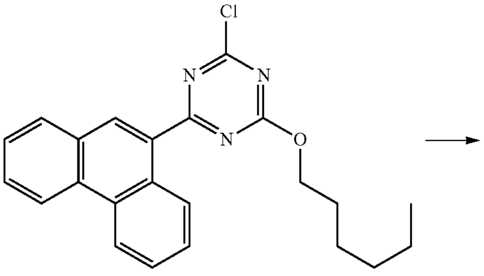

24-3

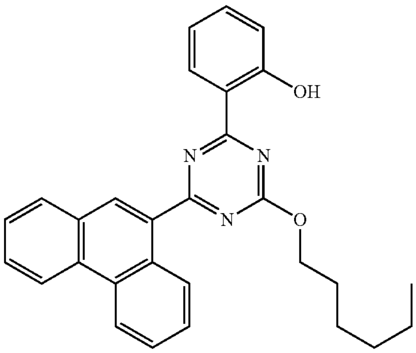

24

Synthesis of Intermediate 24-2

9-bromophenanthrene (5 g) was mixed in 50 mL of THF, and then the reaction temperature was decreased to −78° C. n-BuLi (8 mL, 2.43 M in hexane) was slowly dropped and the mixture was stirred for 1 hour while maintaining the reaction temperature. Cyanuric chloride (3.6 g) was mixed in 15 mL of THF, and then slowly added dropwise to the reaction container. After 3 hours, the reaction was quenched with a saturated ammonium chloride aqueous solution, and was extracted with ethyl acetate three times. The separated filtrate was dried with anhydrous magnesium sulfate, and then was distilled under reduced pressure to obtain residues. The residues thus obtained were recrystallized with MC to obtain Intermediate 24-2 (5.8 g, yield: 91%) The produced compound was identified to be Intermediate 24-2 by using LC-MS. ($C_{17}H_9Cl_2N_3$, calculated value: 325.02, measured value: 325.01).

Synthesis of Intermediate 24-3

Intermediate 24-3 (6 g, yield: 86%) was obtained in the same manner as the synthesis of Intermediate 15-3 except that Intermediate 24-2 (5.8 g) and n-hexanol (1.9 g) were used. The produced compound was identified to be Intermediate 24-3 by using LC-MS. ($C_{23}H_{22}ClN_3O$, calculated value: 391.15, measured value: 391.16).

Synthesis of Compound 24

Compound 24 (6.1 g, yield: 88%) was obtained in the same manner as the synthesis of Compound 2 except that Intermediate 24-3 (6 g) was used. The produced compound was identified to be Compound 24 by using LC-MS. ($C_{29}H_{27}N_3O_2$, calculated value: 449.21, measured value: 449.25).

(5) Synthesis of Compound 35 of Compound Group 2

Compound 35 of Compound Group 2 of the light absorber according to an example may be synthesized by Reaction Scheme 2-5 below, for example.

Reaction Scheme 2-5

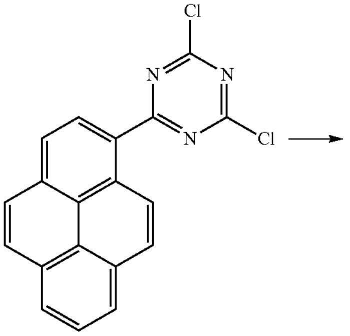

15-2

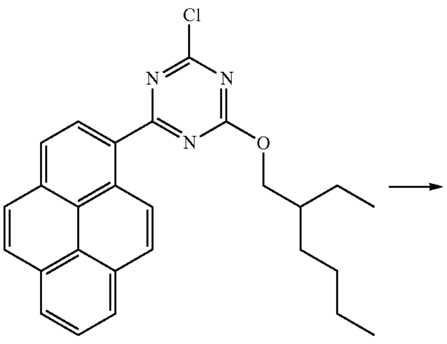

35-1

-continued

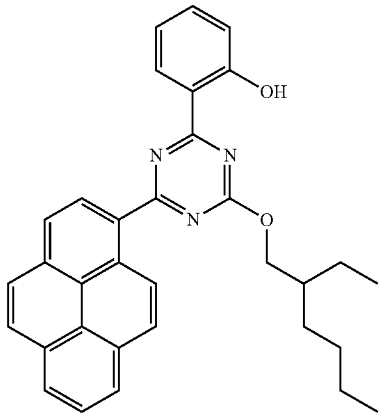

35

Synthesis of Intermediate 35-1

Intermediate 35-1 (3.8 g, yield: 86%) was obtained in the same manner as the synthesis of Intermediate 20-1 except that Intermediate 15-2 (3.5 g) and 2-ethylhexan-1-ol (1.3 g) were used. The produced compound was identified to be Intermediate 35-1 by using LC-MS. ($C_{27}H_{26}ClN_3O$, calculated value: 443.18, measured value: 443.19).

Synthesis of Compound 35

Compound 35 (3.5 g, yield: 81%) was obtained in the same manner as the synthesis of Compound 2 except that Intermediate 35-1 (3.8 g) was used. The produced compound was identified to be Compound 35 by using LC-MS. ($C_{33}H_{31}N_3O_2$, calculated value: 501.24, measured value: 501.25).

(6) Synthesis of Compound 40 of Compound Group 2

Compound 40 of Compound Group 2 of the light absorber according to an example may be synthesized by Reaction Scheme 2-6 below, for example.

Reaction Scheme 2-6

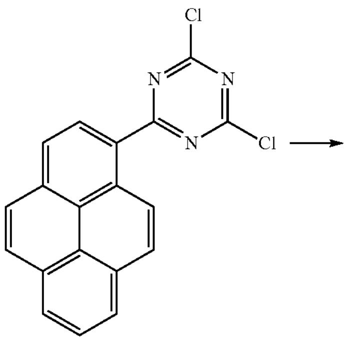

15-2

-continued

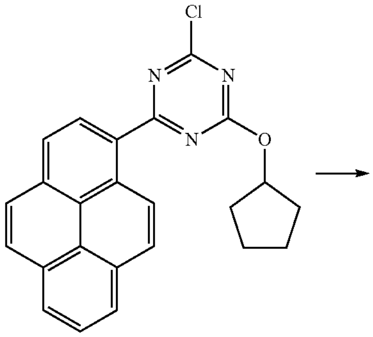

40-1

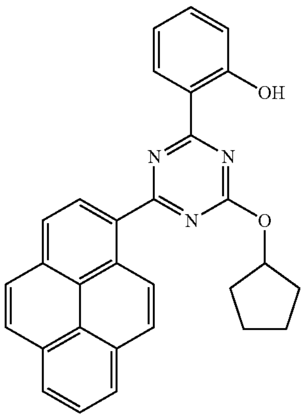

40

Synthesis of Intermediate 40-1

Intermediate 40-1 (3.7 g, yield: 93%) was obtained in the same manner as the synthesis of Intermediate 20-1 except that Intermediate 15-2 (3.5 g) and 2-ethylhexan-1-ol (860 mg) were used. The produced compound was identified to be Intermediate 40-1 by using LC-MS. ($C_{24}H_{18}ClN_3O$, calculated value: 399.11, measured value: 399.12).

Synthesis of Compound 40

Compound 40 (3.6 g, yield: 85%) was obtained in the same manner as the synthesis of Compound 2 except that Intermediate 40-1 (3.7 g) was used. The produced compound was identified to be Compound 40 by using LC-MS. ($C_{30}H_{23}N_3O_2$, calculated value: 457.18, measured value: 457.20).

(7) Synthesis of Compound 75 of Compound Group 2

Compound 75 of Compound Group 2 of the light absorber according to an example may be synthesized by Reaction Scheme 2-7 below, for example.

Reaction Scheme 2-7

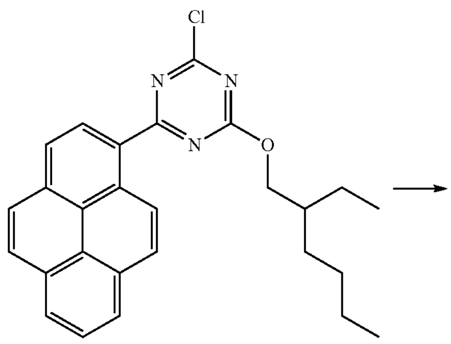

35-1

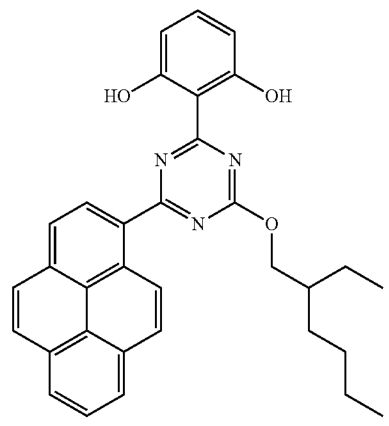

75

Compound 75 (3 g, yield: 86%) was obtained in the same manner as the synthesis of Compound 2 except that Intermediate 35-1 (3 g) and 2-(4,4,5,5-tetramethyl-1,3,2-dioxaborolan-2-yl)benzene-1,3-diol (1.4 g) were used. The produced compound was identified to be Compound 75 by using LC-MS. ($C_{33}H_{31}N_3O_3$, calculated value: 517.24, measured value: 517.29).

(8) Synthesis of Compound 94 of Compound Group 2

Compound 94 of Compound Group 2 of the light absorber according to an example may be synthesized by Reaction Scheme 2-8 below, for example.

Reaction Scheme 2-8

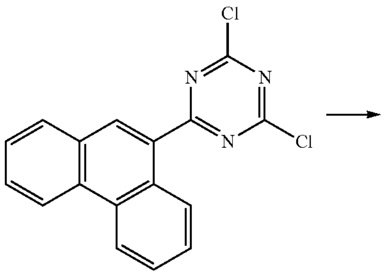

24-2

-continued

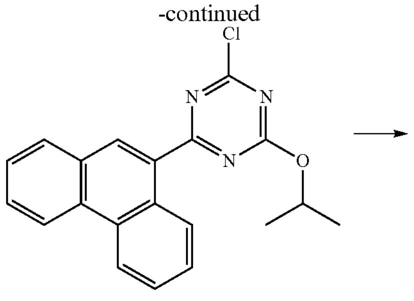

94-1

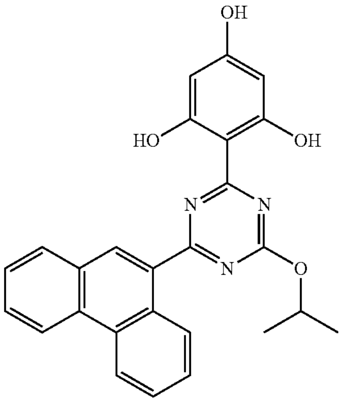

94

Synthesis of Intermediate 94-1

Intermediate 94-1 (3.7 g, yield: 53%) was obtained in the same manner as the synthesis of Intermediate 24-3 except that Intermediate 24-2 (6.5 g) and isopropyl alcohol (1.2 g) were used. The produced compound was identified to be Intermediate 94-1 by using LC-MS. ($C_{20}H_{16}ClN_3O$, calculated value: 349.1, measured value: 349.15).

Synthesis of Compound 94

Compound 94 (2.8 g, yield: 64%) was obtained in the same manner as the synthesis of Compound 2 except that Intermediate 94-1 (3.5 g) and 2-(4,4,5,5-tetramethyl-1,3,2-dioxaborolan-2-yl)benzene-1,3,5-triol (2.7 g) were used. The produced compound was identified to be Compound 94 by using LC-MS. ($C_{26}H_{21}N_3O_4$, calculated value: 439.16, measured value: 439.18).

(9) Synthesis of Compound 102 of Compound Group 2

Compound 102 of Compound Group 2 of the light absorber according to an example may be synthesized by Reaction Scheme 2-9 below, for example.

Reaction Scheme 2-9

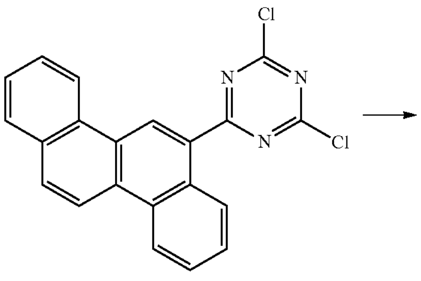

2-3

-continued

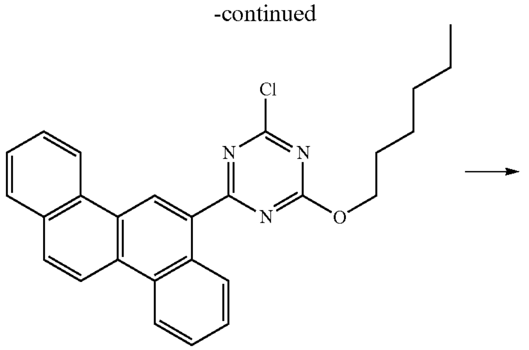

102-1

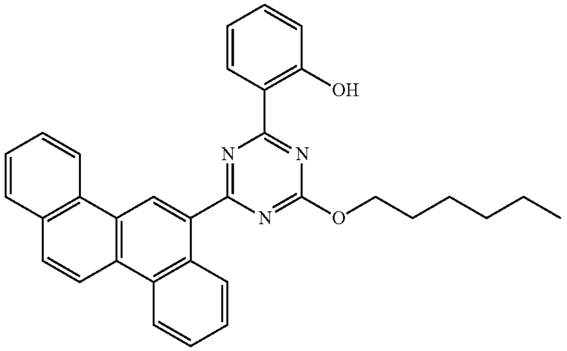

102

Synthesis of Intermediate 102-1

Intermediate 102-1 (3.3 g, yield: 75%) was obtained in the same manner as the synthesis of Intermediate 24-3 except that Intermediate 2-3 (3.8 g) and n-hexan-1-ol (1.1 g) were used. The produced compound was identified to be Intermediate 102-1 by using LC-MS. ($C_{27}H_{24}ClN_3O$, calculated value: 441.16, measured value: 441.19).

Synthesis of Compound 102

Compound 102 (2.8 g, yield: 76%) was obtained in the same manner as the synthesis of Compound 2 except that Intermediate 102-1 (3.3 g) was used. The produced compound was identified to be Compound 102 by using LC-MS. ($C_{33}H_{29}N_3O_2$, calculated value: 499.23, measured value: 499.26).

(10) Synthesis of Compound 154 of Compound Group 2

Compound 154 of Compound Group 2 of the light absorber according to an example may be synthesized by Reaction Scheme 2-10 below, for example.

Reaction Scheme 2-10

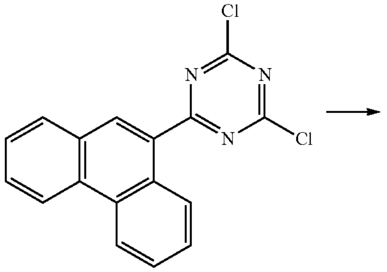

24-2

-continued

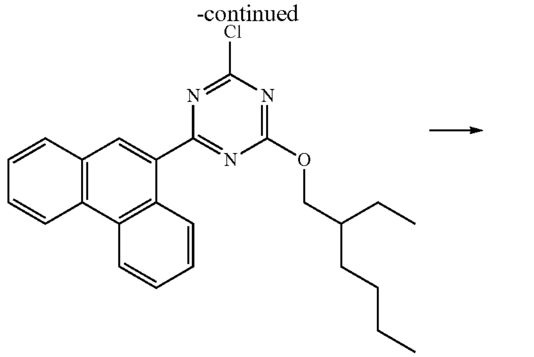

154-1

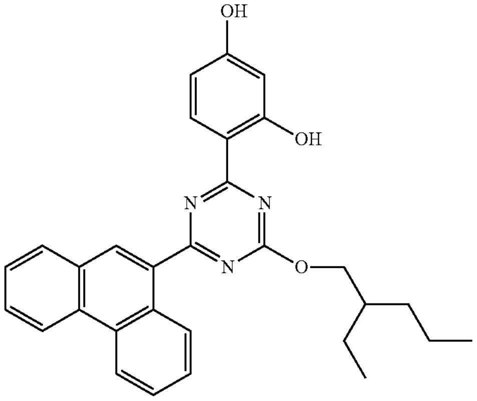

154

Synthesis of Intermediate 154-1

Intermediate 154-1 (3.2 g, yield: 76%) was obtained in the same manner as the synthesis of Intermediate 24-3 except that Intermediate 24-2 (3.3 g) and 2-ethylhexan-1-ol (1.3 g) were used. The produced compound was identified to be Intermediate 154-1 by using LC-MS. ($C_{25}H_{26}ClN_3O$, calculated value: 419.18, measured value: 419.20).

Synthesis of Compound 154

Compound 154 (3.2 g, yield: 83%) was obtained in the same manner as the synthesis of Compound 2 except that Intermediate 154-1 (3.3 g) and 4-(4,4,5,5-tetramethyl-1,3,2-dioxaborolan-2-yl)benzene-1,3-diol (1.8 g) were used. The produced compound was identified to be Compound 154 by using LC-MS. ($C_{30}H_{29}N_3O_3$, calculated value: 479.22, measured value: 479.23).

(11) Synthesis of Compound 169 of Compound Group 2

Compound 169 of Compound Group 2 of the light absorber according to an example may be synthesized by Reaction Scheme 2-11 below, for example.

Reaction Scheme 2-11

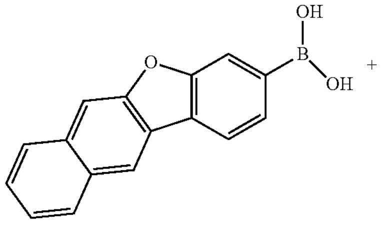

169-1

-continued

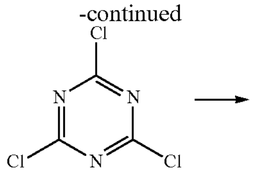

2-2

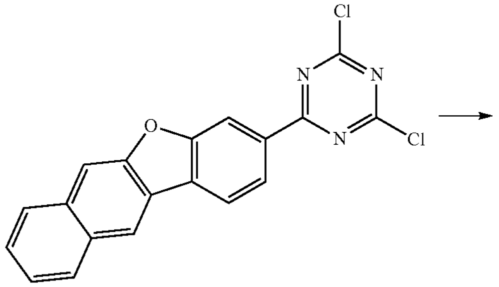

169-2

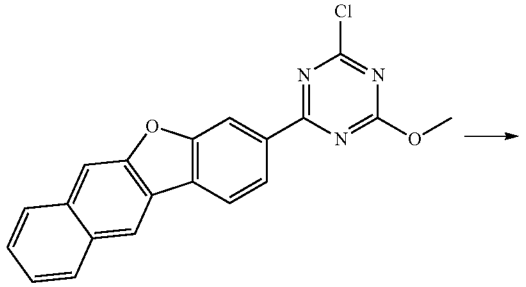

169-3

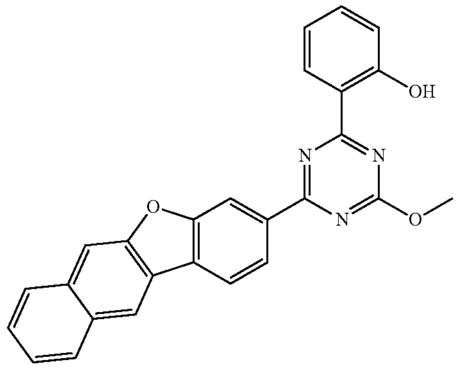

169

Synthesis of Intermediate 169-2

Intermediate 169-2 (4.3 g, yield: 59%) was obtained in the same manner as the synthesis of Intermediate 2-3 except that Intermediate 169-1 (5.2 g) (disclosed in the prior document WO2014141725A1) and Compound 2-2 (3.6 g) were used. The produced compound was identified to be Intermediate 169-2 by using LC-MS. ($C_{19}H_9Cl_2N_{30}$, calculated value: 365.01, measured value: 365.04).

Synthesis of Intermediate 169-3

Intermediate 169-3 (3.2 g, yield: 81%) was obtained in the same manner as the synthesis of Intermediate 2-4 except that Intermediate 169-2 (4.3 g) was used. The produced compound was identified to be Intermediate 169-3 by using LC-MS. ($C_{20}H_{12}ClN_3O_2$, calculated value: 361.06, measured value: 361.12).

Synthesis of Compound 169

Compound 169 (2.8 g, yield: 76%) was obtained in the same manner as the synthesis of Compound 2 except that Intermediate 169-3 (3.2 g) was used. The produced compound was identified to be Compound 169 by using LC-MS. ($C_{26}H_{17}N_3O_3$, calculated value: 419.13, measured value: 419.16).

(12) Synthesis of Compound 227 of Compound Group 2

Compound 227 of Compound Group 2 of the light absorber according to an example may be synthesized by Reaction Scheme 2-12 below, for example.

Reaction Scheme 2-12

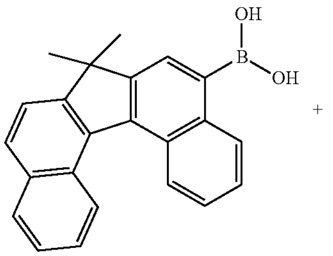

227-1

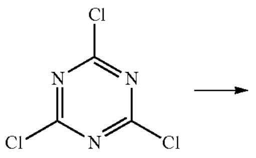

2-2

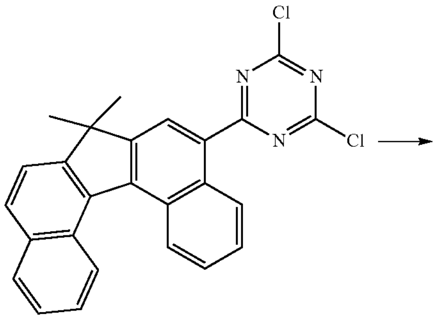

227-2

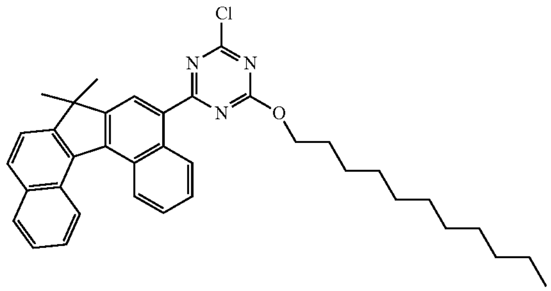

227-3

-continued

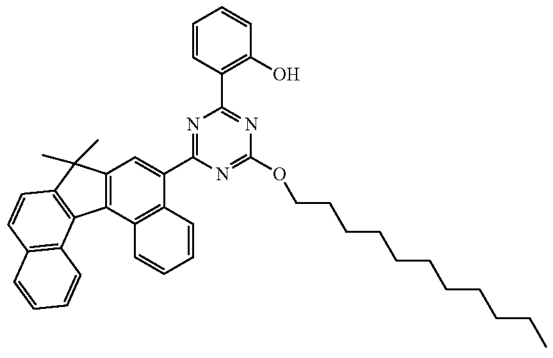

227

Synthesis of Intermediate 227-2

Intermediate 227-2 (3.6 g, yield: 81%) was obtained in the same manner as the synthesis of Intermediate 2-3 except that Intermediate 227-1 (3.4 g) and Compound 2-2 (2 g) were used. The produced compound was identified to be Intermediate 227-2 by using LC-MS. ($C_{26}H_{17}Cl_2N_3$, calculated value: 441.08, measured value: 441.09).

Synthesis of Intermediate 227-3

Intermediate 227-3 (3.9 g, yield: 83%) was obtained in the same manner as the synthesis of Intermediate 24-3 except that Intermediate 227-2 (3.6 g) and undecan-1-ol (1.4 g) were used. The produced compound was identified to be Intermediate 227-3 by using LC-MS. ($C_{37}H_{40}ClN_3O$, calculated value: 577.29, measured value: 577.30).

Synthesis of Compound 227

Compound 227 (3.3 g, yield: 77%) was obtained in the same manner as the synthesis of Compound 2 except that Intermediate 227-3 (3.9 g) was used. The produced compound was identified to be Compound 227 by using LC-MS. ($C_{43}H_{45}N_3O_2$, calculated value: 635.35, measured value: 635.39).

(13) Synthesis of Compound 280 of Compound Group 2

Compound 280 of Compound Group 2 of the light absorber according to an example may be synthesized by Reaction Scheme 2-13 below, for example.

Reaction Scheme 2-13

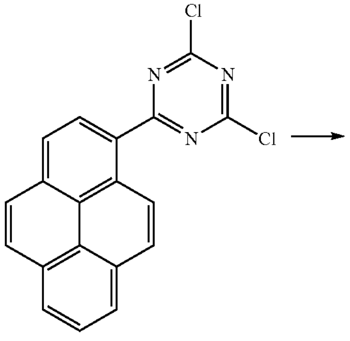

15-2

-continued

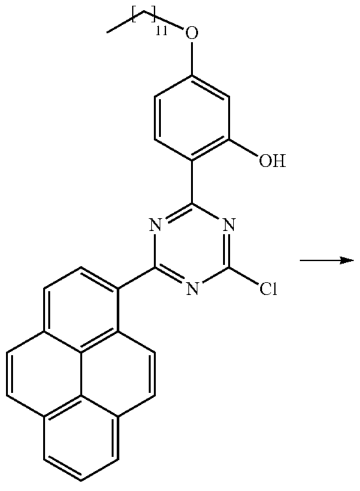

280-1

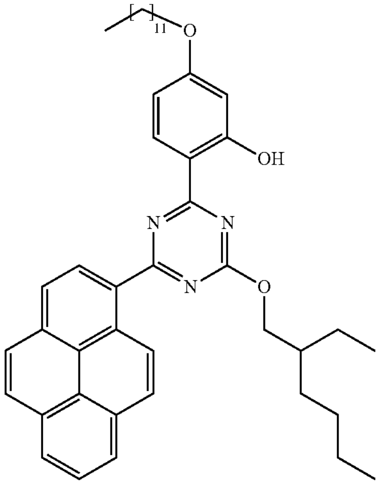

280

Synthesis of Intermediate 280-1

Intermediate 15-2 (3.5 g) and 3-(dodecyloxy)phenol (2.8 g) were mixed in 100 mL of methylene chloride, and then $AlCl_3$ (1.4 g) was slowly added dropwise thereto at 0° C. The reaction temperature was increased to 40° C., and the mixture was refluxed and stirred for 3 hours. When the reaction was completed, the reaction was quenched with water at 0° C., and the reaction solution was extracted with MC three times. The obtained filtrate was dried with anhydrous magnesium sulfate, filtered, and distilled at reduced pressure to obtain Intermediate 280-1 (3.2 g, yield: 54%). The produced compound was identified to be Intermediate 280-1 by using LC-MS. ($C_{37}H_{38}ClN_3O$—$_2$, calculated value: 591.27, measured value: 591.28).

Synthesis of Compound 280

Compound 280 (2.4 g, yield: 67%) was obtained in the same manner as the synthesis of Intermediate 24-3 except that Intermediate 280-1 (3.2 g) and 2-ethylhexan-1-ol (0.7 g) were used. The produced compound was identified to be Compound 280 by using LC-MS. ($C_{45}H_{55}N_3O_3$, calculated value: 685.42, measured value: 685.43).

(14) Synthesis of Compound 295 of Compound Group 2

Compound 295 of Compound Group 2 of the light absorber according to an example may be synthesized by Reaction Scheme 2-14 below, for example.

Reaction Scheme 2-14

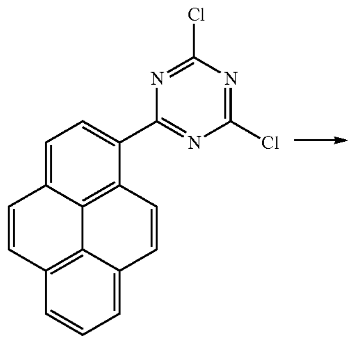

15-2

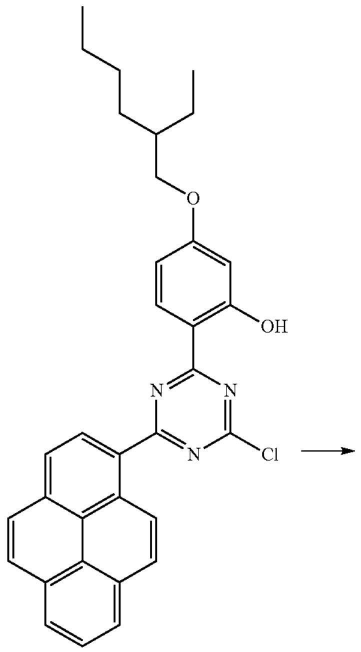

295-1

-continued

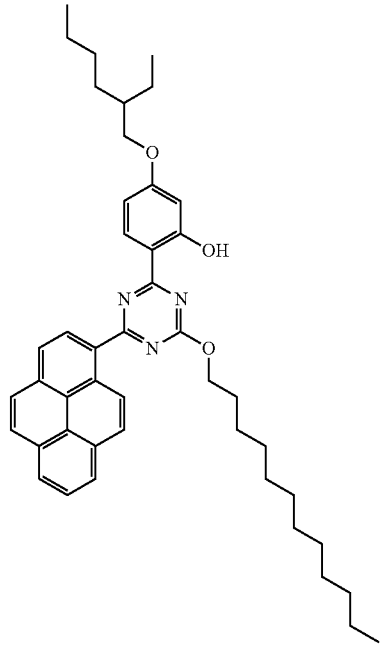

295

Synthesis of Intermediate 295-1

Intermediate 295-1 (3.7 g, yield: 68%) was obtained in the same manner as the synthesis of Intermediate 280-1 except that 3-((2-ethylhexyl)oxy)phenol (2.2 g) was used. The produced compound was identified to be Intermediate 295-1 by using LC-MS. ($C_{33}H_{30}ClN_3O$—$_2$, calculated value: 535.2, measured value: 535.21).

Synthesis of Compound 295

Compound 295 (3.9 g, yield: 84%) was obtained in the same manner as the synthesis of Intermediate 24-3 except that Intermediate 295-1 (3.7 g) and n-dodecanol (1.3 g) were used. The produced compound was identified to be Compound 295 by using LC-MS. ($C_{45}H_{55}N_3O_3$, calculated value: 685.42, measured value: 685.43).

(15) Synthesis of Compound 299 of Compound Group 2

Compound 299 of Compound Group 2 of the light absorber according to an example may be synthesized by Reaction Scheme 2-15 below, for example.

Reaction Scheme 2-15

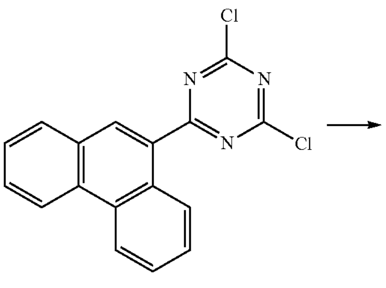

24-2

-continued

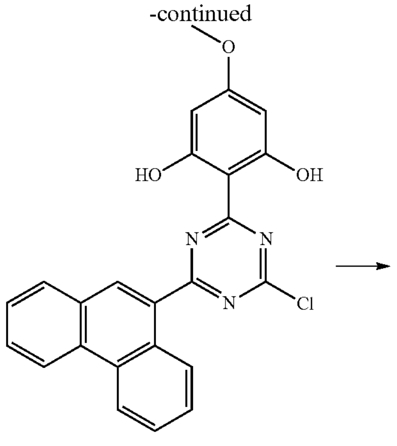

299-1

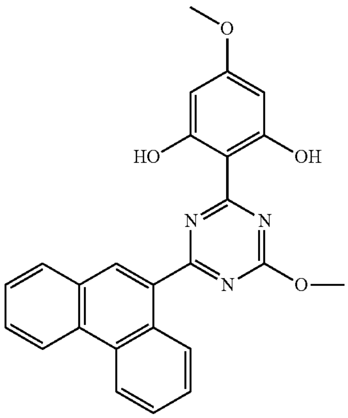

299

Synthesis of Intermediate 299-1

Intermediate 299-1 (3 g, yield: 71%) was obtained in the same manner as the synthesis of Intermediate 280-1 except that Intermediate 24-2 and 5-methoxybenzene-1,3-diol (1.4 g) were used. The produced compound was identified to be Intermediate 299-1 by using LC-MS. ($C_{24}H_{16}ClN_3O$—$_3$, calculated value: 429.09, measured value: 429.12)

Synthesis of Compound 299

Compound 299 (2.3 g, yield: 76%) was obtained in the same manner as the synthesis of Intermediate 2-4 except that Intermediate 299-1 (3 g) and 2-ethylhexan-1-ol (0.74 g) were used. The produced compound was identified to be Compound 299 by using LC-MS. ($C_{25}H_{19}N_3O_4$, calculated value: 425.14, measured value: 425.15)

(16) Synthesis of Compound 320 of Compound Group 2

Compound 320 of Compound Group 2 of the light absorber according to an example may be synthesized by Reaction Scheme 2-16 below, for example.

Reaction Scheme 2-16

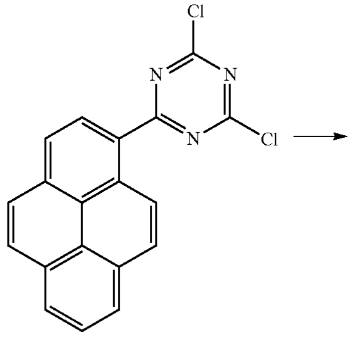

15-2

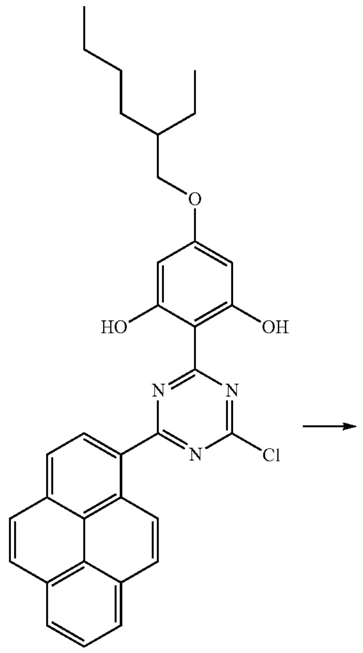

320-1

-continued

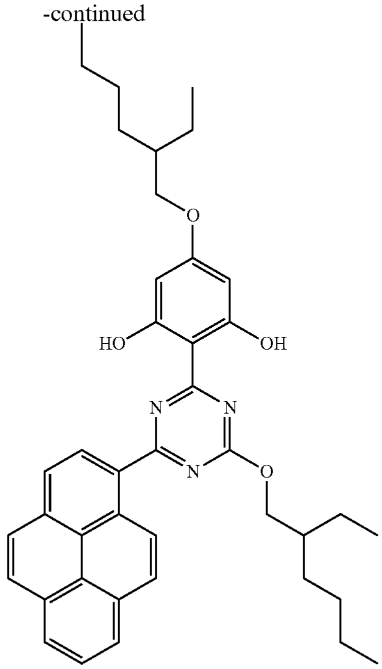

320

Synthesis of Intermediate 320-1

Intermediate 320-1 (3.1 g, yield: 57%) was obtained in the same manner as the synthesis of Intermediate 280-1 except that 5-((2-ethylhexyl)oxy)benzene-1,3-diol (2.4 g) was used. The produced compound was identified to be Intermediate 320-1 by using LC-MS. ($C_{33}H_{30}ClN_3O—_3$, calculated value: 551.20, measured value: 551.23).

Synthesis of Compound 320

Compound 320 (2.4 g, yield: 66%) was obtained in the same manner as the synthesis of Intermediate 24-3 except that Intermediate 320-1 (3.1 g) and 2-ethylhexan-1-ol (0.74 g) were used. The produced compound was identified to be Compound 320 by using LC-MS. ($C_{41}H_{47}N_3O_4$, calculated value: 645.36, measured value: 645.39).

(17) NMR Data of Compounds of Compound Group 2

NMR data on the Example Compounds synthesized by the above-described synthesis method are listed in Table 2 below:

TABLE 2

| Example Compounds | NMR (400 hz) |
|---|---|
| Compound 2 of Compound Group 2 | 9.61(brs, 1H), 9.27(s, 1H), 9.08(d, 1H), 8.84(d, 1H), 8.17(d, 1H), 7.92(m, 2H), 7.81-7.54(m, 6H), 7.32(t, 1H), 7.06(d, 1H), 7.02-7.00(m, 2H), 3.85(s, 3H) |
| Compound 15 of Compound Group 2 | 9.61(brs, 1H), 8.52(d, 1H), 8.31(d, 1H), 8.16(d, 1H), 8.08-8.04(m, 4H), 7.92(m, 1H), 7.7-7.55(m, 2H), 7.32(t, 1H), 7.06-7.00(m, 2H), 5.24(m, 1H), 1.35(d, 2H) |
| Compound 20 of Compound Group 2 | 15.30(s, 1H), 8.73(d, 1H), 8.31(d, 1H), 8.21-7.88 (m, 7H), 7.86(d, 1H), 7.40(m, 1H), 7.08-7.00(m,2H) 4.64(t, 2H), 2.06(m, 2H), 1.16(t, 3H) |
| Compound 24 of Compound Group 2 | 15.30(s, 1H), 9.01(s, 1H), 8.81(d, 1H), 8.46(d, 1H), 7.97-7.95(m, 2H), 7.79-7.36(m, 5H), 7.07-7.00(m, 2H), 4.67(t, 2H), 1.94-1.85(m, 2H), 1.68-1.58(m, 2H), 1.29-1.23(m, 4H) 0.97-0.98(m, 3H) |
| Compound 35 of Compound Group 2 | 15.30(s, 1H), 8.74(d, 1H), 8.31(d, 1H), 8.19-7.86(m, 8H), 7.40(m, 1H), 7.08-7.00(m, 2H), 4.29(d, 1H), 4.17(d, 1H), 2.00-1.74(m, H), 1.68-1.59(m, H), 1.43-1.18(m, H), 0.89(q, 3H) |
| Compound 40 of Compound Group 2 | 15.30(s, 1H), 8.73(d, 1H), 8.31(d, 1H), 8.22-7.94(m, 6H), 7.88(d, 1H), 7.40-7.34(m, 1H), 7.10-7.00(m, 2H), 5.86(m, 1H), 2.26-2.16(m, 2H), 1.93-1.74(m, 4H), 1.72-1.62(m, 2H) |
| Compound 75 of Compound Group 2 | 15.30(s, 2H), 8.75(d, 1H), 8.31(d, 1H), 8.16-8.02(m, 6H), 7.86(d, 1H), 7.16(t, 1H), 6.17(d, 2H), 4.28(ab, 2H), 2.00-1.80(m, 2H), 1.71-1.60(m, 1H), 1.48-1.19(m, 6H), 0.91(t, 3H), 0.84(t, 3H) |
| Compound 94 of Compound Group 2 | 12.81(s, 3H), 9.01(m, 1H), 8.85-8.76(m, 2H), 8.46-8.44(m, 1H), 7.98-7.95(m, 1H), 7.82-7.77(m, 1H), 7.69-7.60(m, 2H), 7.56(dt, 1H), 5.88(s, 2H), 5.50(m, 1H), 1.37(d, 3H) |
| Compound 102 of Compound Group 2 | 15.30(s, 1H), 9.46(s, 1H), 8.76-8.65(m, 3H), 8.02-7.96(m, 2H), 7.81(t, 1H), 7.65-7.56(m, 3H), 7.40(m, 1H), 7.08-7.00(m, 2H), 4.67(t, 2H), 1.95-1.91(m, 2H), 1.66-1.58(m, 2H), 1.32-1.24(m, 4H), 0.96-0.87(m, 3H) |
| Compound 154 of Compound Group 2 | 10.90(s, 2H), 9.01(s, 1H), 8.81(d, 2H), 8.46(m, 1H), 8.22(d, 1H), 7.98(d, 1H), 7.78(t, 1H), 7.66-7.53(m, 3H), 6.53(s, 1H), 6.31(d, 1H), 4.36(ab, 2H), 2.20(m, 1H), 1.43-1.20(m, 6H), 0.96-0.87(m, 6H) |
| Compound 169 of Compound Group 2 | 15.30(s, 1H), 8.65(m, 1H), 8.63(m, 1H), 8.36(m, 1H), 8.23-8.20(m, 1H), 8.14(s, 1H), 8.07-8.00(m, 2H), 7.91-7.86(m, 1H), 7.42-7.35(m, 3H), 7.07(t, 1H), 7.02(dd, 1H), 4.01 (s, 3H) |
| Compound 227 of Compound Group 2 | 15.30(s, 1H), 8.62(s, 1H), 8.41(td, 1H), 7.98(dd, 1H), 7.77(d, 1H), 7.74(m, 1H), 7.69(dt, 1H), 7.48-7.32(m, 5H), 7.26(dt, H), 7.16(dt, 1H), 7.06(t, 1H), 7.00(dd, 1H), 4.57(t, 2H), 1.90(p, 2H), 1.68(s, 6H), 1.58(p, 2H), 1.35-1.22(m, 14H), 0.87(t, 3H) |

TABLE 2-continued

| Example Compounds | NMR (400 hz) |
|---|---|
| Compound 280 of Compound Group 2 | 15.30(s, 1H), 8.74(s, 1H), 8.31(d, 1H), 8.19(d, 1H), 8.15-8.08(m, 4H), 8.01(m, 1H), 7.88(d, 1H), 7.86(dd, 1H), 6.33(m, 1H), 4.30(ab, 2H), 3.89(t, 2H), 1.99-1.90(m, 1H), 1.85-1.75(m, 3H), 1.69-1.60(m, 1H), 1.51-1.19(m, 24H), 0.91-0.83(m, 9H) |
| Compound 295 of Compound Group 2 | 15.30(s, 1H), 8.74(d, 1H), 8.31(d, 1H), 8.19-8.08(m, 5H), 8.02(t, 1H), 7.88(d, 1H), 7.83(dd, 1H), 6.36(dd, H), 6.31(t, 1H), 4.59(t, 2H), 4.09(dd, 1H), 3.88(d, 1H), 1.94-1.74(m, 4H), 1.63-1.51(m, 3H), 1.39-1.15(m, 22H), 0.90-0.85(m, 9H) |
| Compound 299 of Compound Group 2 | 15.30(s, 2H), 9.04(m, 1H), 8.81-8.79(m, 2H), 8.46-8.44(m, 2H), 7.98-7.96(m, 1H), 7.82(t, 1H), 7.69-7.52(m, 3H), 5.77(s, 2H), 4.01(s, 3H), 3.77(s, 3H) |
| Compound 320 of Compound Group 2 | 15.30(s, 2H), 8.73(d, 1H), 8.31(d, 1H), 8.19-8.13(m, 3H), 8.10(t, 1H), 8.02-7.99(m, 2H) 5.75(s, 2H), 4.29(d, 1H), 4.18(m, 1H), , 4.13-4.12(m, H), 4.11(d, 1H), 3.95(dd, 1H) 1.99-1.90(m, 2H), 1.87-1.72(m, 2H), 1.69-1.54(m, 2H), 1.42-1.14(m, 12H), 0.91-0.85(m, 12H) |

2. Absorbance Evaluation of Light Absorber

To evaluate the absorbance of the light absorber of an example, the transmittance of the organic film including the light absorber of an example was evaluated at each of 405 nm wavelength and 430 nm wavelength. The light absorber compounds used in Examples and Comparative Examples are listed in Table 3.

TABLE 3

Compound Group 1 Compound 2

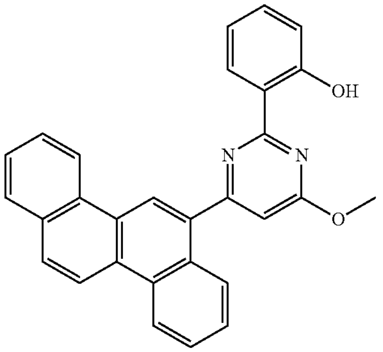

2

Compound Group 1 Compound 15

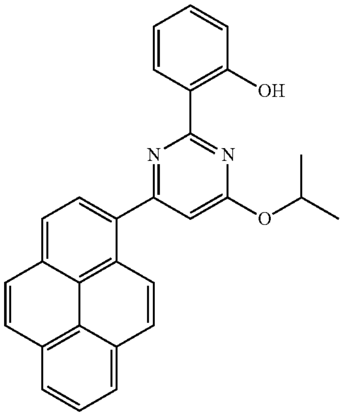

15

TABLE 3-continued

Compound Group 1 Compound 25

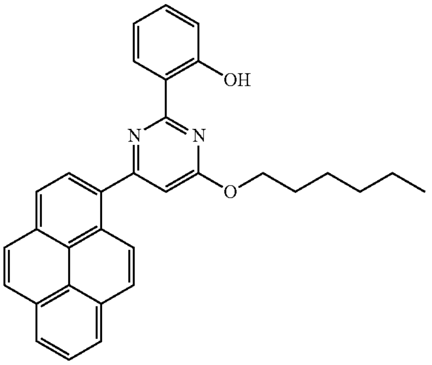

25

Compound Group 1 Compound 36

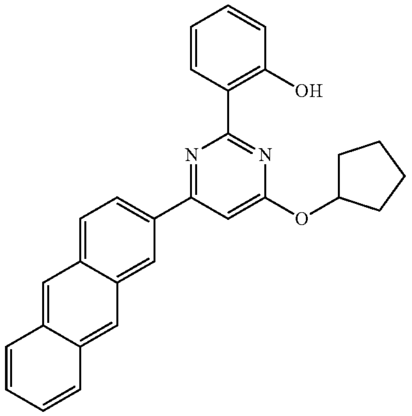

36

TABLE 3-continued
Compound Group 1 Compound 56
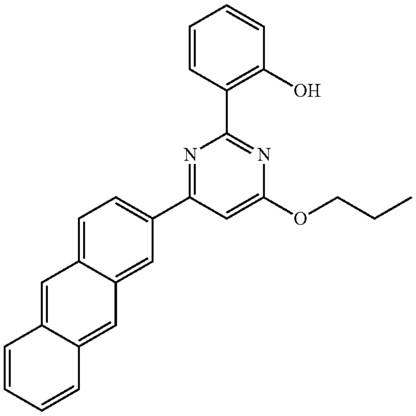
56
Compound Group 1 Compound 78
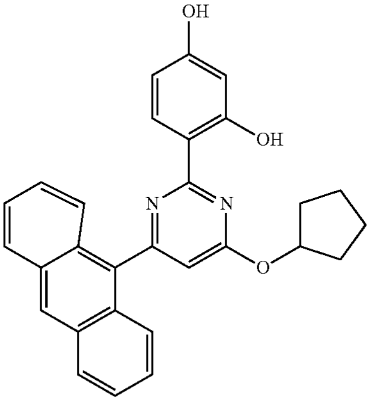
78
Compound Group 1 Compound 95
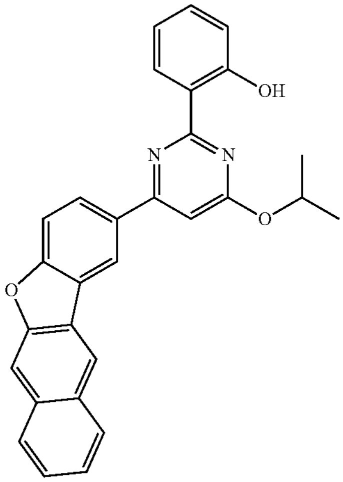
95
TABLE 3-continued
Compound Group 1 Compound 115
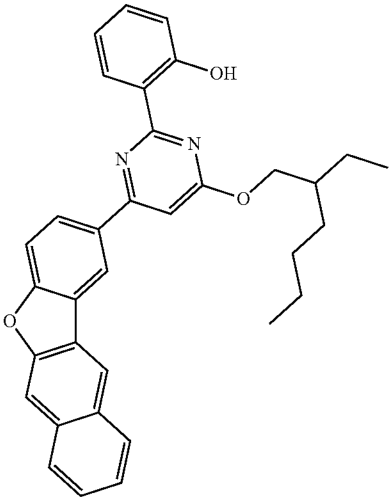 [SMILES: CCCCC(CC)COc1cc(-c2ccc3oc4cc5ccccc5cc4c3c2)nc(-c2ccccc2O)n1]
115
Compound Group 1 Compound 148
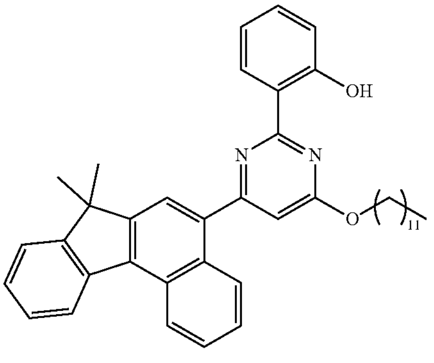
148
Compound Group 1 Compound 177
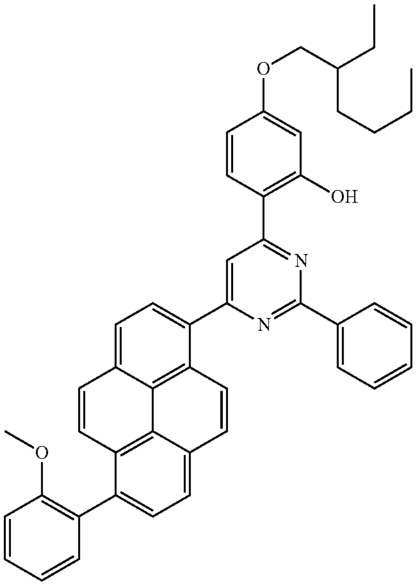 [SMILES: CCCCC(CC)COc1ccc(-c2cc(-c3ccc4ccc5c(-c6ccccc6OC)ccc6ccc3c4c65)nc(-c3ccccc3)n2)c(O)c1]
177

TABLE 3-continued
Compound Group 2 Compound 2
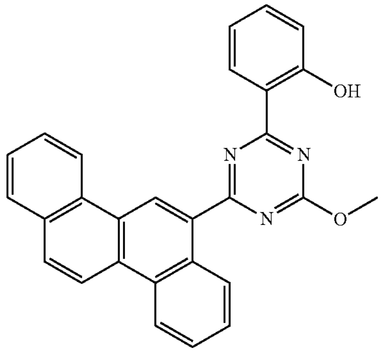 [SMILES: COc1nc(-c2ccccc2O)nc(-c2cc3c4ccccc4ccc3c3ccccc23)n1]
2
Compound Group 2 Compound 15
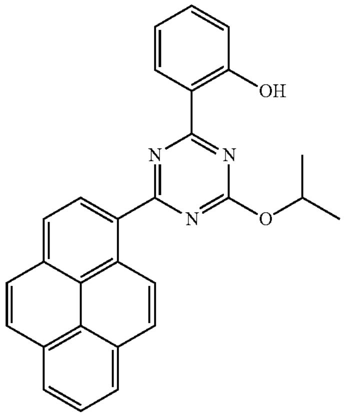 [SMILES: CC(C)Oc1nc(-c2ccccc2O)nc(-c2ccc3ccc4cccc5ccc2c3c45)n1]
15
Compound Group 2 Compound 20
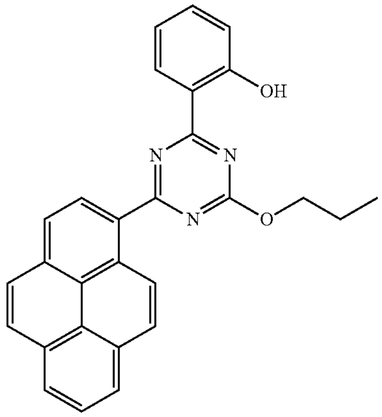 [SMILES: CCCOc1nc(-c2ccccc2O)nc(-c2ccc3ccc4cccc5ccc2c3c45)n1]
20
TABLE 3-continued
Compound Group 2 Compound 24
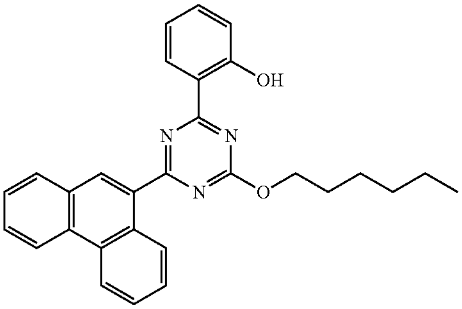 [SMILES: CCCCCCOc1nc(-c2ccccc2O)nc(-c2cc3ccccc3c3ccccc23)n1]
24
Compound Group 2 Compound 35
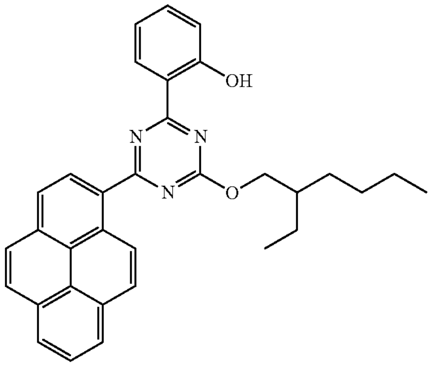 [SMILES: CCCCC(CC)COc1nc(-c2ccccc2O)nc(-c2ccc3ccc4cccc5ccc2c3c45)n1]
35
Compound Group 2 Compound 40
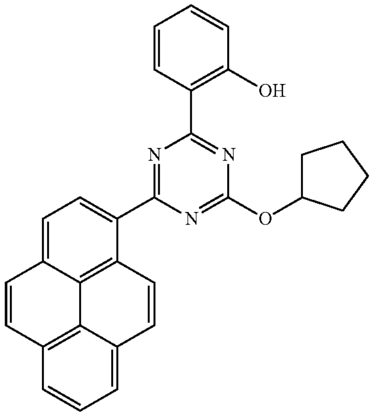 [SMILES: Oc1ccccc1-c1nc(OC2CCCC2)nc(-c2ccc3ccc4cccc5ccc2c3c45)n1]
40
Compound Group 2 Compound 75
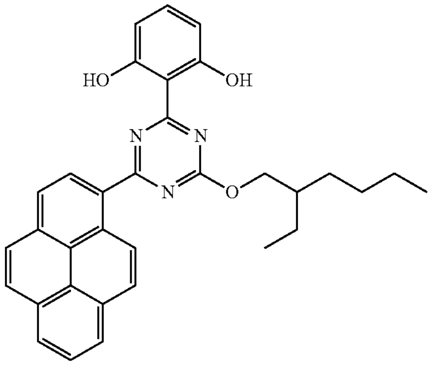 [SMILES: CCCCC(CC)COc1nc(-c2c(O)cccc2O)nc(-c2ccc3ccc4cccc5ccc2c3c45)n1]
75

TABLE 3-continued
Compound Group 2 Compound 94
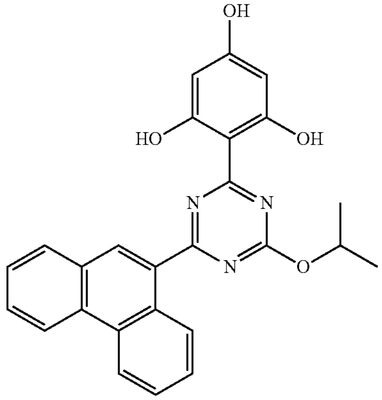 [SMILES: CC(C)Oc1nc(-c2c(O)cc(O)cc2O)nc(-c2cc3ccccc3c3ccccc23)n1]
94
Compound Group 2 Compound 102
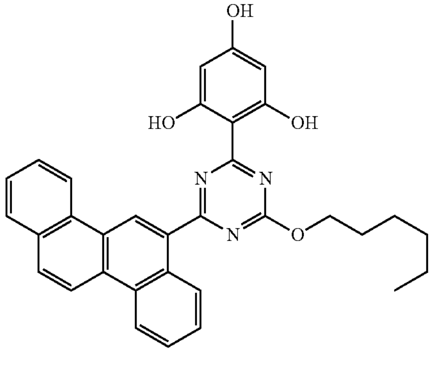 [SMILES: CCCCCCOc1nc(-c2c(O)cc(O)cc2O)nc(-c2cc3c4ccccc4ccc3c3ccccc23)n1]
102
Compound Group 2 Compound 154
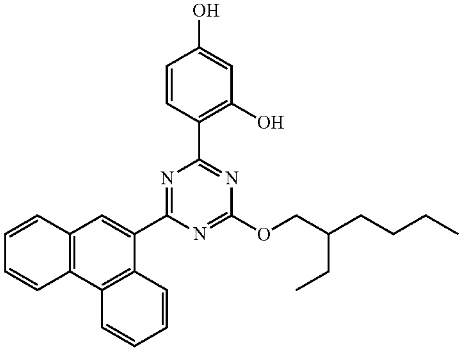 [SMILES: CCCCC(CC)COc1nc(-c2ccc(O)cc2O)nc(-c2cc3ccccc3c3ccccc23)n1]
154
Compound Group 2 Compound 169
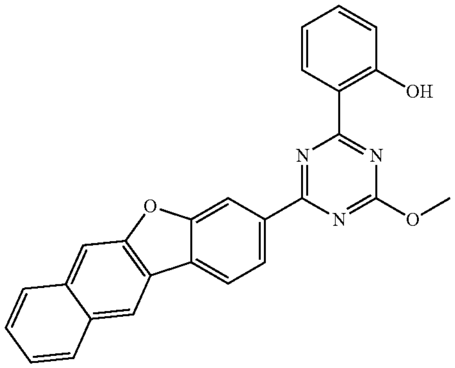 [SMILES: COc1nc(-c2ccc3c(c2)oc2cc4ccccc4cc23)nc(-c2ccccc2O)n1]
19
TABLE 3-continued
Compound Group 2 Compound 227
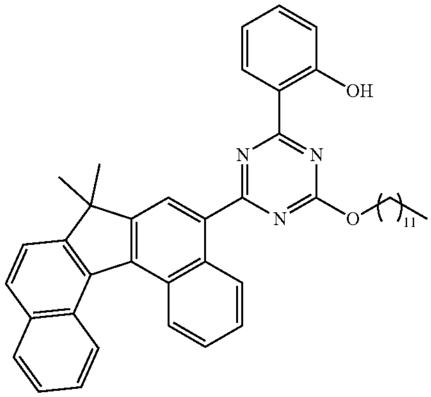
227
Compound Group 2 Compound 280
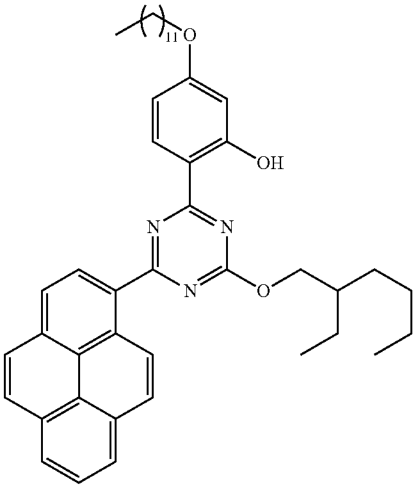
280
Compound Group 2 Compound 295
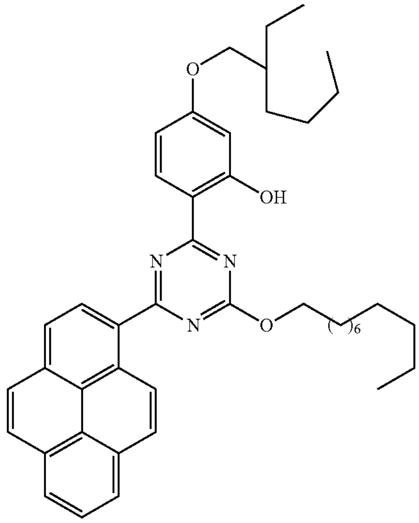
295

TABLE 3-continued

| | |
|---|---|
| Compound Group 2 Compound 299 | 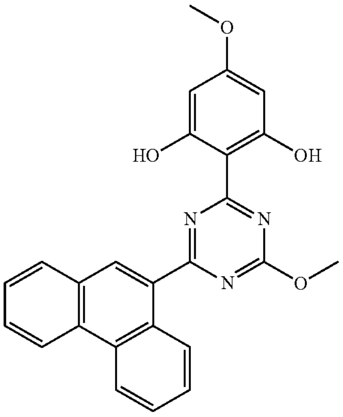 [SMILES: COc1cc(O)c(-c2nc(OC)nc(-c3cc4ccccc4c4ccccc34)n2)c(O)c1] 299 |
| Compound Group 2 Compound 320 | 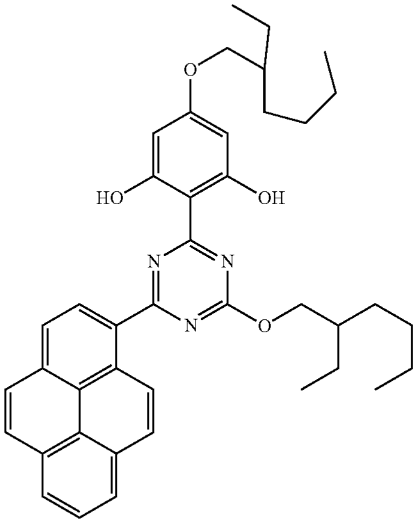 [SMILES: CCCCC(CC)COc1cc(O)c(-c2nc(OCC(CC)CCCC)nc(-c3ccc4ccc5cccc6ccc3c4c56)n2)c(O)c1] 320 |
| Comparative Example Compound C1 | 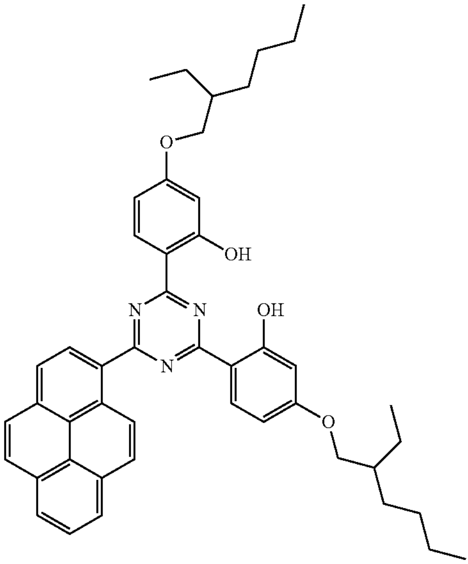 [SMILES: CCCCC(CC)COc1ccc(-c2nc(-c3ccc(OCC(CC)CCCC)cc3O)nc(-c3ccc4ccc5cccc6ccc3c4c56)n2)c(O)c1] C1 |

TABLE 3-continued

| | |
|---|---|
| Comparative Example Compound C2 | 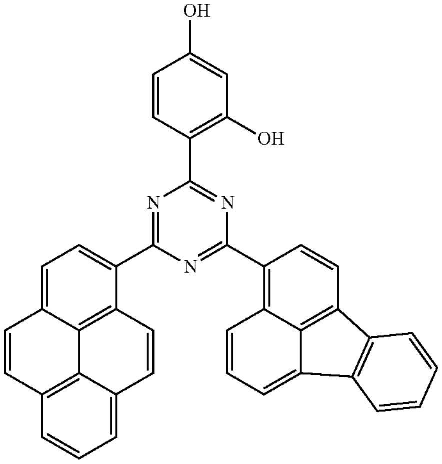 C2 |
| Comparative Example Compound C3 | 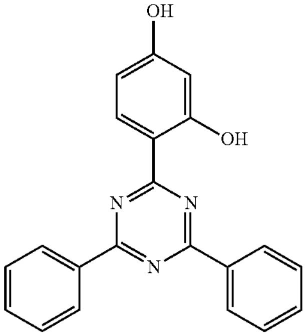 C3 |

Table 4 shows the light transmittance at each of 405 nm wavelength and 430 nm in Examples and Comparative Examples, and the evaluation results listed in Table 4 show transmittance in the case where the polarizing member was added on the organic film including Example and Comparative Example Compounds. The transmittance was measured by UV-Vis spectrophotometer (Lambda 650, PerkinElmer Inc.), and the measured wavelength range was 300-780 nm.

TABLE 4

| Division | Example Compounds | Transmittance (%) (@ 405 nm) | Transmittance (%) (@ 430 nm) |
|---|---|---|---|
| Example 1-1 | Compound Group 1 Compound 2 | 3.6 | 24.2 |
| Example 1-2 | Compound Group 1 Compound 15 | 3.4 | 33.3 |
| Example 1-3 | Compound Group 1 Compound 25 | 3.5 | 34.6 |
| Example 1-4 | Compound Group 1 Compound 36 | 3.0 | 30.0 |
| Example 1-5 | Compound Group 1 Compound 56 | 2.9 | 31.5 |
| Example 1-6 | Compound Group 1 Compound 78 | 2.6 | 27.5 |
| Example 1-7 | Compound Group 1 Compound 95 | 2.3 | 24.3 |
| Example 1-8 | Compound Group 1 Compound 115 | 2.2 | 21.2 |
| Example 1-9 | Compound Group 1 Compound 148 | 2.4 | 23.2 |

TABLE 4-continued

| Division | Example Compounds | Transmittance (%) (@ 405 nm) | Transmittance (%) (@ 430 nm) |
|---|---|---|---|
| Example 1-10 | Compound Group 1 Compound 177 | 2.1 | 28.5 |
| Example 2-1 | Compound Group 2 Compound 2 | 3.6 | 24.2 |
| Example 2-2 | Compound Group 2 Compound 15 | 3.4 | 33.3 |
| Example 2-3 | Compound Group 2 Compound 20 | 3.5 | 34.6 |
| Example 2-4 | Compound Group 2 Compound 24 | 3.3 | 31.5 |
| Example 2-5 | Compound Group 2 Compound 35 | 3.0 | 30.0 |
| Example 2-6 | Compound Group 2 Compound 40 | 2.6 | 27.5 |
| Example 2-7 | Compound Group 2 Compound 75 | 2.3 | 24.3 |
| Example 2-8 | Compound Group 2 Compound 94 | 2.2 | 21.2 |
| Example 2-9 | Compound Group 2 Compound 102 | 2.4 | 23.2 |
| Example 2-10 | Compound Group 2 Compound 154 | 3.5 | 27.2 |
| Example 2-11 | Compound Group 2 Compound 169 | 4.0 | 33.2 |
| Example 2-12 | Compound Group 2 Compound 227 | 3.6 | 31.2 |
| Example 2-13 | Compound Group 2 Compound 280 | 3.4 | 29.6 |
| Example 2-14 | Compound Group 2 Compound 295 | 3.5 | 28.6 |
| Example 2-15 | Compound Group 2 Compound 299 | 2.7 | 29.3 |
| Example 2-16 | Compound Group 2 Compound 320 | 2.5 | 30.2 |
| Comparative Example 1 | Comparative Example Compound C1 | 0.8 | 5.3 |
| Comparative Example 2 | Comparative Example Compound C2 | 0.5 | 3.2 |
| Comparative Example 3 | Comparative Example Compound C3 | 1.5 | 6.08 |

Referring to the results of Table 4, it may be confirmed that the Examples including the organic films using the light absorbers according to an example show high transmittance values at 430 nm compared to Comparative Examples. That is, Examples show higher transmittance values in the case where the polarizing members are added on the organic films including Example and Comparative Example Compounds, and thus the transmittances at 430 nm of the organic films included Examples are higher than those of the organic films included in Comparative Examples.

Referring to the results of Table 4, it may be confirmed that Examples have relatively high transmittance values at a wavelength of 430 nm, and thus the transmittances of light in a blue wavelength region are higher than those of Comparative Examples. Therefore, it may be confirmed that Examples show low transmittance values at a wavelength of 405 nm, and thus UV light or a portion of visible light is effectively absorbed in the organic film. Moreover, it may be confirmed that Examples show relatively high transmittance values at a wavelength of 430 nm, and thus light in a blue wavelength region is minimally absorbed in the organic film, thereby minimizing the reduction of efficiency emitted from the light-emitting device. That is, Examples have similar absorption rate of UV light to Comparative Examples, but have an excellent reliability characteristic and reduce the degree of the light absorption in the blue wavelength region, thereby exhibiting excellent display quality compared to Comparative Examples.

The light absorber of an example may include a hexagonal heterocycle containing two or more nitrogen atoms as a ring-forming atom and three different substituents which are substituted at the hexagonal heterocycle, thereby efficiently absorbing UV light and a portion of visible light. That is, the light absorber of an example may include the pyrimidine core or the triazine core, the first substituent that is a phenyl group substituted with at least one hydroxyl group, the second substituent that is a condensed ring group in which three or more rings are condensed, and the third substituent that is a substituted or unsubstituted oxy group or a substituted or unsubstituted thio group, to form an organic film having a transmittance of 10% or less at 405 nm wavelength, a transmittance of 70% or more at 430 nm wavelength, and a transmittance of 97% or more at 450 nm wavelength.

The light absorber according to an embodiment of the present invention has excellent degree of the light absorption with respect to UV light and a portion of visible light, and the light-emitting device of the display apparatus including the same in the encapsulation member may exhibit good efficiency and an excellent service life characteristic because the deterioration due to external light is efficiently prevented.

Although the inventive concept has been described with reference to a preferred embodiment of the inventive concept, it will be understood that the inventive concept should not be limited to these preferred embodiments but various changes and modifications can be made by those skilled in the art without departing from the spirit and scope of the inventive concept.

Accordingly, the technical scope of the inventive concept is not intended to be limited to the contents set forth in the detailed description of the specification, but is intended to be defined by the appended claims.

INDUSTRIAL APPLICABILITY

The present invention relates to a light absorber having excellent light absorption with respect to UV light and a portion of visible light, and to a light-emitting device including the same in the encapsulation member and having good efficiency and an excellent service life characteristic, and industrial applicability is high.

The invention claimed is:

1. A display apparatus comprising:

a light-emitting device comprising a first electrode, a second electrode facing the first electrode, and a plurality of organic layers between the first electrode and the second electrode; and an encapsulation member on the light-emitting device and comprising a light absorber, wherein the light absorber comprises a hexagonal heterocycle comprising two or more nitrogen atoms as ring-forming atoms, and first to third substituents substituted at the hexagonal heterocycle, the first to third substituents being different from one another, the first substituent is a substituted phenyl group comprising at least one hydroxyl group, and the second substituent is a substituted or unsubstituted anthracene group, a substituted or unsubstituted phenanthrene, a substituted or unsubstituted pyrene group, a substituted or unsubstituted chrysene group, a substituted or unsubstituted dibenzofuran derivative, a substituted or unsubstituted carbazole derivative, or a substituted or unsubstituted fluorene derivative, wherein a substituent of the substituted or unsubstituted dibenzofuran derivative, a substituent of the substituted or unsubstituted carbazole derivative, and a substituent of the substituted or unsubstituted fluorene derivative are each independently a hydrogen atom, an alkyl group having 1 to 20 carbon atoms, an alkenyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or adjacent groups are bonded to each other to form a ring, and wherein when the hexagonal heterocycle comprises three nitrogen atoms as ring-forming atoms, then the third substituent is a substituted or unsubstituted alkoxy group having 1 to 20 carbon atoms, a substituted or unsubstituted aryloxy group having 6 to 30 ring-forming carbon atoms, a substituted or unsubstituted alkylthio group having 1 to 20 carbon atoms, or a substituted or unsubstituted arylthio group having 6 to 30 ring-forming carbon atoms.

2. The display apparatus of claim 1, wherein the encapsulation member comprises at least one organic film and at least one inorganic film, and the at least one organic film comprises the light absorber.

3. The display apparatus of claim 2, wherein the at least one organic film and the at least one inorganic film are alternately laminated, and the at least one organic film comprises:

a first organic film to absorb light in a first wavelength region; and a second organic film to absorb light in a second wavelength region different from the light in the first wavelength region.

4. The display apparatus of claim 1, wherein the encapsulation member covers the light-emitting device.

5. The display apparatus of claim 1, further comprising a polarizing member on the encapsulation member.

6. The display apparatus of claim 1, wherein the encapsulation member comprises:

a first inorganic film adjacent to the second electrode;

a second inorganic film on the first inorganic film; and an organic film between the first inorganic film and the second inorganic film, the organic film comprising the light absorber, wherein the organic film has a transmittance of 10% or less at about 405 nm wavelength, a transmittance of 70% or more at about 430 nm wavelength, and a transmittance of 97% or more at about 450 nm wavelength.

7. The display apparatus of claim 1, wherein the plurality of organic layers comprises:

a hole transport region on the first electrode;

an emission layer on the hole transport region; and an electron transport region on the emission layer.

8. The display apparatus of claim 1, further comprising a light blocking layer on the encapsulation member.

9. The display apparatus of claim 1, wherein the hexagonal heterocycle is triazine or pyrimidine.

10. The display apparatus of claim 1, wherein the first substituent is represented by at least one among Formulae H1 to H5:

H1

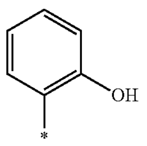

-continued

H2

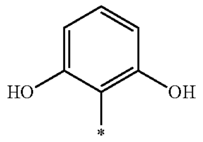

H3

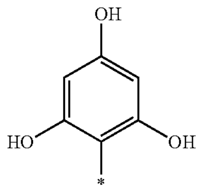

H4

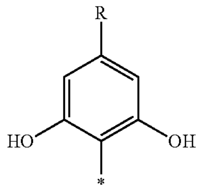

H5

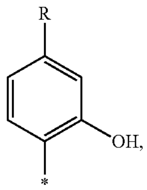

and wherein R, in Formulae H4 and H5, is a substituted or unsubstituted alkoxy group having 1 to 20 carbon atoms.

11. The display apparatus of claim 1, wherein the light absorber is represented by Formula 1 or Formula 2:

[Formula 1]

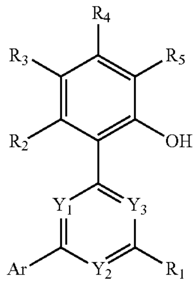

[Formula 2]

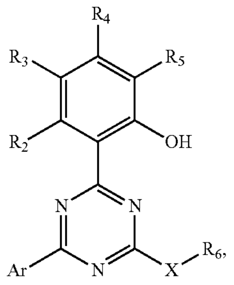

and wherein, in Formula 1 and Formula 2,

Ar is a substituted or unsubstituted anthracene group, a substituted or unsubstituted phenanthrene, a substituted or unsubstituted pyrene group, a substituted or unsubstituted chrysene group, a substituted or unsubstituted dibenzofuran derivative, a substituted or unsubstituted carbazole derivative, or a substituted or unsubstituted fluorene derivative, a substituent of the substituted or unsubstituted dibenzofuran derivative, a substituent of the substituted or unsubstituted carbazole derivative, and a substituent of the substituted or unsubstituted fluorene derivative are each independently a hydrogen atom, an alkyl group having 1 to 20 carbon atoms, an alkenyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or adjacent groups are bonded to each other to form a ring, and $R_2$ to $R_5$ are each independently a hydrogen atom, a deuterium atom, a halogen atom, a cyano group, a substituted or unsubstituted alkyl group having 1 to 30 carbon atoms, a substituted or unsubstituted alkoxy group having 1 to 20 carbon atoms, a substituted or unsubstituted aryloxy group having 6 to 30 ring-forming carbon atoms, a substituted or unsubstituted alkylamine group having 1 to 30 carbon atoms, a substituted or unsubstituted arylamine group having 6 to 30 ring-forming carbon atoms, a substituted or unsubstituted heterocyclic group having 2 to 30 ring-forming carbon atoms, or a substituted or unsubstituted aryl group having 6 to 30 ring-forming carbon atoms, in Formula 1, two among $Y_1$ to $Y_3$ are N and the remaining one among $Y_1$ to $Y_3$ is CH, and $R_1$ is a substituted or unsubstituted alkoxy group having 1 to 20 carbon atoms, a substituted or unsubstituted aryloxy group having 6 to 30 ring-forming carbon atoms, a substituted or unsubstituted alkylthio group having 1 to 20 carbon atoms, or a substituted or unsubstituted arylthio group having 6 to 30 ring-forming carbon atoms, and in Formula 2, X is O or S, and $R_6$ is a substituted or unsubstituted alkyl group having 1 to 30 carbon atoms, a substituted or unsubstituted heterocyclic group having 2 to 30 ring-forming carbon atoms, or a substituted or unsubstituted aryl group having 6 to 30 ring-forming carbon atoms.

12. The display apparatus of claim 11, wherein Formula 1 is represented by at least one among Formula 1-1 to Formula 1-4:

[Formula 1-1]

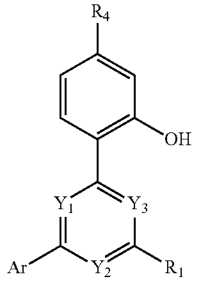

-continued

[Formula 1-2]

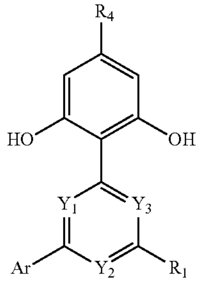

[Formula 1-3]

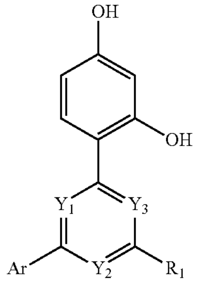

[Formula 1-4]

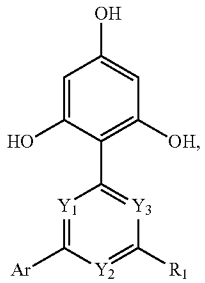

wherein, in Formula 1-1 to Formula 1-4, Ar, $Y_1$ to $Y_3$, $R_1$, and $R_4$ are the same as defined in Formula 1.

13. The display apparatus of claim 11, wherein Formula 2 is represented by at least one among Formula 2-1 to Formula 2-4:

[Formula 2-1]

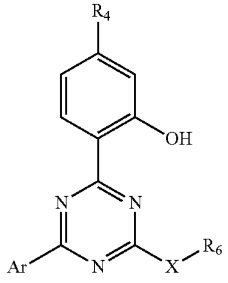

[Formula 2-2]

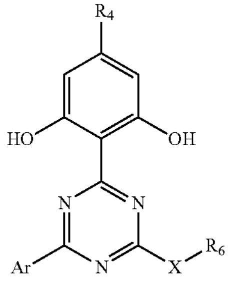

-continued

[Formula 2-3]

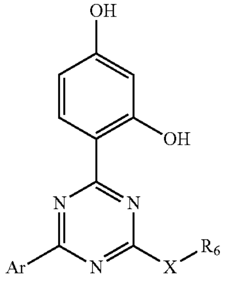

[Formula 2-4]

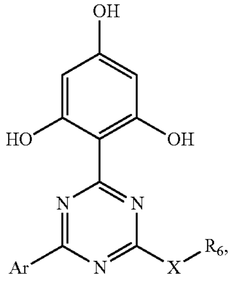

and wherein, in Formula 2-1 to Formula 2-4, X, Ar, $R_4$, and $R_6$ are the same as defined in Formula 2.

14. The display apparatus of claim 11, wherein Ar is represented by at least one among Ar-a to Ar-h:

Ar-a

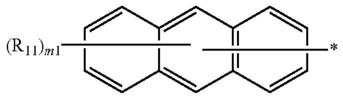

Ar-b

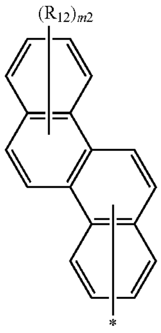

Ar-c

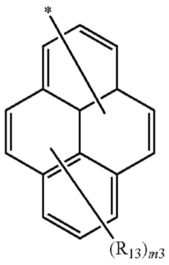

Ar-d

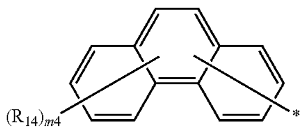

-continued

Ar-e

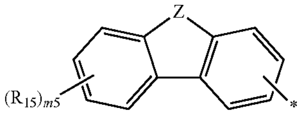

Ar-f

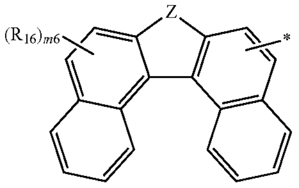

Ar-g

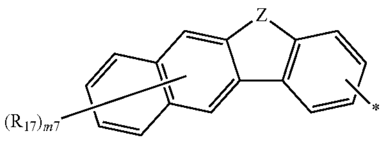

Ar-h

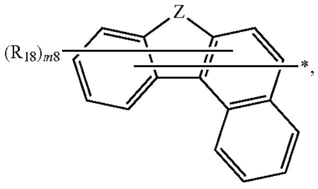

and wherein, in Ar-e to Ar-h, Z is O, S, $NR_a$, or $CR_bR_c$, and $R_a$ to $R_c$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and in Ar-a to Ar-h, $R_{11}$ to $R_{18}$ are each independently a hydrogen atom, a deuterium atom, a halogen atom, an alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and m1 to m8 are each independently an integer of 0 to 4.

15. The display apparatus of claim 11, wherein Formula 1 is represented by at least one among Formula 1-A to Formula 1-C:

[Formula 1-A]

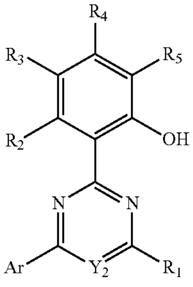

-continued
[Formula 1-B]
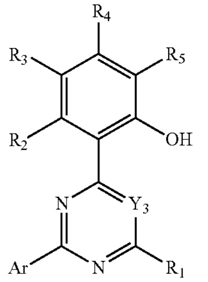
[Formula 1-C]
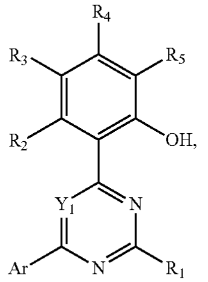
and
wherein, in Formula 1-A to Formula 1-C, $Y_1$ to $Y_3$, Ar, and $R_1$ to $R_5$ are the same as defined in Formula 1.
16. The display apparatus of claim 1, wherein the light absorber comprises at least one among the compounds represented by Compound Group 1 and Compound Group 2:
Compound Group 1
1
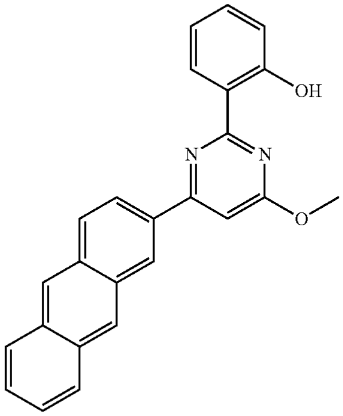
2
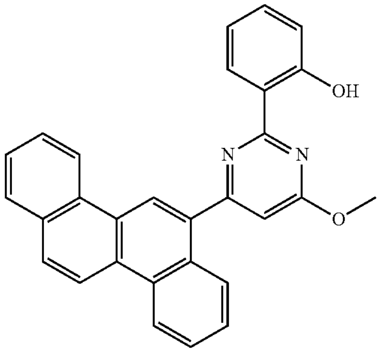
-continued
3
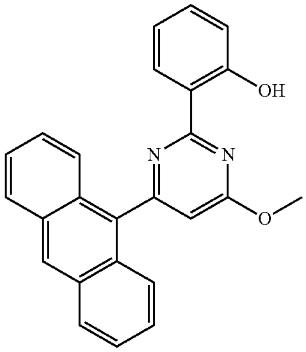
4
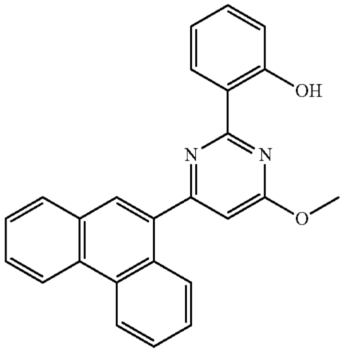
5
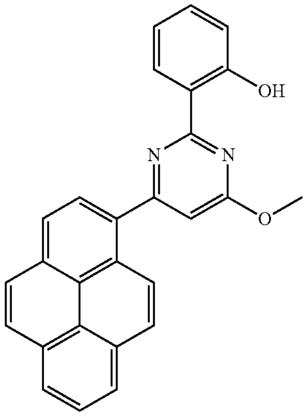
6
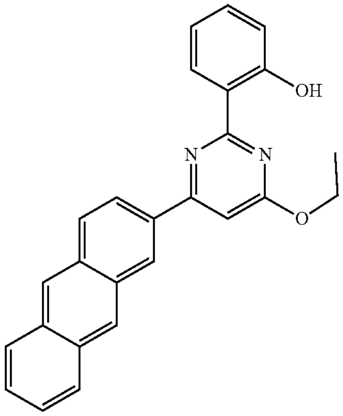

7
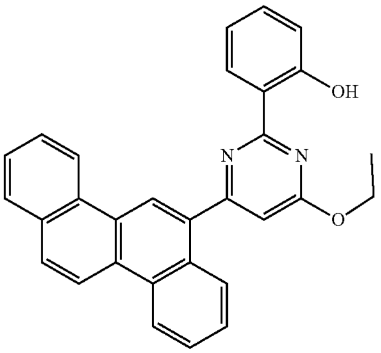
8
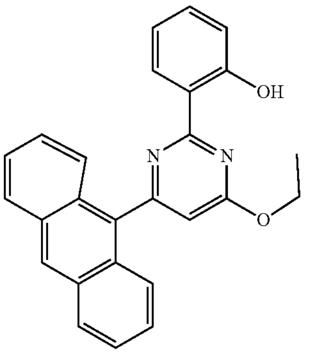
9
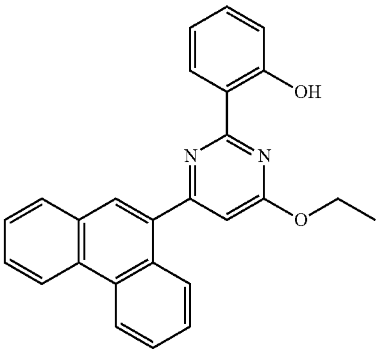
10
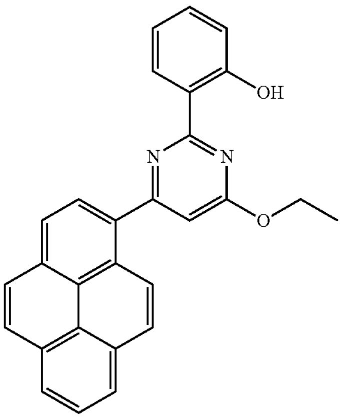
11
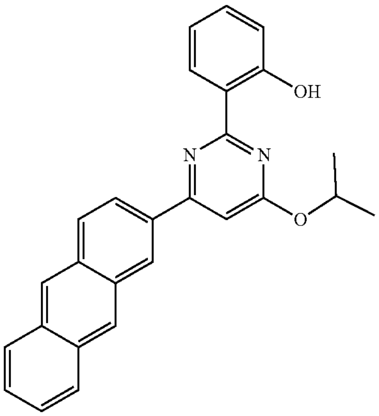
12
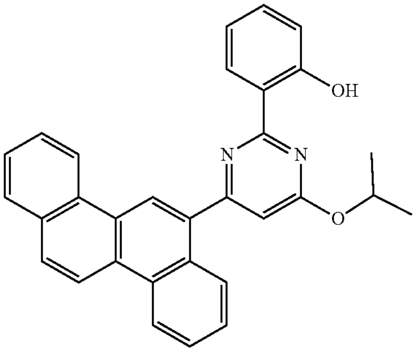
13
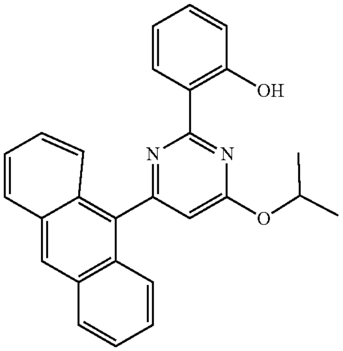
14
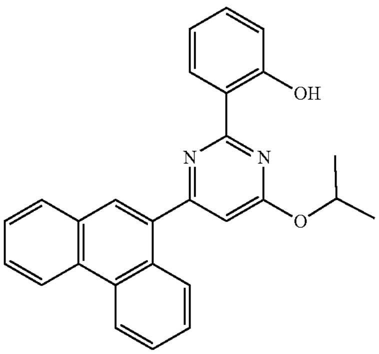

-continued
15
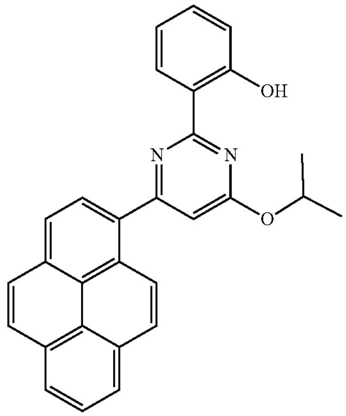
16
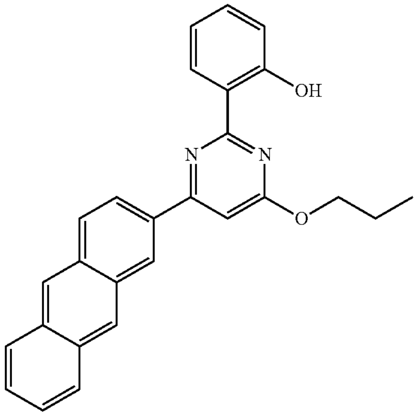
17
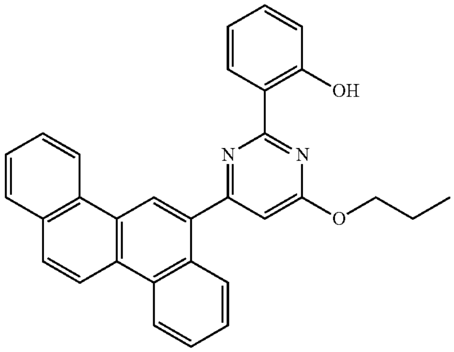
18
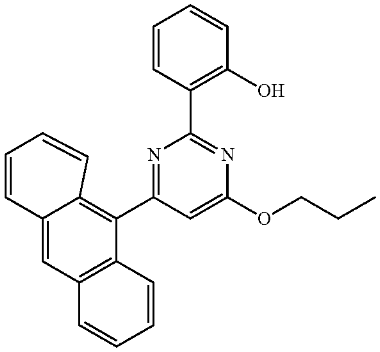
-continued
19
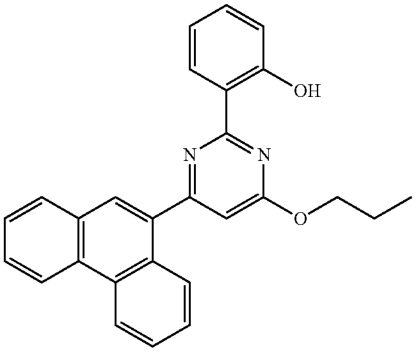
20
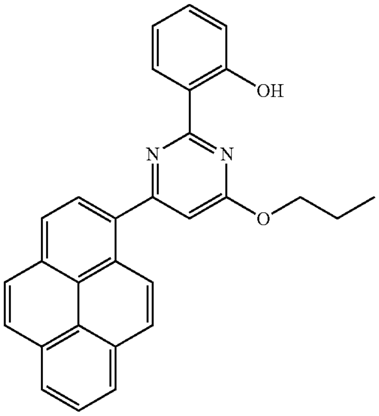
21
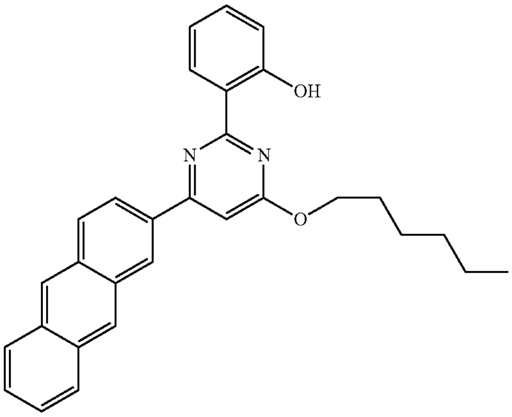
22
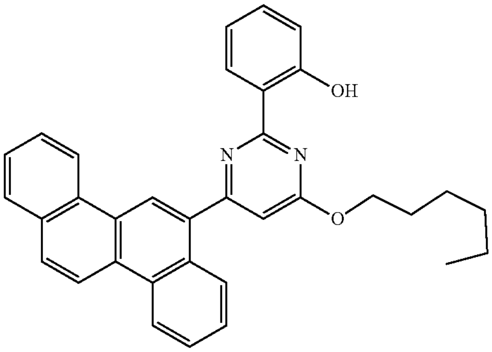

-continued
23
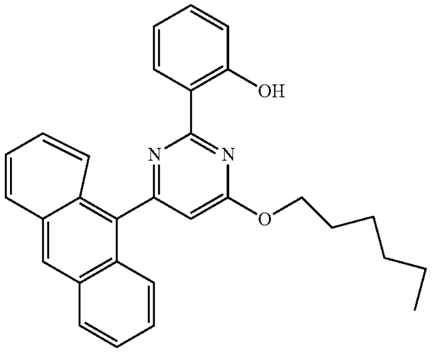
24
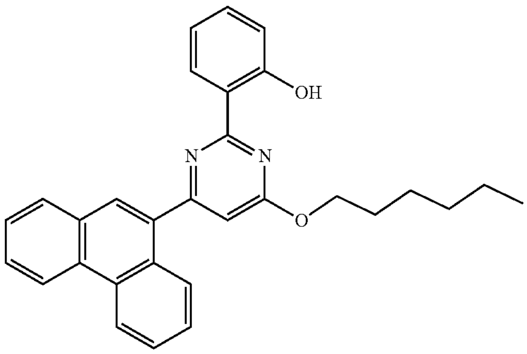
25
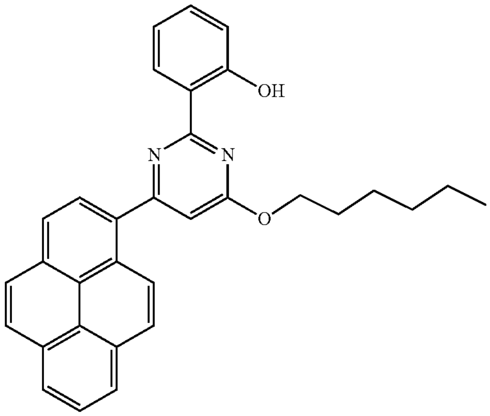
26
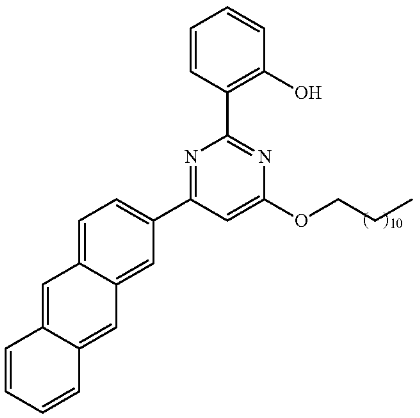
-continued
27
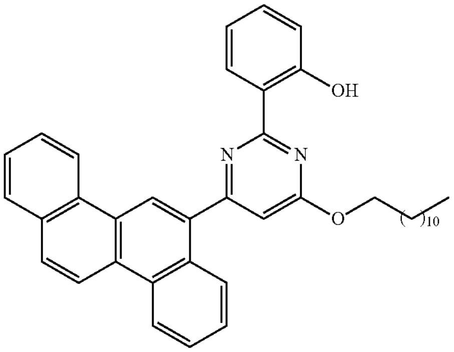
28
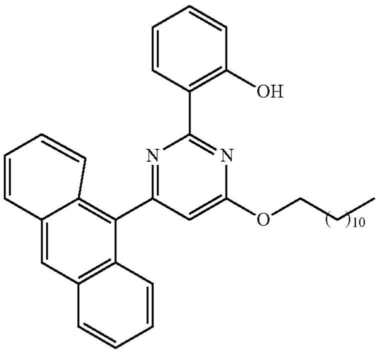
29
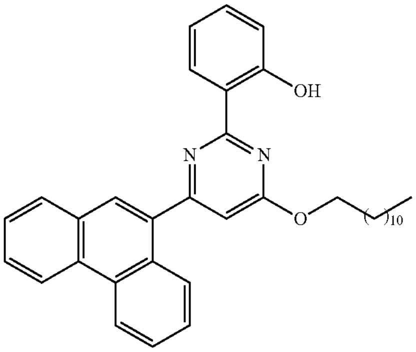
30
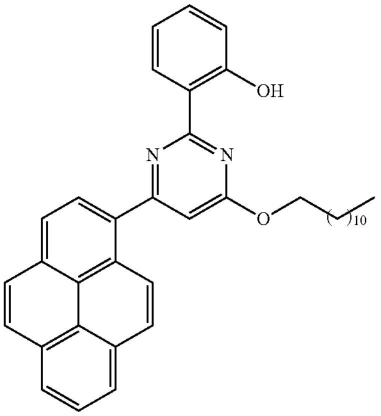

-continued
31
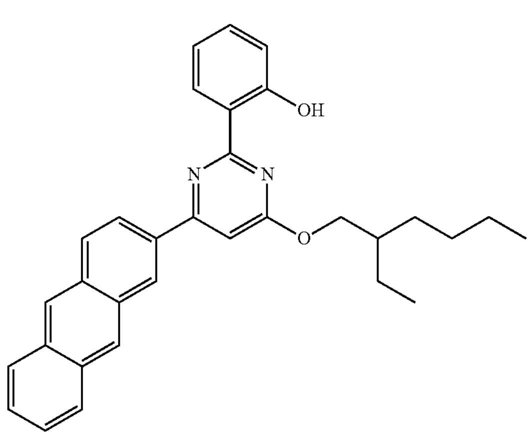
32
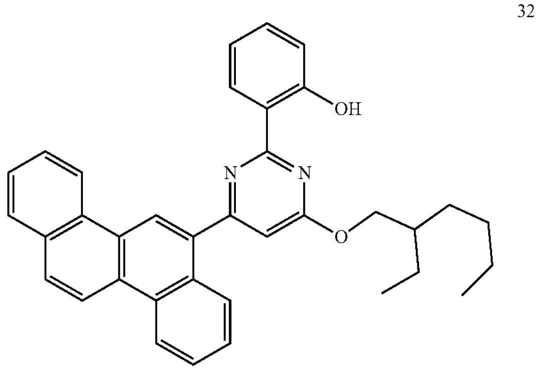
33
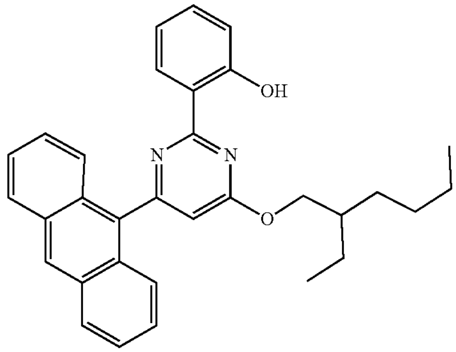
34
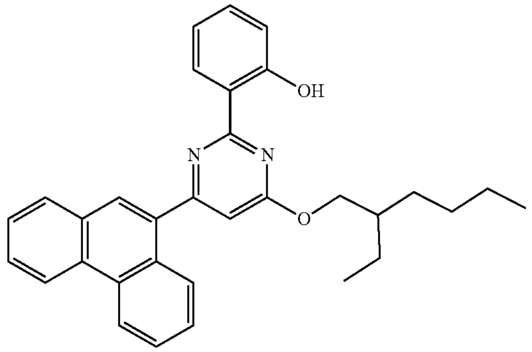
-continued
35
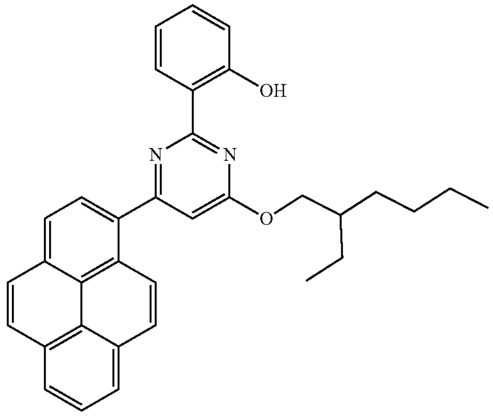
36
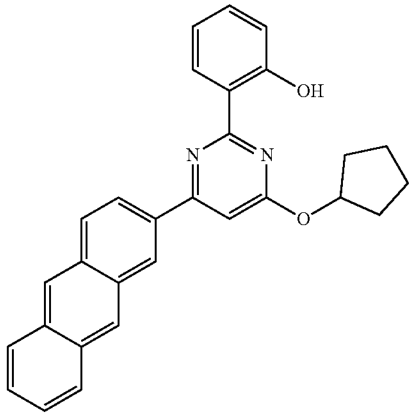
37
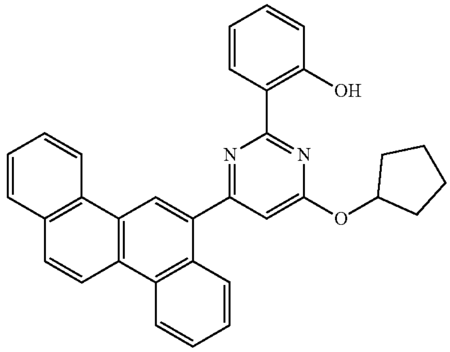
38
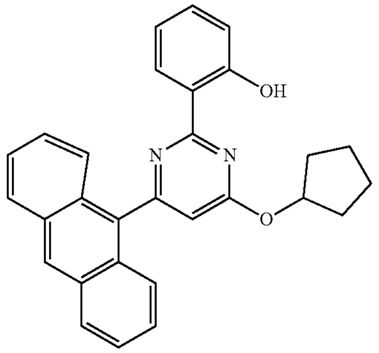

-continued
39
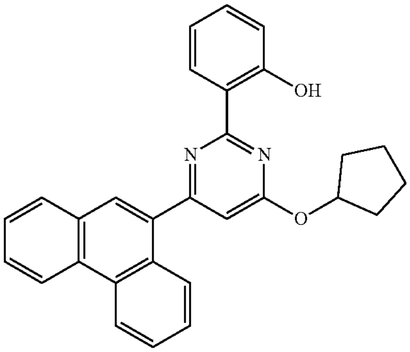
40
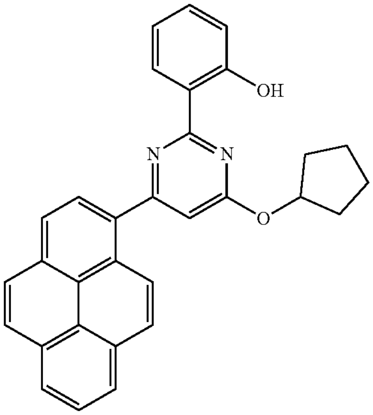
41
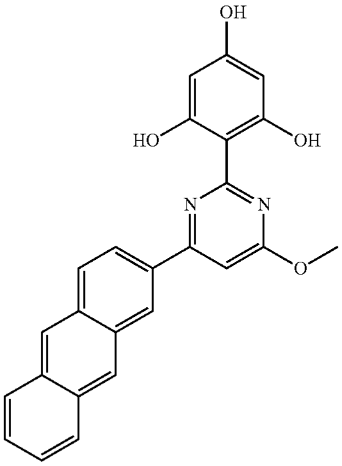
42
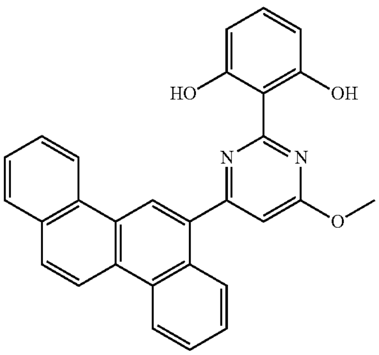
-continued
43
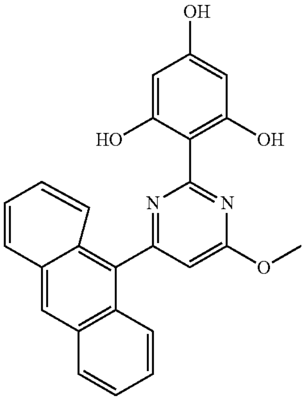
44
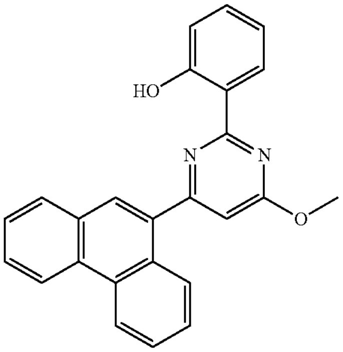
45
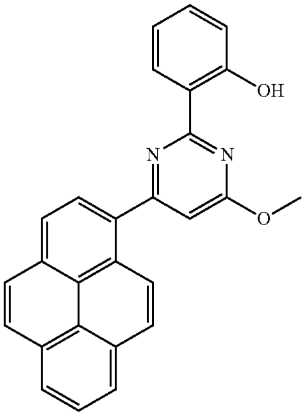
46
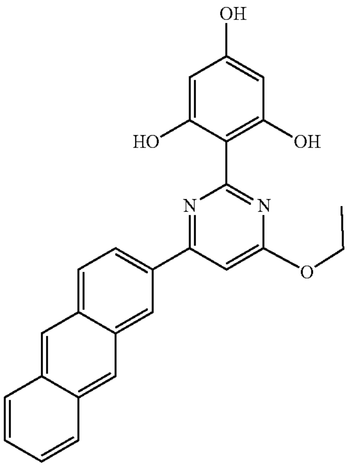

-continued
47
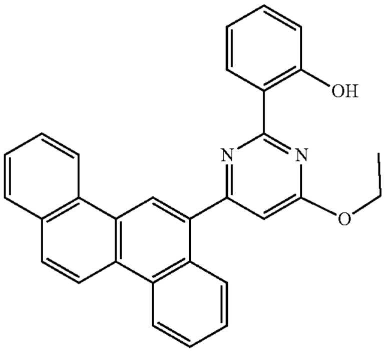
48
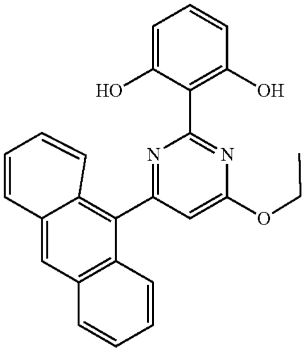
49
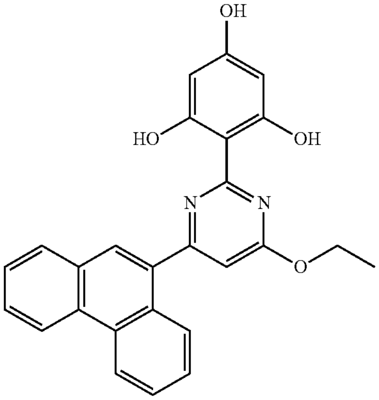
50
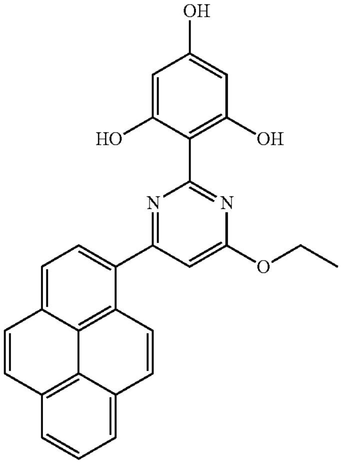
-continued
51
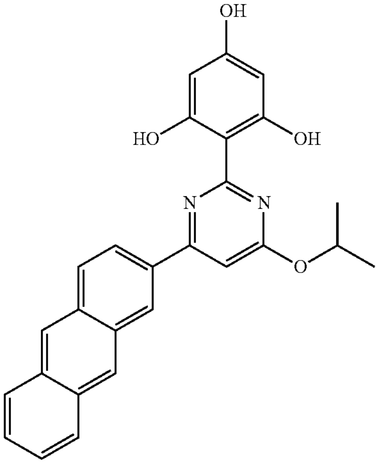
52
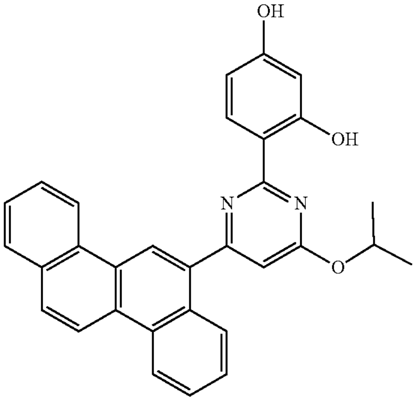
53
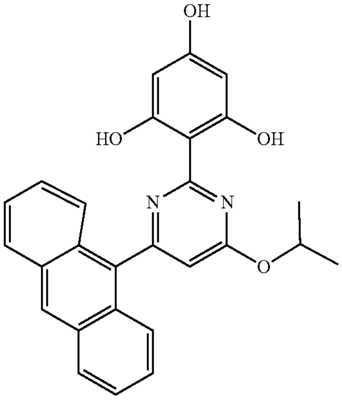
54
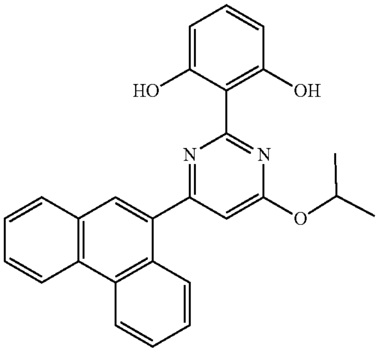

55
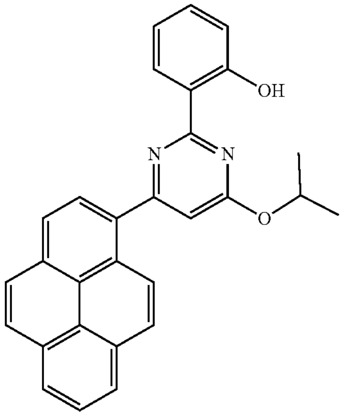
56
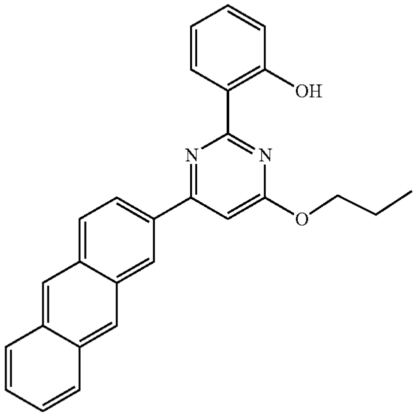
57
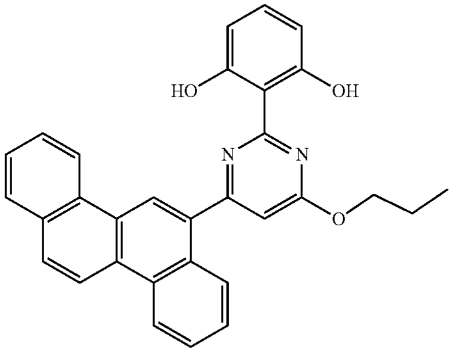
58
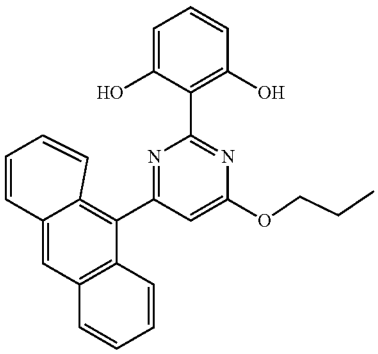
59
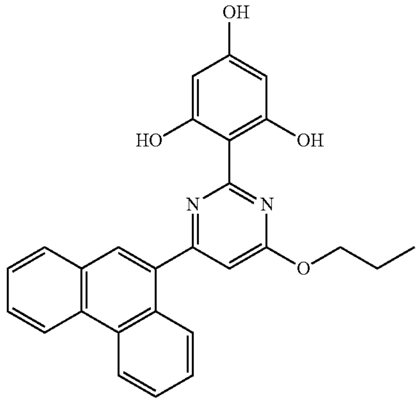
60
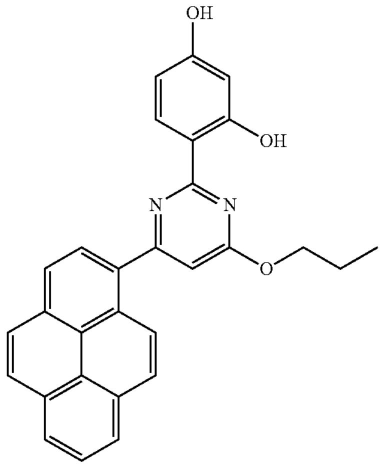
61
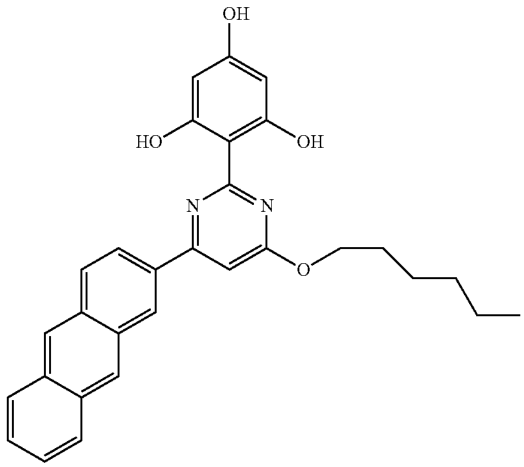

-continued
62
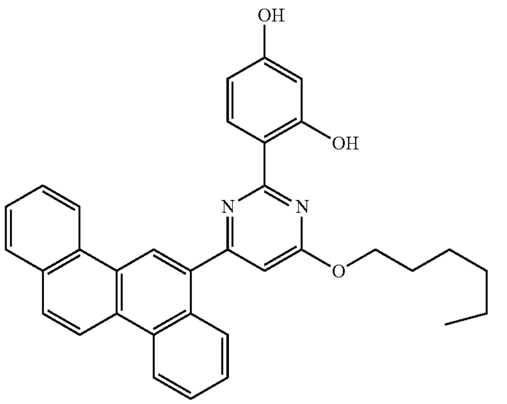
63
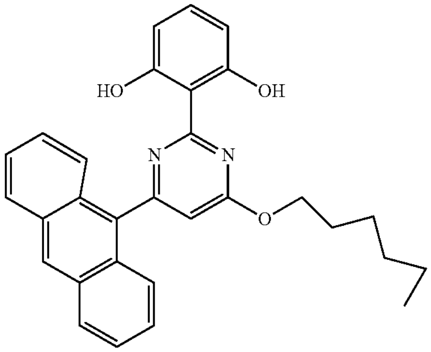
64
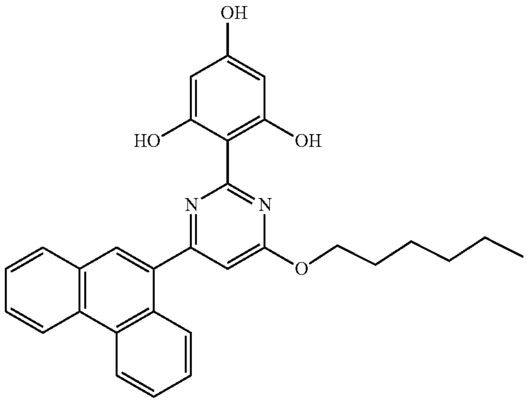
65
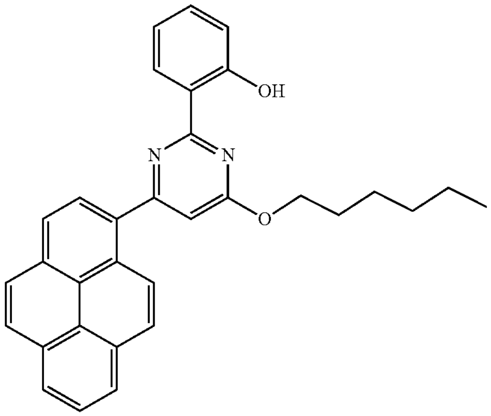
-continued
66
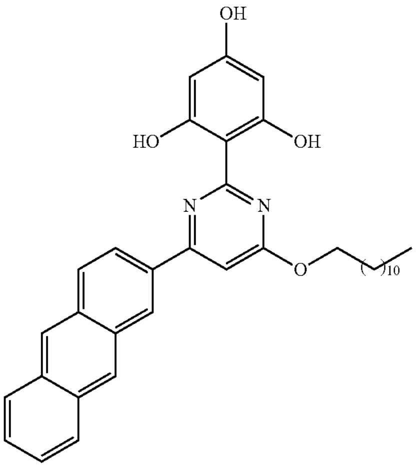
67
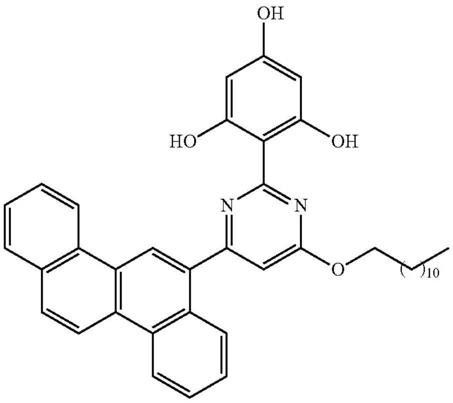
68
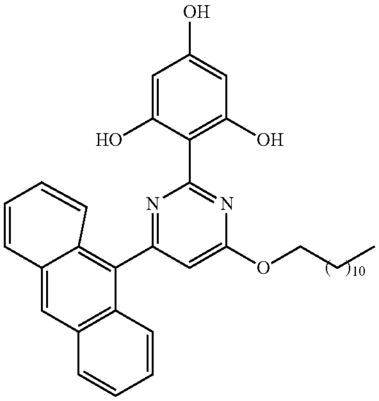

-continued
69
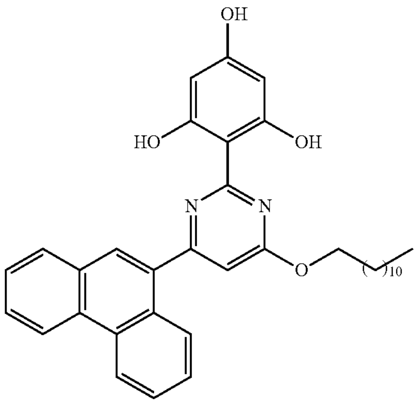
70
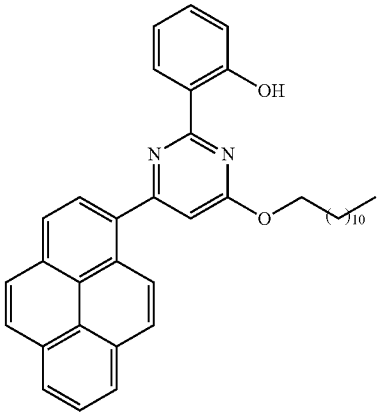
71
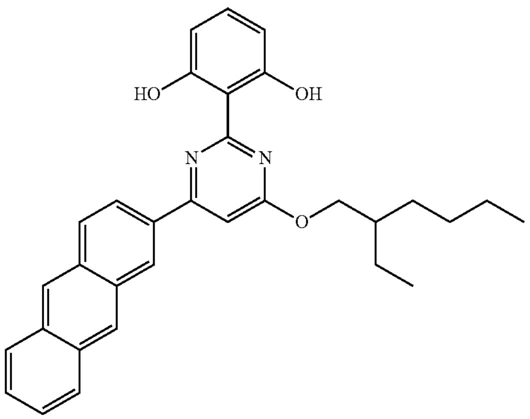
-continued
72
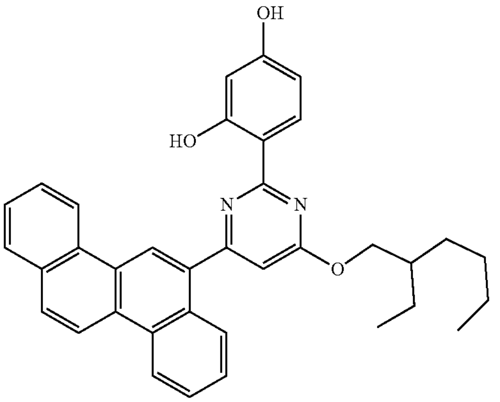
73
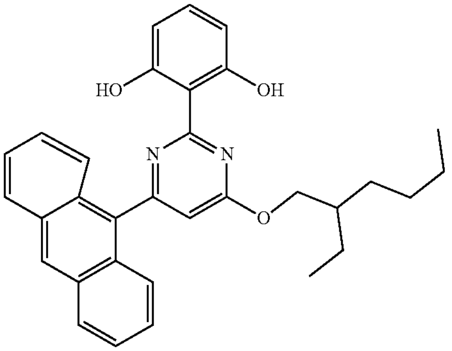
74
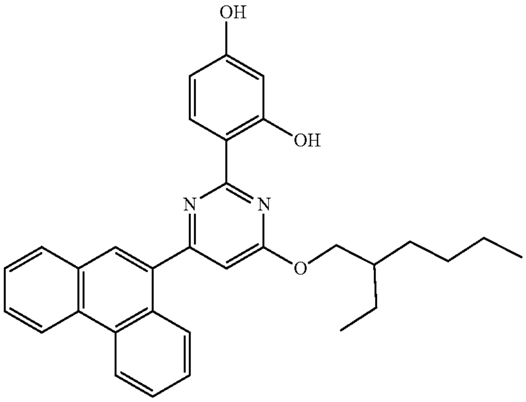
75
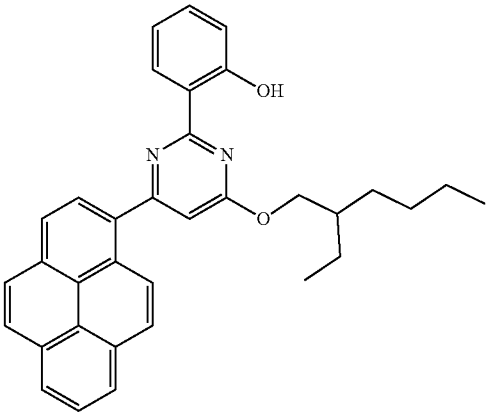

-continued
76
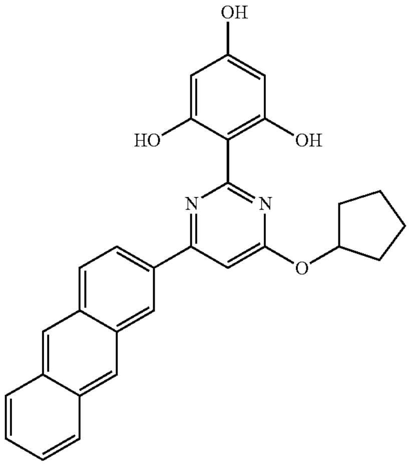
77
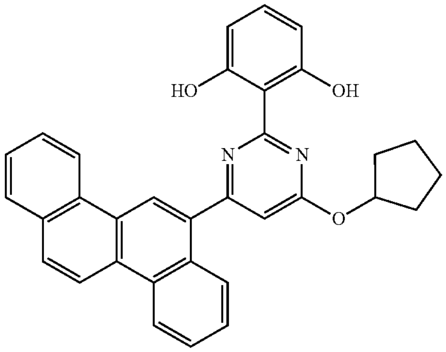
78
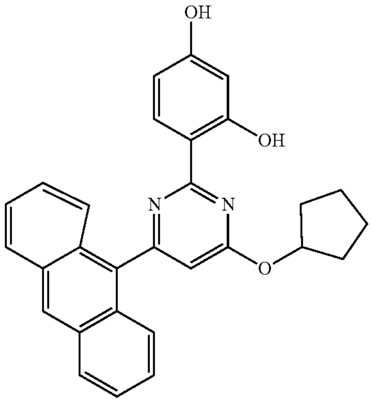
79
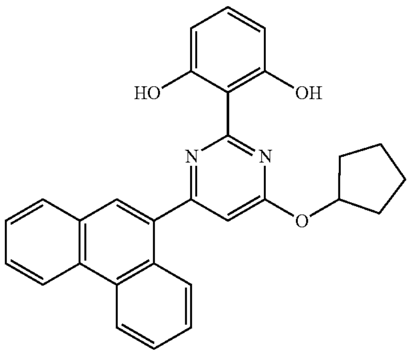
-continued
80
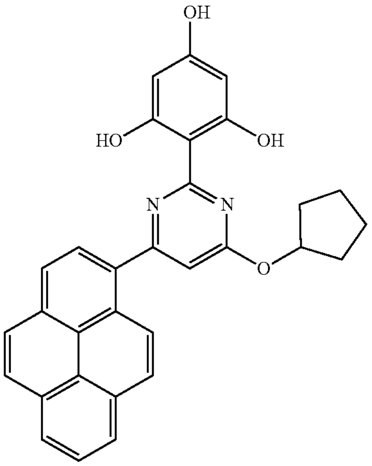
81
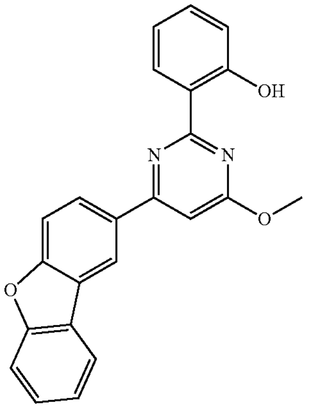
82
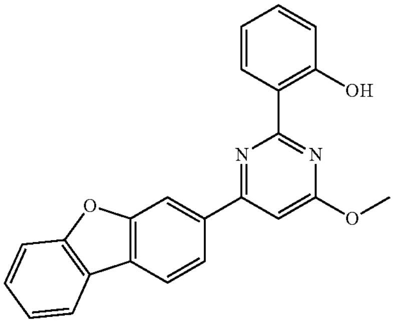
83
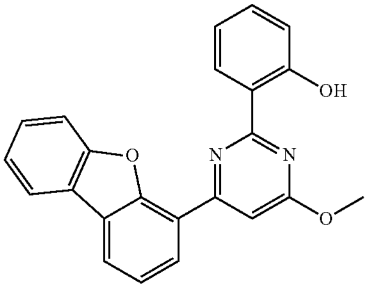

84
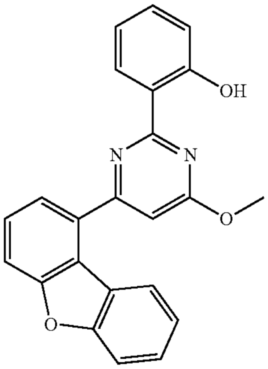
85
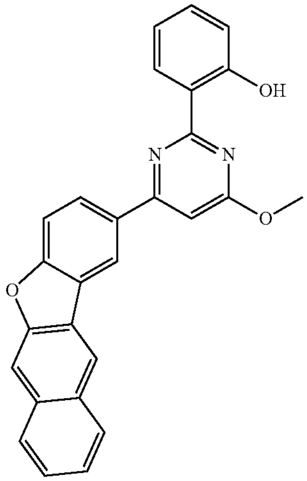
86
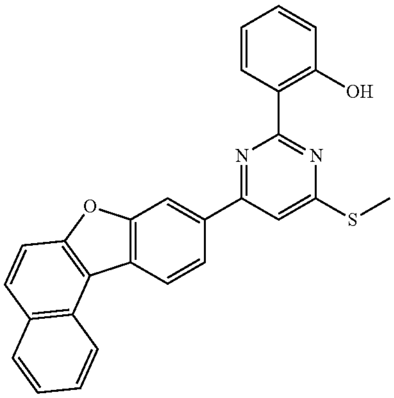
87
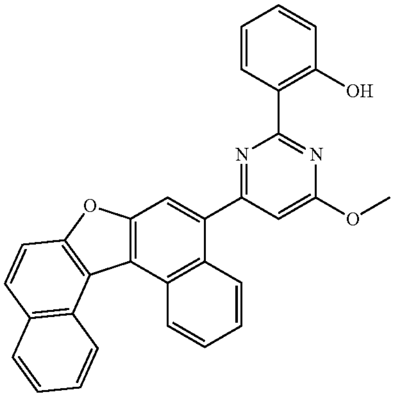
88
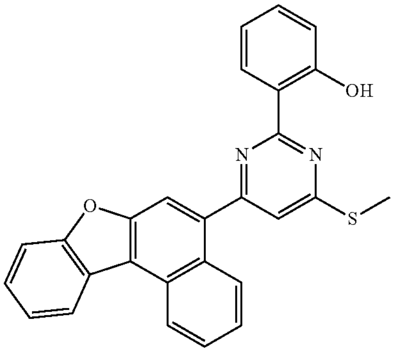
89
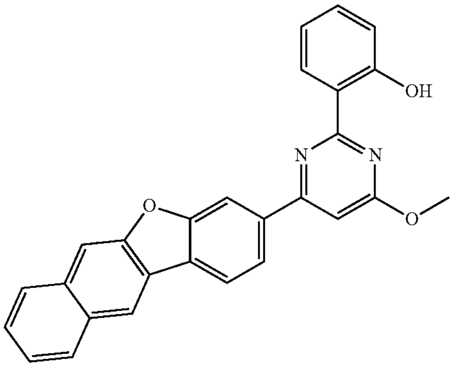
90
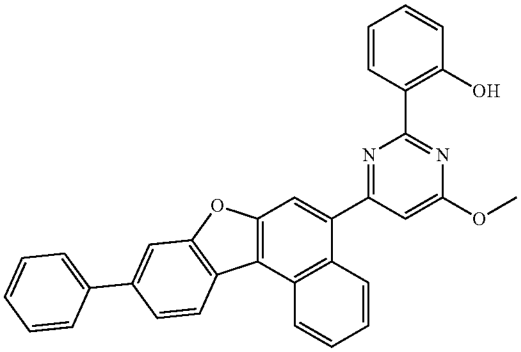
91
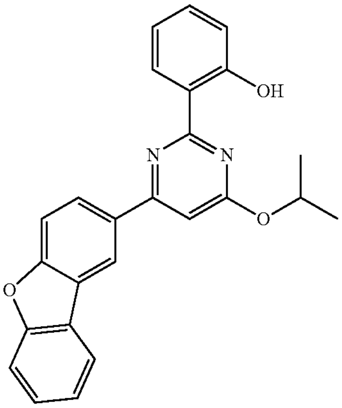

-continued
92
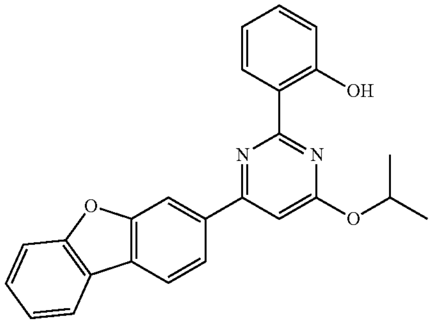
93
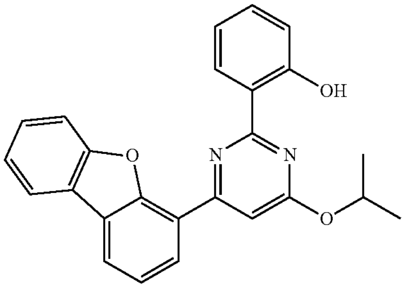
94
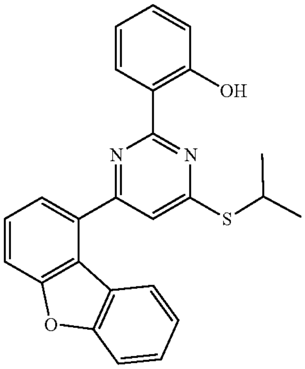
95
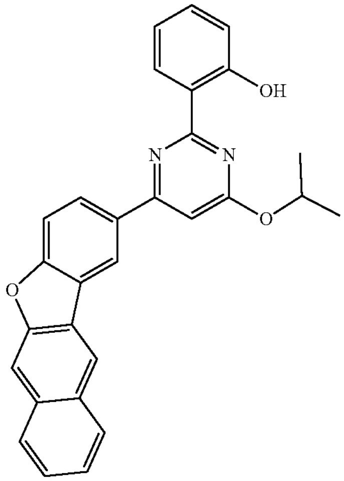
-continued
96
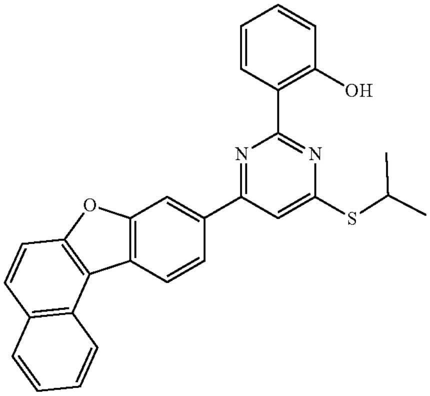
97
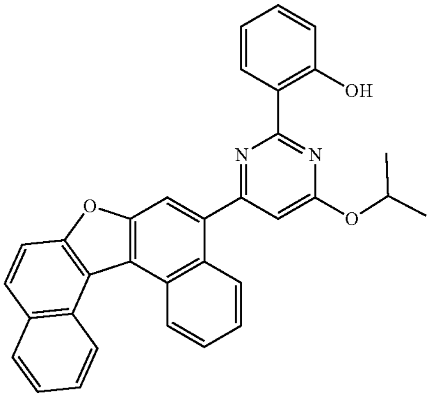
98
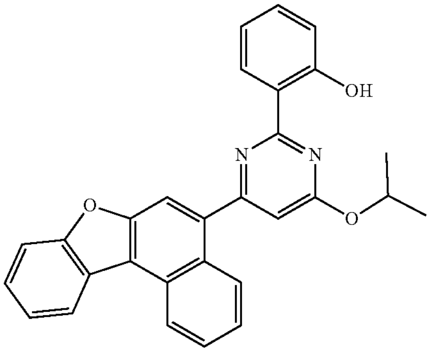
99
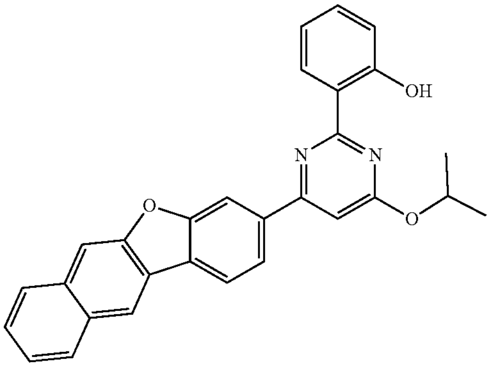

-continued
100
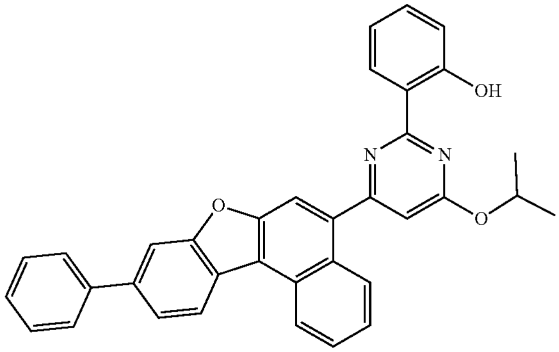
101
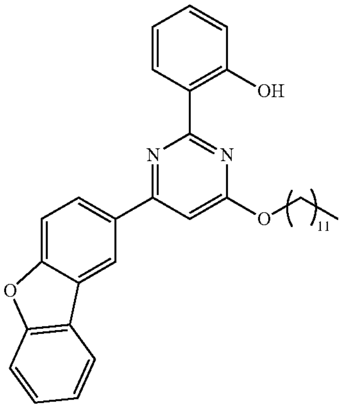
102
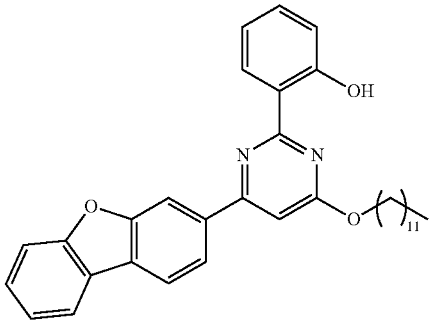
103
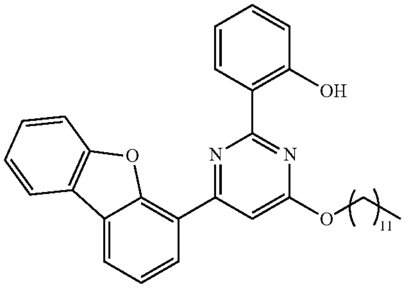
-continued
104
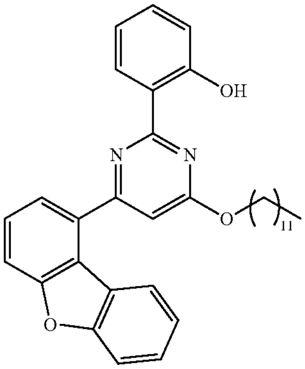
105
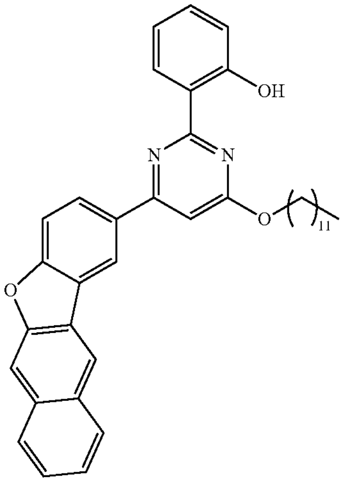
106
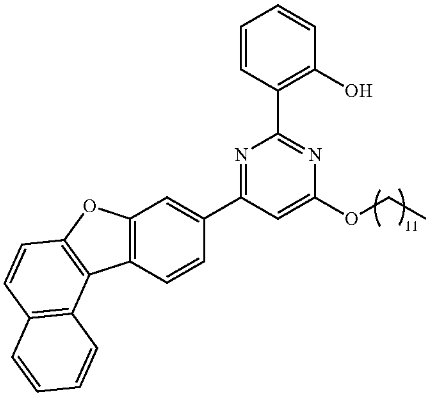
107
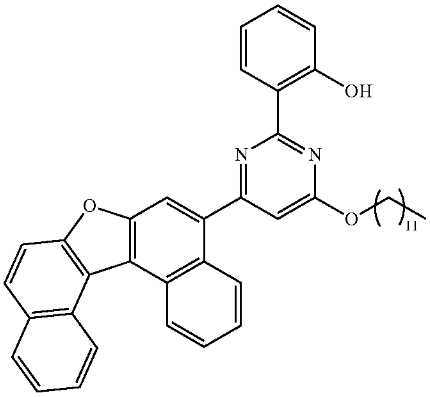

-continued
108
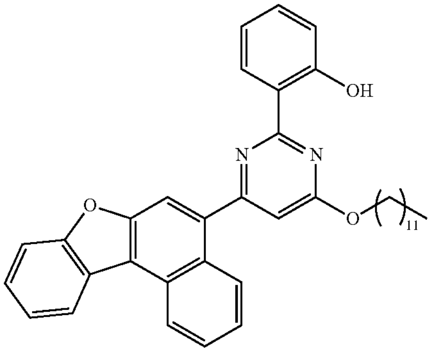
109
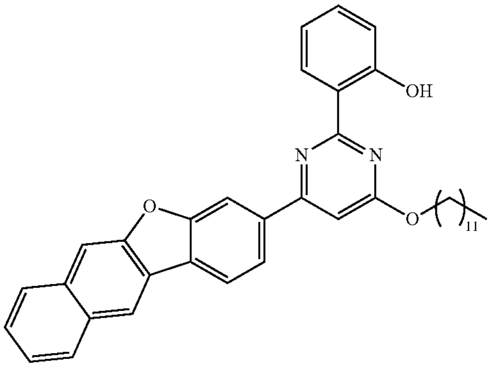
110
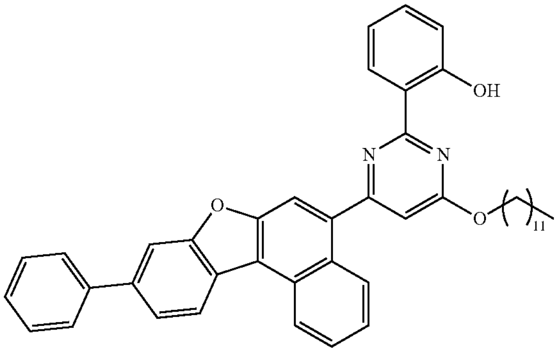
111
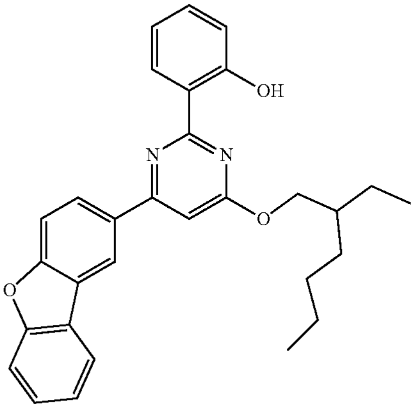
-continued
112
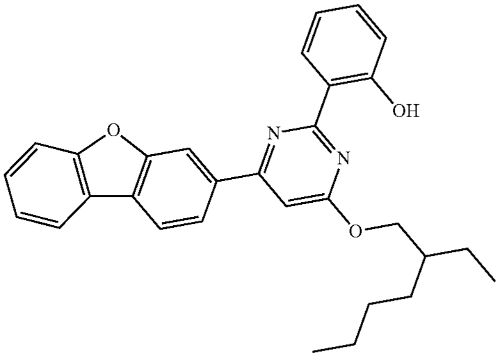
113
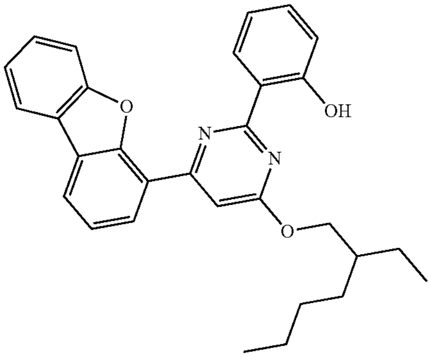
114
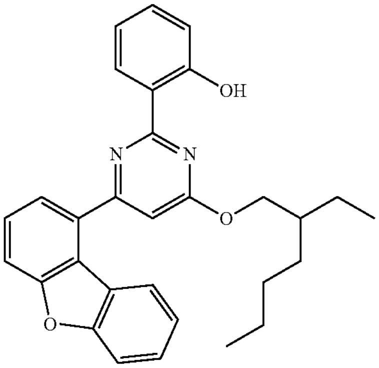
115
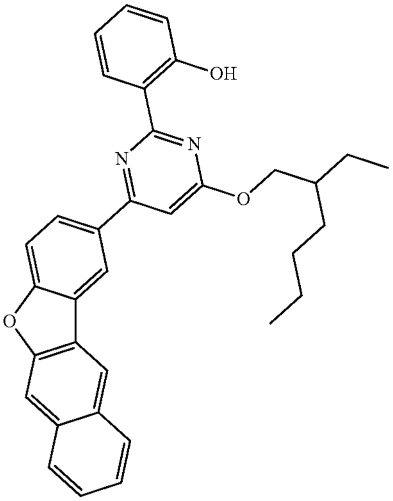

-continued
116
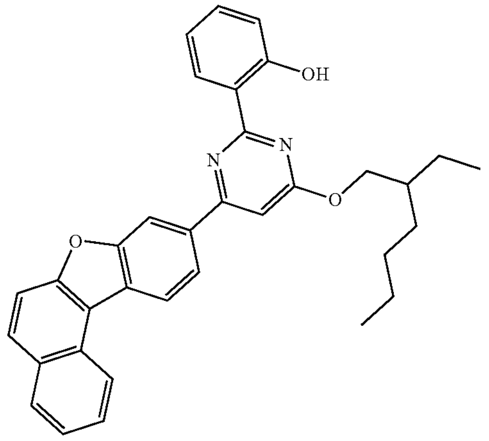
117
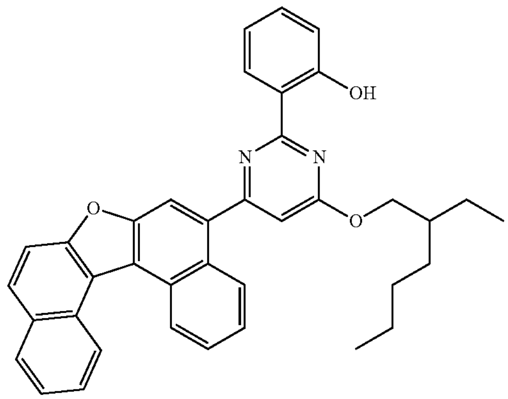
118
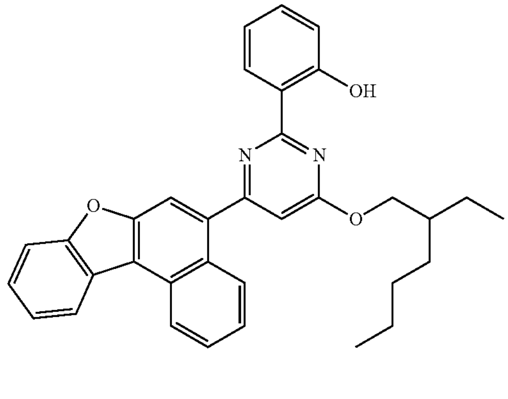
-continued
119
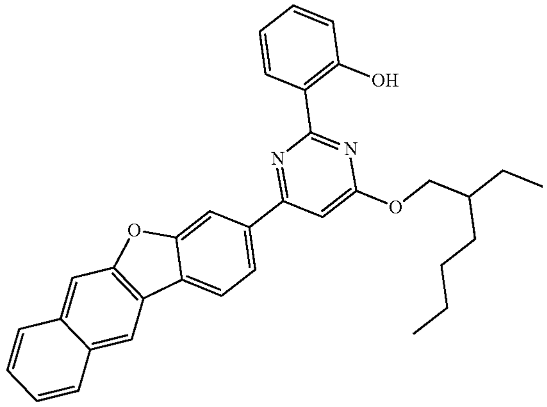
120
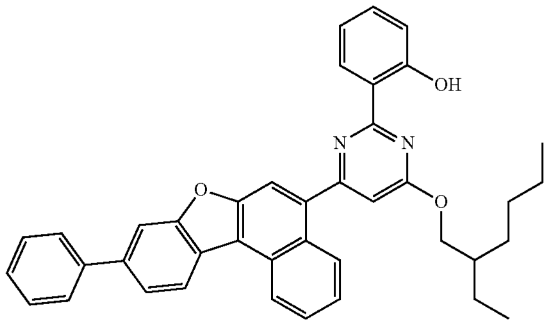
121
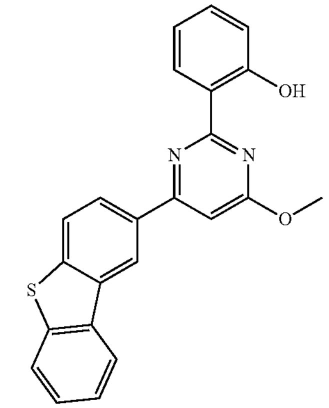
122
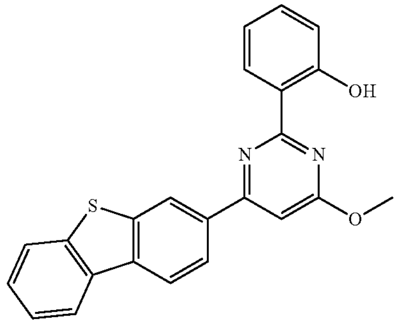

-continued
123
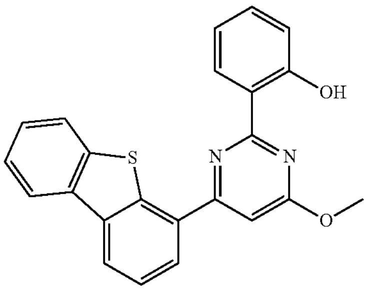
124
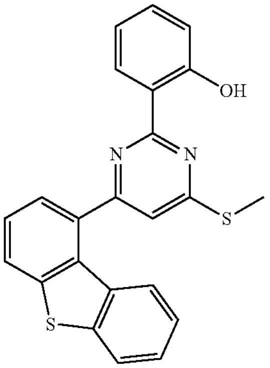
125
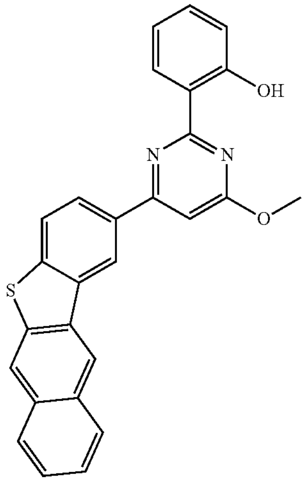
126
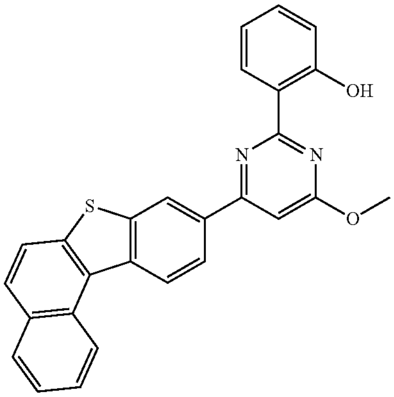
-continued
127
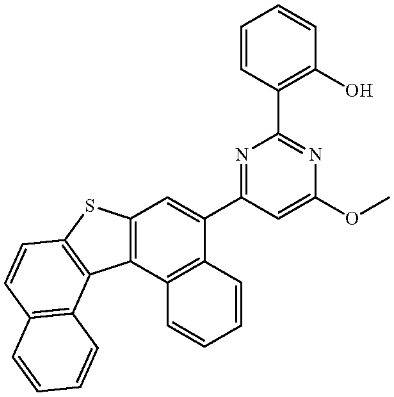
128
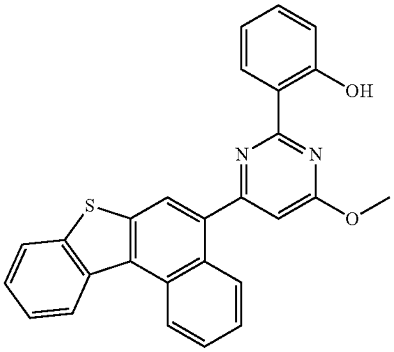
129
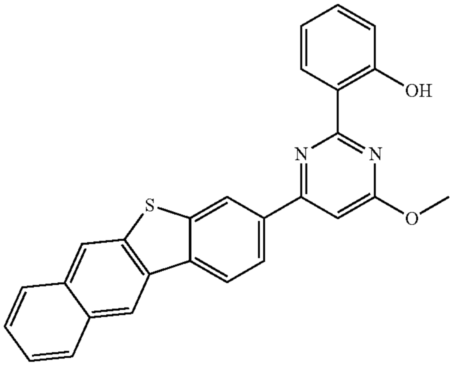
130
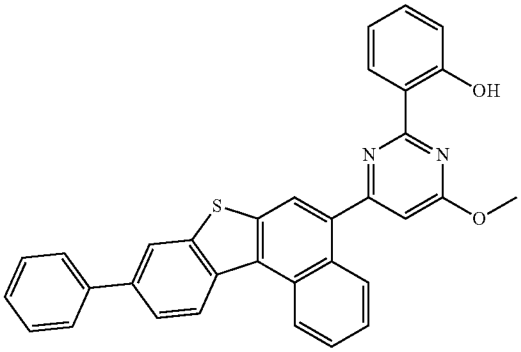

-continued
131
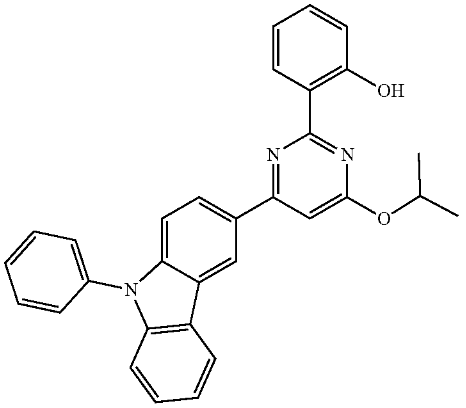
132
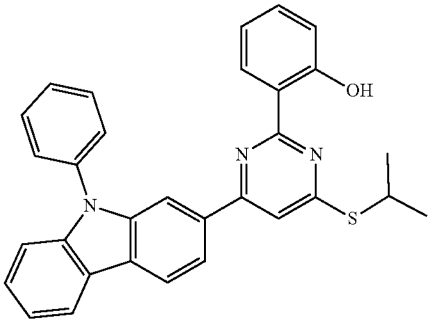
133
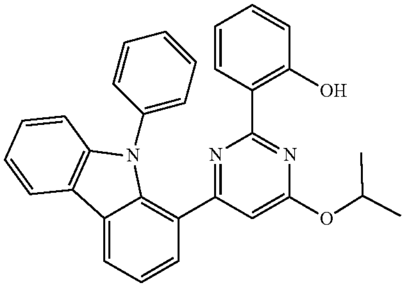
134
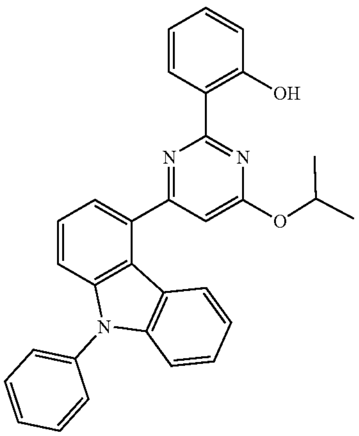
-continued
135
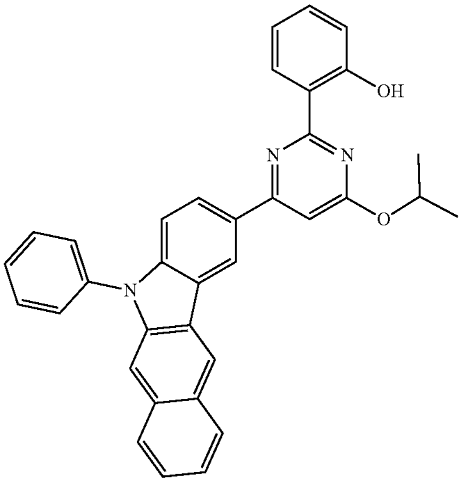
136
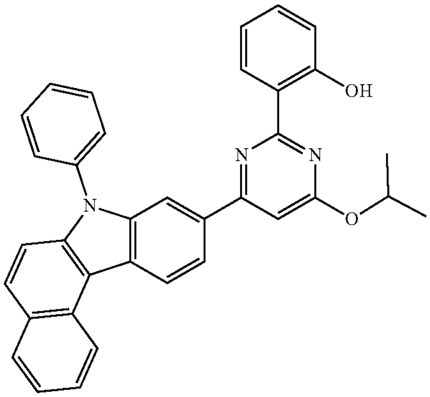
137
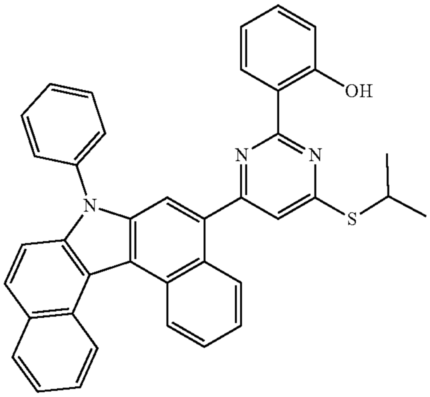
138
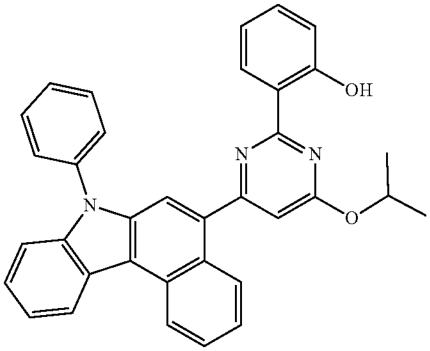

-continued
139
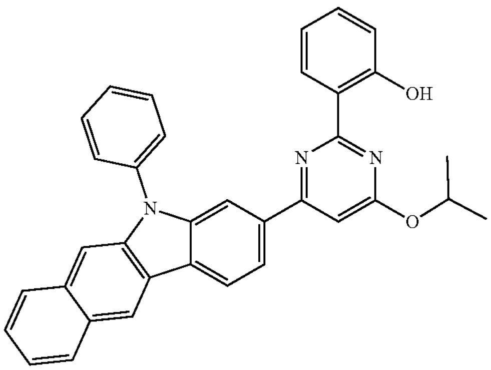
140
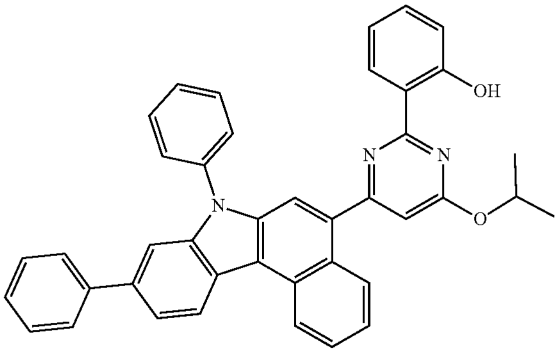
141
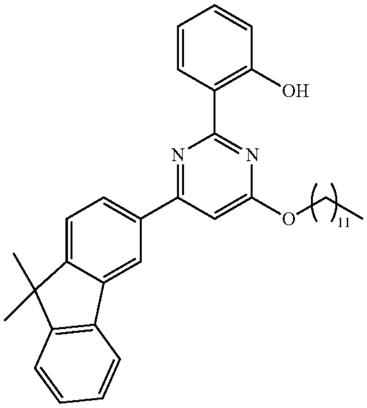
142
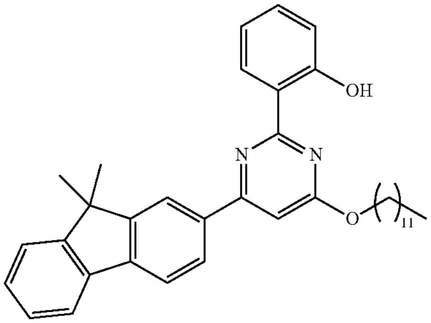
-continued
143
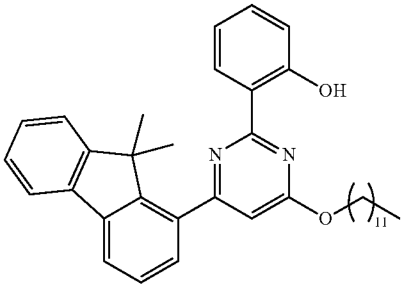
144
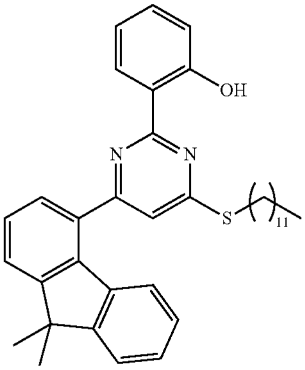
145
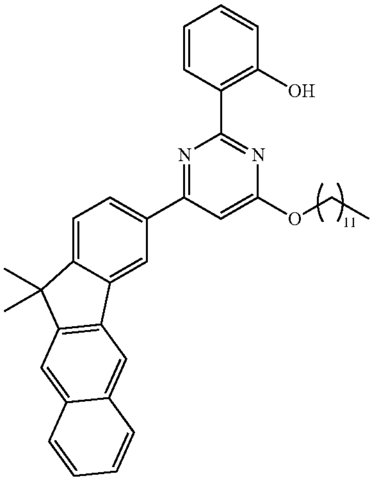
146
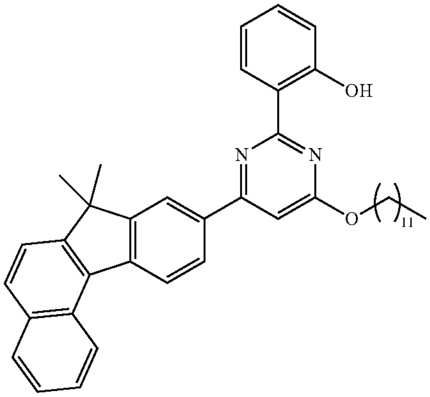

-continued
147
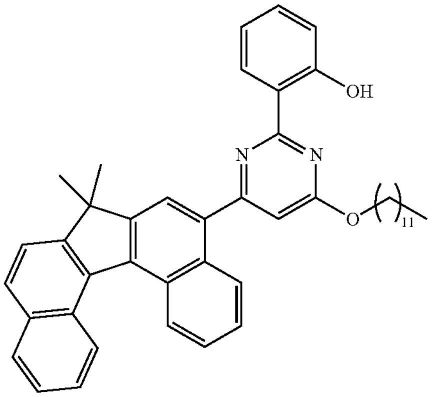
148
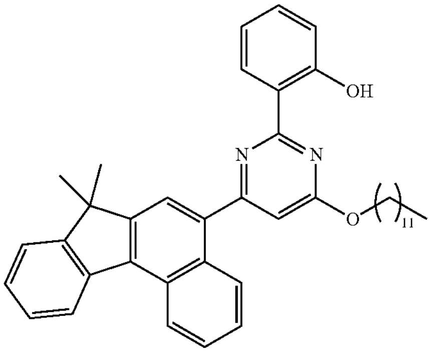
149
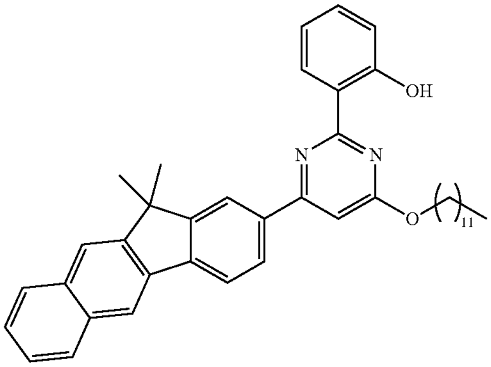
150
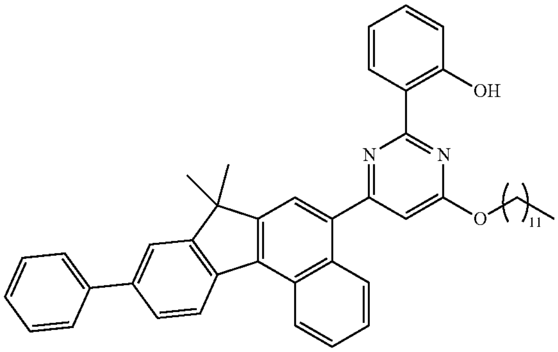
-continued
151
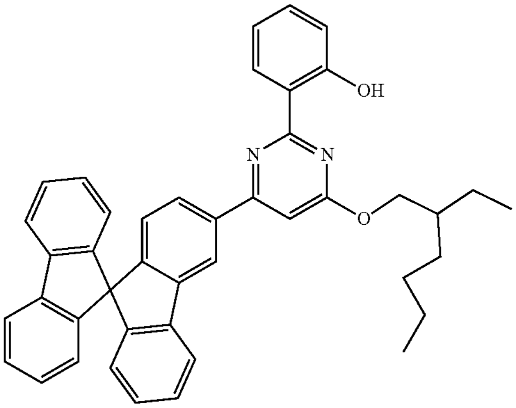
152
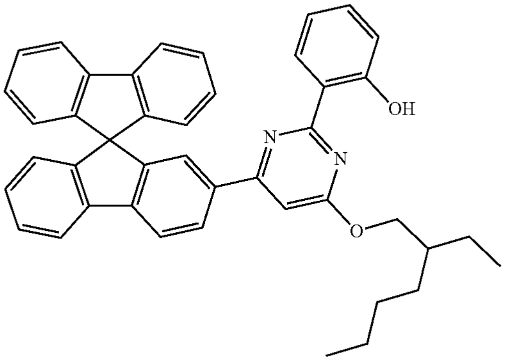
153
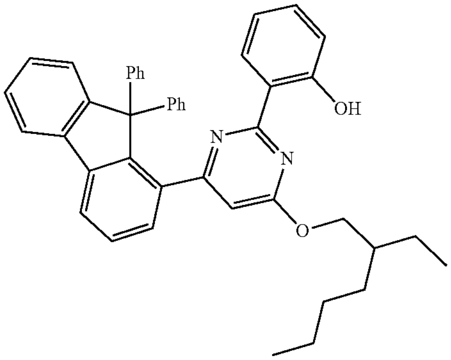
154
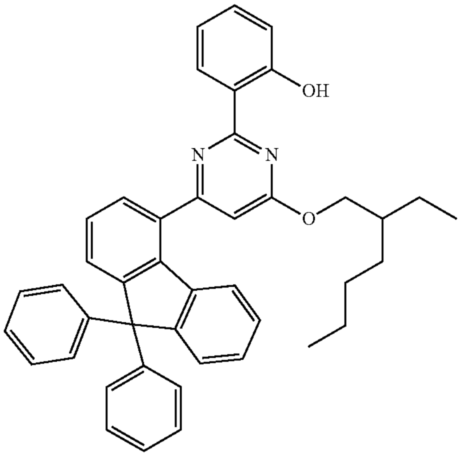

-continued
155
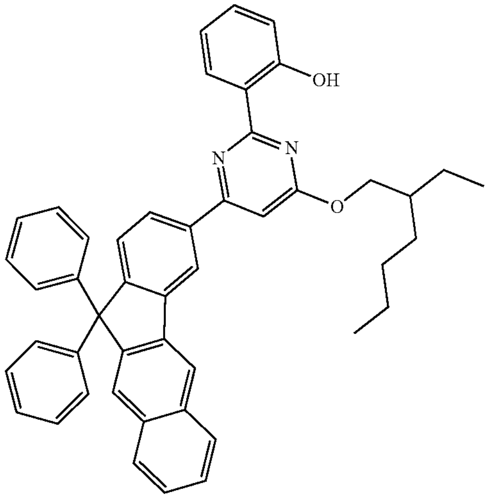
156
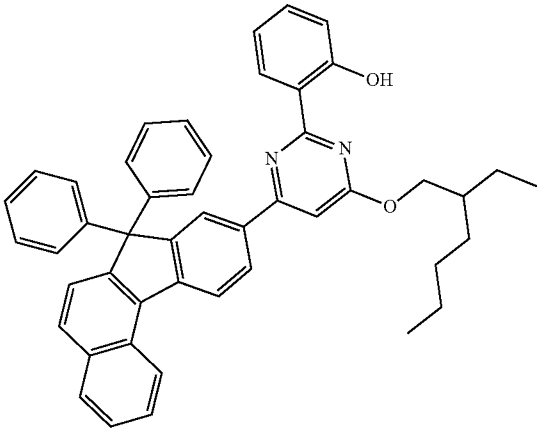
157
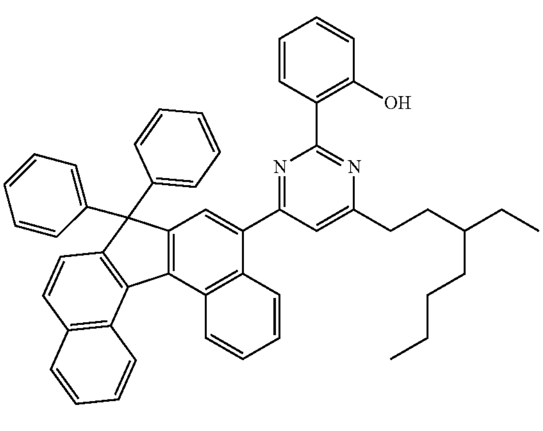
-continued
158
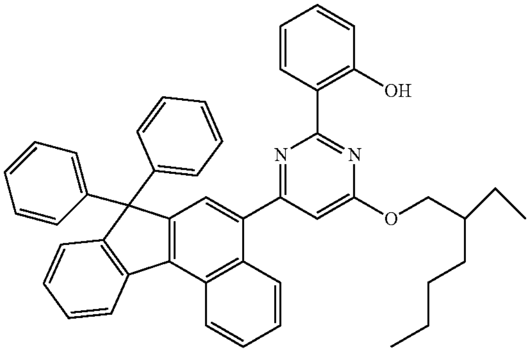
159
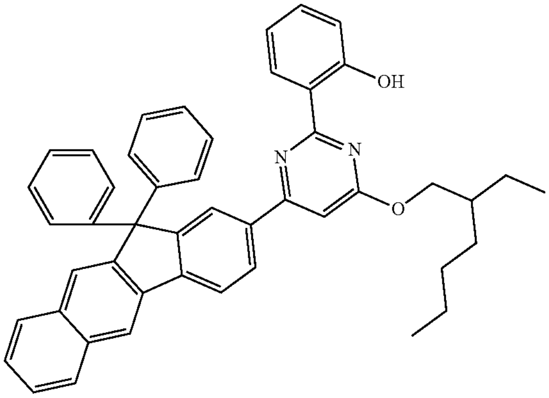
160
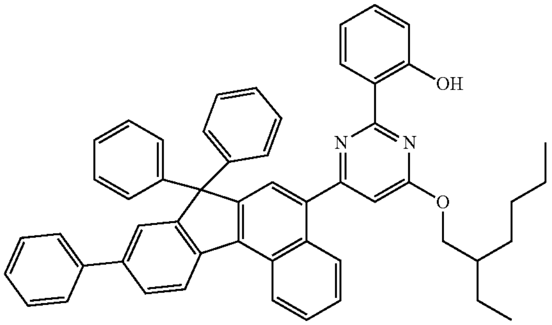
161
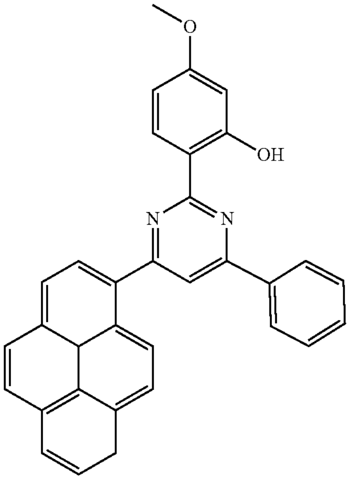

-continued
162
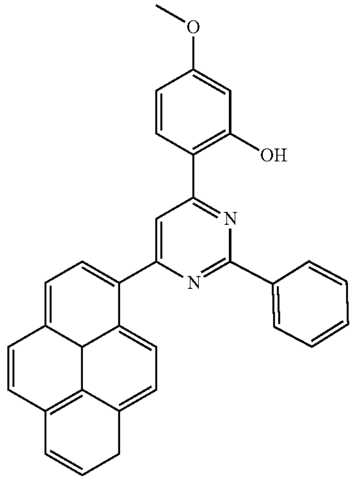
163
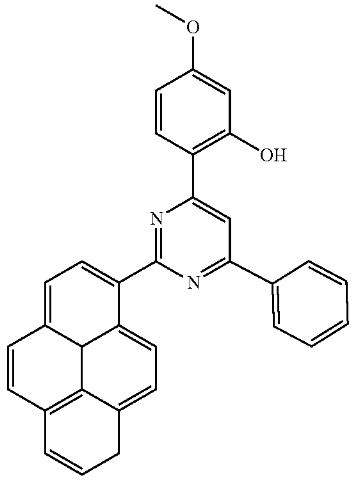
164
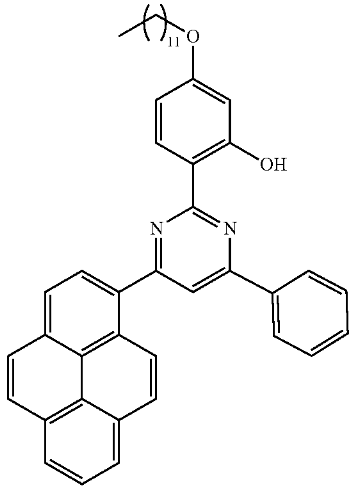
-continued
165
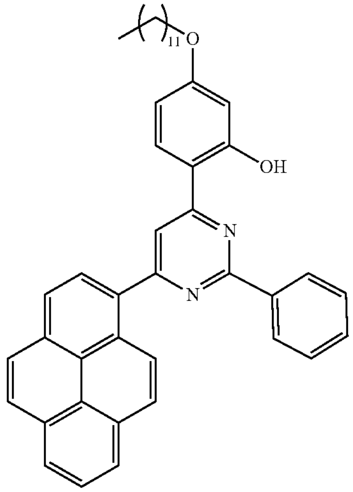
166
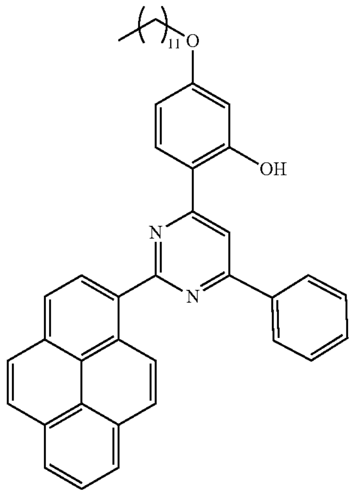
167
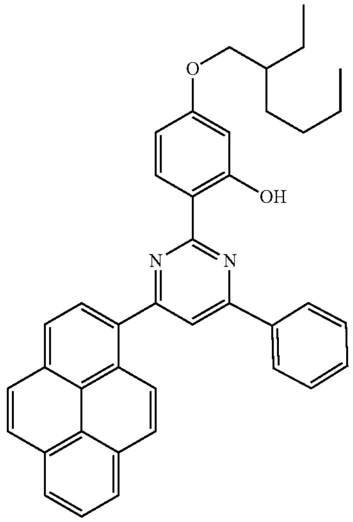

-continued
168
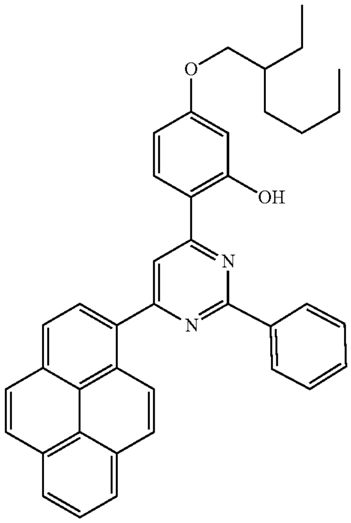
169
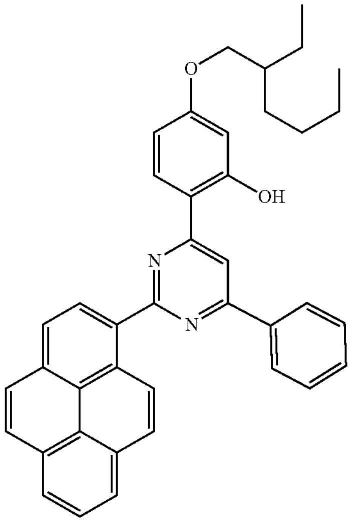
170
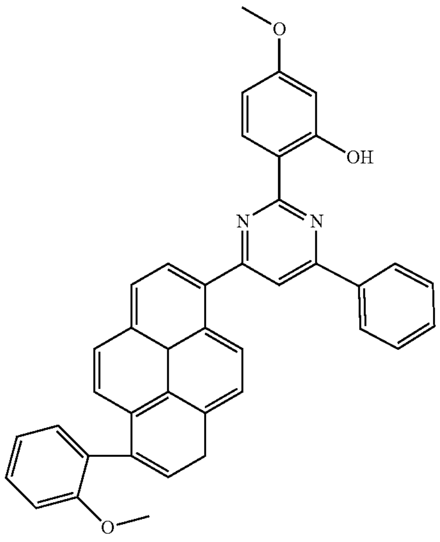
-continued
171
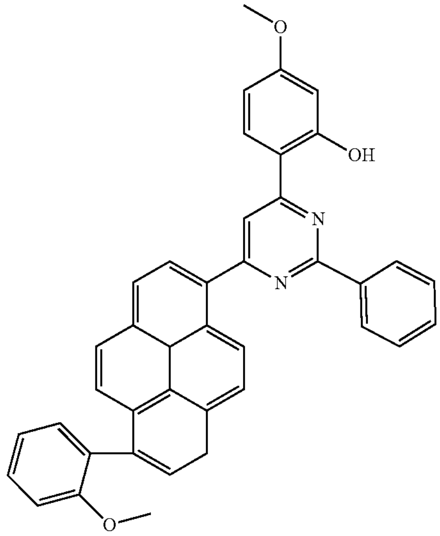
172
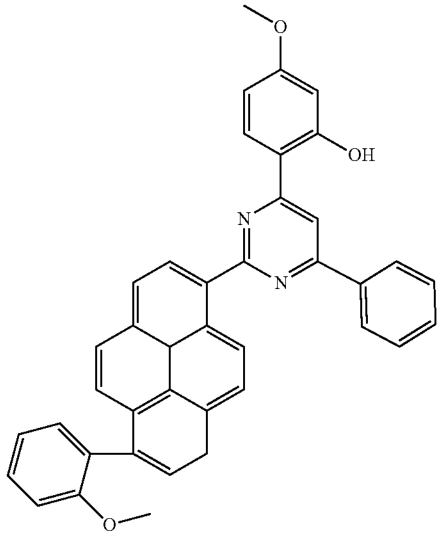
173
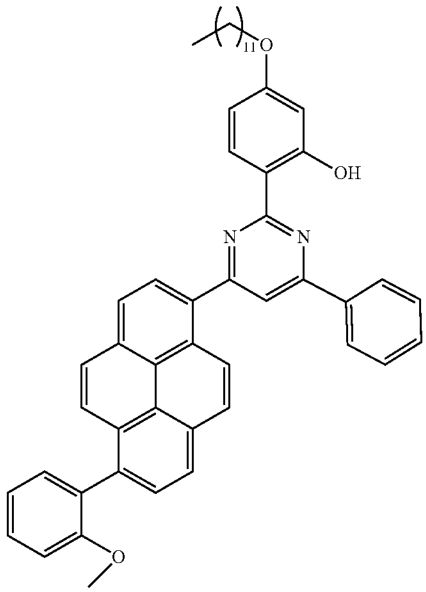

-continued
174
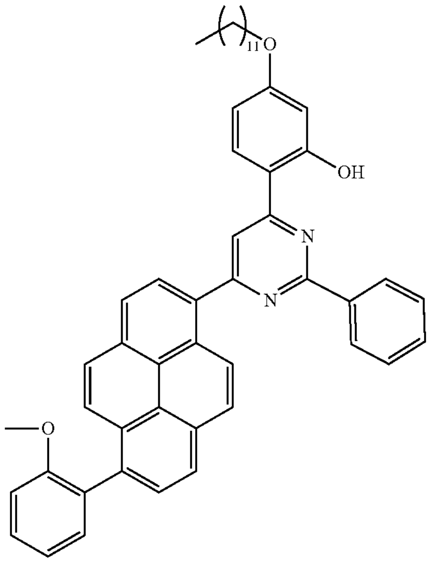
175
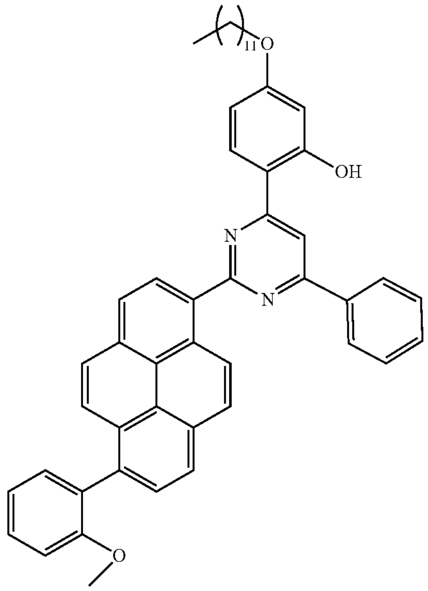
-continued
176
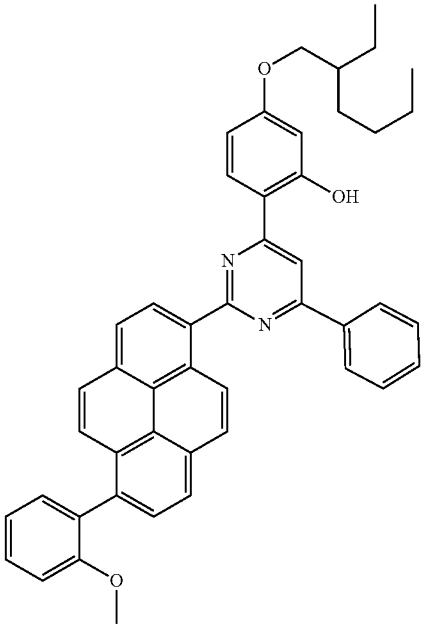
177
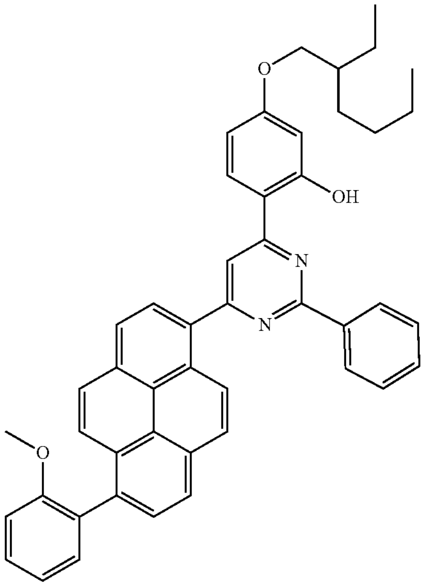

-continued
178
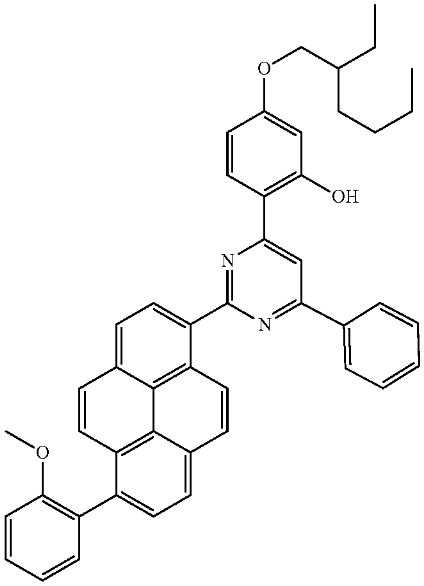
[Compound Group 2]
1
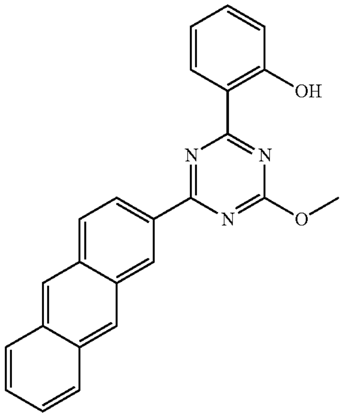
2
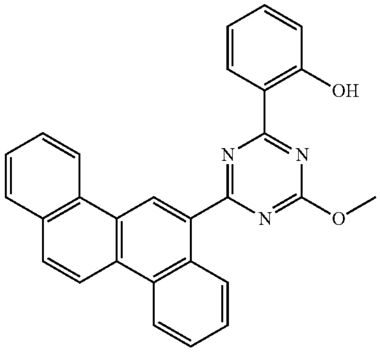
-continued
3
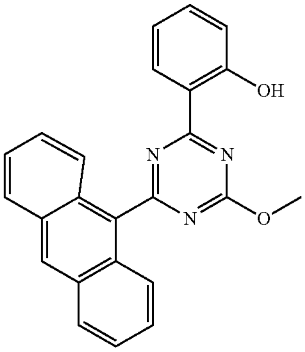
4
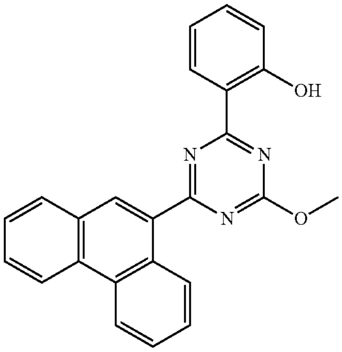
5
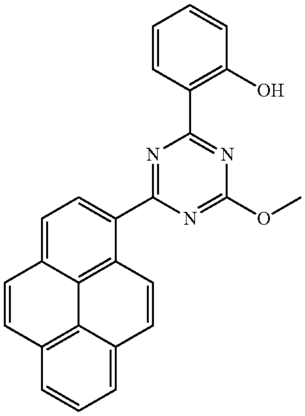
6
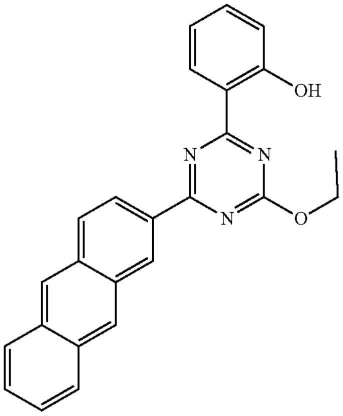

-continued
7
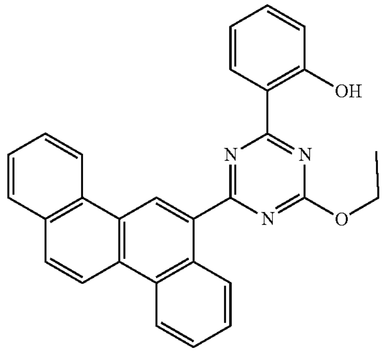
8
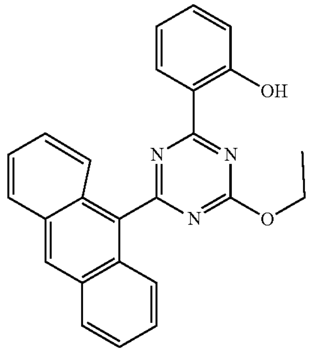
9
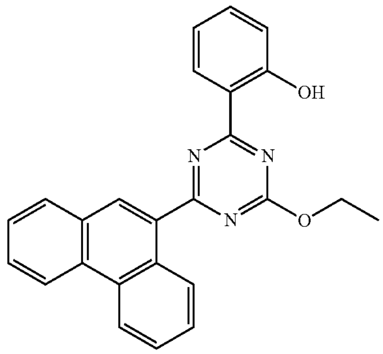
10
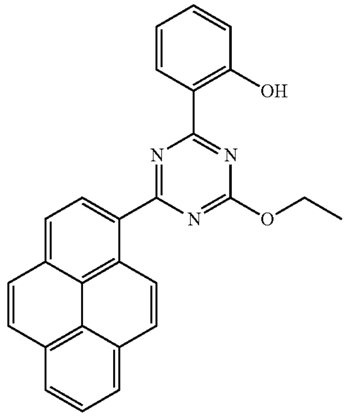
-continued
11
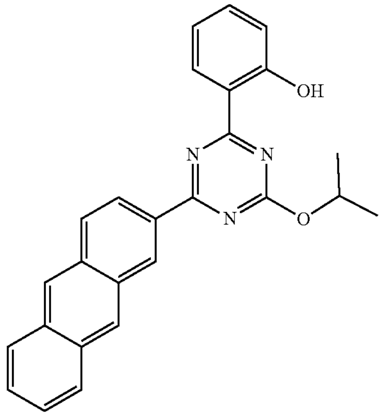
12
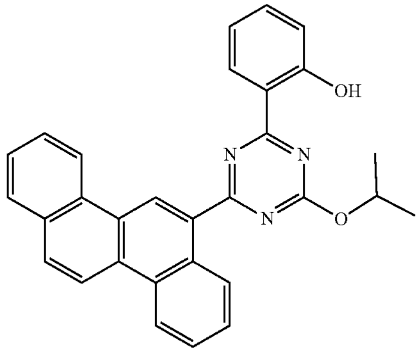
13
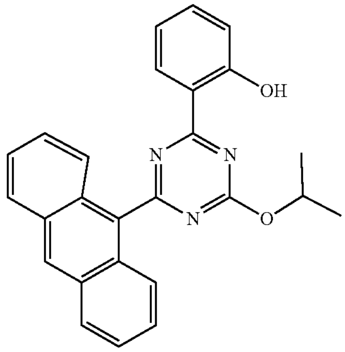
14
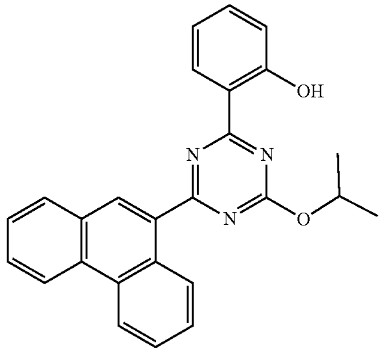

-continued
15
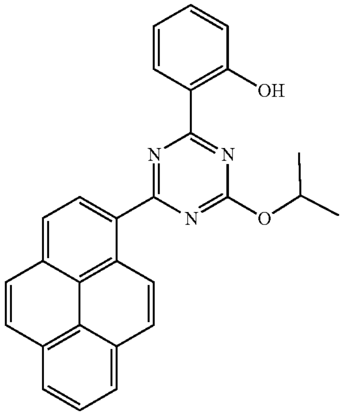
16
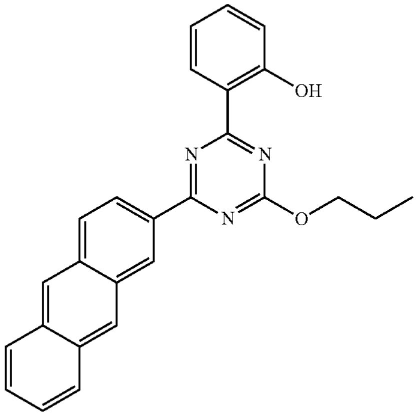
17
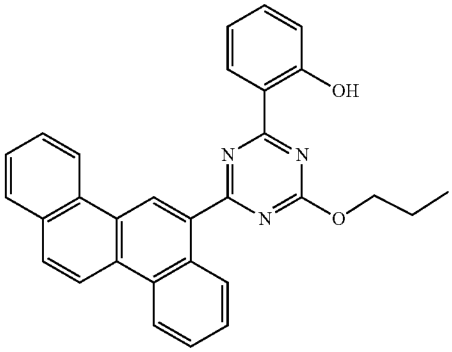
18
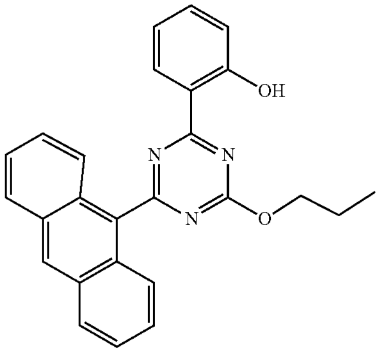
-continued
19
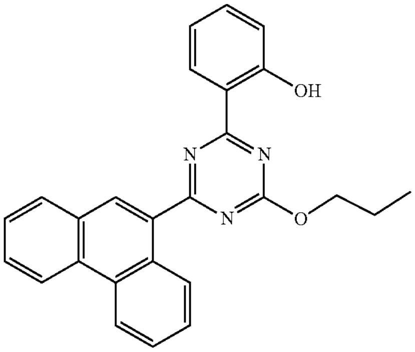
20
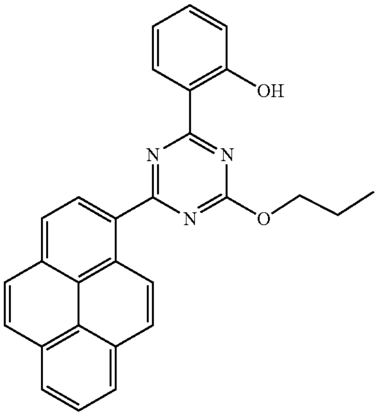
21
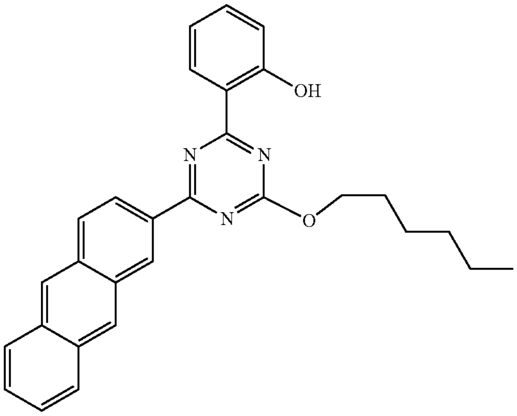
22
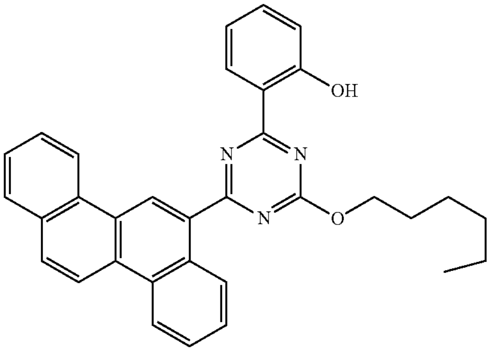

-continued
23
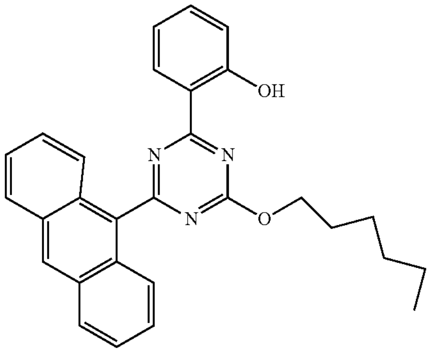
24
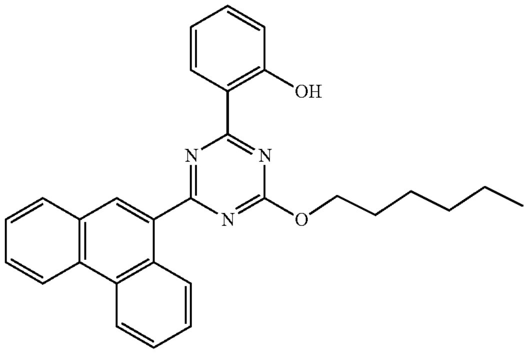
25
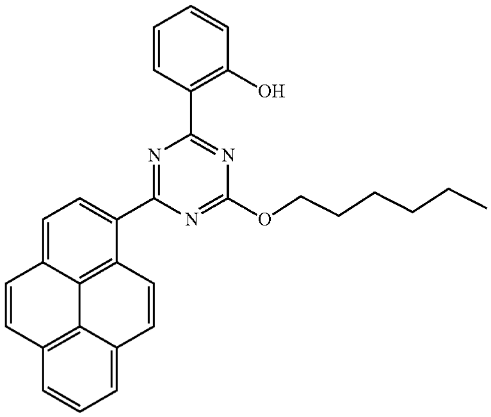
26
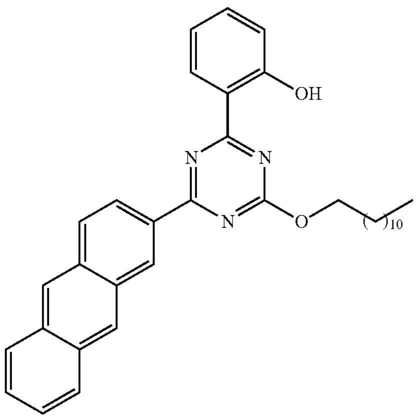
-continued
27
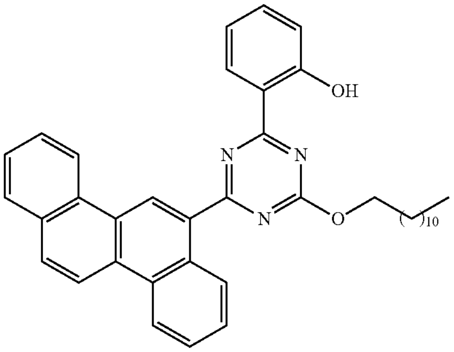
28
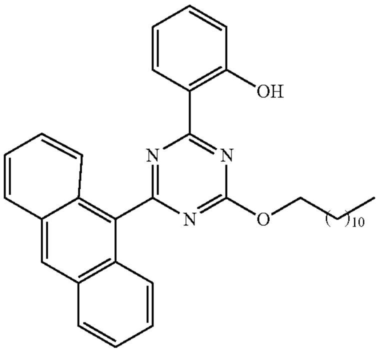
29
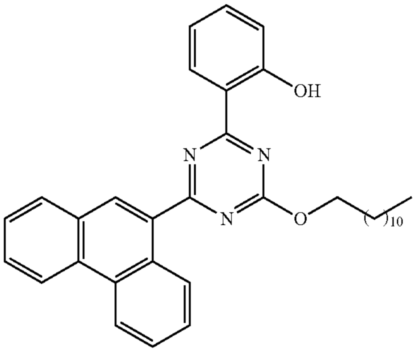
30
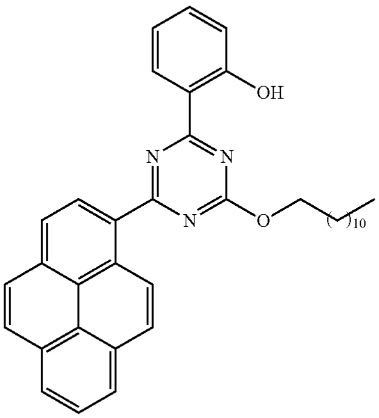

-continued
31
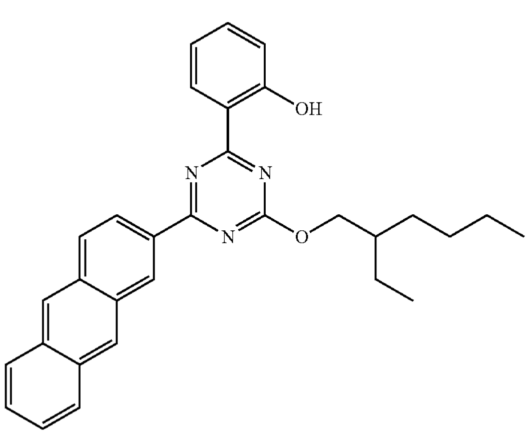
32
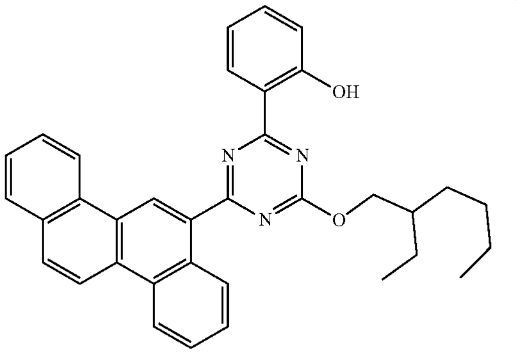
33
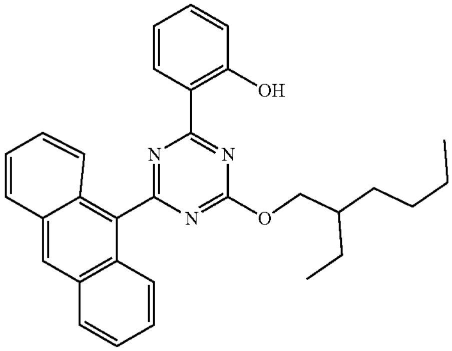
34
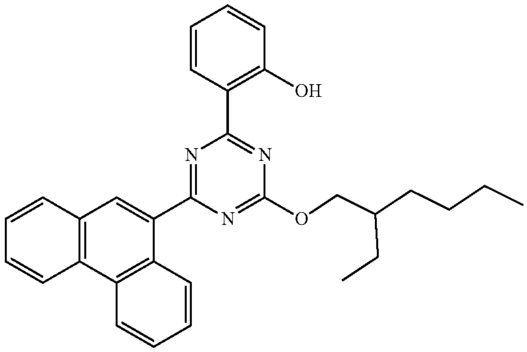
-continued
35
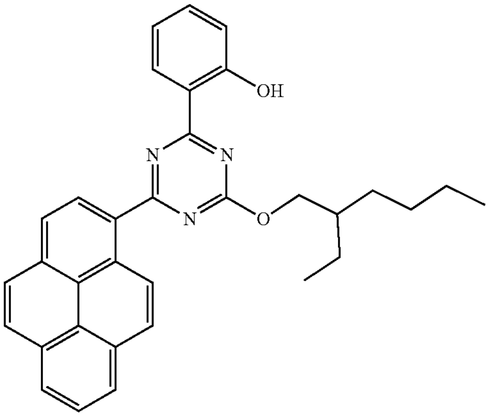
36
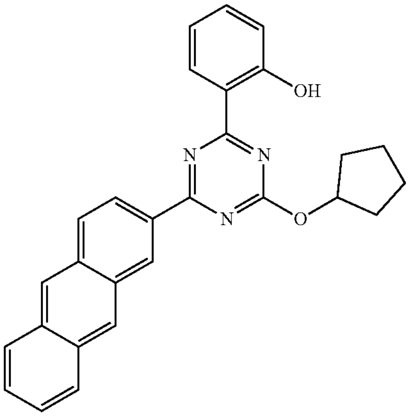
37
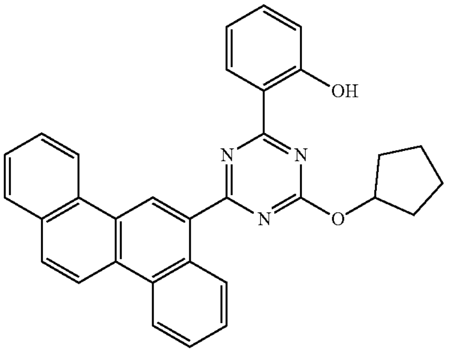
38
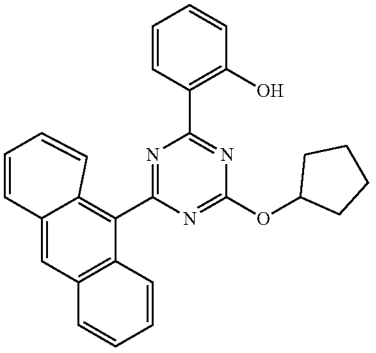

-continued
39
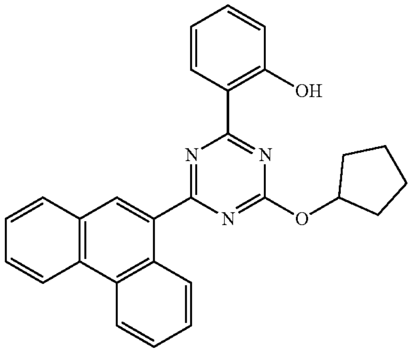
40
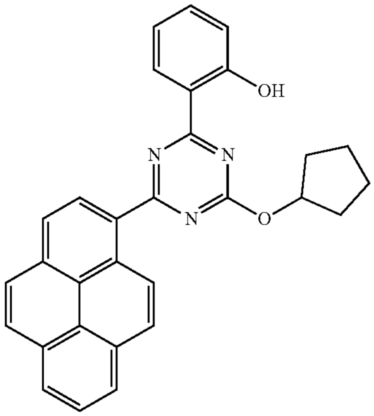
41
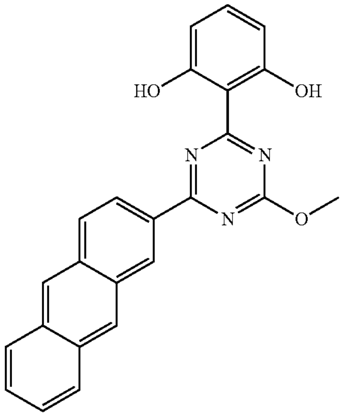
42
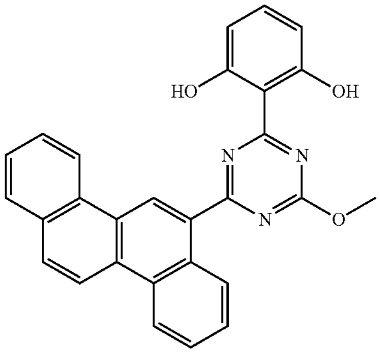
-continued
43
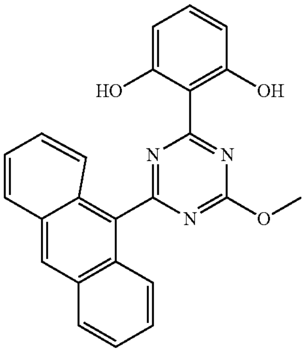
44
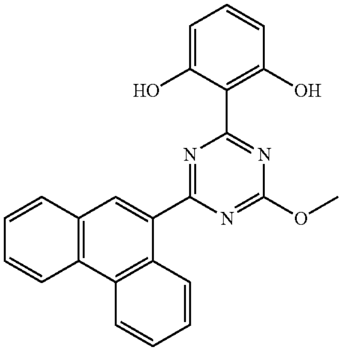
45
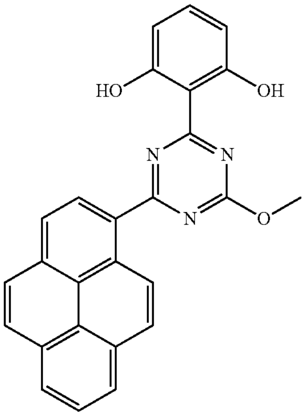
46
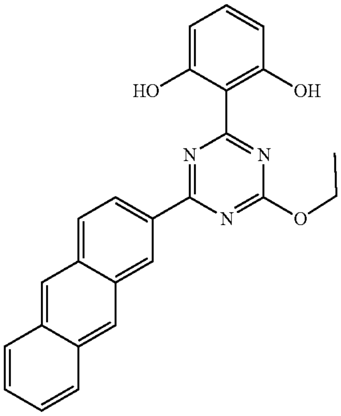

-continued
47
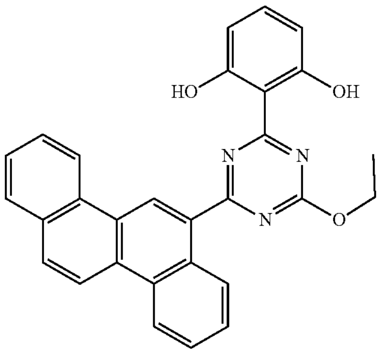
48
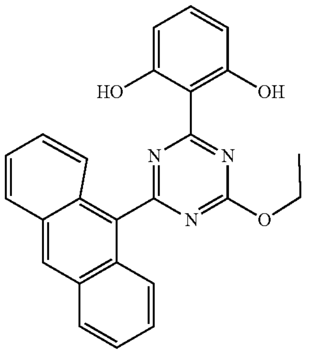
49
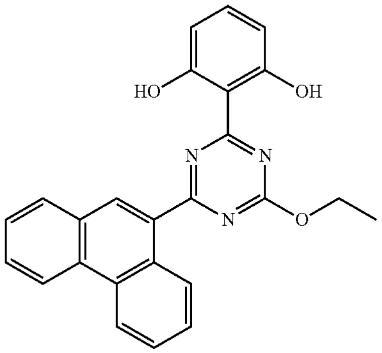
50
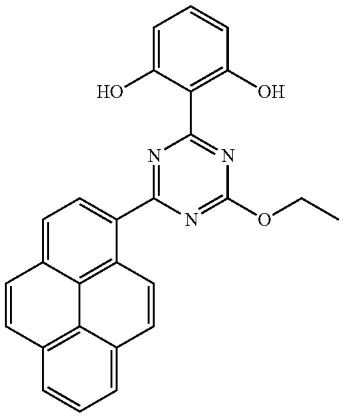
-continued
51
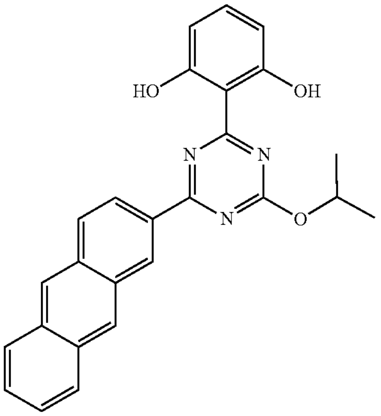
52
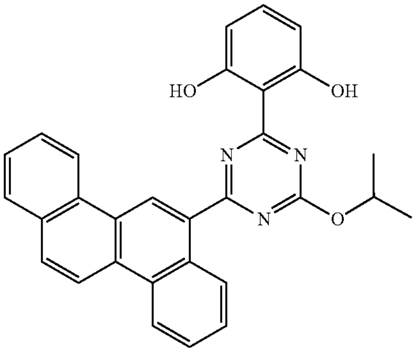
53
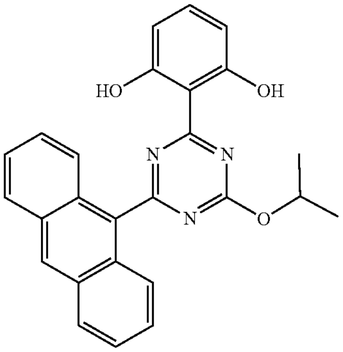
54
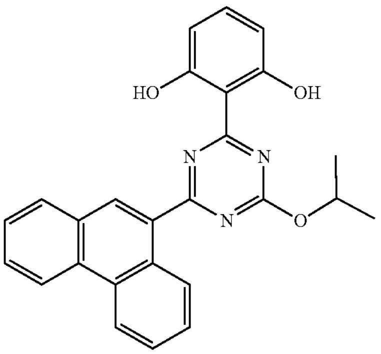

-continued
55
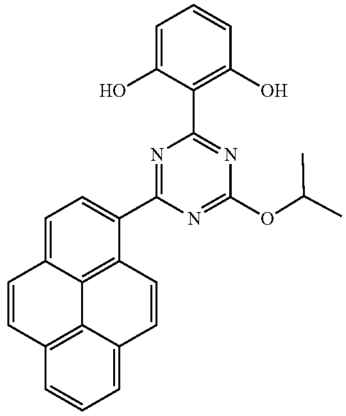
56
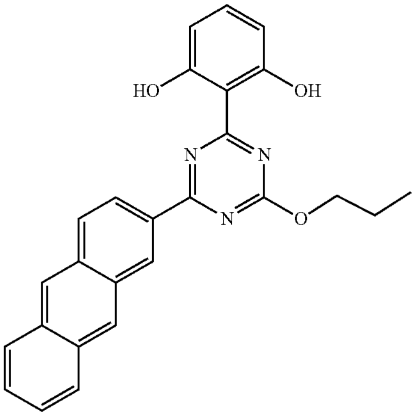
57
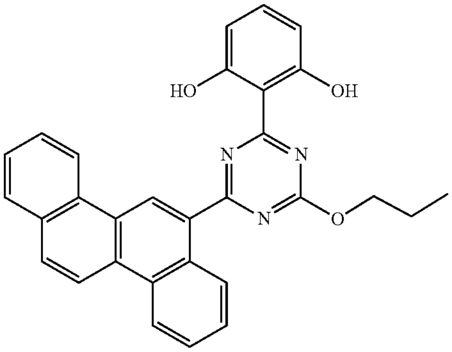
58
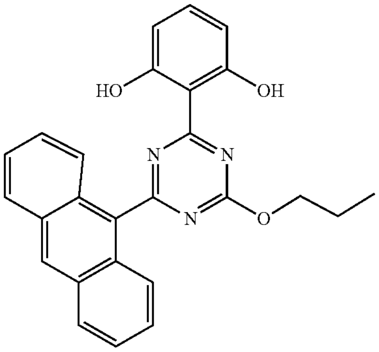
-continued
59
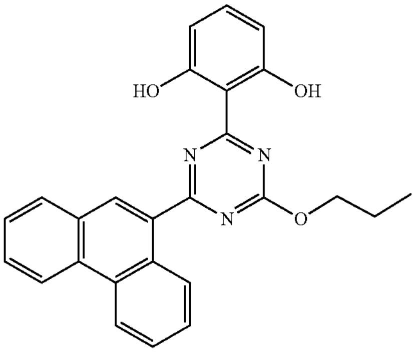
60
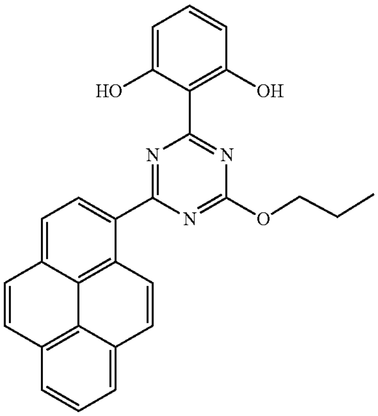
61
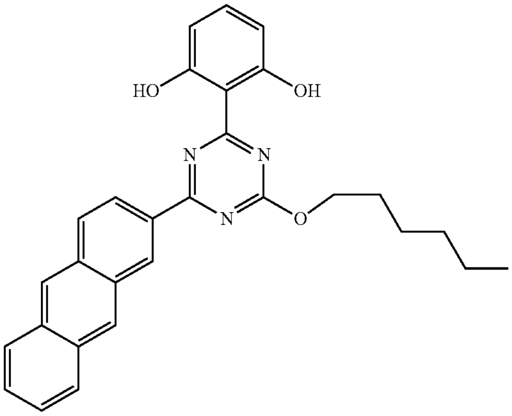
62
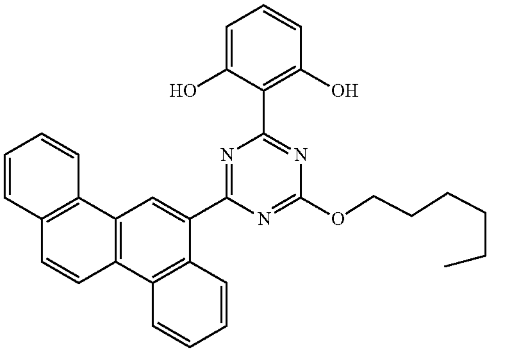

-continued
63
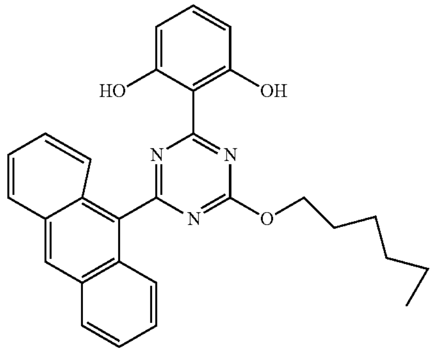
64
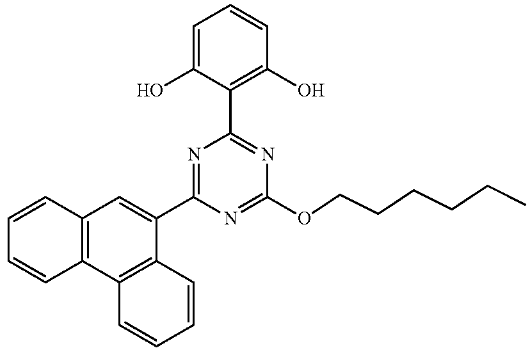
65
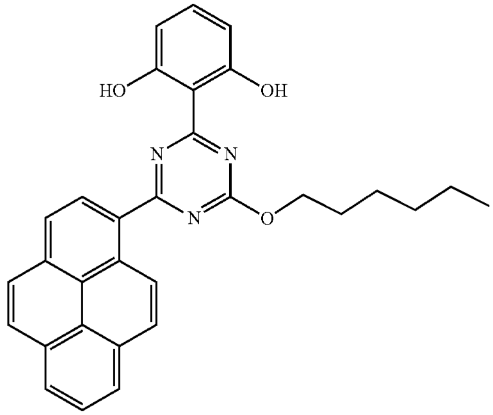
66
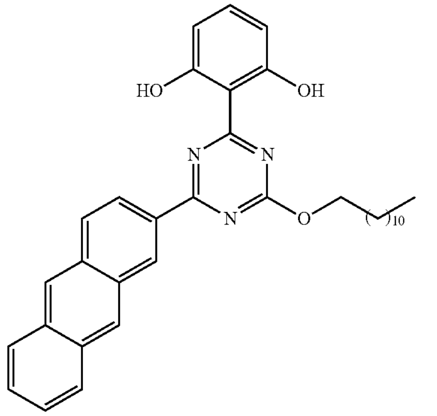
-continued
67
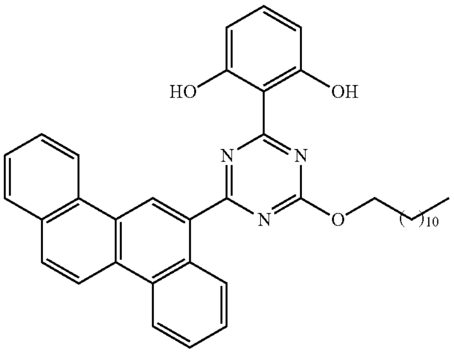
68
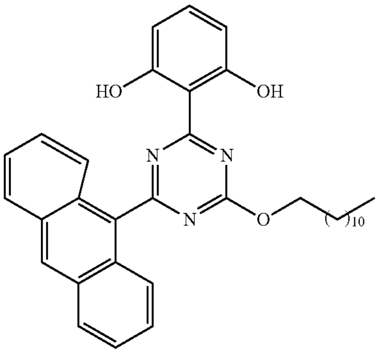
69
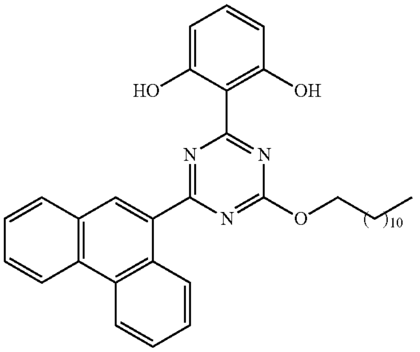
70
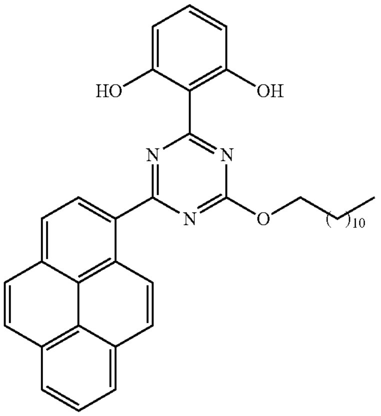

-continued
71
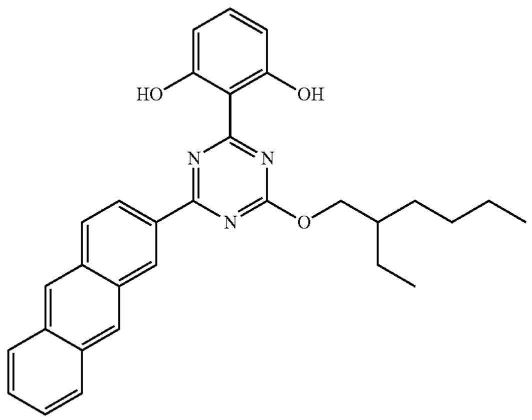
72
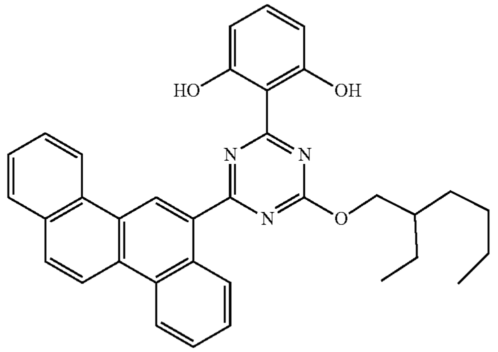
73
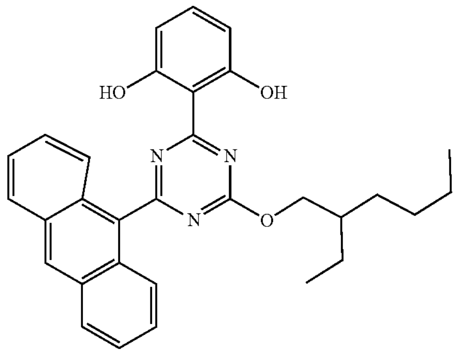
74
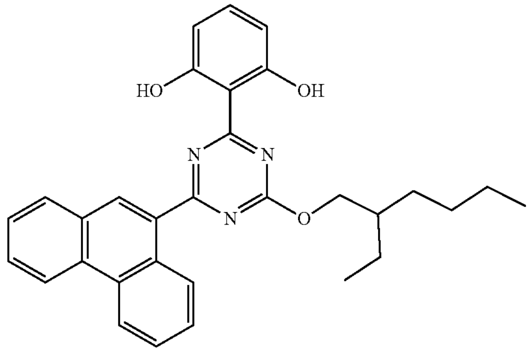
-continued
75
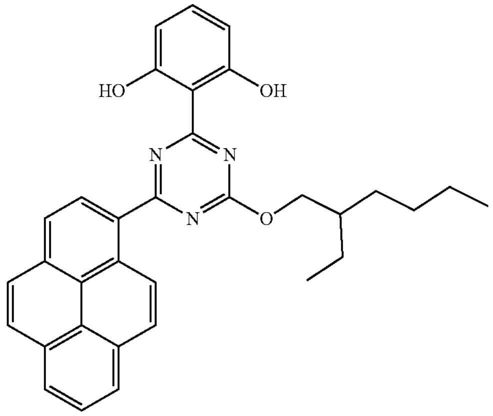
76
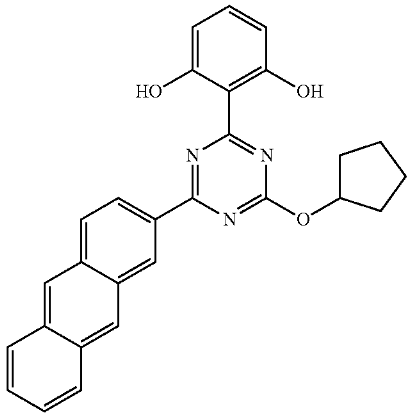
77
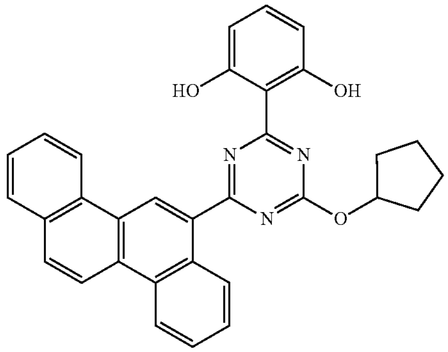
78
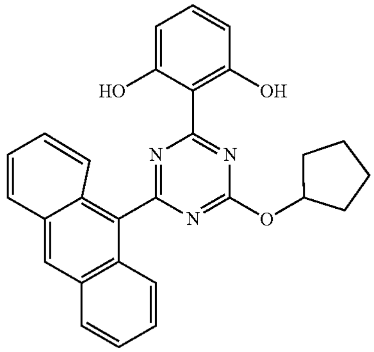

-continued
79
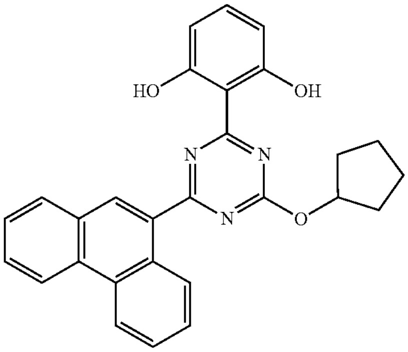
80
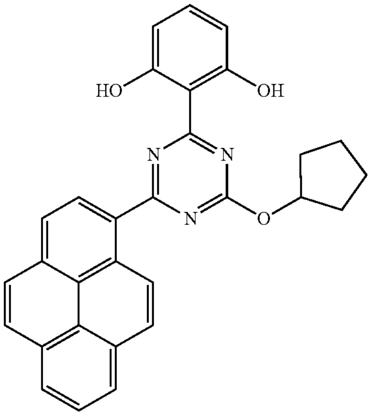
81
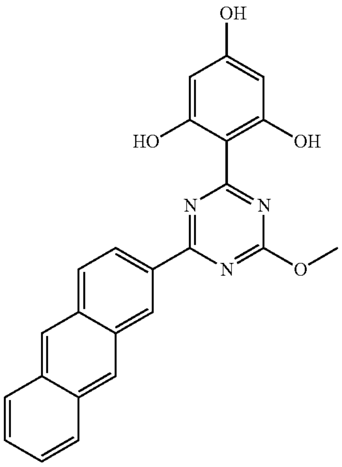
82
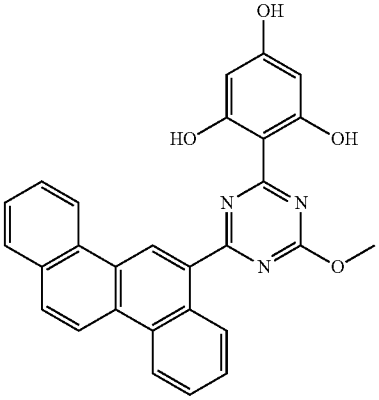
-continued
83
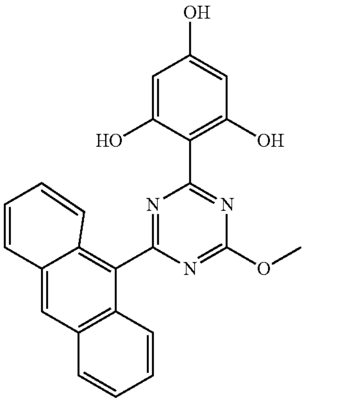
84
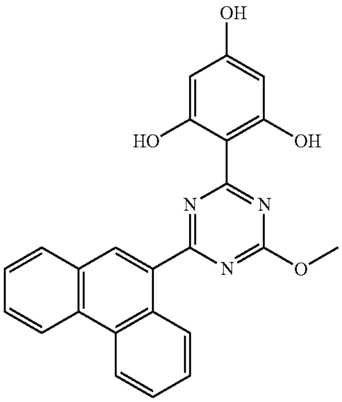
85
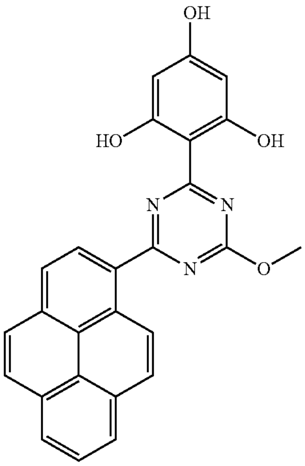

86
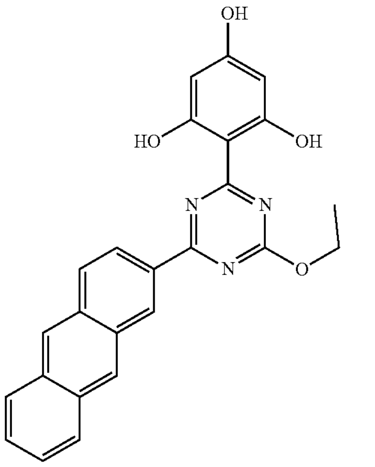
87
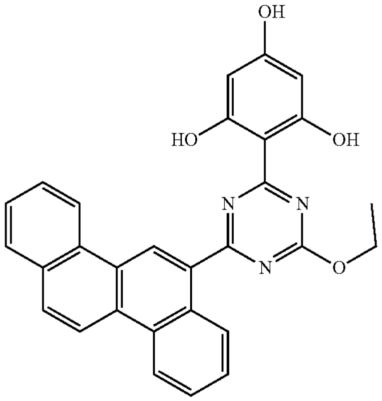
88
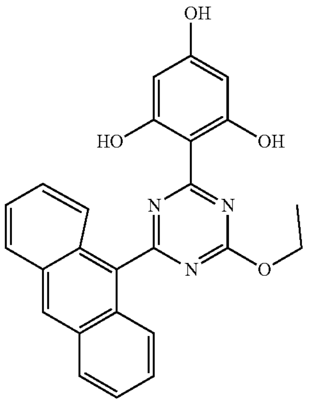
89
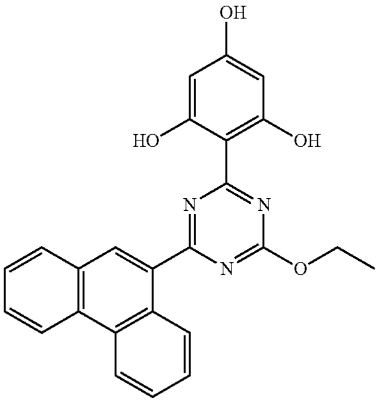
90
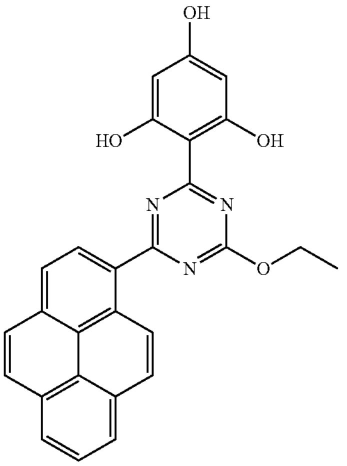
91
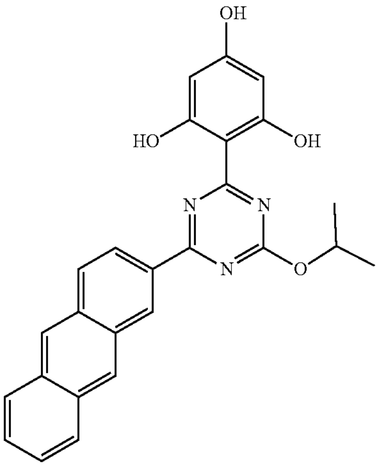

92
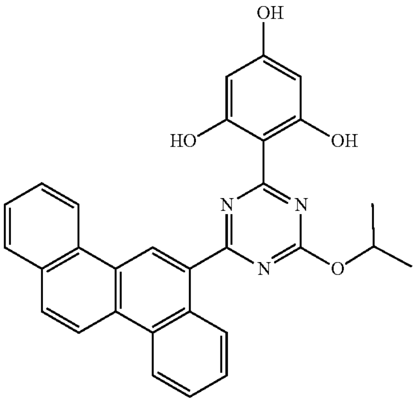
93
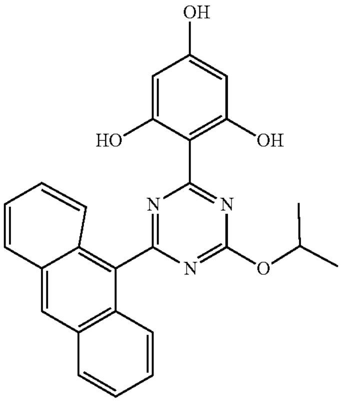
94
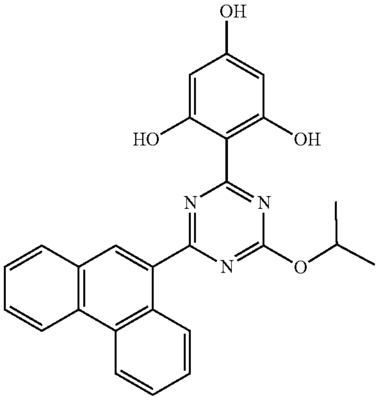
95
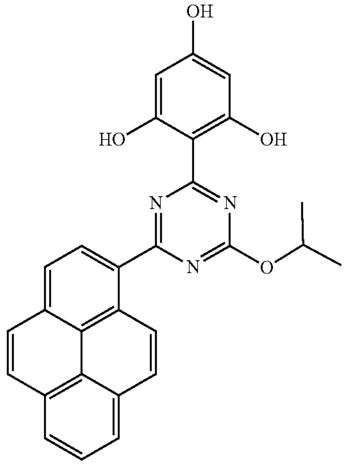
96
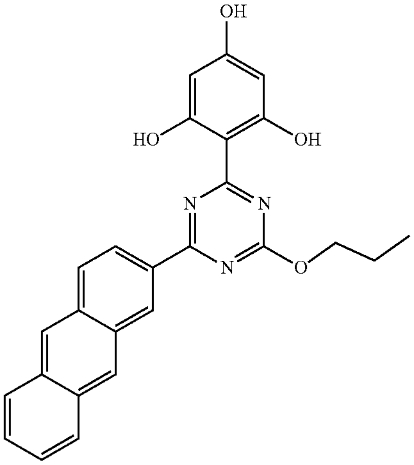
97
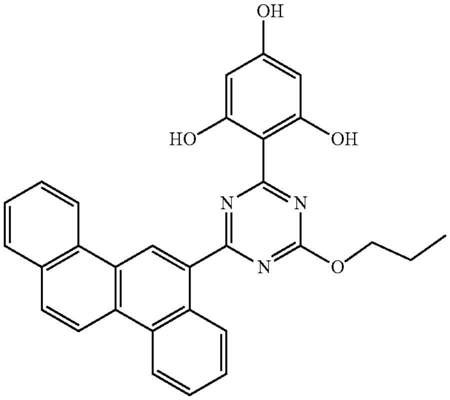

98
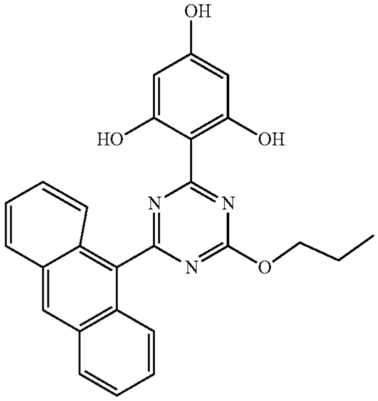
99
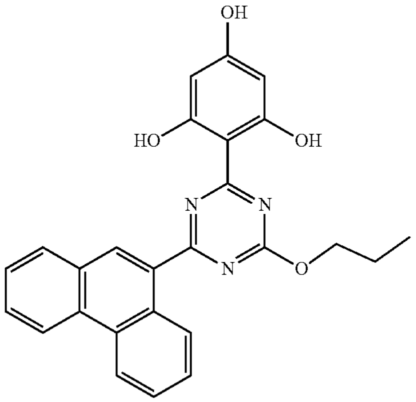
100
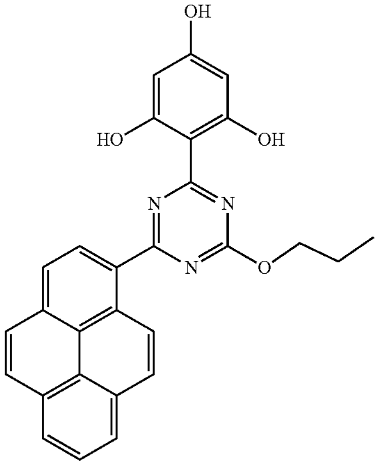
101
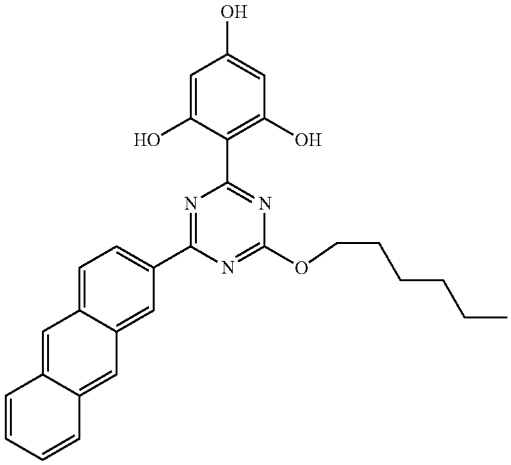
102
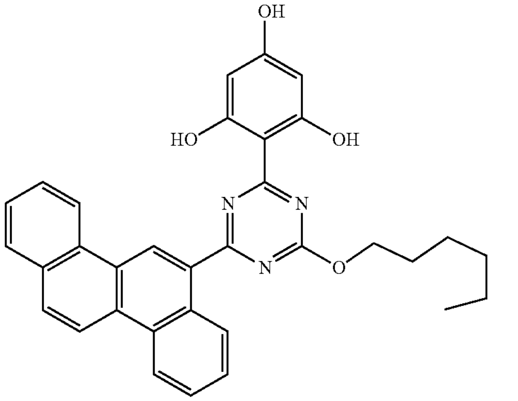
103
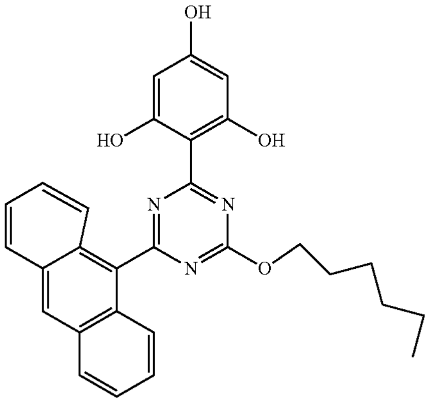

-continued
104
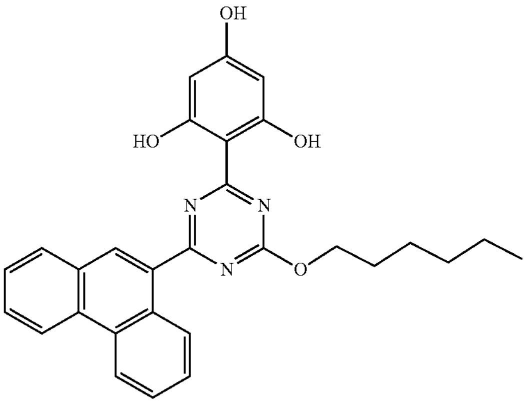
105
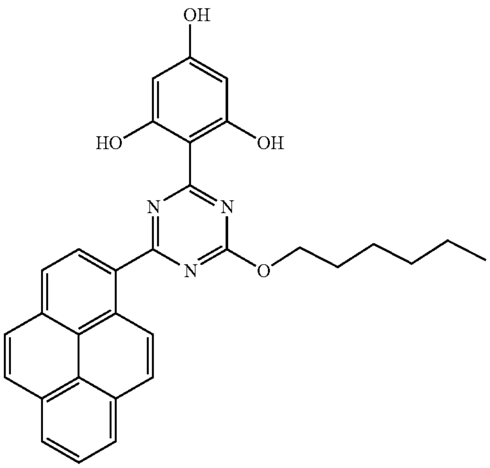
106
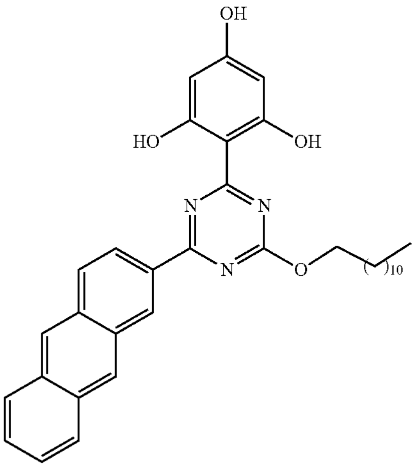
-continued
107
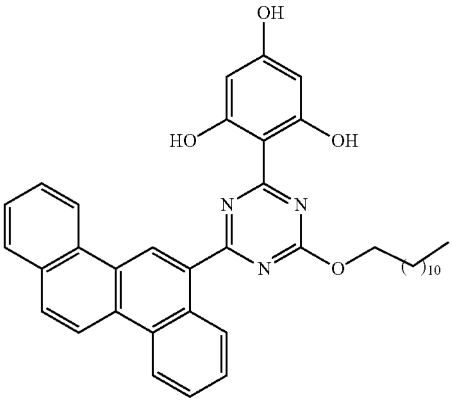
108
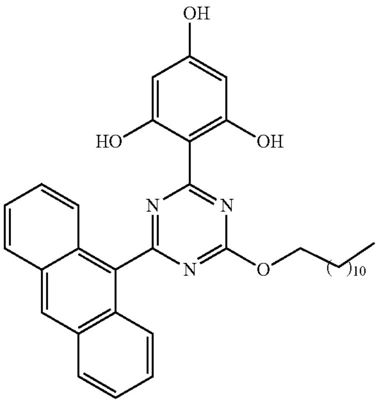
109
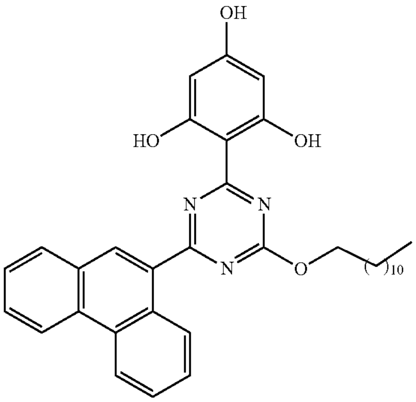

-continued
110
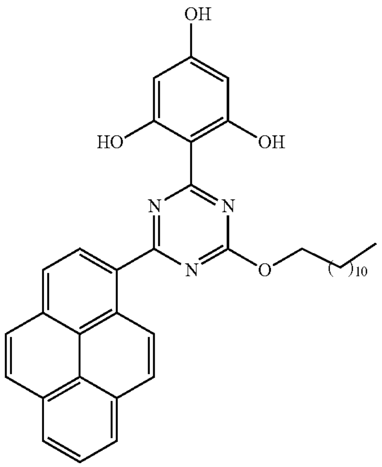
111
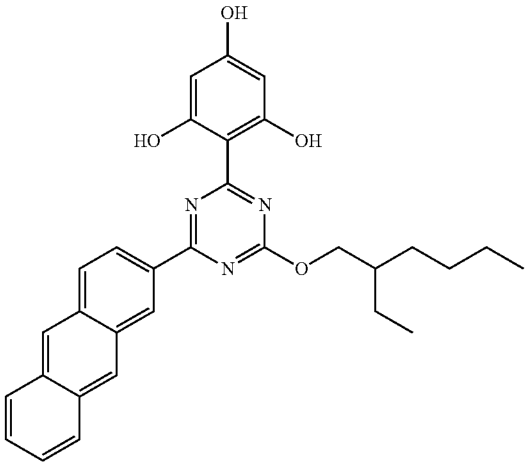
112
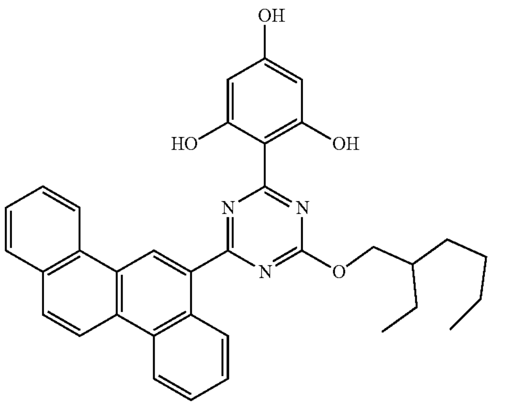
-continued
113
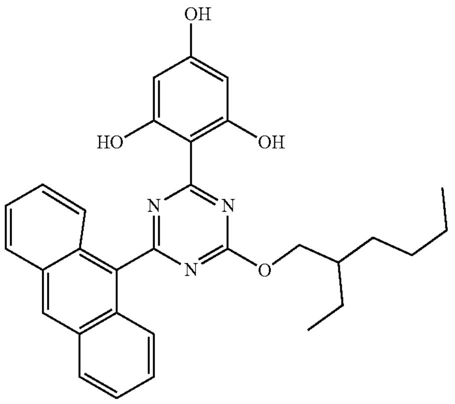
114
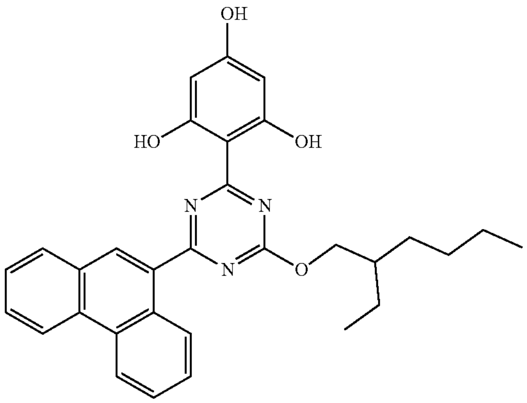
115
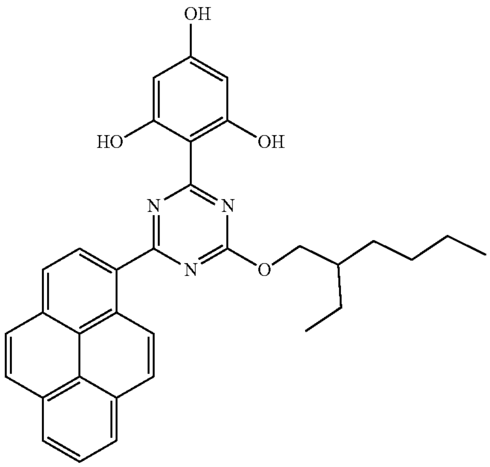

-continued
116
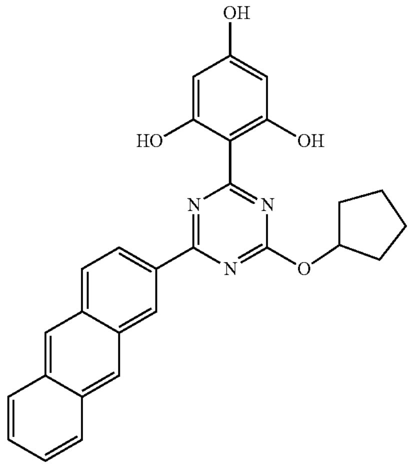
117
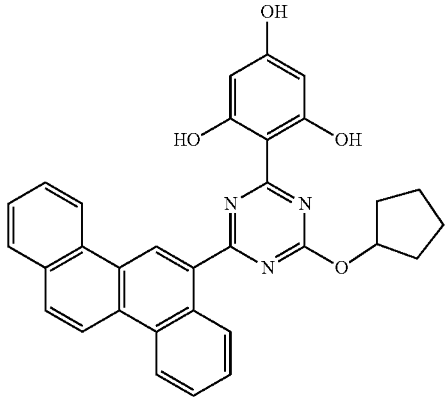
118
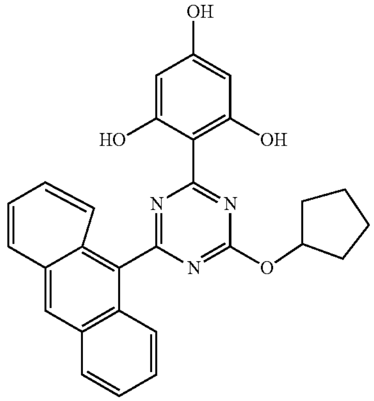
-continued
119
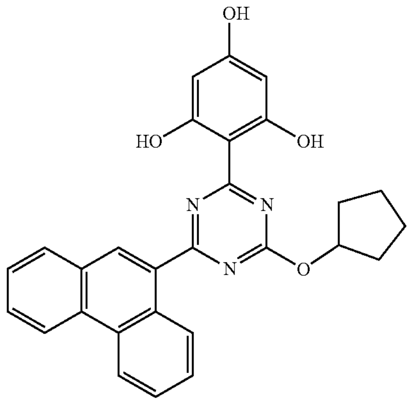
120
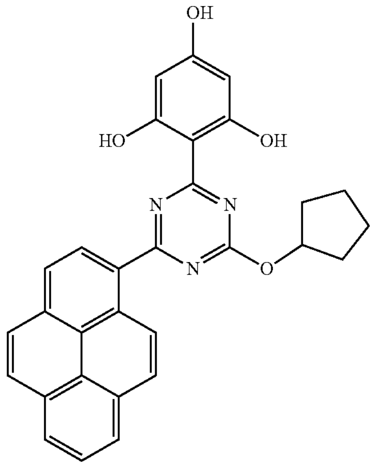
121
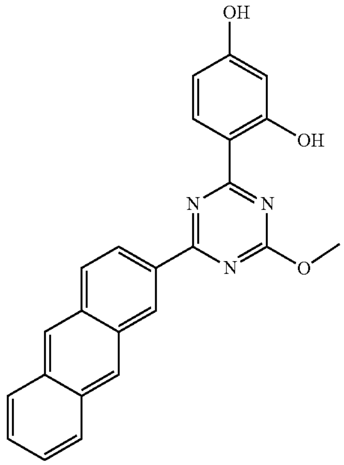

-continued
122
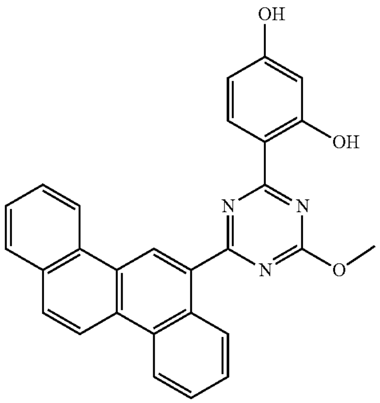
123
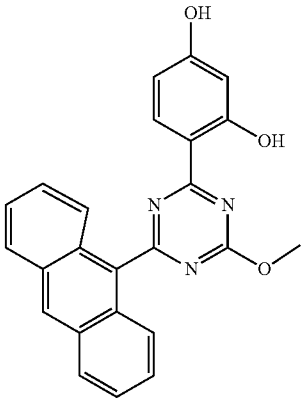
124
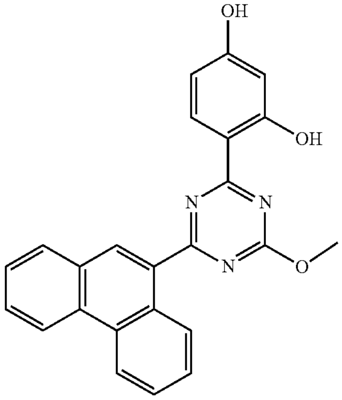
-continued
125
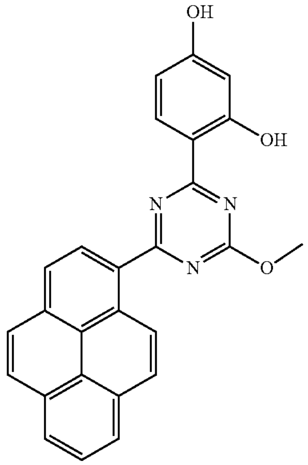
126
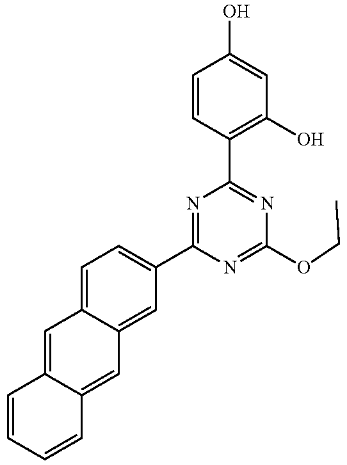
127
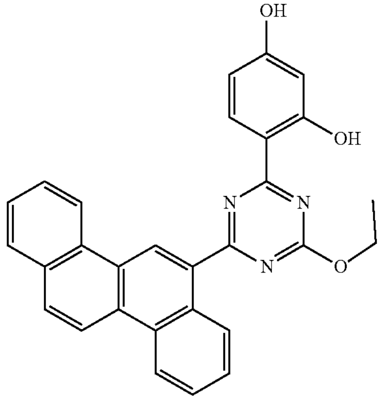

-continued
128
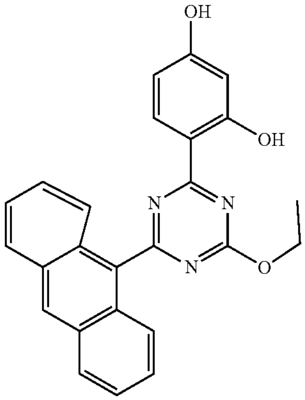
129
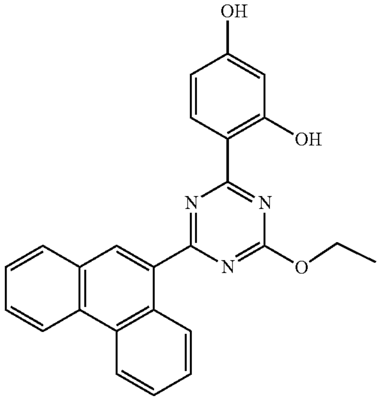
130
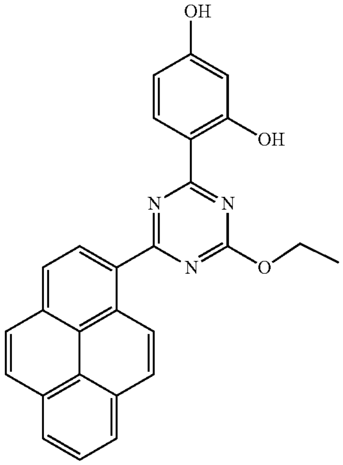
-continued
131
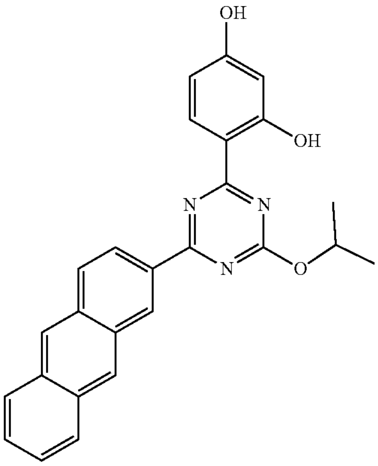
132
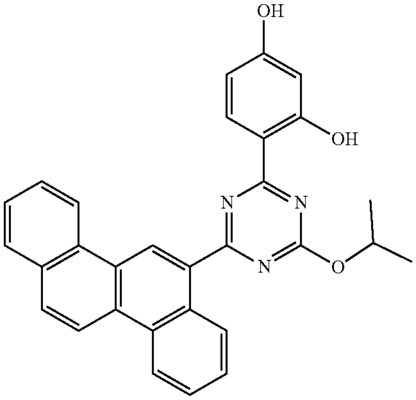
133
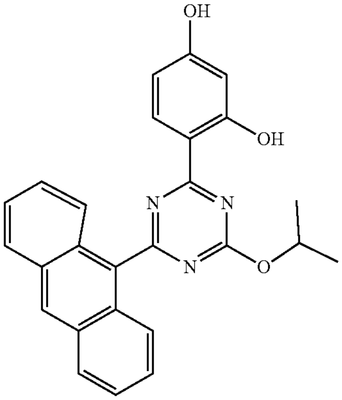

-continued
134
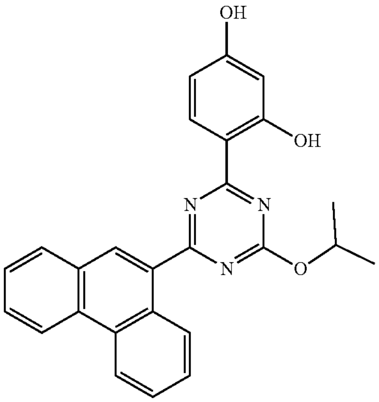
135
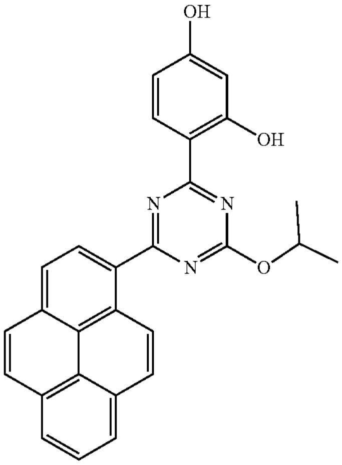
136
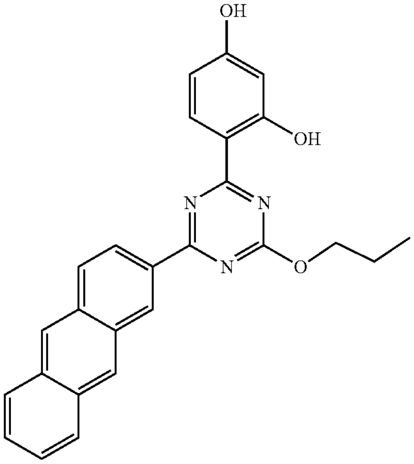
-continued
137
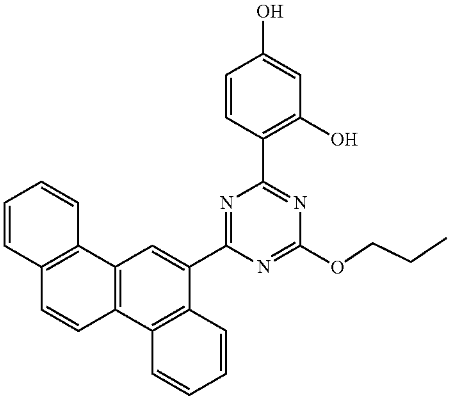
138
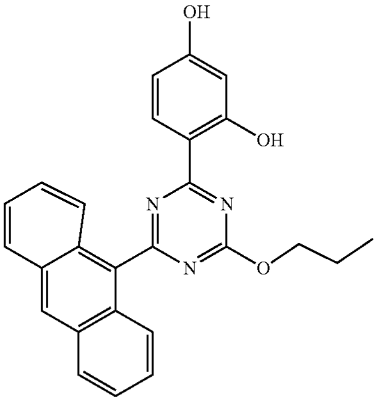
139
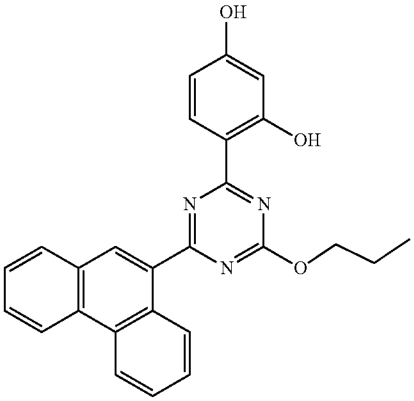

-continued
140
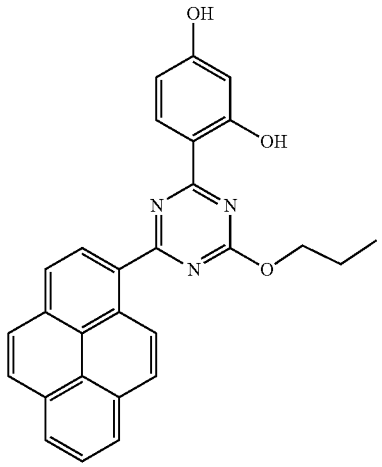
141
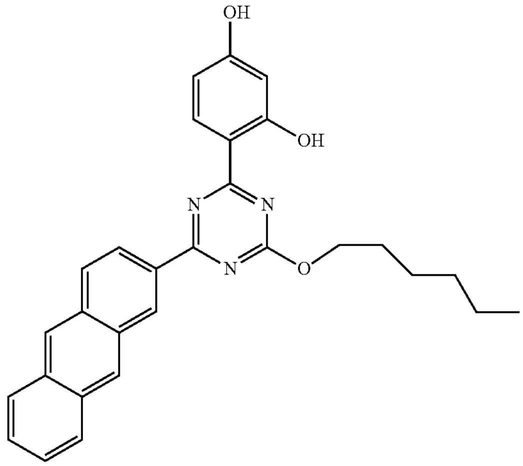
142
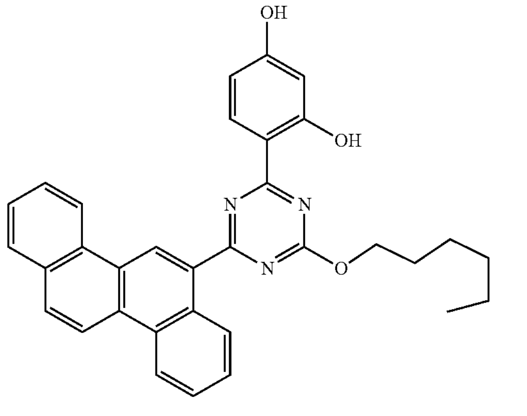
-continued
143
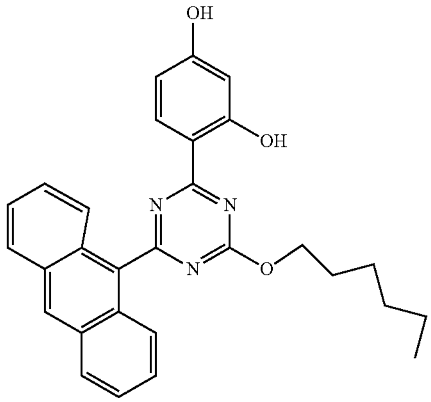
144
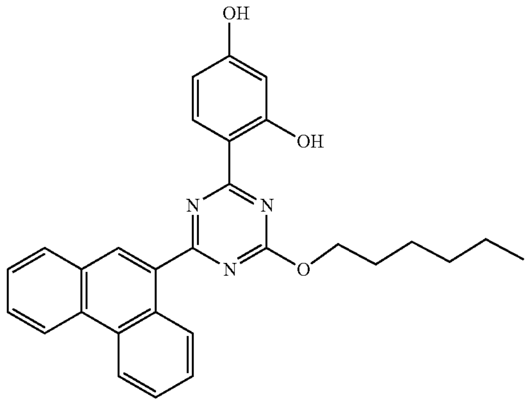
145
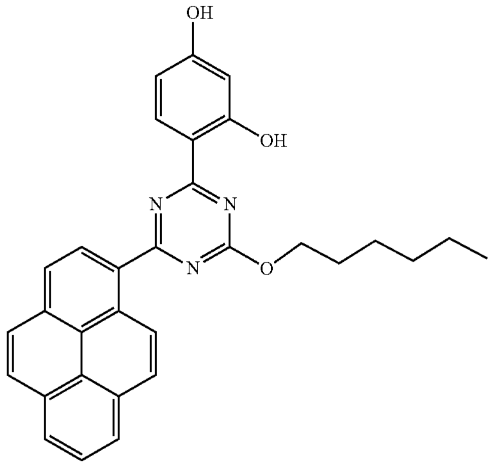

-continued
146
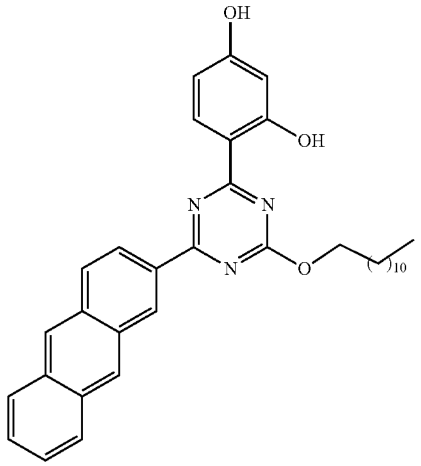
147
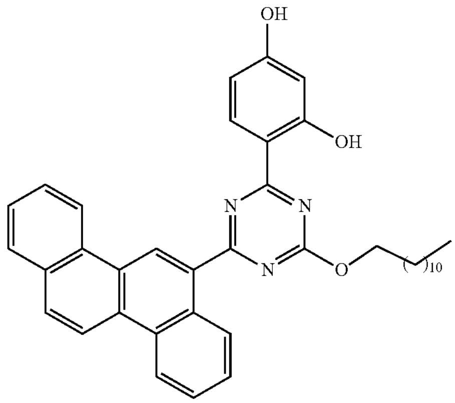
148
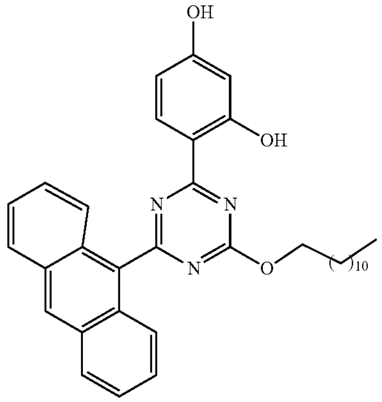
-continued
149
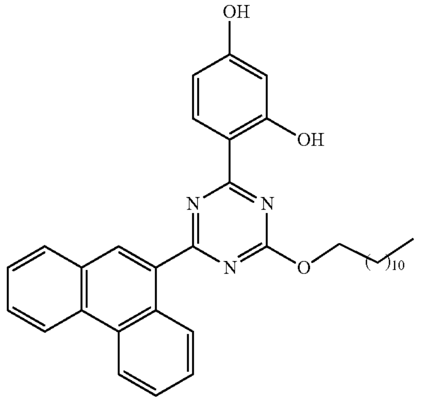
150
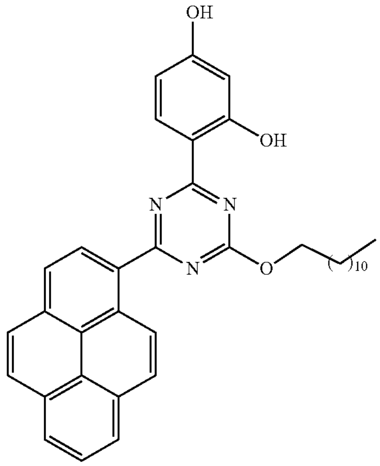
151
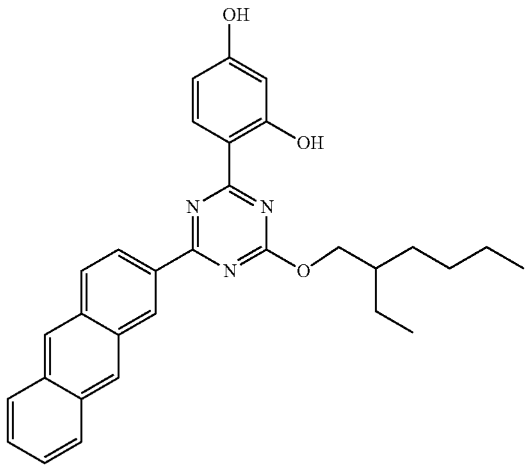

152
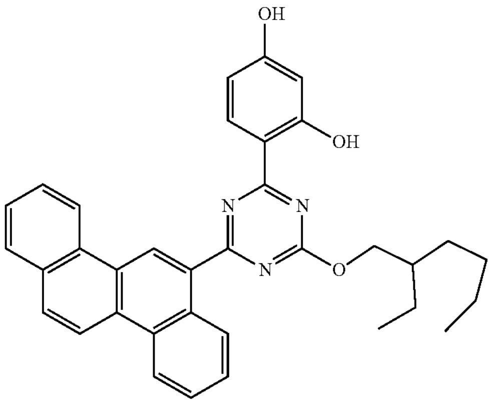
153
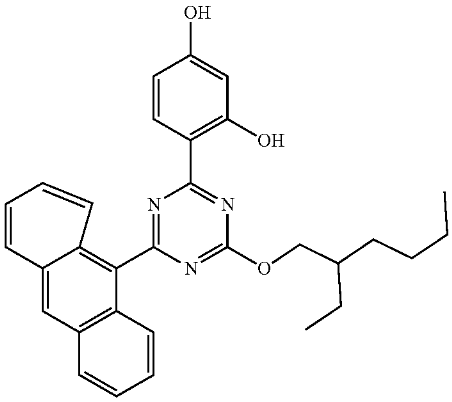
154
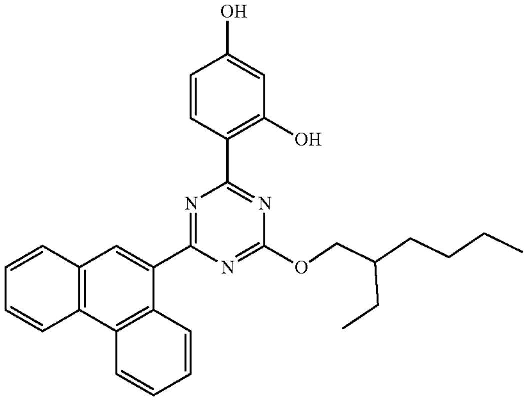
155
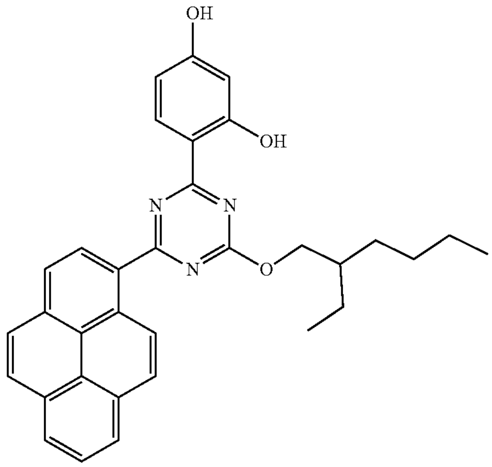
156
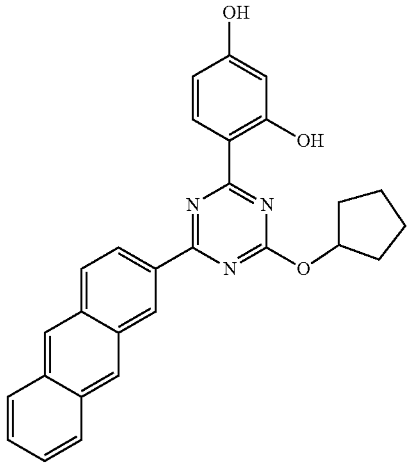
157
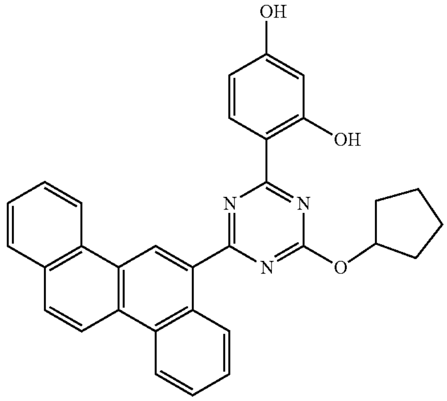

-continued
158
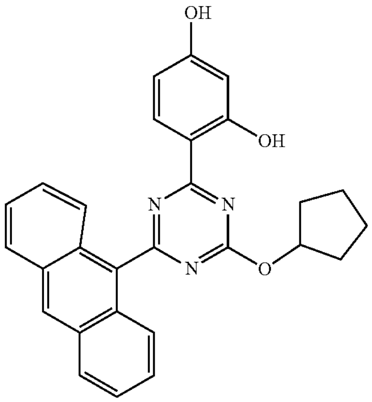
159
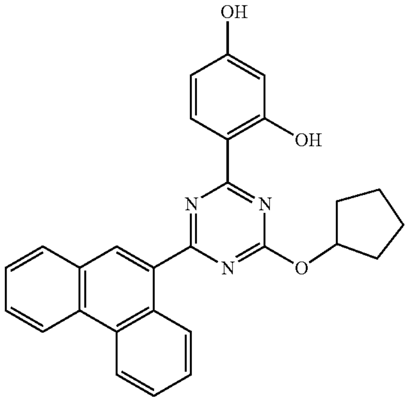
160
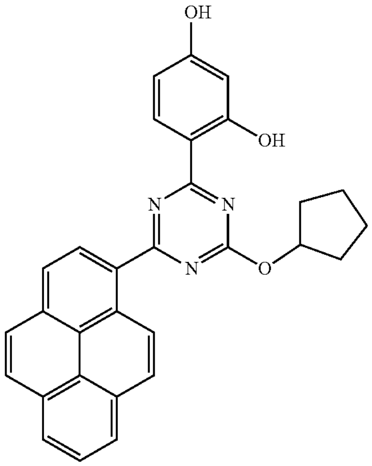
-continued
161
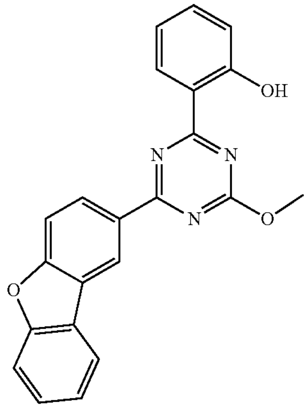
162
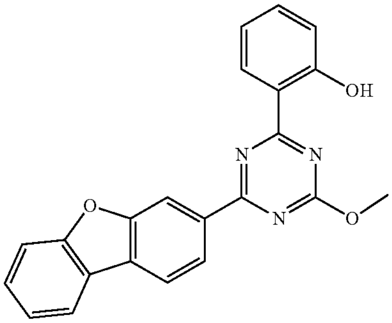
163
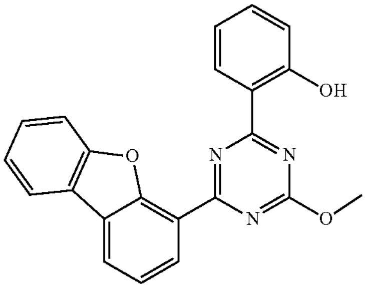
164
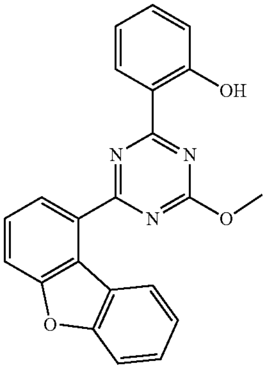

-continued
165
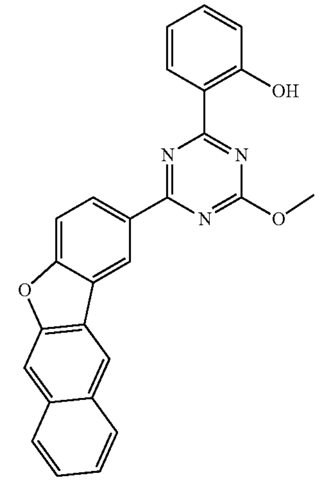
166
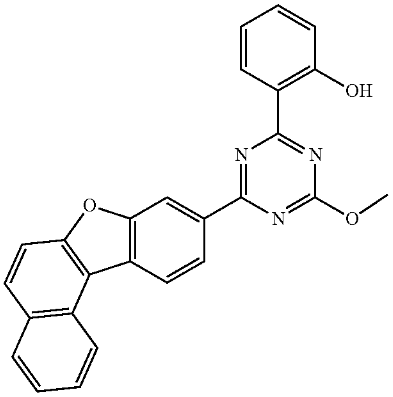
167
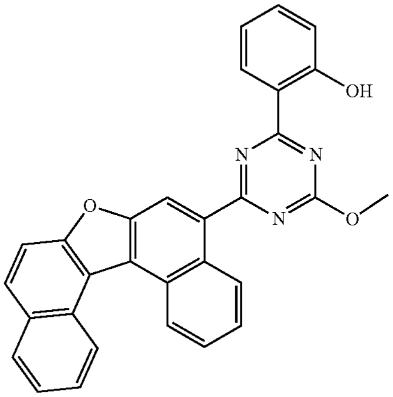
168
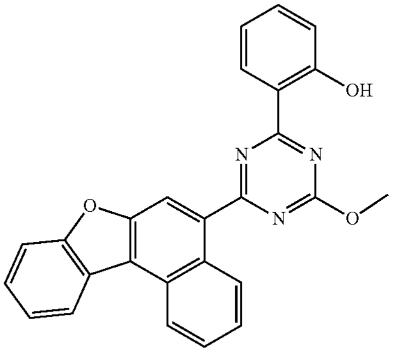
-continued
169
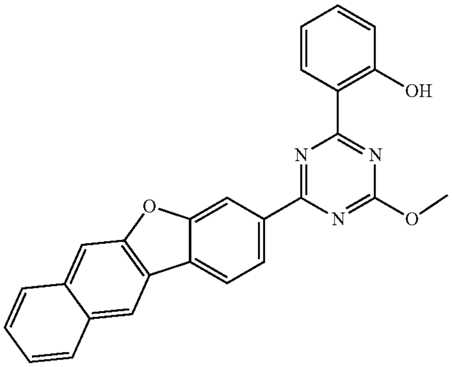
170
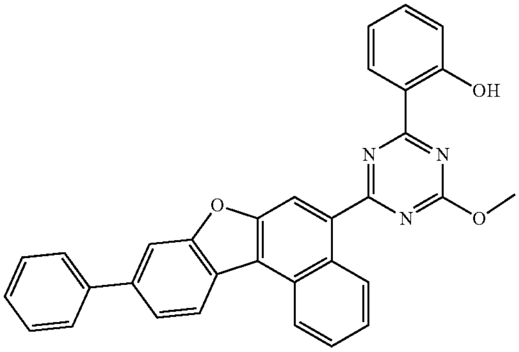
171
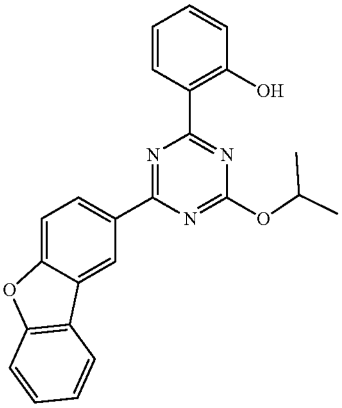
172
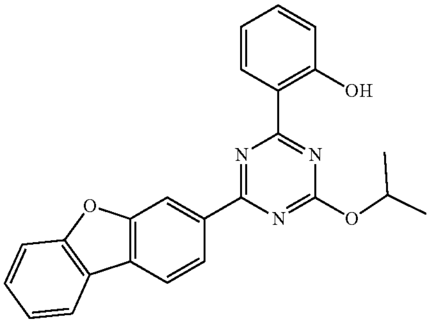

-continued
173
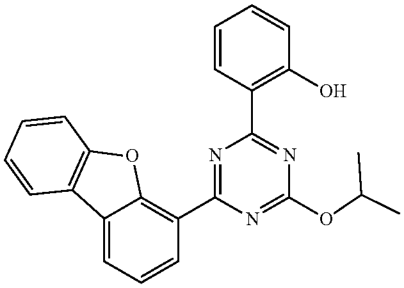
174
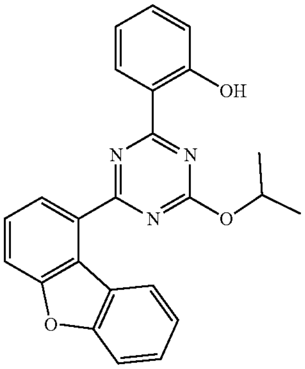
175
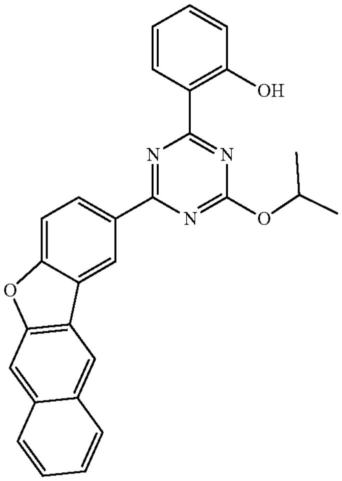
176
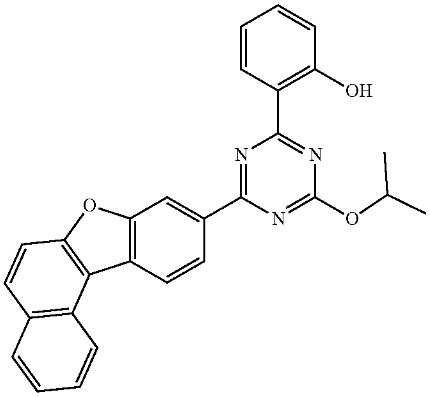
-continued
177
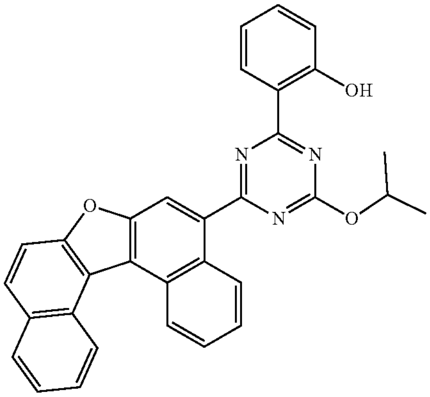
178
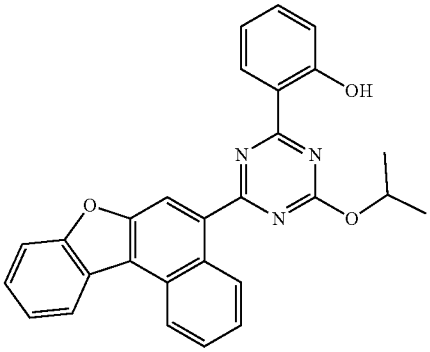
179
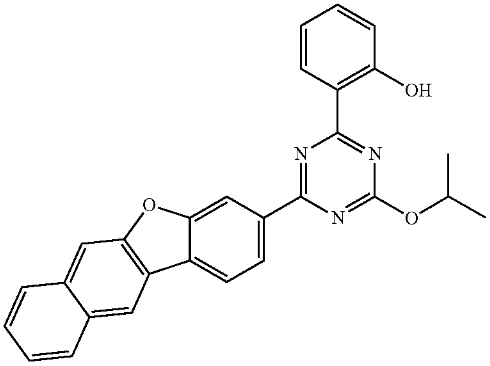
180
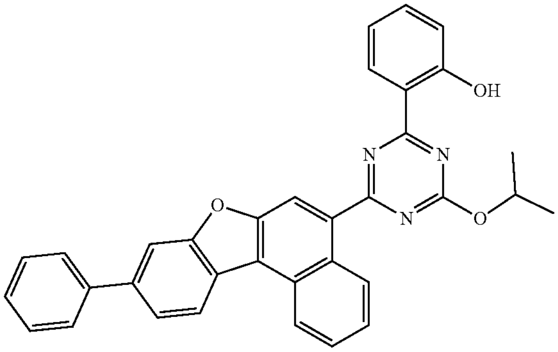

-continued
181
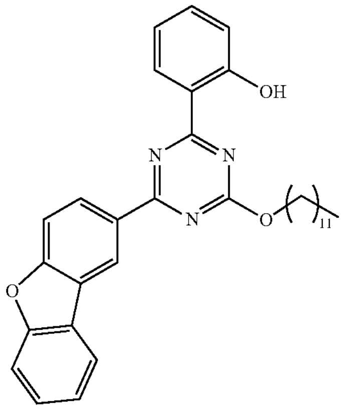
182
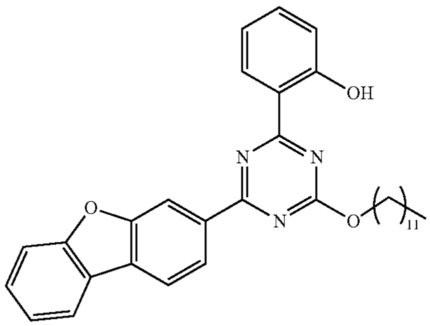
183
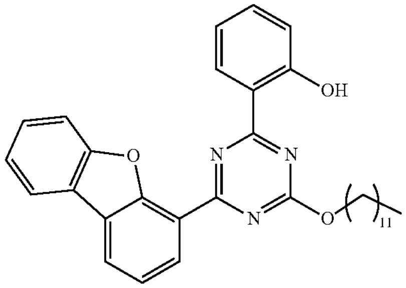
184
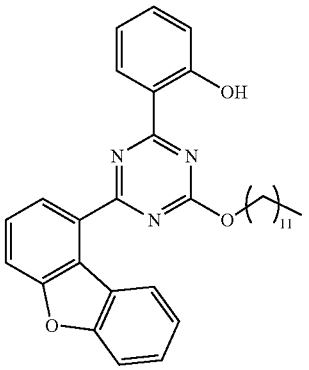
-continued
185
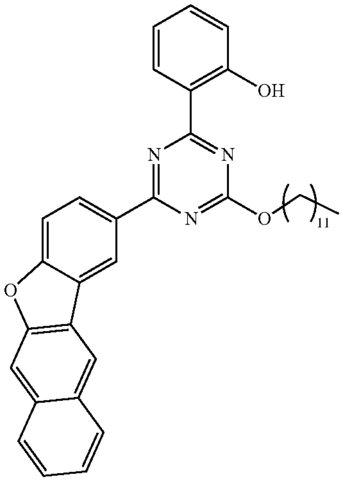
186
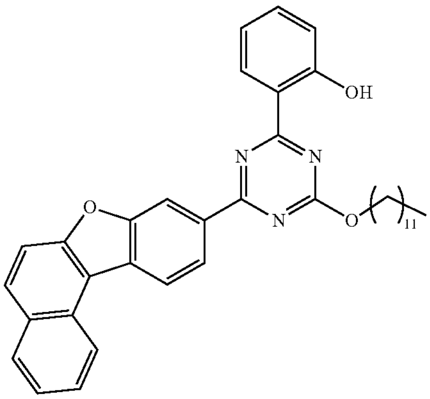
187
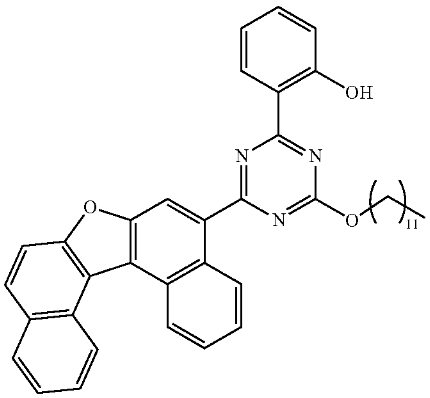
188
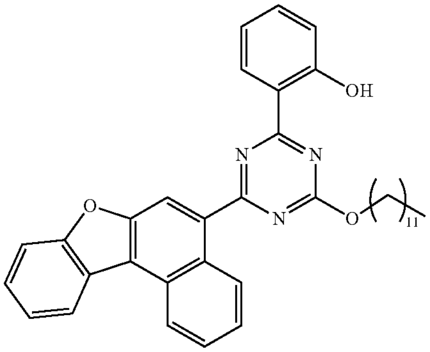

-continued
189
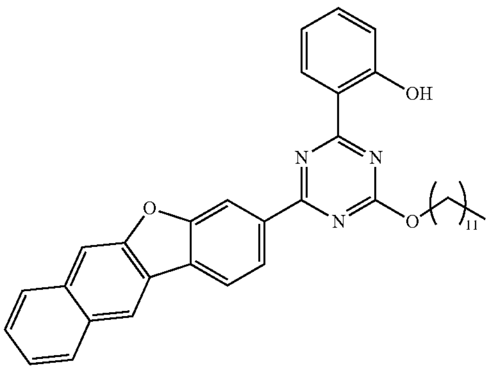
190
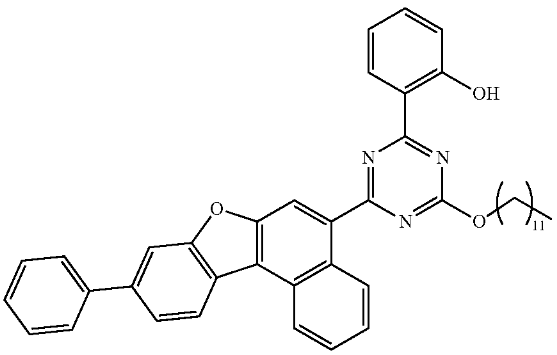
191
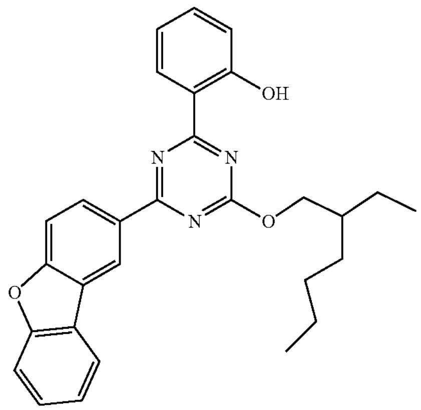
192
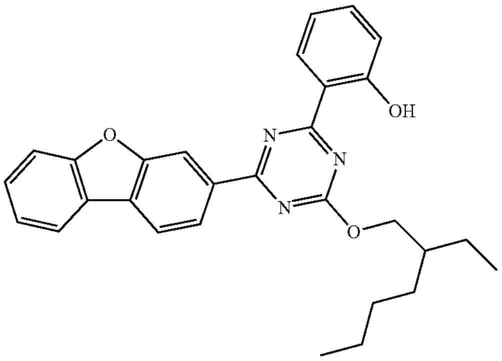
-continued
193
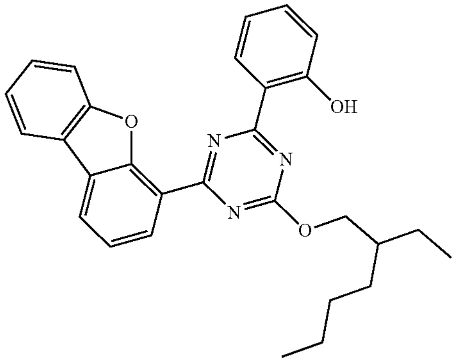
194
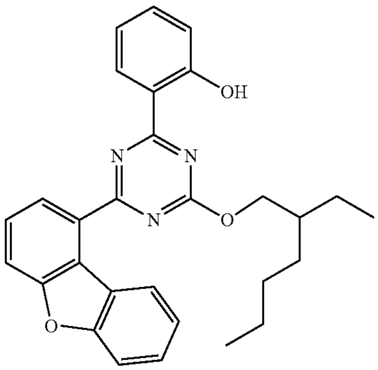
195
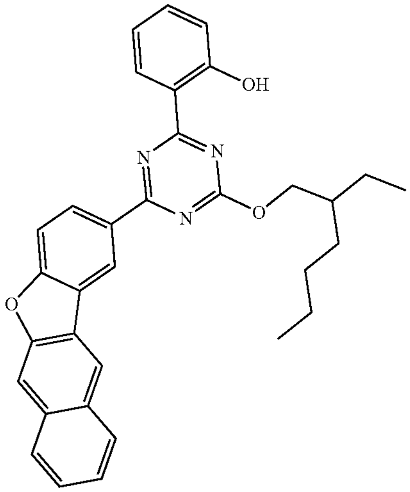
196
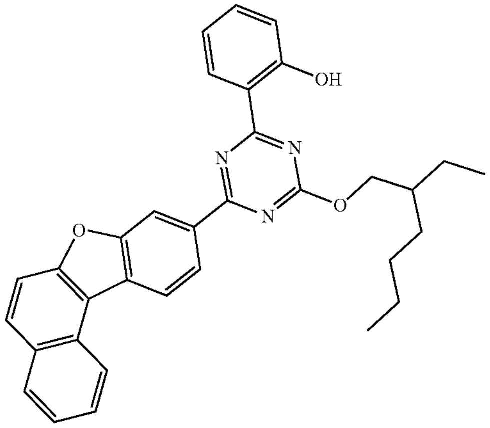

-continued
197
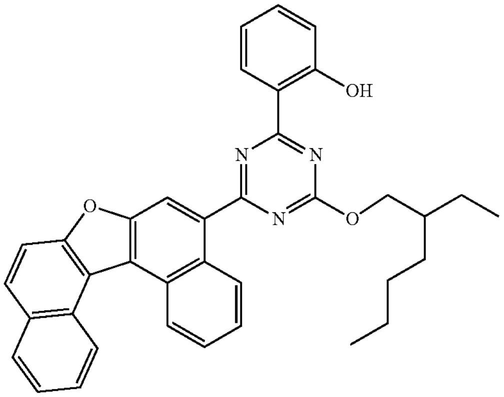
198
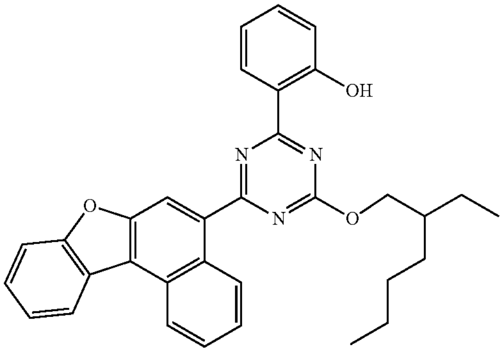
199
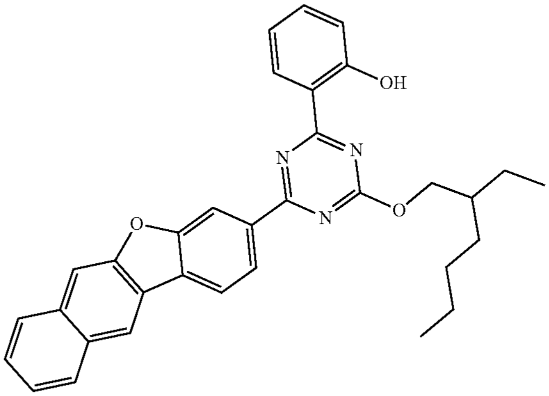
200
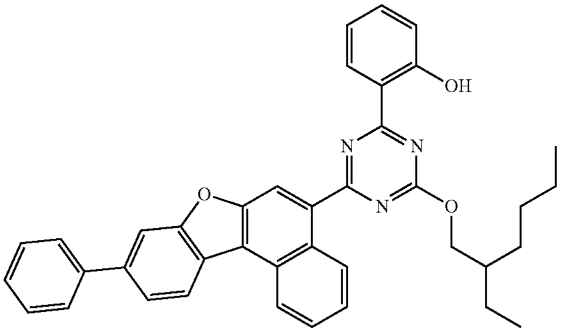
-continued
201
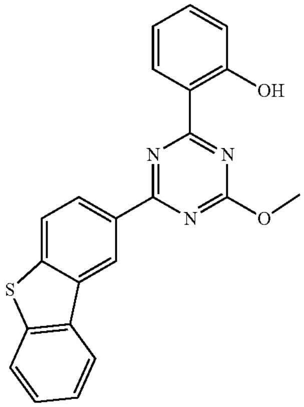
202
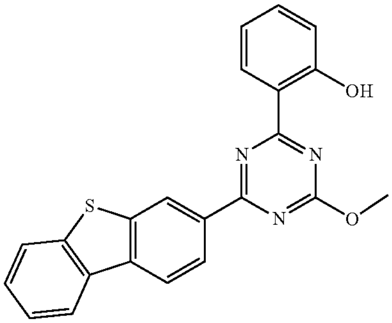
203
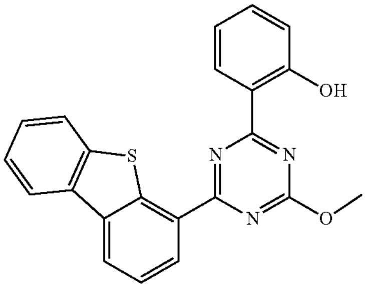
204
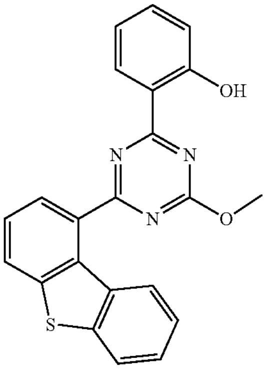

-continued
205
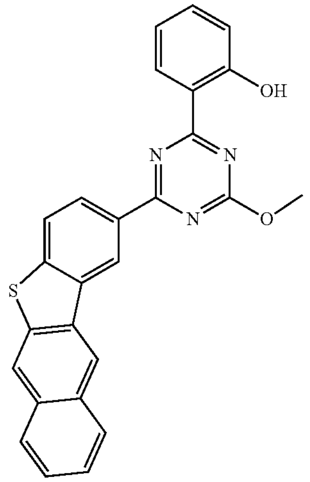
206
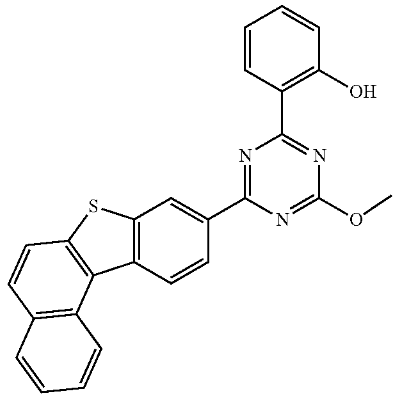
207
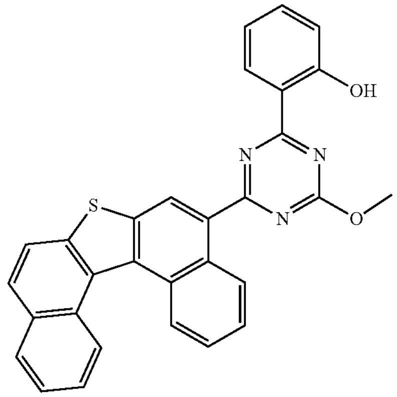
208
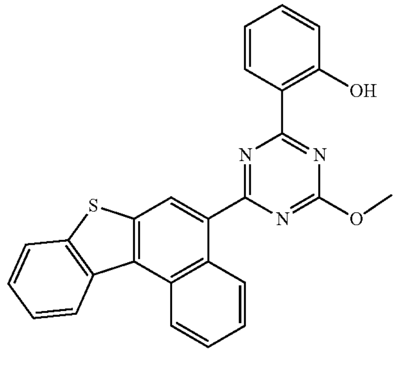
-continued
209
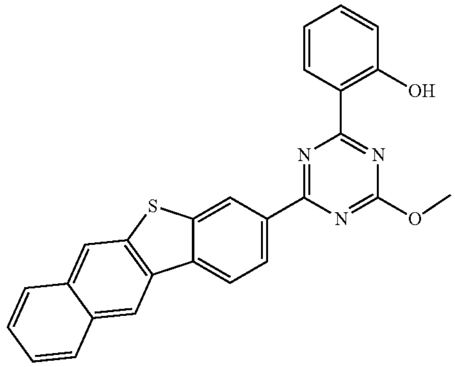
210
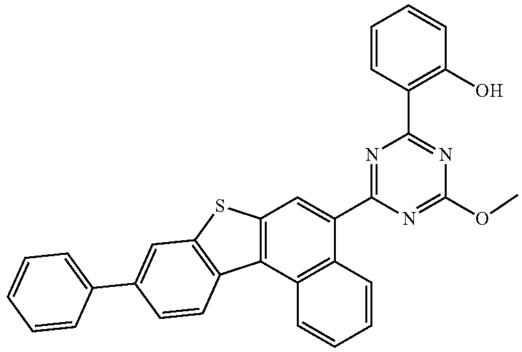
211
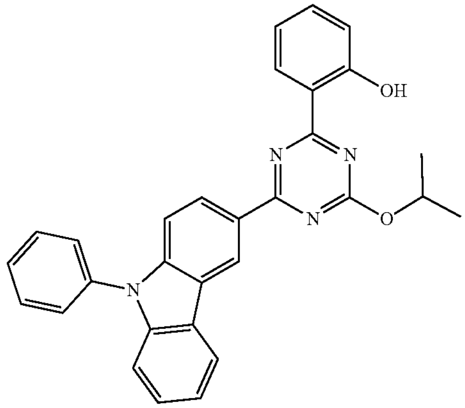
212
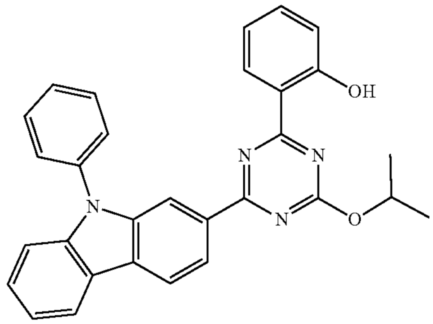

213
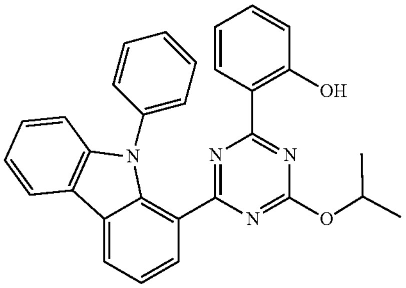
214
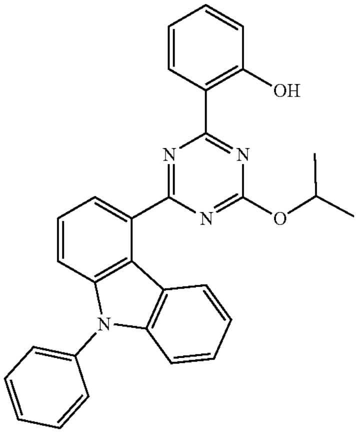
215
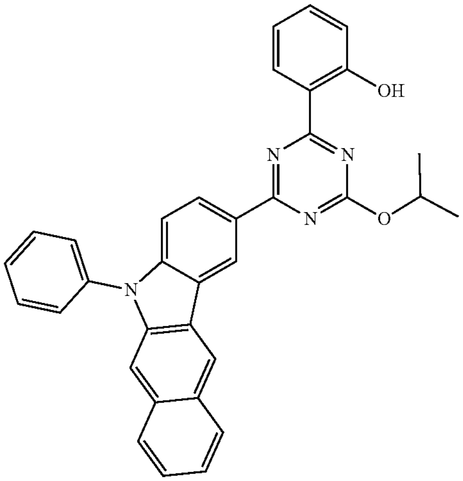
216
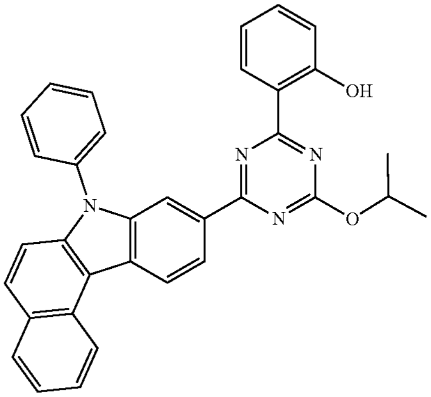
217
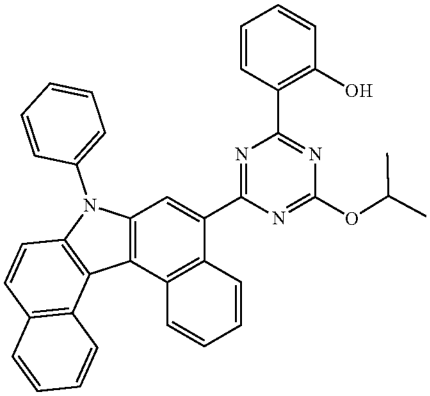
218
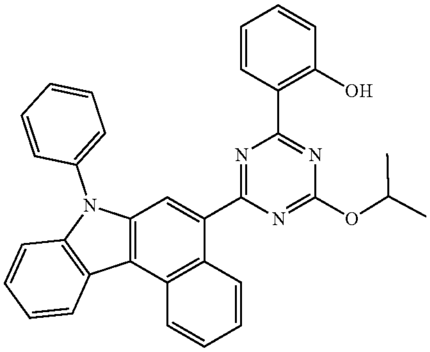
219
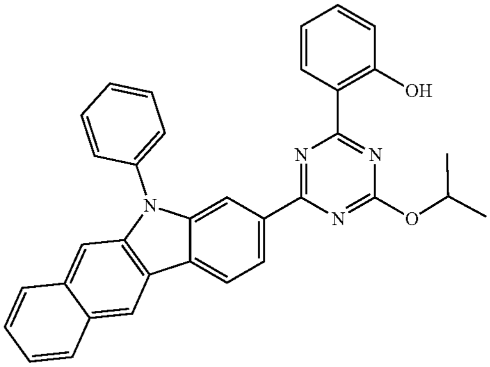
220
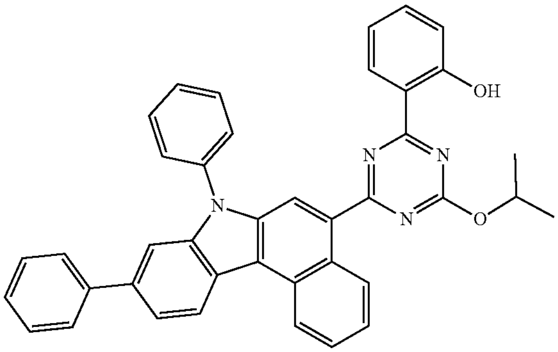

-continued
221
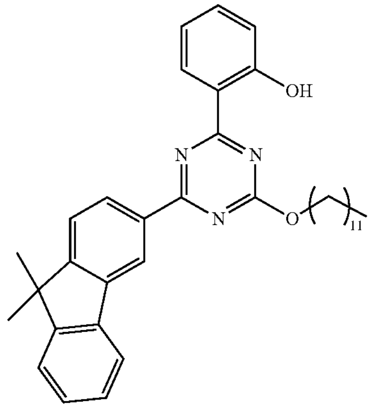
222
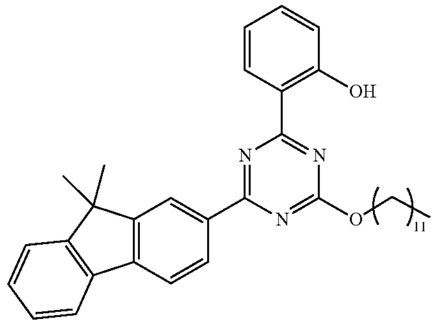
223
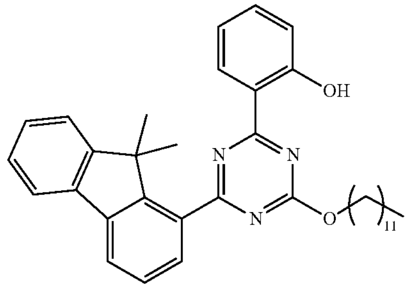
224
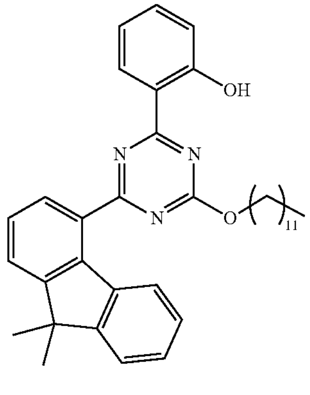
-continued
225
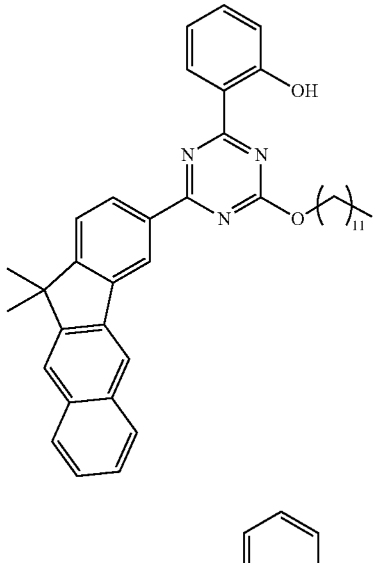
226
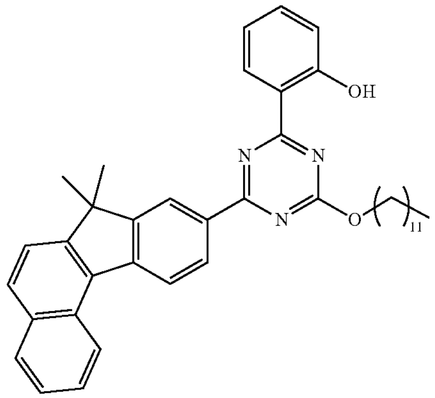
227
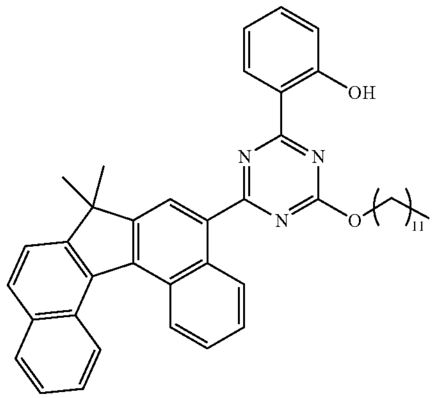
228
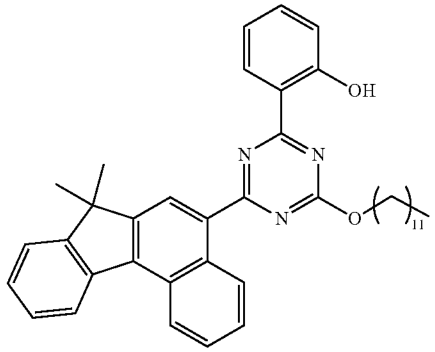

-continued
229
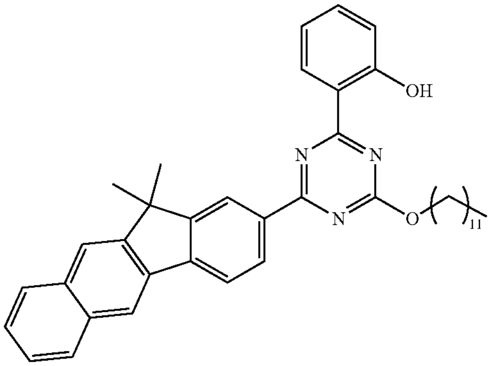
230
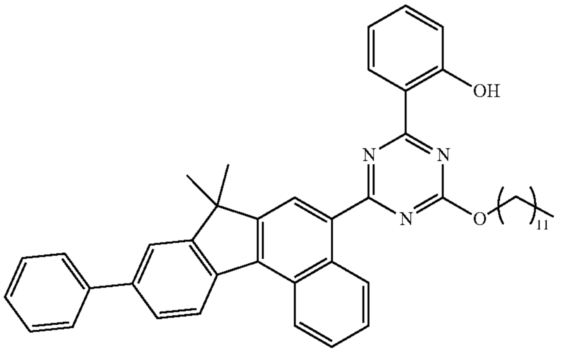
231
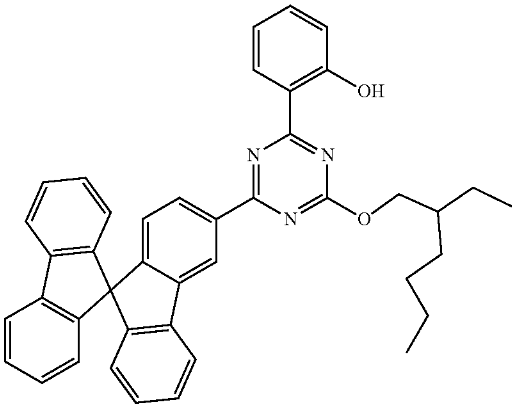
232
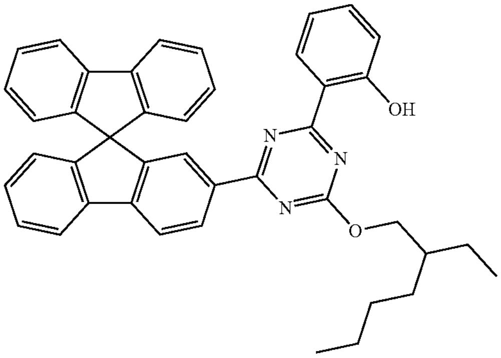
-continued
233
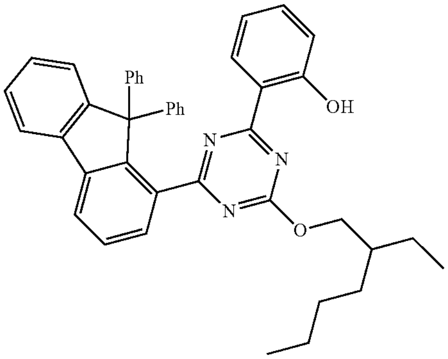
234
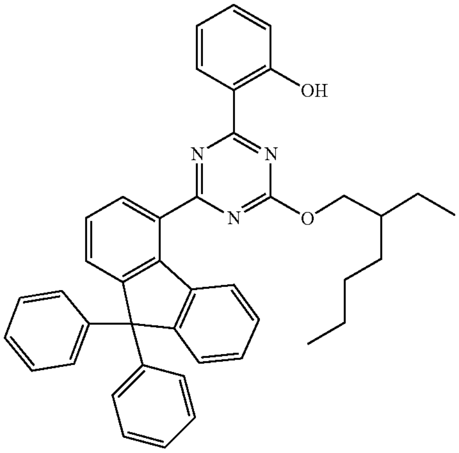
235
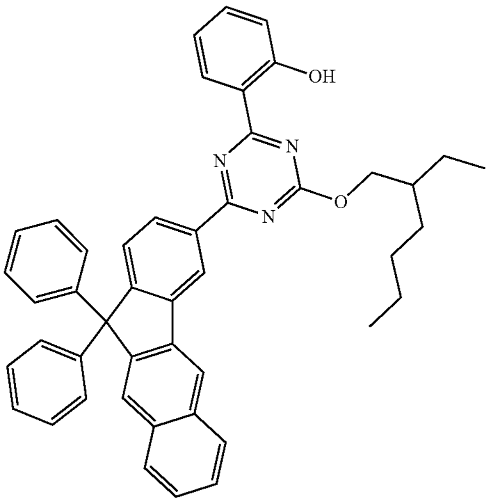

-continued
236
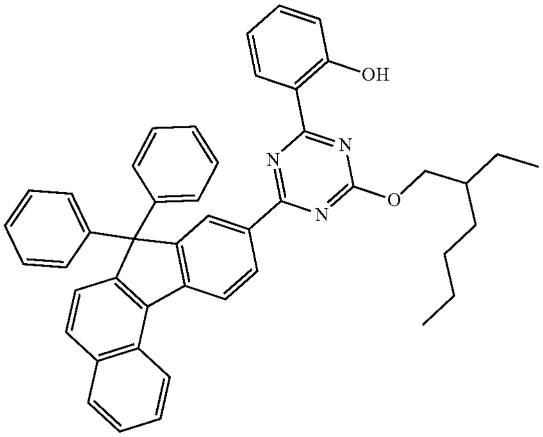
237
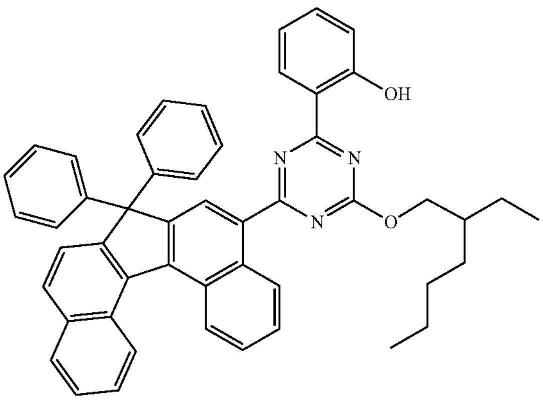
238
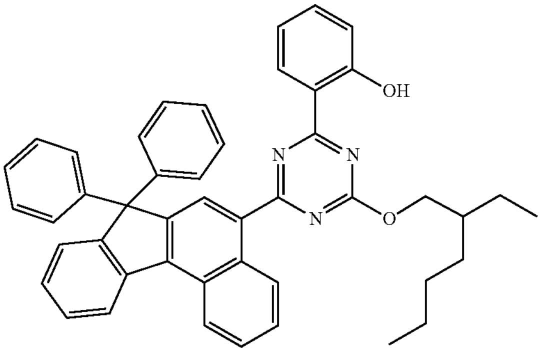
-continued
239
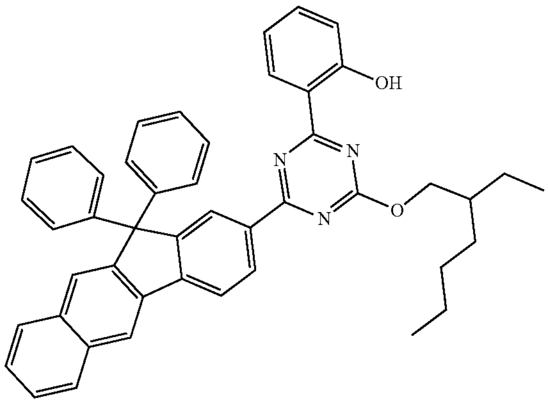
240
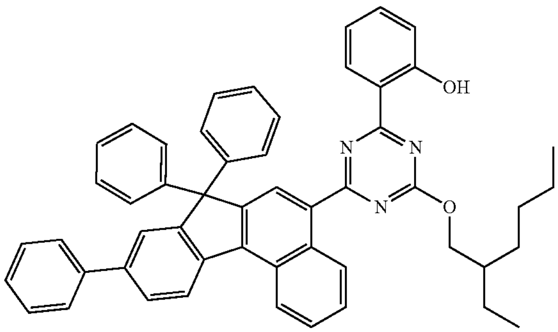
241
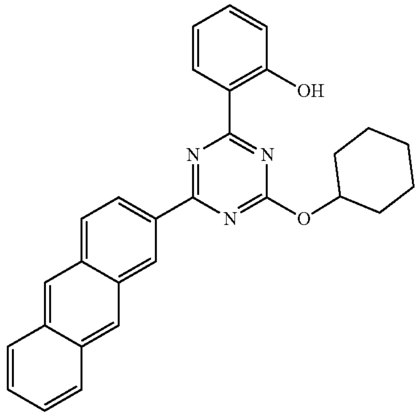
242
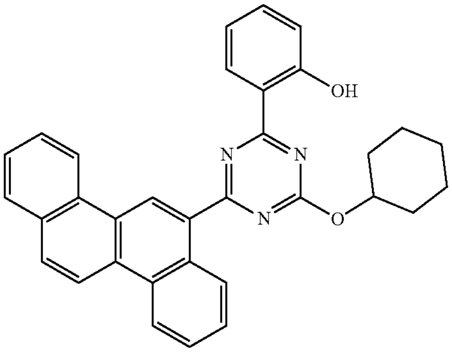

-continued
243
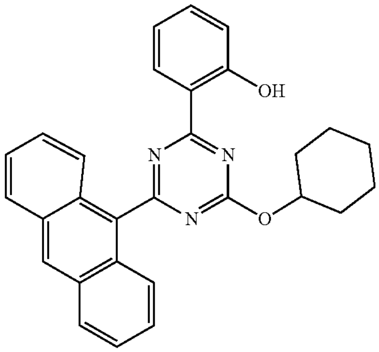
244
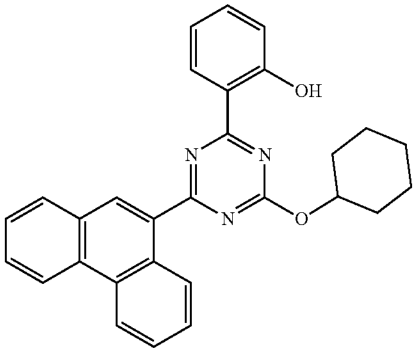
245
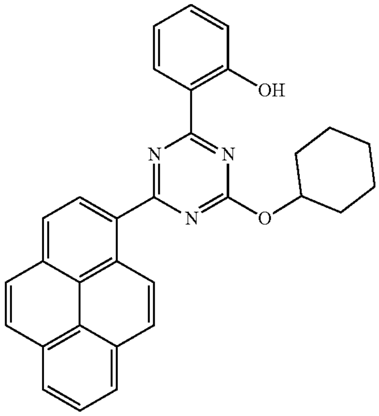
246
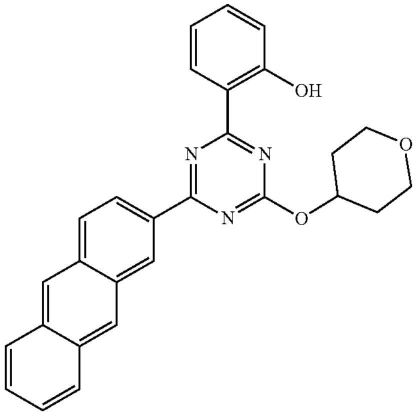
-continued
247
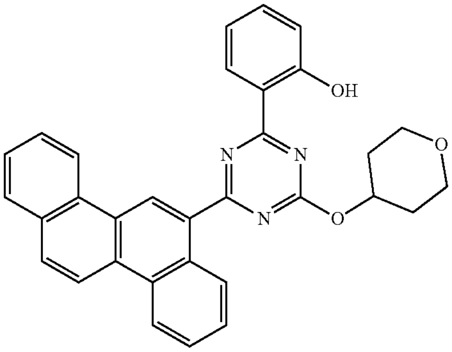
248
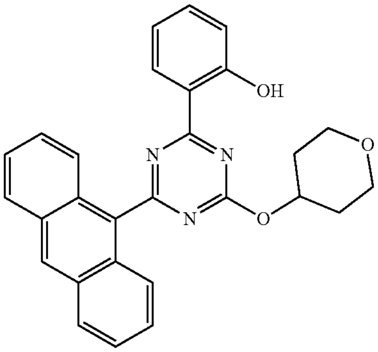
249
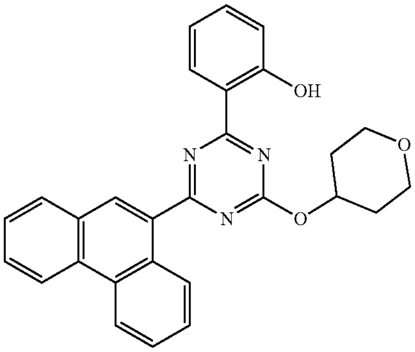
250
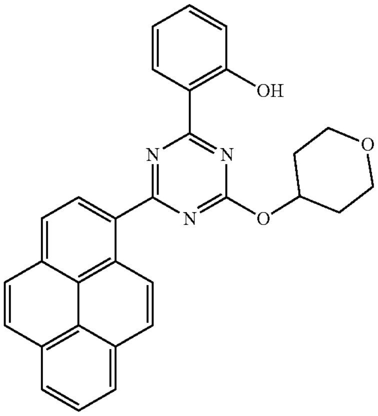

-continued
251
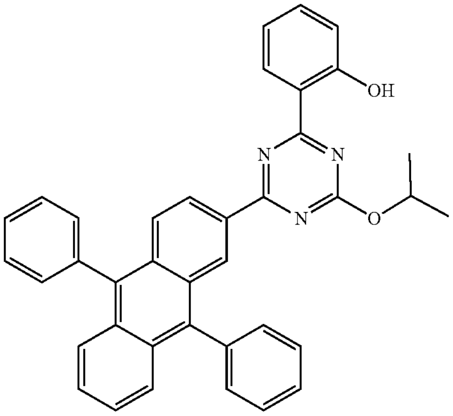
252
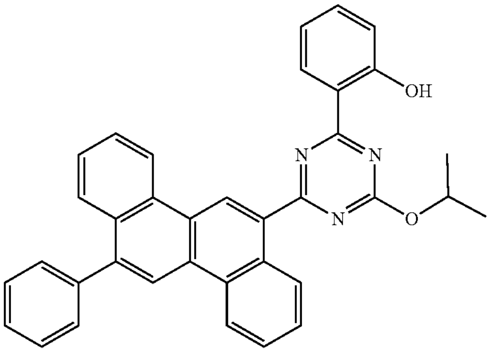
253
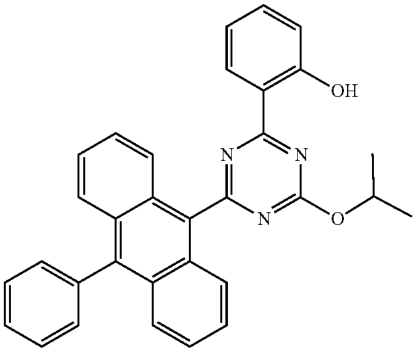
254
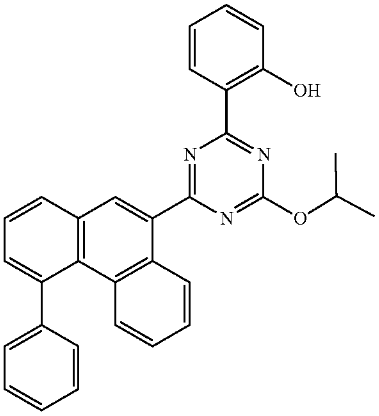
-continued
255
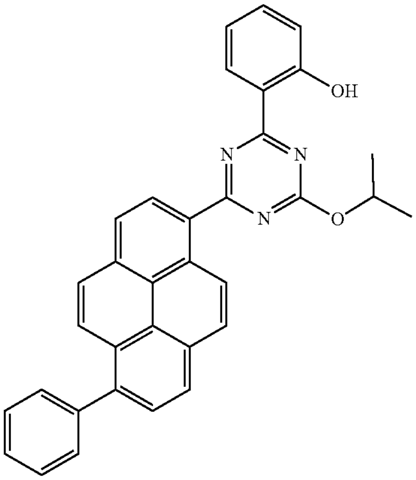
256
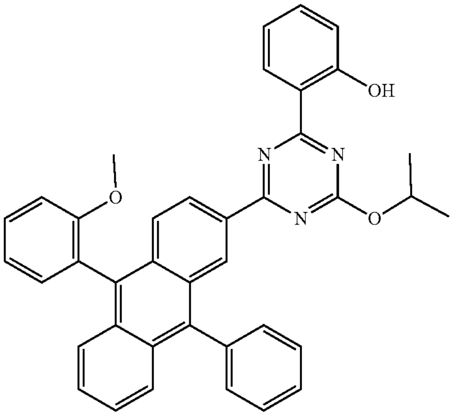
257
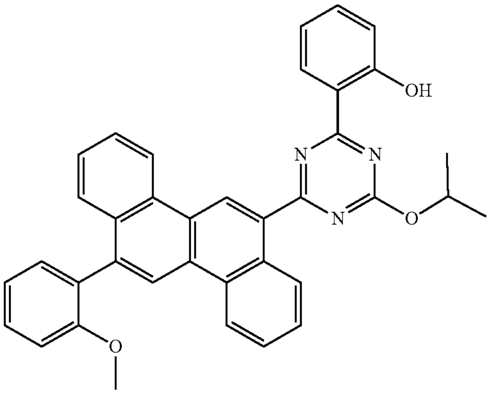

-continued
258
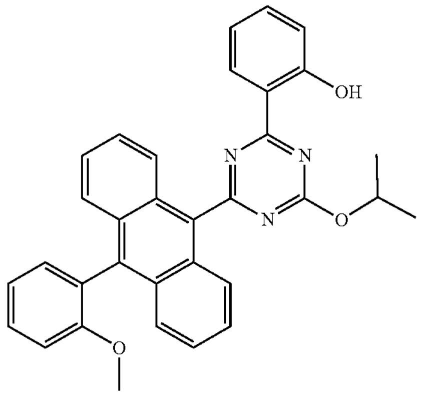
259
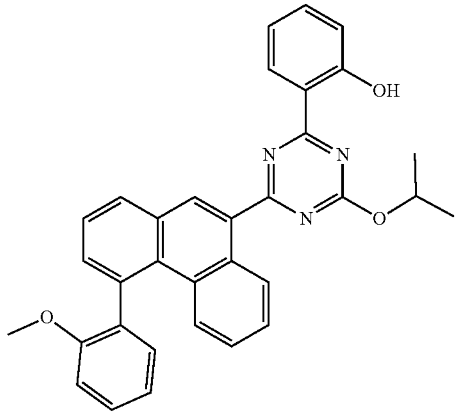
260
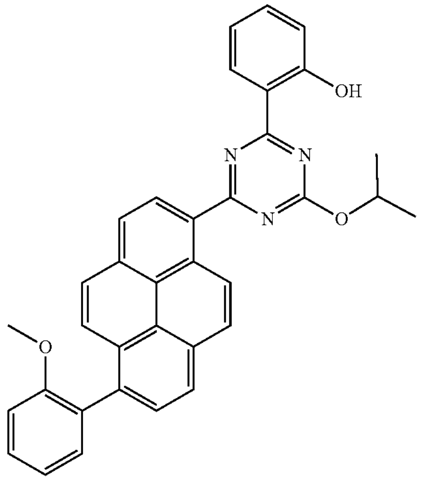
-continued
261
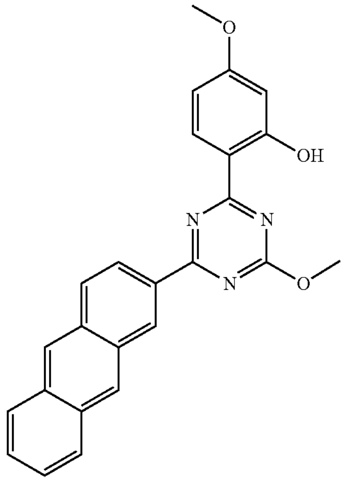
262
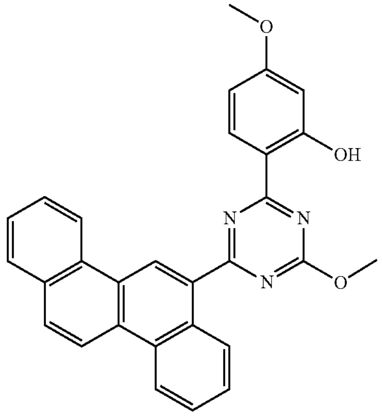
263
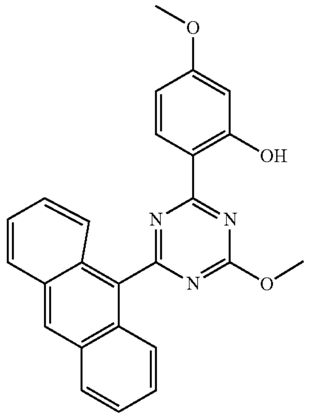

-continued
264
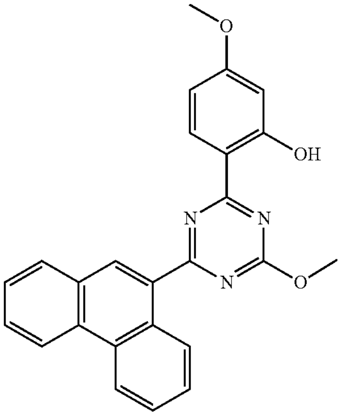
265
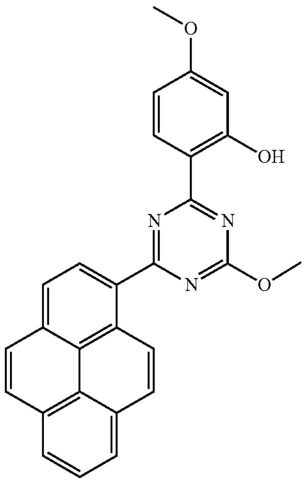
266
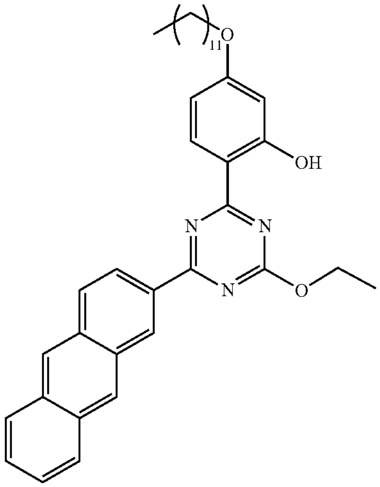
-continued
267
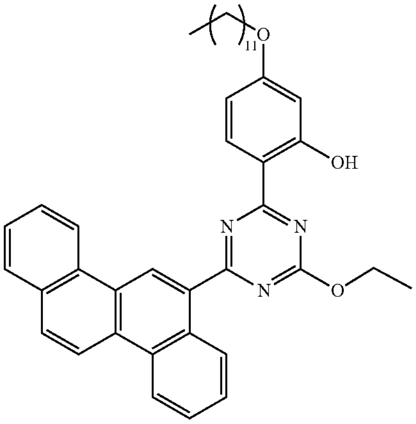
268
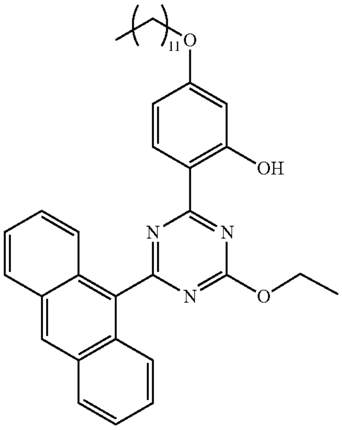
269
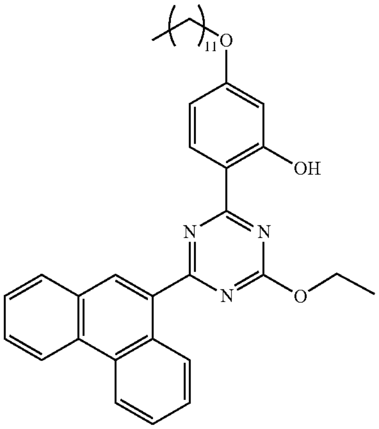

-continued
270
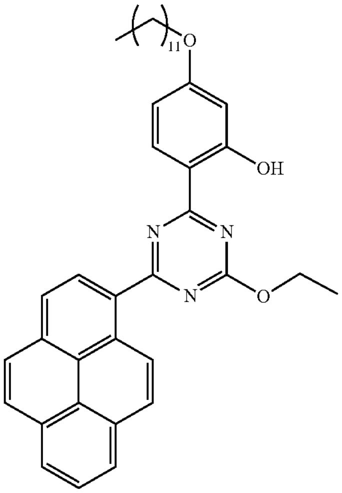
271
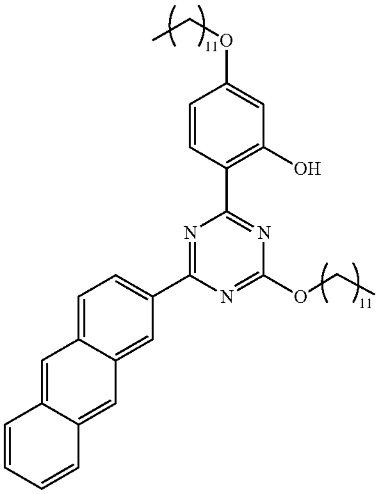
272
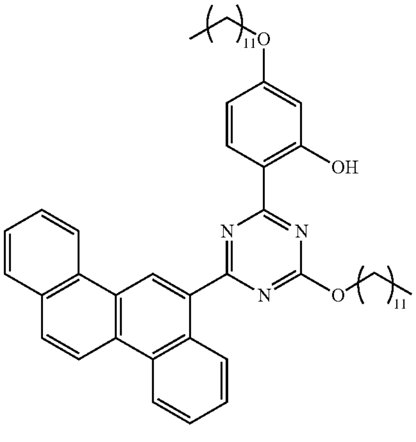
-continued
273
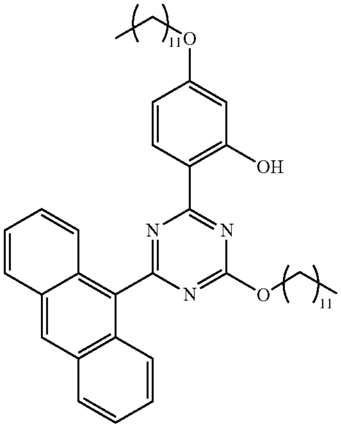
274
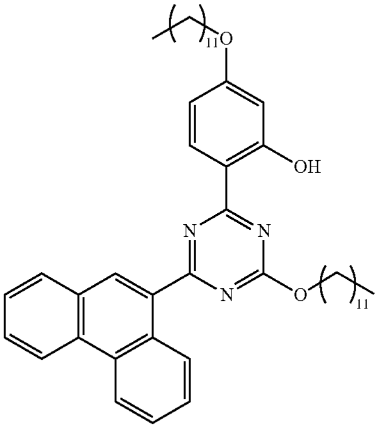
275
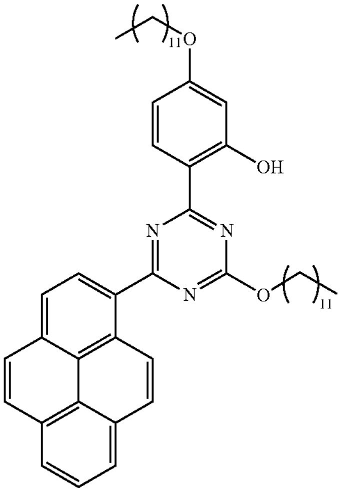

-continued
276
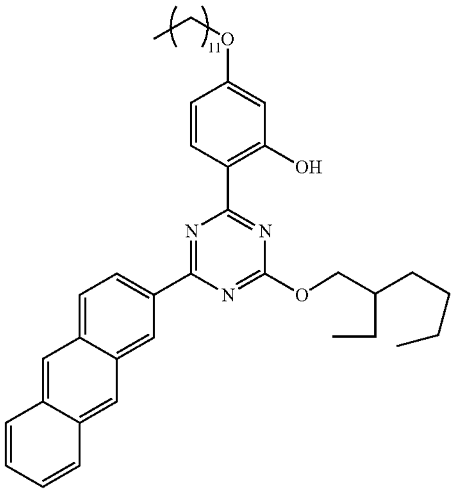
277
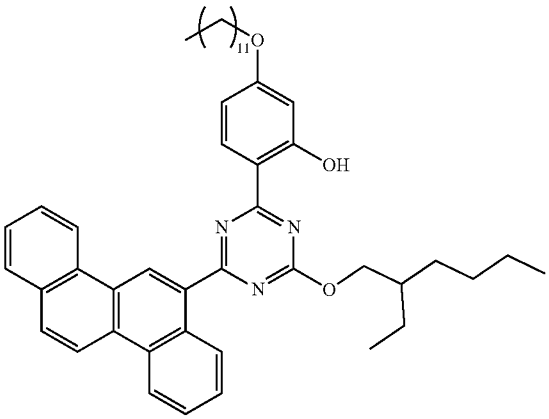
278
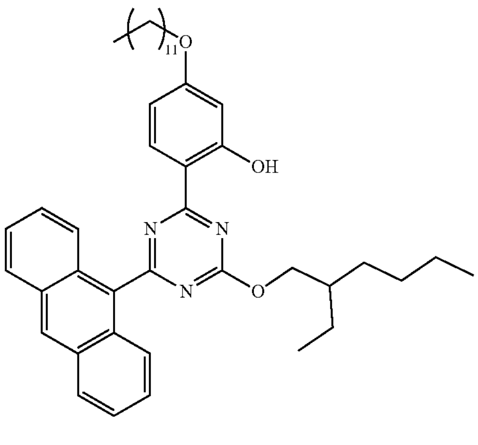
-continued
279
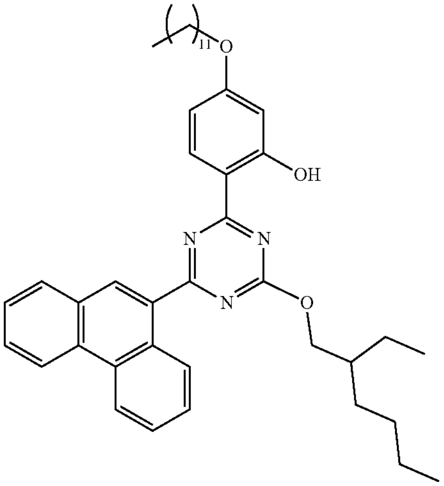
280
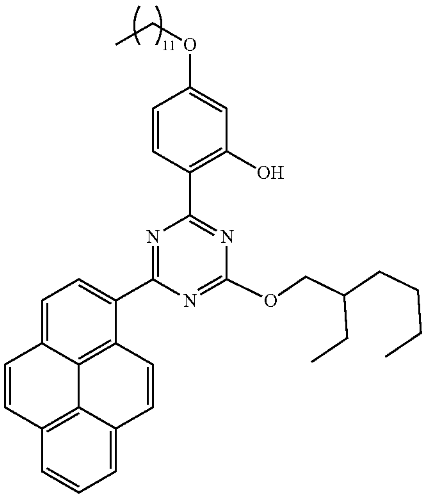
281
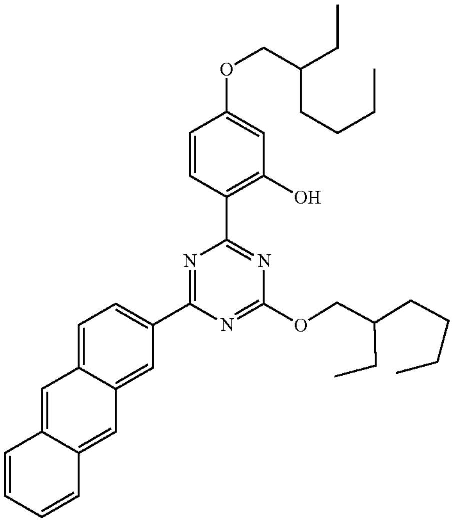

-continued
282
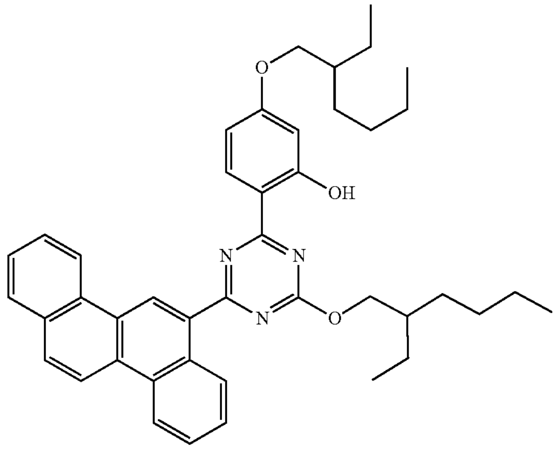
283
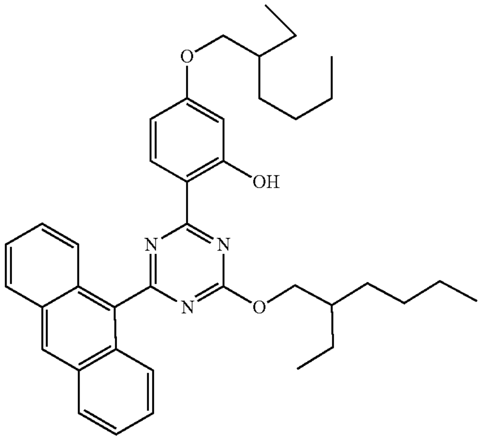
284
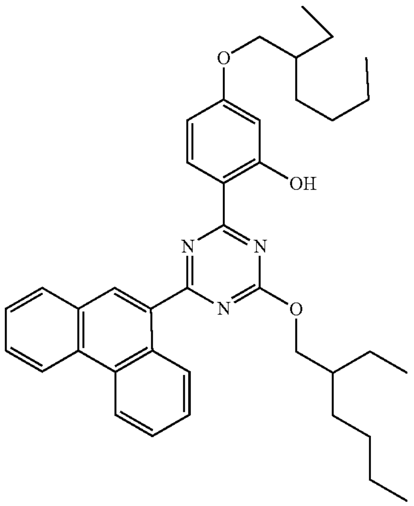
-continued
285
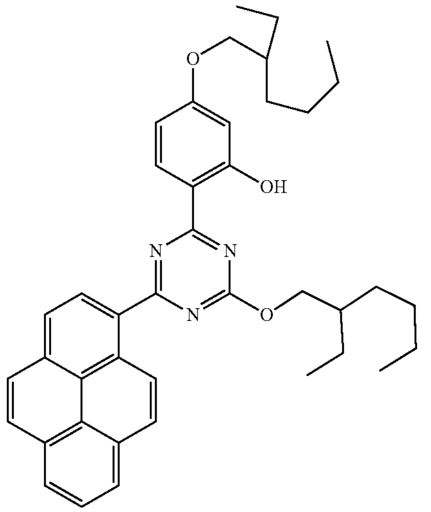
286
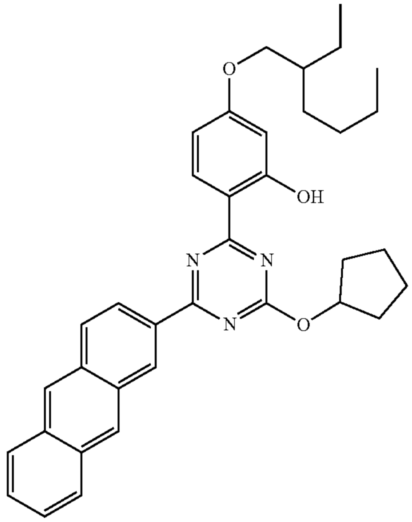
287
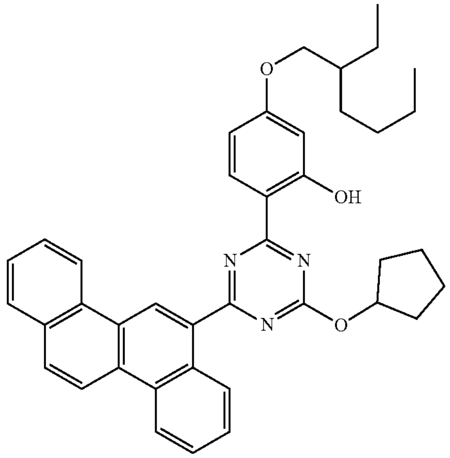

-continued
288
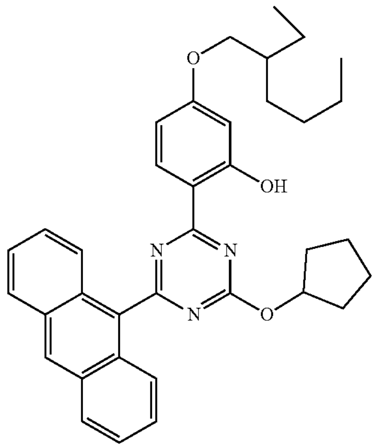
289
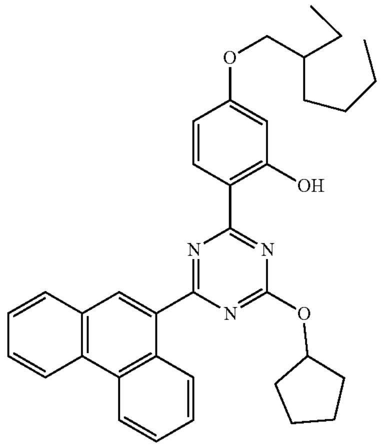
290
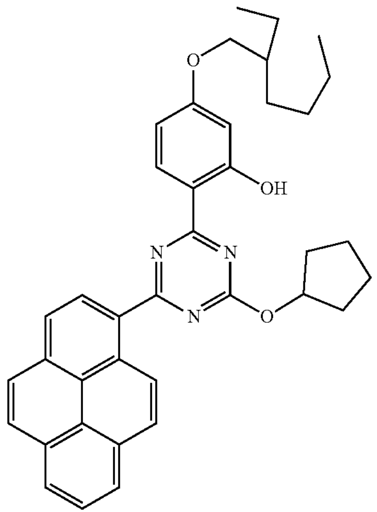
-continued
291
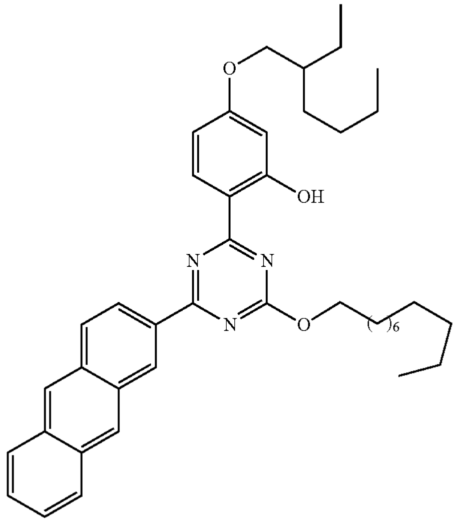
292
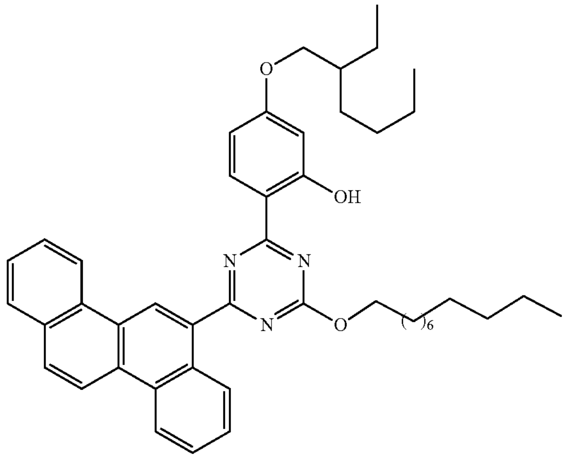
293
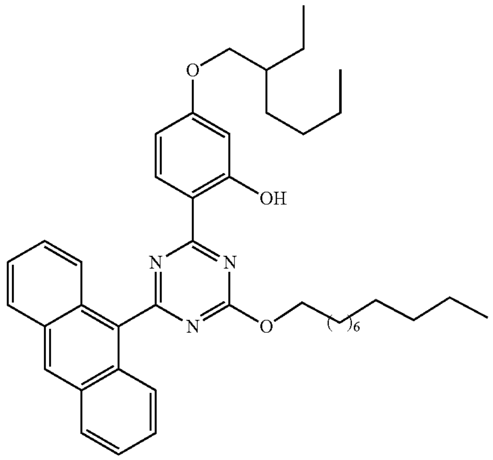

-continued
294
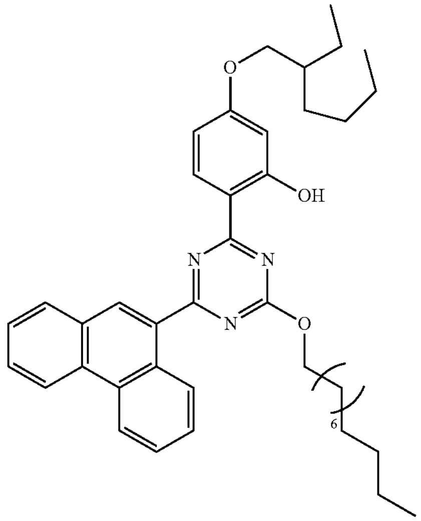
295
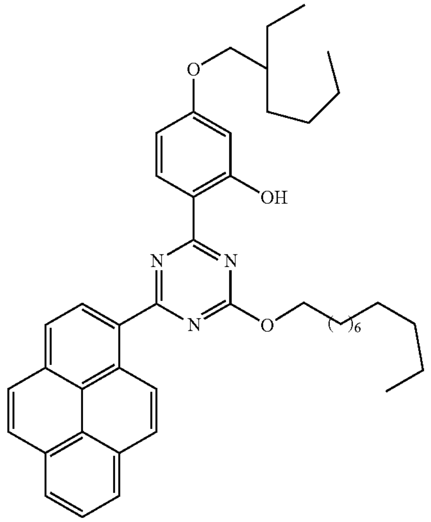
296
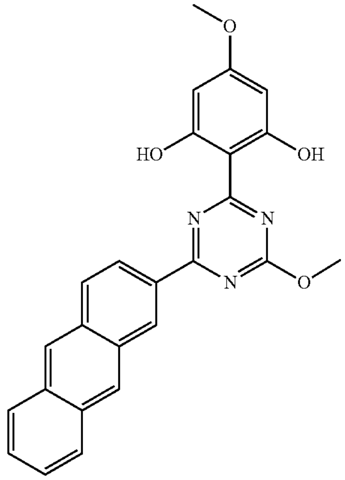
-continued
297
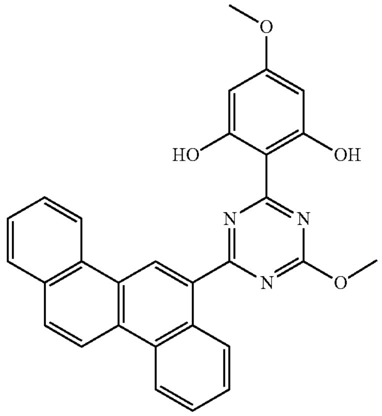
298
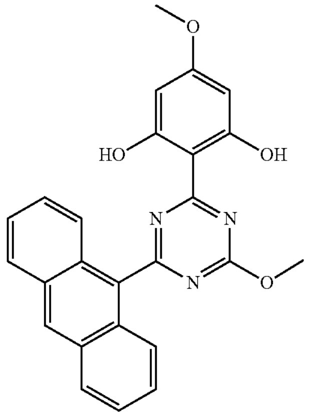
299
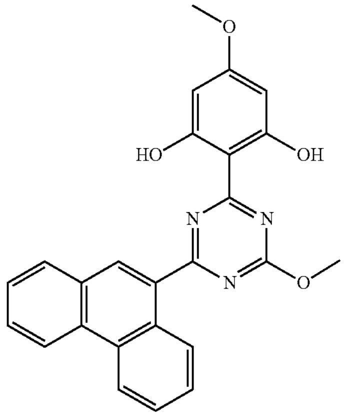

-continued
300
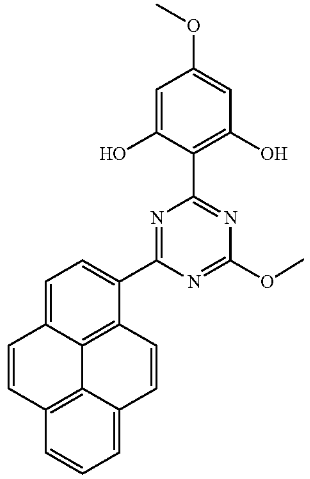
301
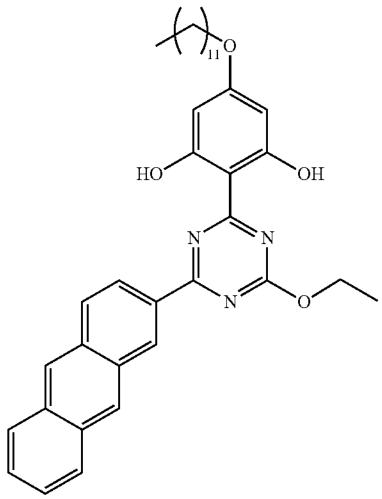
302
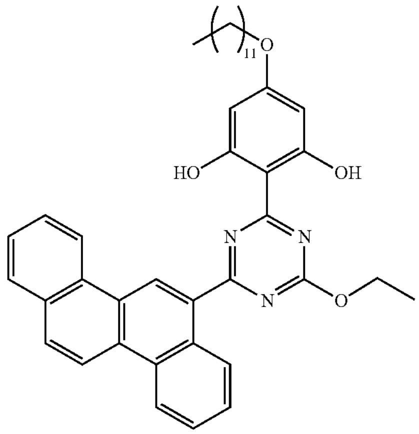
-continued
303
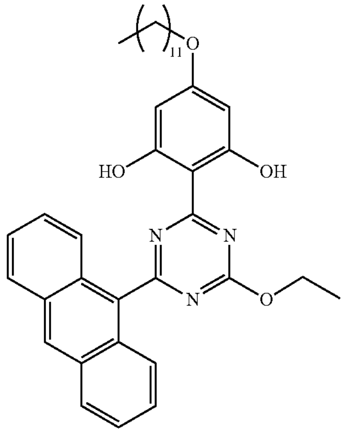
304
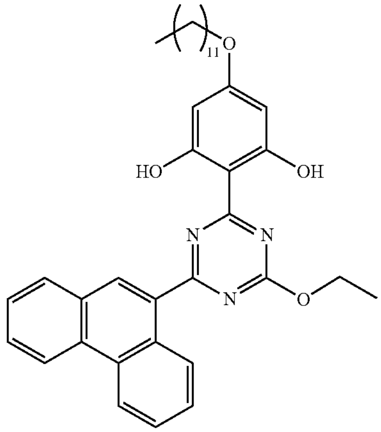
305
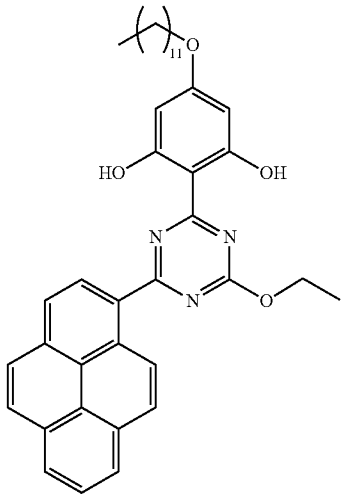

-continued
306
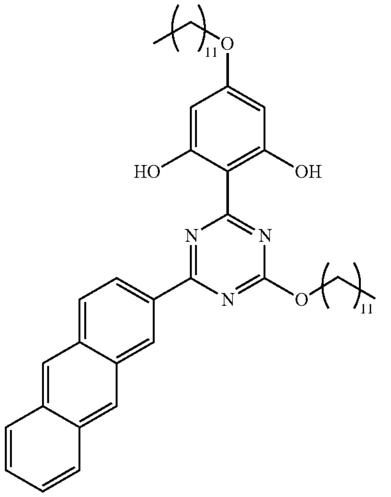
307
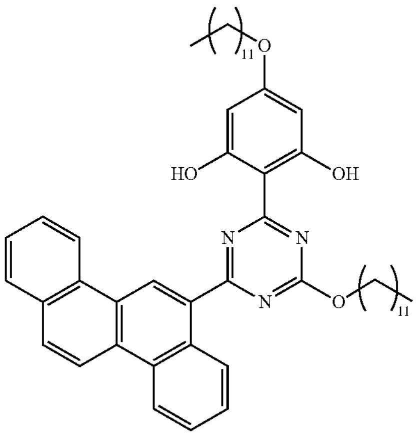
308
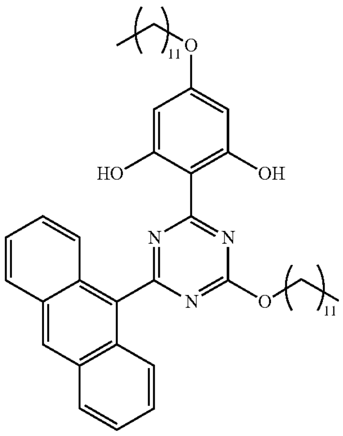
-continued
309
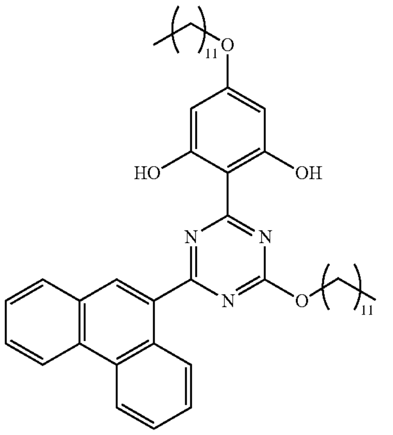
310
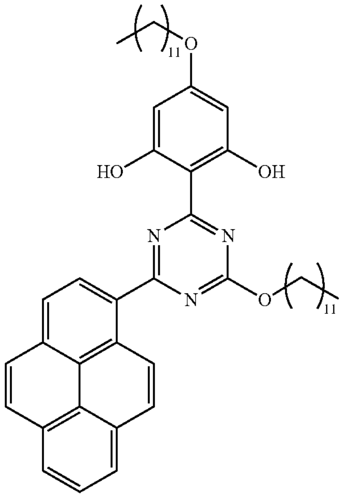
311
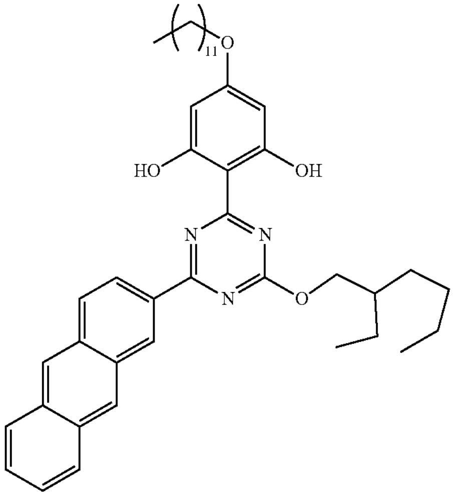

-continued
312
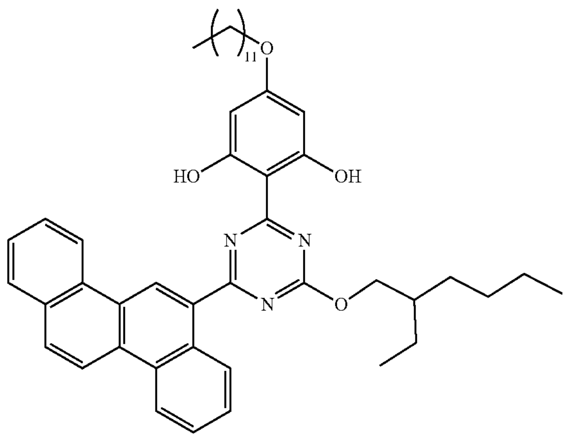
313
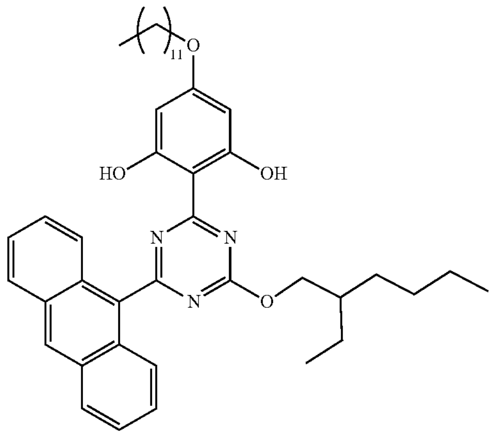
314
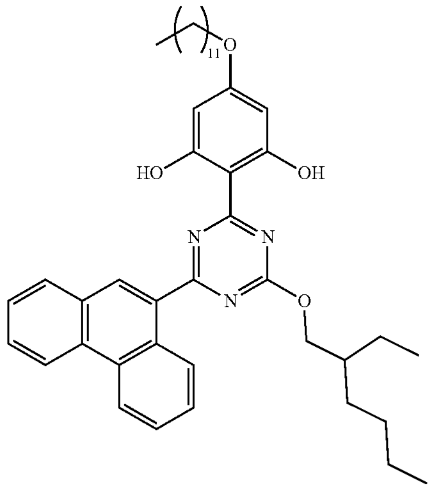
-continued
315
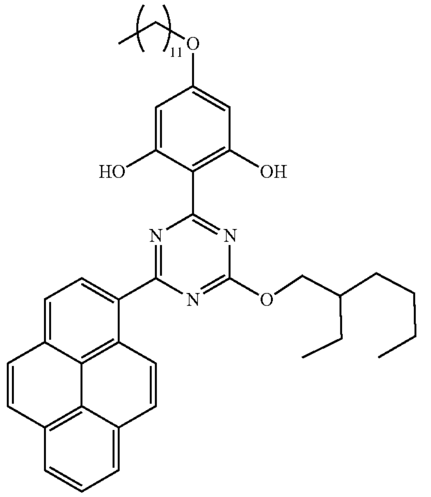
316
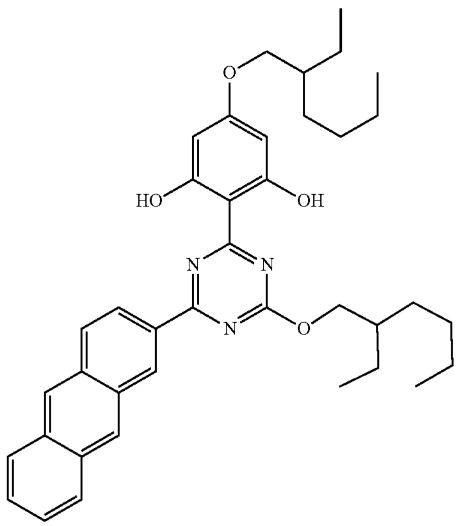
317
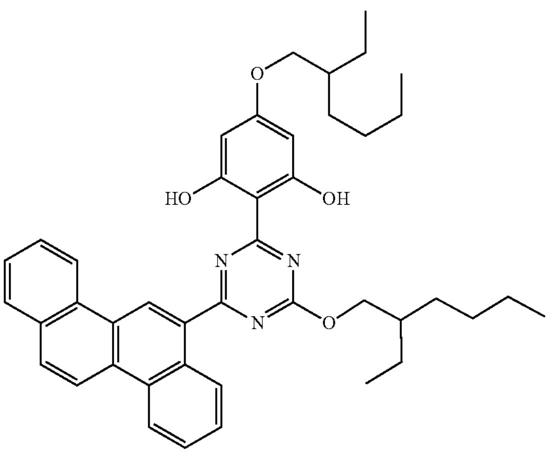

-continued
318
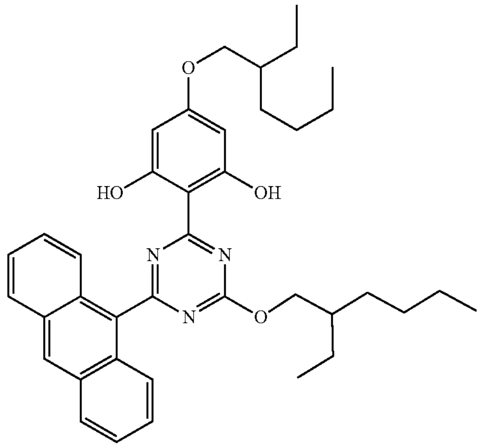
319
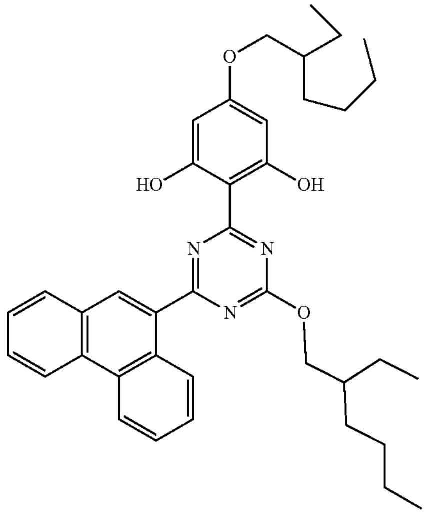
320
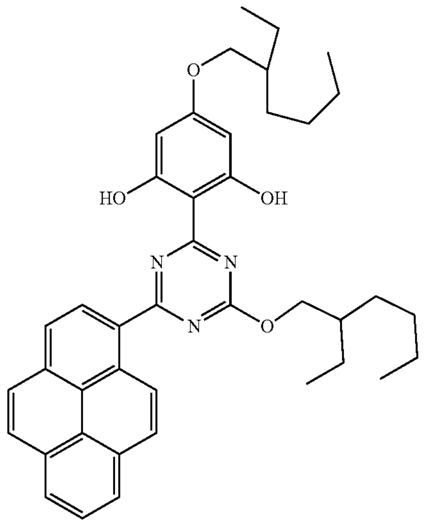
-continued
321
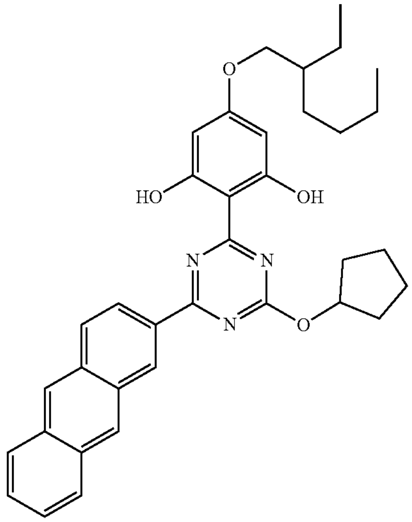
322
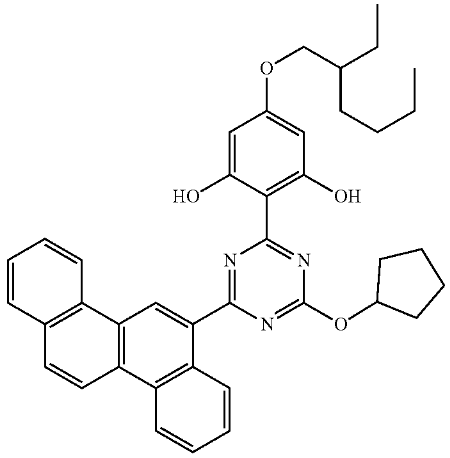
323
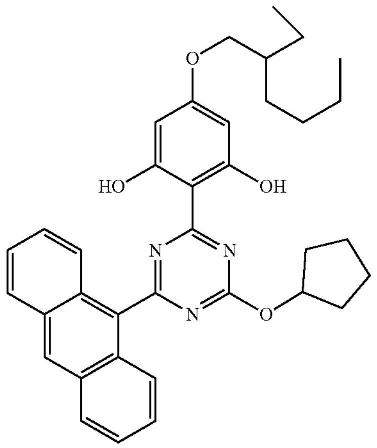

-continued
324
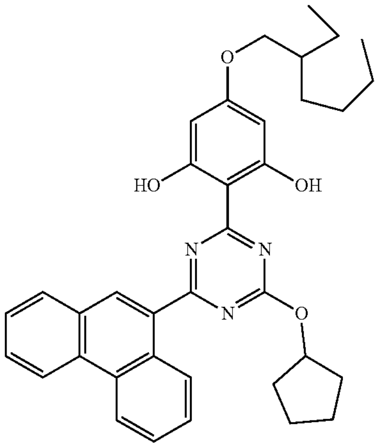
325
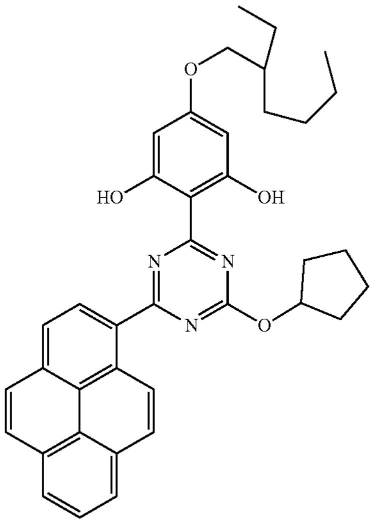
326
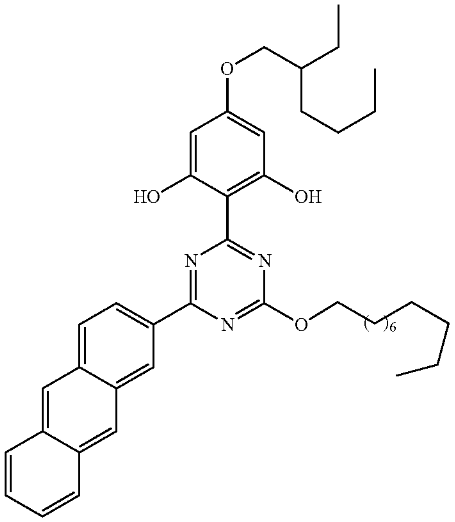
-continued
327
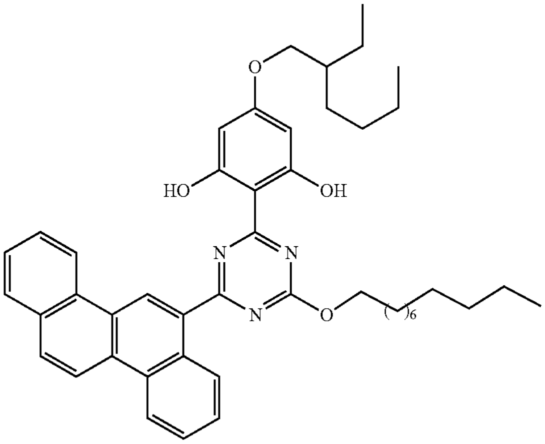
328
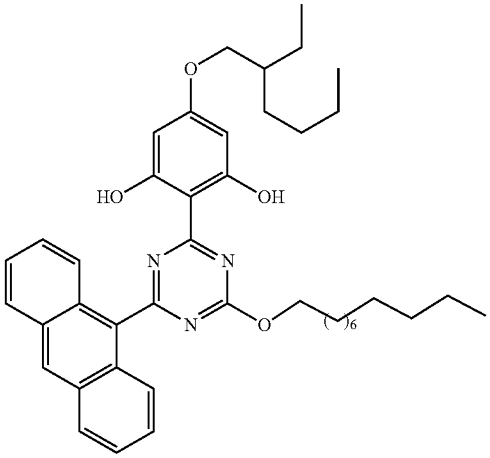
329
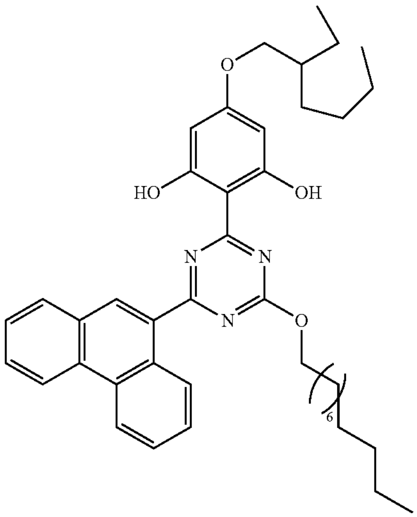

-continued
330
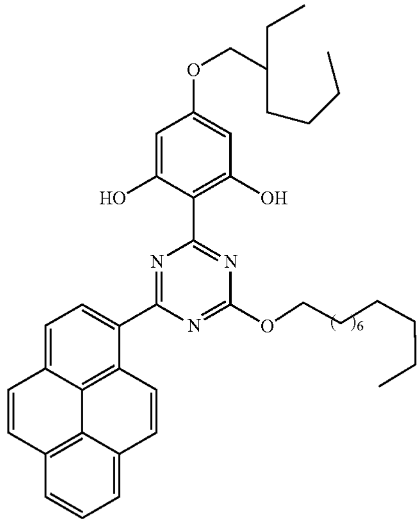
331
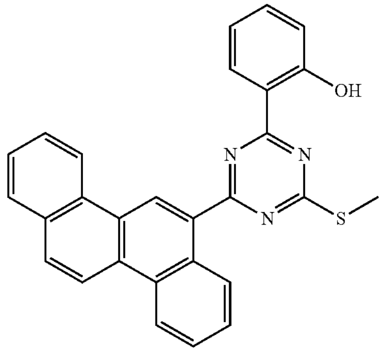
332
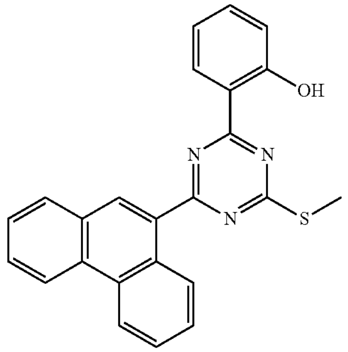
333
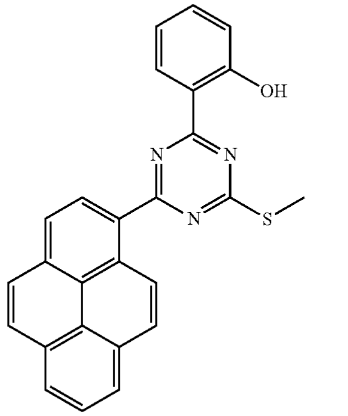
-continued
334
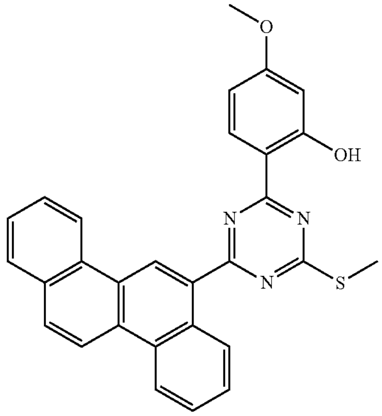
335
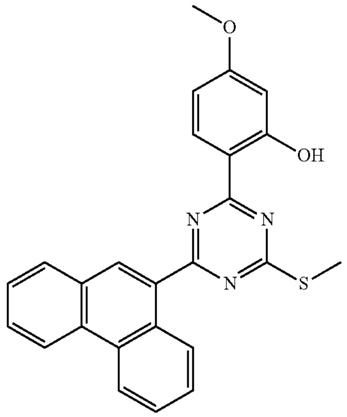
336
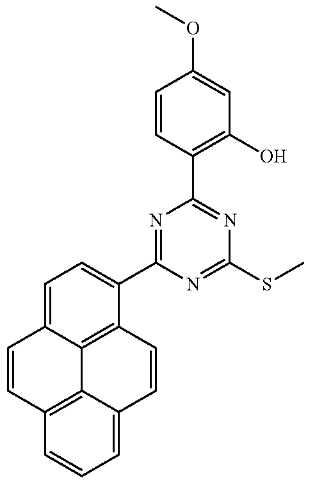

-continued
337
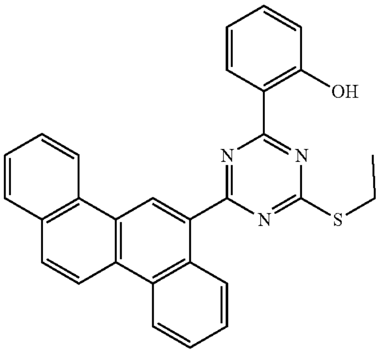
338
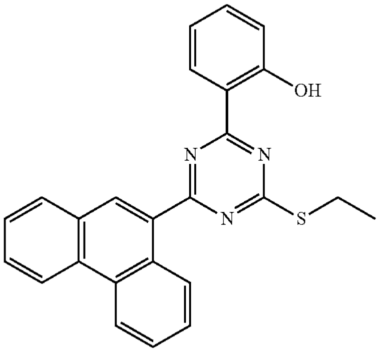
339
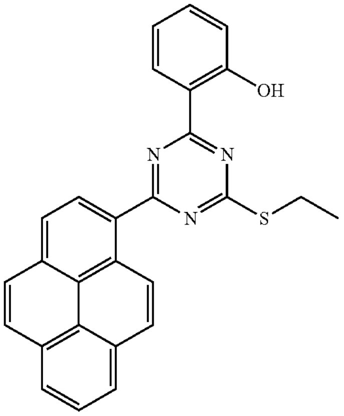
340
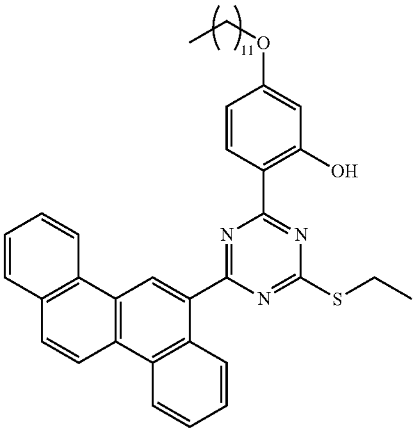
-continued
341
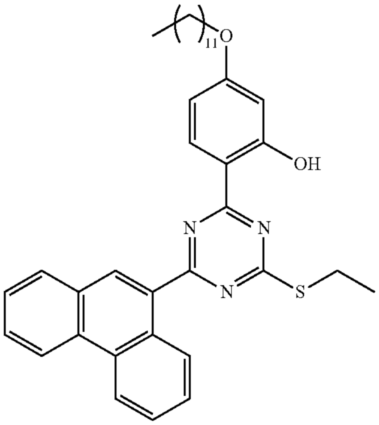
342
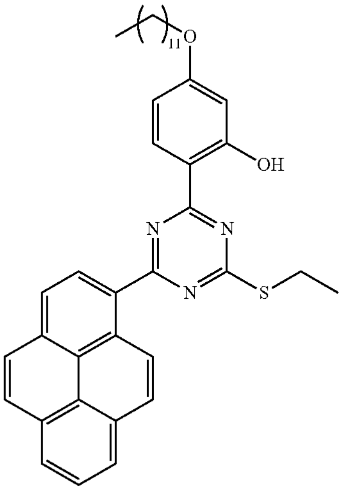
343
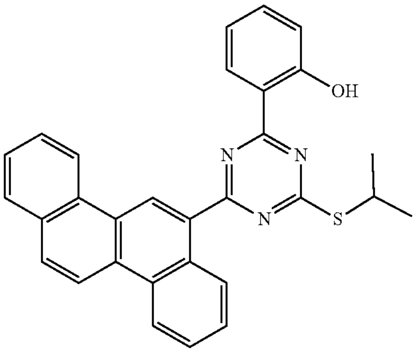
344
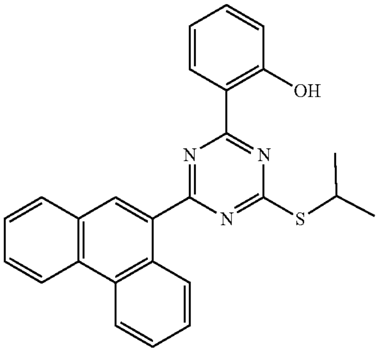

-continued
345
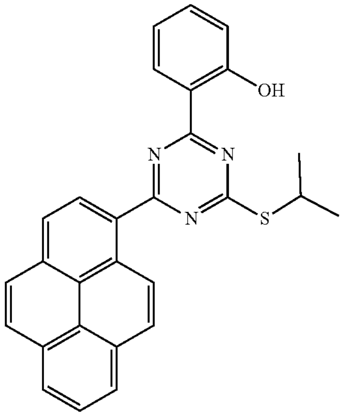
346
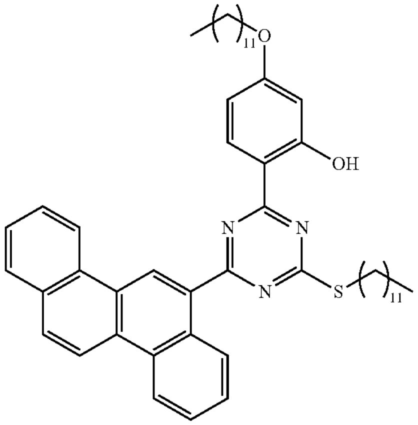
347
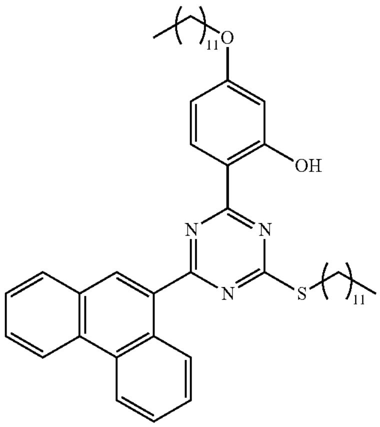
-continued
348
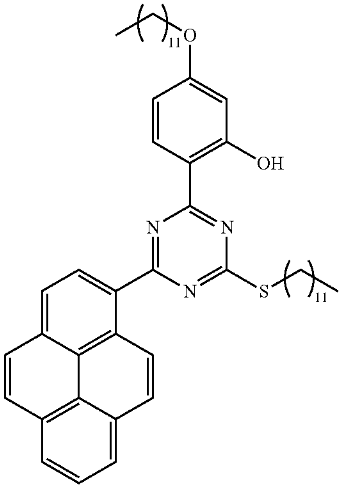
349
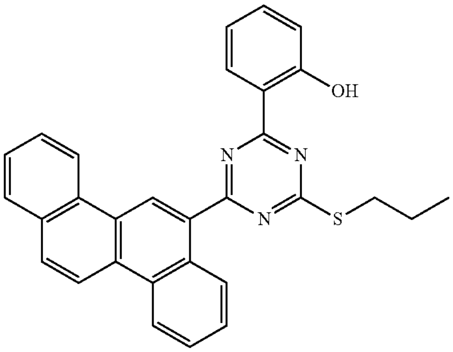
350
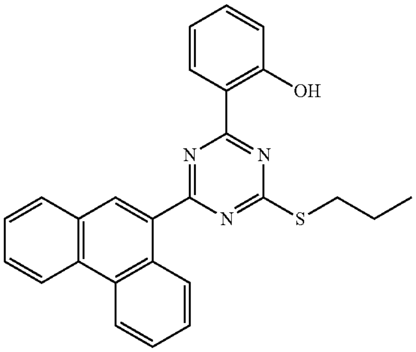
351
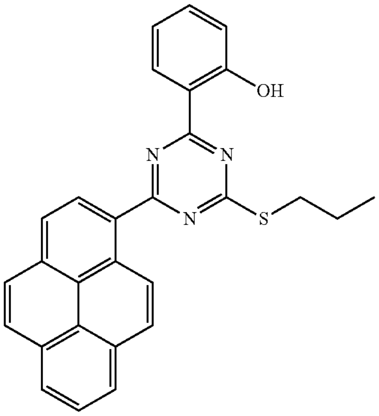

352
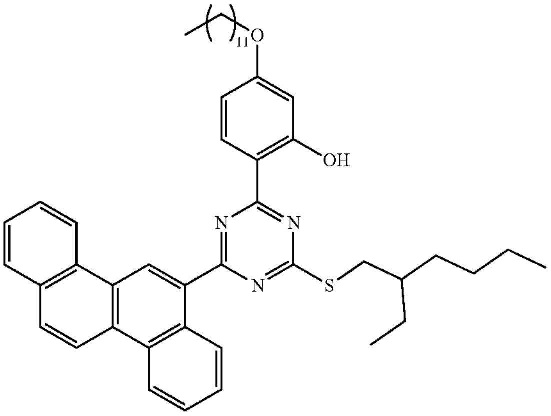
353
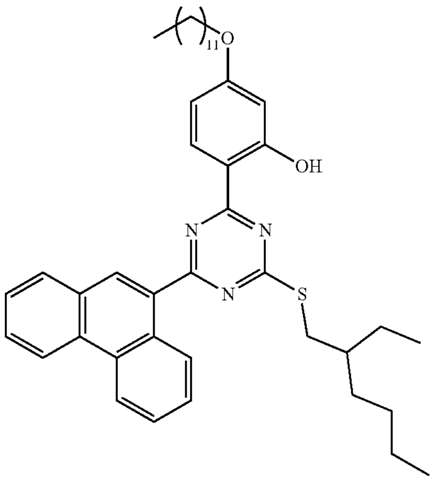
354
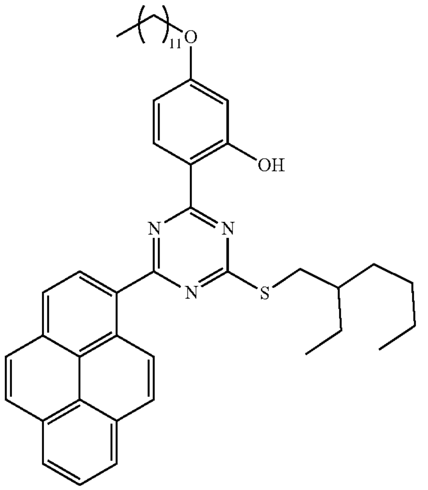
355
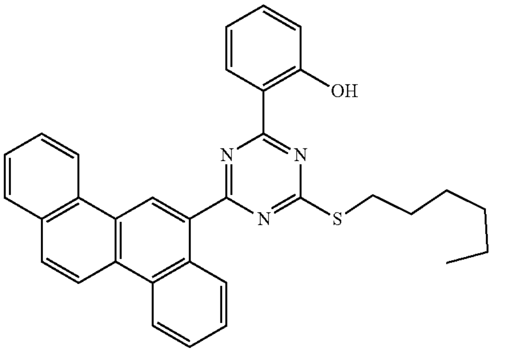
356
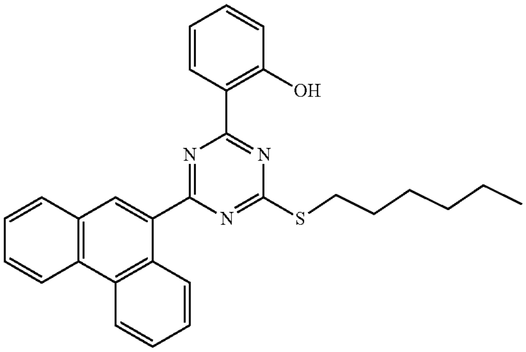
357
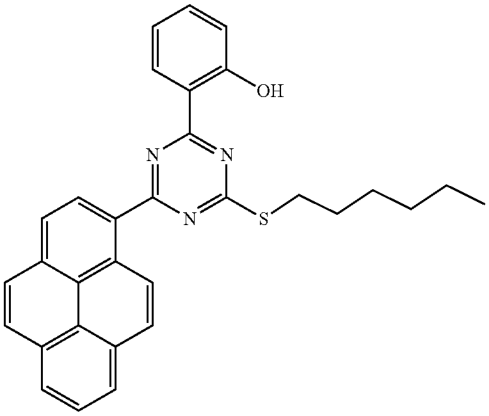
358
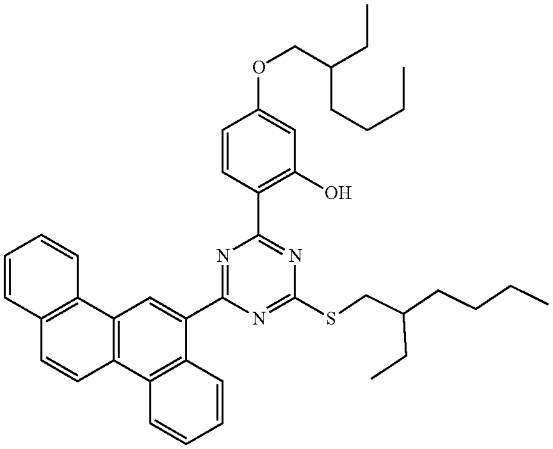

-continued
359
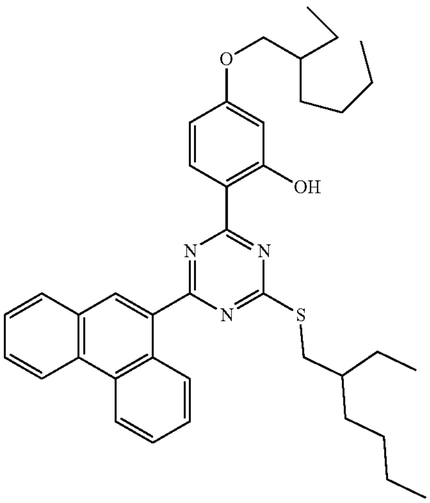
360
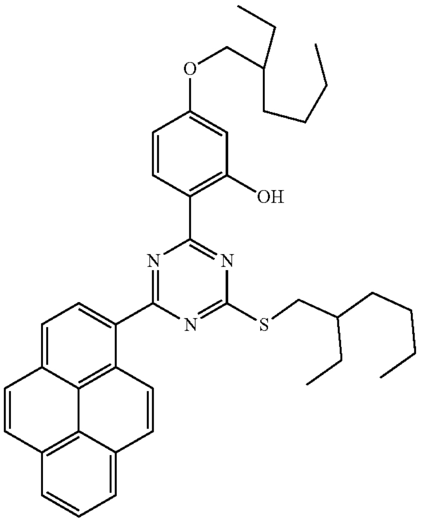
361
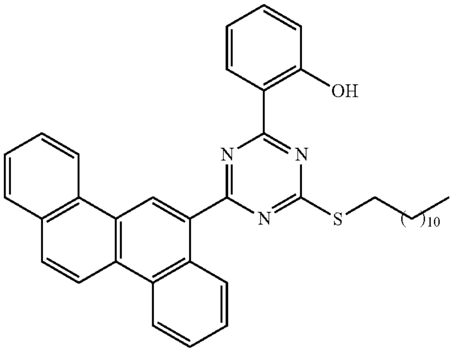
-continued
362
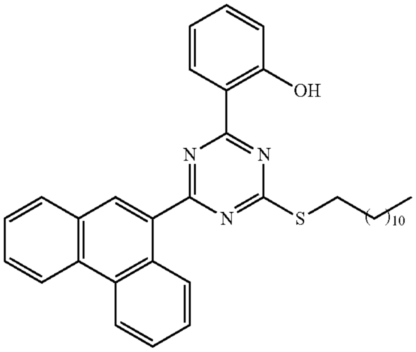
363
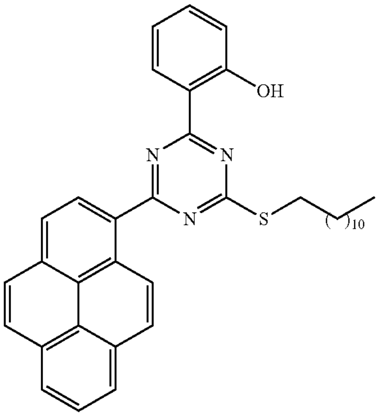
364
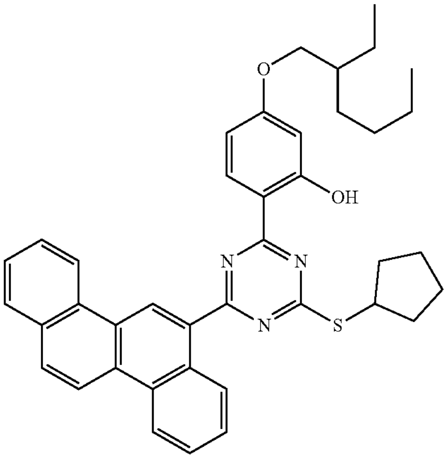

-continued
365
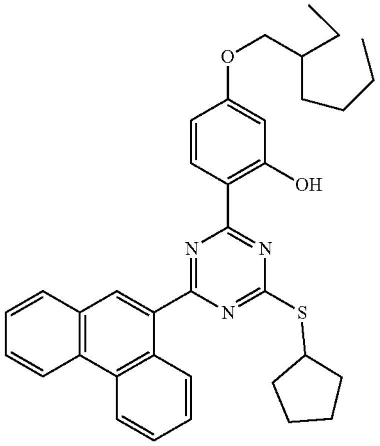
366
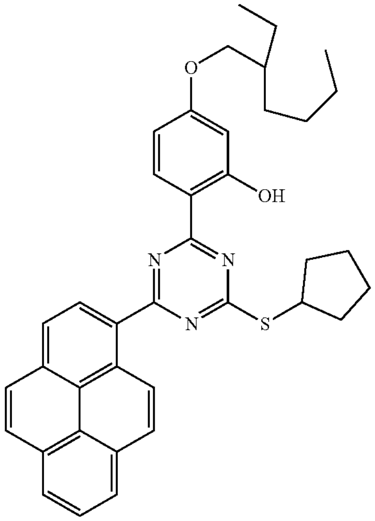
367
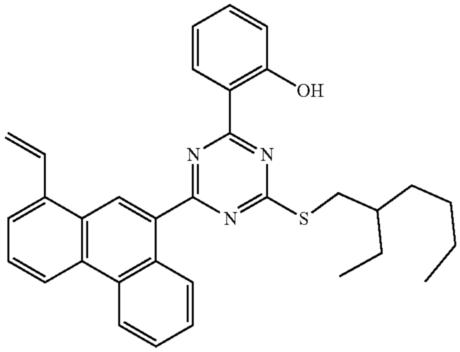
-continued
368
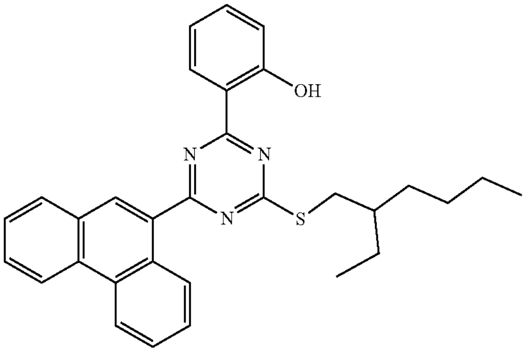
369
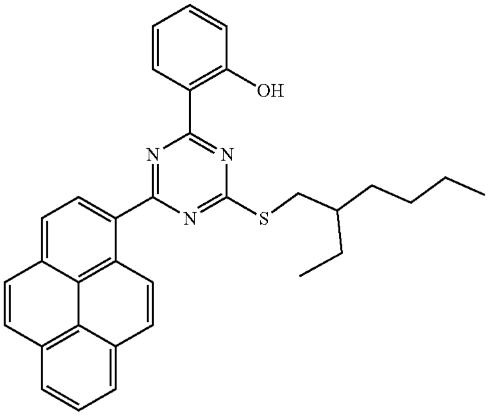
370
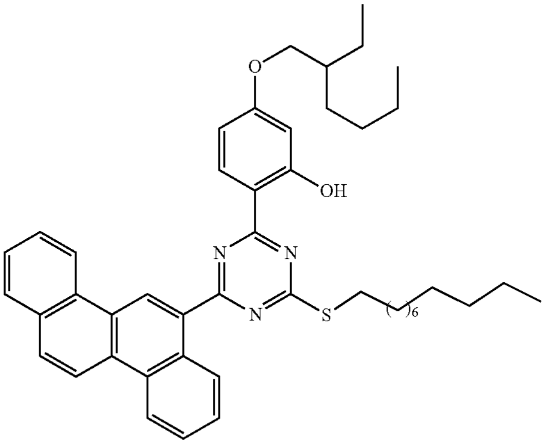

-continued

371

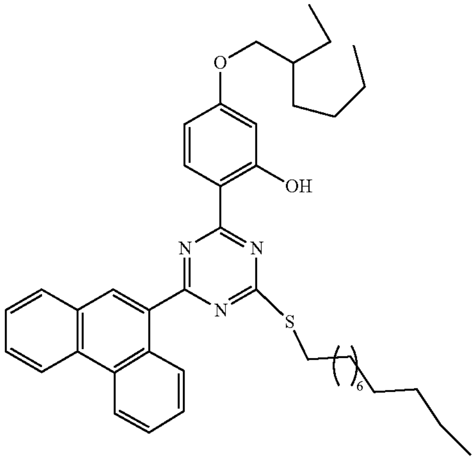

372

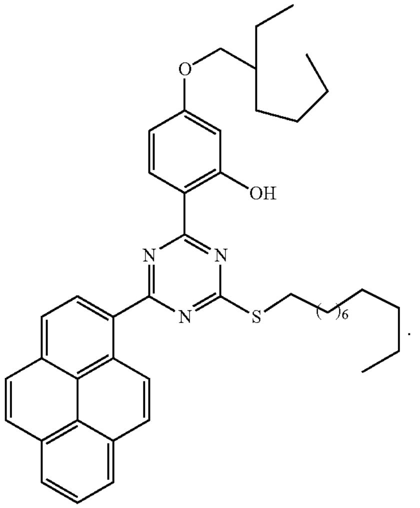

17. A display apparatus comprising:

a light-emitting device comprising a first electrode, a second electrode facing the first electrode, and a plurality of organic layers between the first electrode and the second electrode; and an encapsulation member on the light-emitting device and comprising an organic film comprising a light absorber, wherein the organic film has a transmittance of 10% or less at about 405 nm wavelength, a transmittance of 70% or more at about 430 nm wavelength, and a transmittance of 97% or more at about 450 nm wavelength, the light absorber comprises a hexagonal heterocycle comprising two or more N atoms as ring-forming atoms, and first to third substituents substituted at the hexagonal heterocycle, the first to third substituents being different from one another, the second substituent is substituted or unsubstituted anthracene group, a substituted or unsubstituted phenanthrene, a substituted or unsubstituted pyrene group, a substituted or unsubstituted chrysene group, a substituted or unsubstituted dibenzofuran derivative, a substituted or unsubstituted carbazole derivative, or a substituted or unsubstituted fluorene derivative, a substituent of the substituted or unsubstituted dibenzofuran derivative, a substituent of the substituted or unsubstituted carbazole derivative, and a substituent of the substituted or unsubstituted fluorene derivative are each independently a hydrogen atom, an alkyl group having 1 to 20 carbon atoms, an alkenyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or adjacent groups are bonded to each other to form a ring, and when the hexagonal heterocycle comprises three N atoms as ring-forming atoms, then the third substituent is a substituted or unsubstituted oxy group, or a substituted or unsubstituted thio group.

18. The display apparatus of claim 17, wherein the hexagonal heterocycle is triazine or pyrimidine.

19. The display apparatus of claim 17, wherein the first substituent is a substituted phenyl group comprising at least one hydroxyl group.

20. The display apparatus of claim 17, wherein the first substituent is represented by at least one among Formulae H1 to H5:

H1

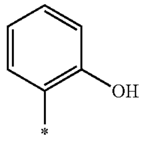

H2

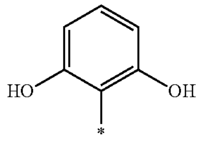

H3

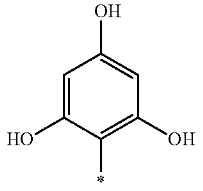

H4

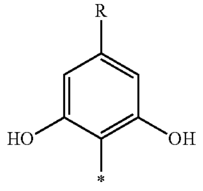

H5

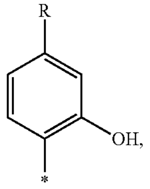

and wherein R in Formulae H4 and H5 is a substituted or unsubstituted alkoxy group having 1 to 20 carbon atoms.

21. The display apparatus of claim 17, wherein the second substituent is represented by at least one among Ar-a to Ar-h:

Ar-a

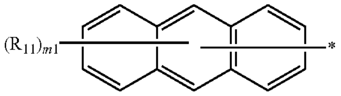

Ar-b

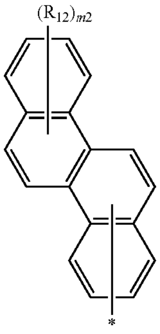

Ar-c

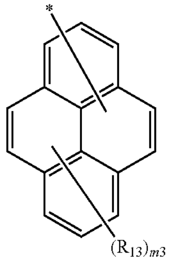

Ar-d

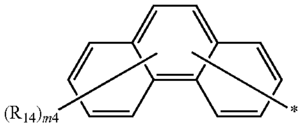

Ar-e

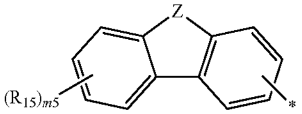

Ar-f

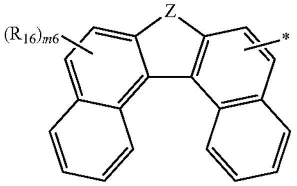

Ar-g

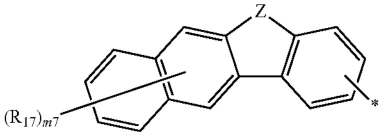

Ar-h

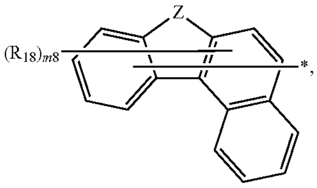

and wherein, in Ar-e to Ar-h, Z is O, S, $NR_a$, or $CR_bR_c$, and $R_a$ to $R_c$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and in Ar-a to Ar-h, $R_{11}$ to $R_{18}$ are each independently a hydrogen atom, a deuterium atom, a halogen atom, an alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and m1 to m8 are each independently an integer of 0 to 4.

22. The display apparatus of claim 17, wherein the third substituent is represented by at least one among S1 to S15:

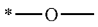

S1

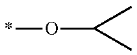

S2

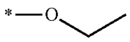

S3

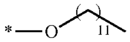

S4

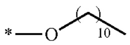

S5

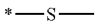

S6

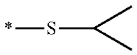

S7

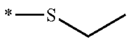

S8

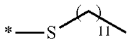

S9

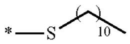

S10

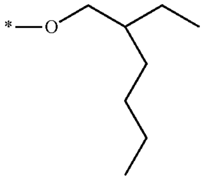

S11

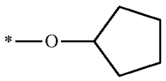

S12

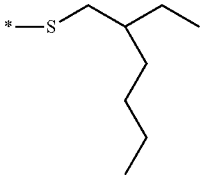

S13

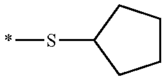

S14

-continued
S15
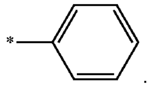
23. The display apparatus of claim 17, wherein the light absorber comprises at least one among the compounds represented by Compound Group 1 and Compound Group 2:
[Compound Group 1]
1
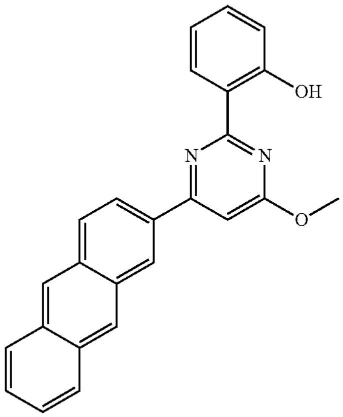
2
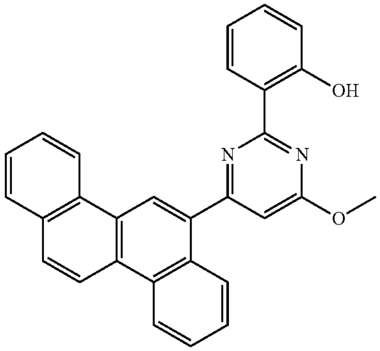
3
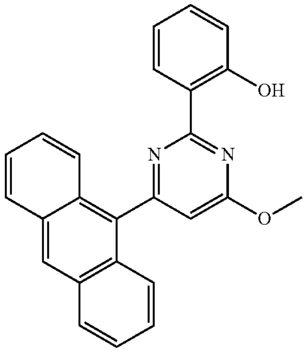
-continued
4
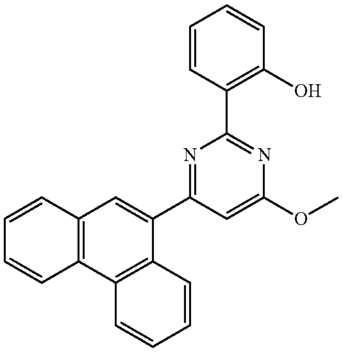
5
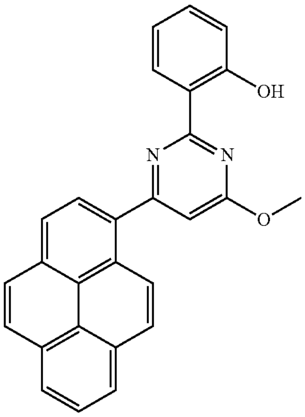
6
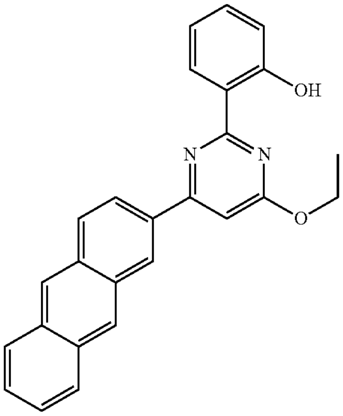
7
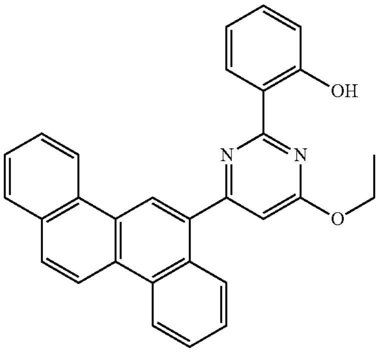

-continued
8
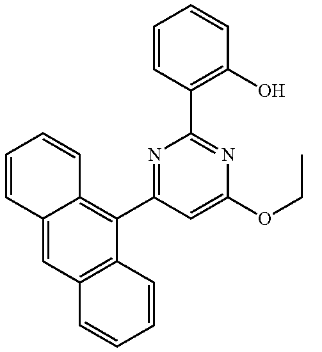
9
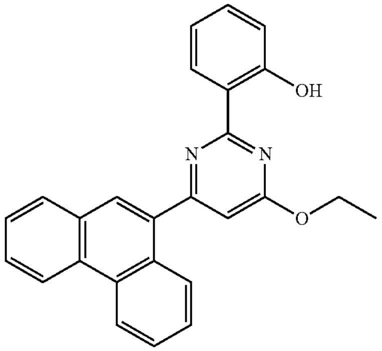
10
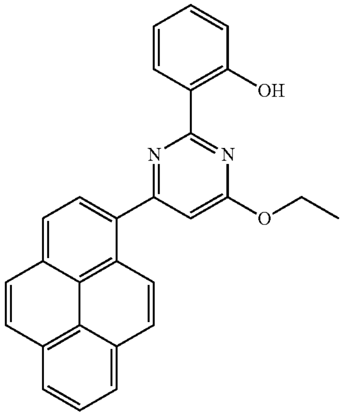
11
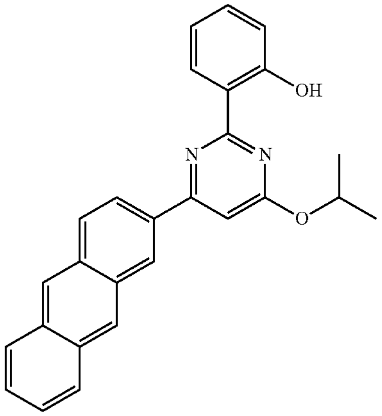
-continued
12
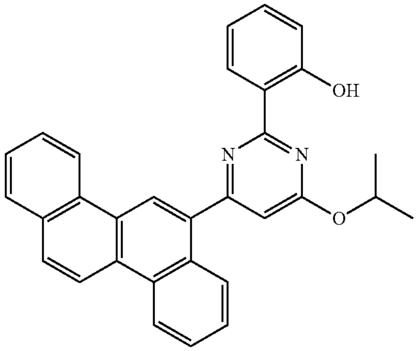
13
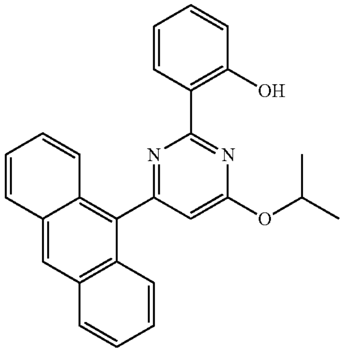
14
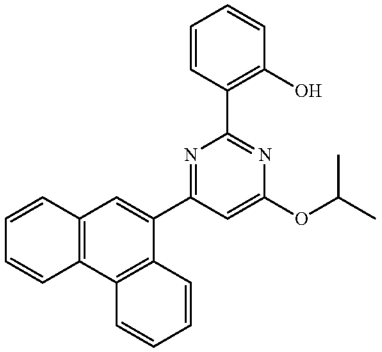
15
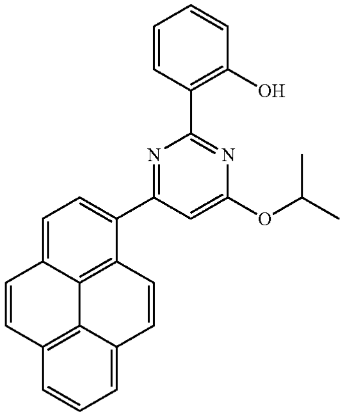

16
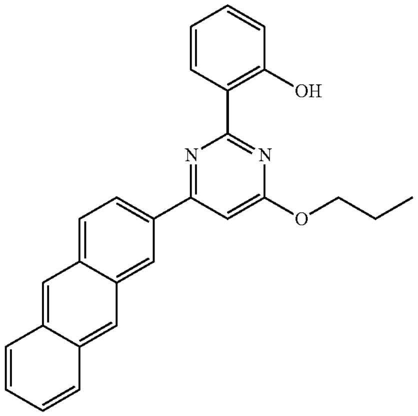
17
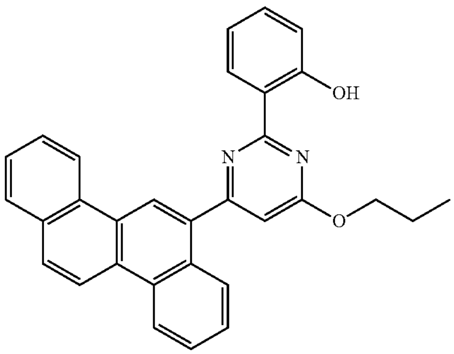
18
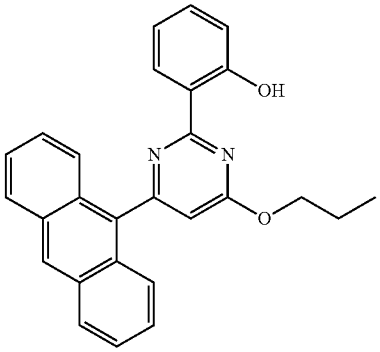
19
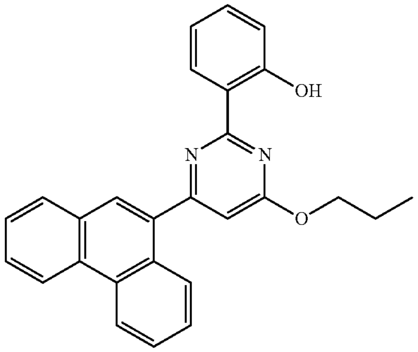
20
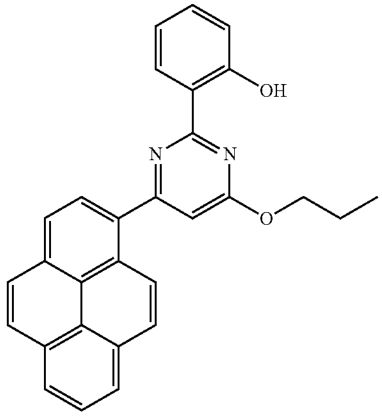
21
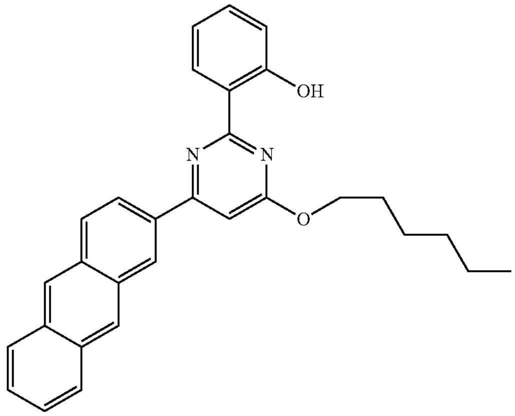
22
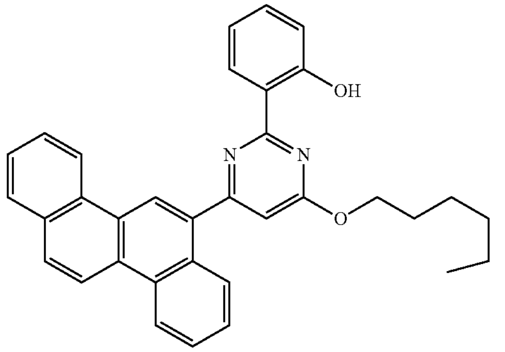
23
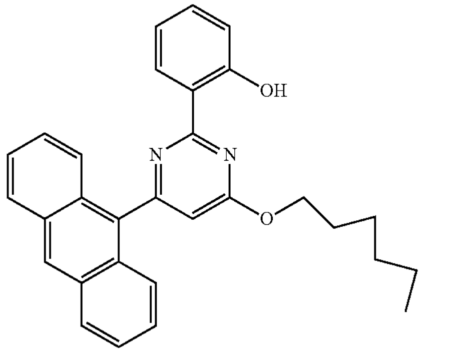

-continued
24
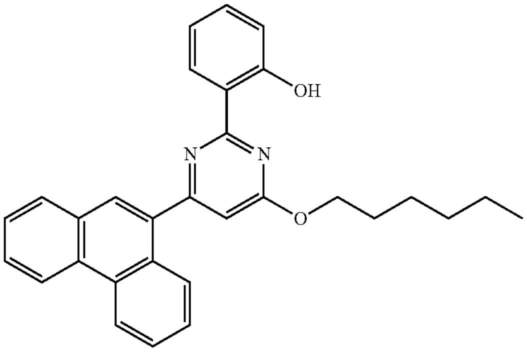
25
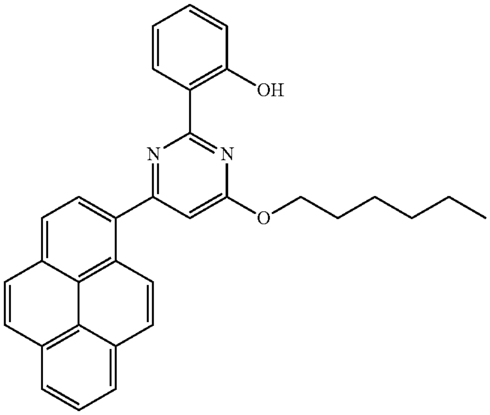
26
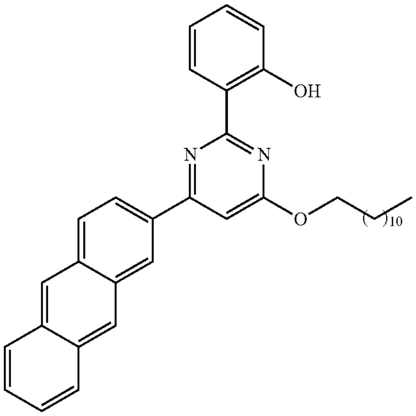
27
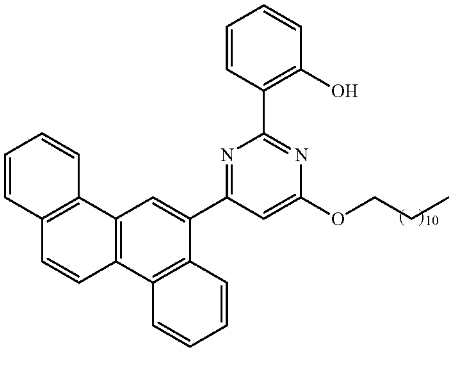
-continued
28
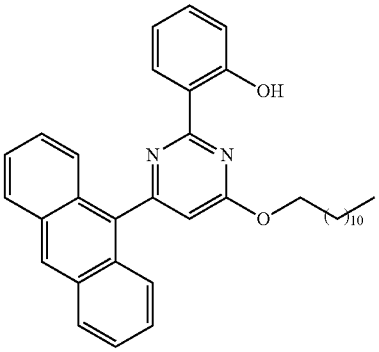
29
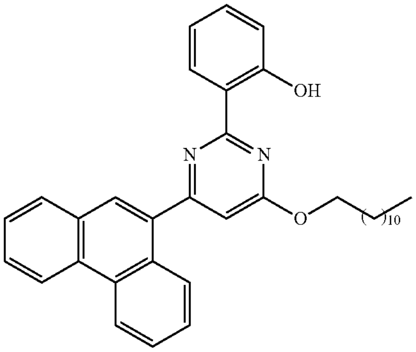
30
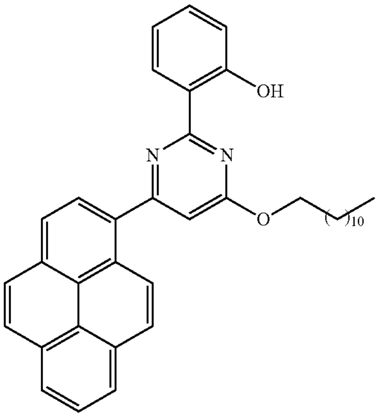
31
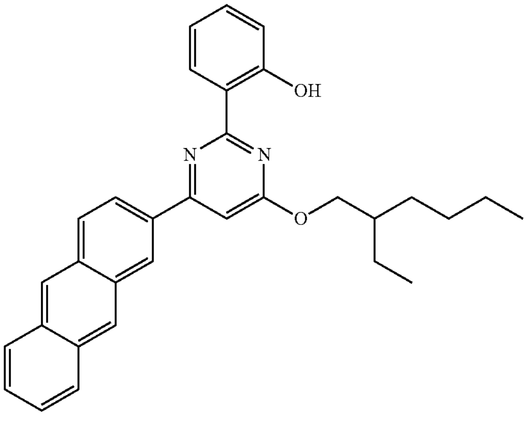

-continued
32
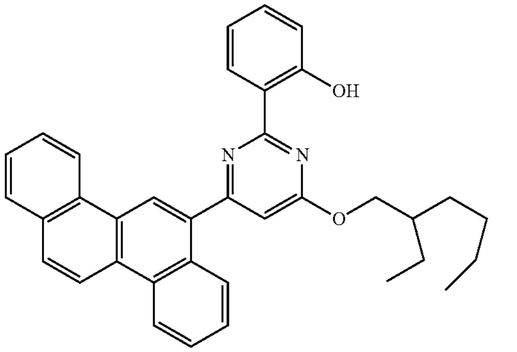
33
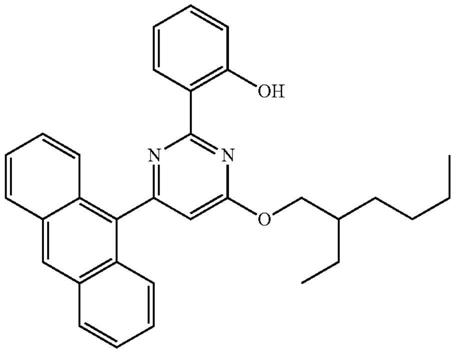
34
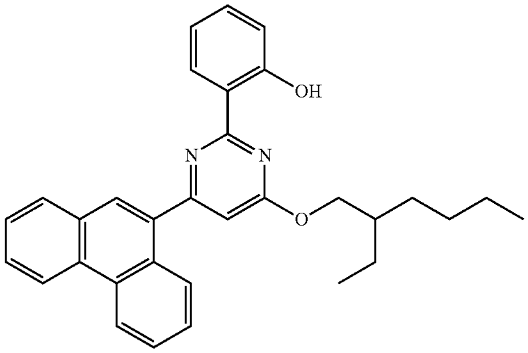
35
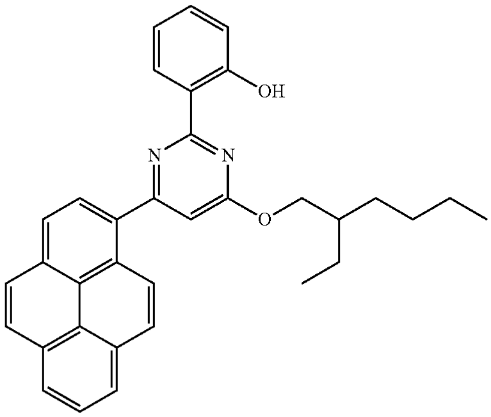
-continued
36
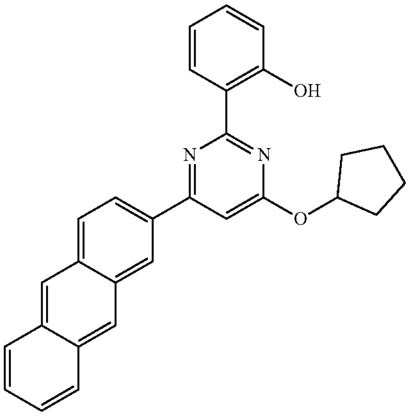
37
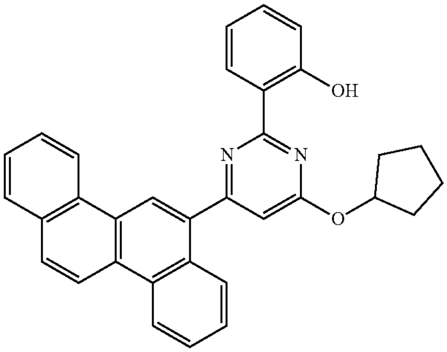
38
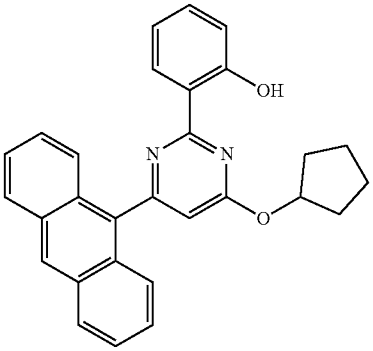
39
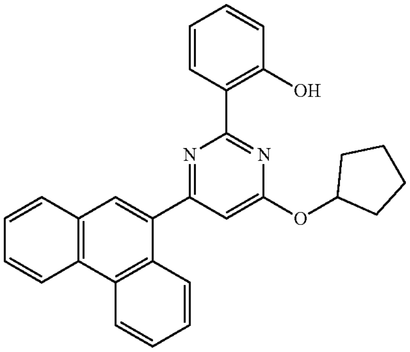

-continued
40
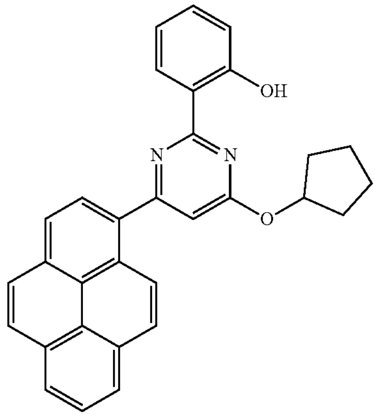
41
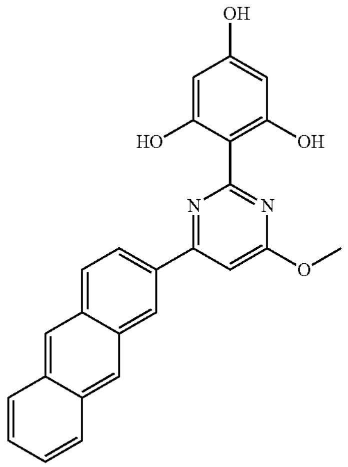
42
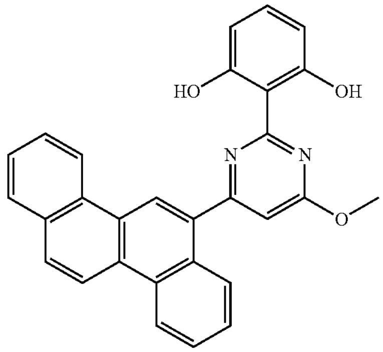
43
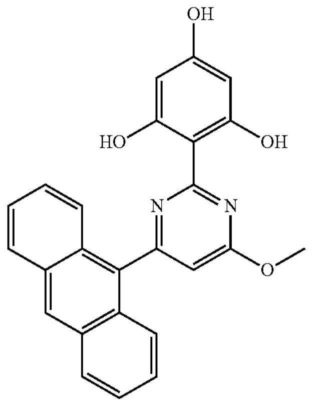
-continued
44
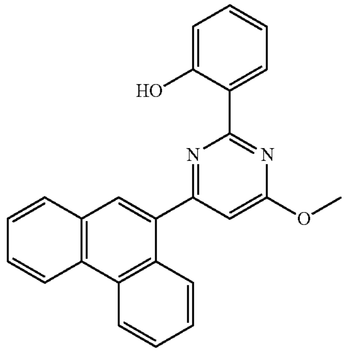
45
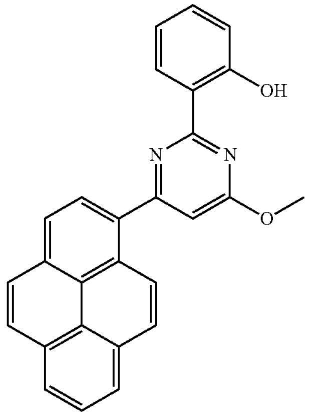
46
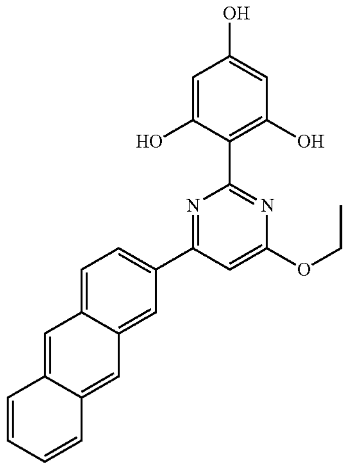
47
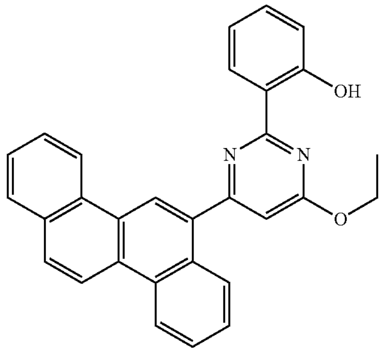

-continued
48
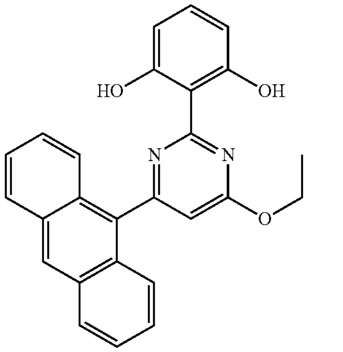
49
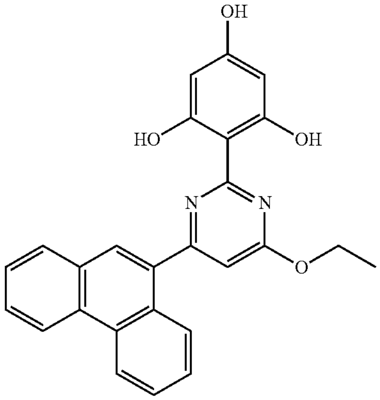
50
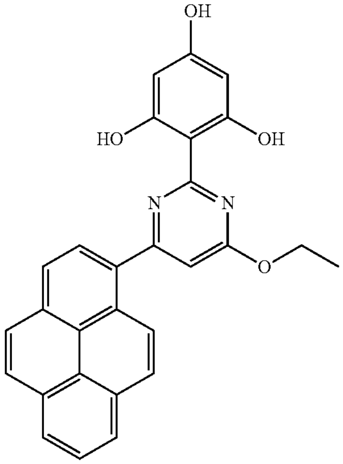
-continued
51
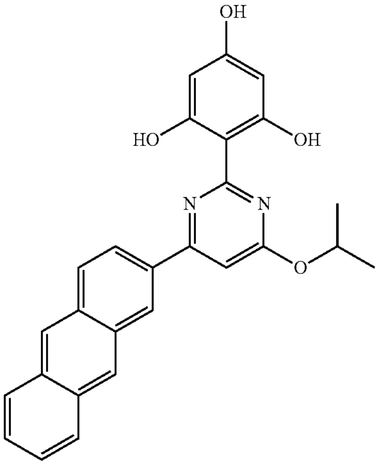
52
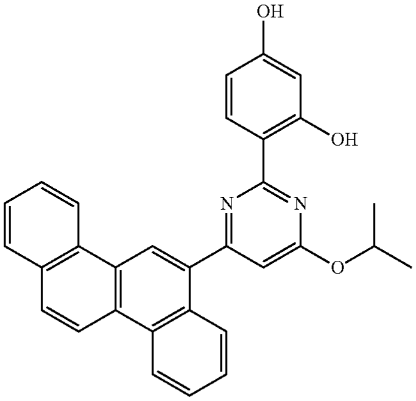
53
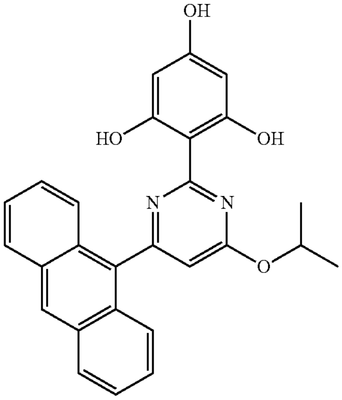
54
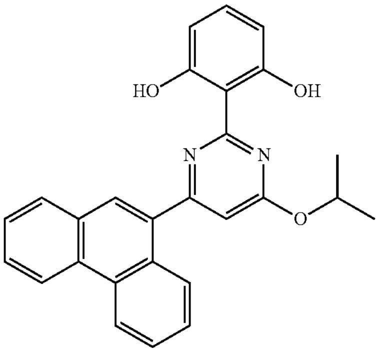

-continued
55
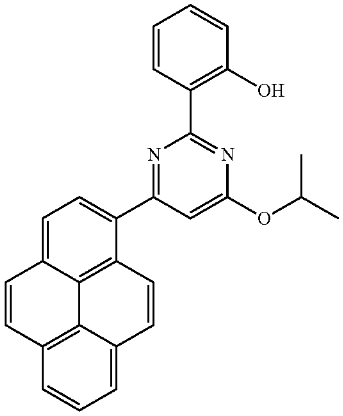
56
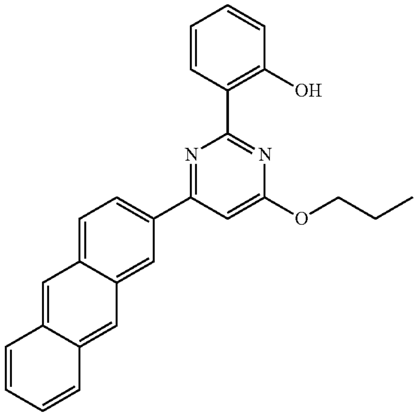
57
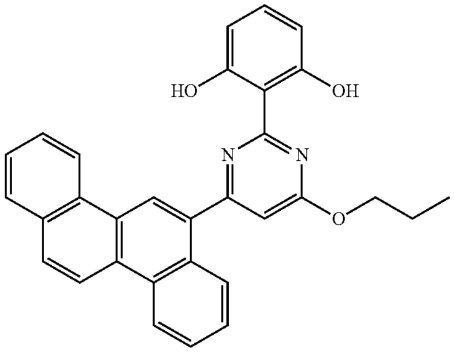
58
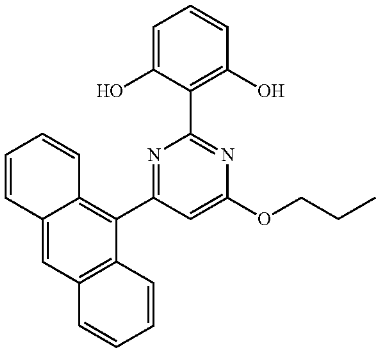
-continued
59
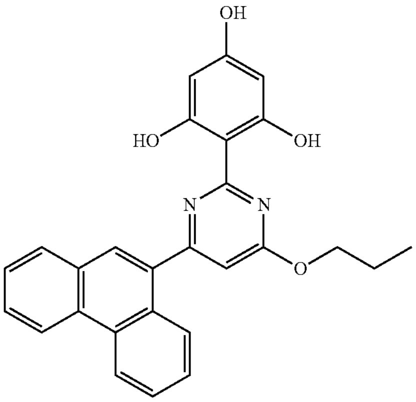
60
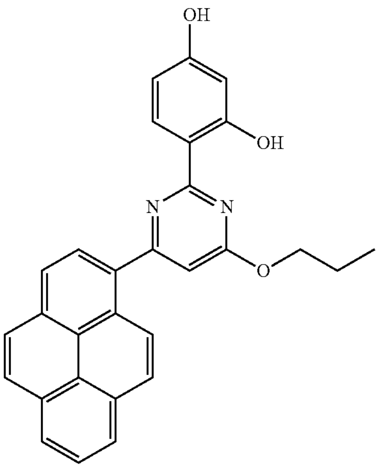
61
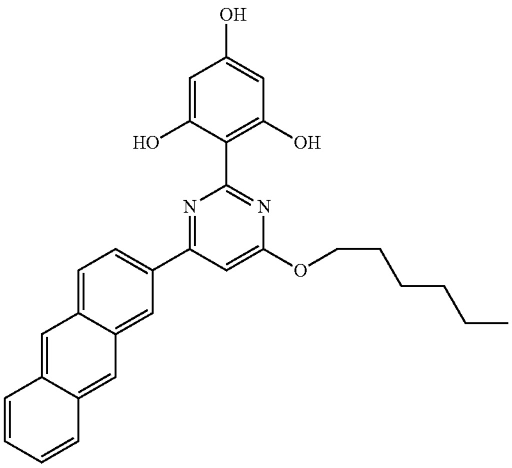

-continued
62
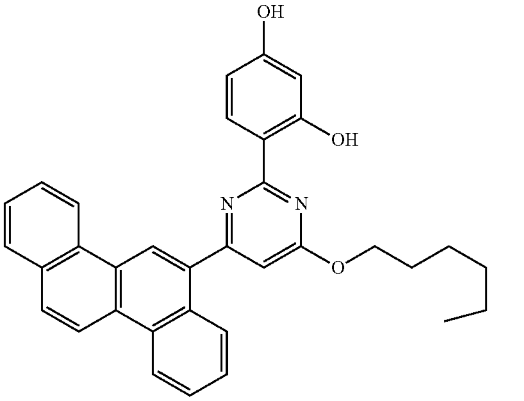
63
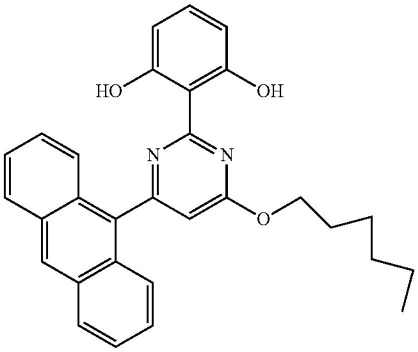
64
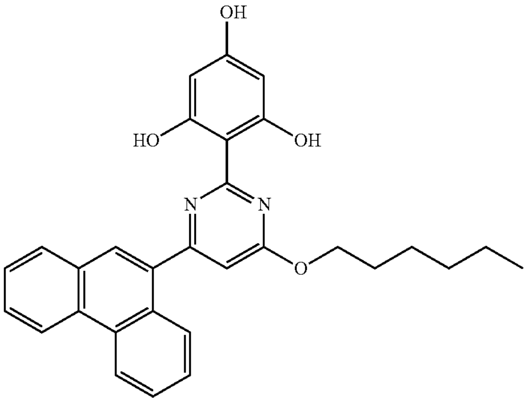
65
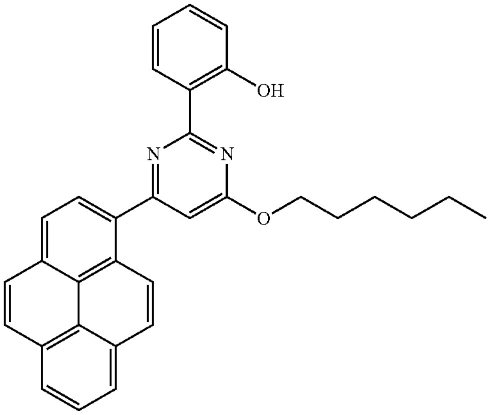
-continued
66
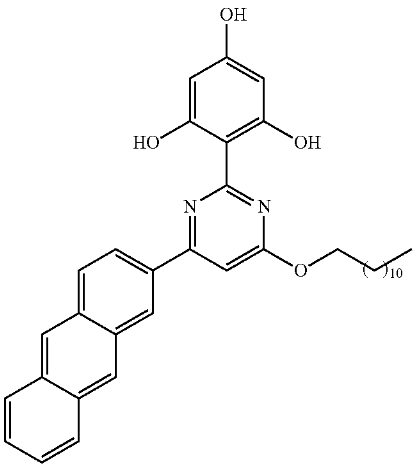
67
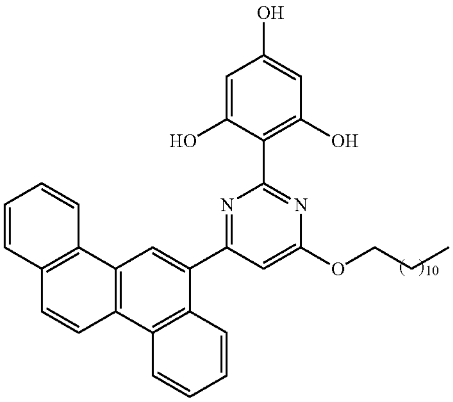
68
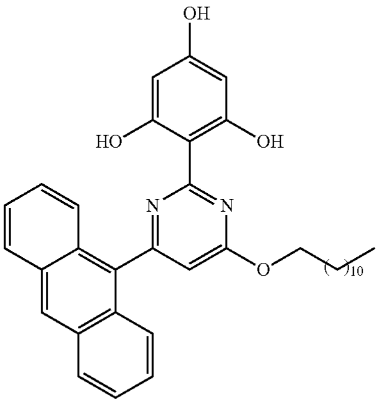

-continued
69
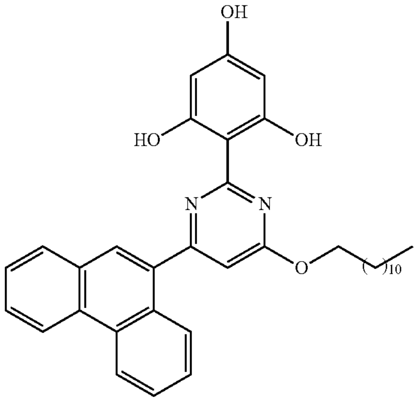
70
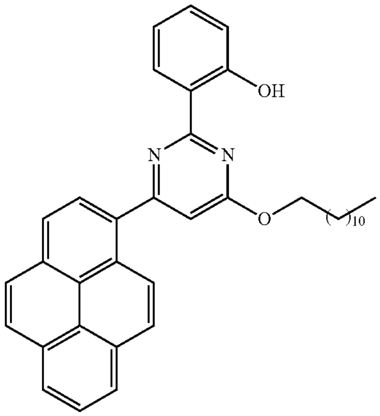
71
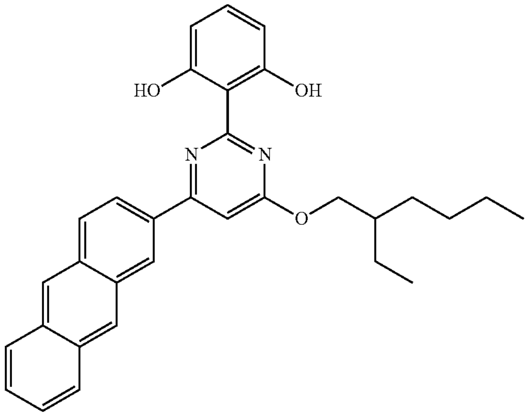
72
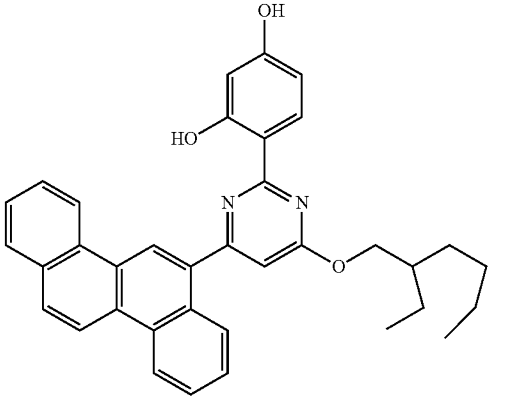
-continued
73
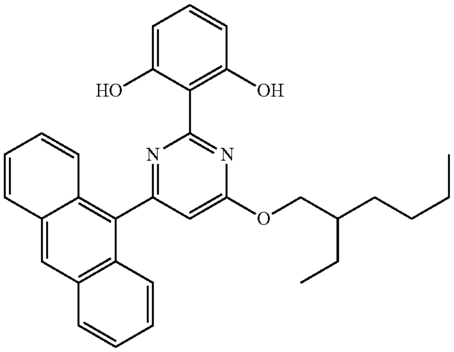
74
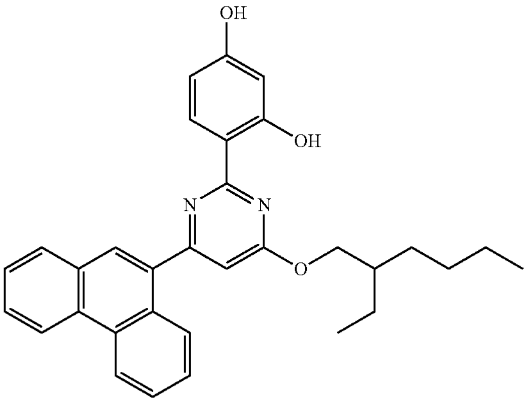
75
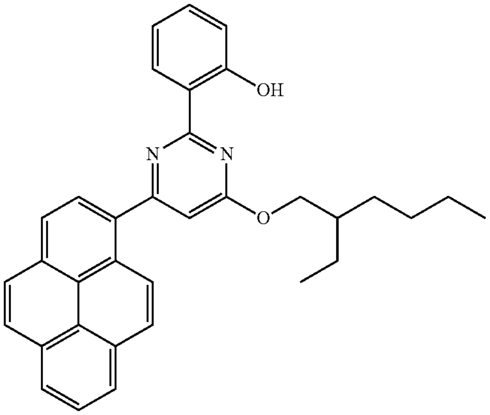

-continued
76
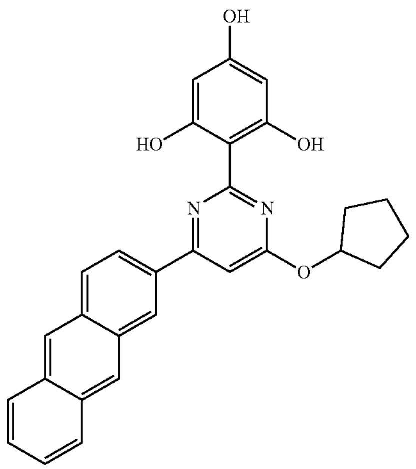
77
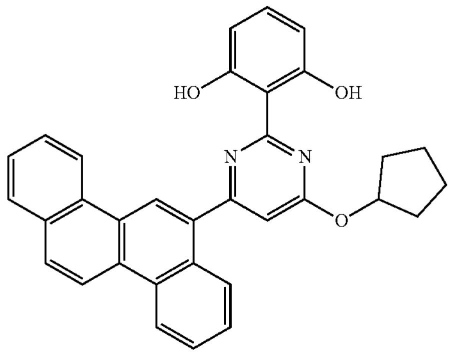
78
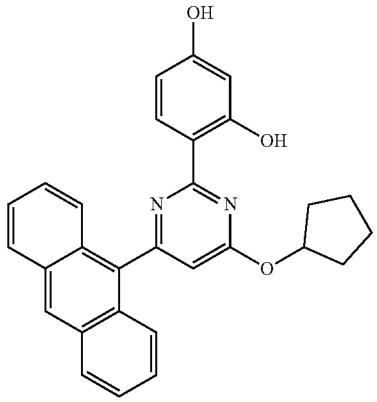
79
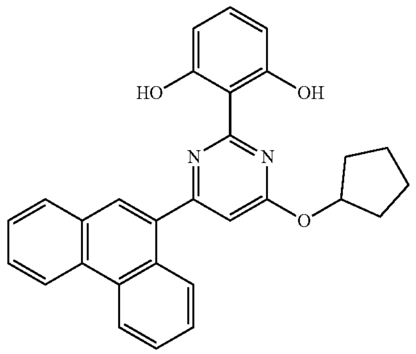
-continued
80
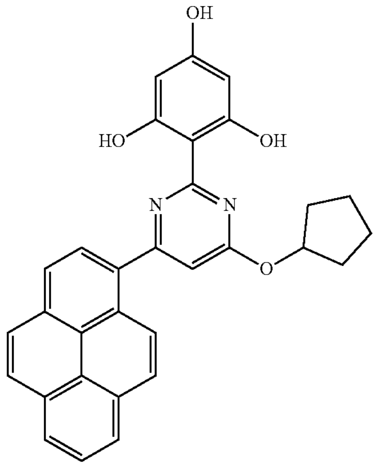
81
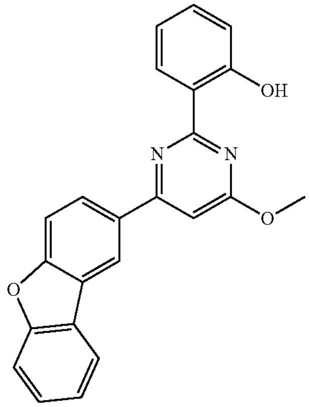
82
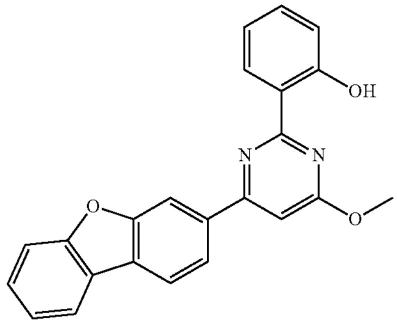
83
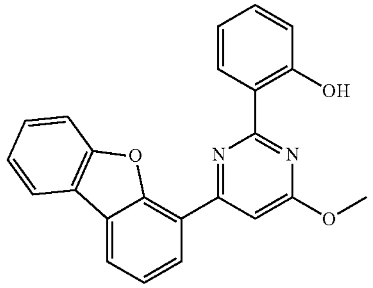

-continued
84
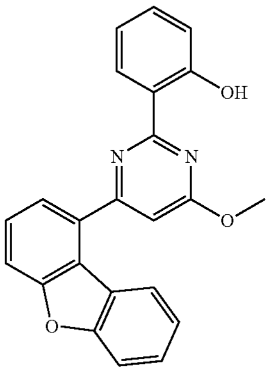
85
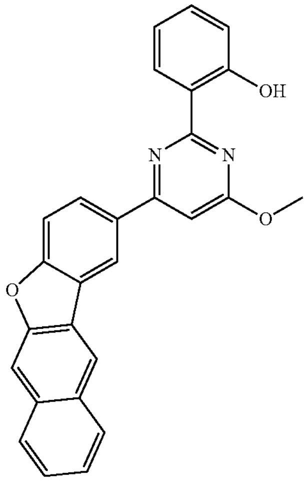
86
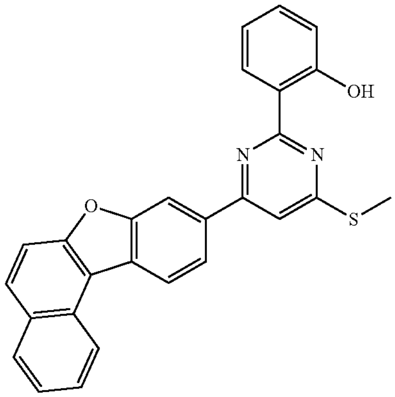
87
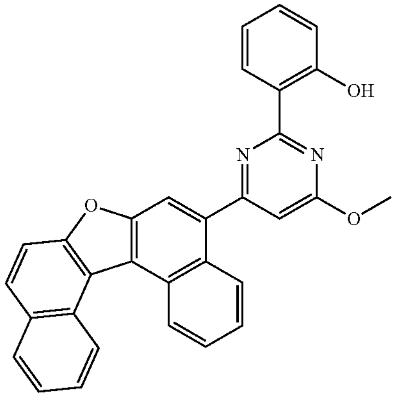
-continued
88
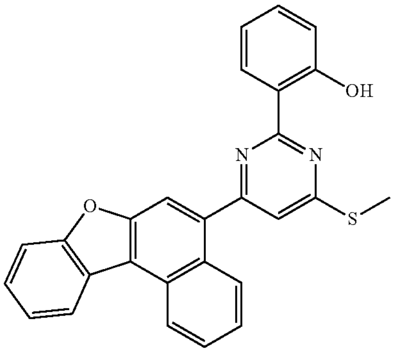
89
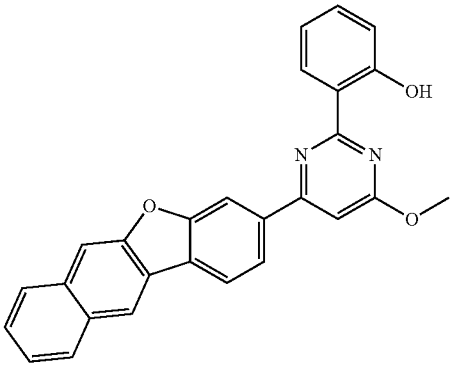
90
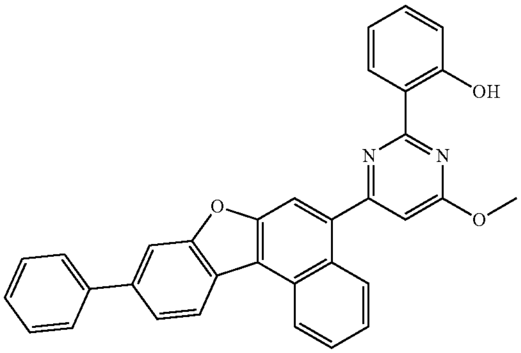
91
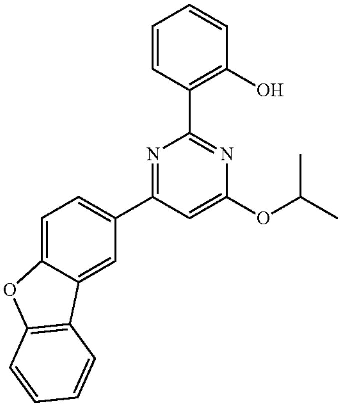

-continued
92
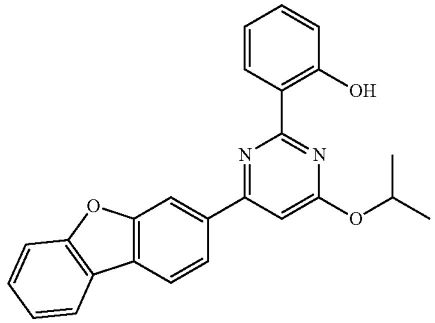
93
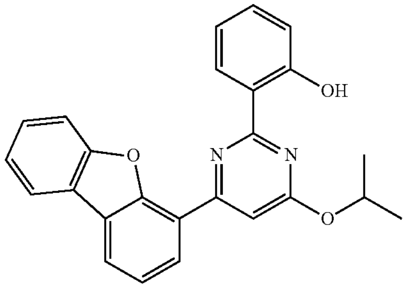
94
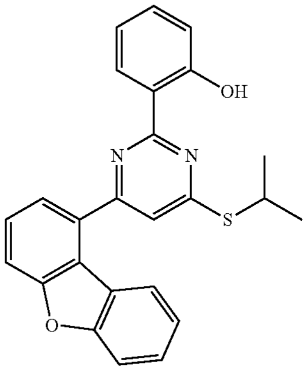
95
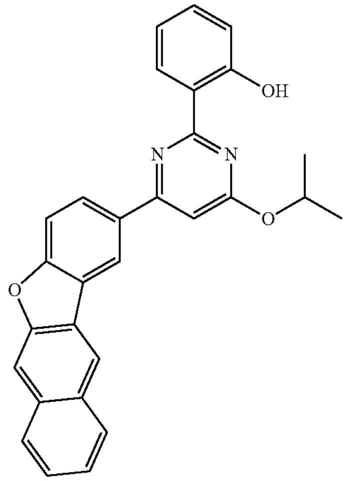
-continued
96
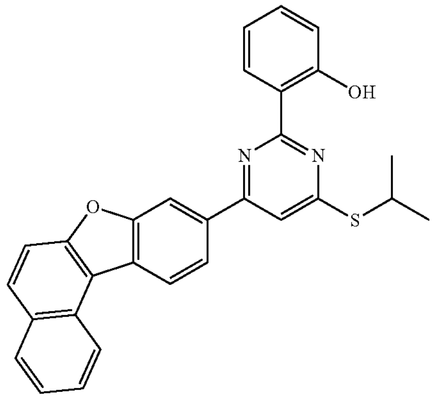
97
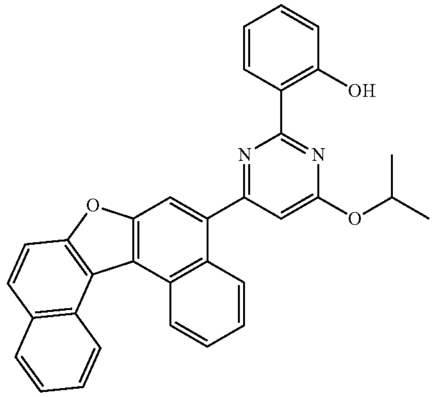
98
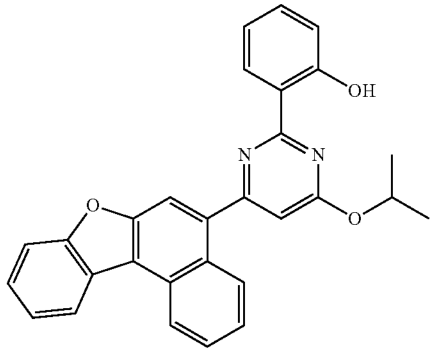
99
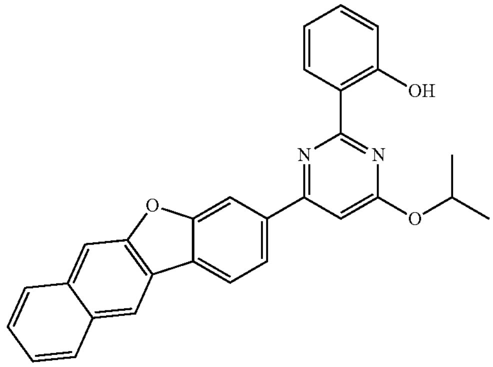

-continued
100
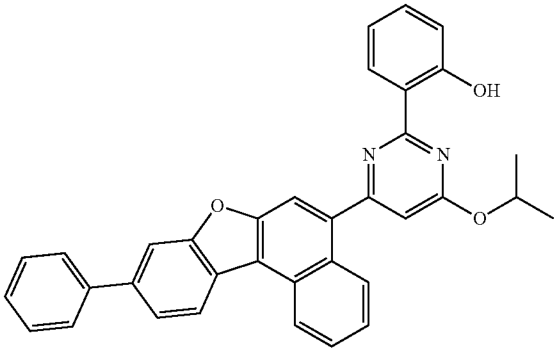
101
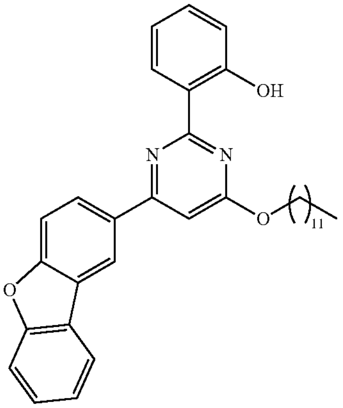
102
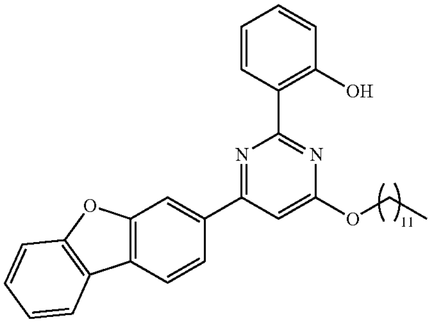
103
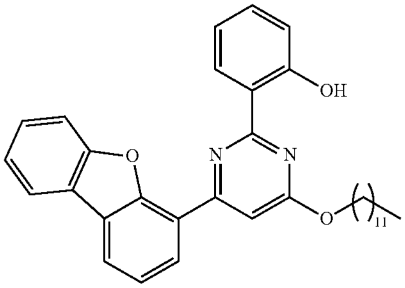
-continued
104
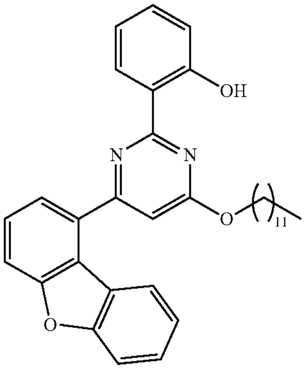
105
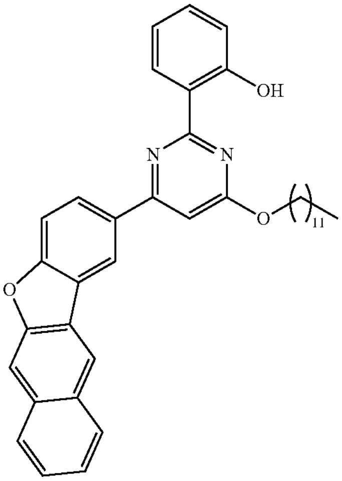
106
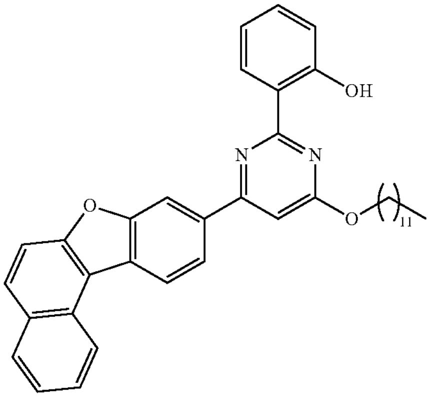
107
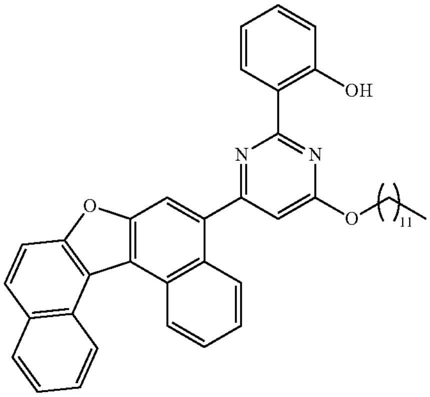

-continued
108
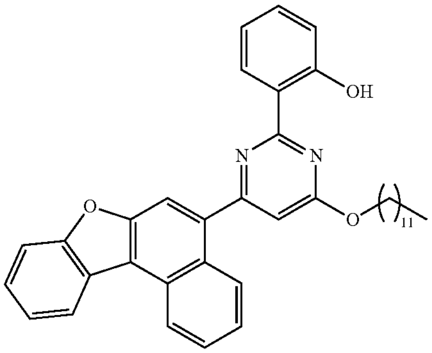
109
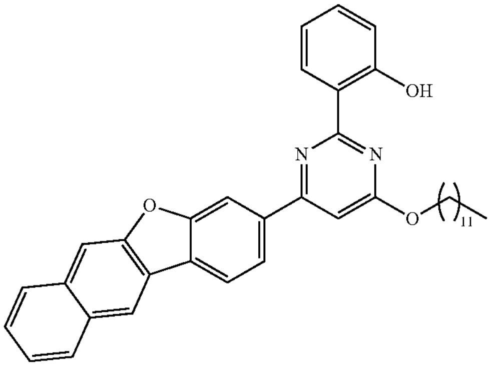
110
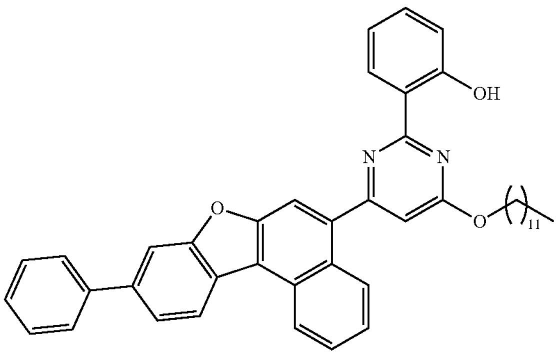
111
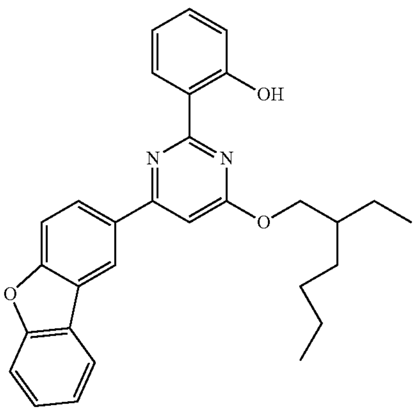
-continued
112
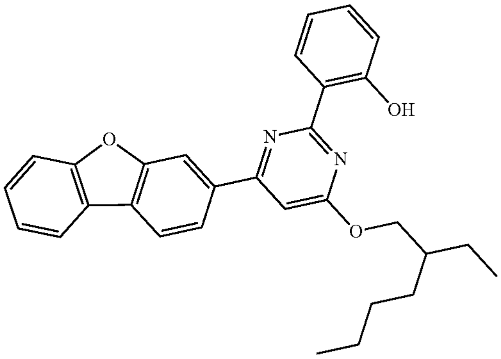
113
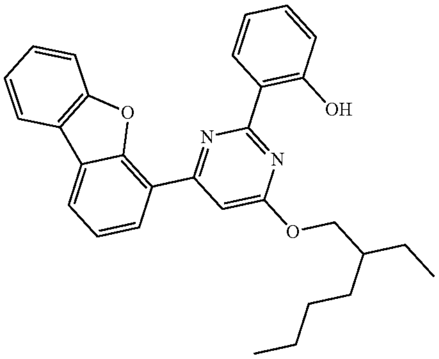
114
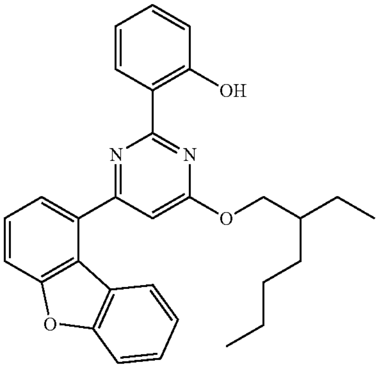
115
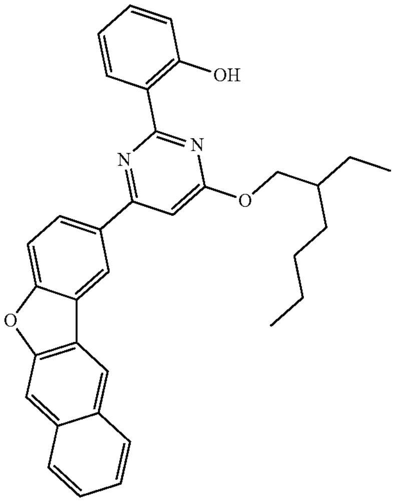

-continued
116
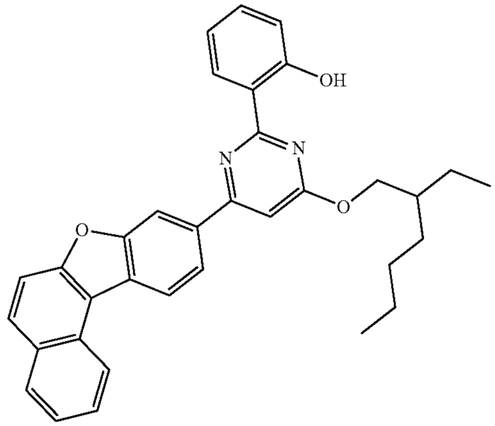
117
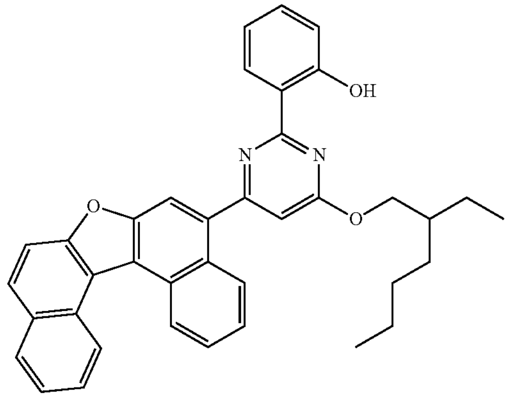
118
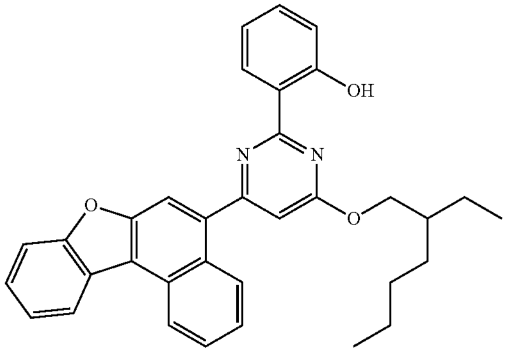
-continued
119
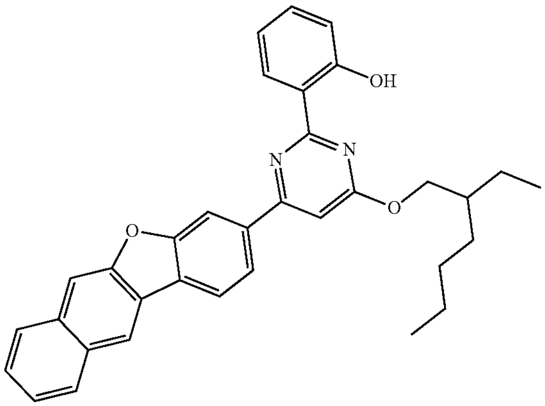
120
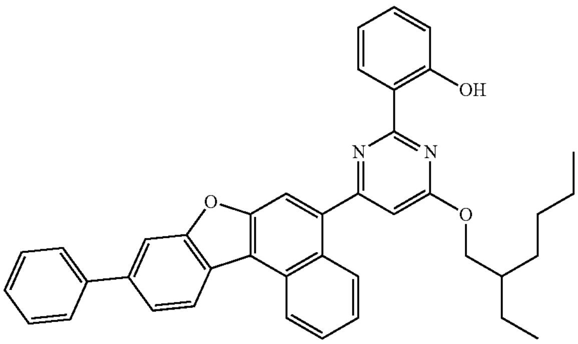
121
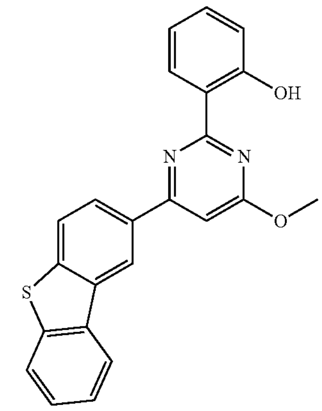
122
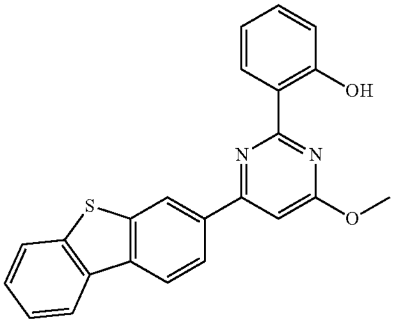

-continued
123
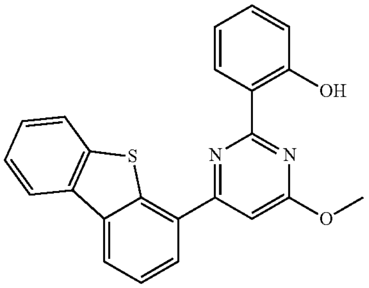
124
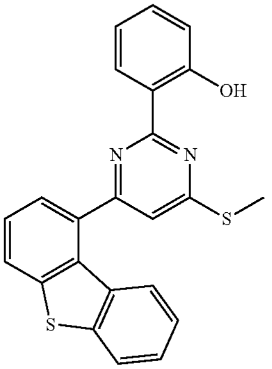
125
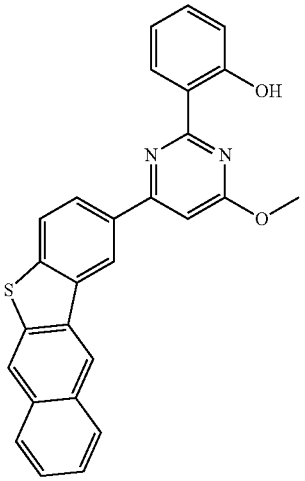
126
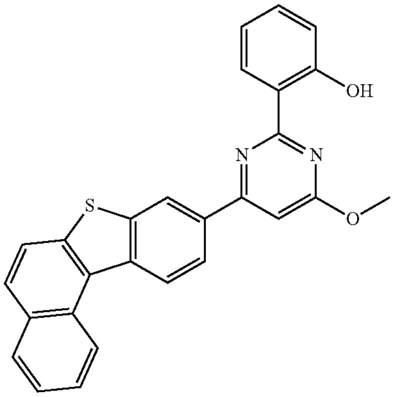
-continued
127
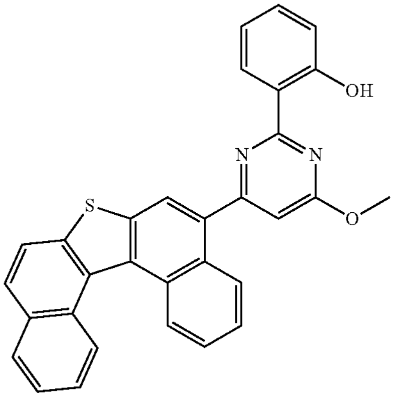
128
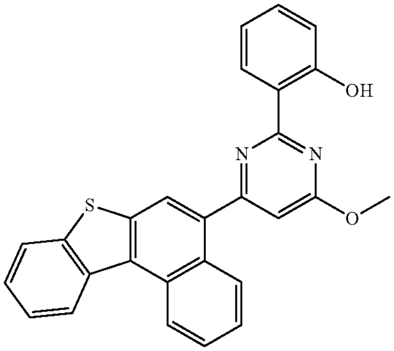
129
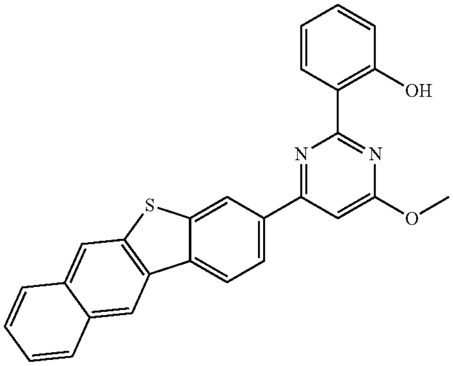
130
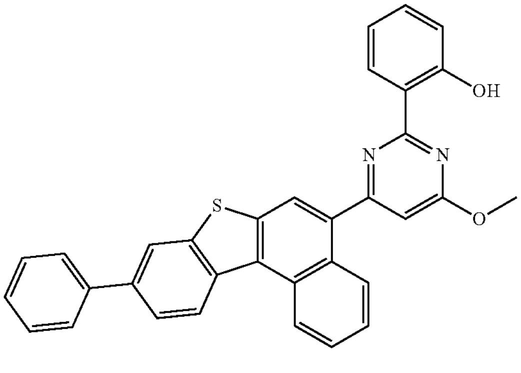

-continued
131
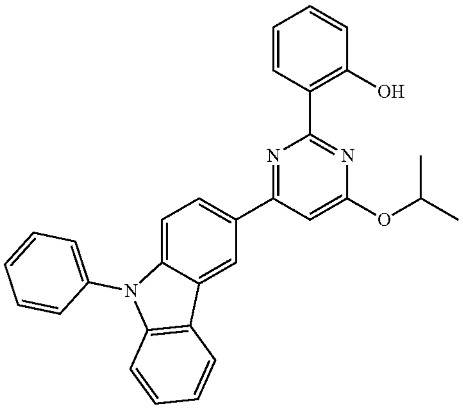
132
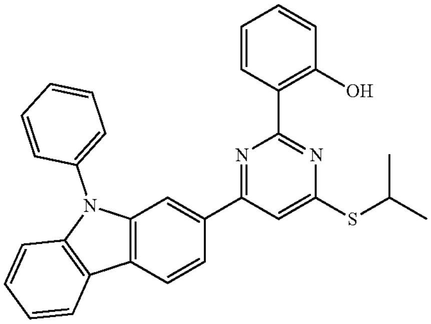
133
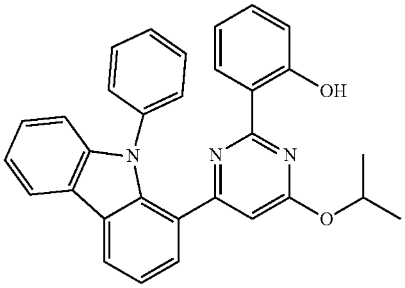
134
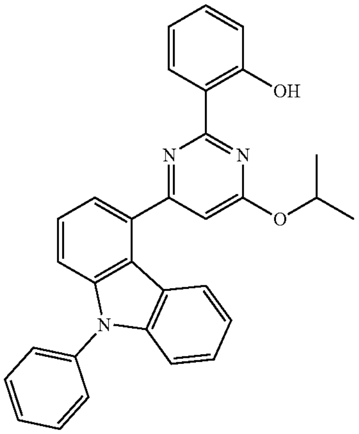
-continued
135
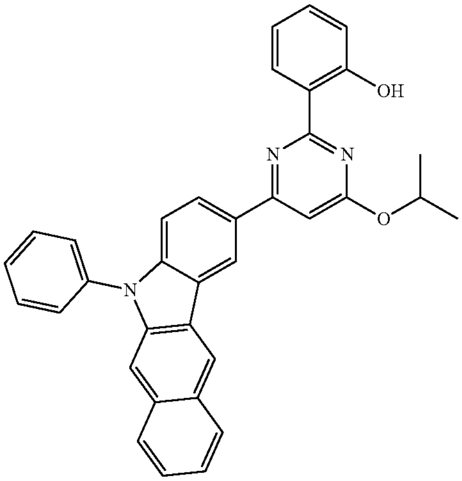
136
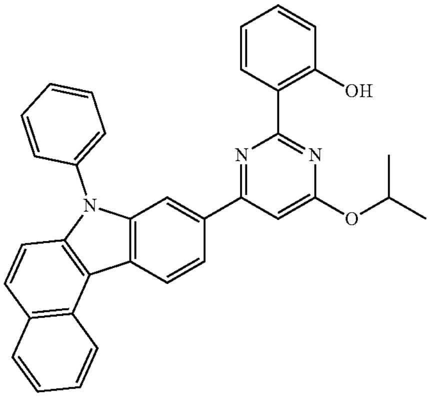
137
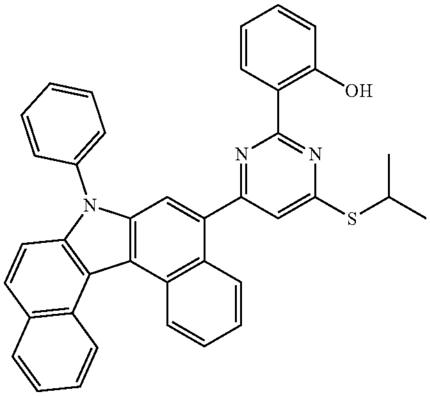
138
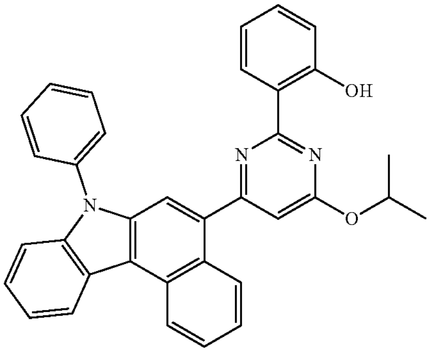

-continued
139
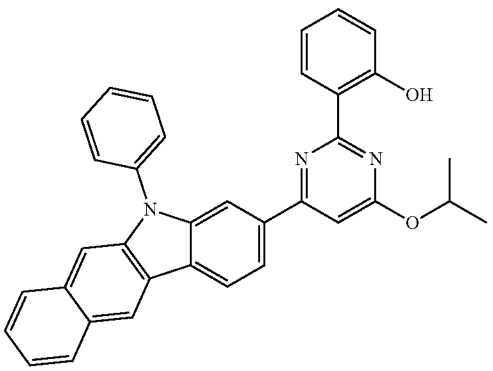
140
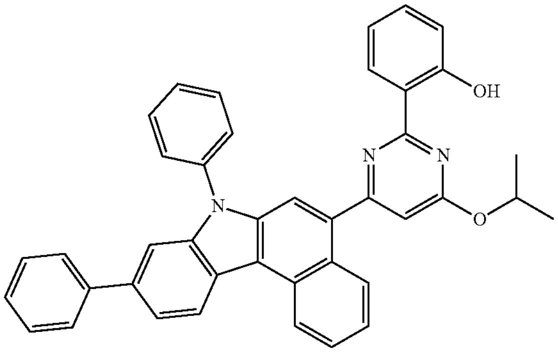
141
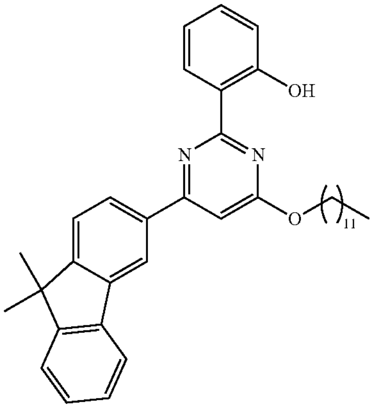
142
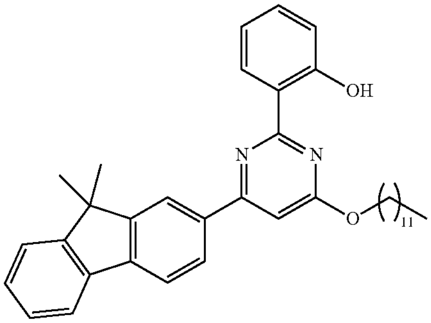
-continued
143
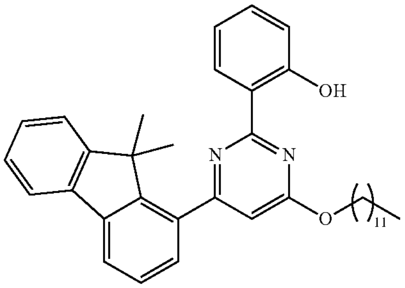
144
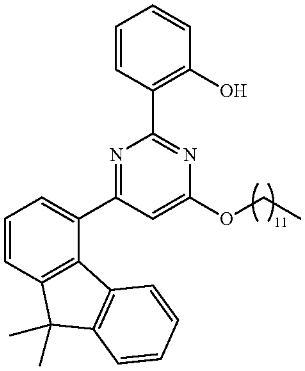
145
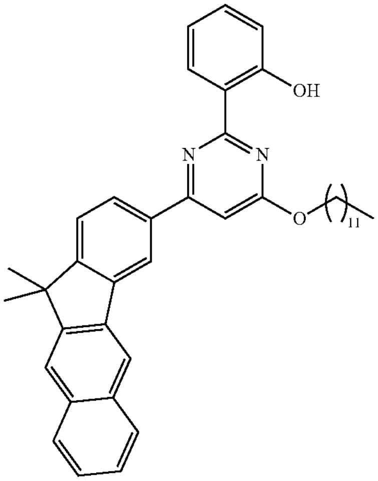
146
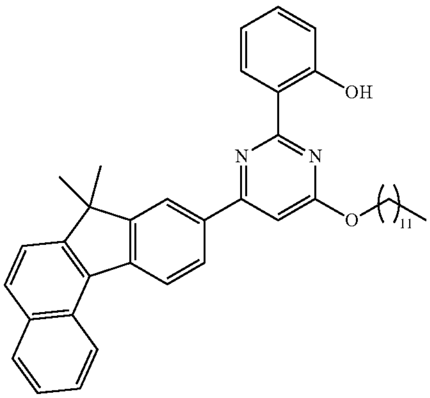

-continued
147
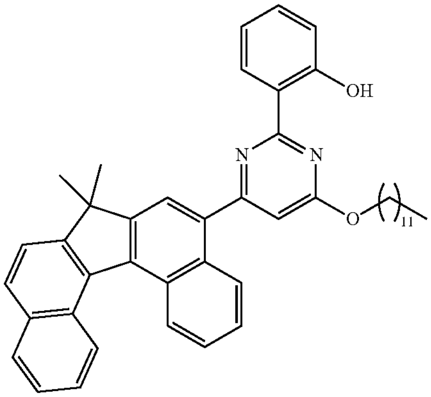
148
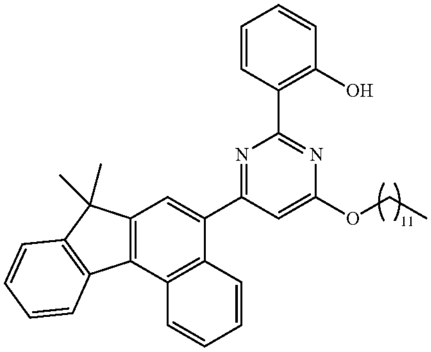
149
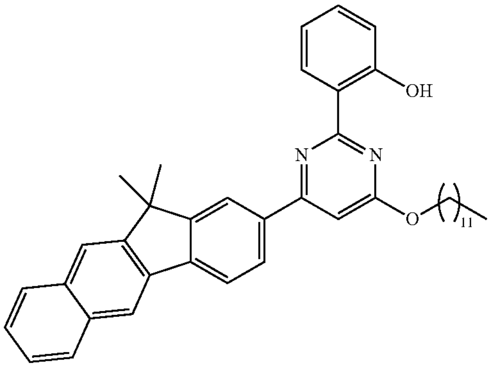
150
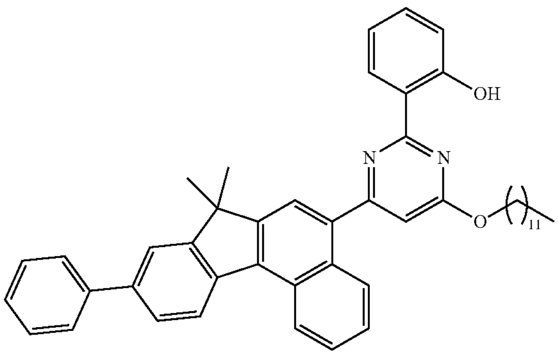
-continued
151
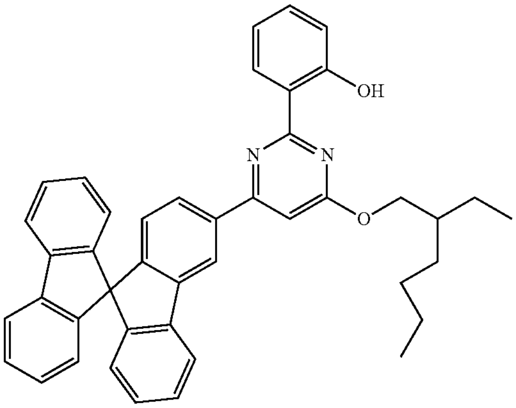
152
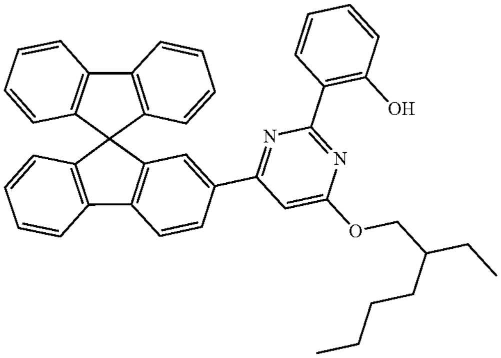
153
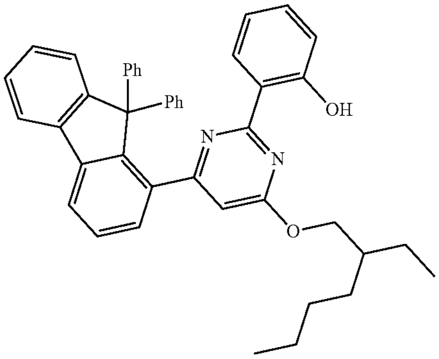
154
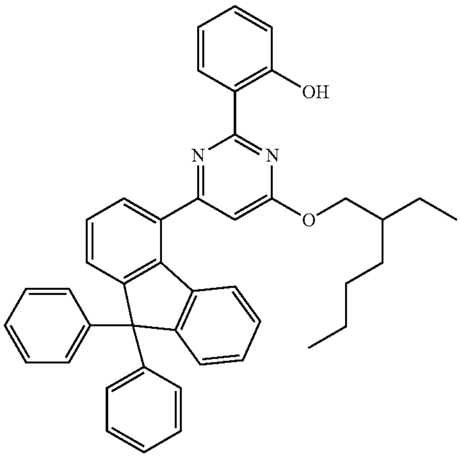

-continued
155
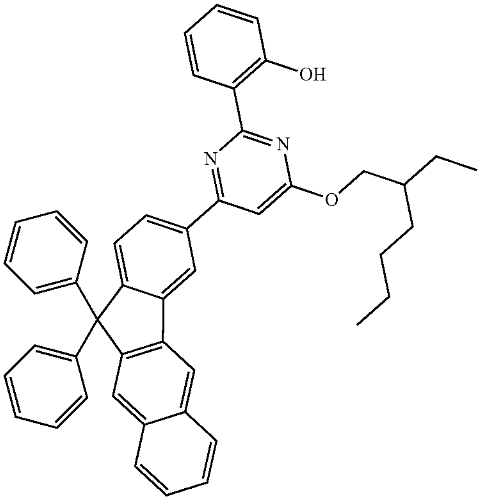
156
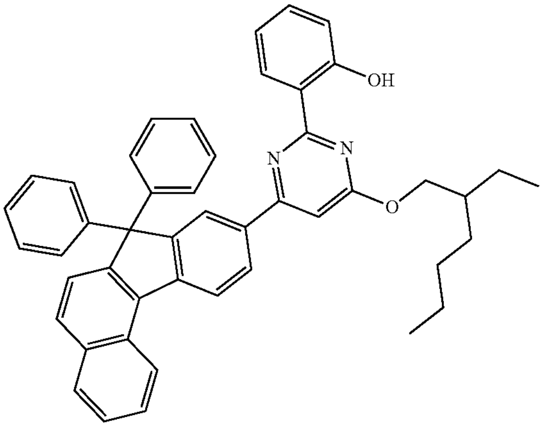
157
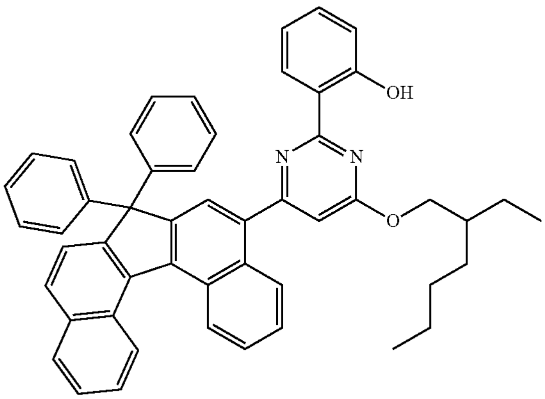
-continued
158
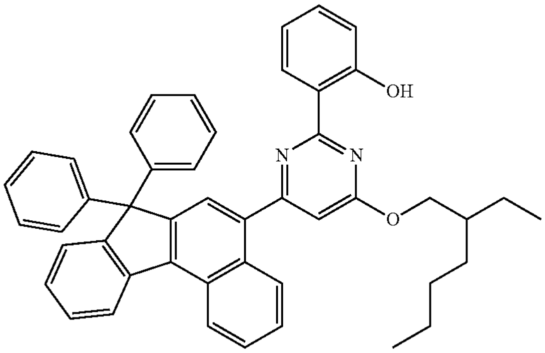
159
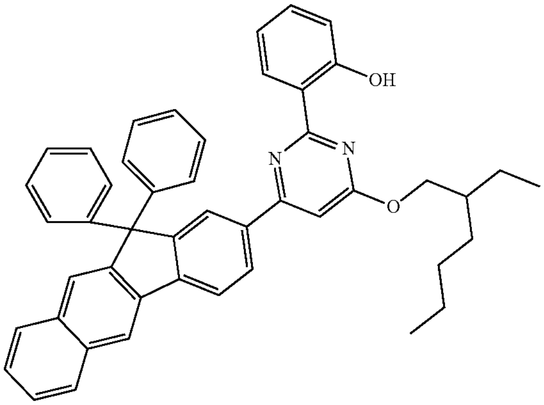
160
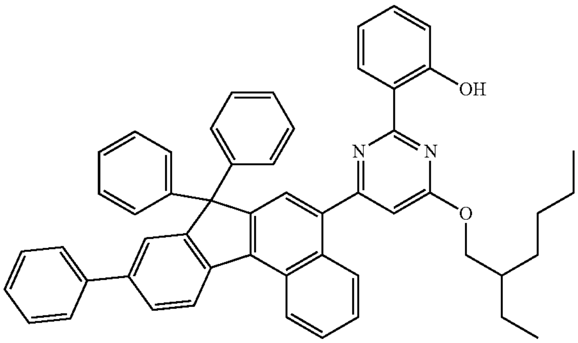
161
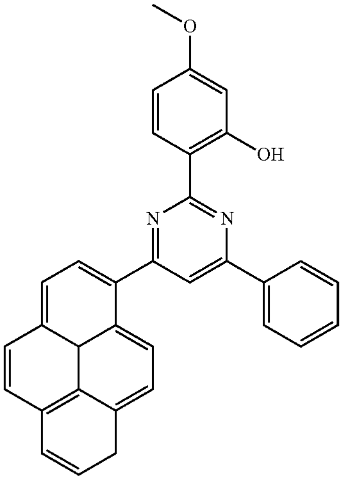

-continued
162
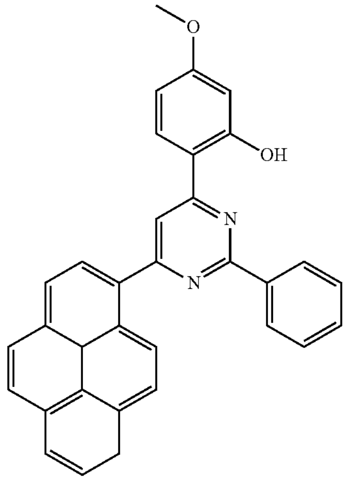
163
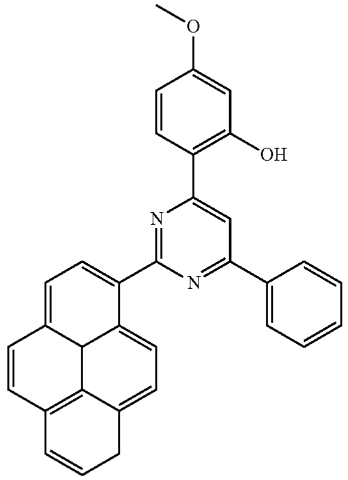
164
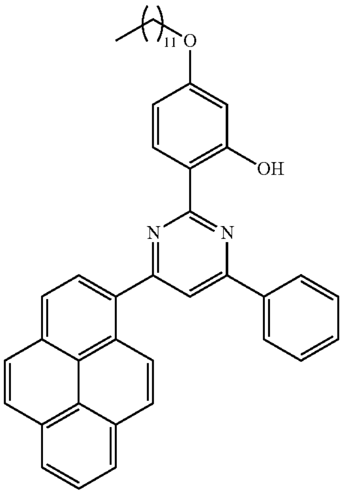
-continued
165
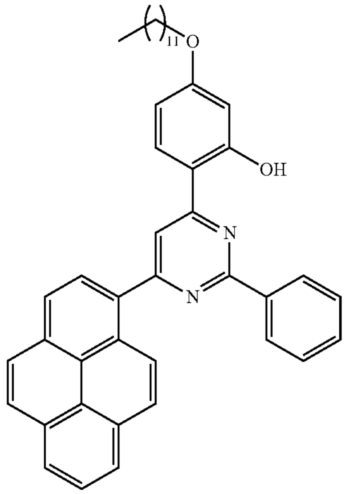
166
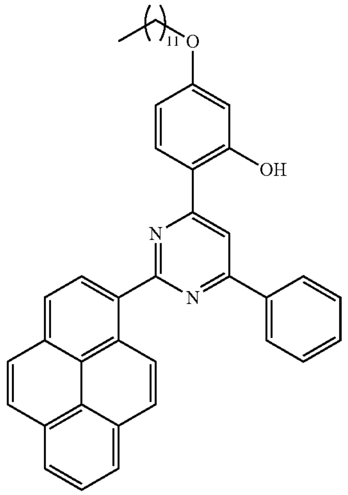
167
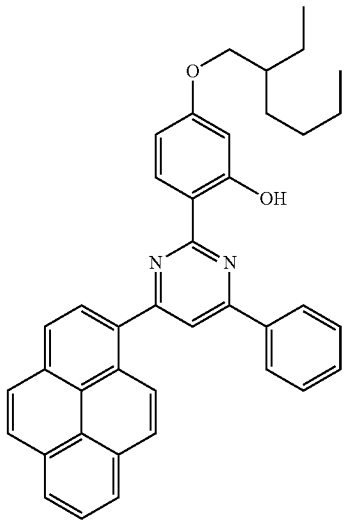

-continued
168
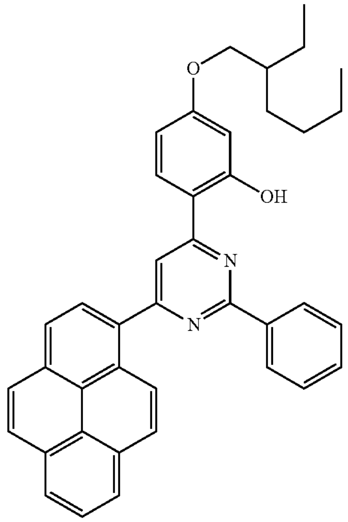
169
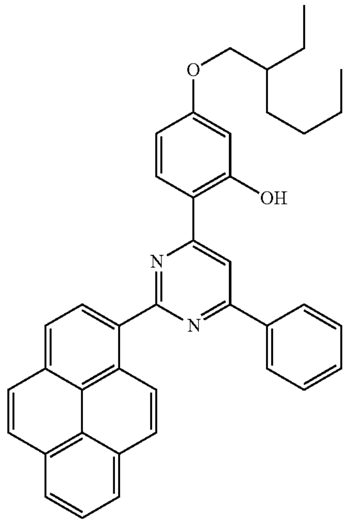
170
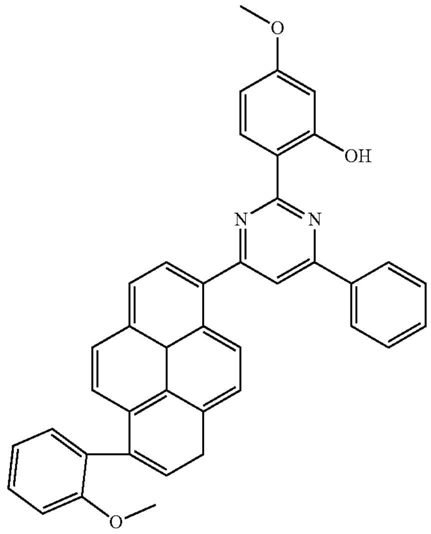
-continued
171
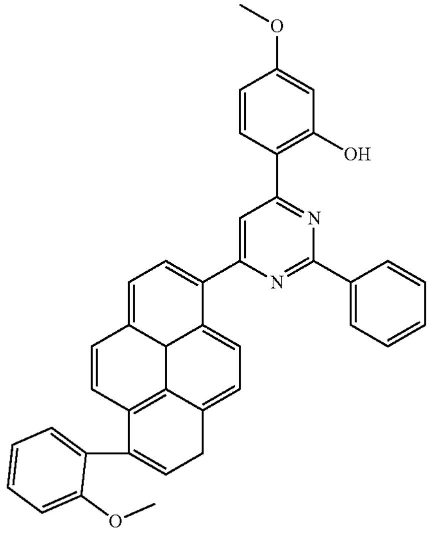
172
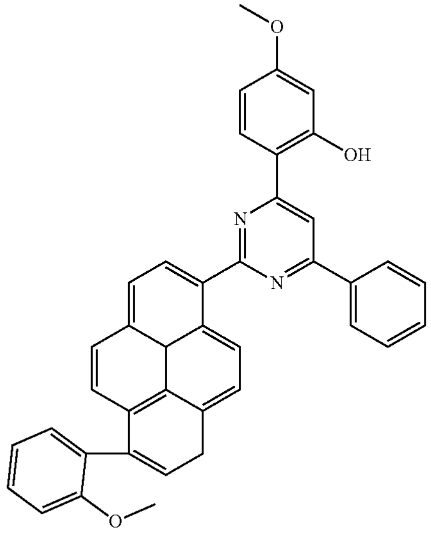
173
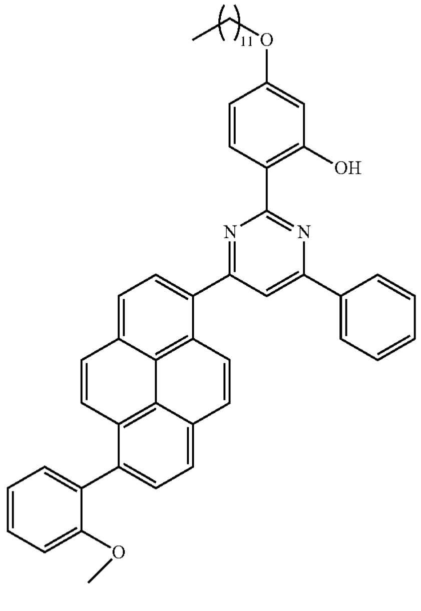

-continued
174
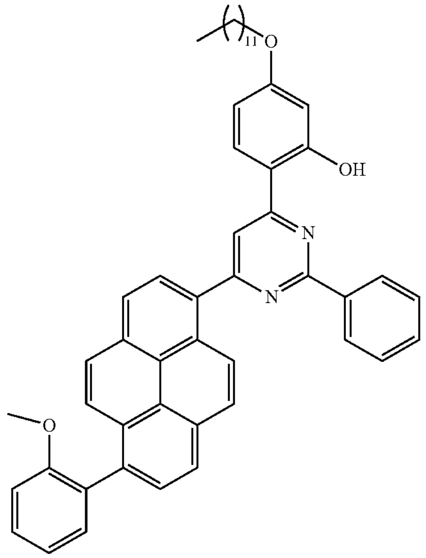
-continued
176
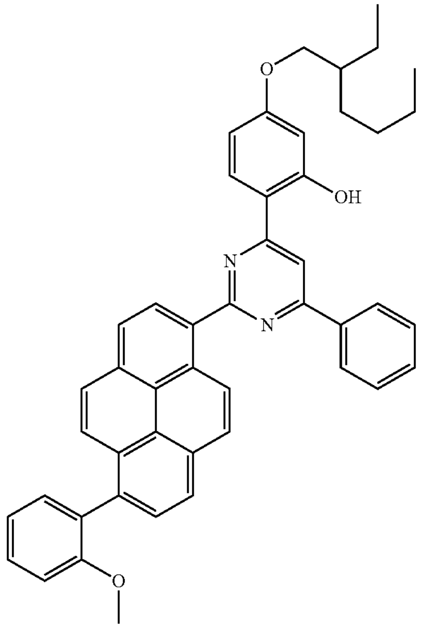
175
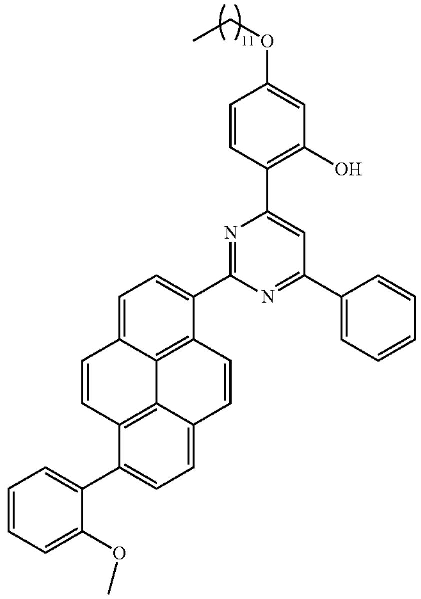
177
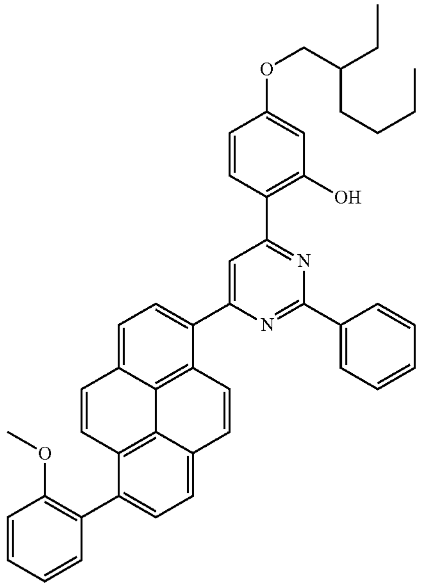

-continued
178
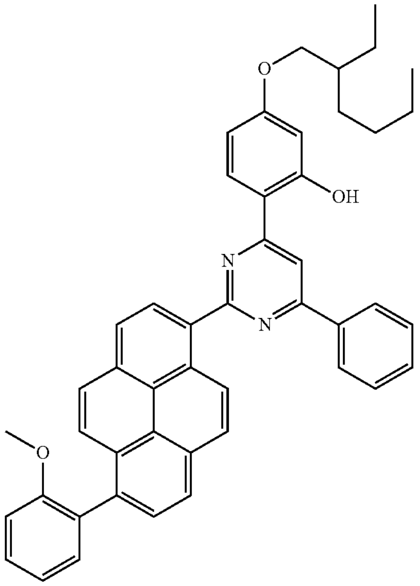
Compound Group 2
1
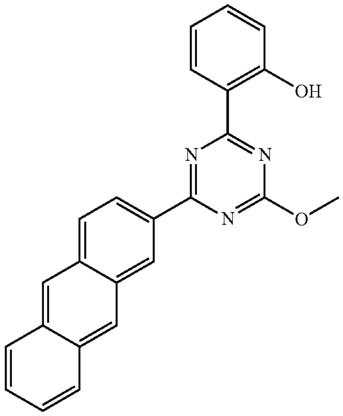
2
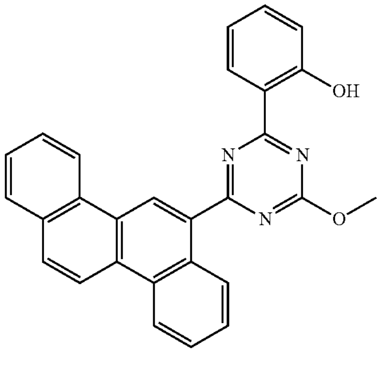
-continued
3
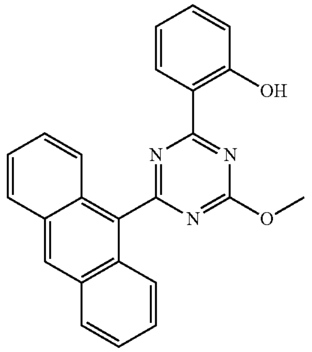
4
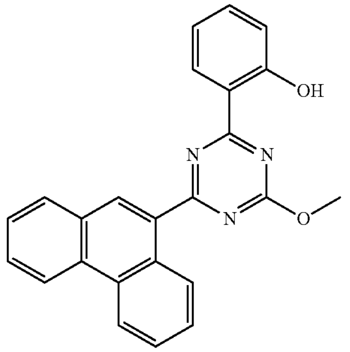
5
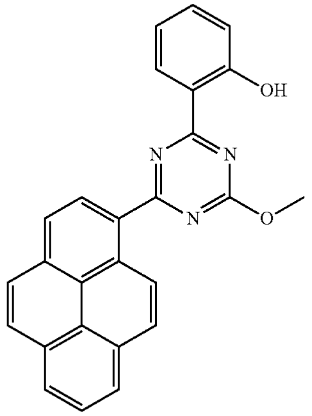
6
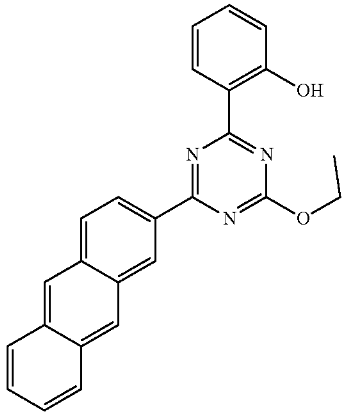

-continued
7
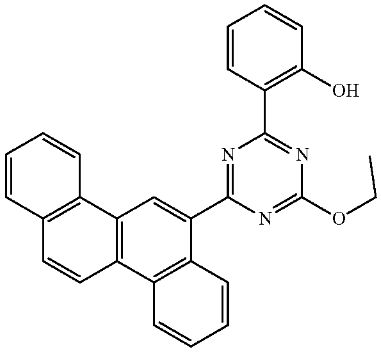
8
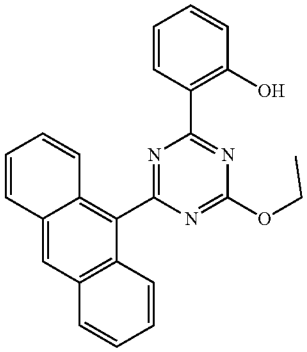
9
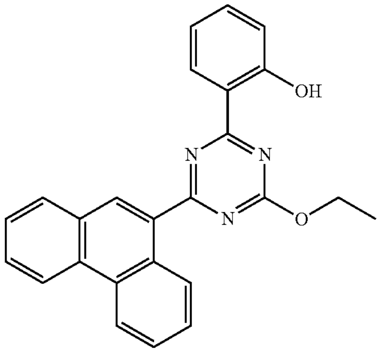
10
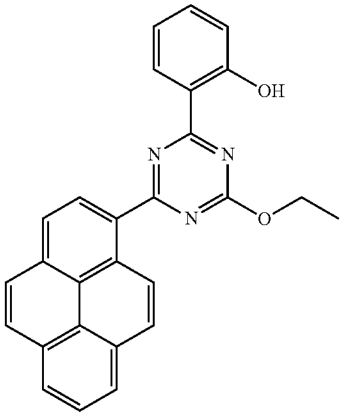
-continued
11
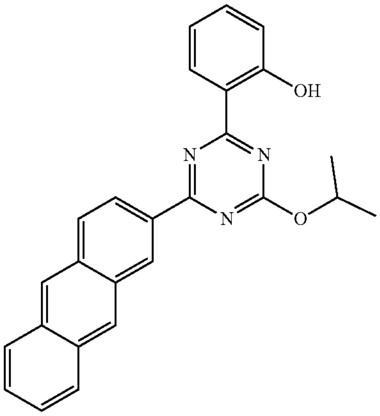
12
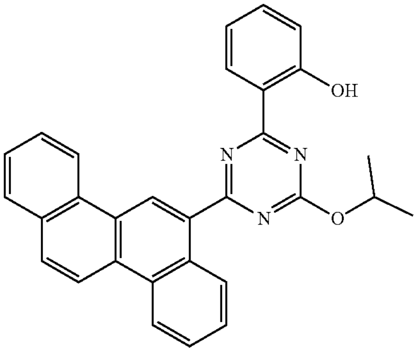
13
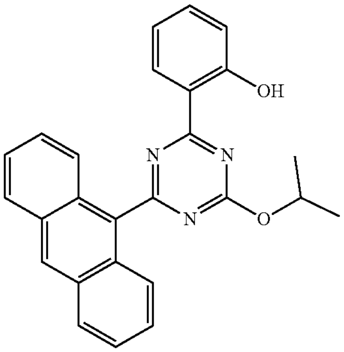
14
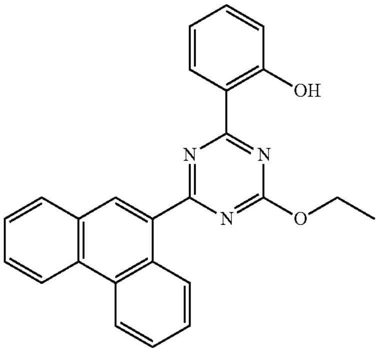

-continued
15
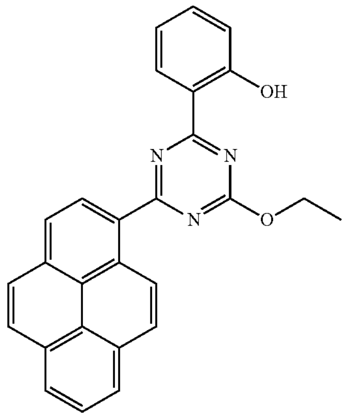
16
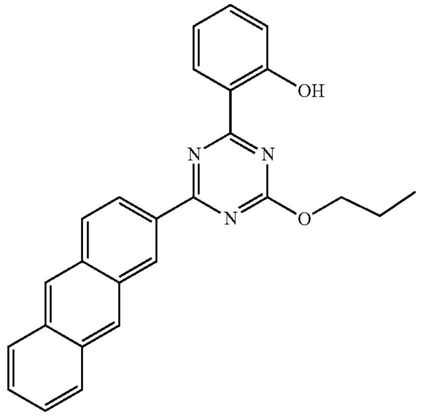
17
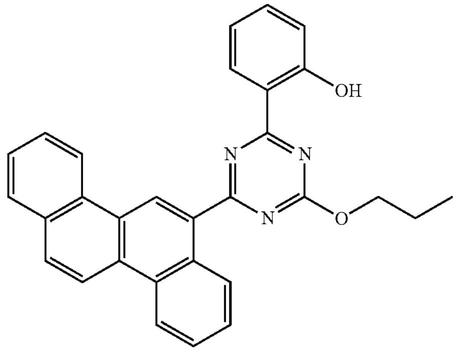
18
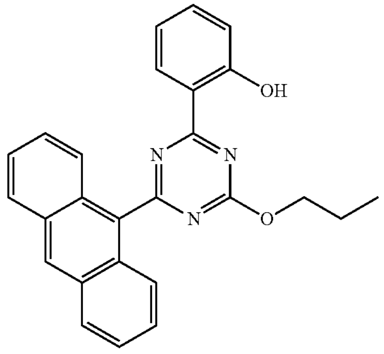
-continued
19
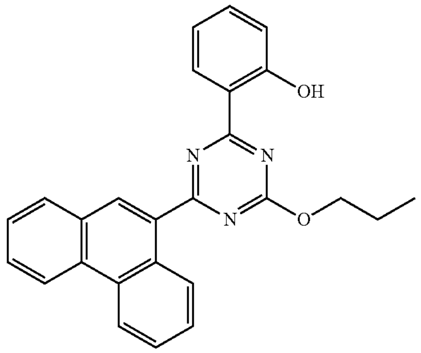
20
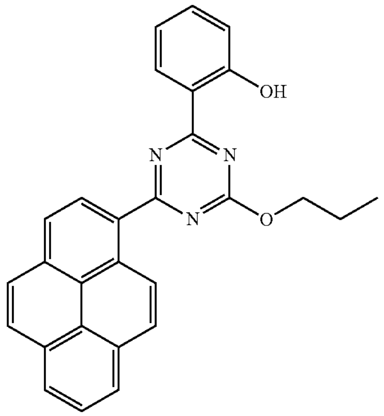
21
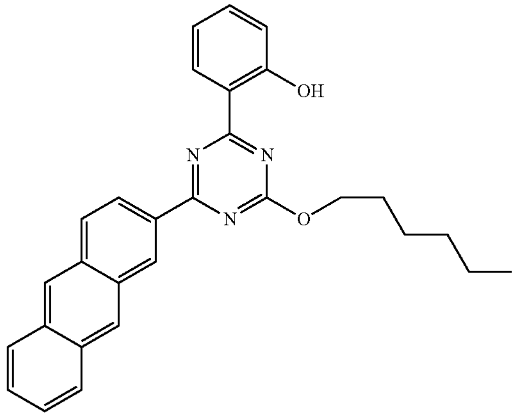
22
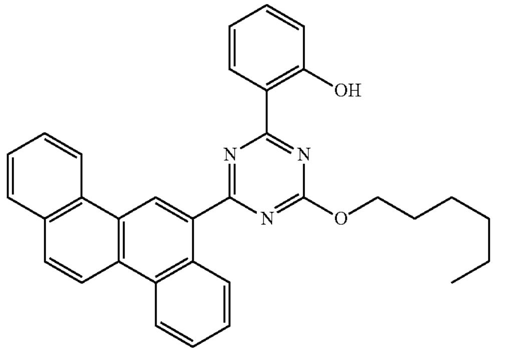

-continued
23
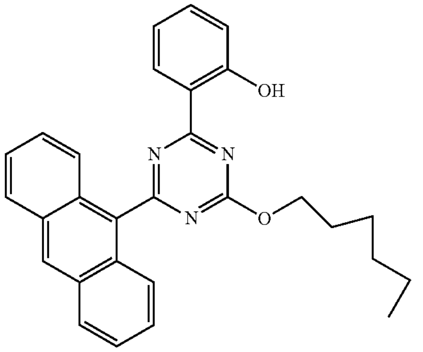
24
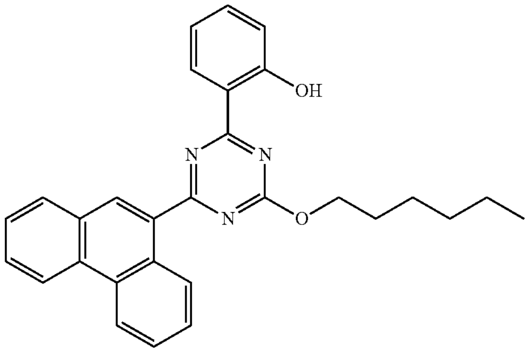
25
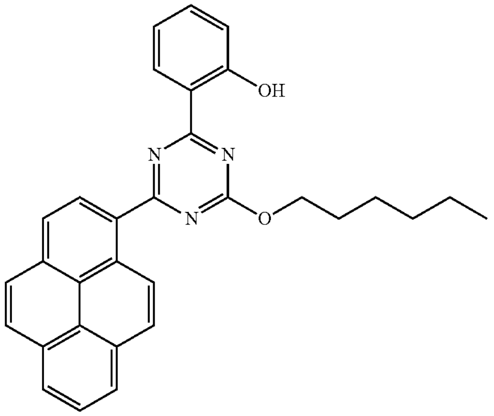
26
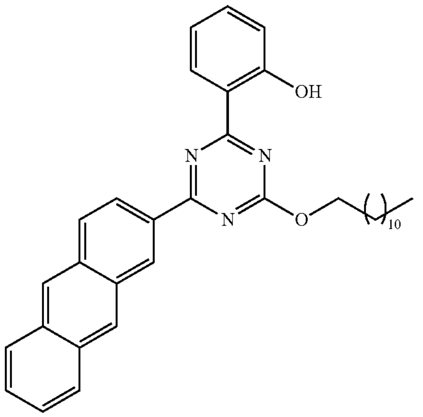
-continued
27
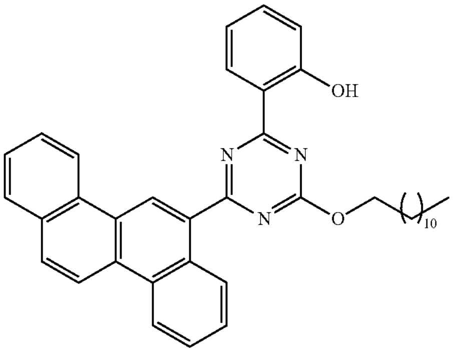
28
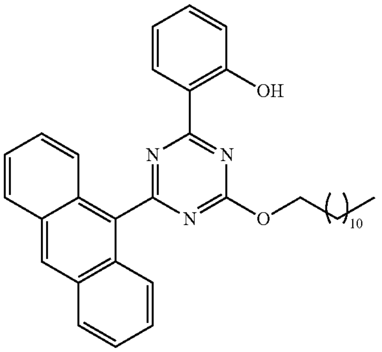
29
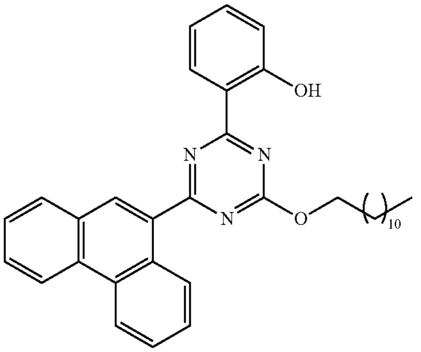
30
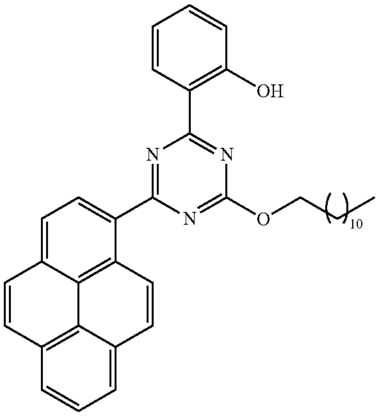

-continued
31
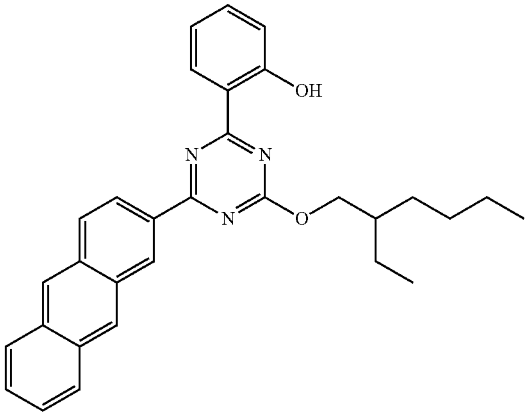
32
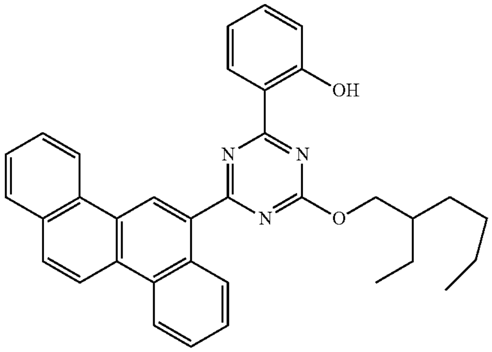
33
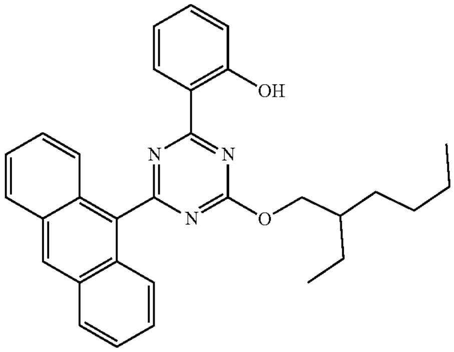
34
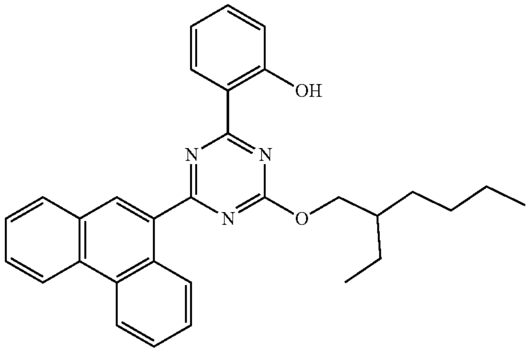
-continued
35
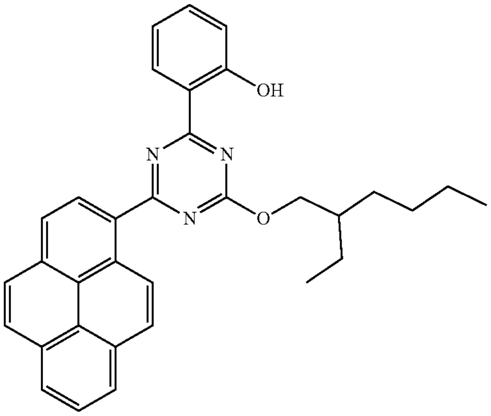
36
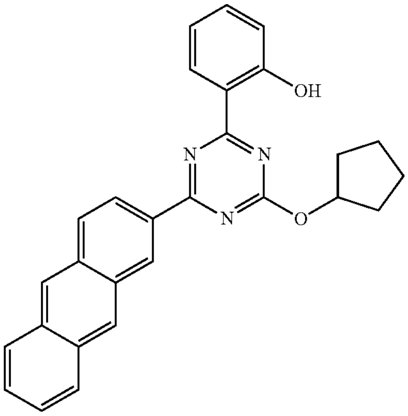
37
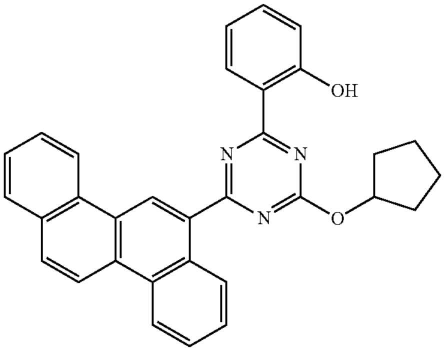
38
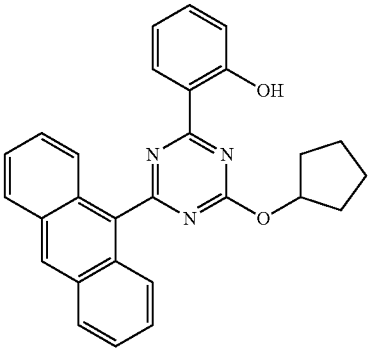

-continued
39
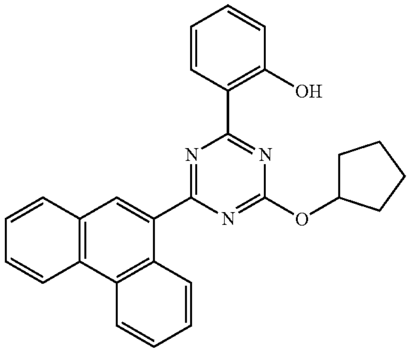
40
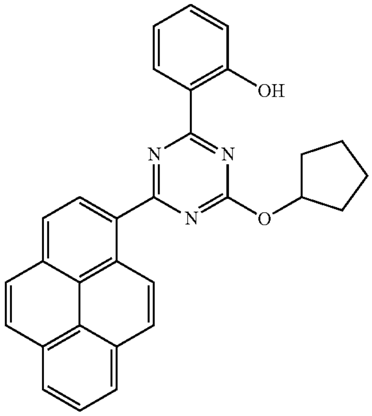
41
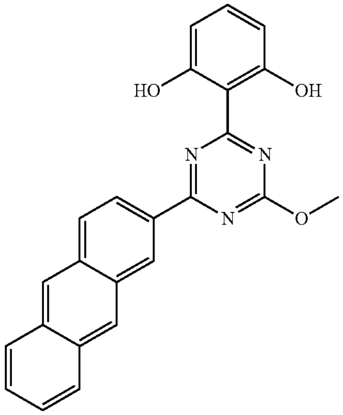
42
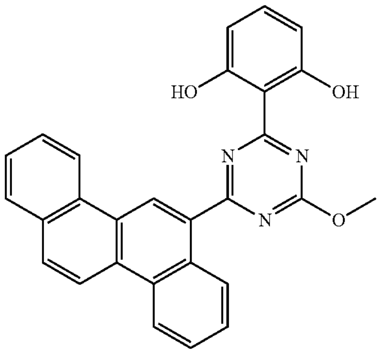
-continued
43
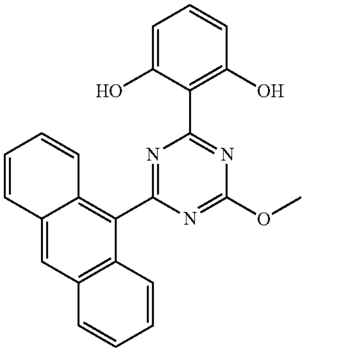
44
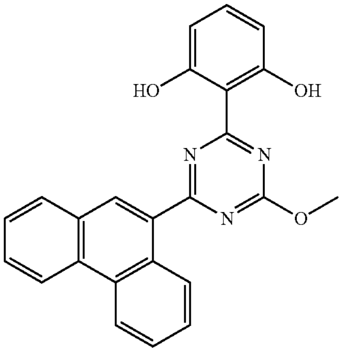
45
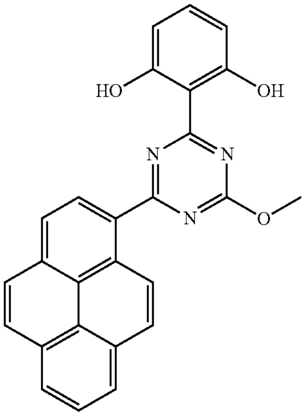
46
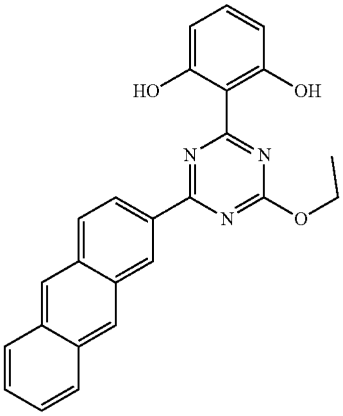

-continued
47
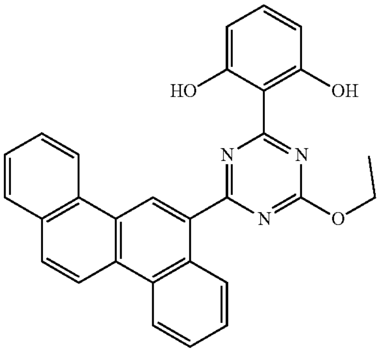
48
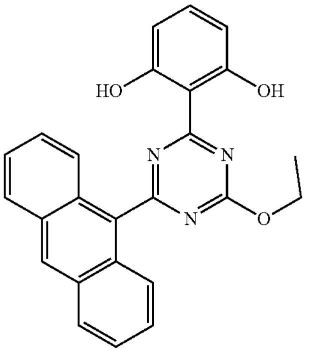
49
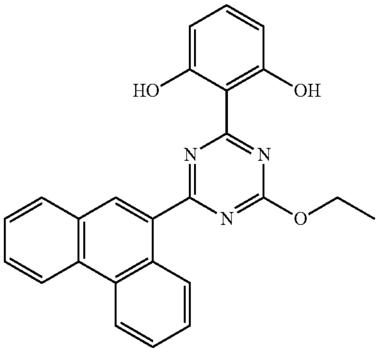
50
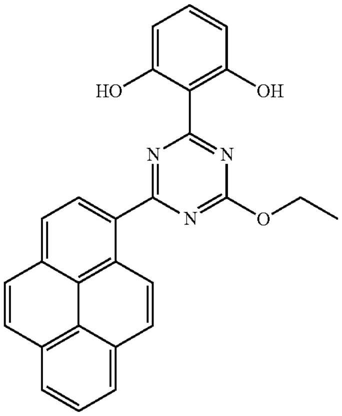
-continued
51
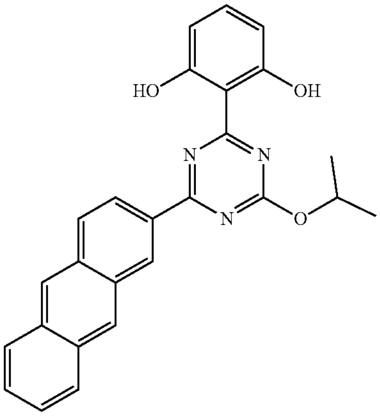
52
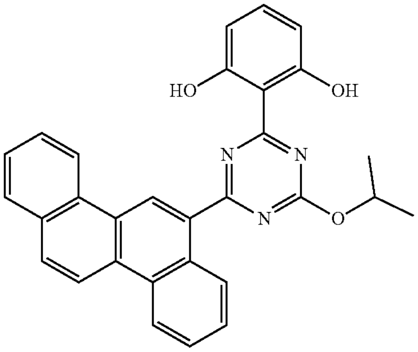
53
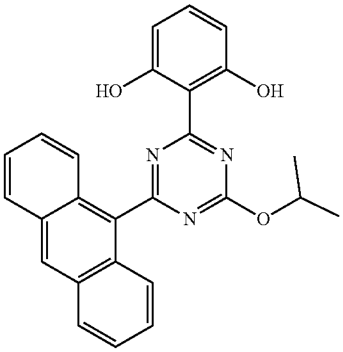
54
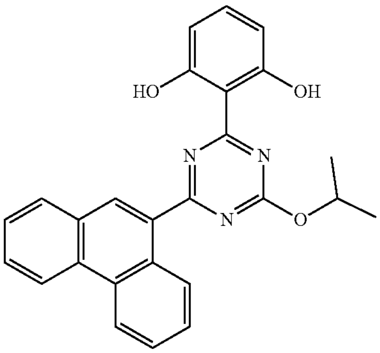

-continued
55
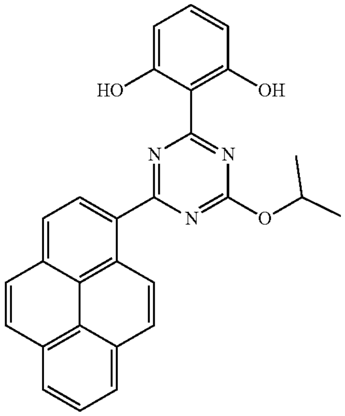
56
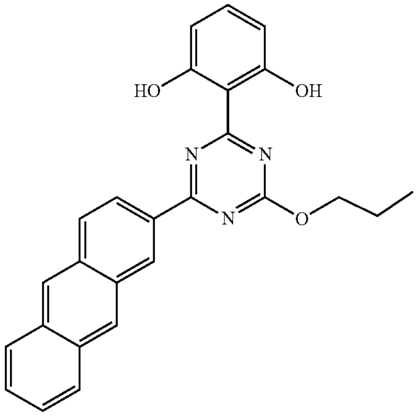
57
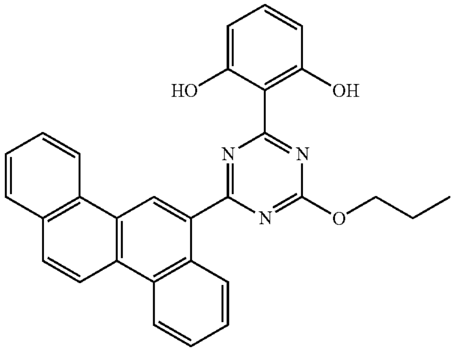
58
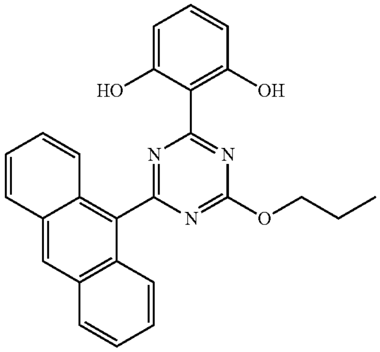
-continued
59
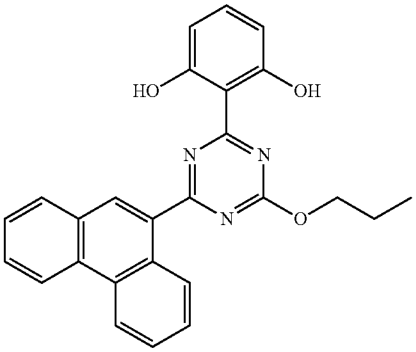
60
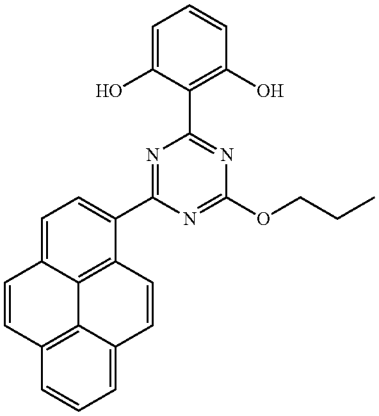
61
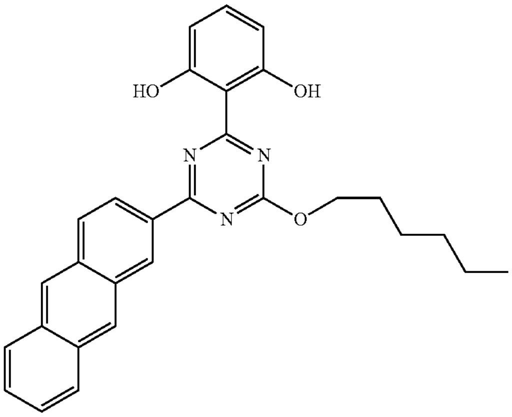
62
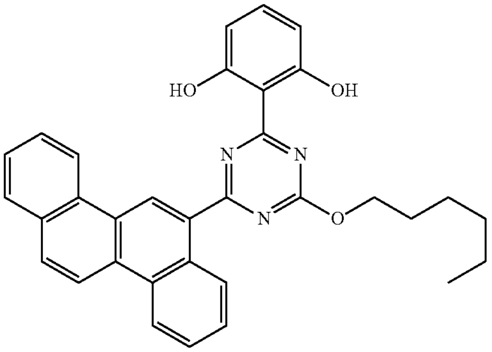

-continued
63
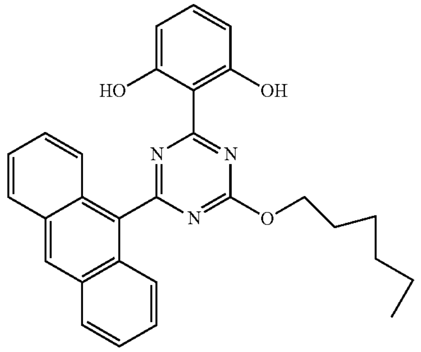
64
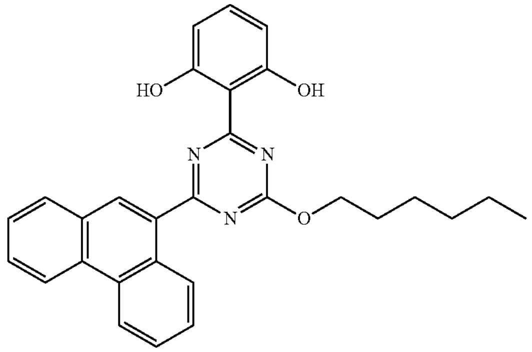
65
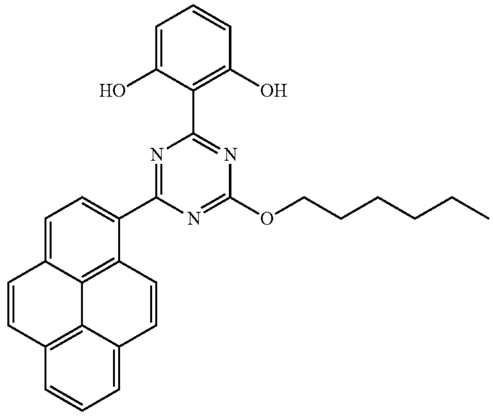
66
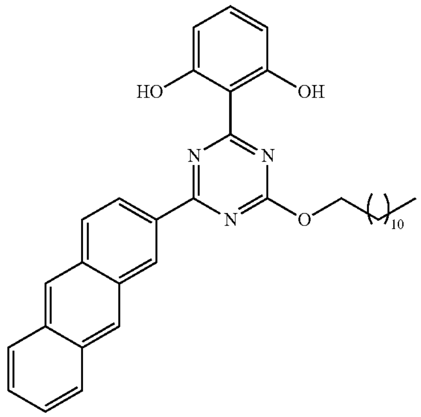
-continued
67
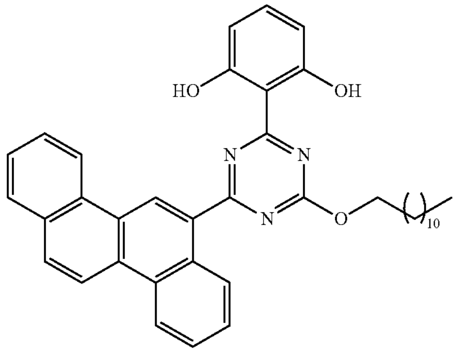
68
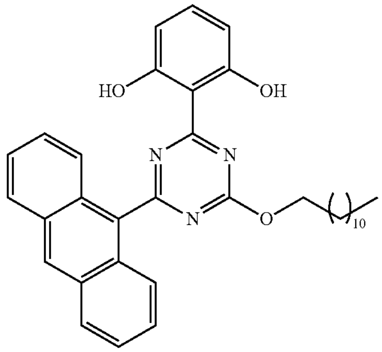
69
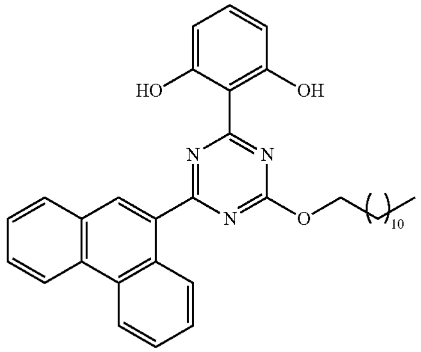
70
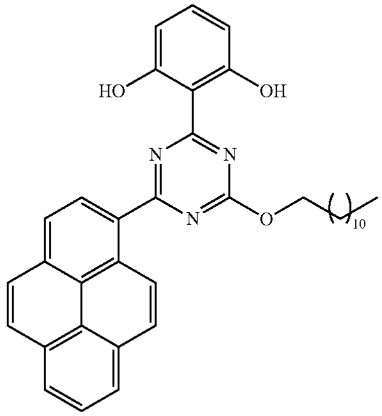

-continued
71
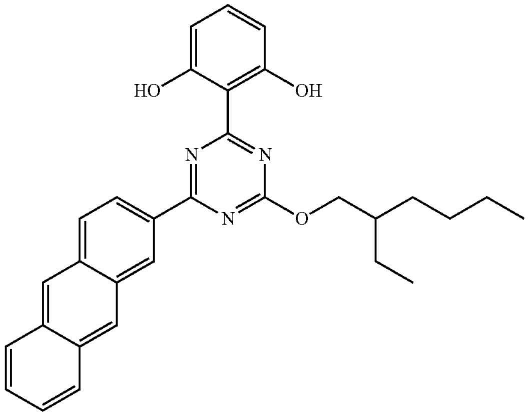
72
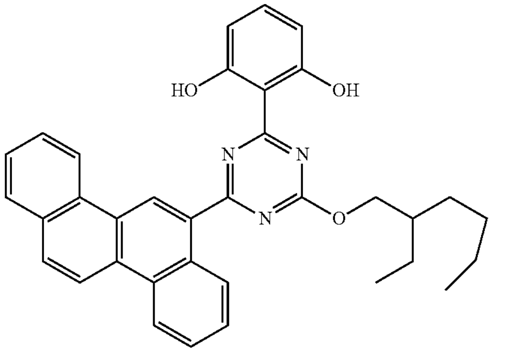
73
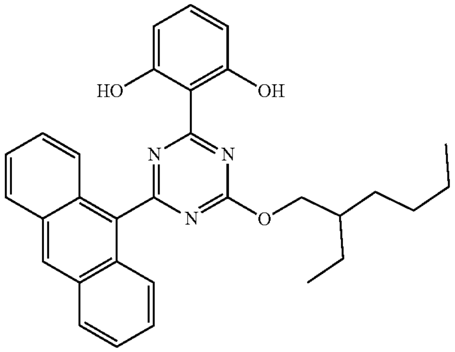
74
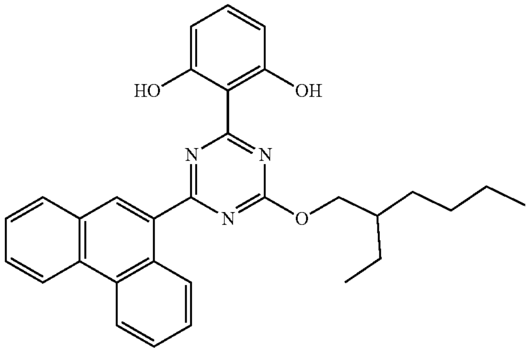
-continued
75
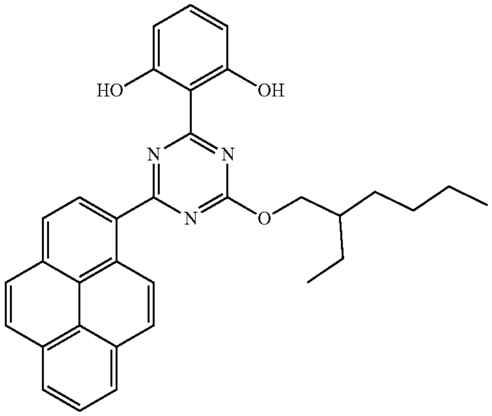
76
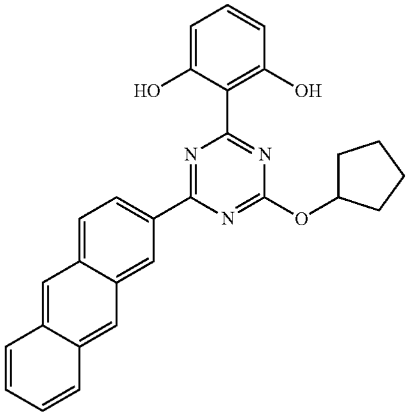
77
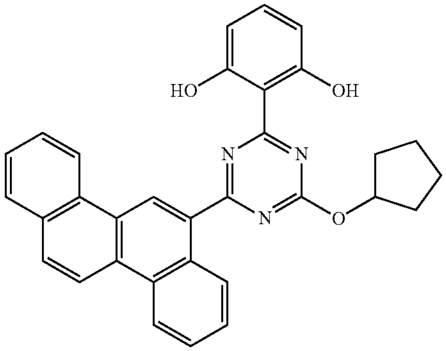
78
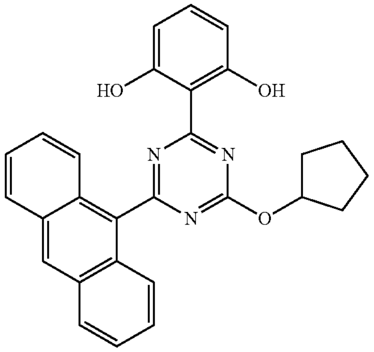

-continued
79
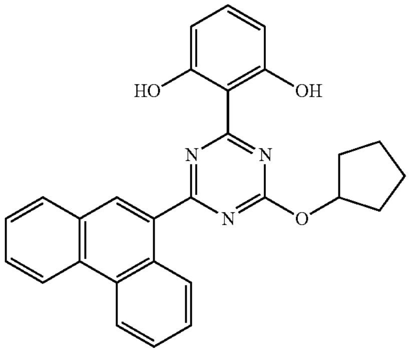
80
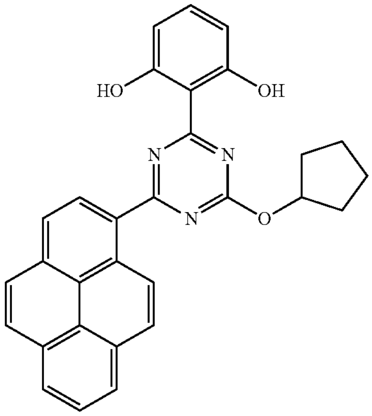
81
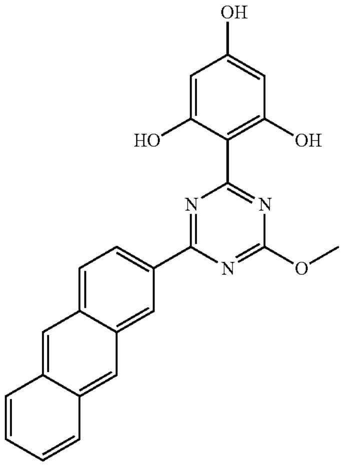
82
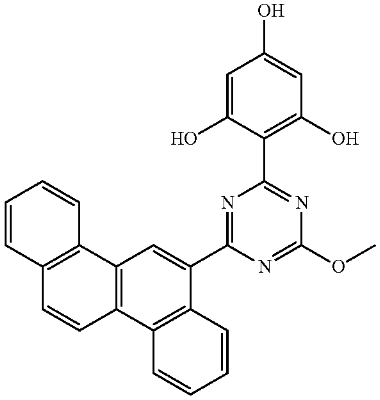
-continued
83
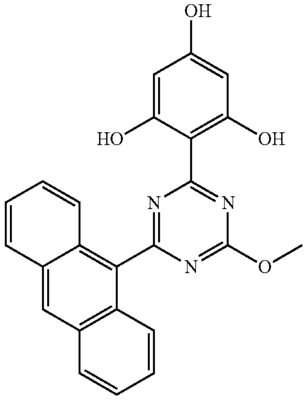
84
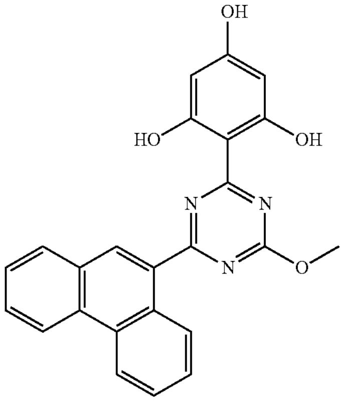
85
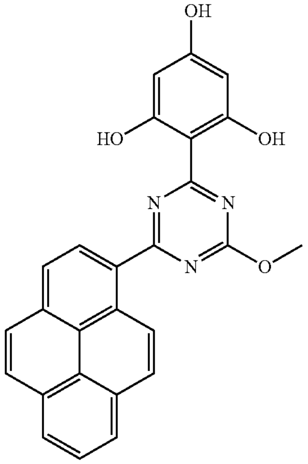

-continued
86
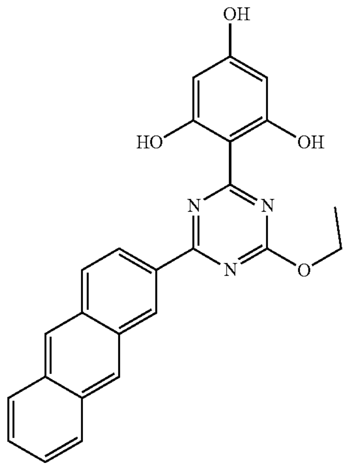
87
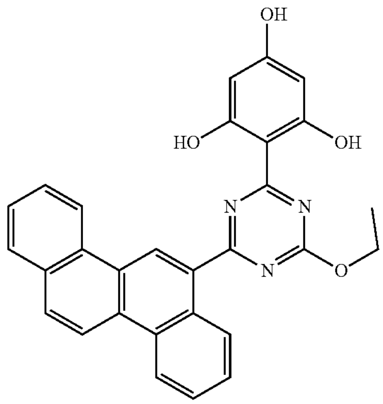
88
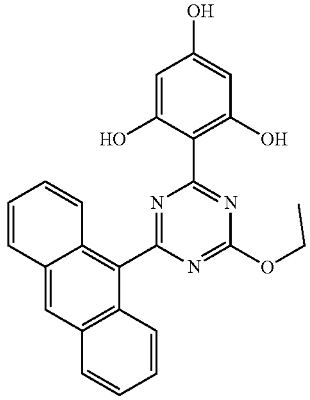
-continued
89
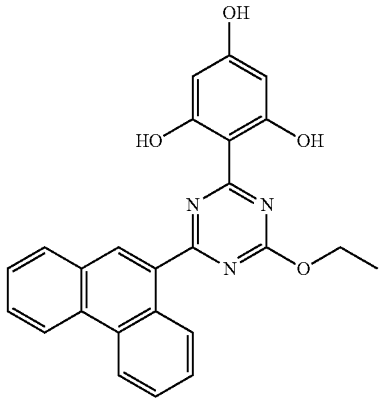
90
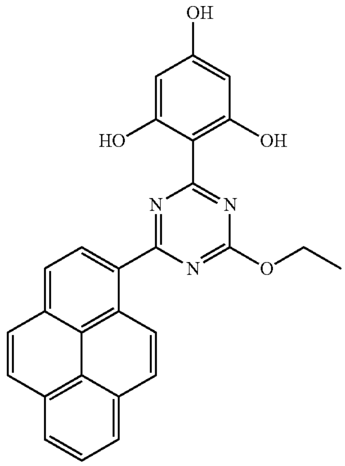
91
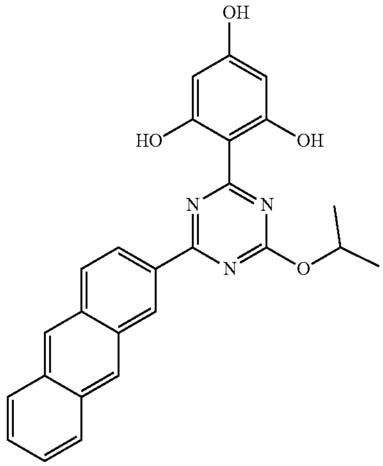

-continued
92
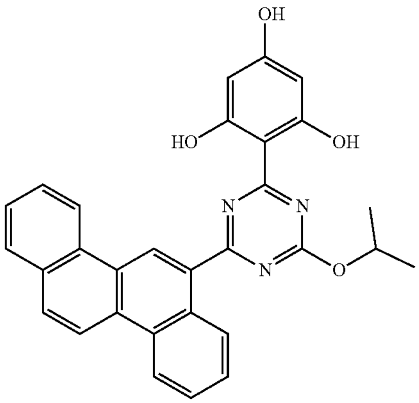
93
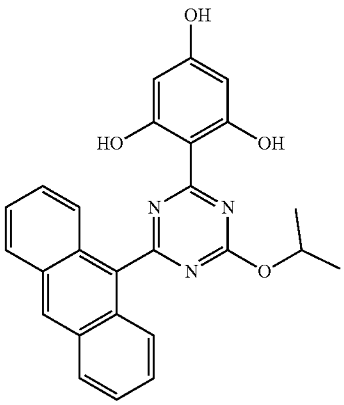
94
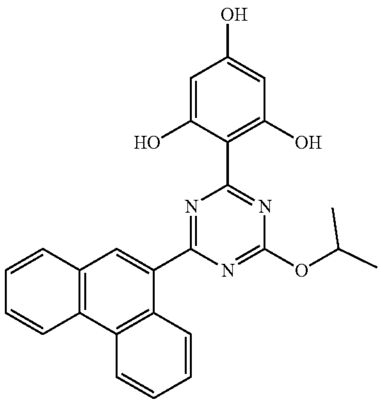
-continued
95
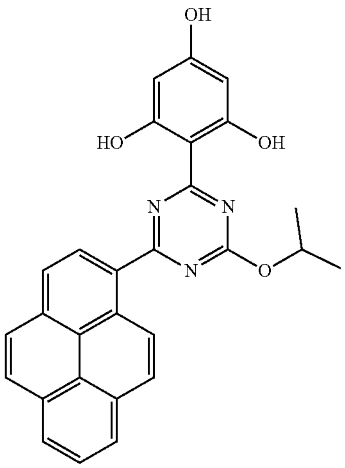
96
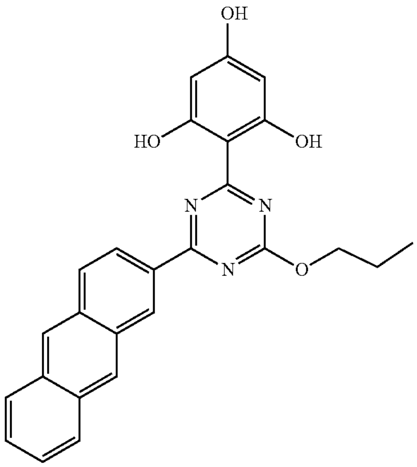
97
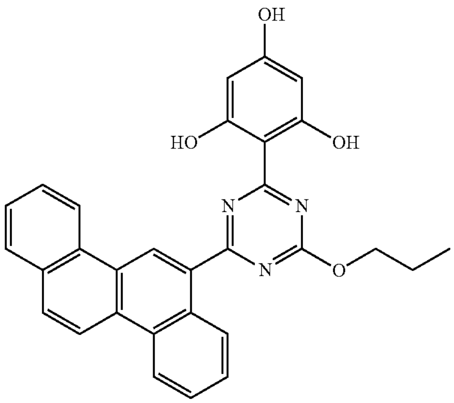

-continued
98
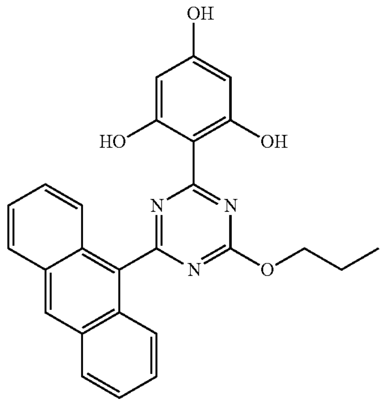
99
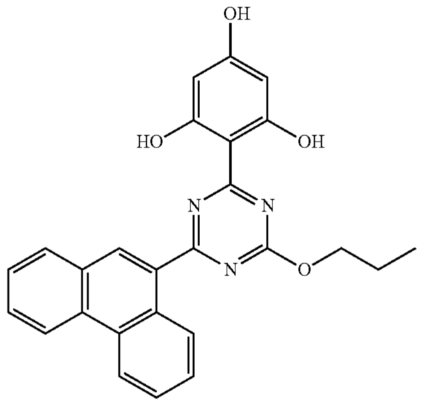
100
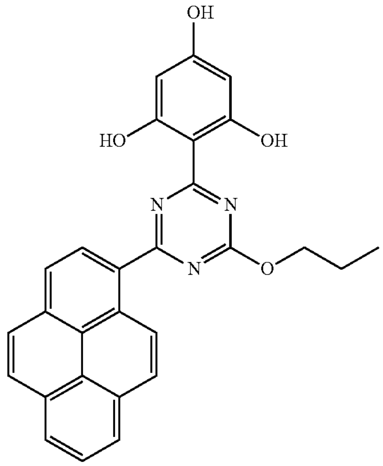
-continued
101
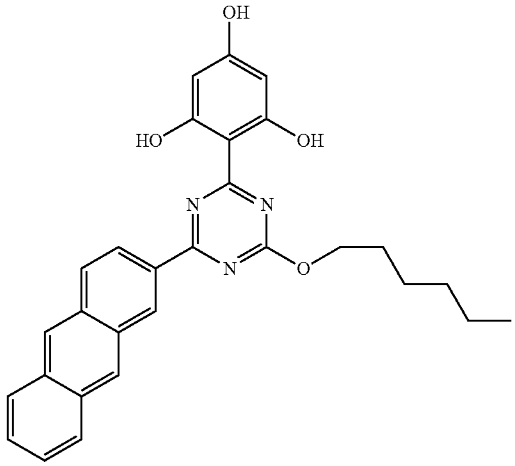
102
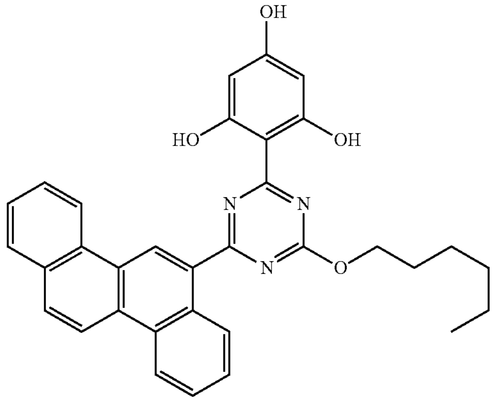
103
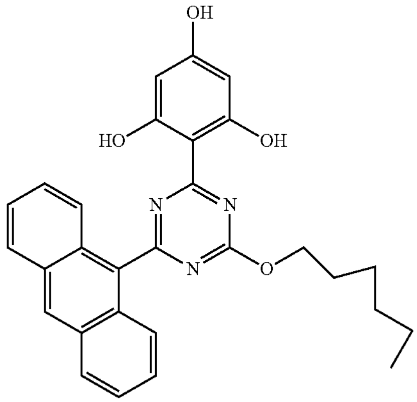

104
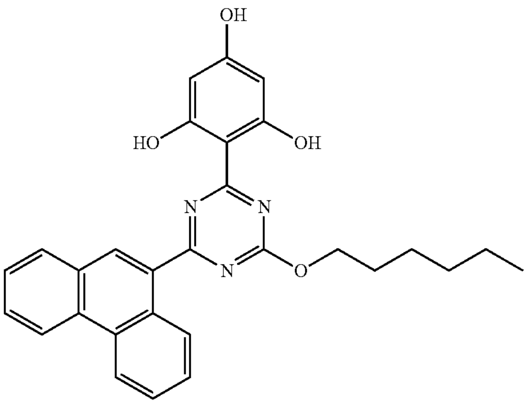
105
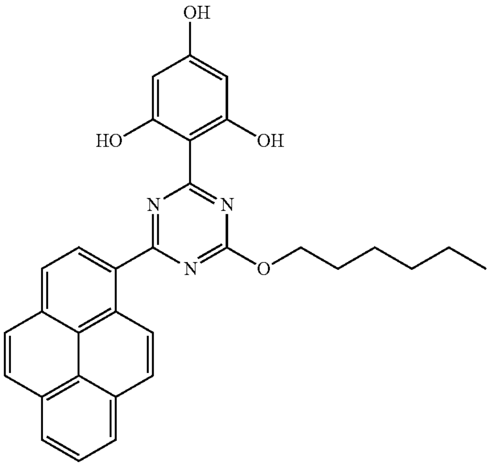
106
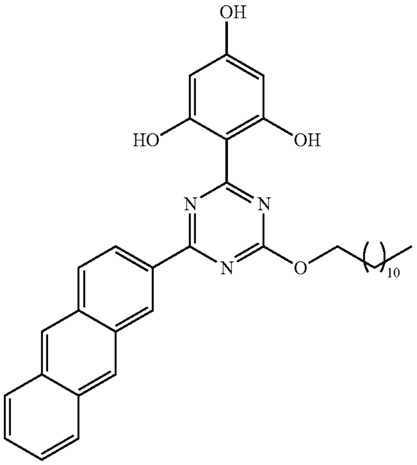
107
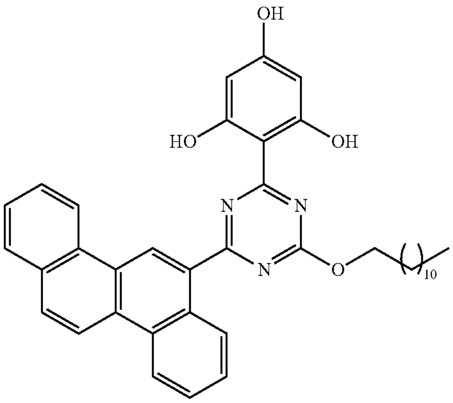
108
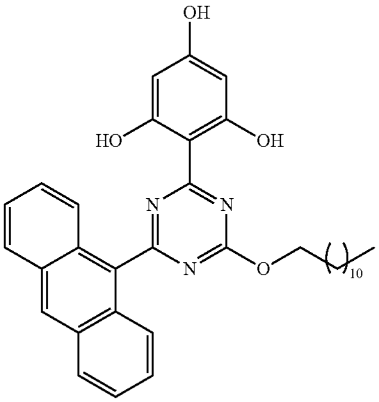
109
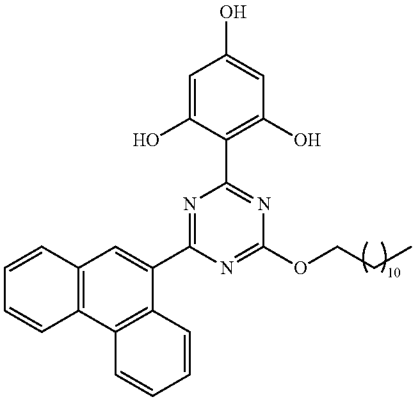

-continued
110
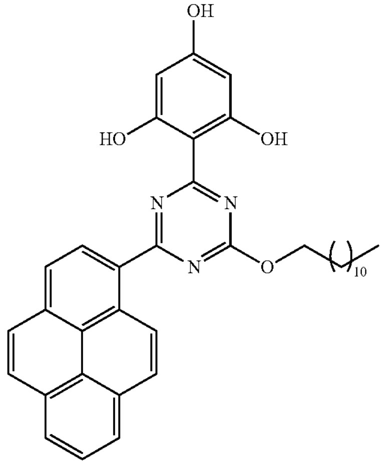
111
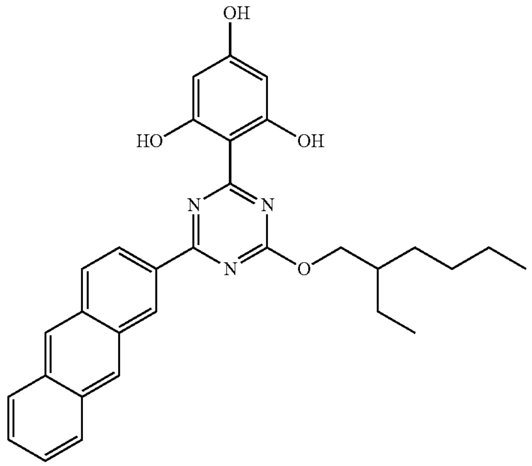
112
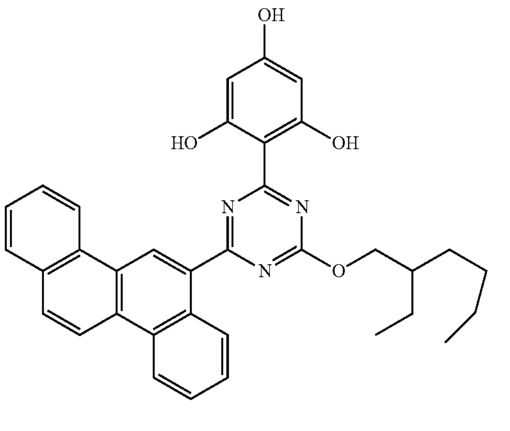
-continued
113
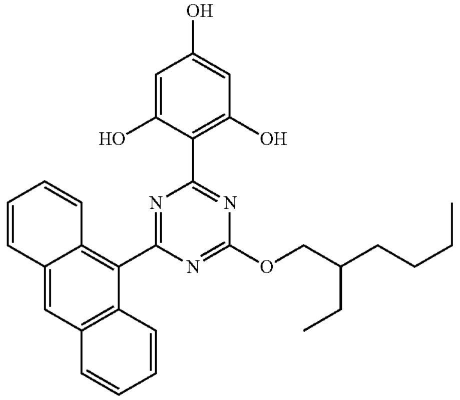
114
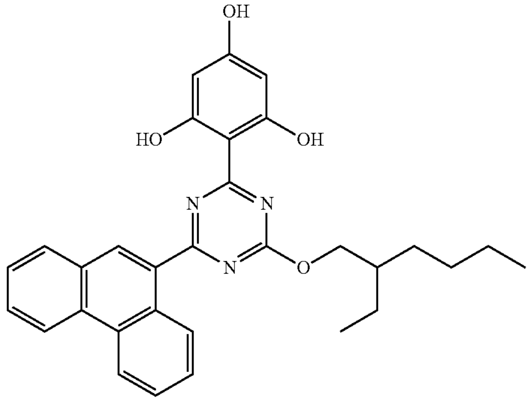
115
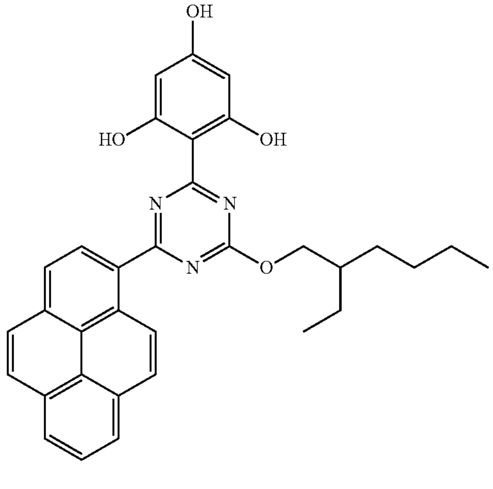

-continued
116
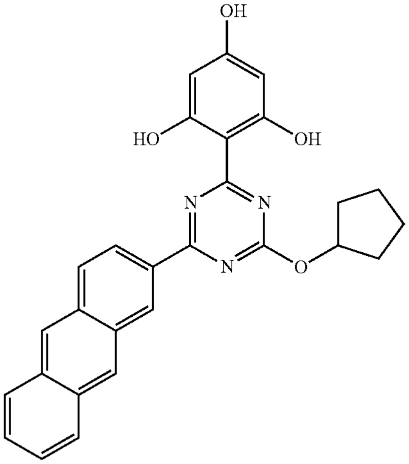
117
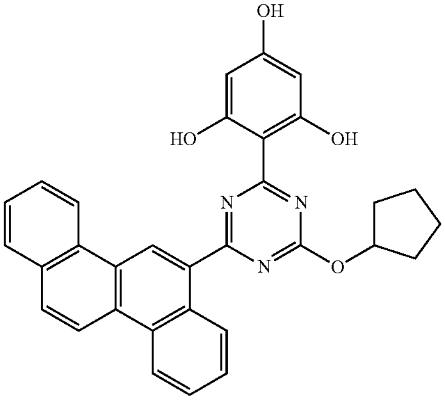
118
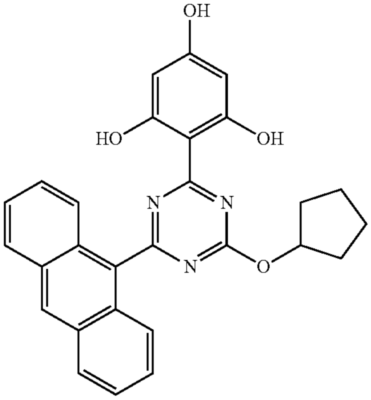
-continued
119
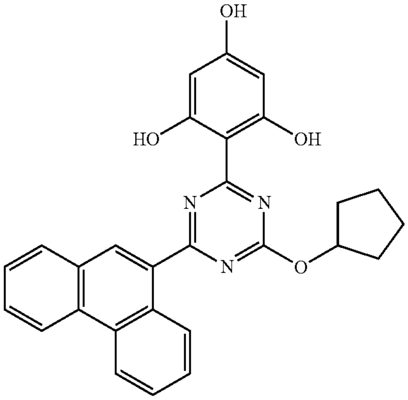
120
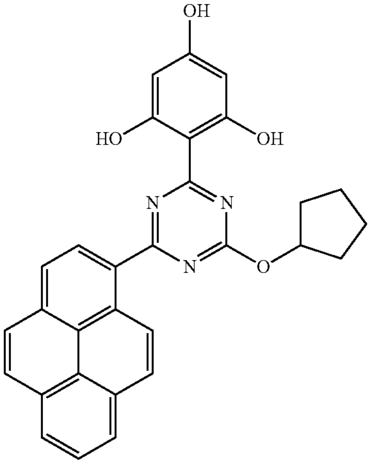
121
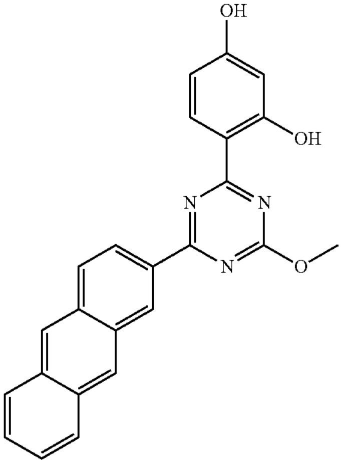

-continued
122
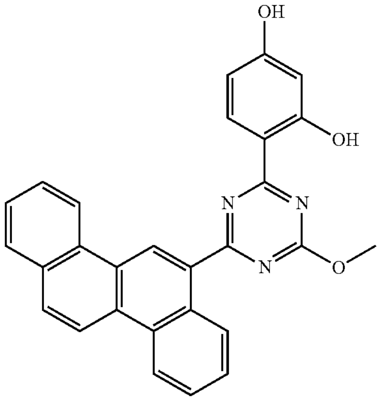
123
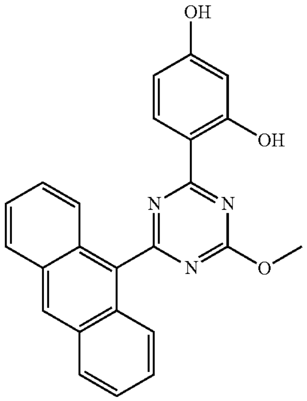
124
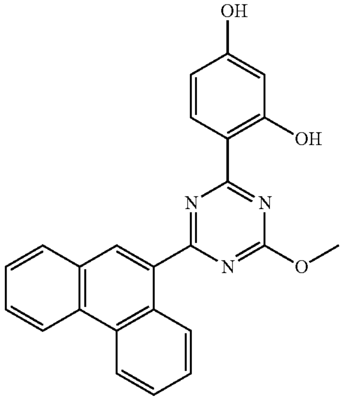
-continued
125
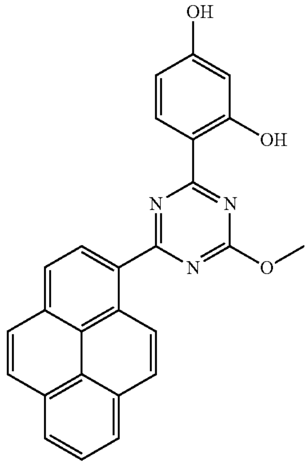
126
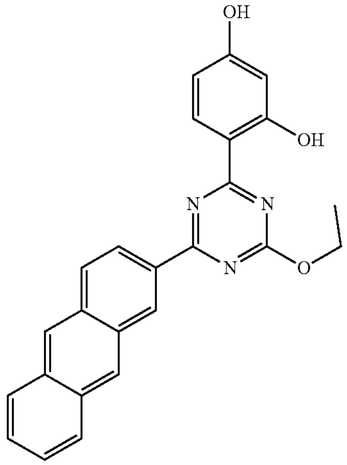
127
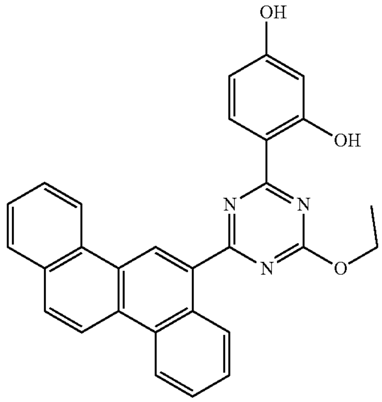

-continued
128
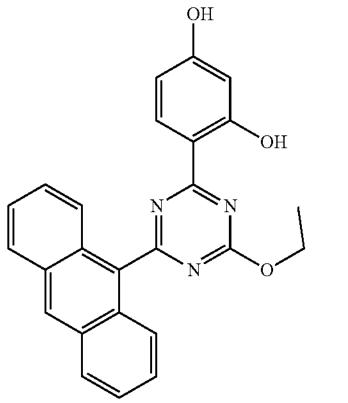
129
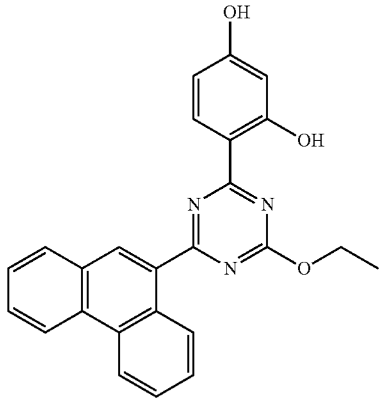
130
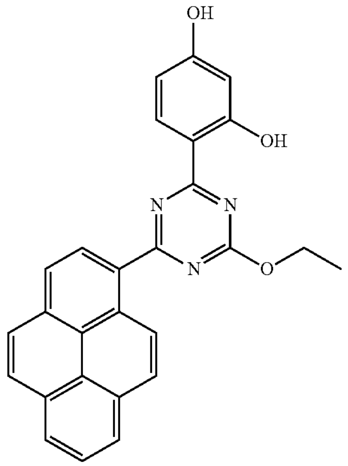
-continued
131
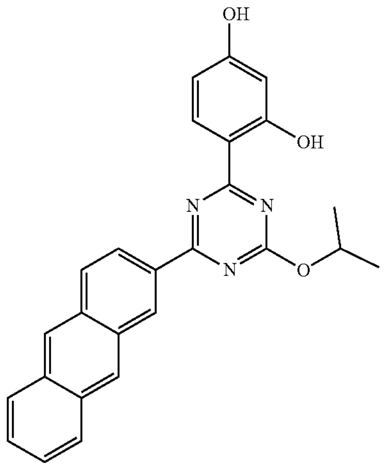
132
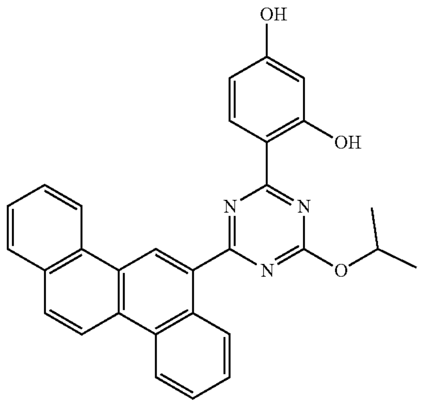
133
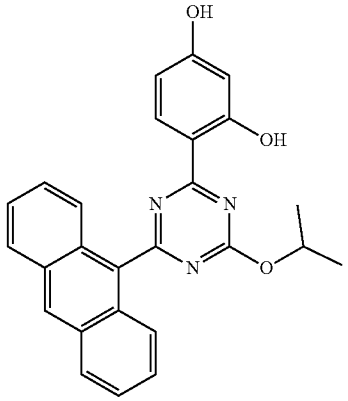

-continued
134
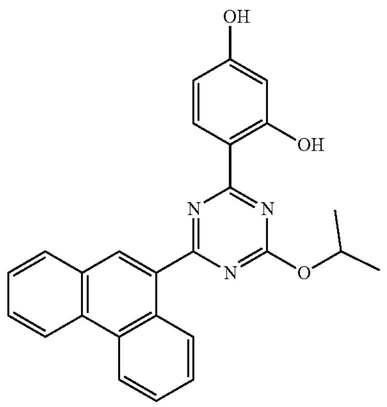
135
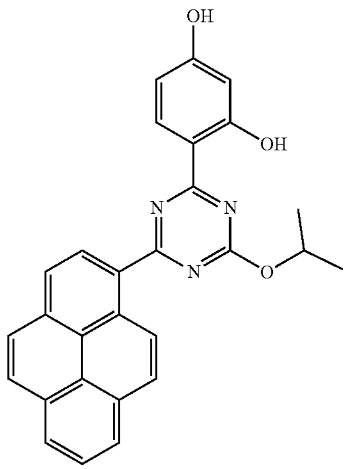
136
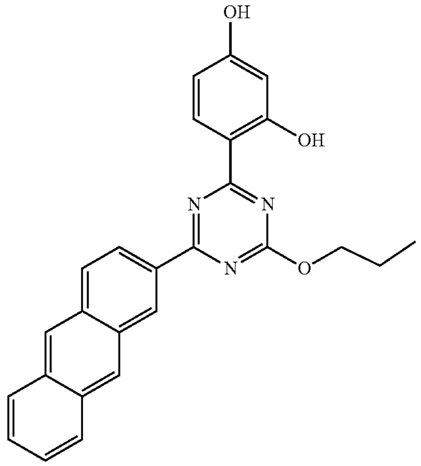
-continued
137
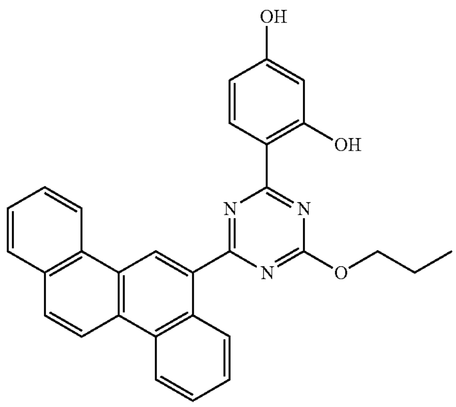
138
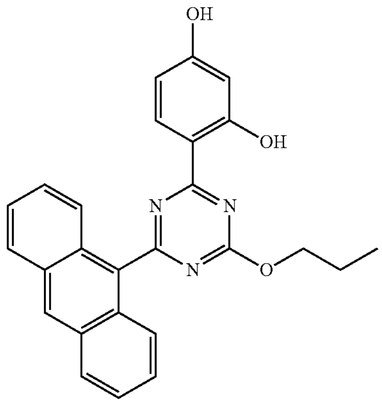
139
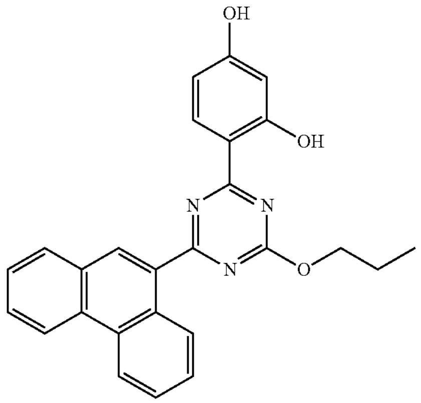

-continued
140
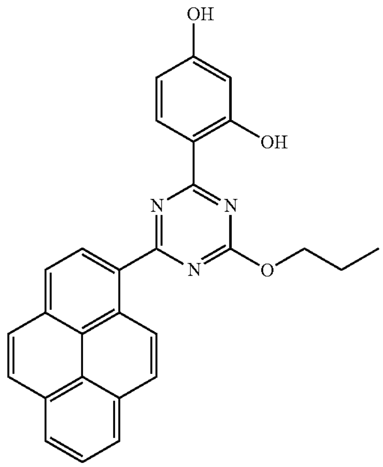
141
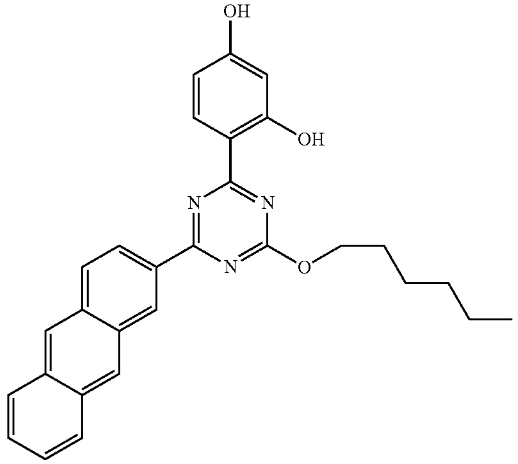
142
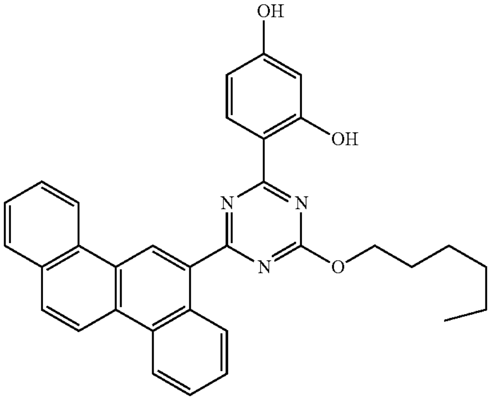
-continued
143
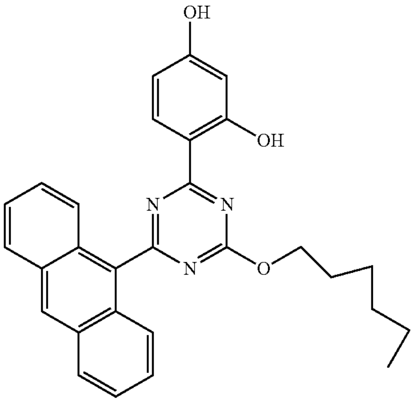
144
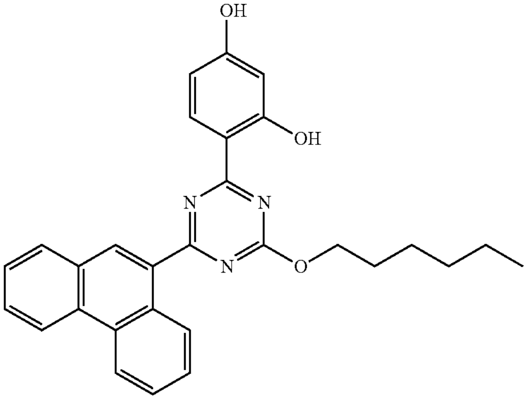
145
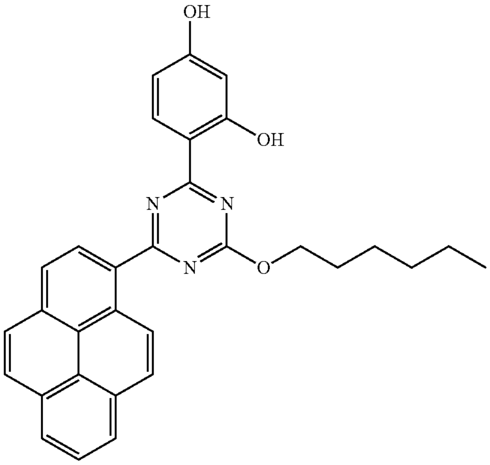

-continued
146
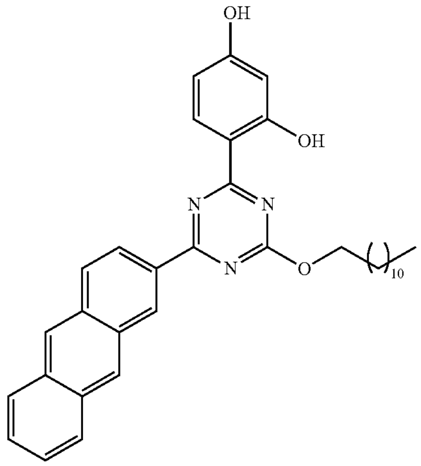
147
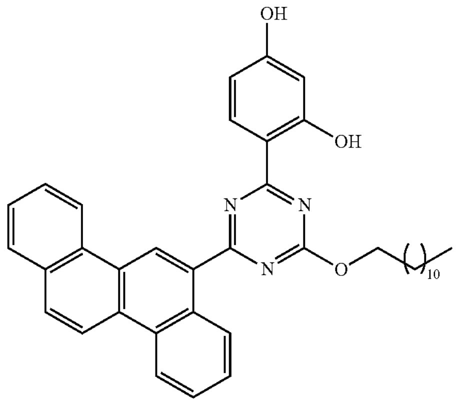
148
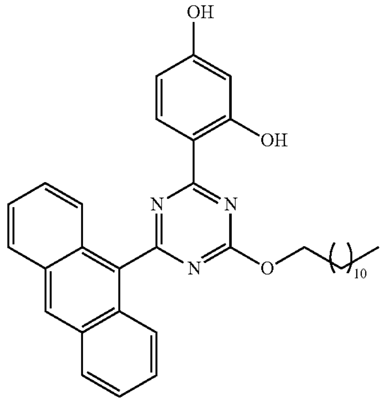
-continued
149
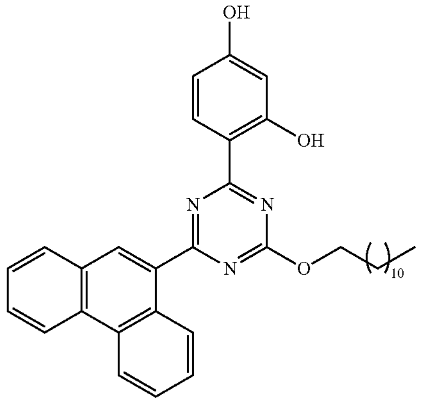
150
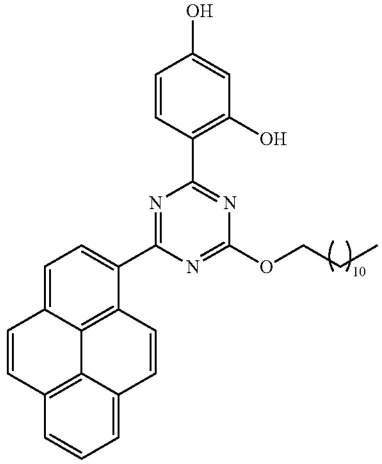
151
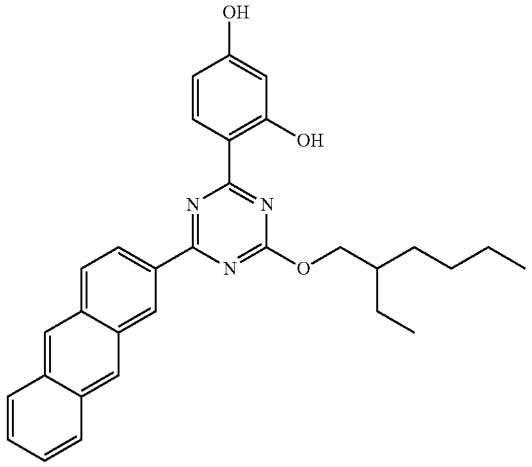

152
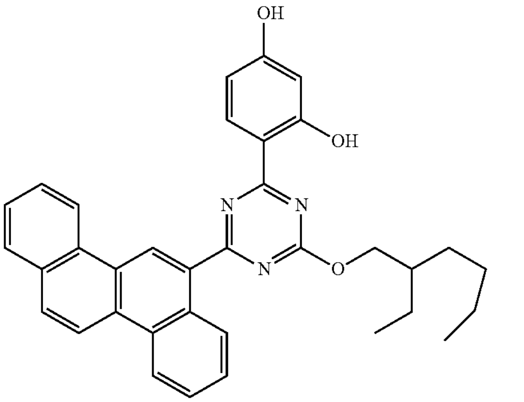
153
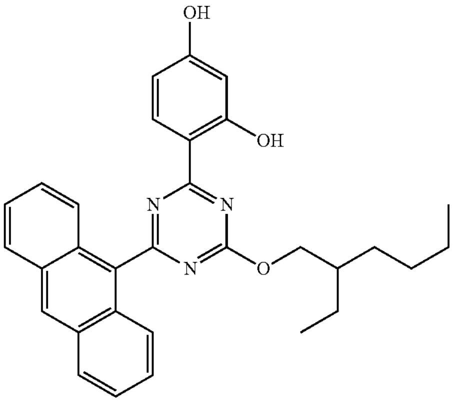
154
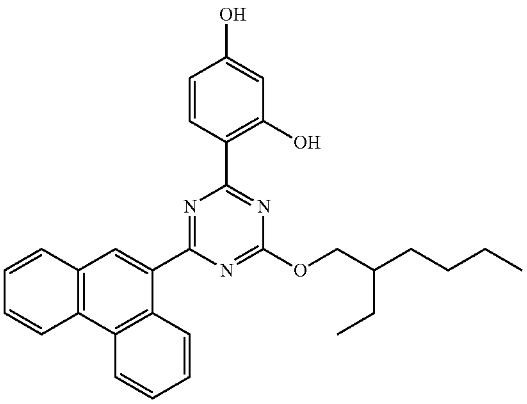
155
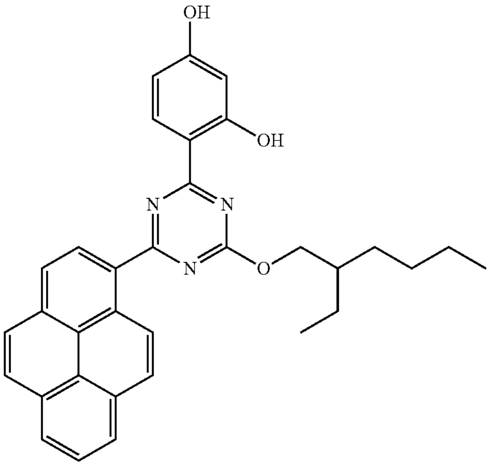
156
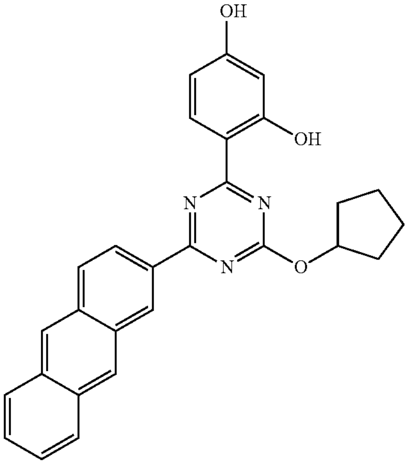
157
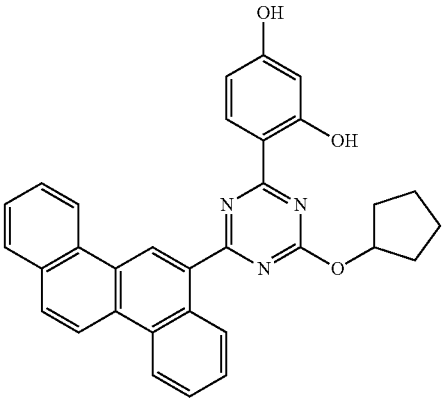

-continued
158
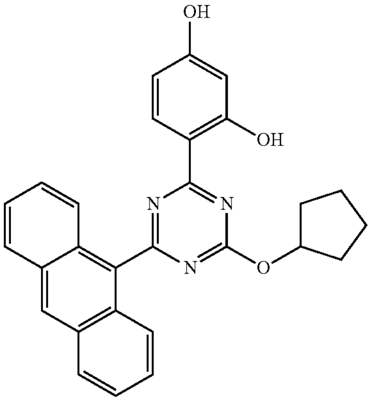
159
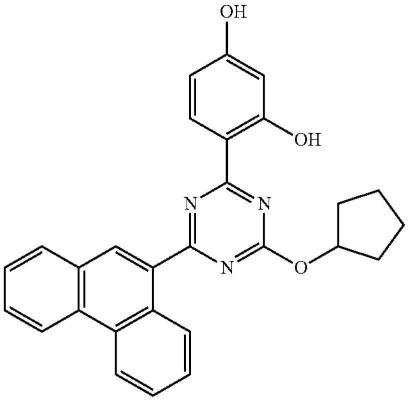
160
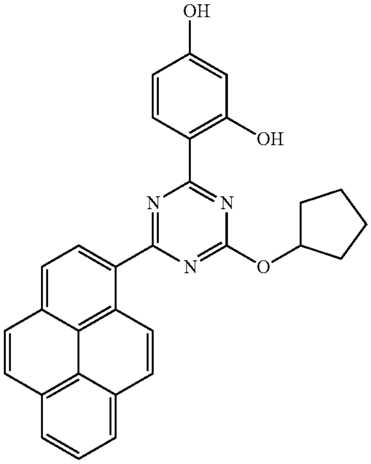
-continued
161
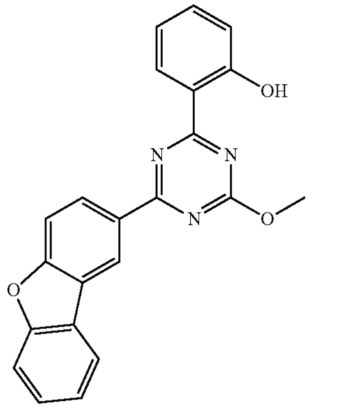
162
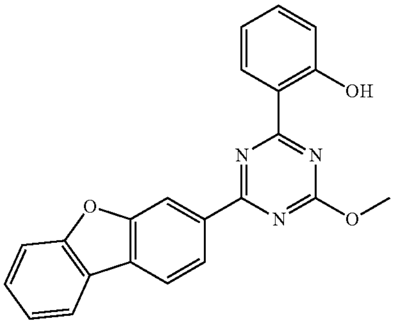
163
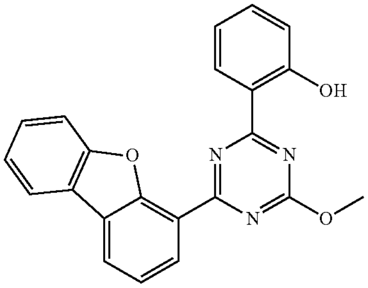
164
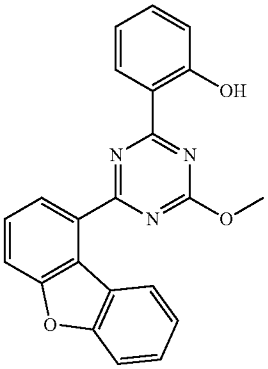

-continued
165
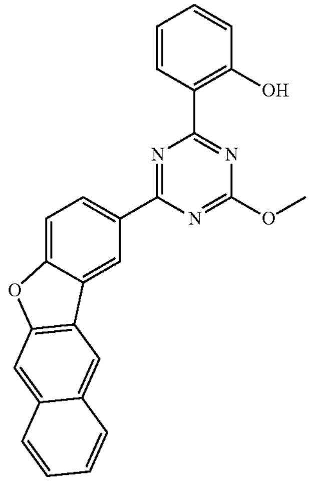
166
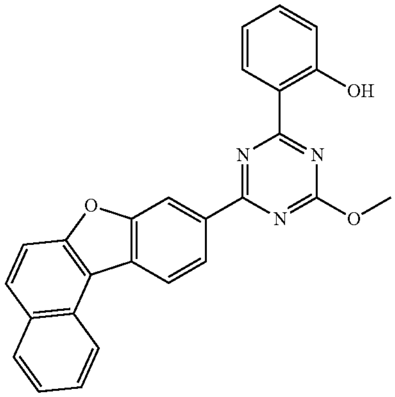
167
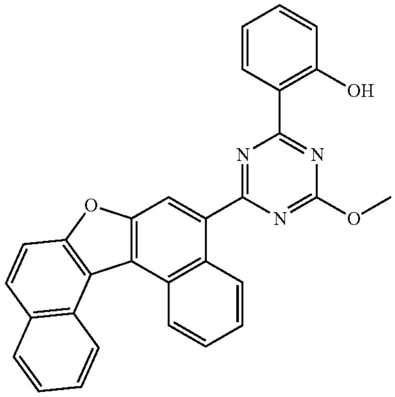
168
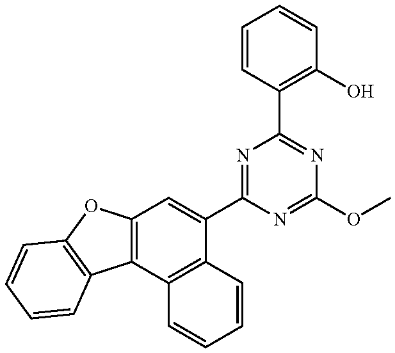
-continued
169
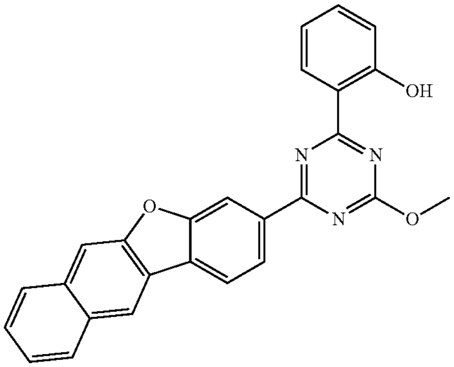
170
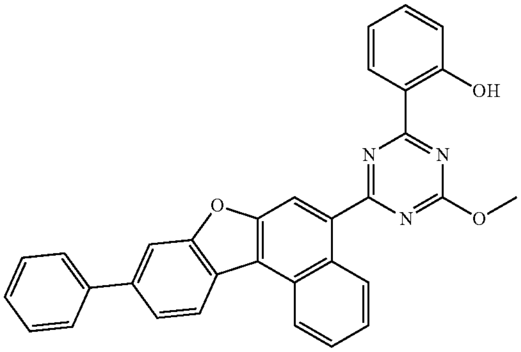
171
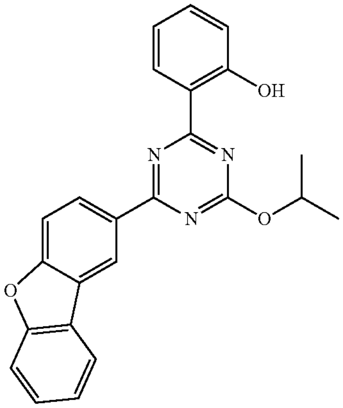
172
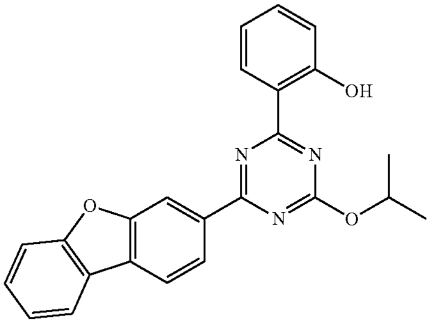

-continued
173
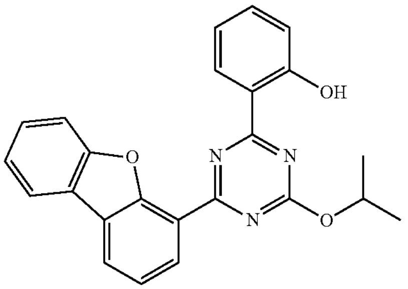
174
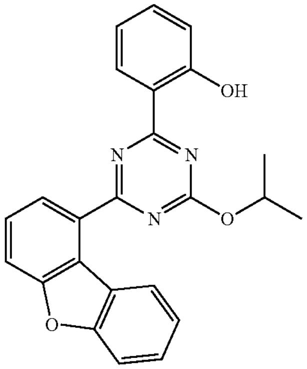
175
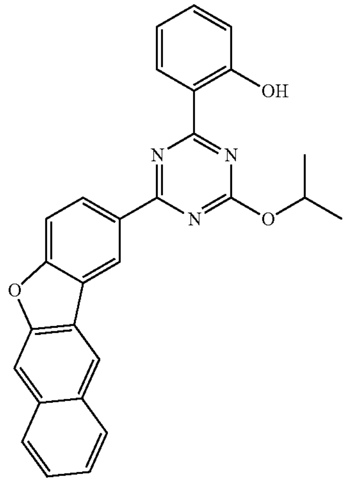
176
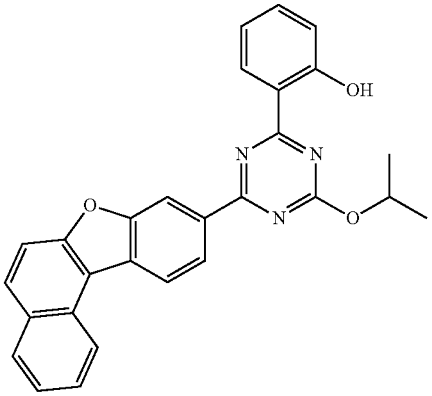
-continued
177
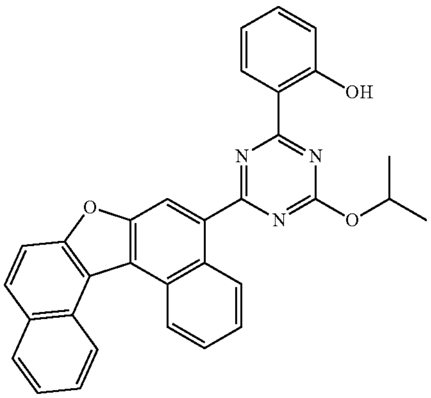
178
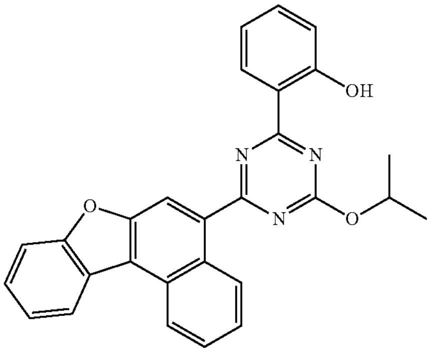
179
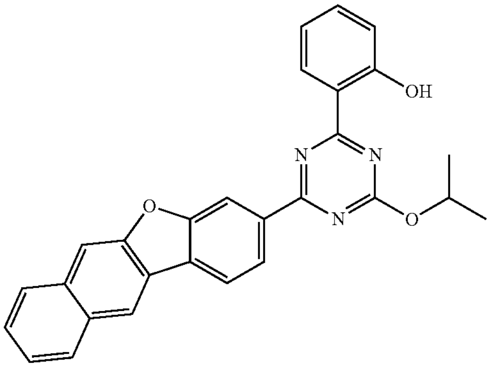
180
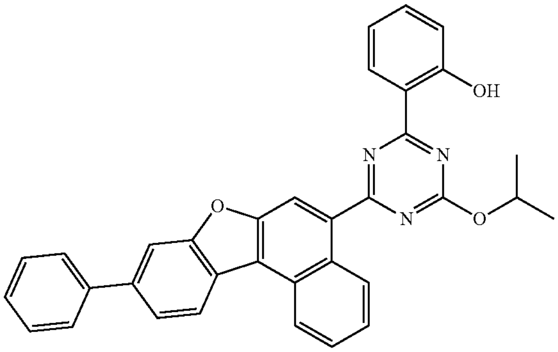

-continued
181
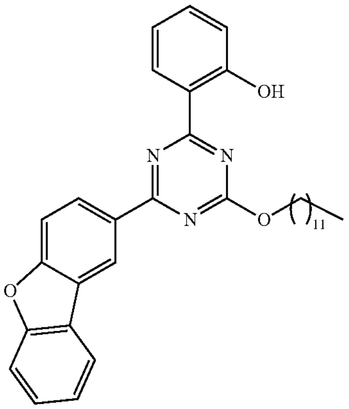
182
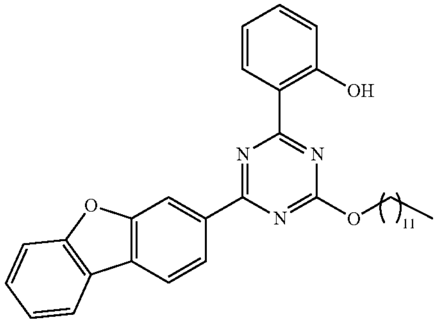
183
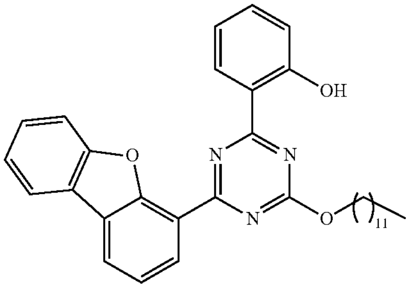
184
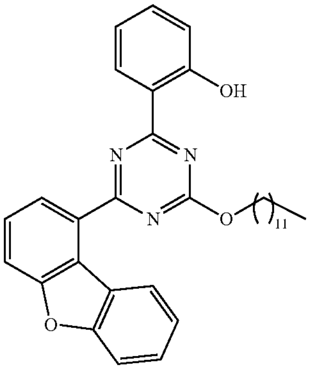
-continued
185
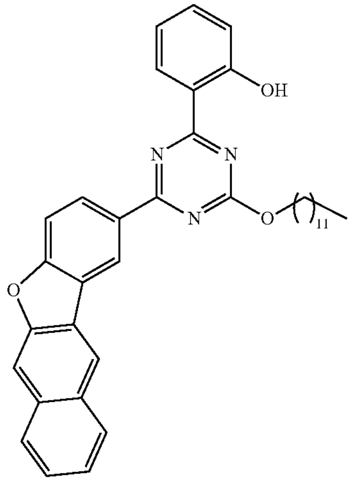
186
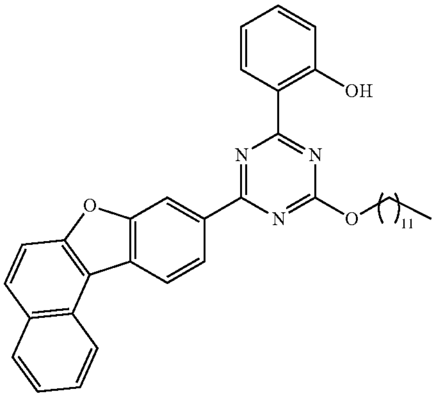
187
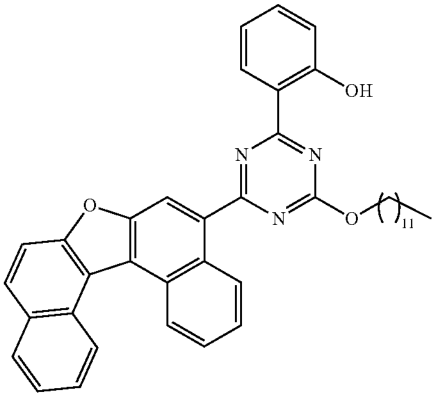
188
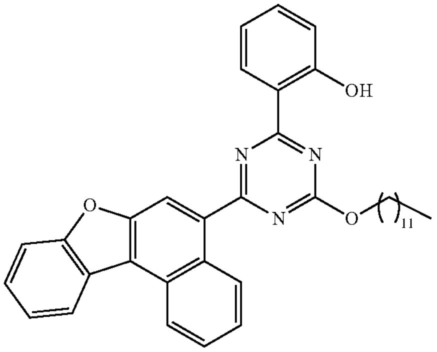

-continued
189
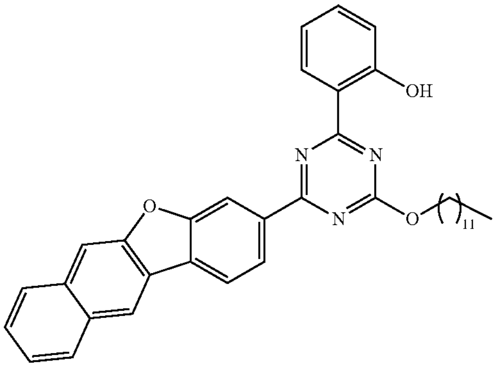
190
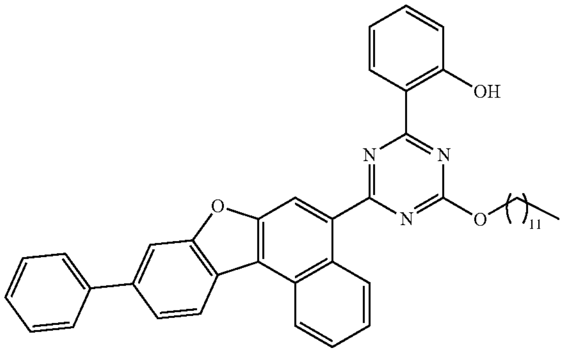
191
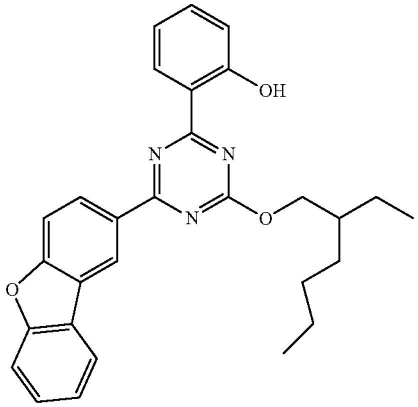
192
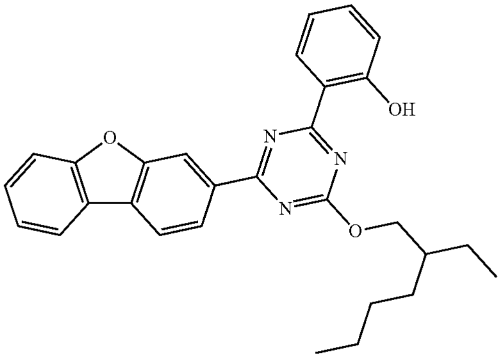
-continued
193
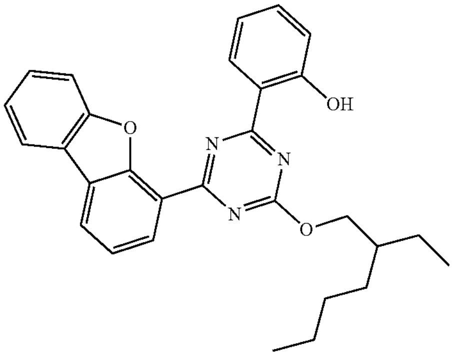
194
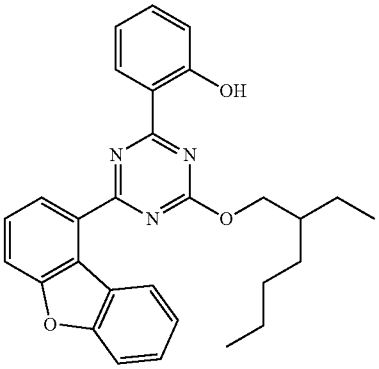
195
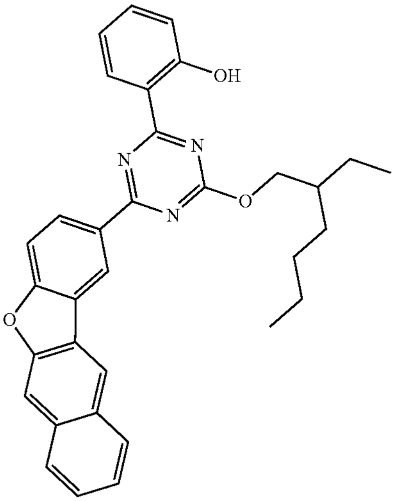

-continued
196
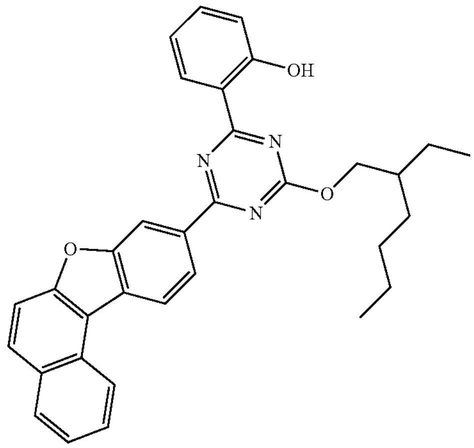
197
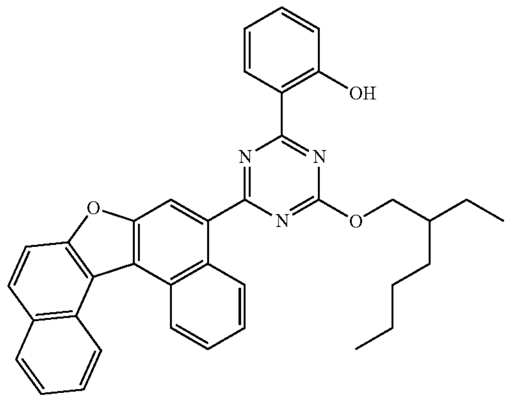
198
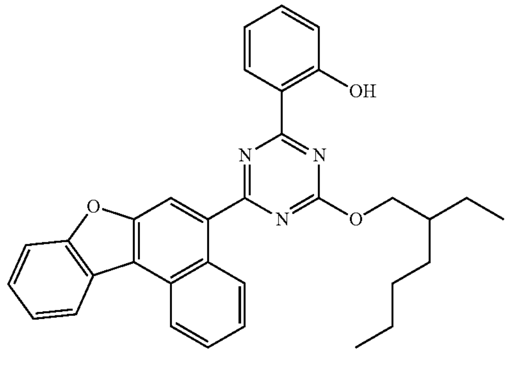
199
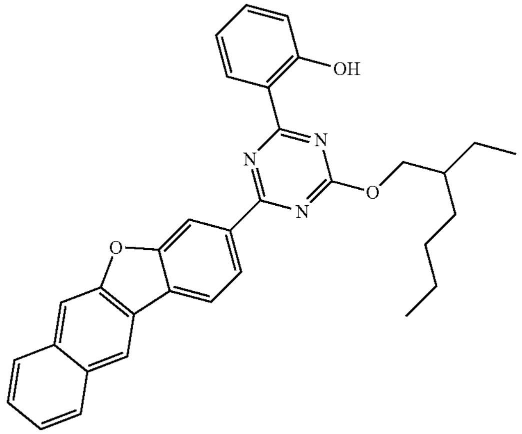
200
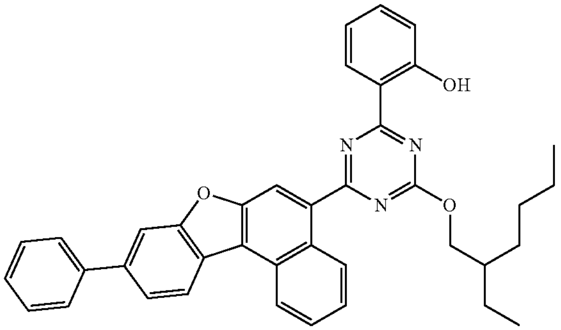
201
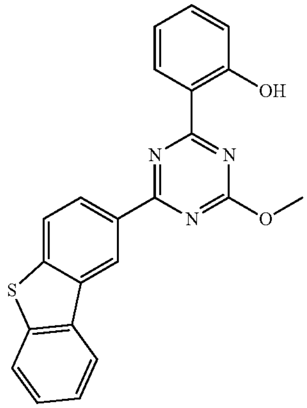
202
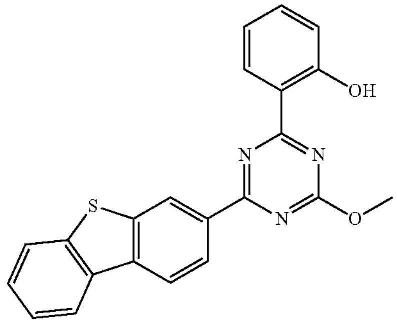

-continued
203
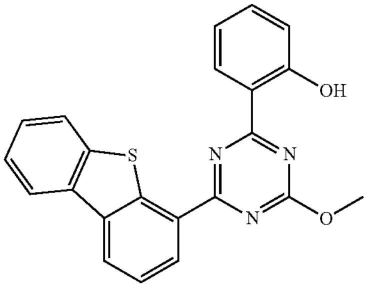
204
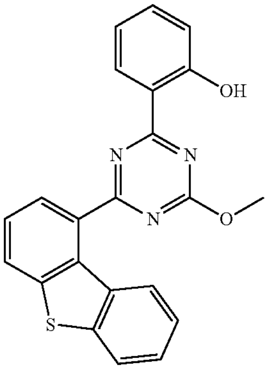
205
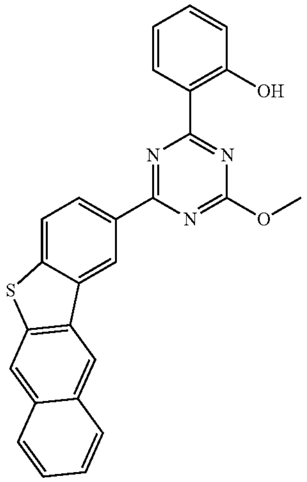
206
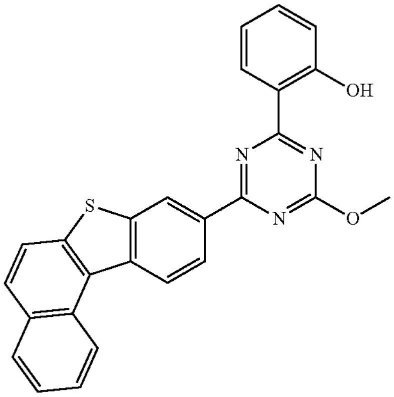
-continued
207
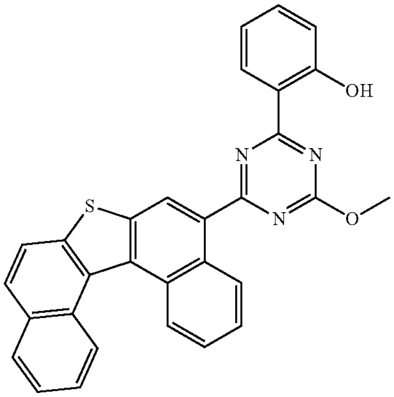
208
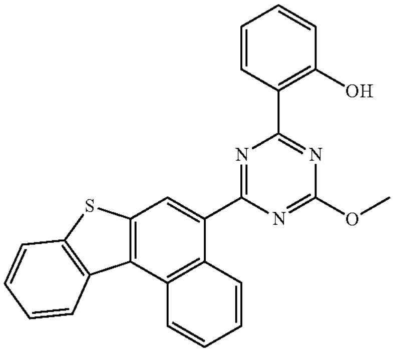
209
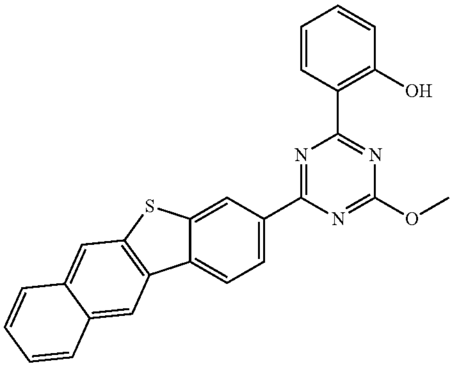
210
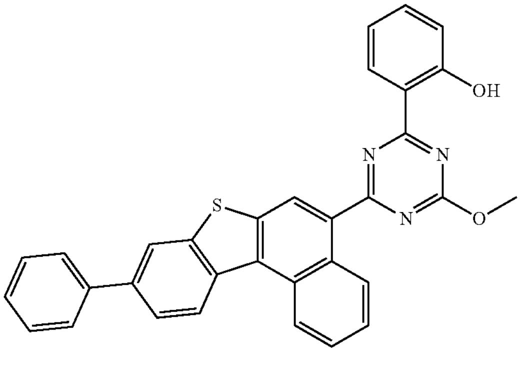

211
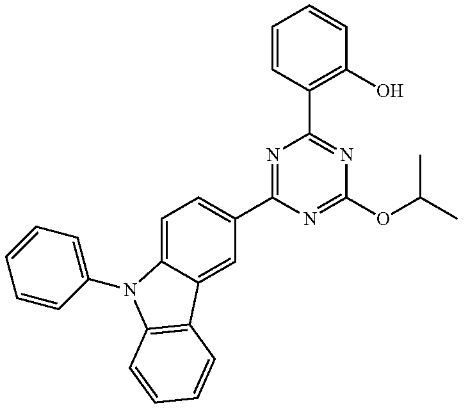
212
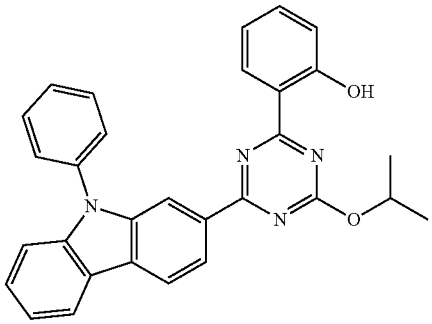
213
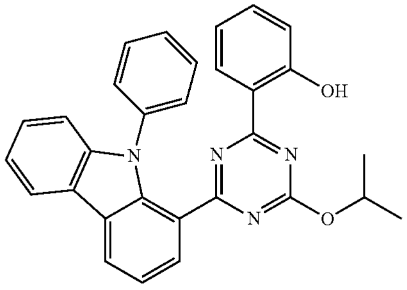
214
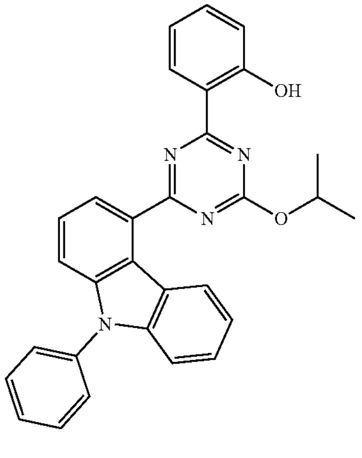
215
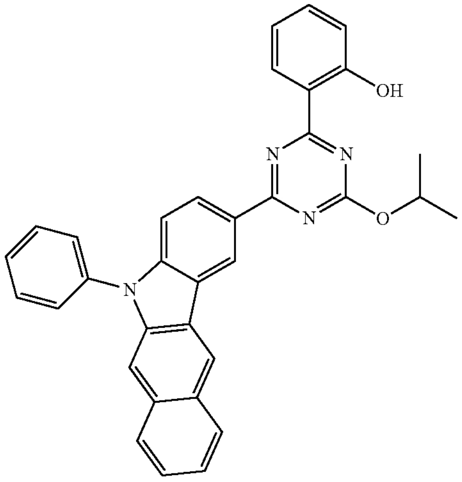
216
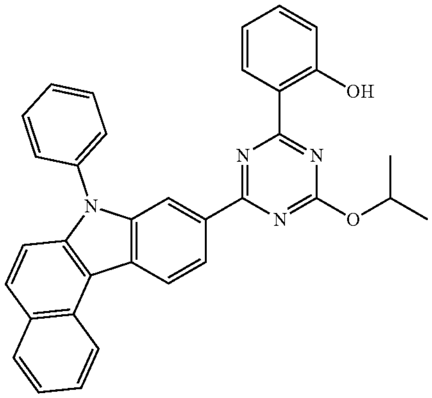
217
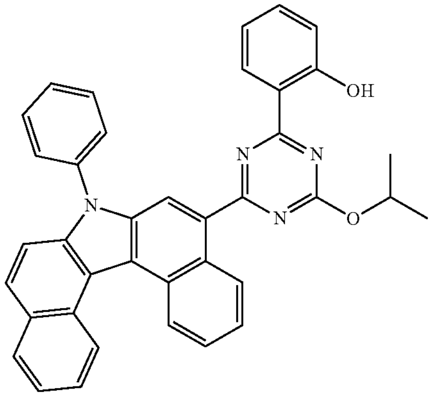
218
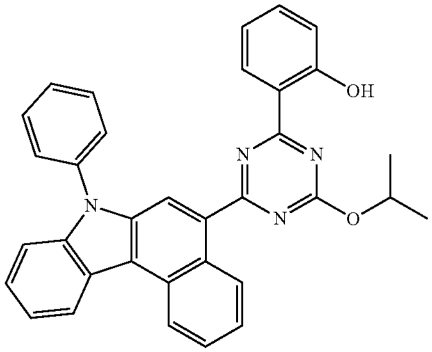

-continued
219
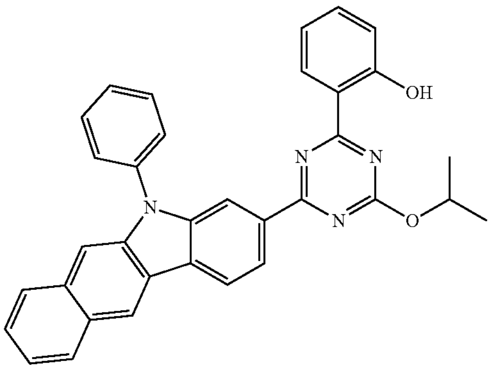
220
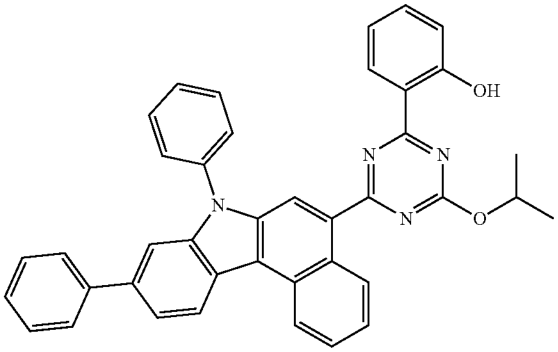
221
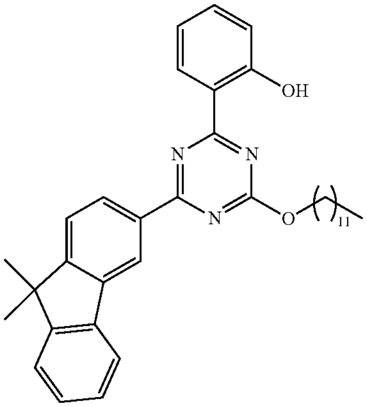
222
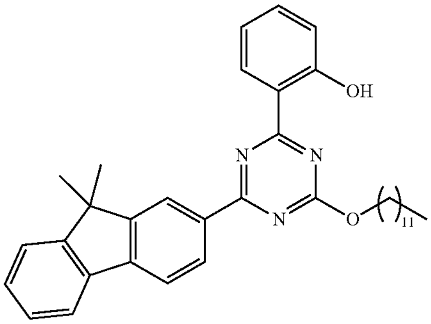
-continued
223
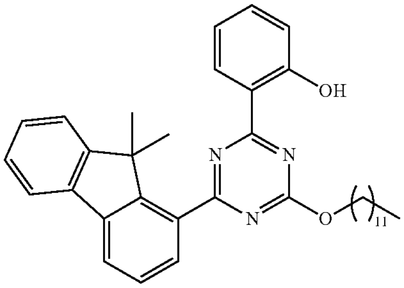
224
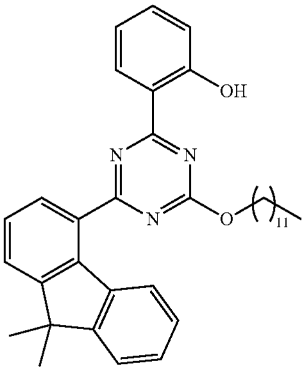
225
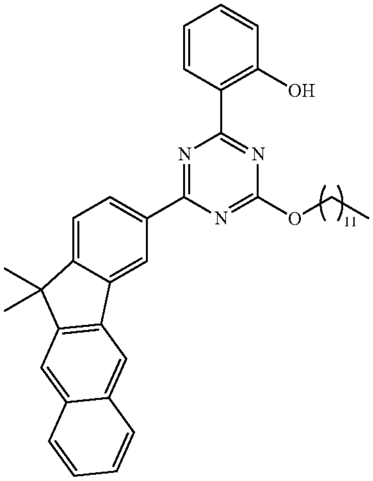
226
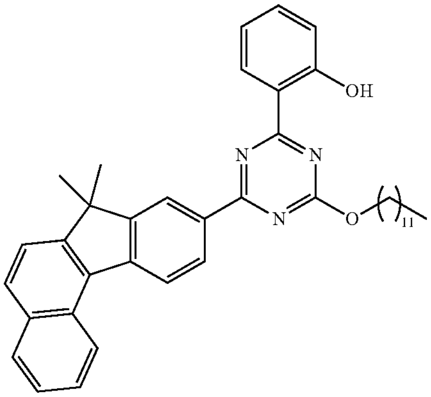

227
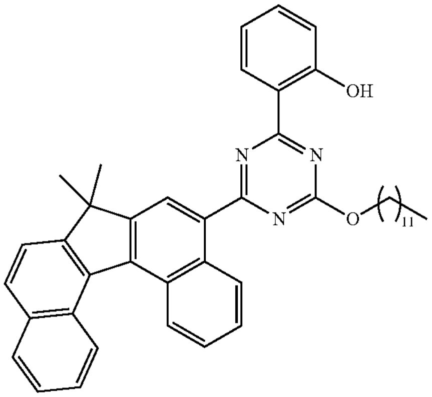
228
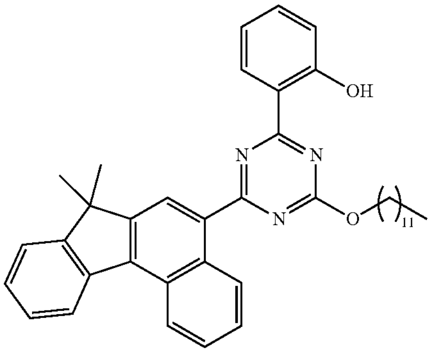
229
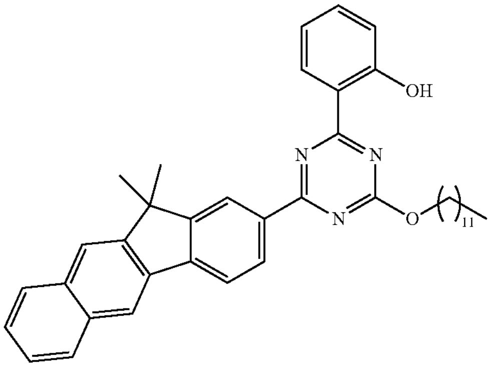
230
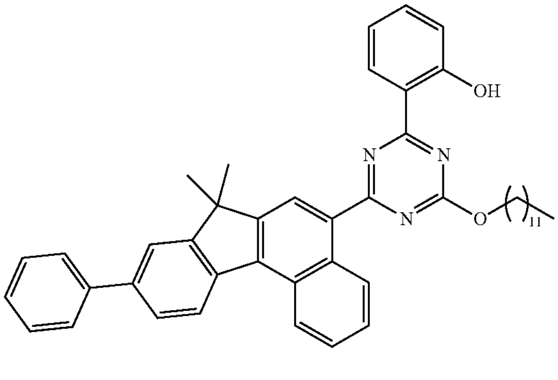
231
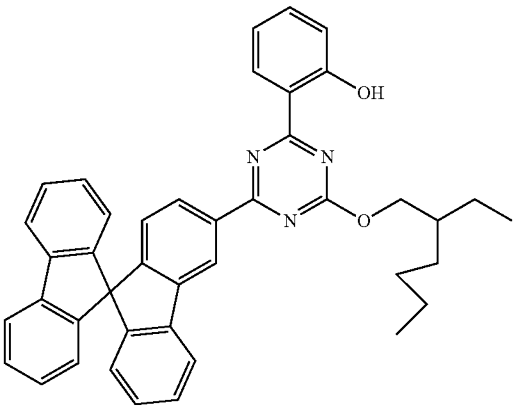
232
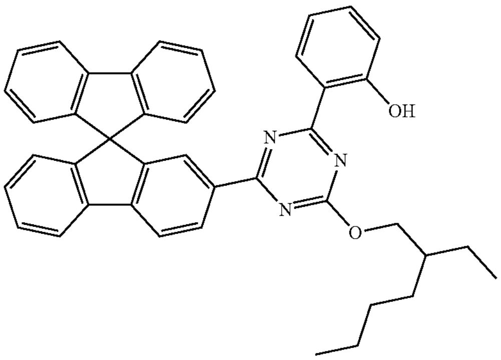
233
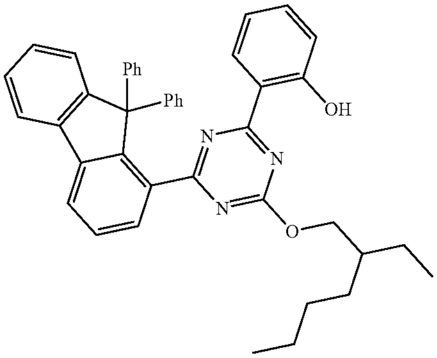
234
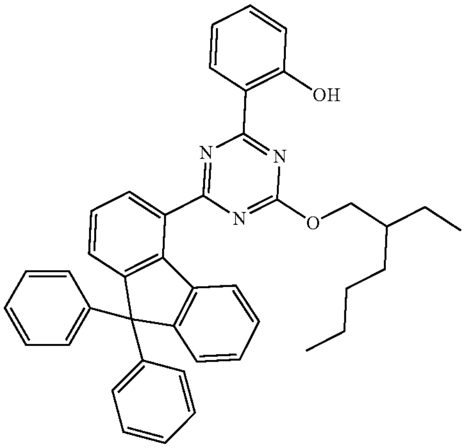

-continued
235
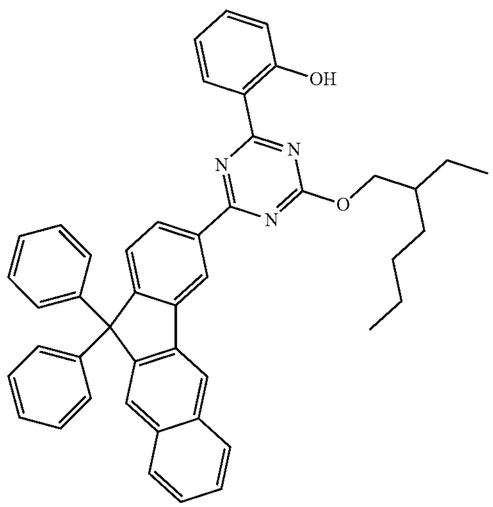
236
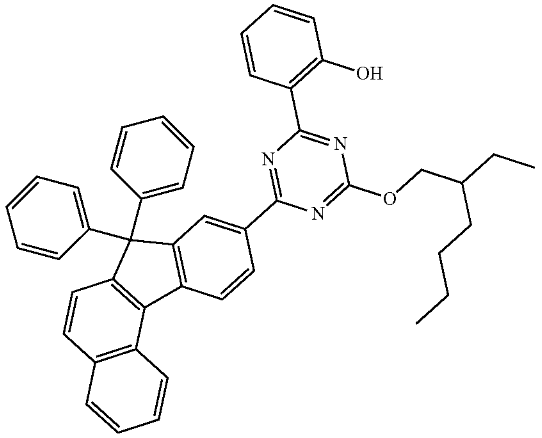
237
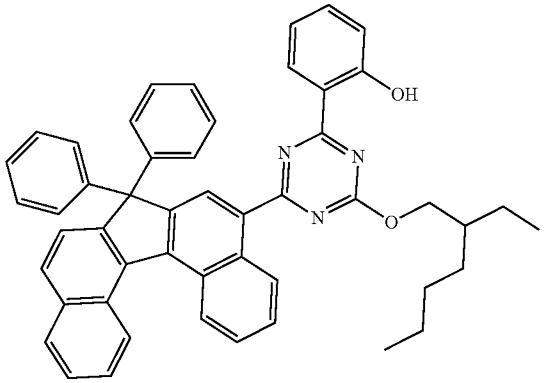
-continued
238
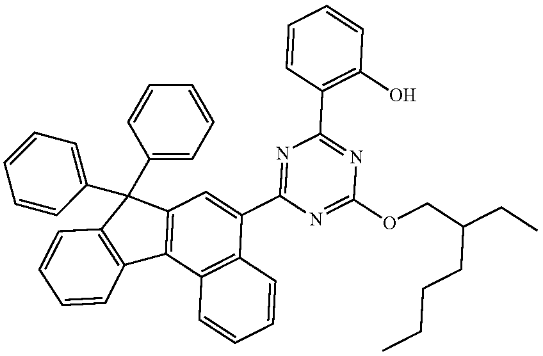
239
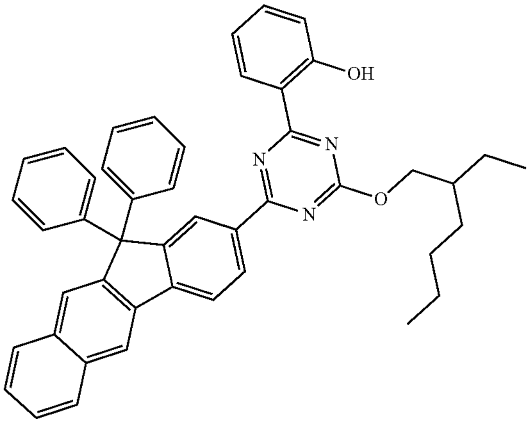
240
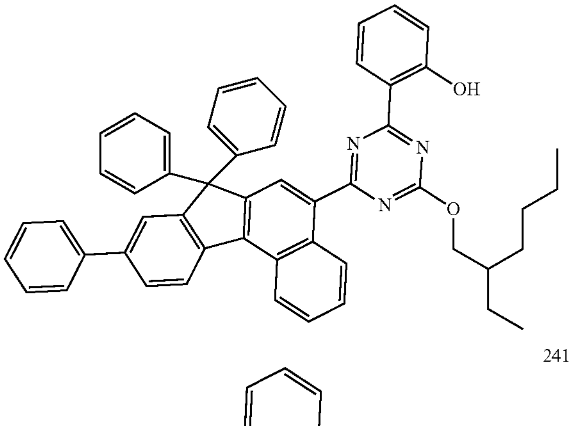
241
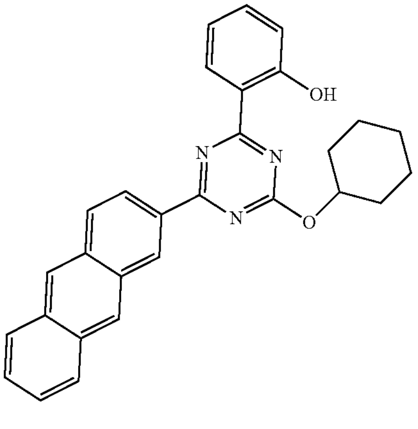

-continued
242
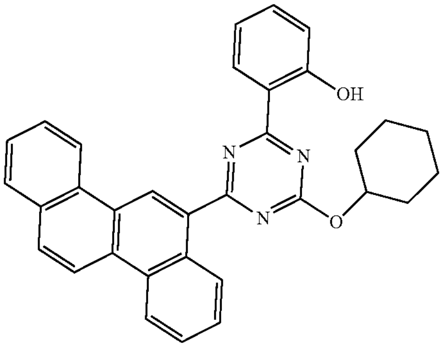
243
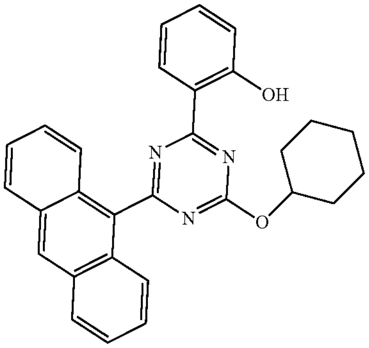
244
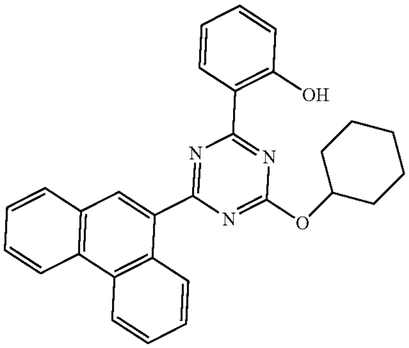
245
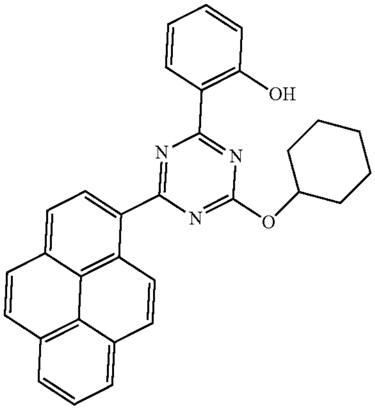
-continued
246
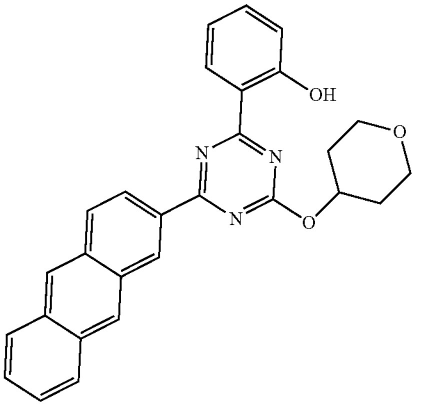
247
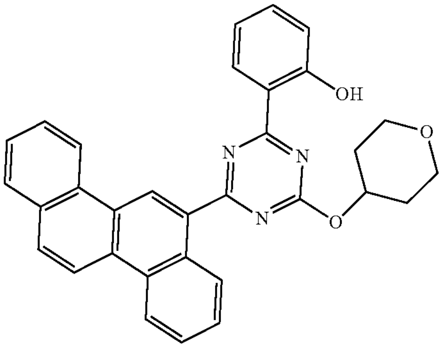
248
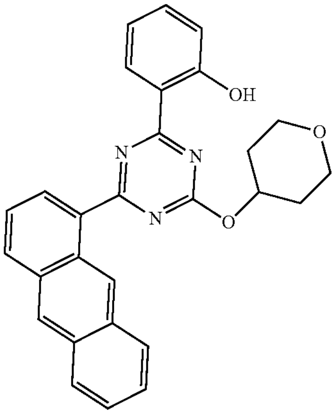
249
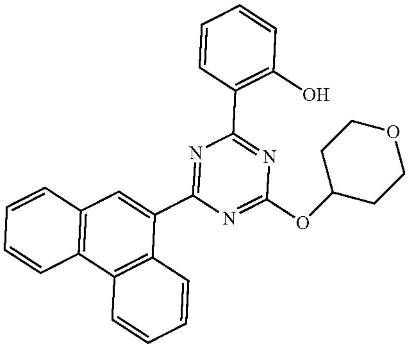

-continued
250
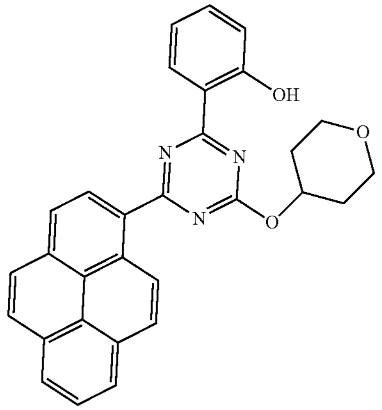
251
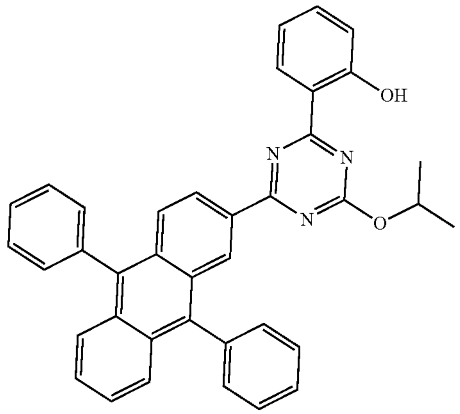
252
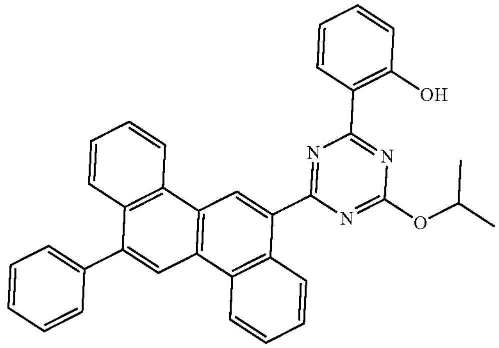
253
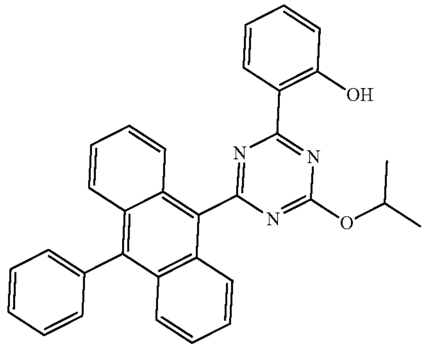
-continued
254
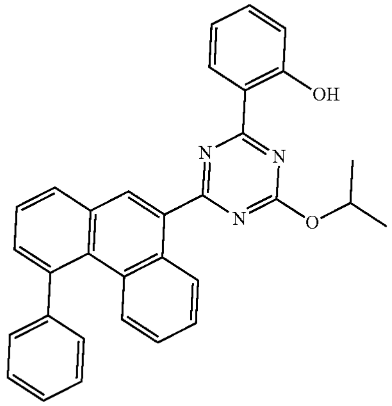
255
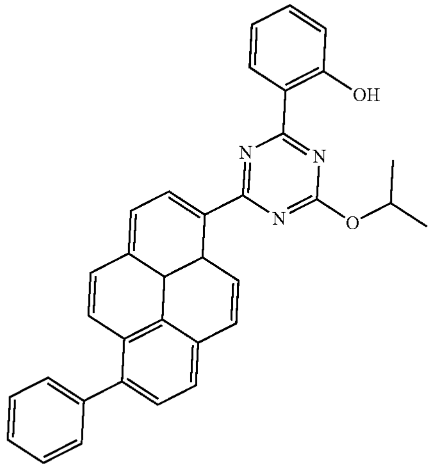
256
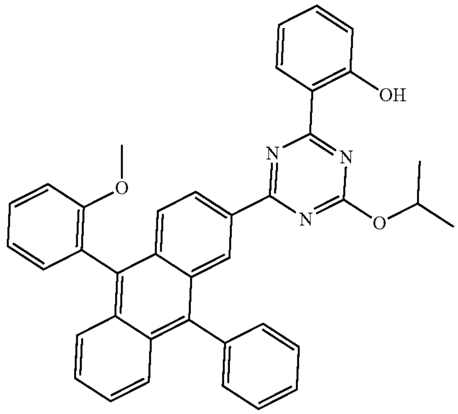

-continued
257
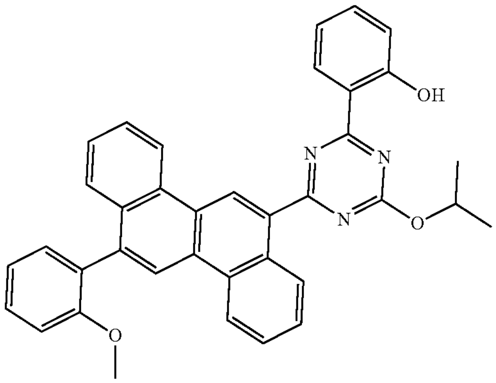
258
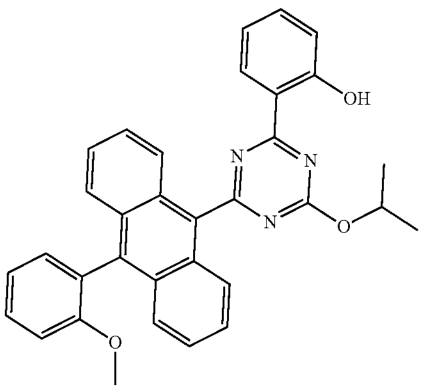
259
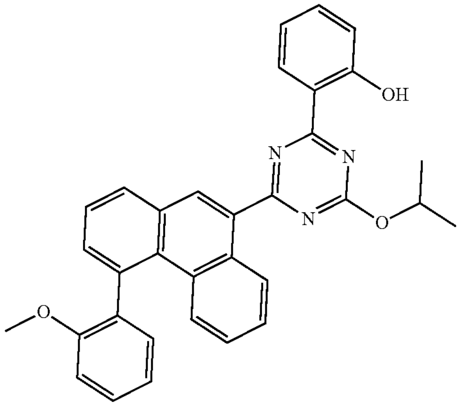
-continued
260
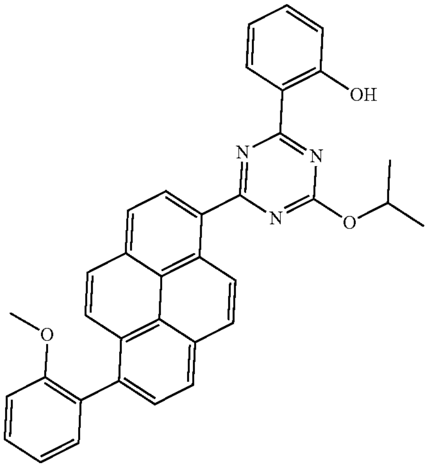
261
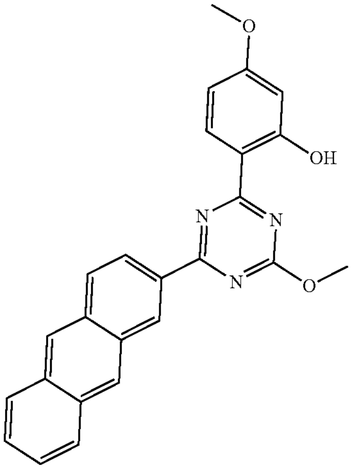
262
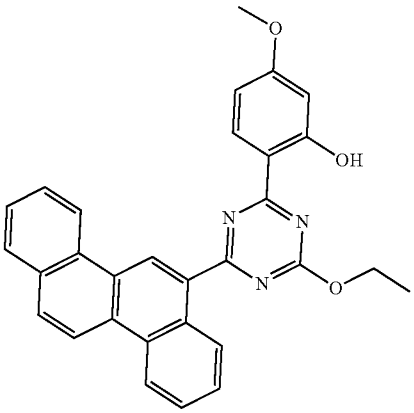

-continued
263
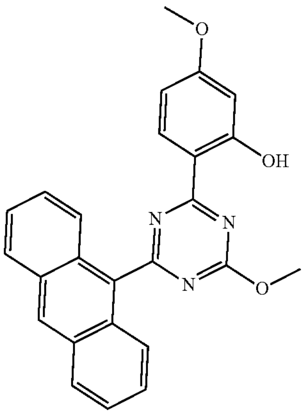
264
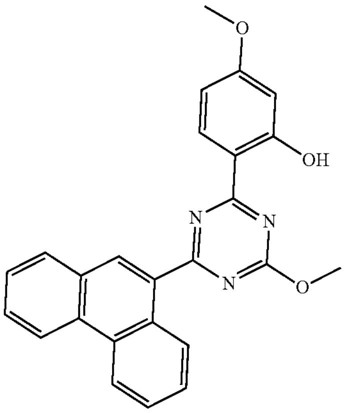
265
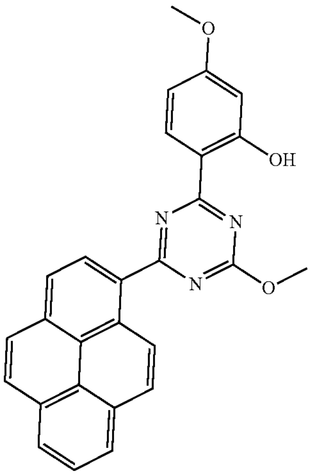
-continued
266
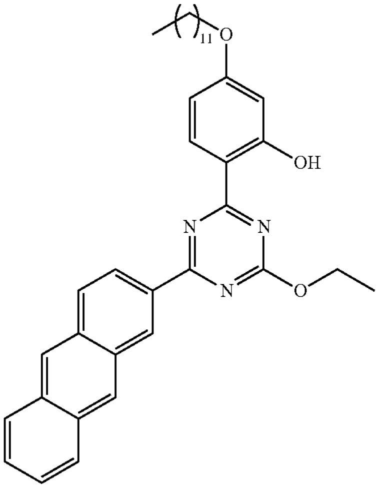
267
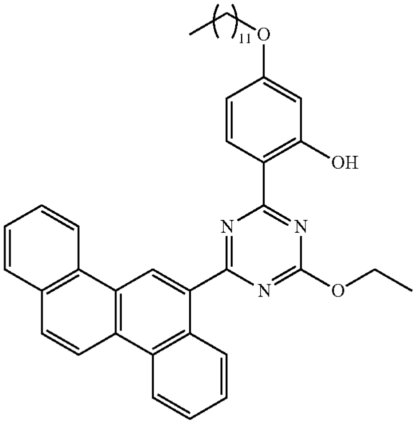
268
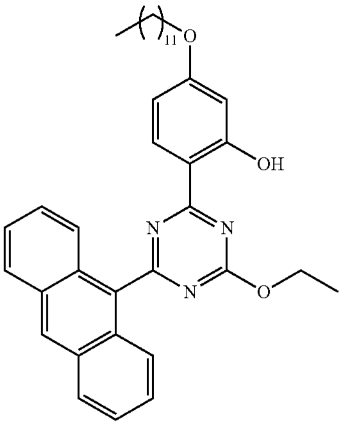

-continued
269
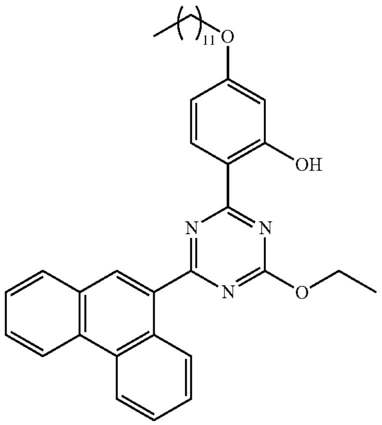
270
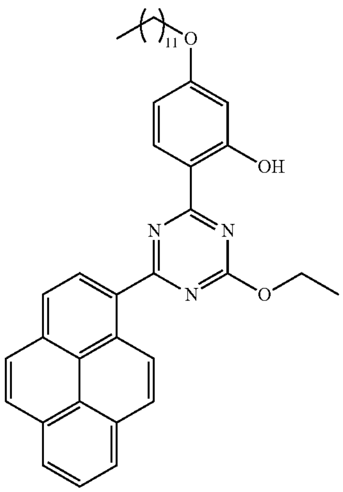
271
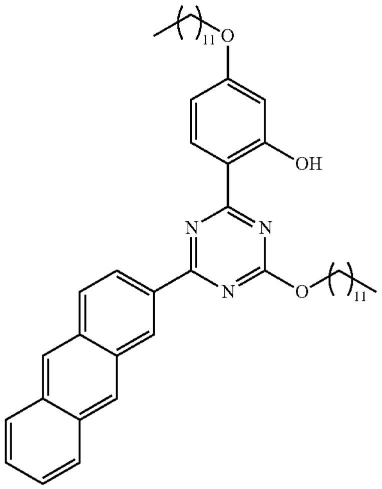
-continued
272
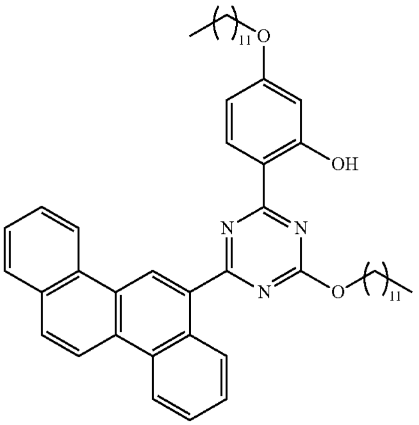
273
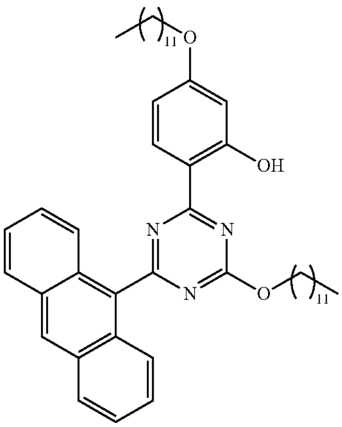
274
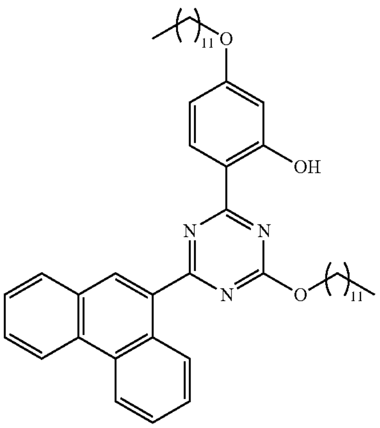

275
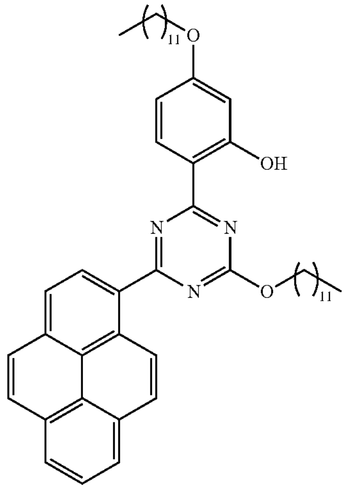
276
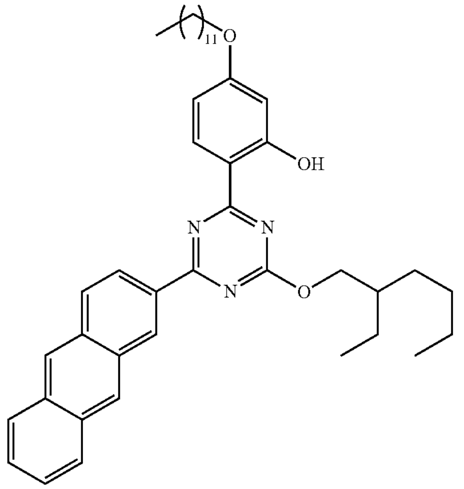
277
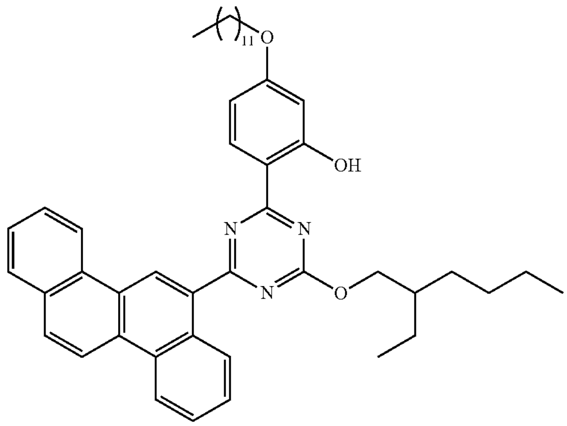
278
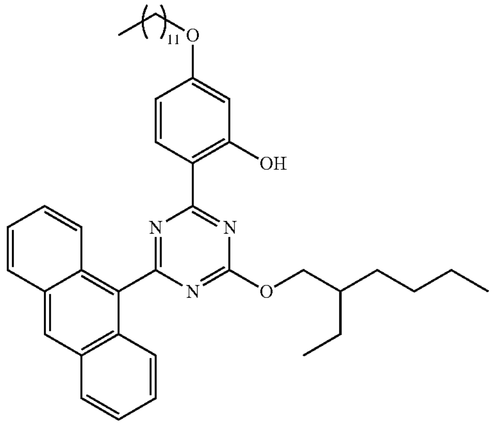
279
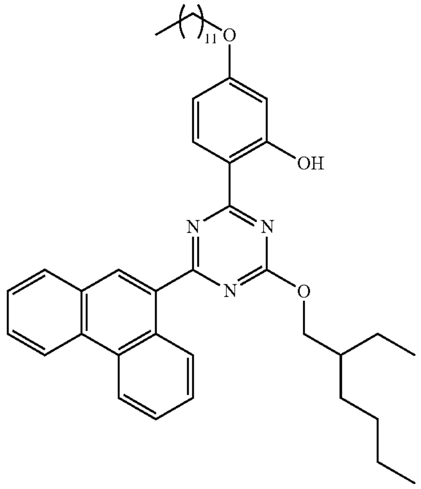
280
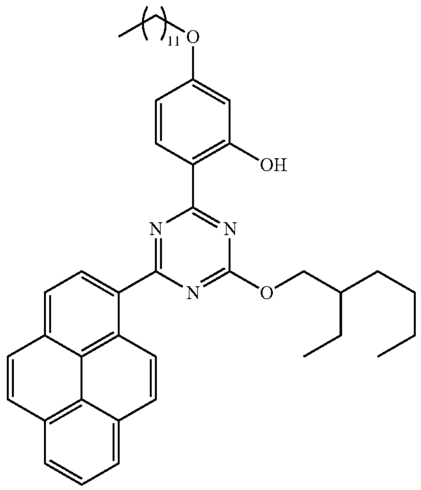

-continued
281
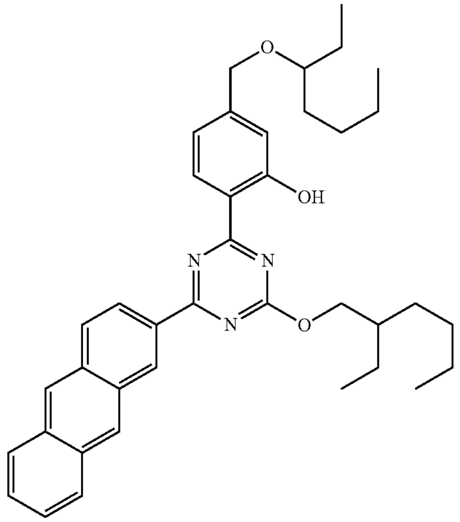
282
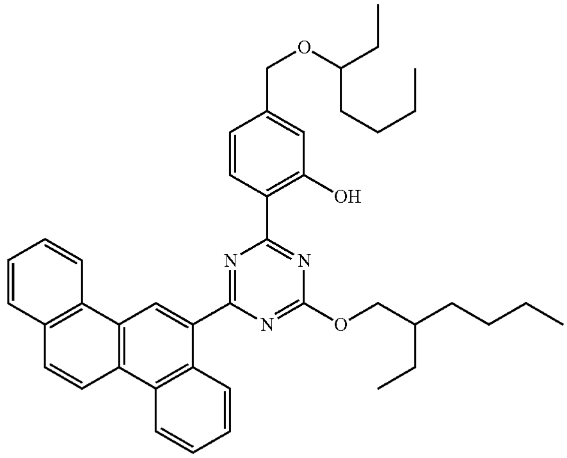
283
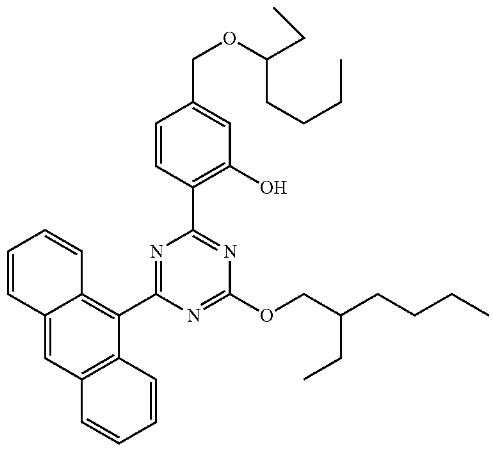
-continued
284
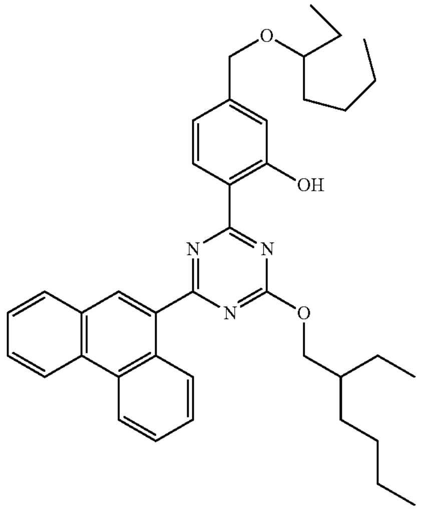
285
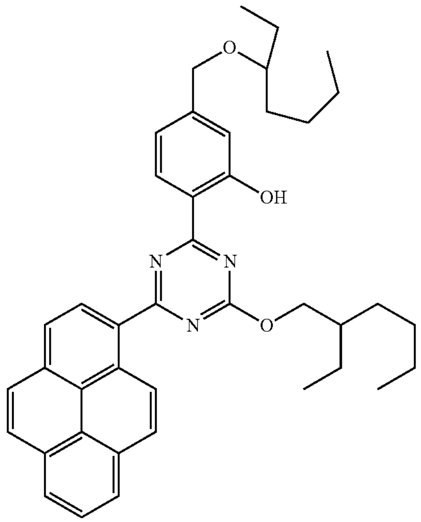
286
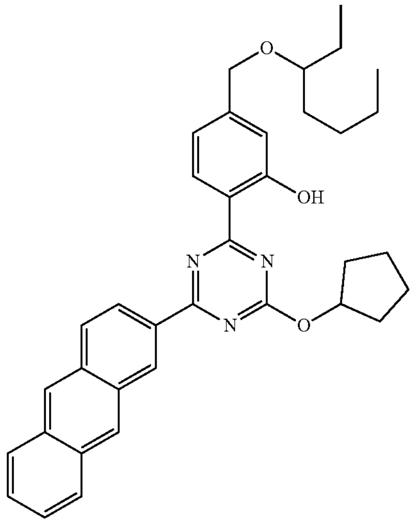

-continued
287
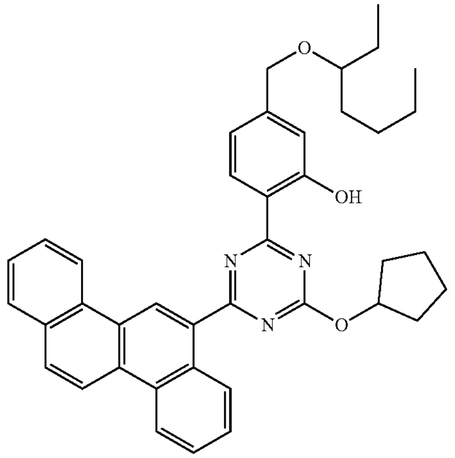
288
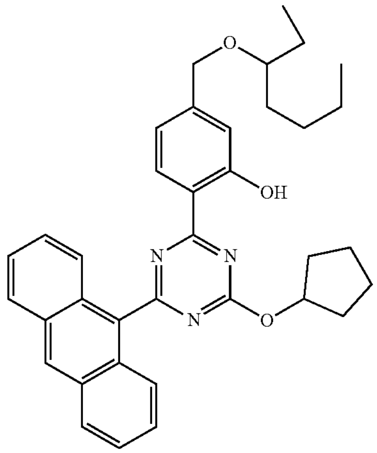
289
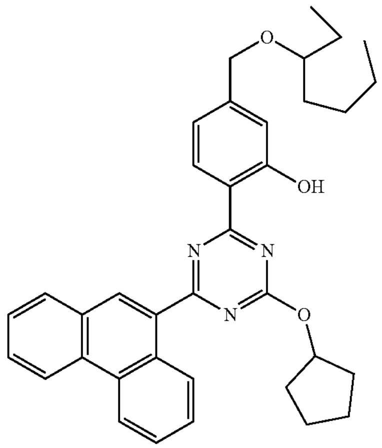
-continued
290
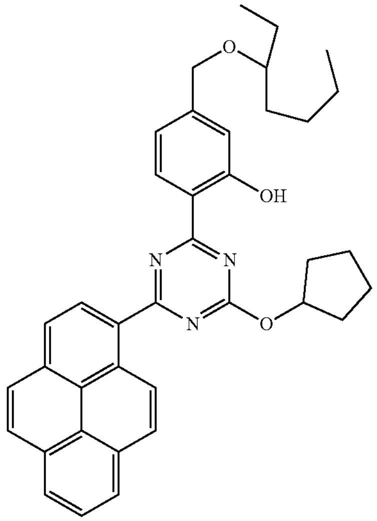
291
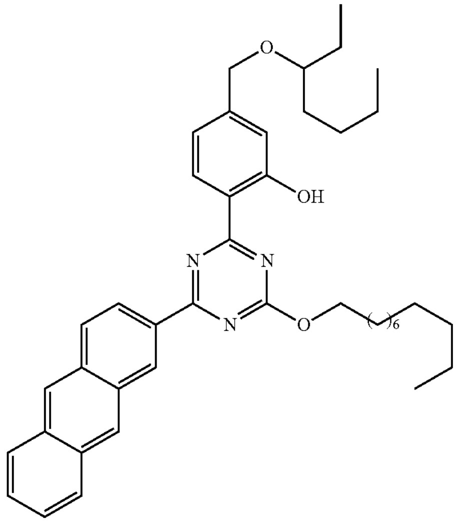
292
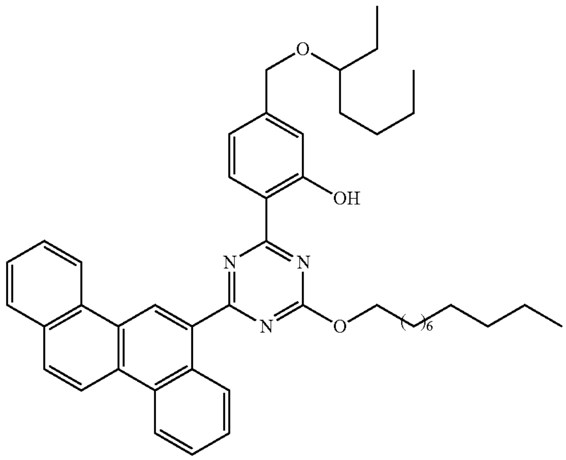

-continued
293
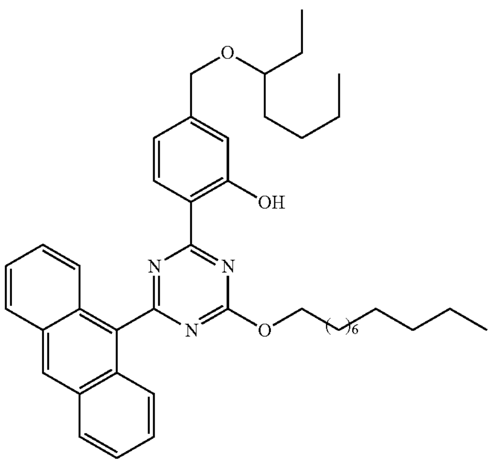
294
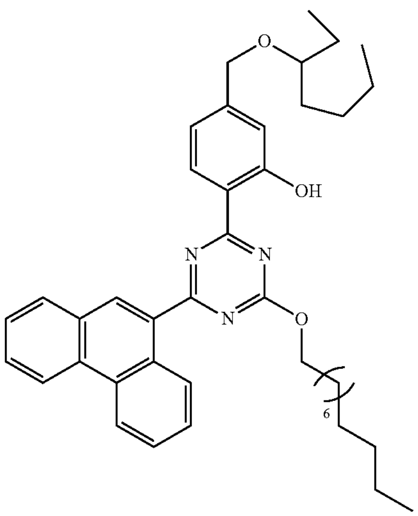
295
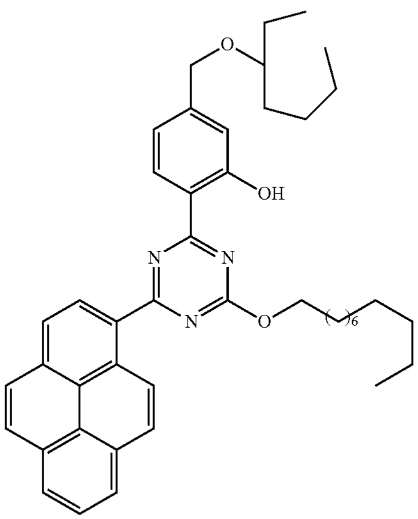
-continued
296
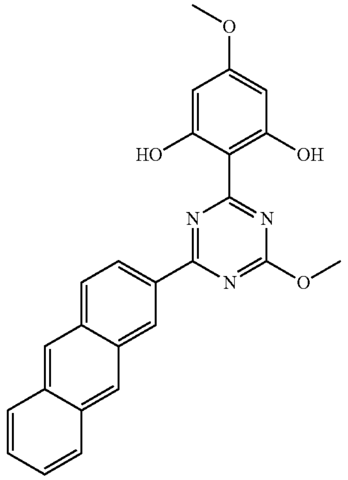
297
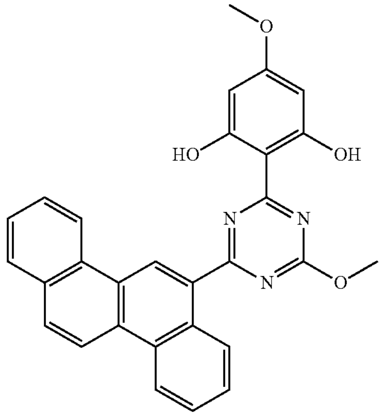
298
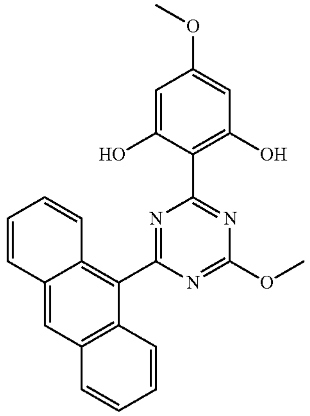

-continued
299
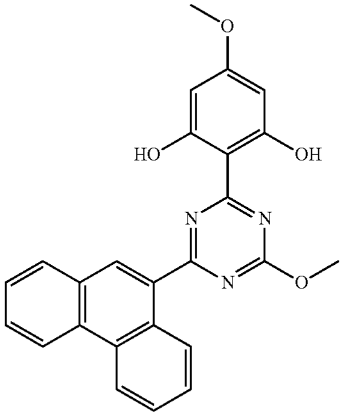
300
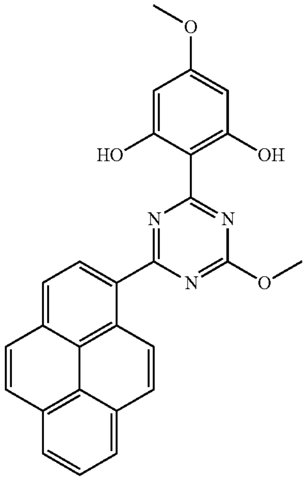
301
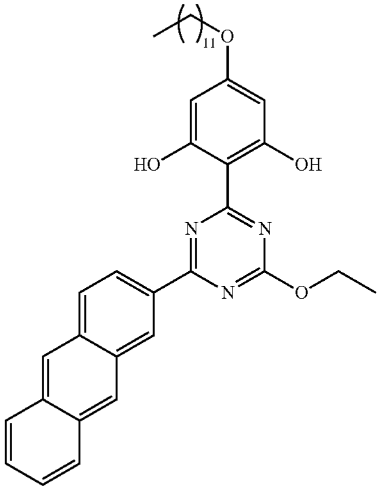
-continued
302
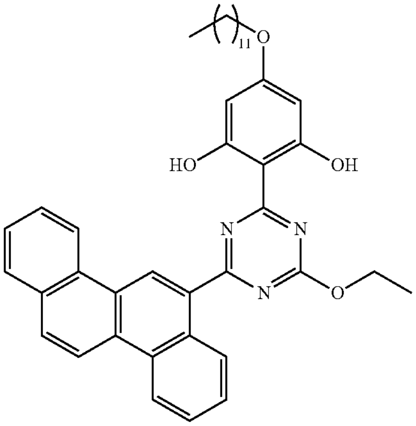
303
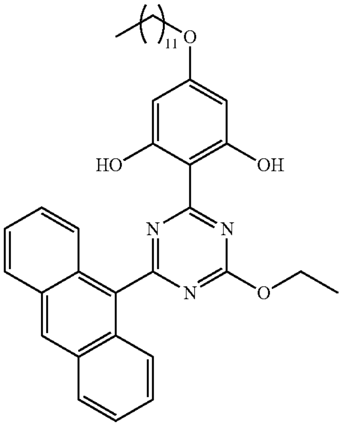
304
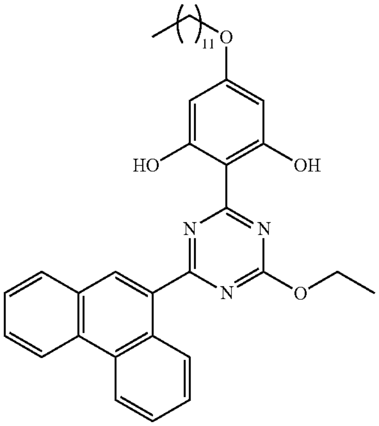

-continued
305
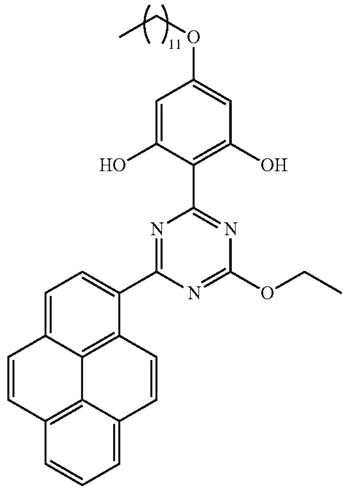
306
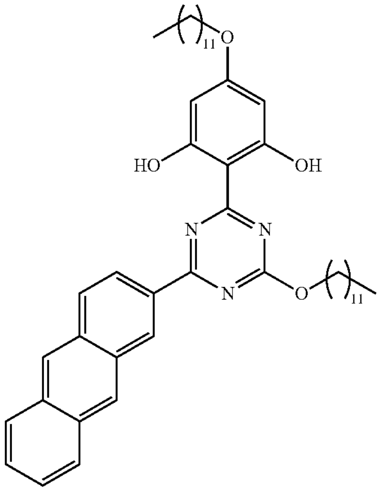
307
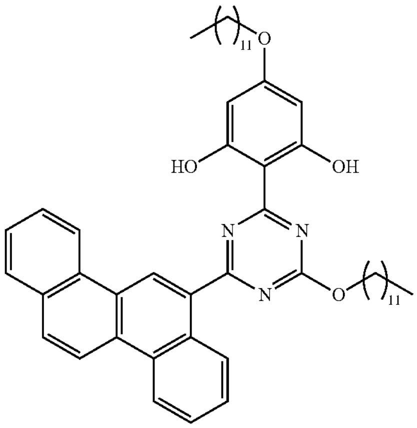
-continued
308
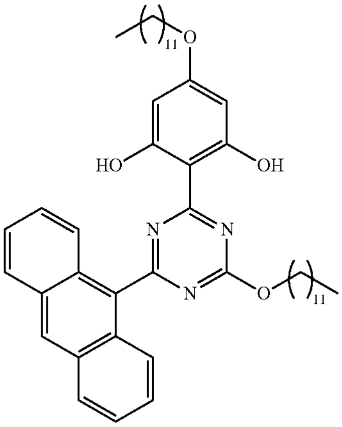
309
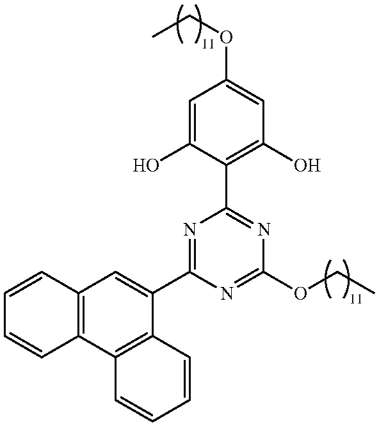
310
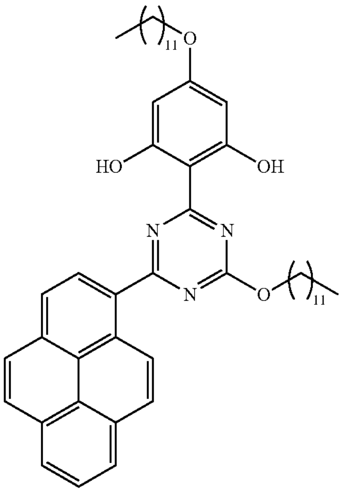

-continued
311
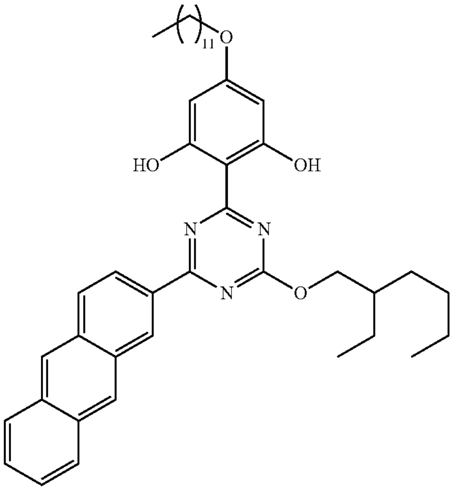
312
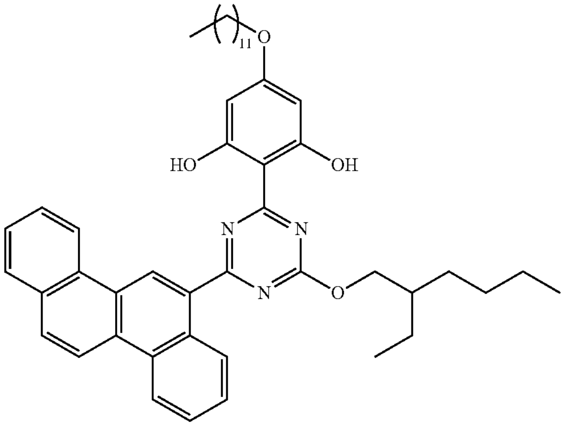
313
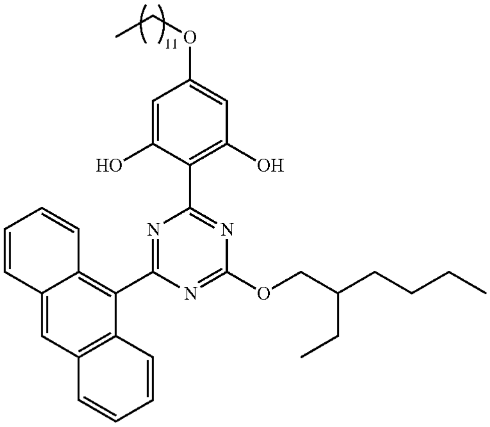
-continued
314
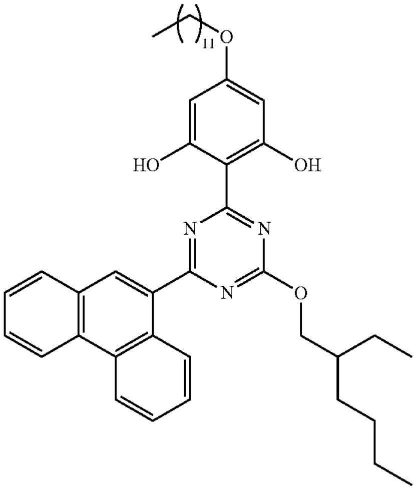
315
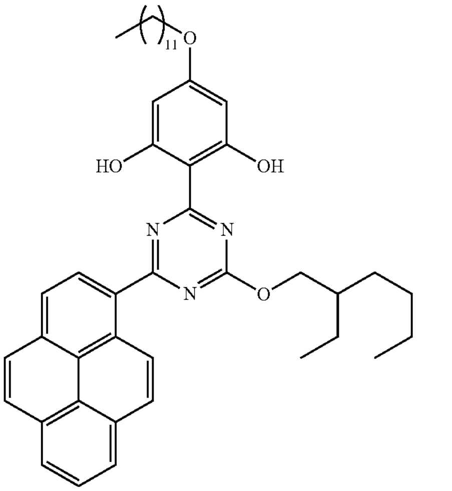
316
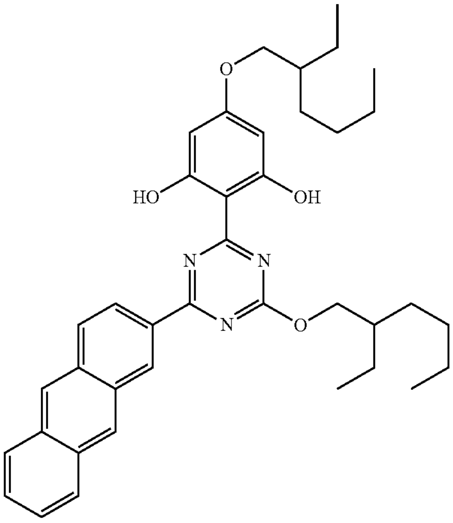

-continued
317
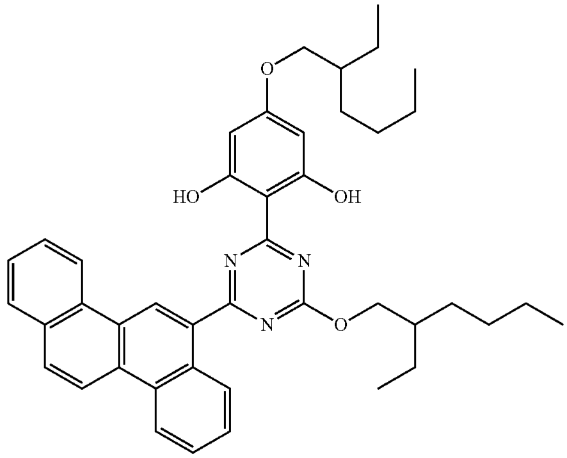
318
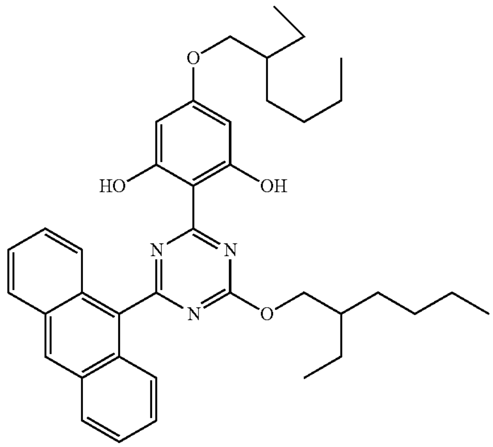
319
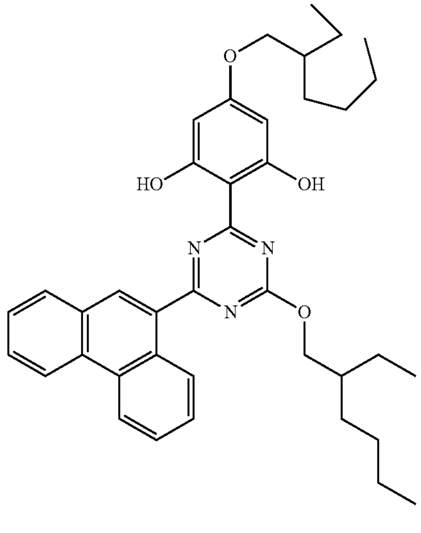
-continued
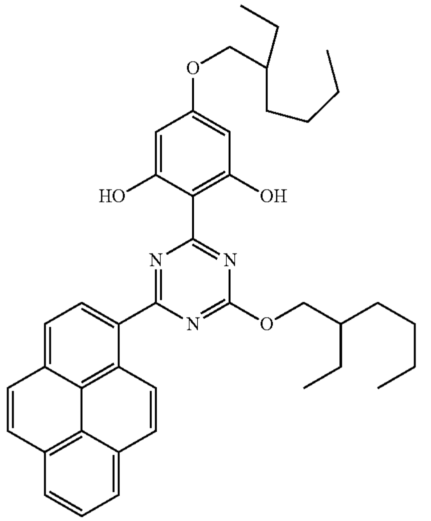
321
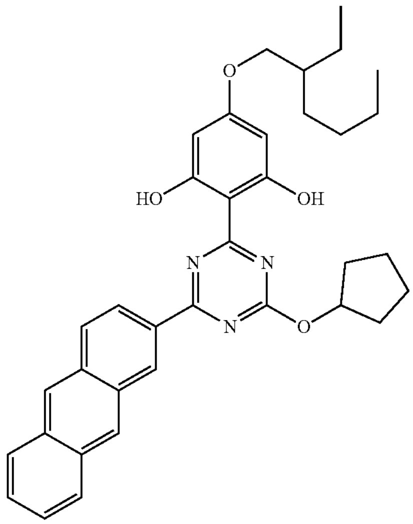
322
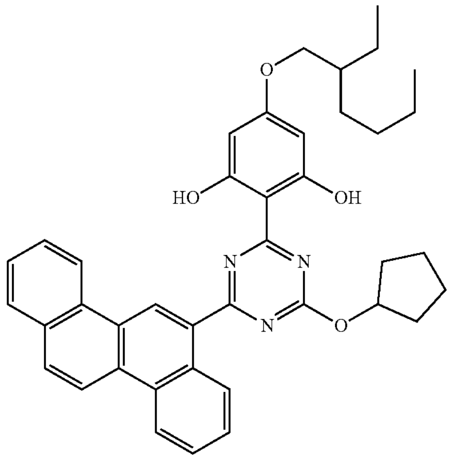

-continued
323
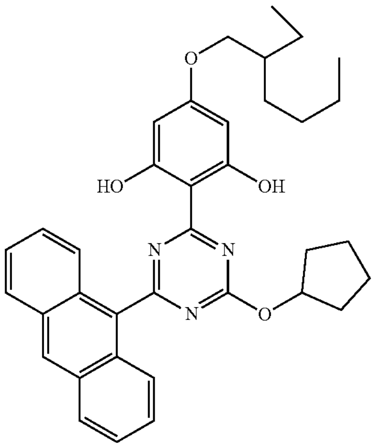
324
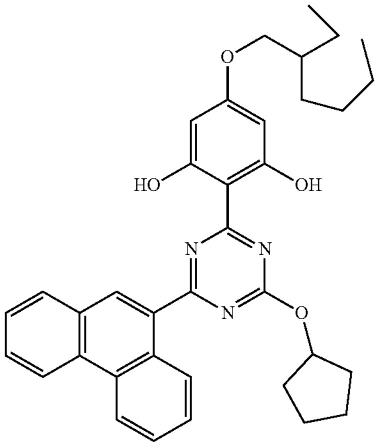
325
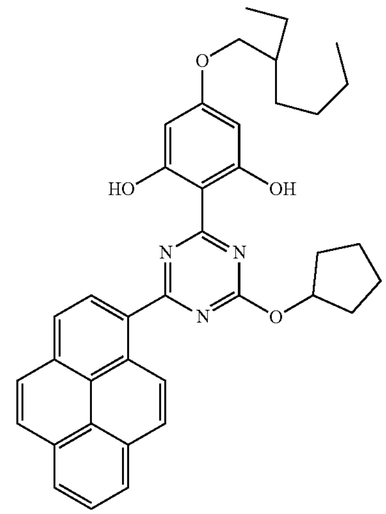
-continued
326
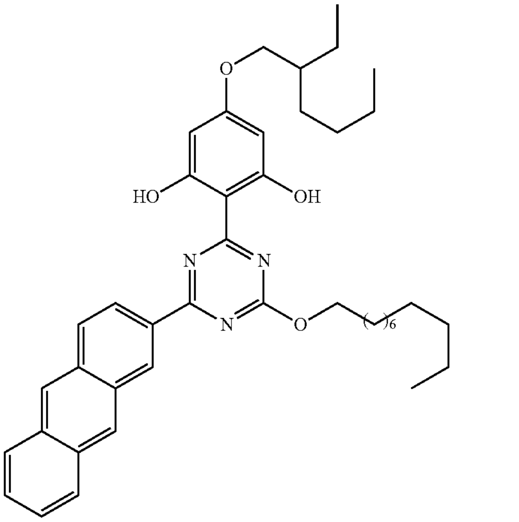
327
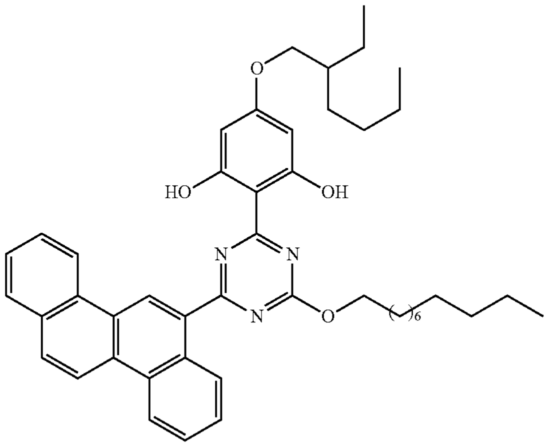
328
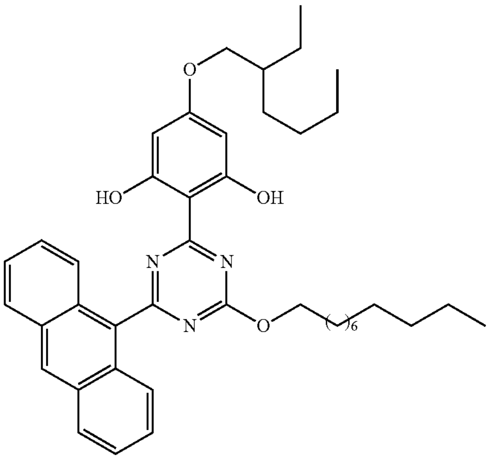

-continued
329
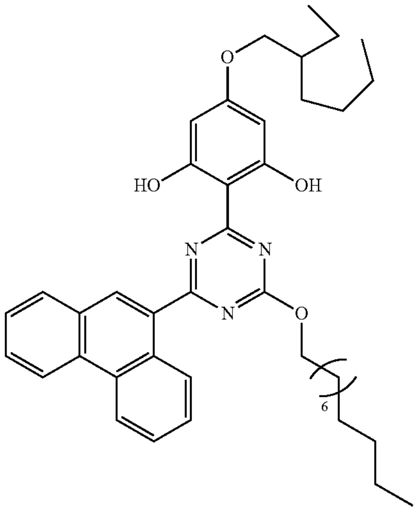
330
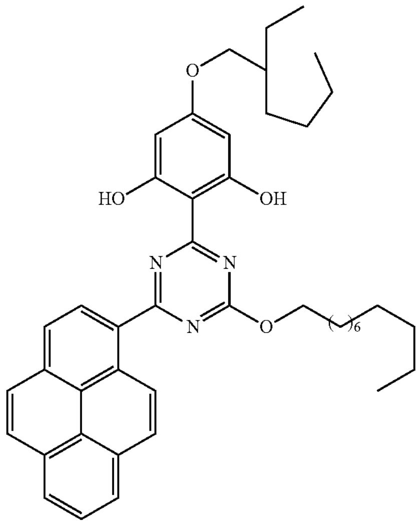
331
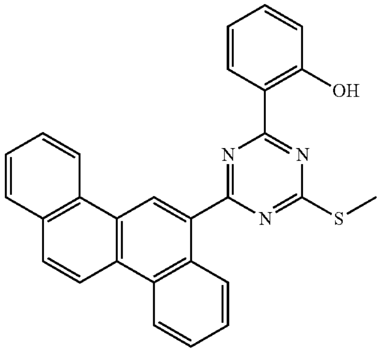
-continued
332
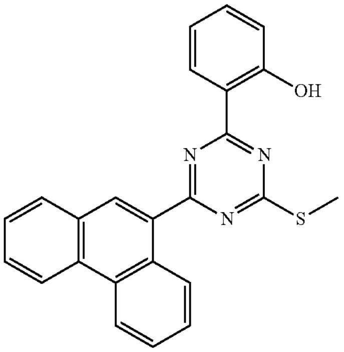
333
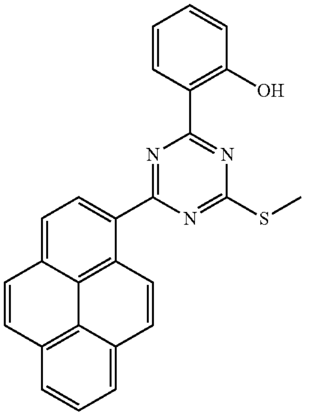
334
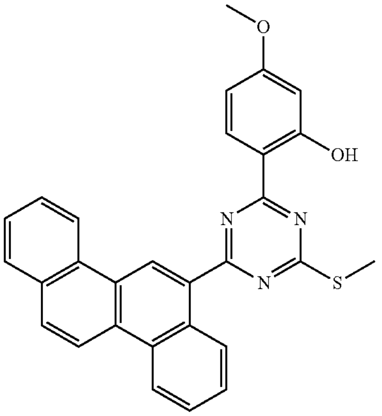
335
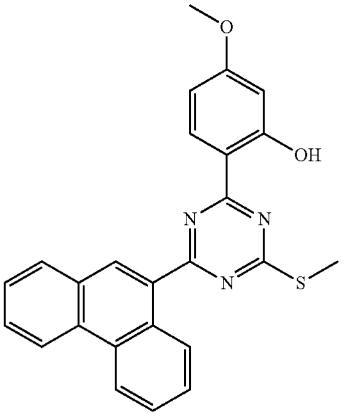

-continued
336
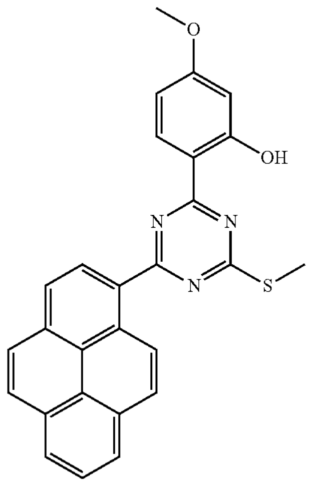
337
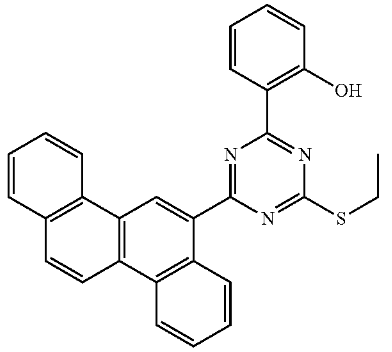
338
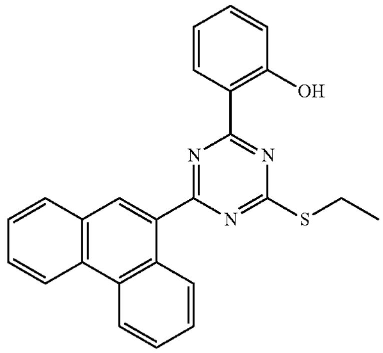
339
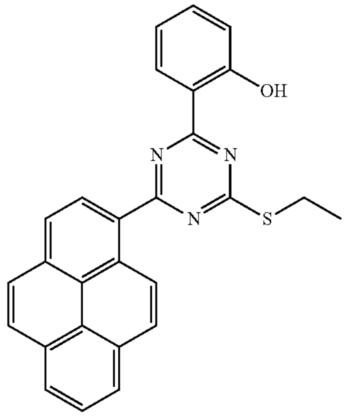
-continued
340
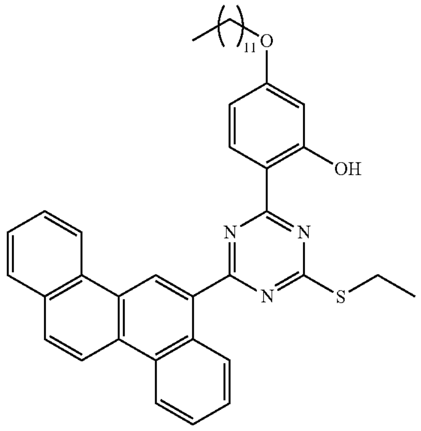
341
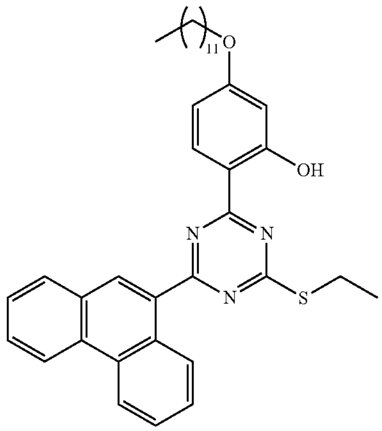
342
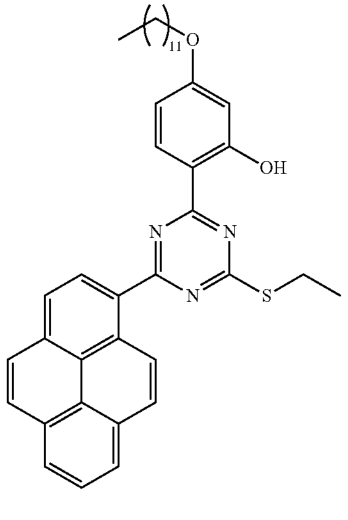

-continued
343
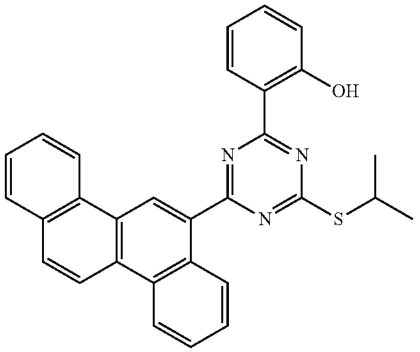
344
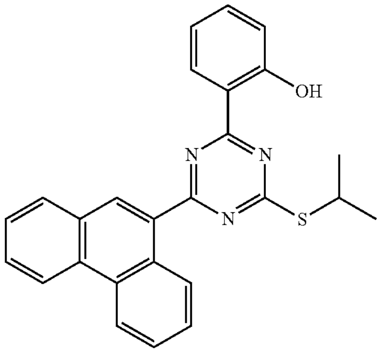
345
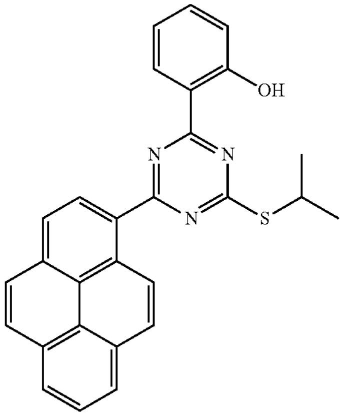
346
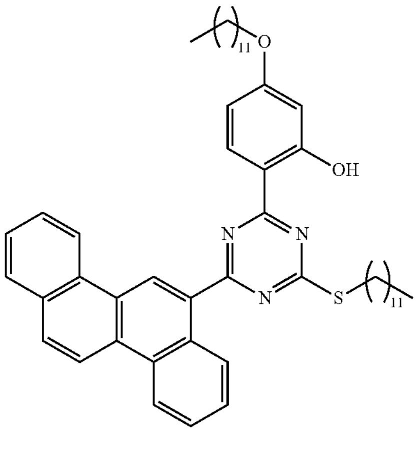
-continued
347
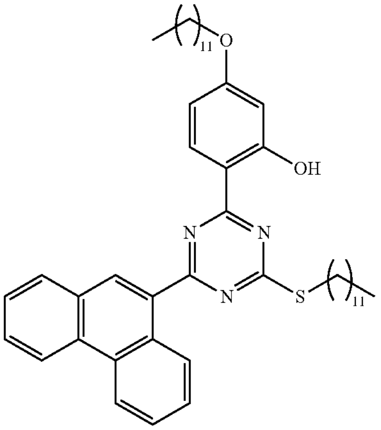
348
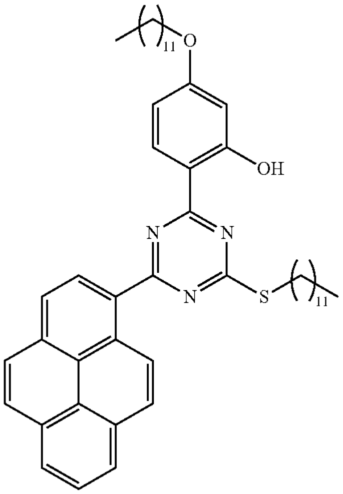
349
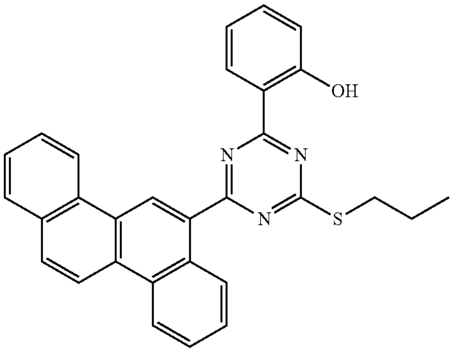
350
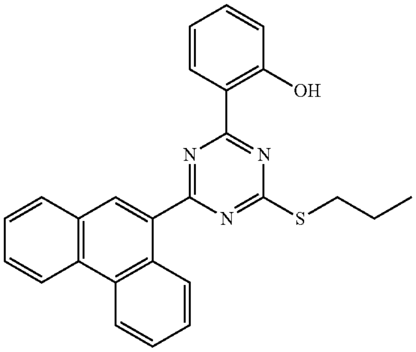

-continued
351
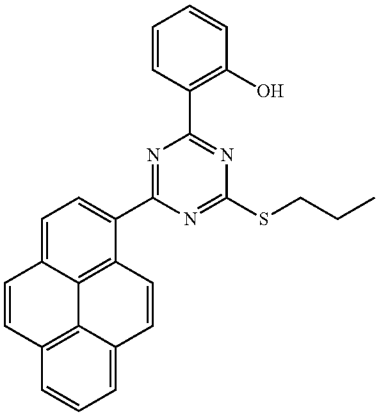
352
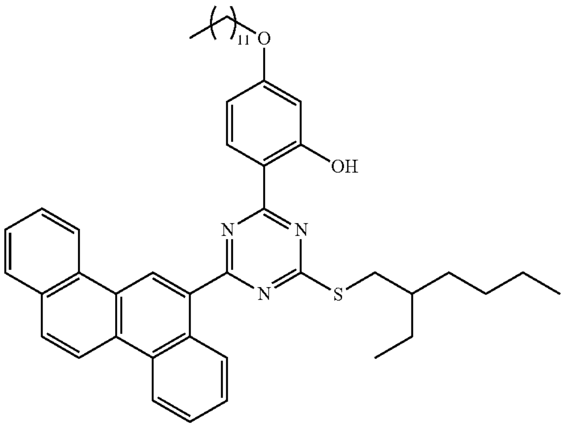
353
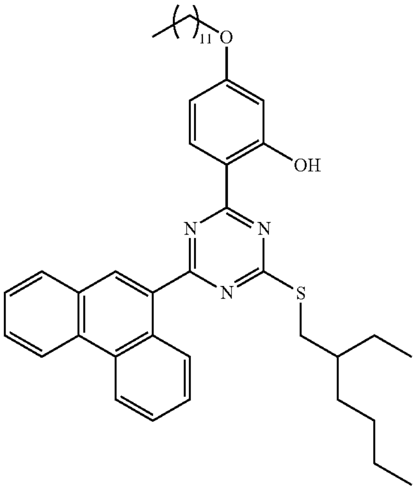
-continued
354
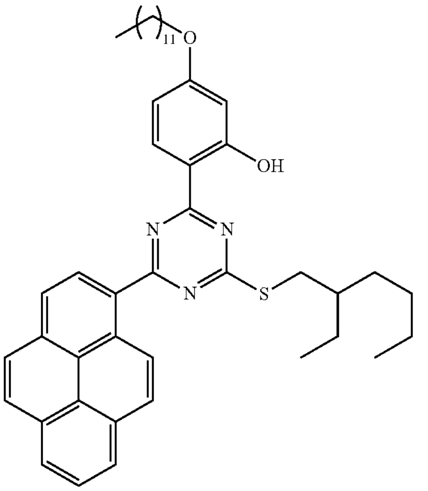
355
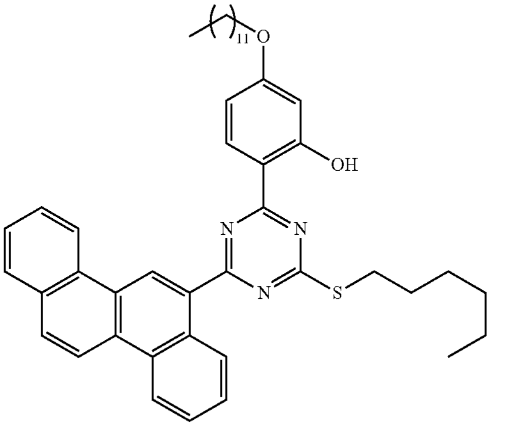
356
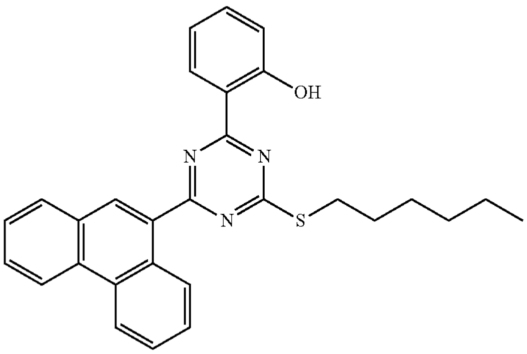

-continued
357
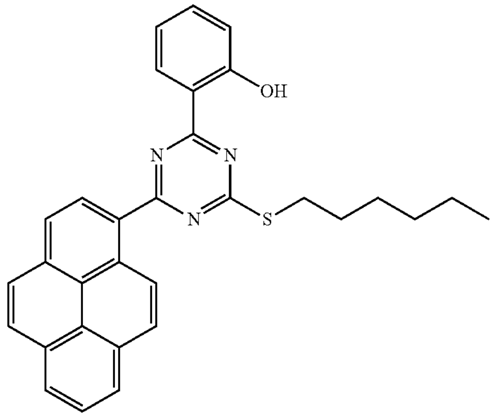
358
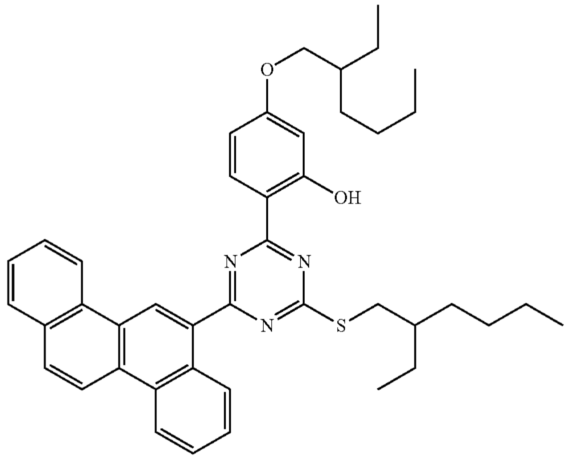
359
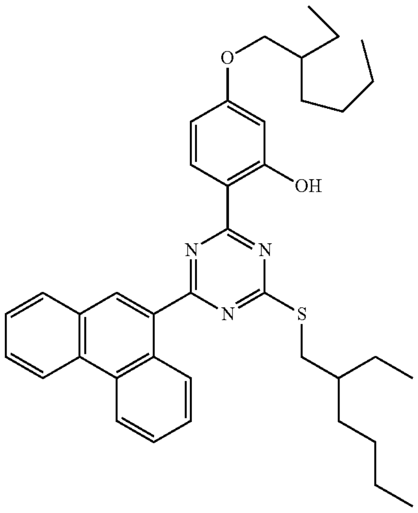
-continued
360
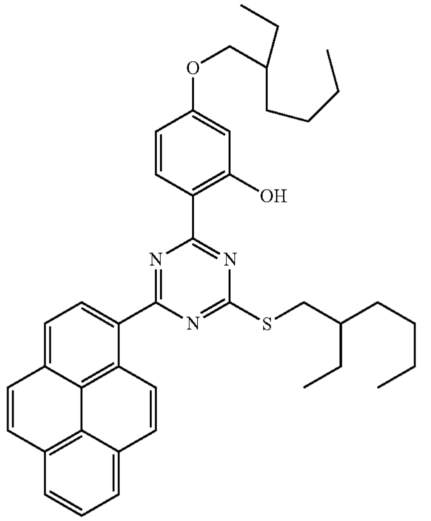
361
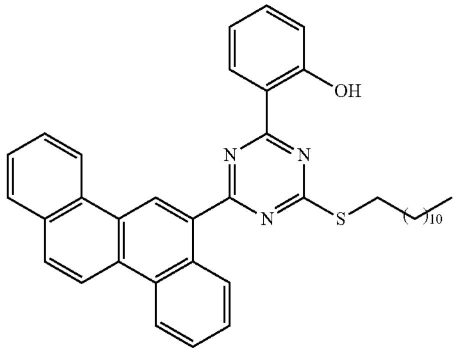
362
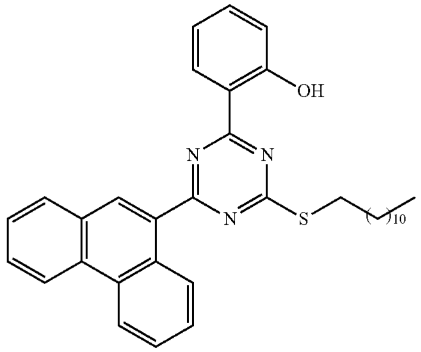
363
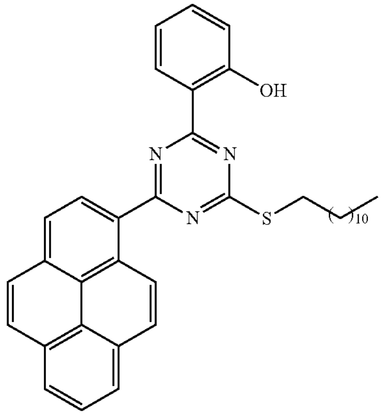

-continued
364
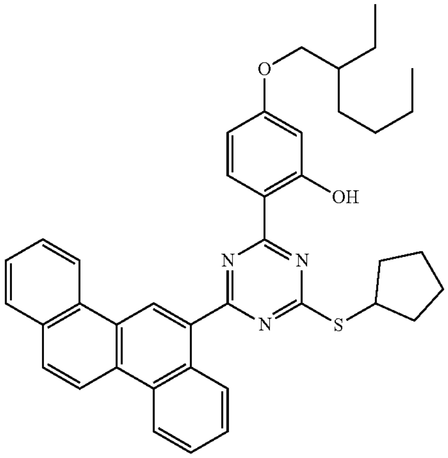
365
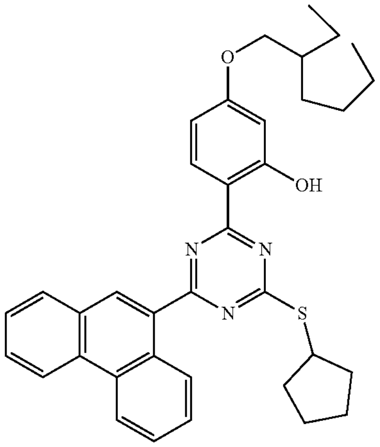
366
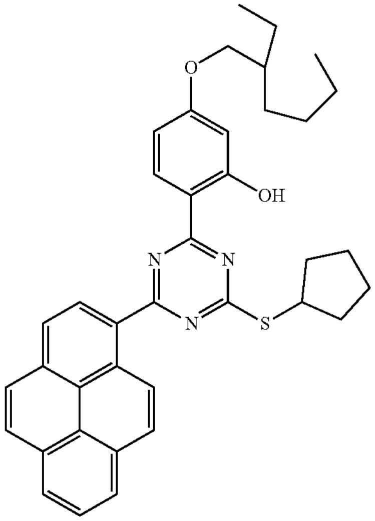
-continued
367
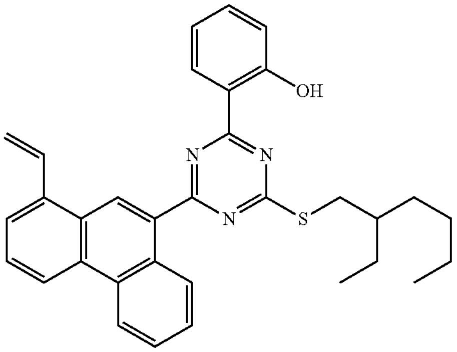
368
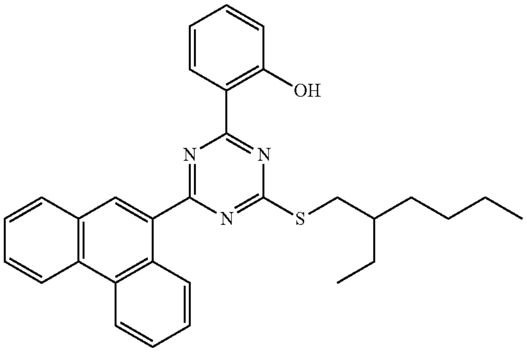
369
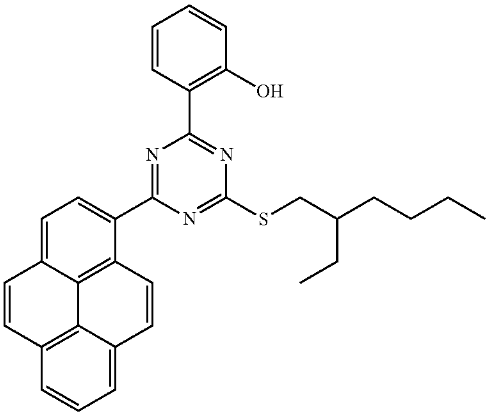
370
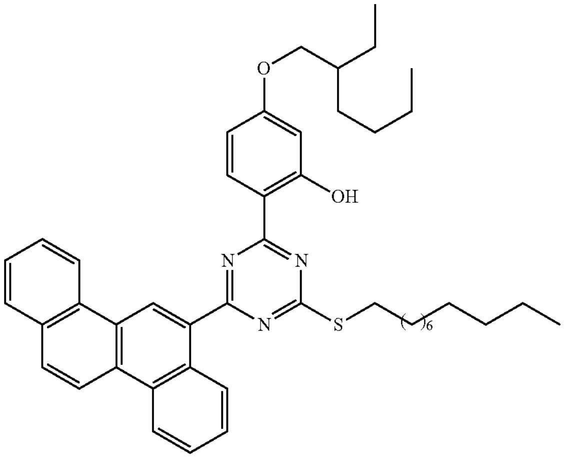

-continued

371

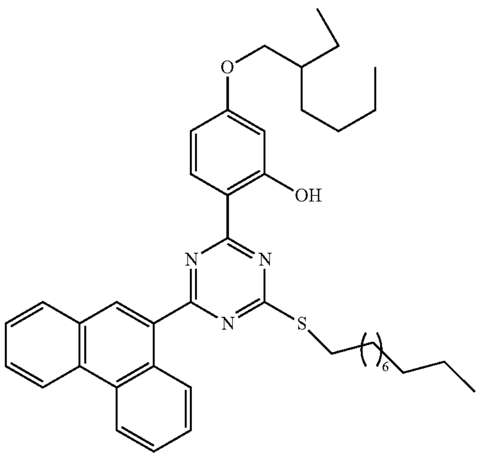

372

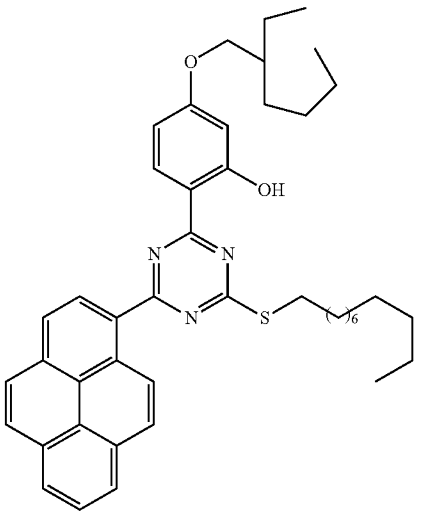

.

24. A light absorber represented by Formula 1 or Formula 2:

[Formula 1]

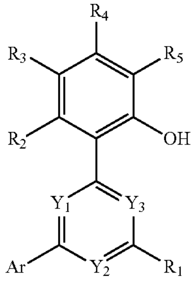

-continued

[Formula 2]

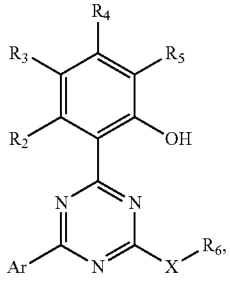

and wherein, in Formula 1 and Formula 2,

Ar is a substituted or unsubstituted anthracene group, a substituted or unsubstituted phenanthrene, a substituted or unsubstituted pyrene group, a substituted or unsubstituted chrysene group, a substituted or unsubstituted dibenzofuran derivative, a substituted or unsubstituted carbazole derivative, or a substituted or unsubstituted fluorene derivative, a substituent of the substituted or unsubstituted dibenzofuran derivative, a substituent of the substituted or unsubstituted carbazole derivative, and a substituent of the substituted or unsubstituted fluorene derivative are each independently a hydrogen atom, an alkyl group having 1 to 20 carbon atoms, an alkenyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or adjacent groups are bonded to each other to form a ring, and $R_2$ to $R_5$ are each independently a hydrogen atom, a deuterium atom, a halogen atom, a cyano group, a substituted or unsubstituted alkyl group having 1 to 30 carbon atoms, a substituted or unsubstituted alkoxy group having 1 to 20 carbon atoms, a substituted or unsubstituted aryloxy group having 6 to 30 ring-forming carbon atoms, a substituted or unsubstituted alkylamine group having 1 to 30 carbon atoms, a substituted or unsubstituted arylamine group having 6 to 30 ring-forming carbon atoms, a substituted or unsubstituted heterocyclic group having 2 to 30 ring-forming carbon atoms, or a substituted or unsubstituted aryl group having 6 to 30 ring-forming carbon atoms, in Formula 1, two among $Y_1$ to $Y_3$ are N and the remaining one among $Y_1$ to $Y_3$ is CH, $R_1$ is a substituted or unsubstituted alkoxy group having 1 to 20 carbon atoms, a substituted or unsubstituted aryloxy group having 6 to 30 ring-forming carbon atoms, a substituted or unsubstituted alkylthio group having 1 to 20 carbon atoms, or a substituted or unsubstituted arylthio group having 6 to 30 ring-forming carbon atoms, and in Formula 2, X is O or S, and $R_6$ is a substituted or unsubstituted alkyl group having 1 to 30 carbon atoms, a substituted or unsubstituted heterocyclic group having 2 to 30 ring-forming carbon atoms, or a substituted or unsubstituted aryl group having 6 to 30 ring-forming carbon atoms.

25. The light absorber of claim 24, wherein Formula 1 is represented by at least one among Formula 1-1 to Formula 1-4:

[Formula 1-1]

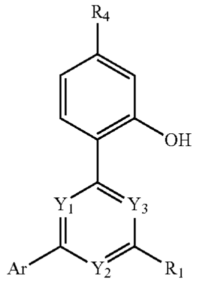

[Formula 1-2]

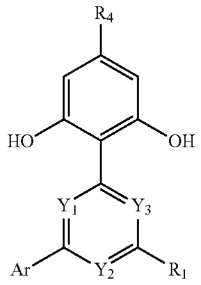

[Formula 1-3]

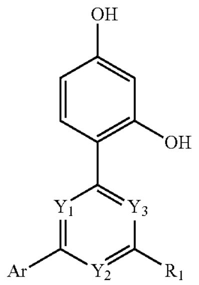

[Formula 1-4]

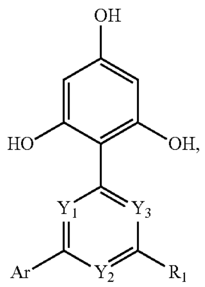

and wherein, in Formula 1-1 to Formula 1-4, Ar, $Y_1$ to $Y_3$, $R_1$, and $R_4$ are the same as defined in Formula 1.

26. The light absorber of claim 24, wherein Formula 2 is represented by at least one among Formula 2-1 to Formula 2-4:

[Formula 2-1]

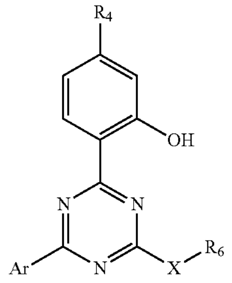

[Formula 2-2]

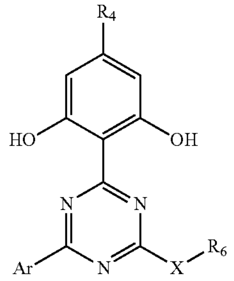

[Formula 2-3]

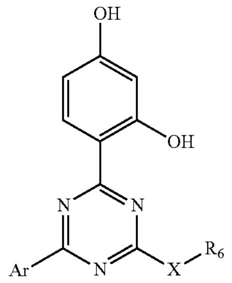

[Formula 2-4]

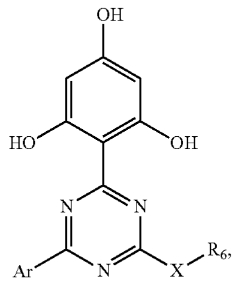

and wherein, in Formula 2-1 to Formula 2-4, X, Ar, $R_4$, and $R_6$ are the same as defined in Formula 1 and Formula 2.

27. The light absorber of claim 24, wherein Formula 1 is represented by at least one among Formula 1-A to Formula 1-C:

[Formula 1-A]

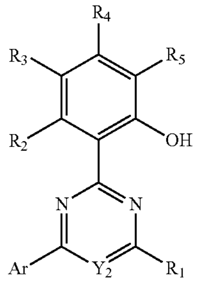

[Formula 1-B]

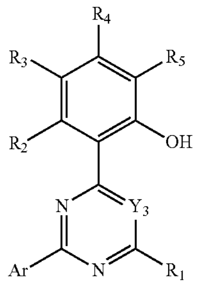

[Formula 1-C]

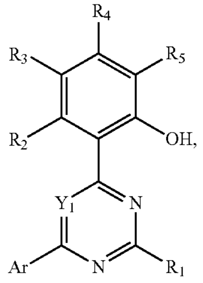

and wherein, in Formula 1-A to Formula 1-C, $Y_1$ to $Y_3$, Ar, and $R_1$ to $R_5$ are the same as defined in Formula 1.

28. The light absorber of claim 24, wherein Ar is represented by at least one among Ar-a to Ar-h:

Ar-a

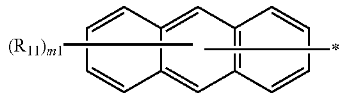

Ar-b

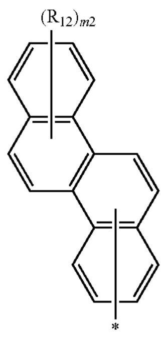

-continued

Ar-c

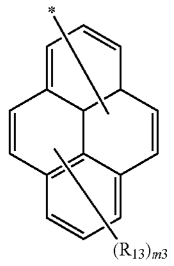

Ar-d

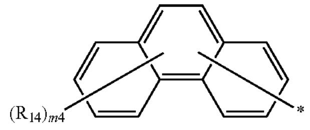

Ar-e

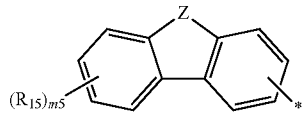

Ar-f

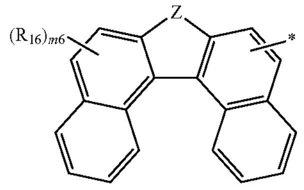

Ar-g

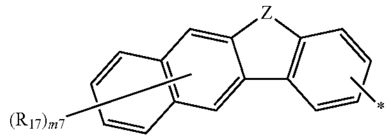

Ar-h

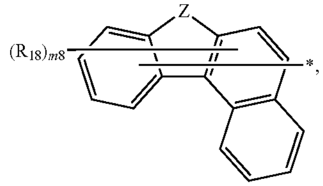

and wherein, in Ar-e to Ar-h, Z is O, S, $NR_a$, or $CR_bR_c$, and $R_a$ to $R_c$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and in Ar-a to Ar-h, $R_{11}$ to $R_{18}$ are each independently a hydrogen atom, a deuterium atom, a halogen atom, an alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and m1 to m8 are each independently an integer of 0 to 4.

29. The light absorber of claim 24, wherein Ar is an unsubstituted anthracene, an unsubstituted phenanthrene, an unsubstituted pyrene, or an unsubstituted chrysene.

30. The light absorber of claim 24, wherein $R_1$ is represented by at least one among S1 to S15:

S1
S2
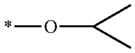
S3
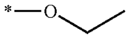
S4
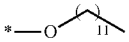
S5
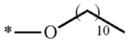
S6
S7
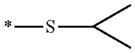
S8
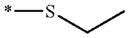
S9
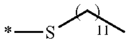
S10
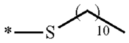
S11
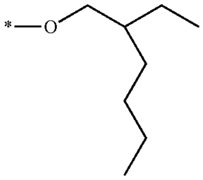
S12
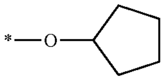
S13
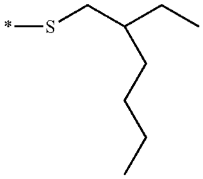
S14
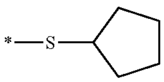
S15
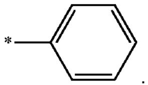
.
31. The light absorber of claim 24, wherein the light absorber represented by Formula 1 is at least one among the compounds represented by Compound Group 1 and Compound Group 2:
Compound Group 1
1
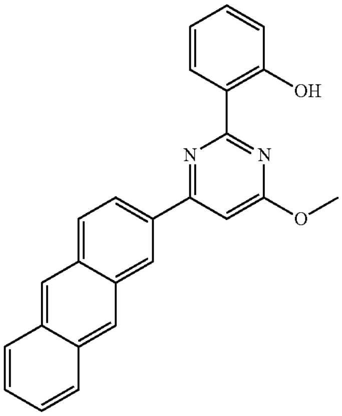
2
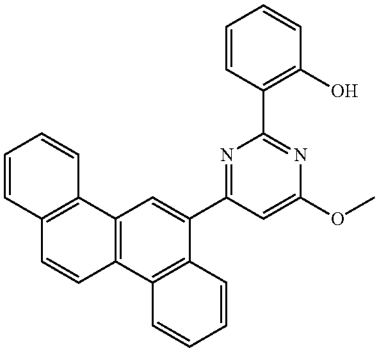
3
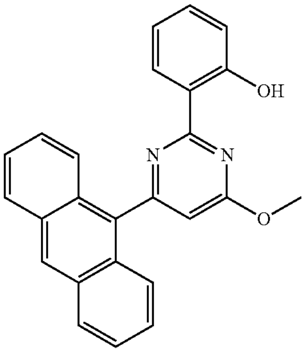
4
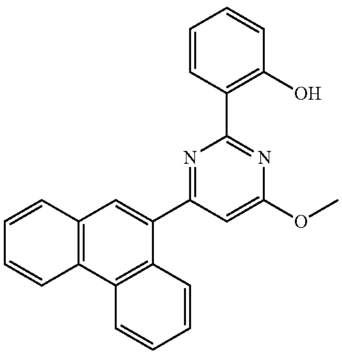

-continued
5
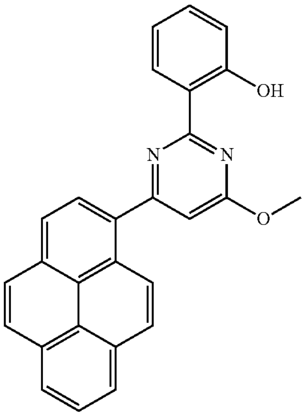
6
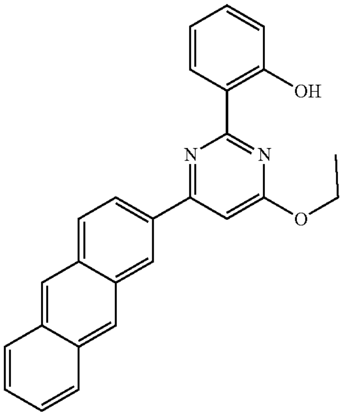
7
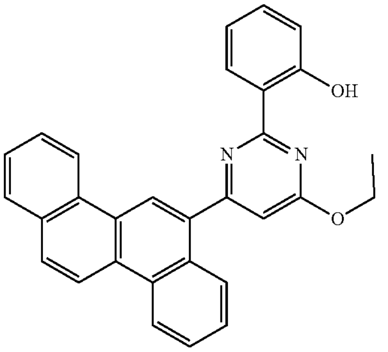
8
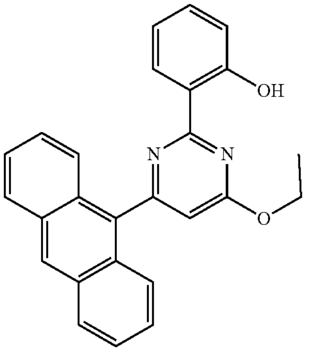
-continued
9
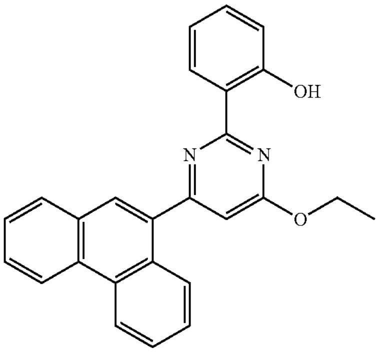
10
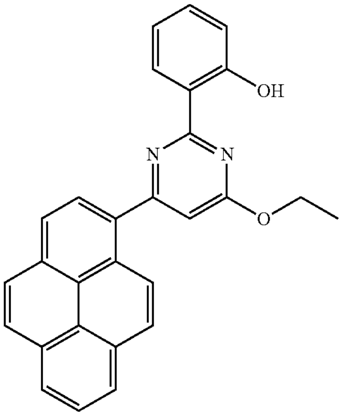
11
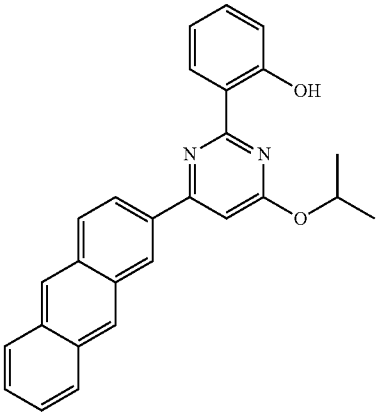
12
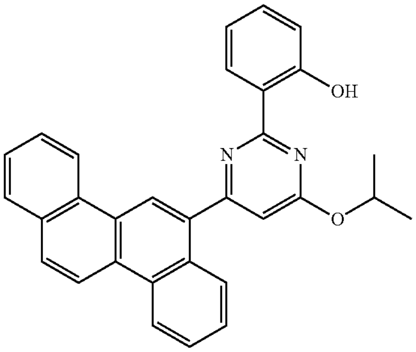

-continued
13
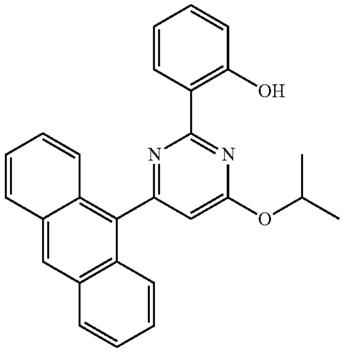
14
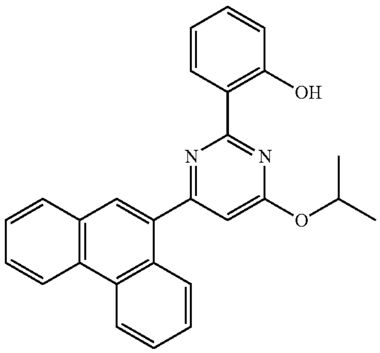
15
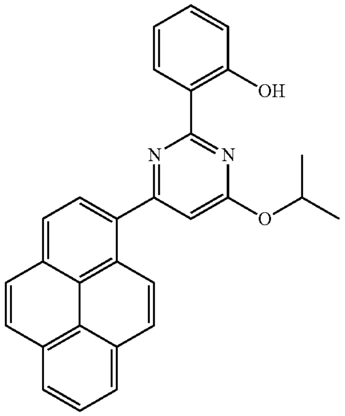
16
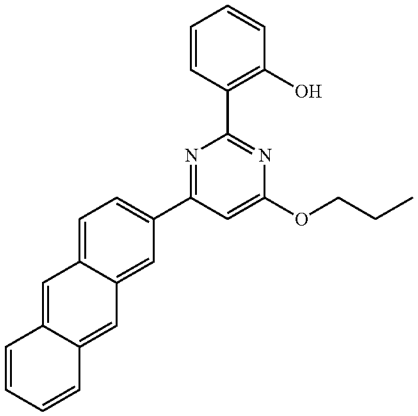
-continued
17
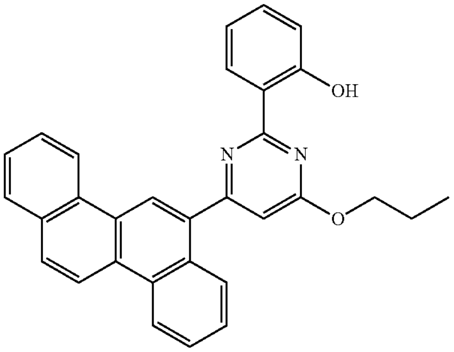
18
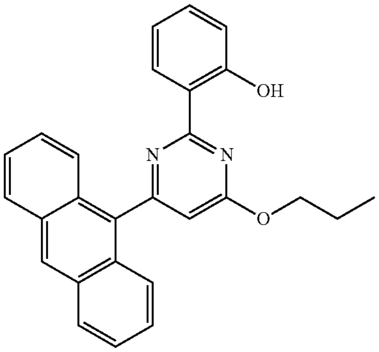
19
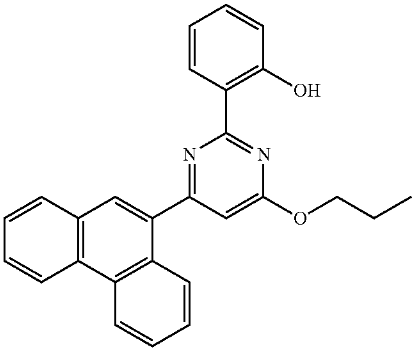
20
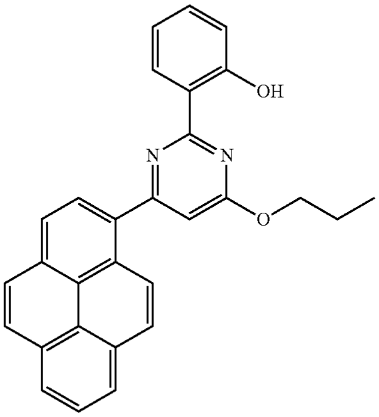

21
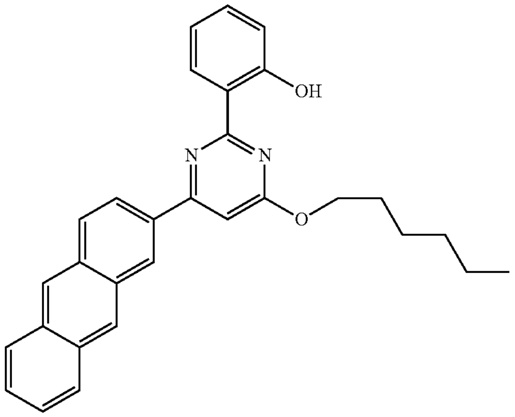
22
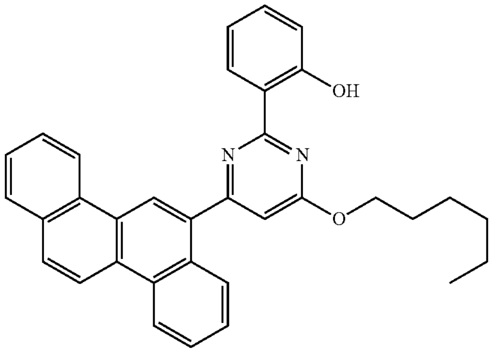
23
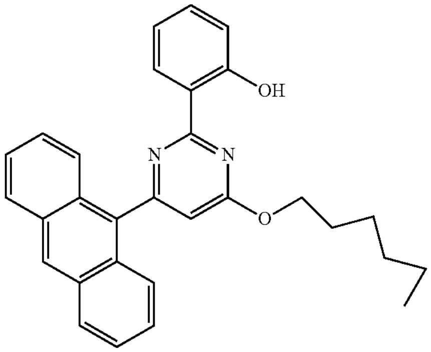
24
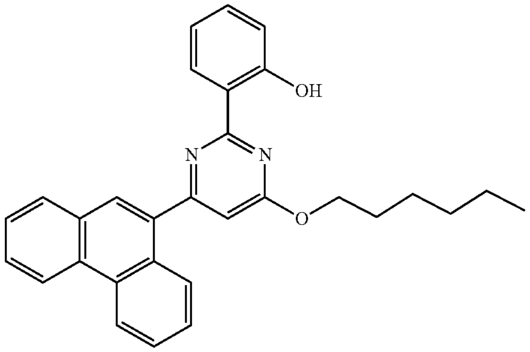
25
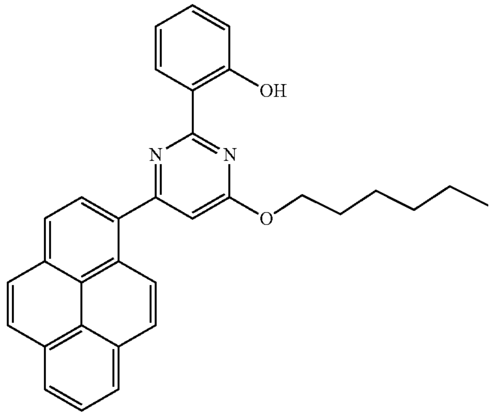
26
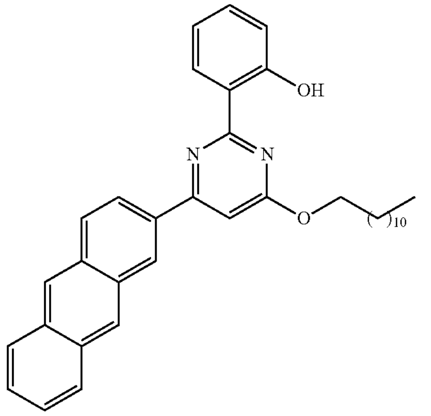
27
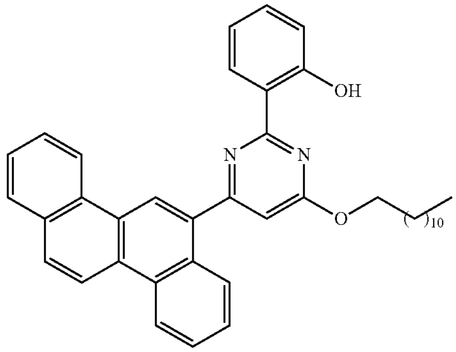
28
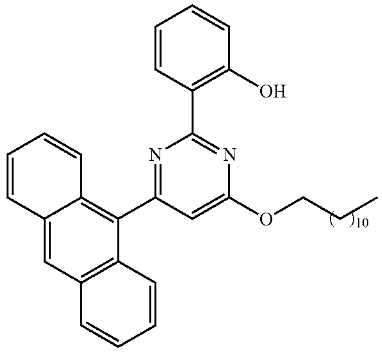

29
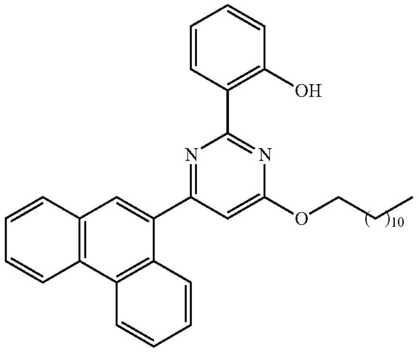
30
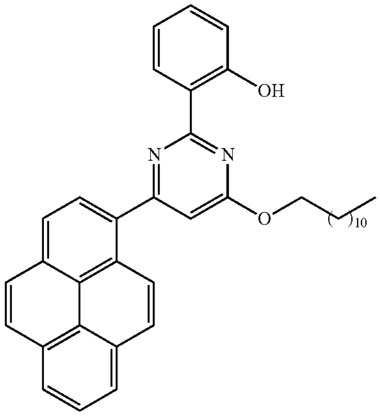
31
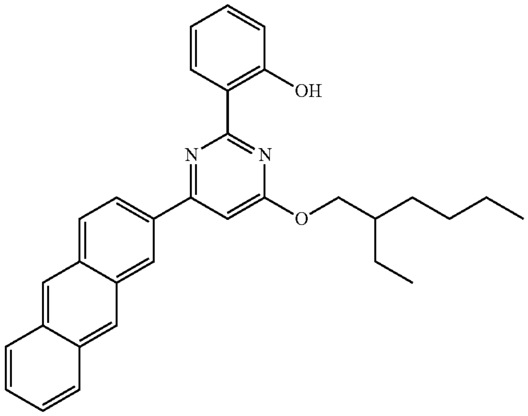
32
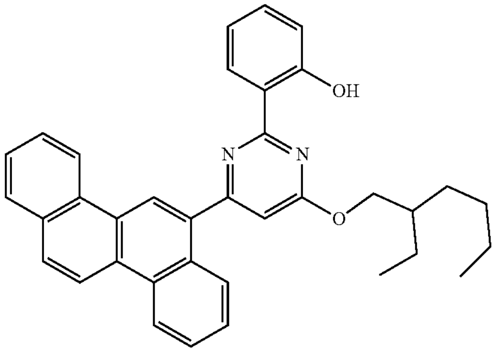
33
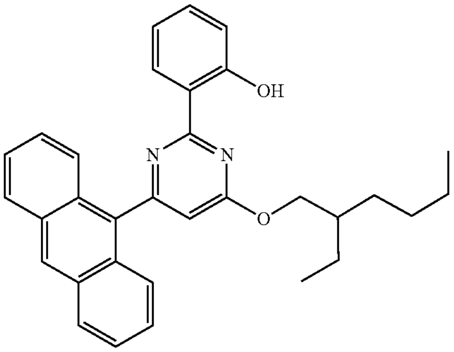
34
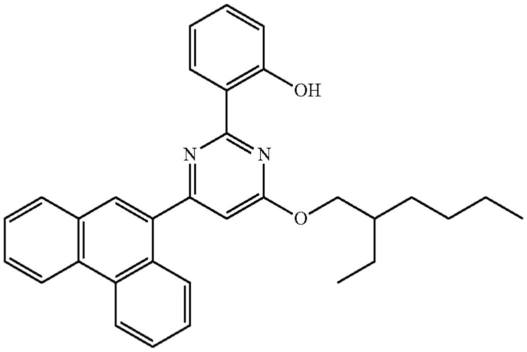
35
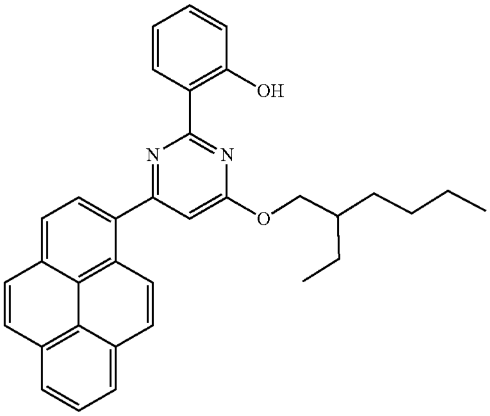
36
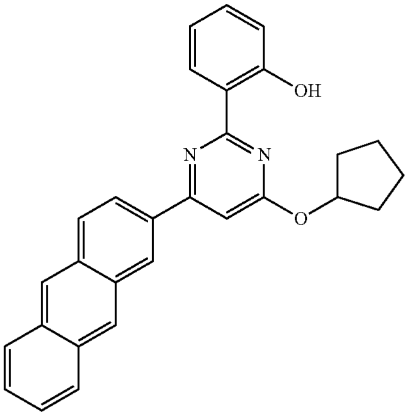

-continued
37
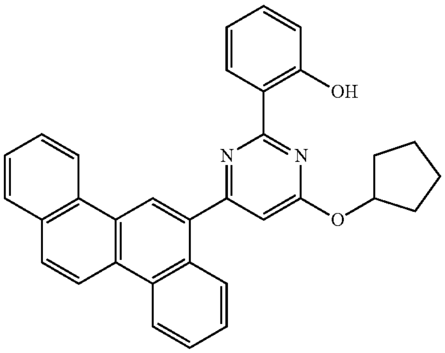
38
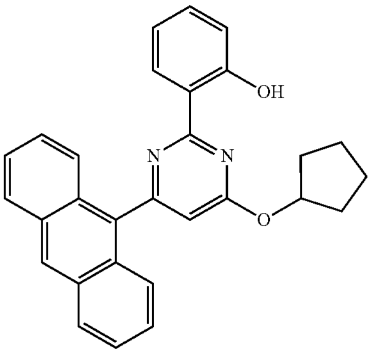
39
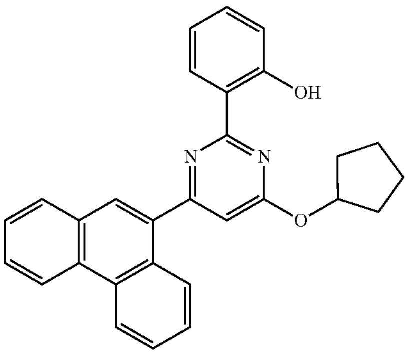
40
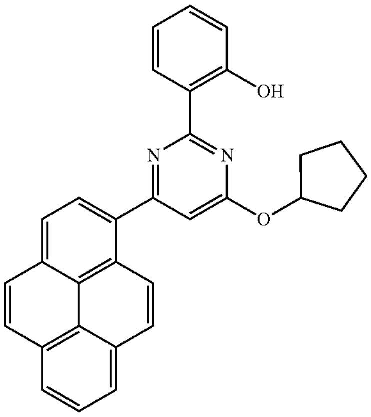
-continued
41
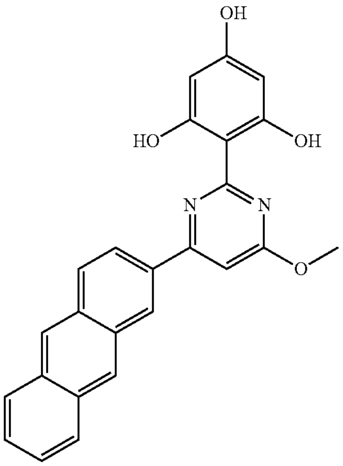
42
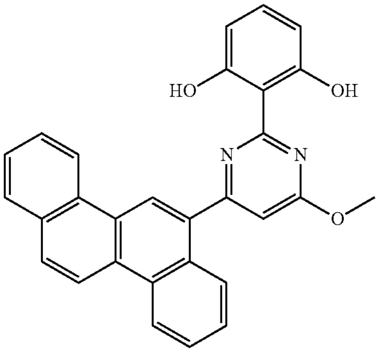
43
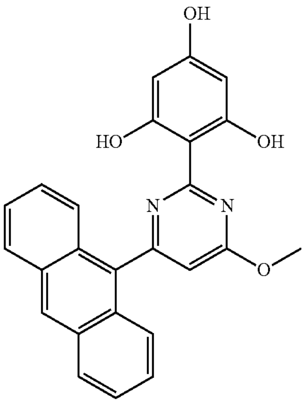
44
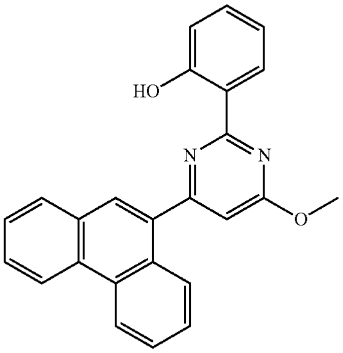

-continued
45
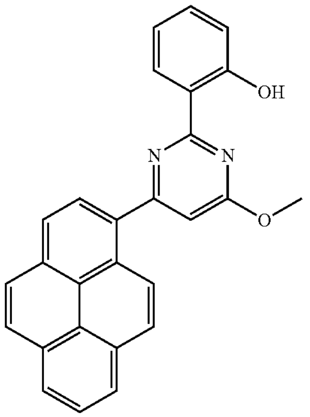
46
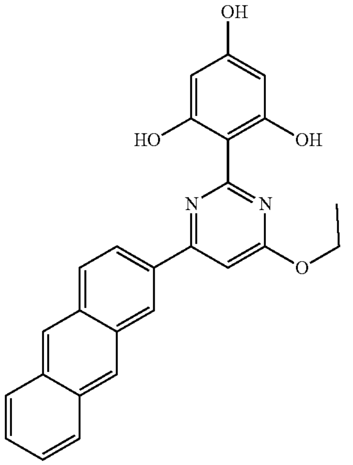
47
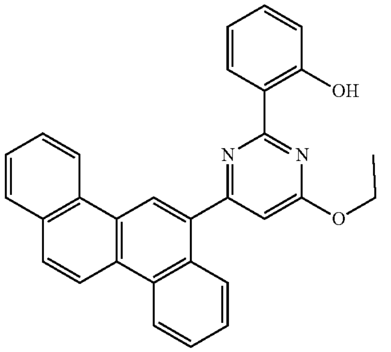
48
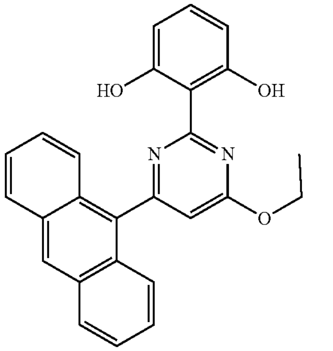
-continued
49
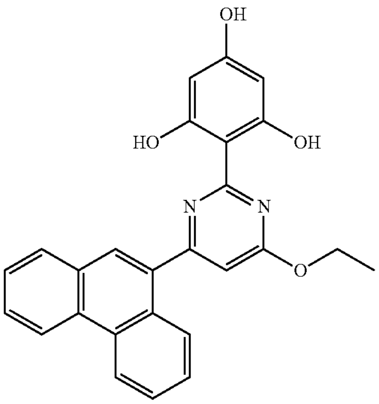
50
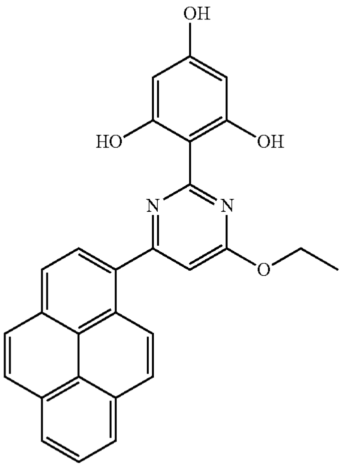
51
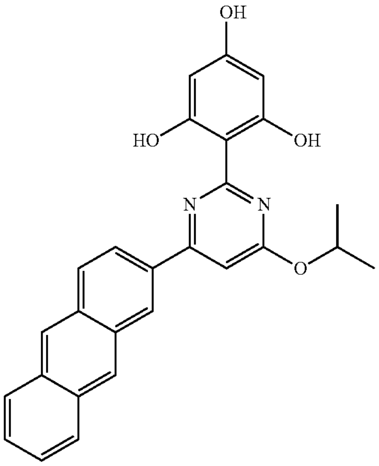

-continued
52
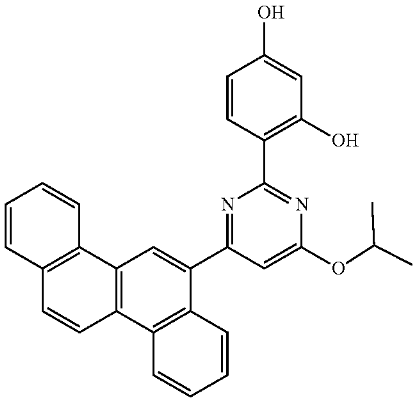
53
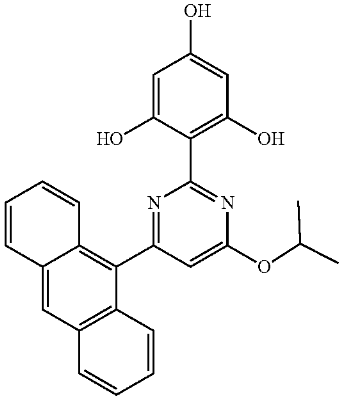
54
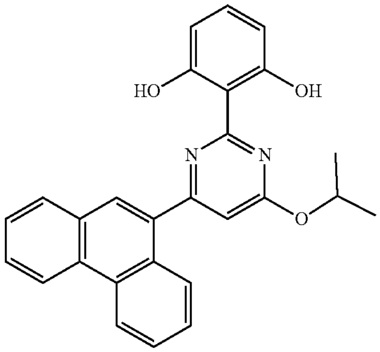
55
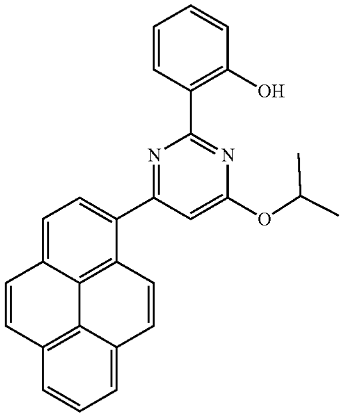
-continued
56
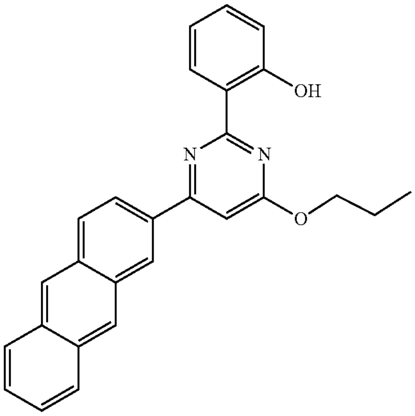
57
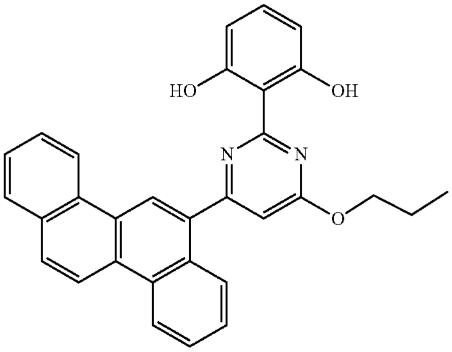
58
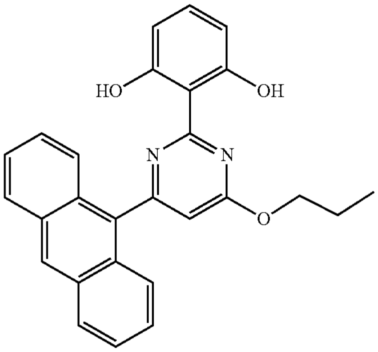
59
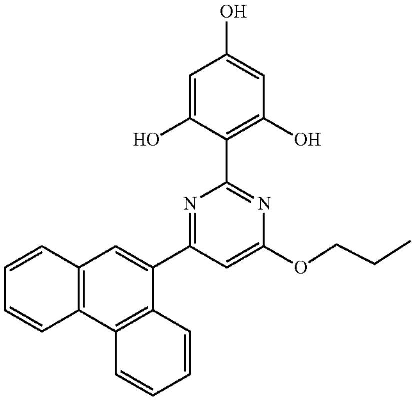

-continued
60
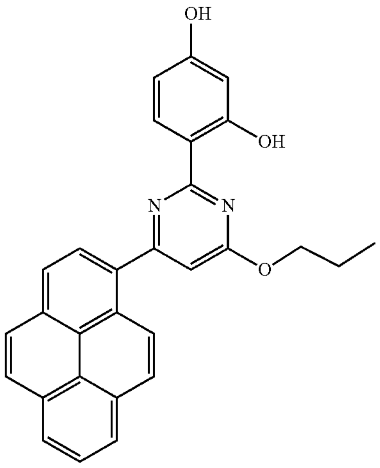
61
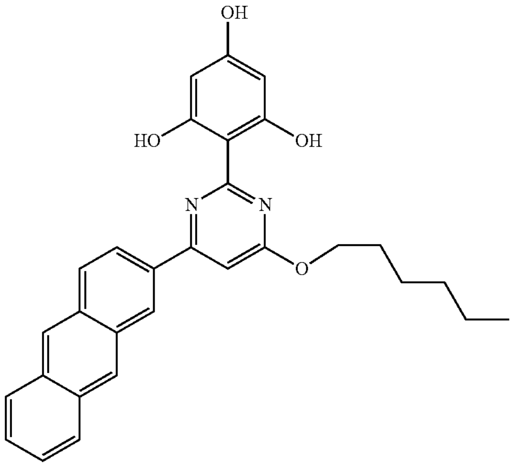
62
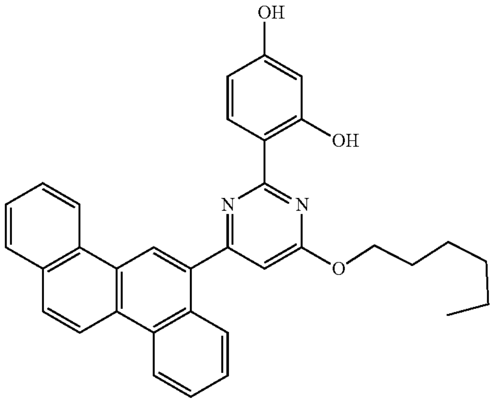
-continued
63
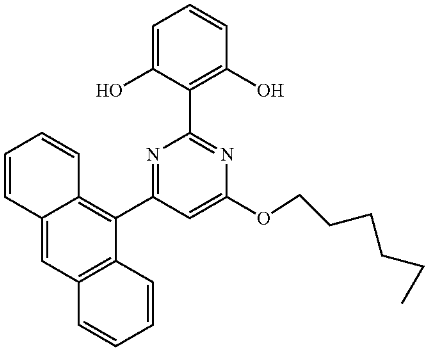
64
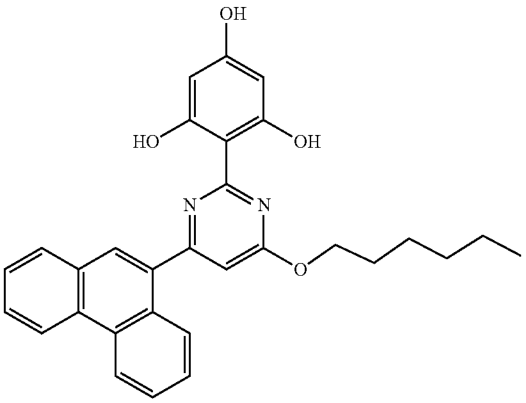
65
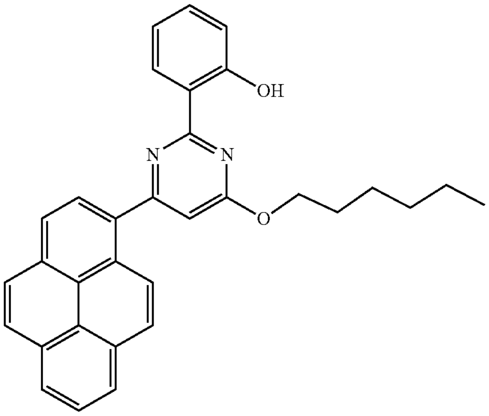

-continued
66
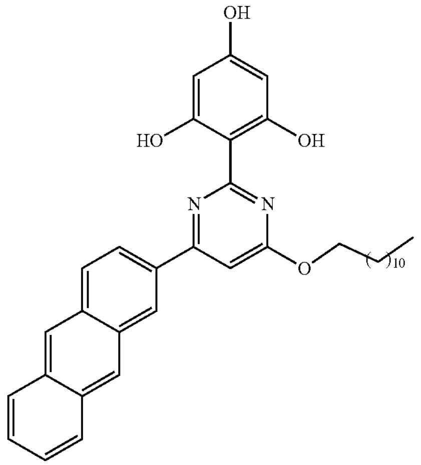
67
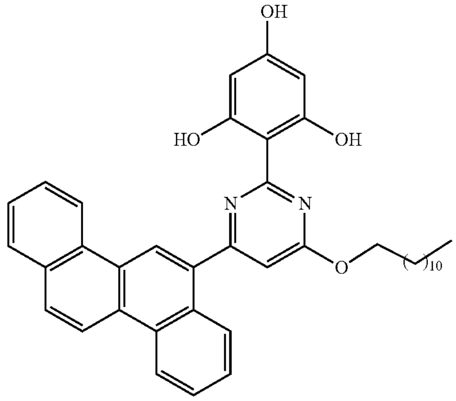
68
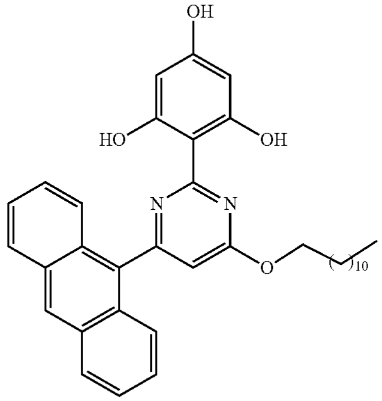
-continued
69
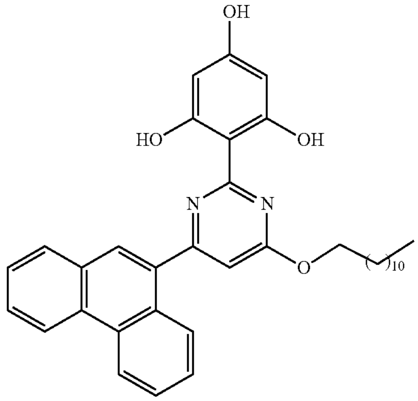
70
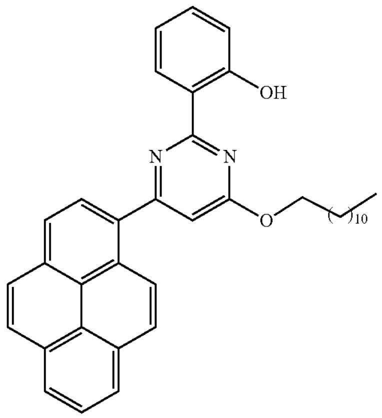
71
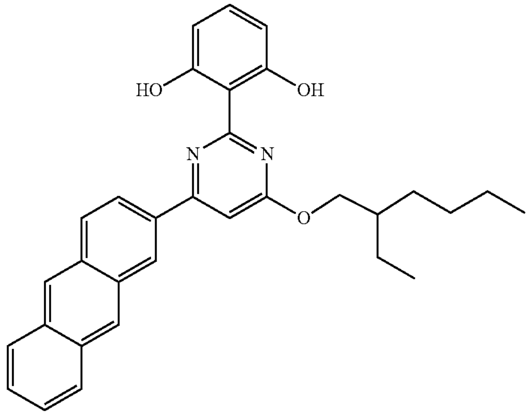

-continued
72
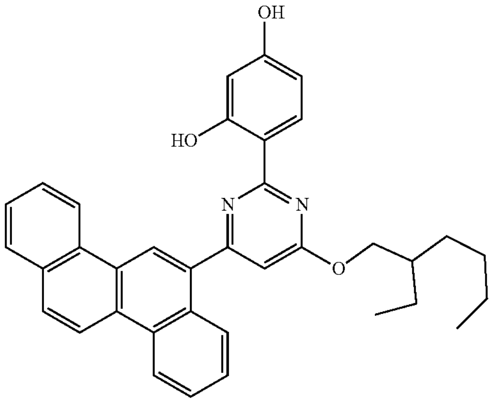
73
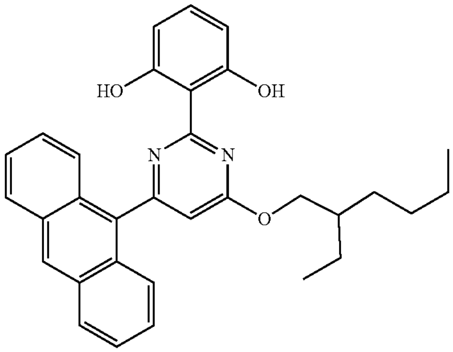
74
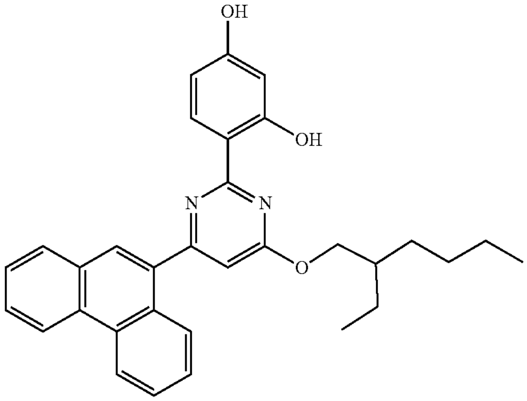
75
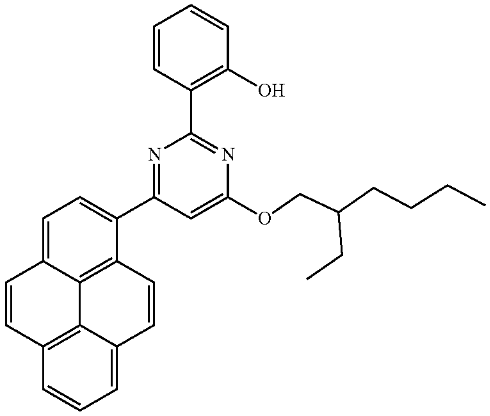
-continued
76
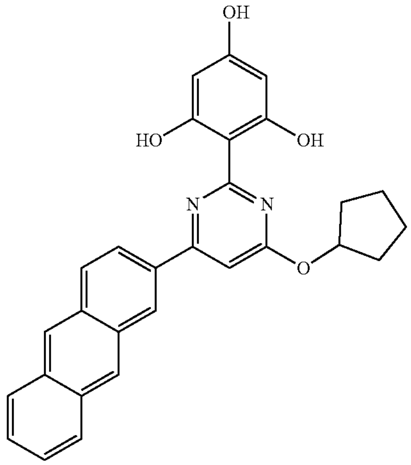
77
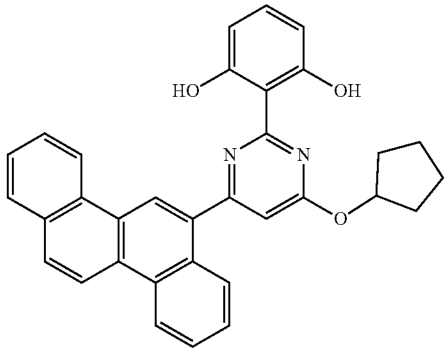
78
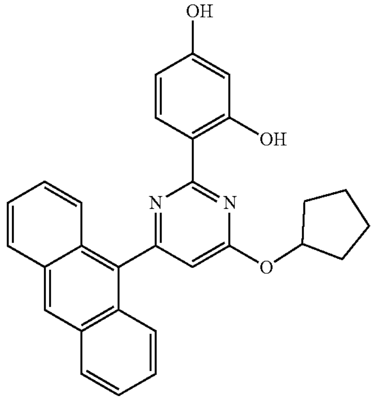
79
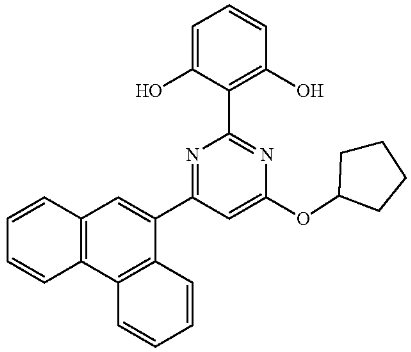

-continued
80
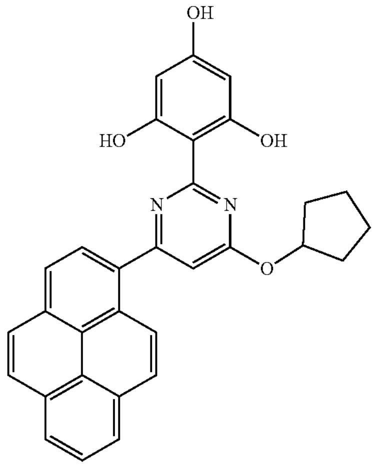
81
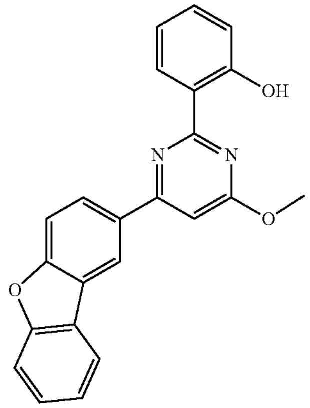
82
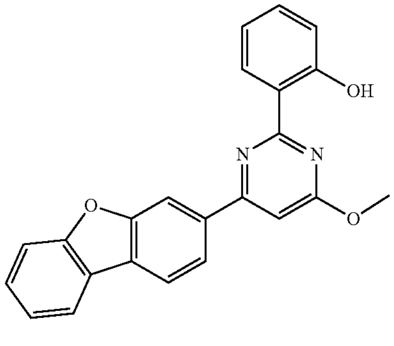
83
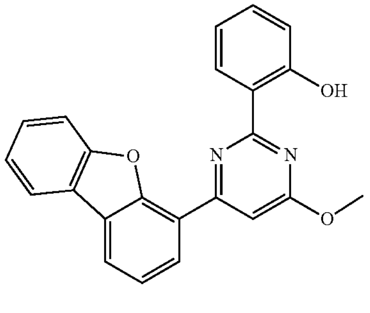
-continued
84
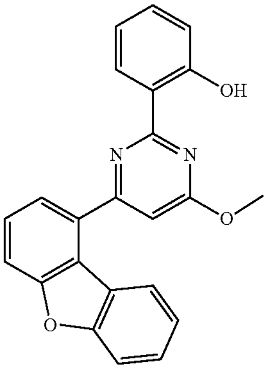
85
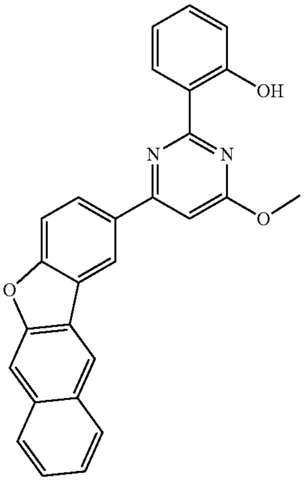
86
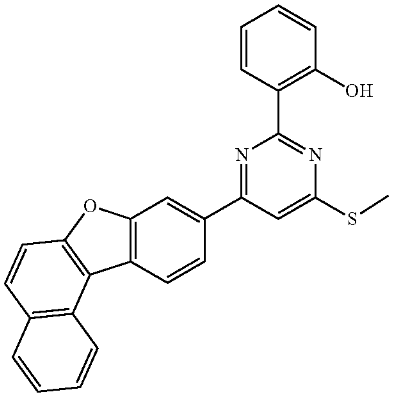
87
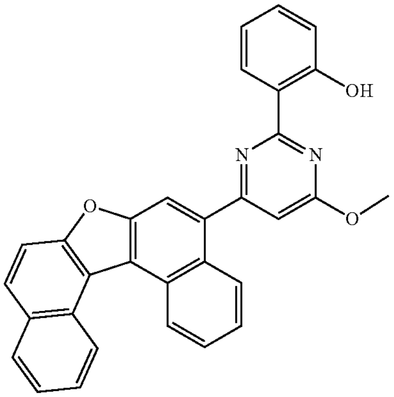

-continued
88
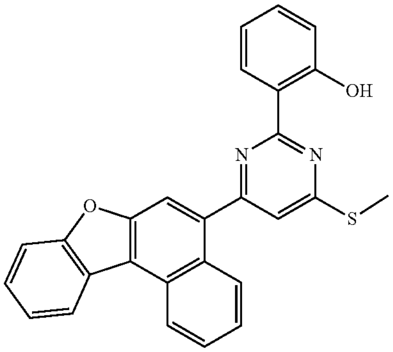
89
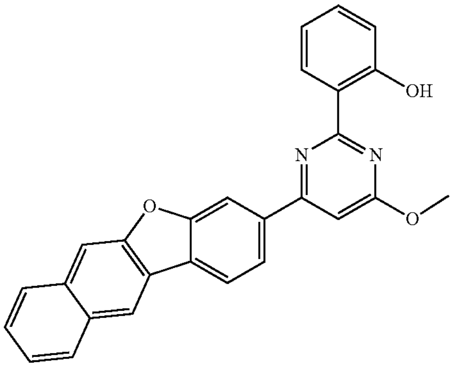
90
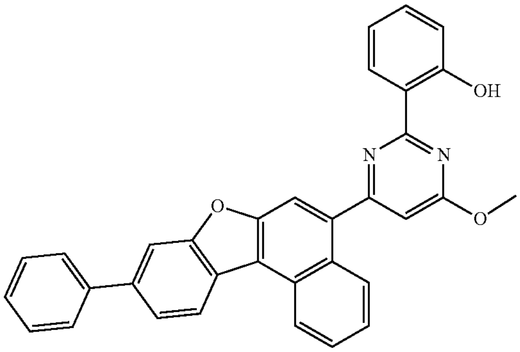
91
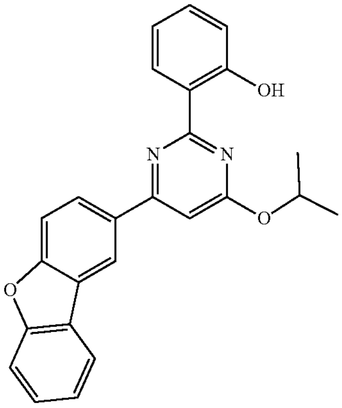
-continued
92
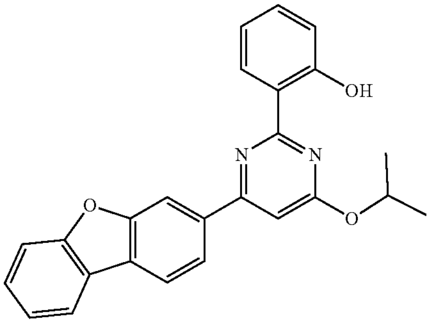
93
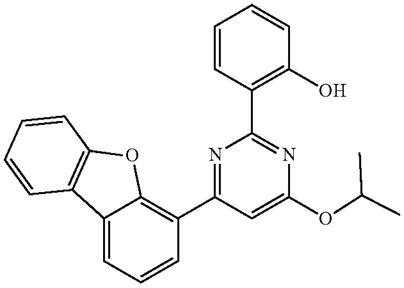
94
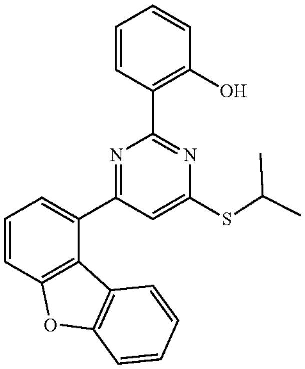
95
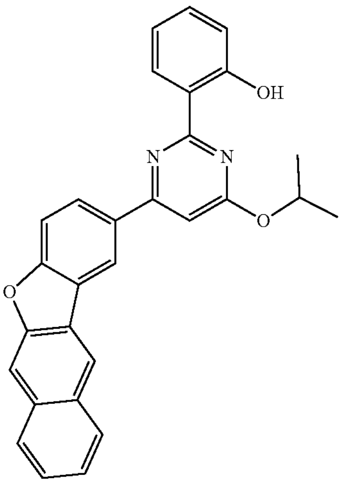

-continued
96
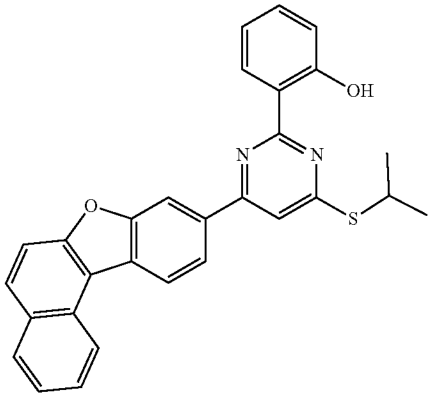
97
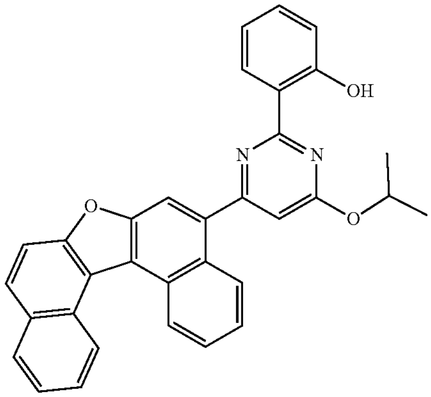
98
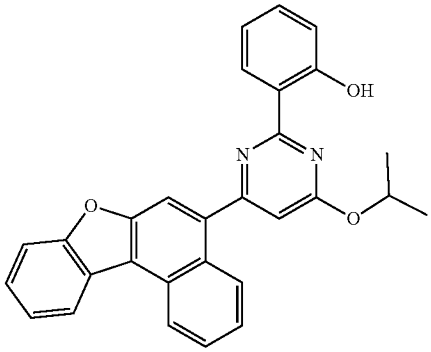
99
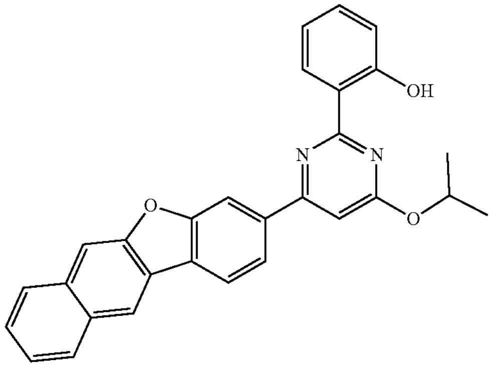
-continued
100
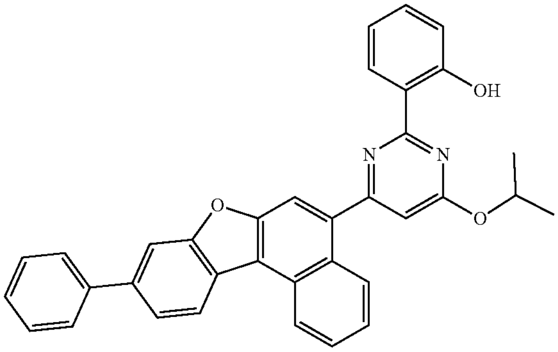
101
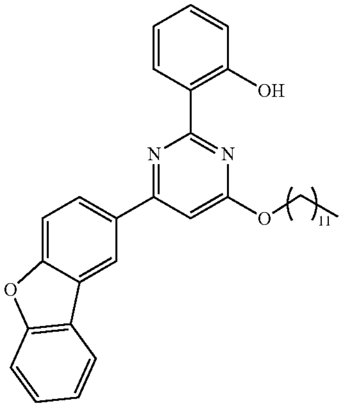
102
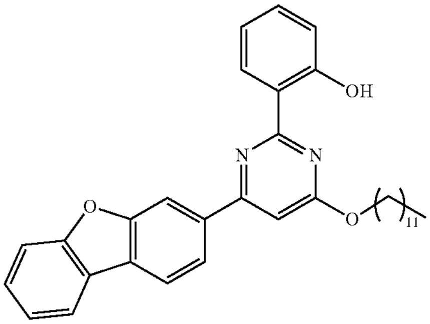
103
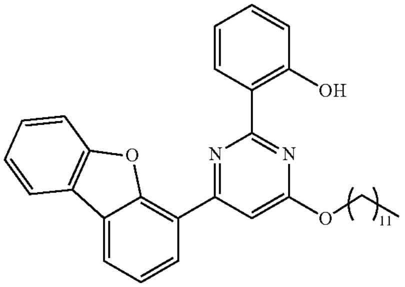

104
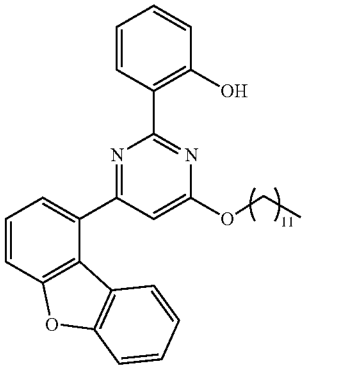
105
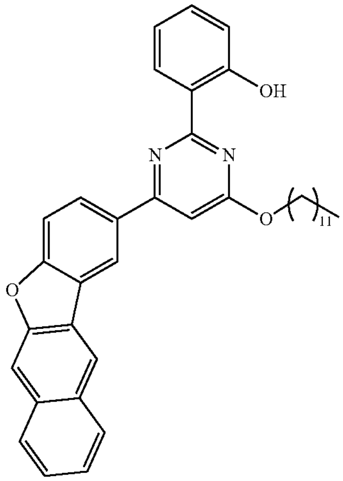
106
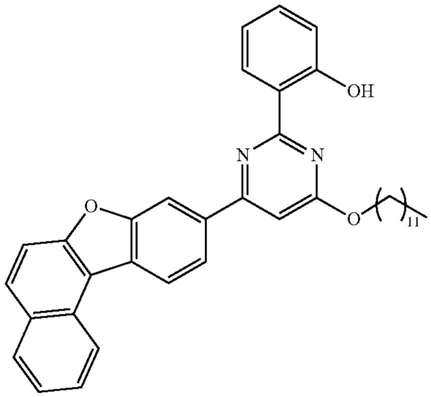
107
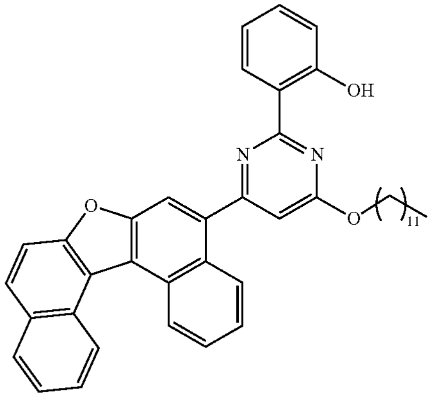
108
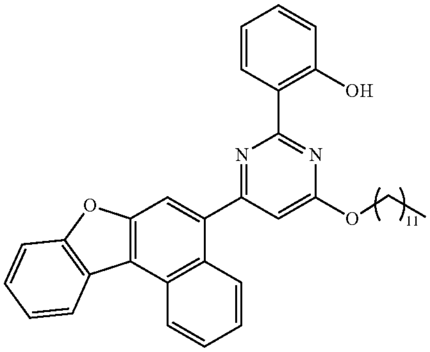
109
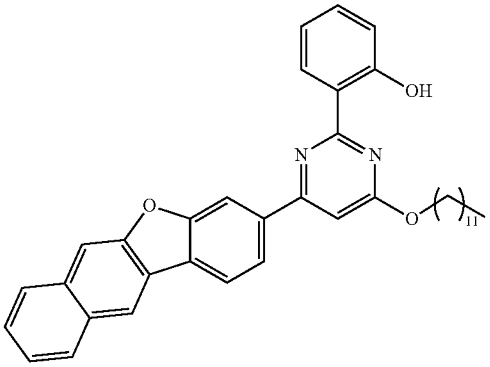
110
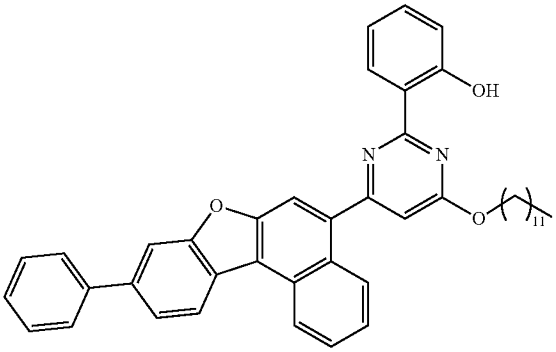
111
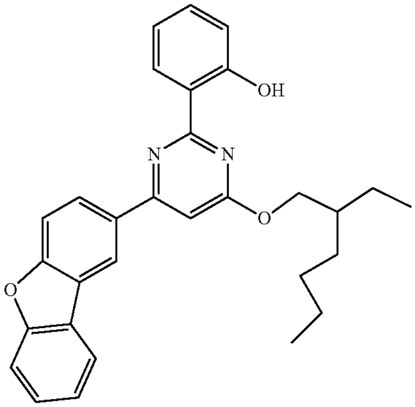

-continued
112
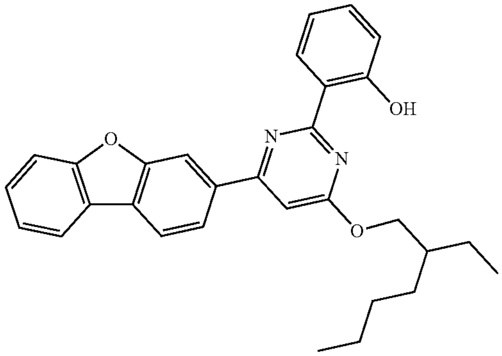
113
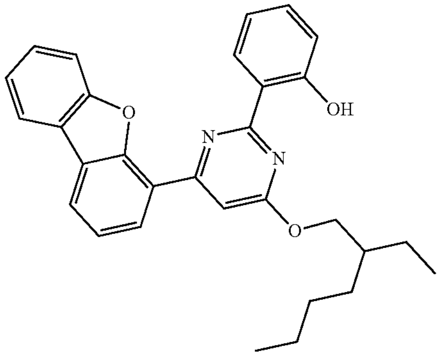
114
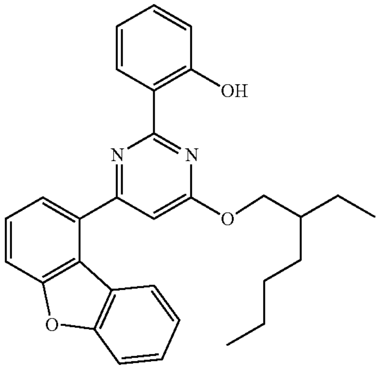
115
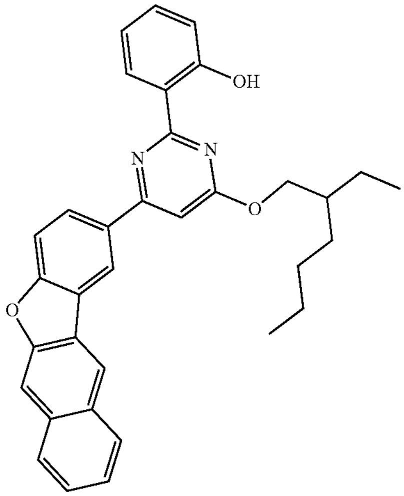
-continued
116
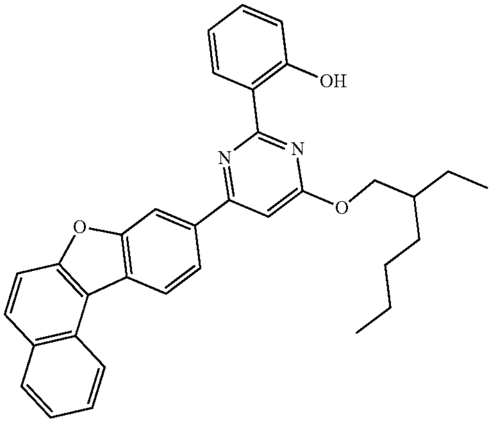
117
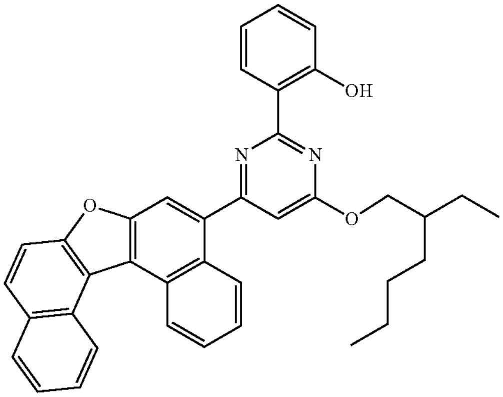
118
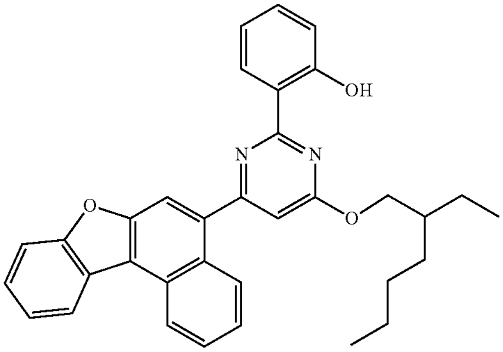

-continued
119
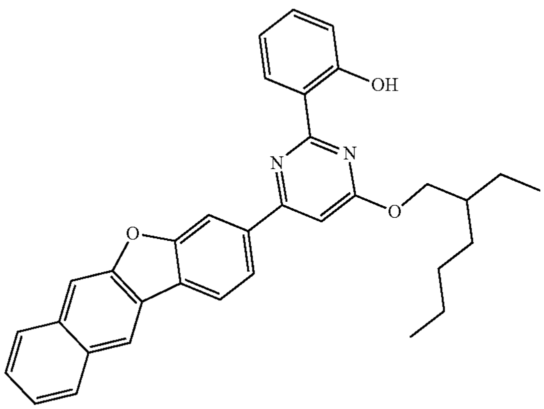
120
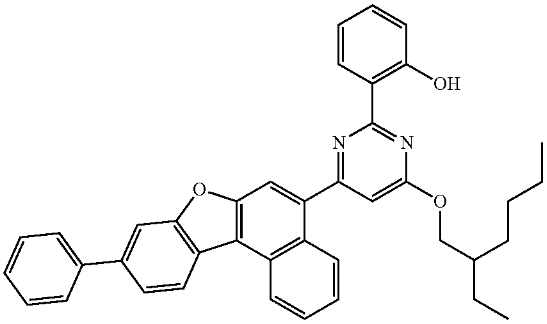
121
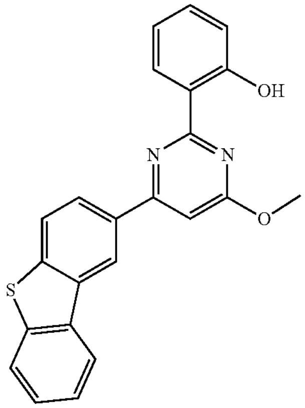
122
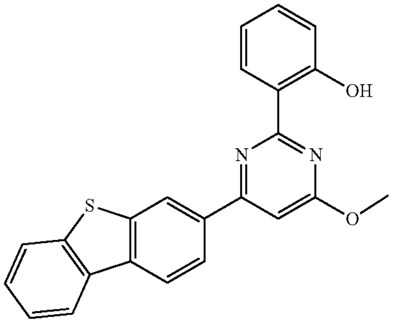
-continued
123
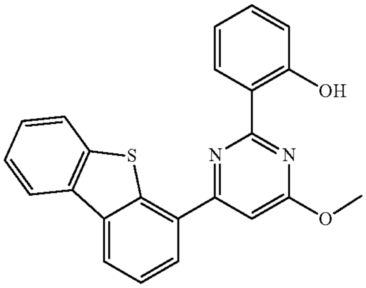
124
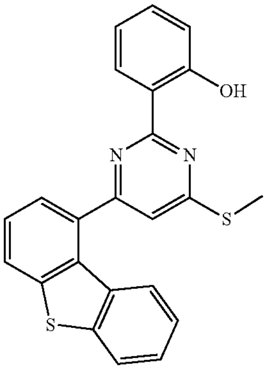
125
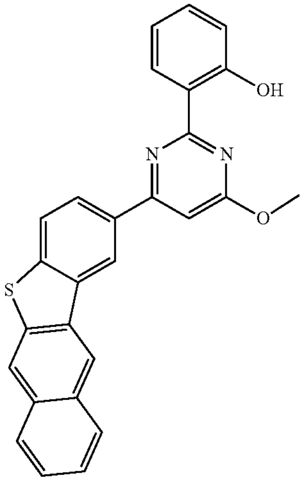
126
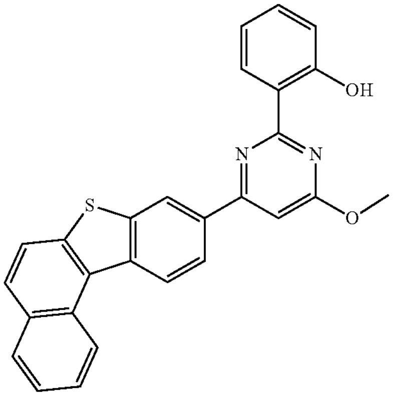

-continued
127
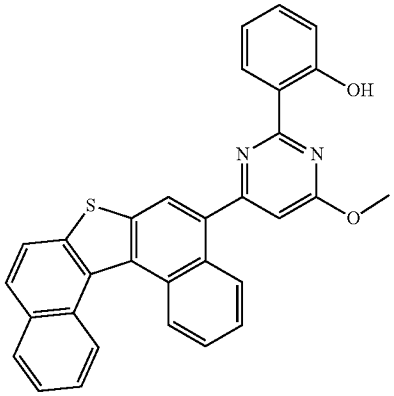
128
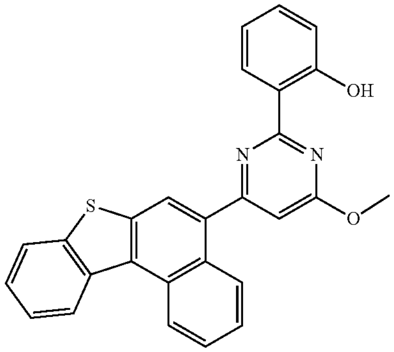
129
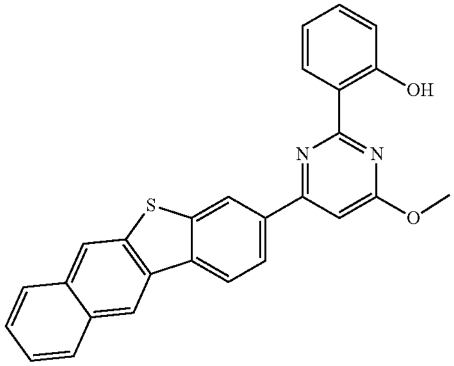
130
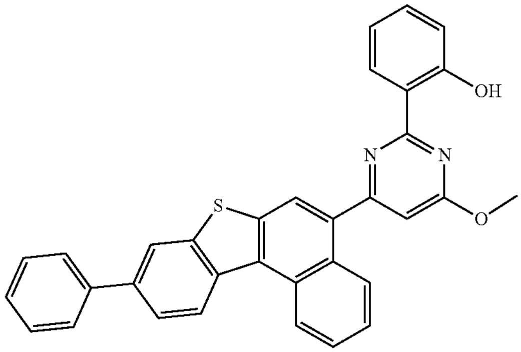
-continued
131
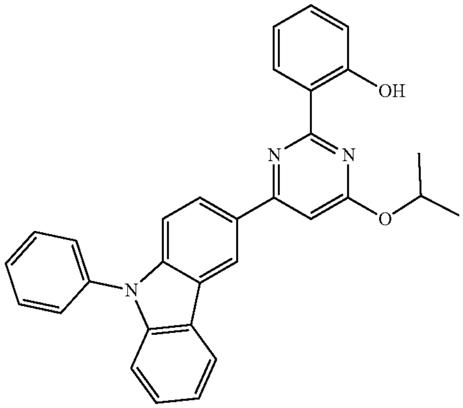
132
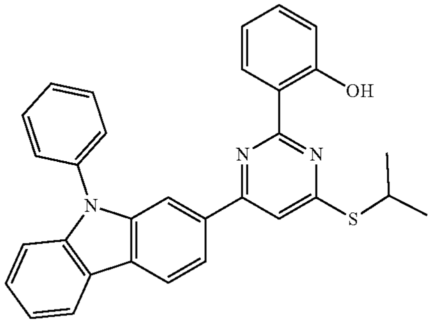
133
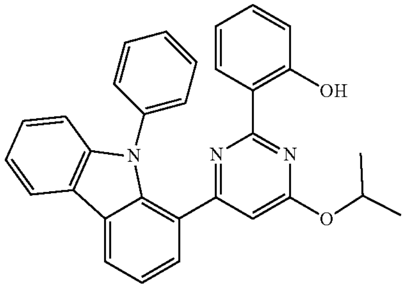
134
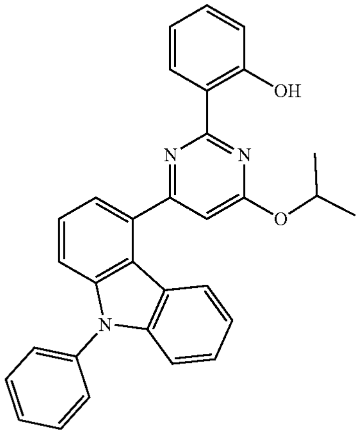

-continued
135
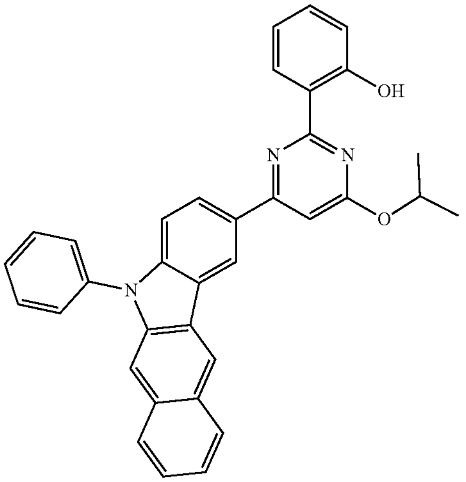
136
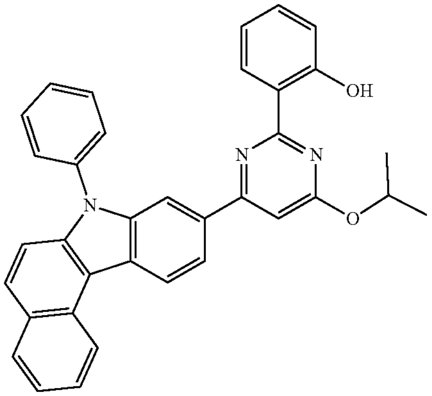
137
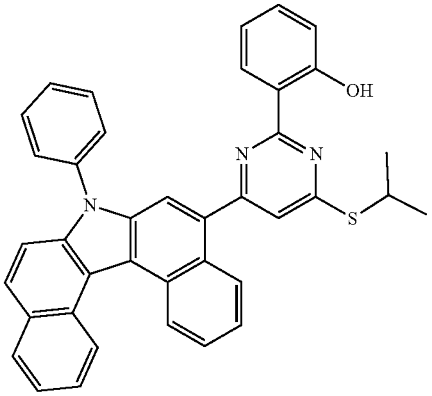
138
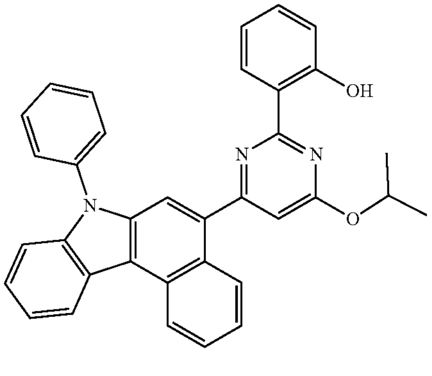
-continued
139
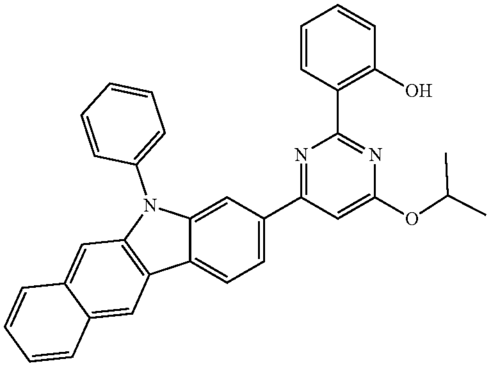
140
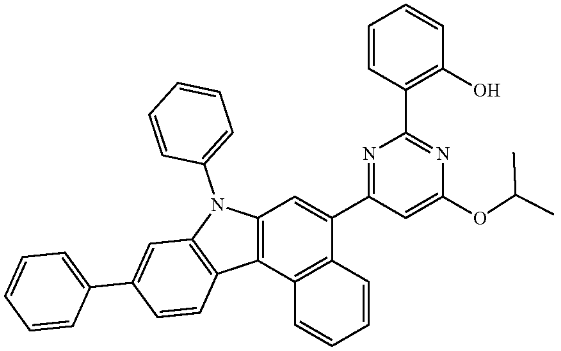
141
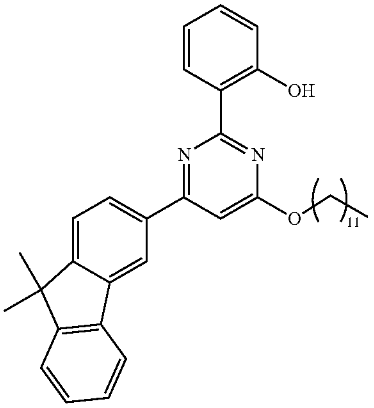
142
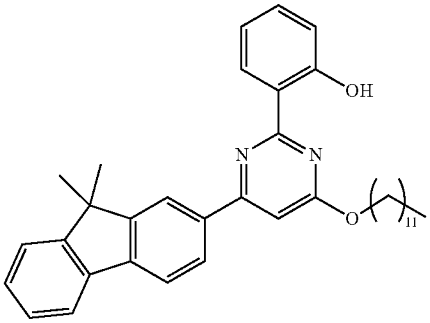

-continued
143
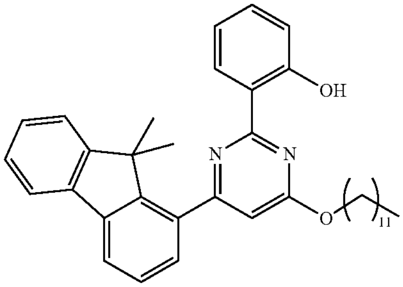
144
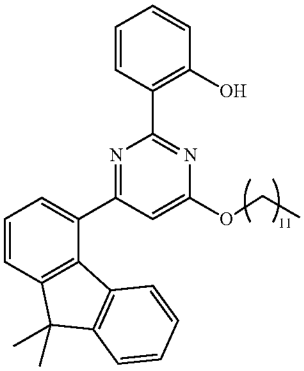
145
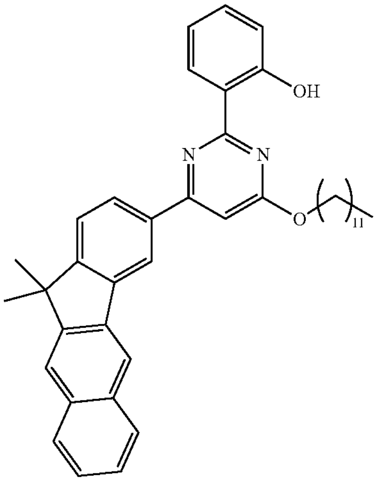
146
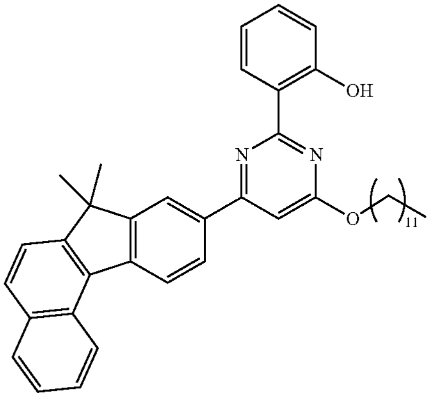
-continued
147
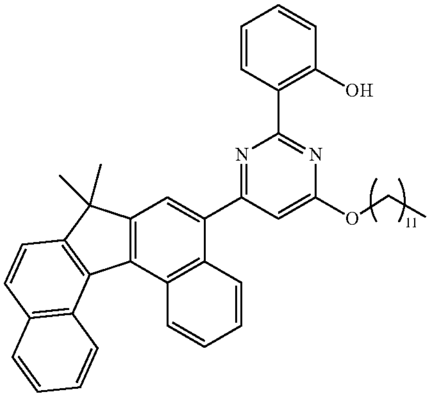
148
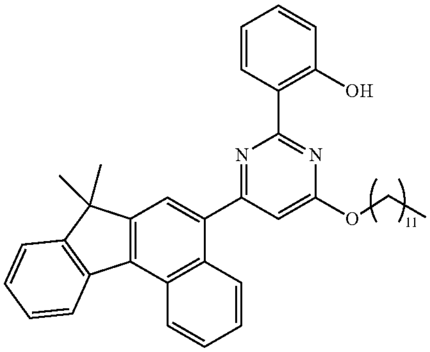
149
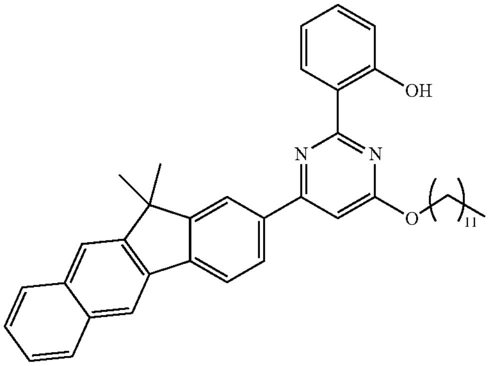
150
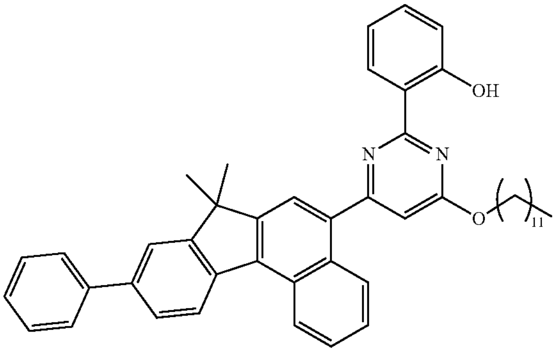

-continued
151
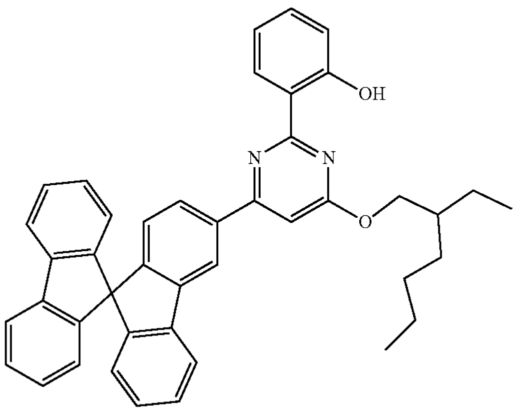
152
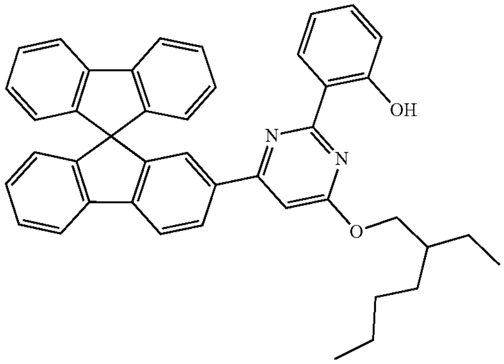
153
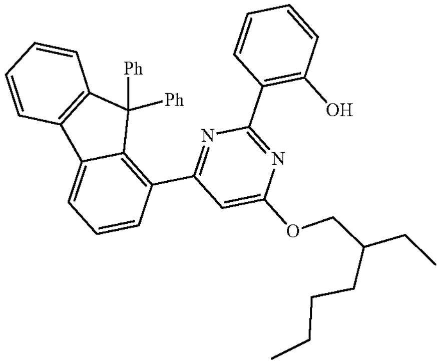
154
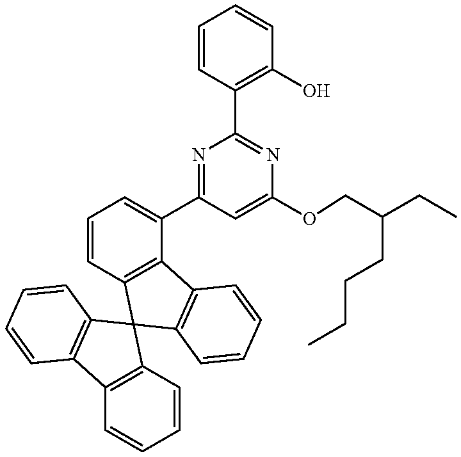
-continued
155
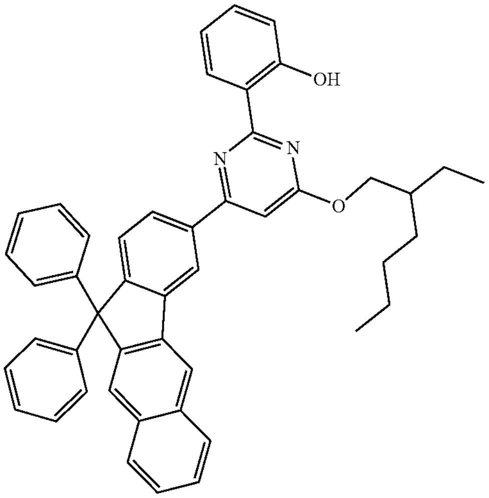
156
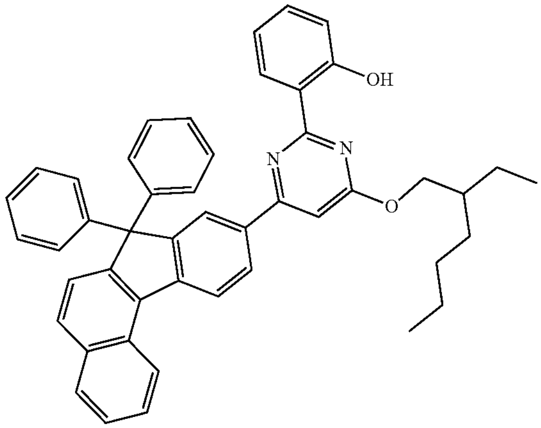
157
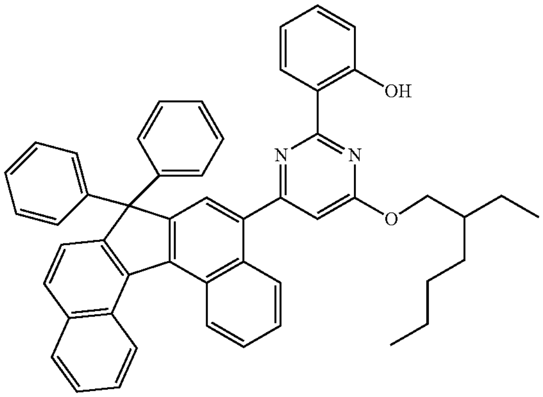

-continued
158
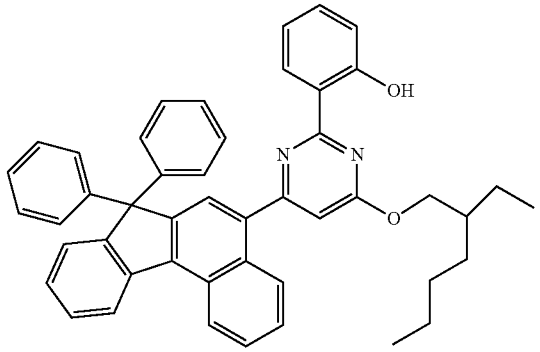
159
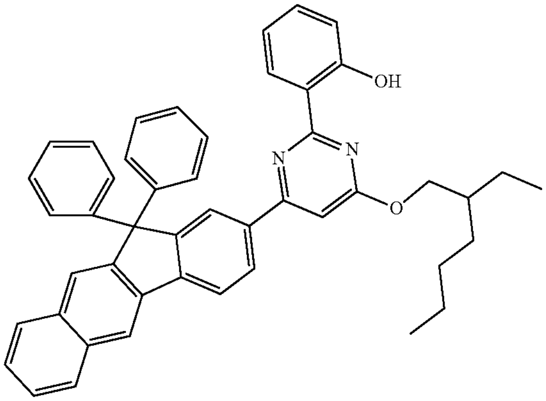
160
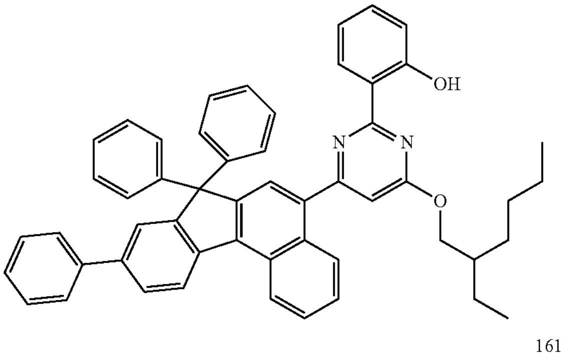
161
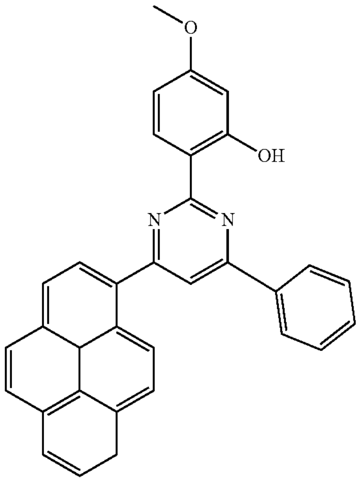
-continued
162
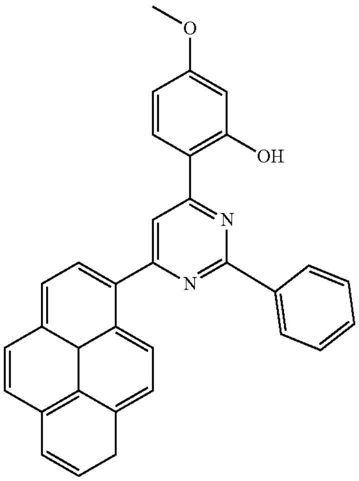
163
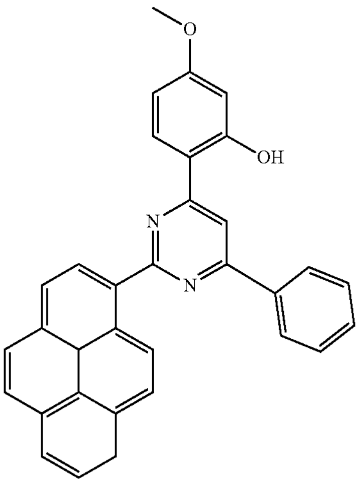
164
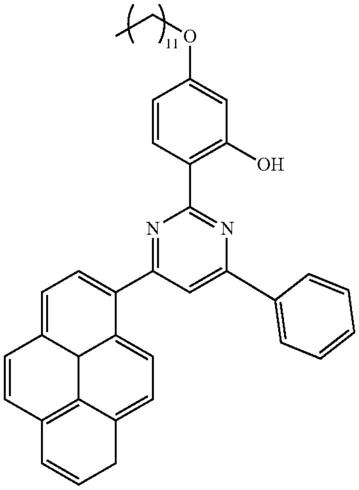

-continued
165
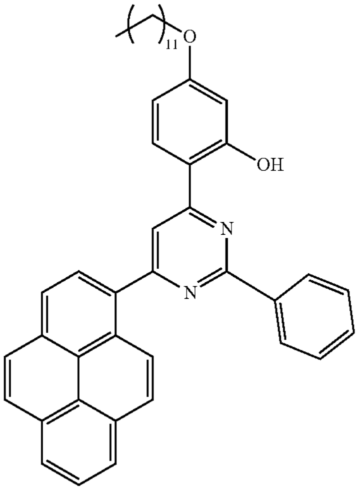
166
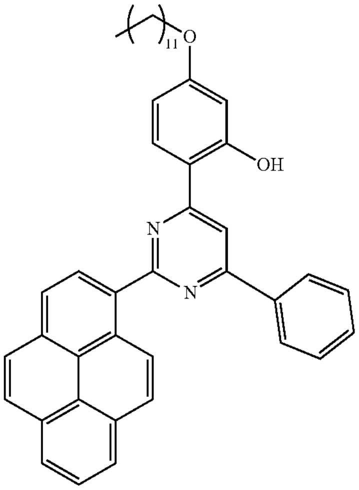
167
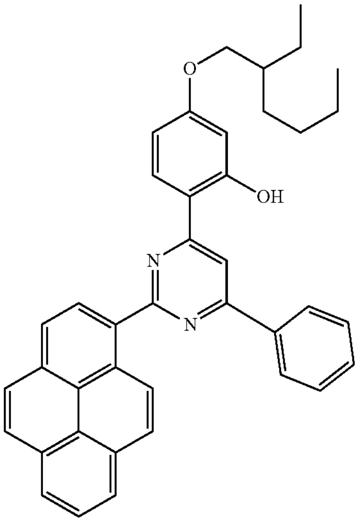
-continued
168
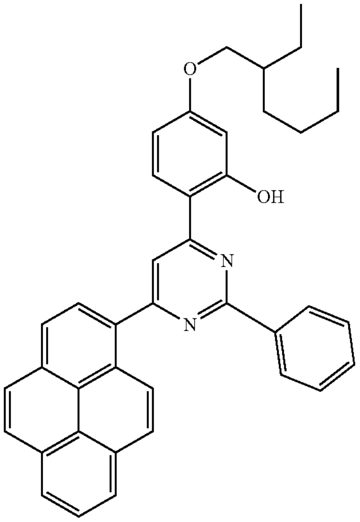
169
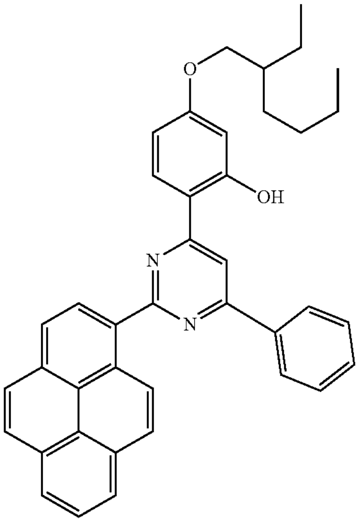
170
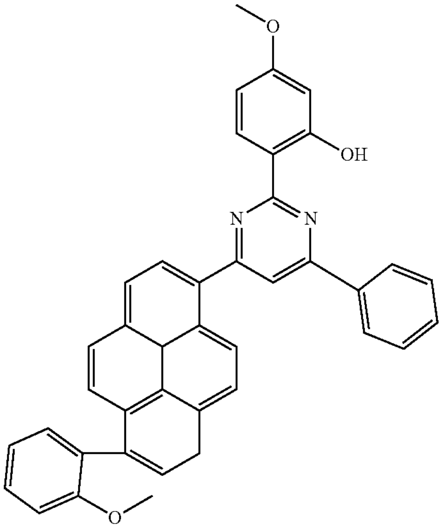

171
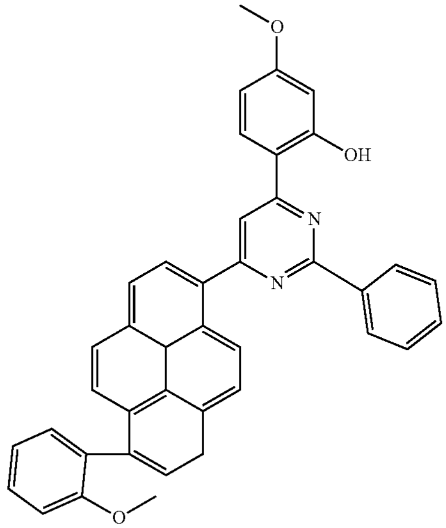
172
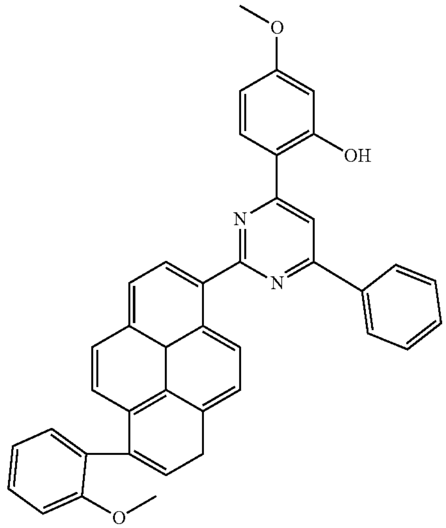
173
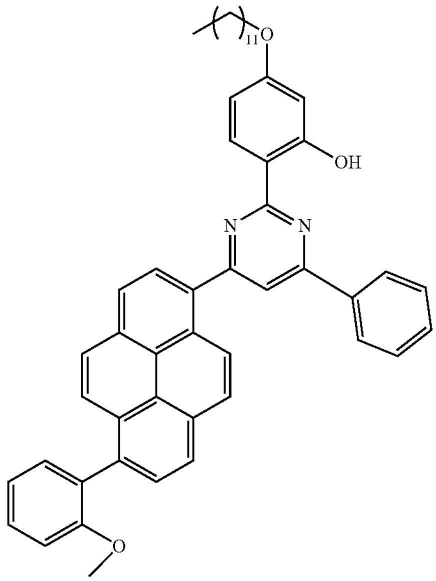
174
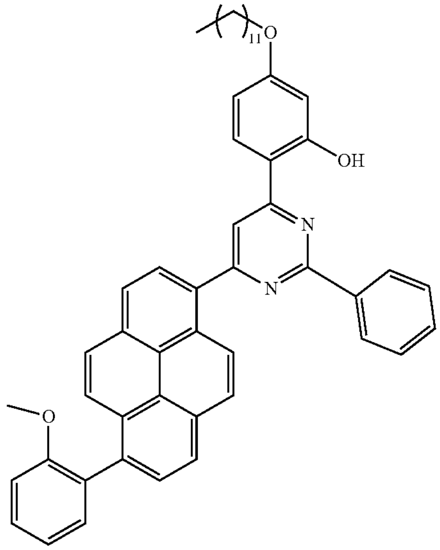
175
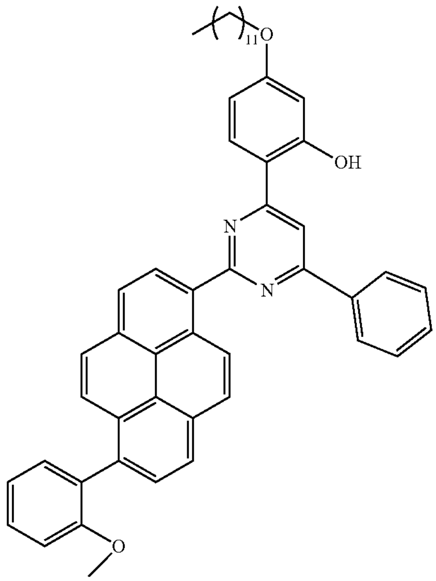

176
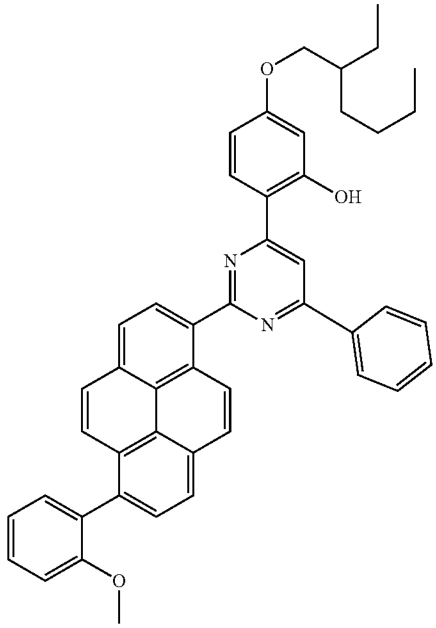
177
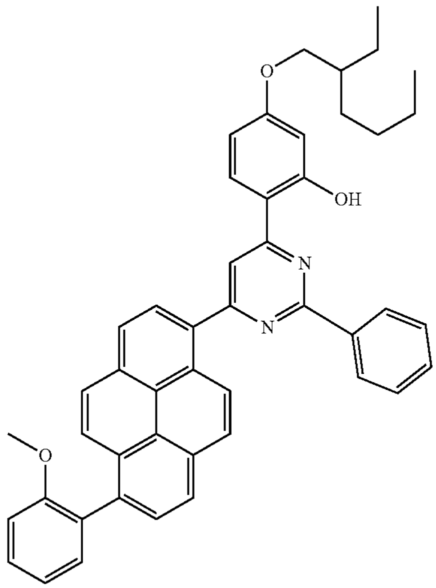
178
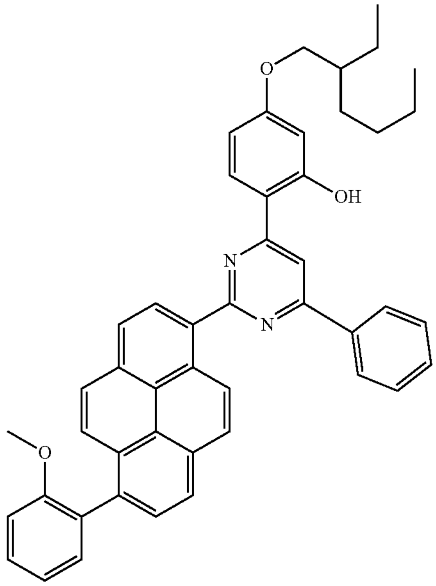
Compound Group 2
1
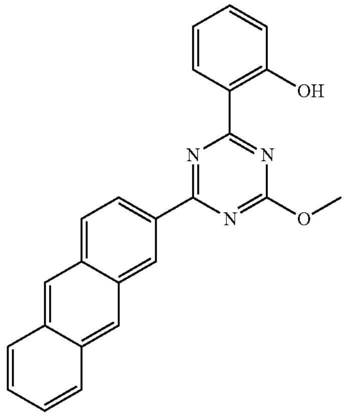
2
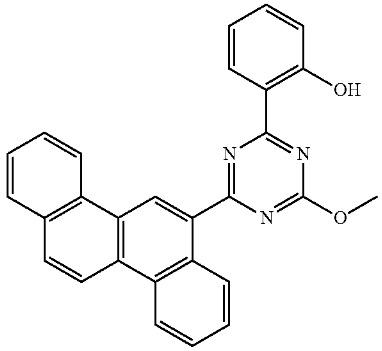

-continued
3
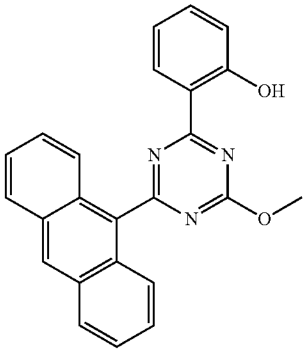
4
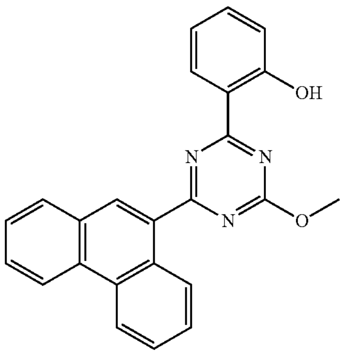
5
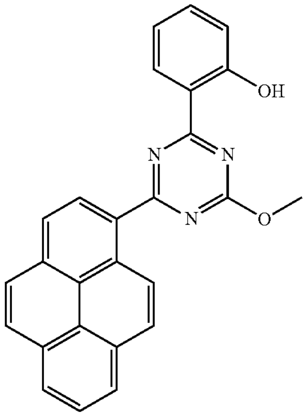
6
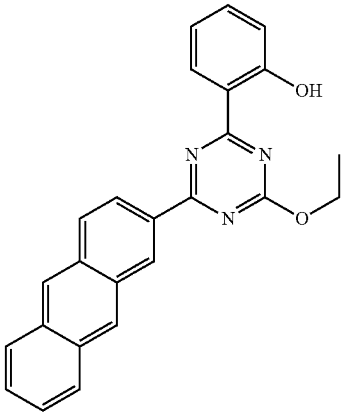
-continued
7
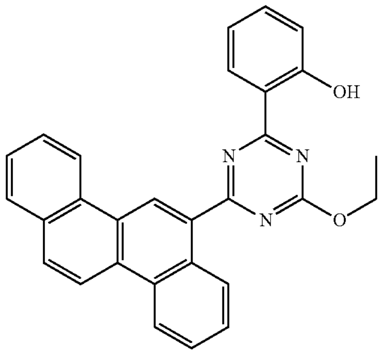
8
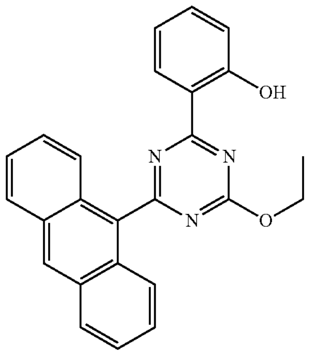
9
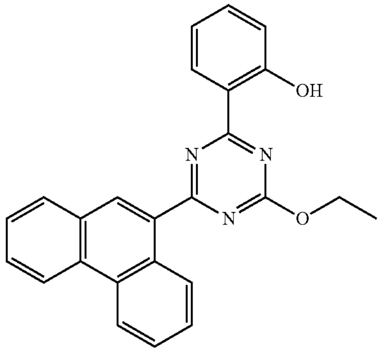
10
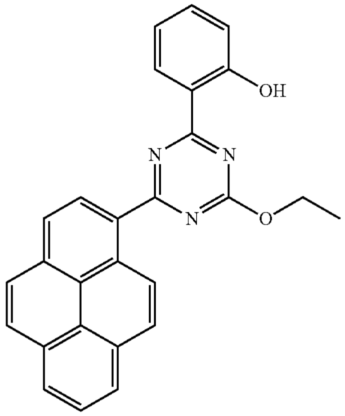

-continued
11
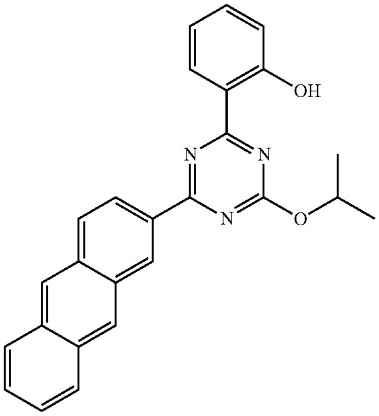
12
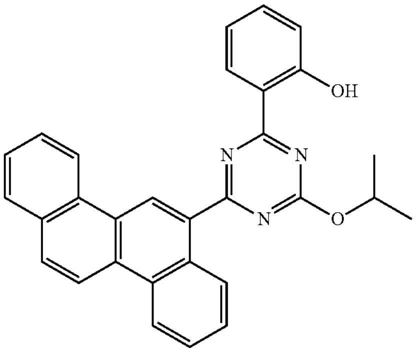
13
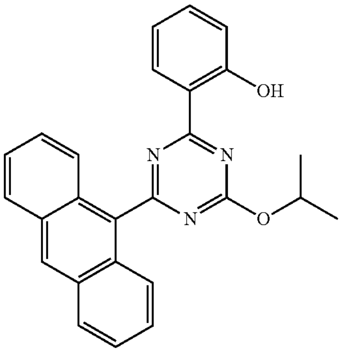
14
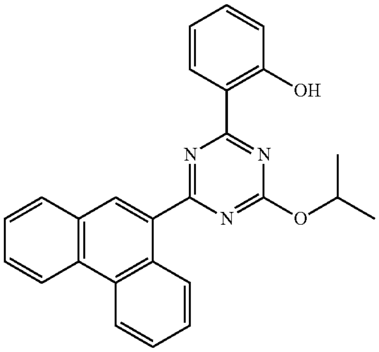
-continued
15
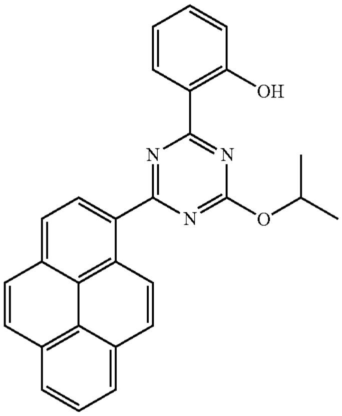
16
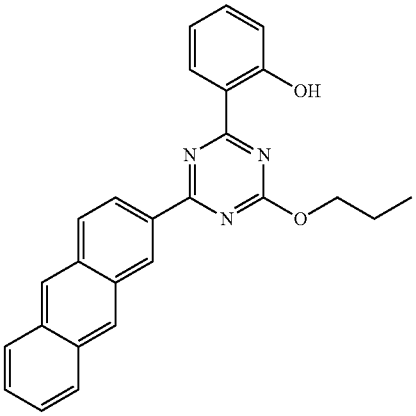
17
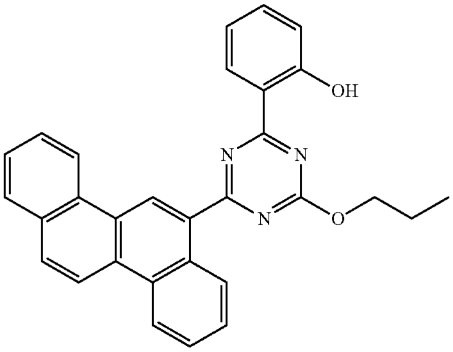
18
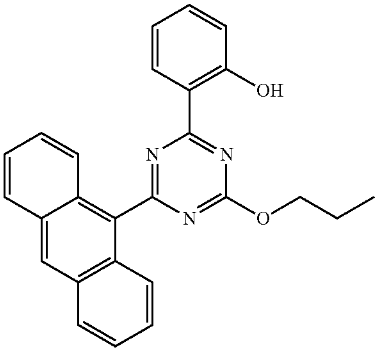

-continued
19
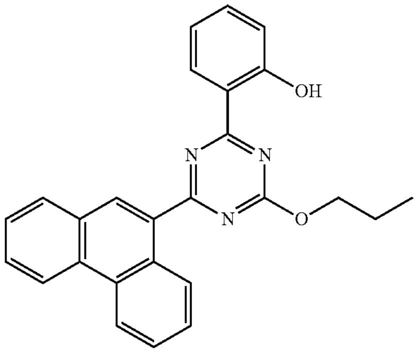
20
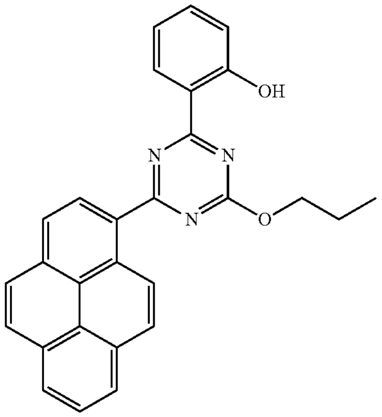
21
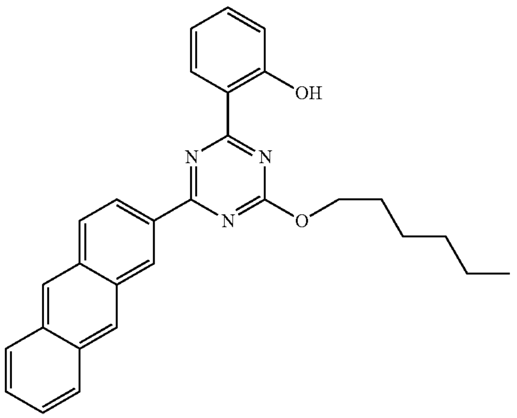
22
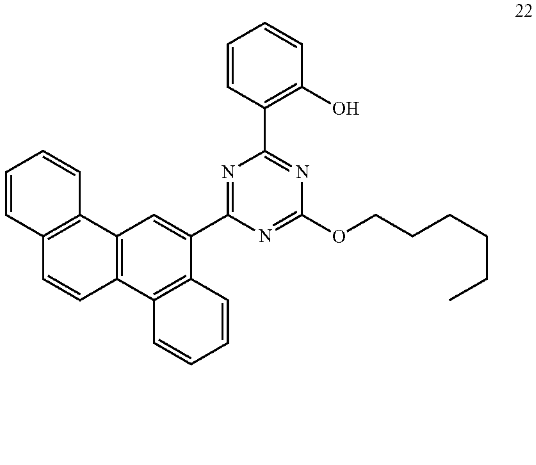
-continued
23
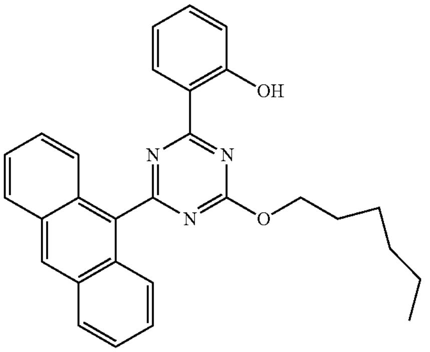
24
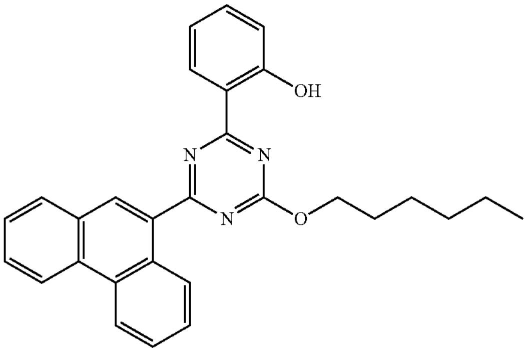
25
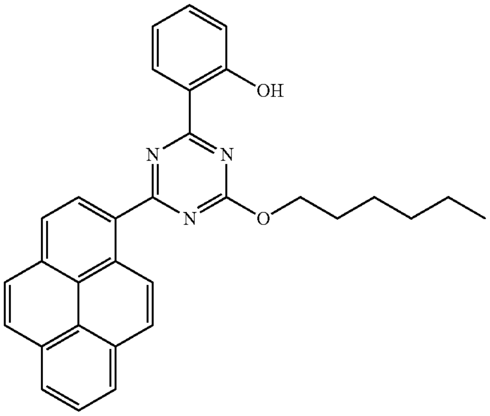
26
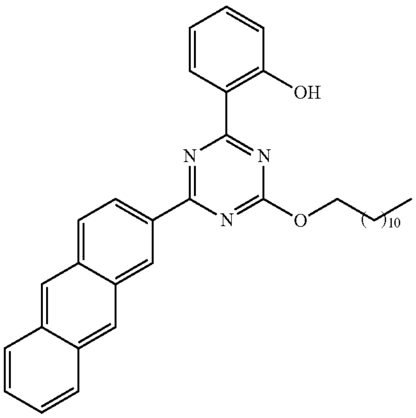

27
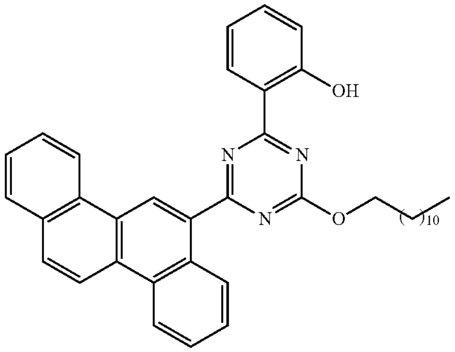
28
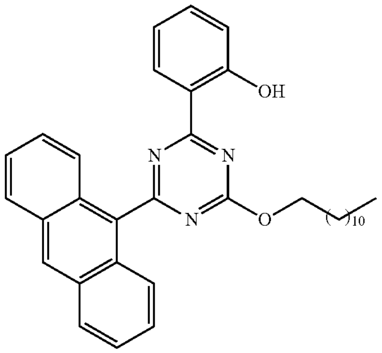
29
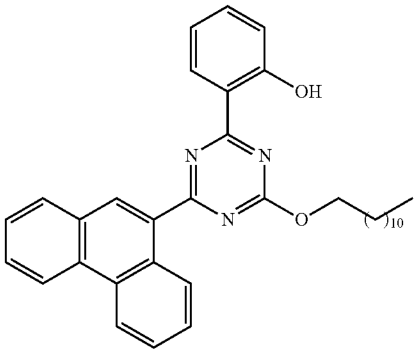
30
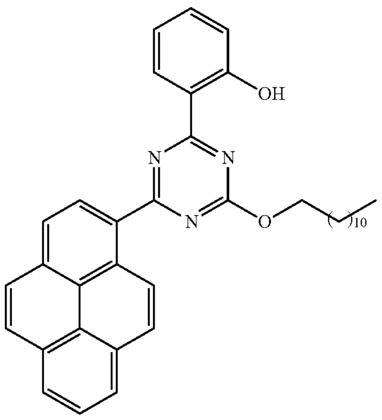
31
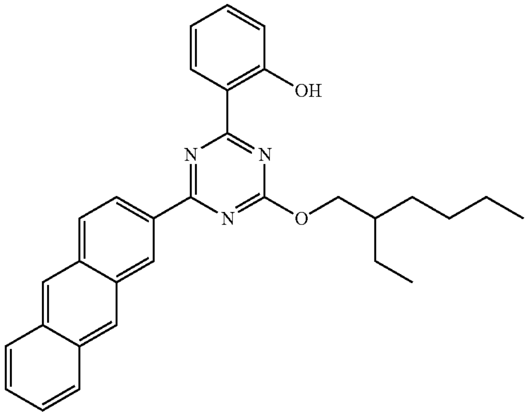
32
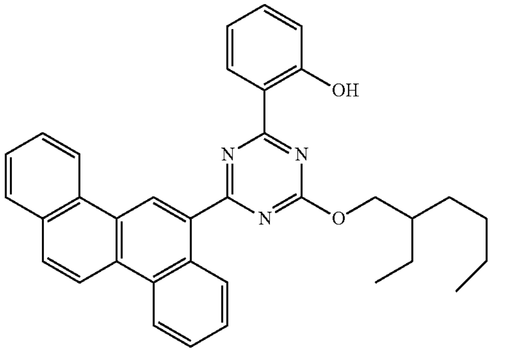
33
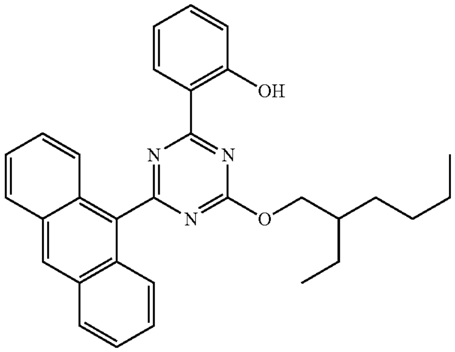
34
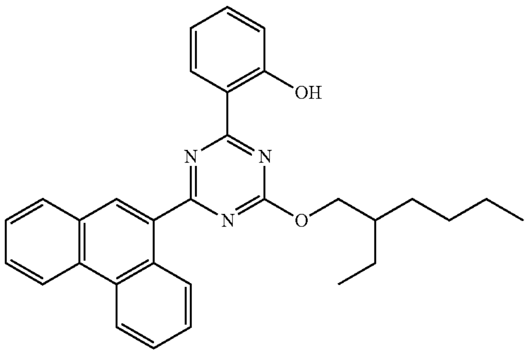

-continued
35
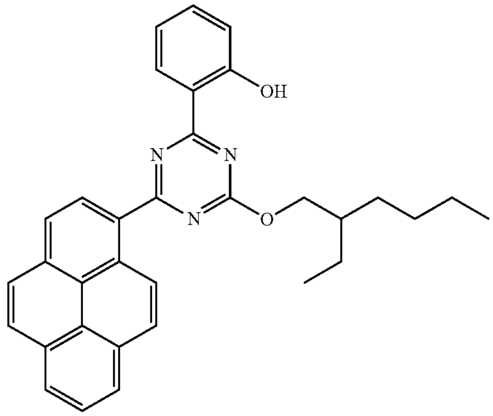
36
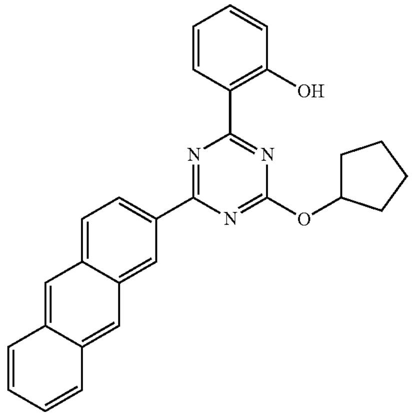
37
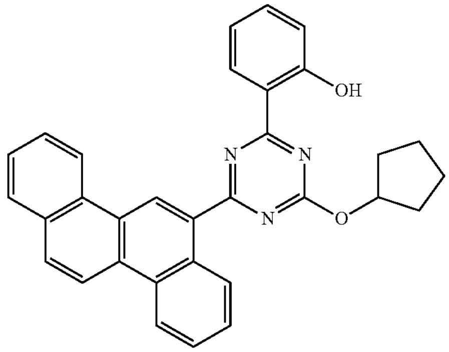
38
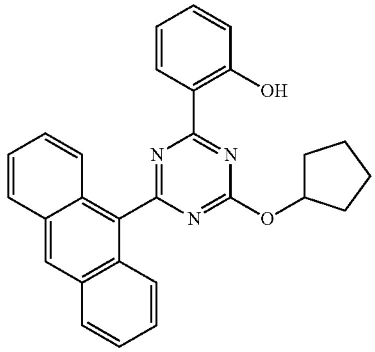
-continued
39
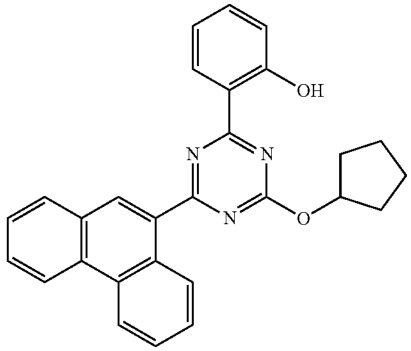
40
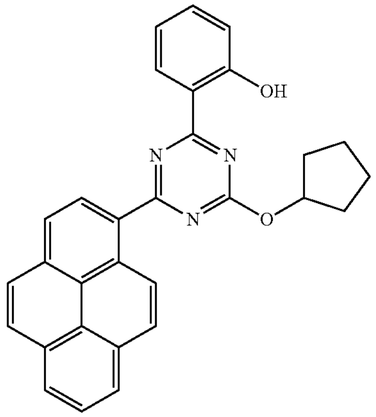
41
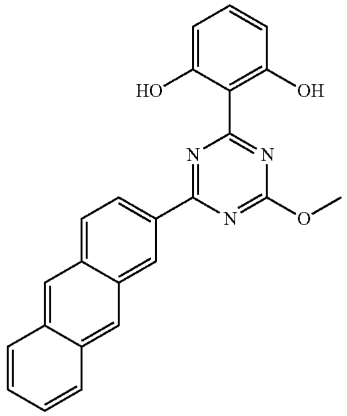
42
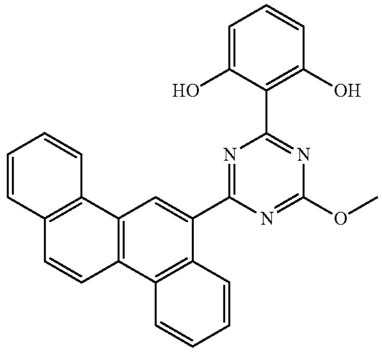

-continued
43
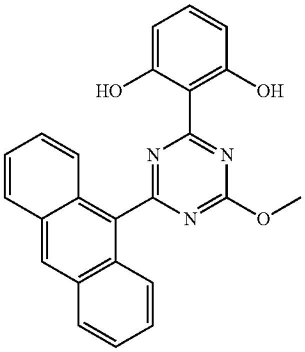
44
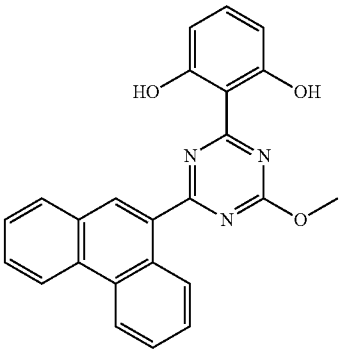
45
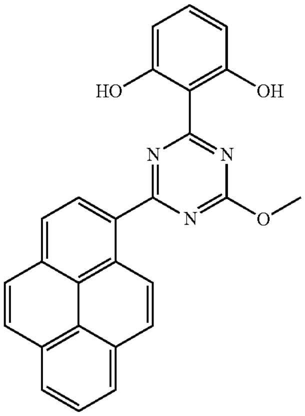
46
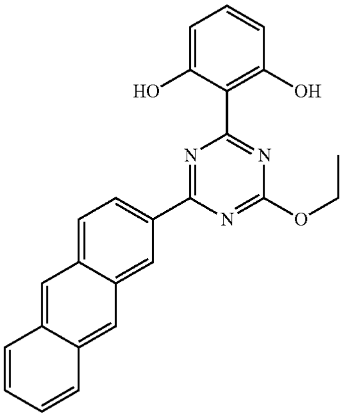
-continued
47
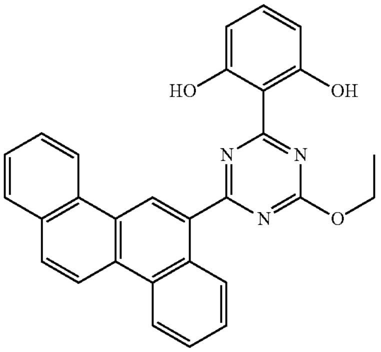
48
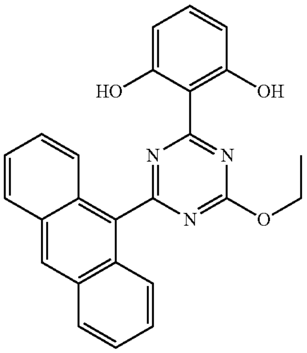
49
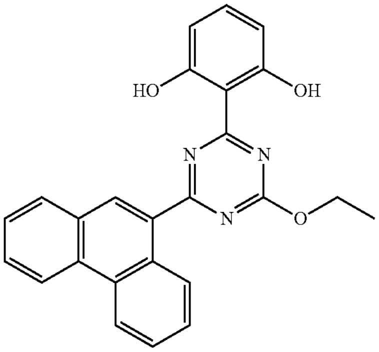
50
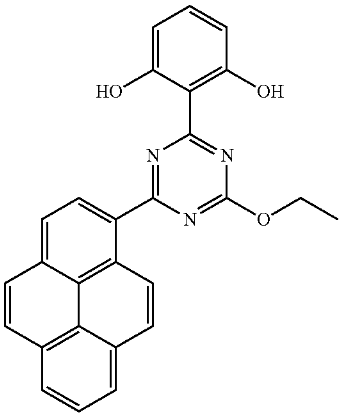

-continued
51
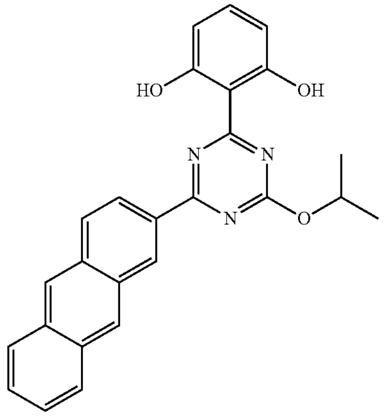
52
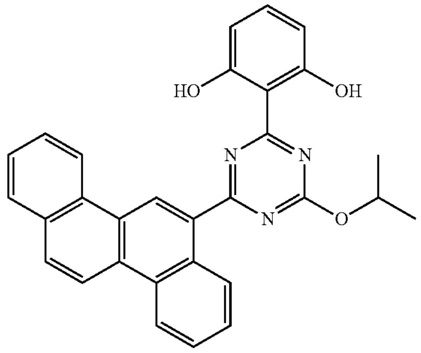
53
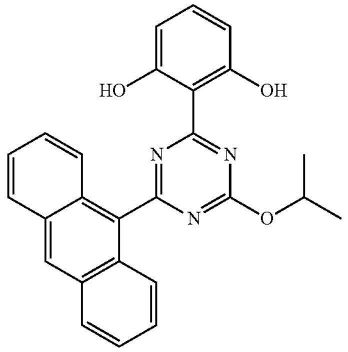
54
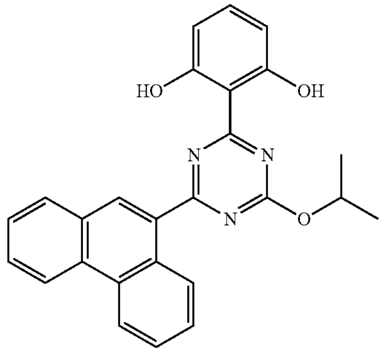
-continued
55
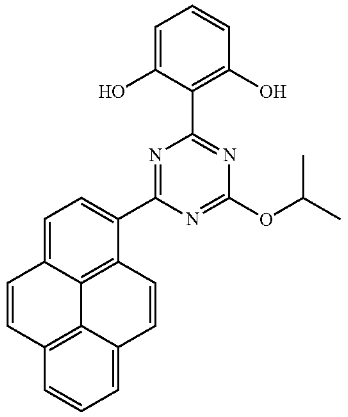
56
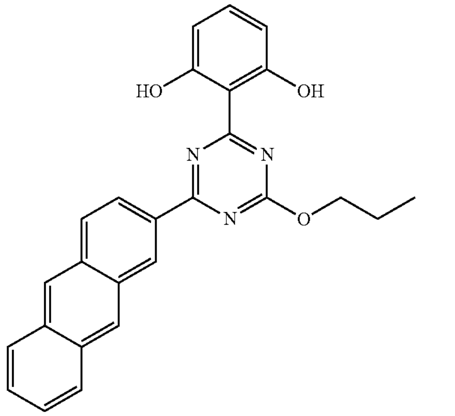
57
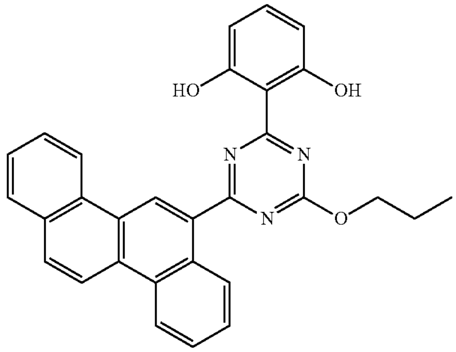
58
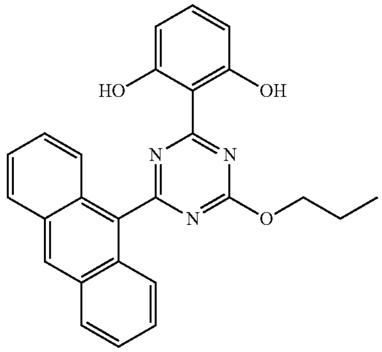

-continued
59
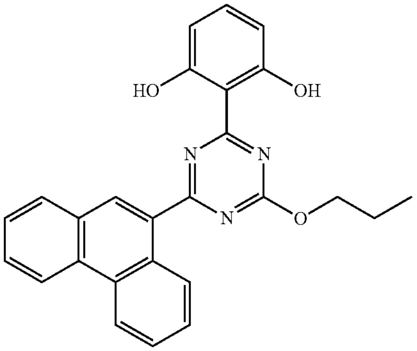
60
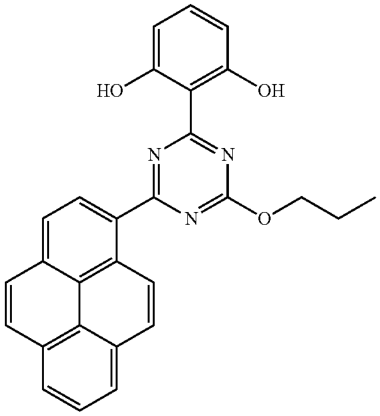
61
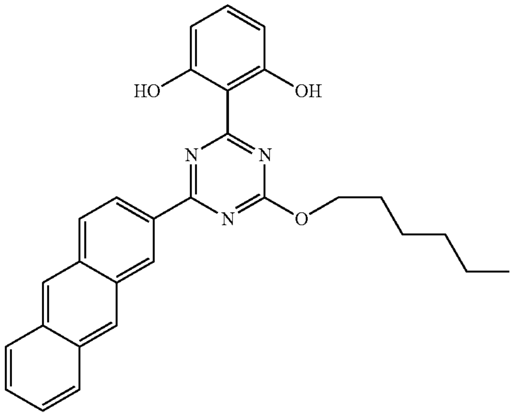
62
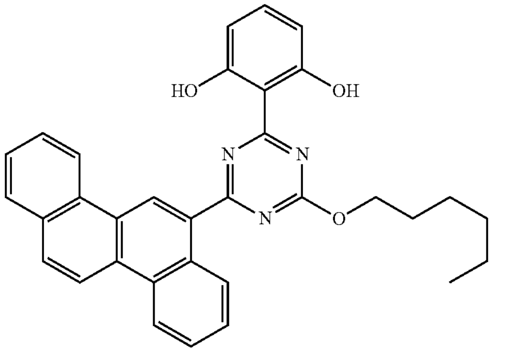
-continued
63
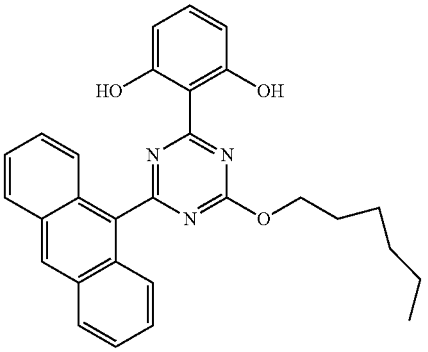
64
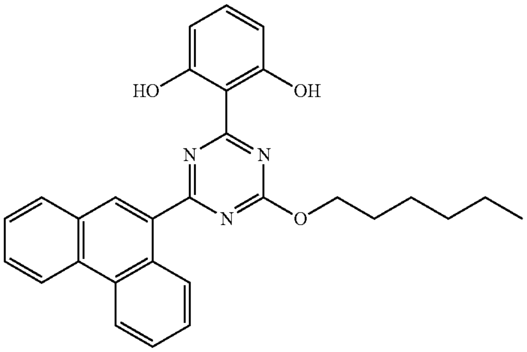
65
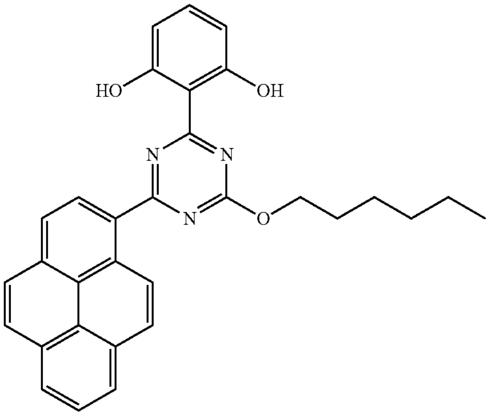
66
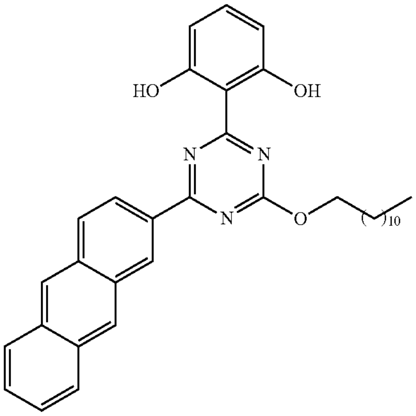

-continued
67
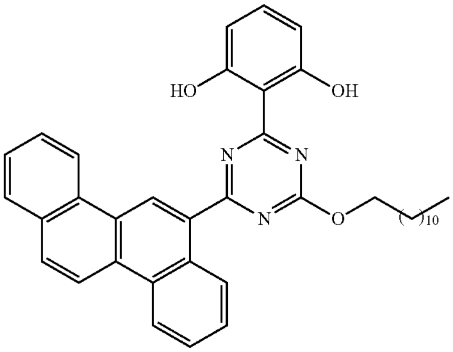
68
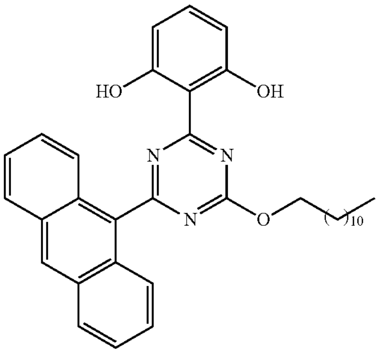
69
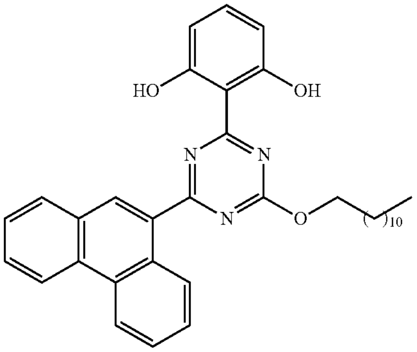
70
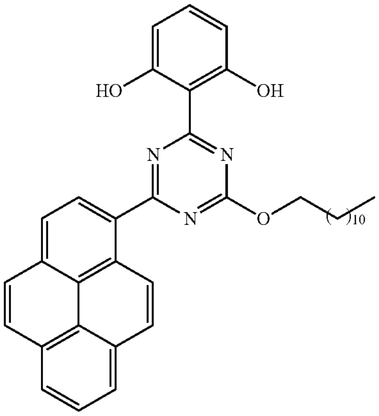
-continued
71
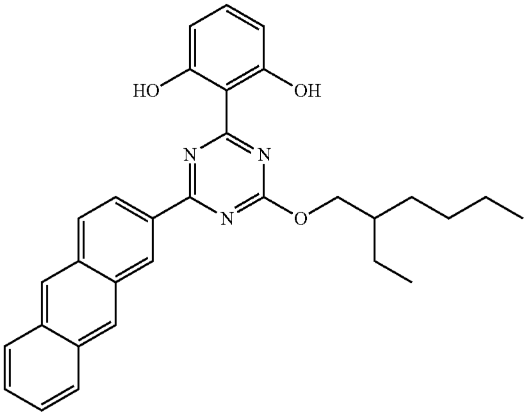
72
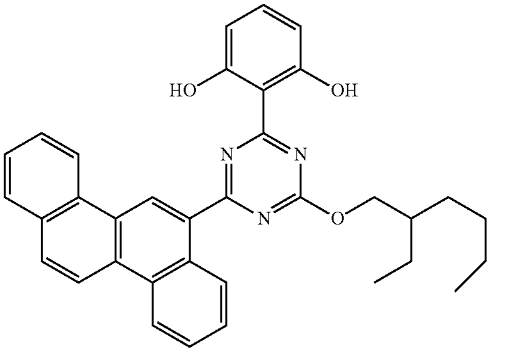
73
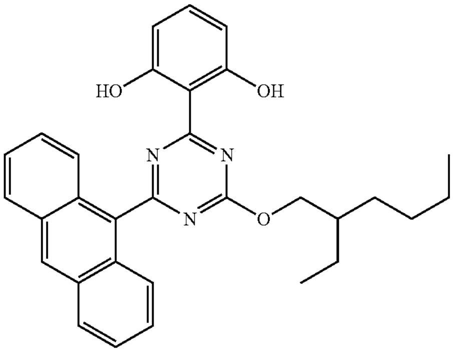
74
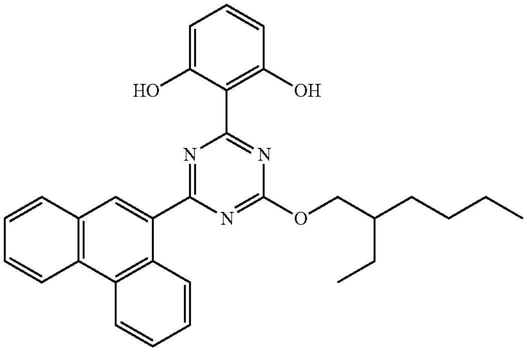

-continued
75
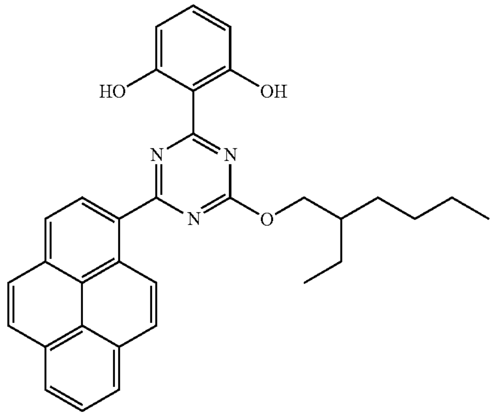
76
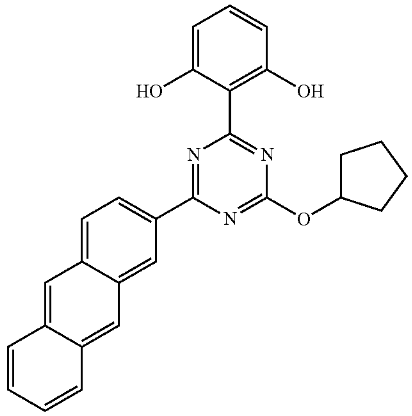
77
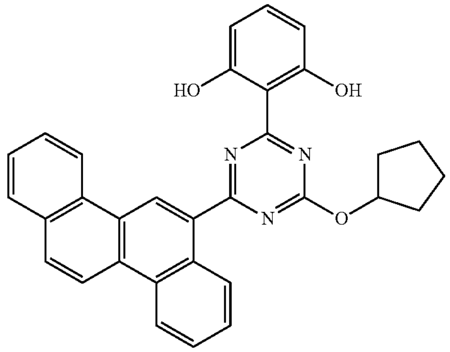
78
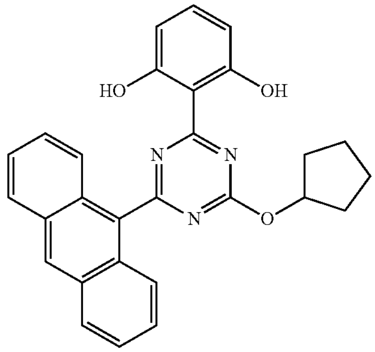
-continued
79
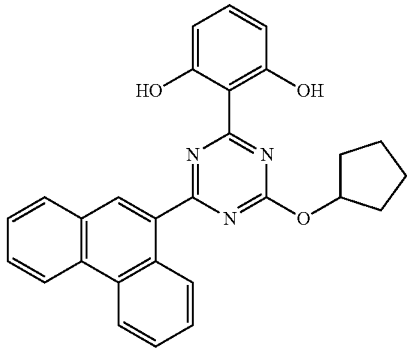
80
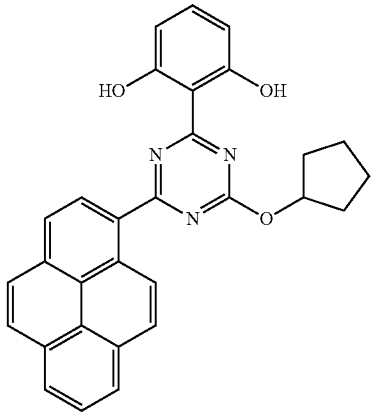
81
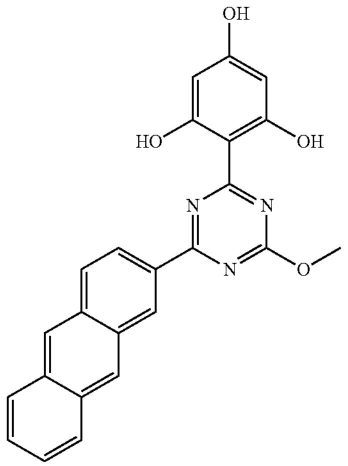
82
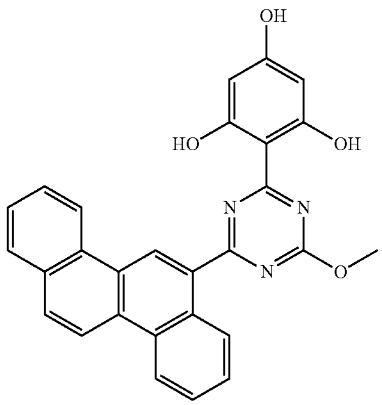

-continued
83
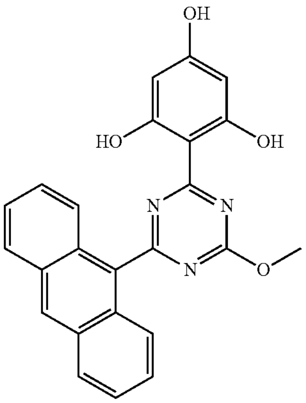
84
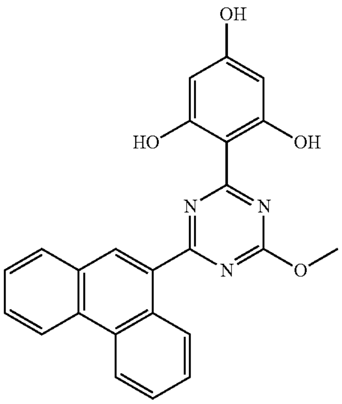
85
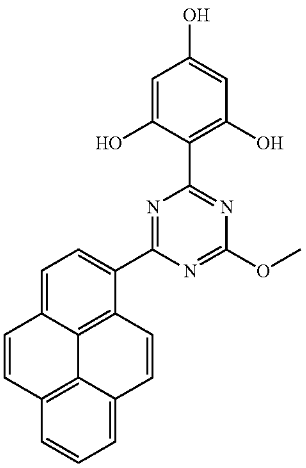
-continued
86
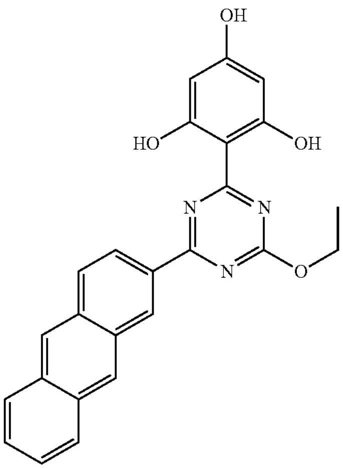
87
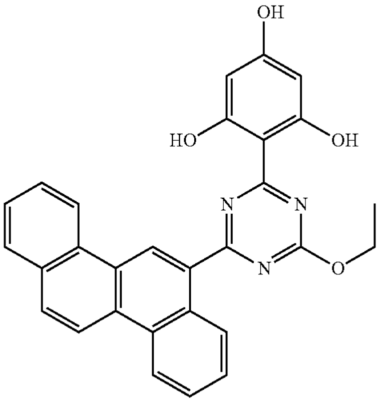
88
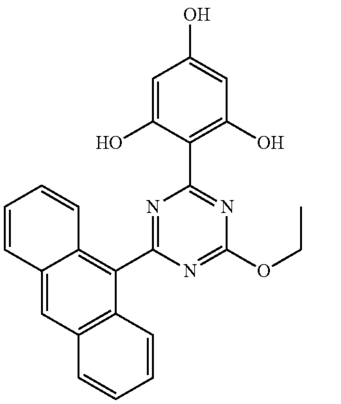

-continued
89
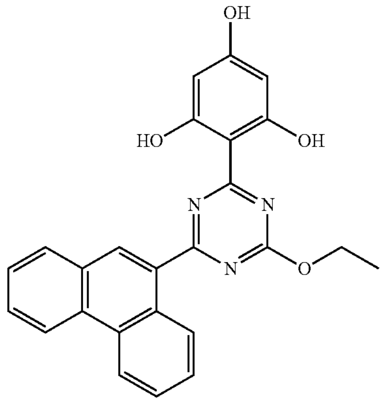
90
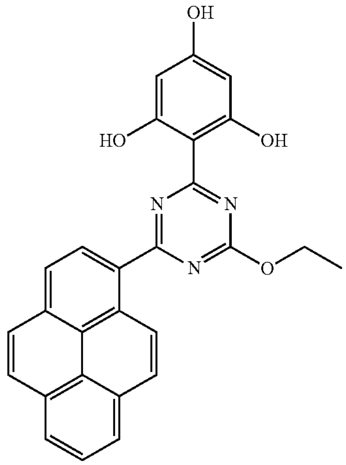
91
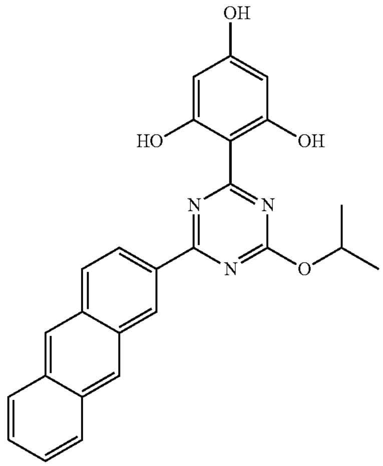
-continued
92
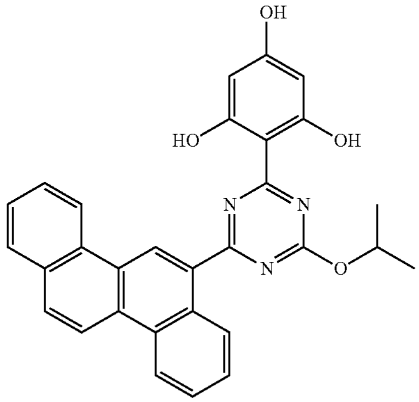
93
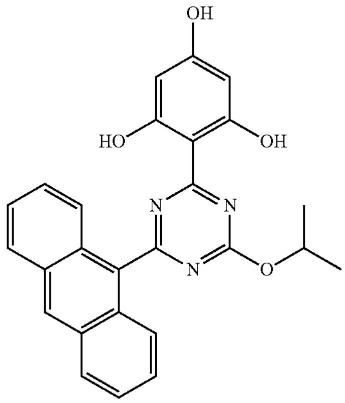
94
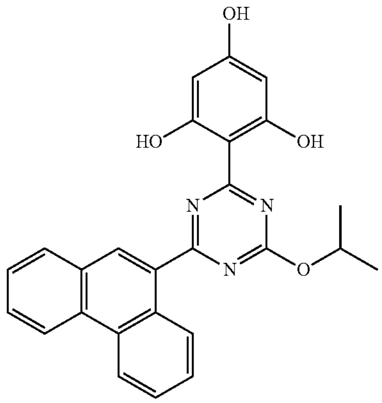

-continued
95
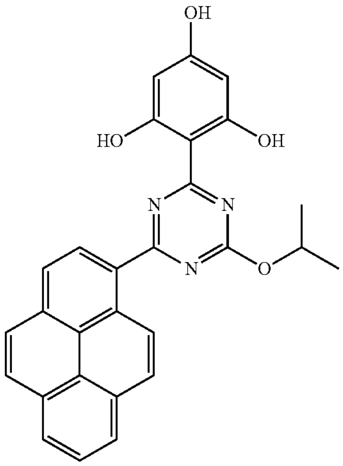
96
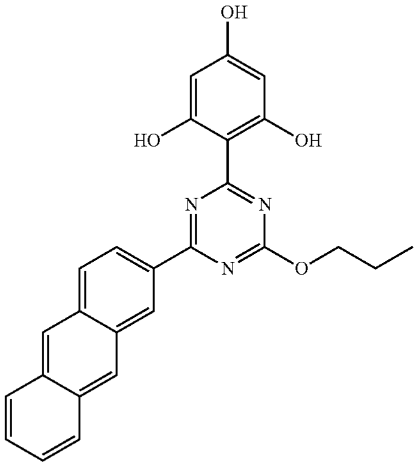
97
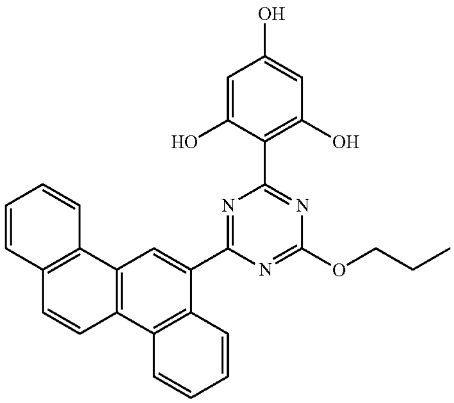
-continued
98
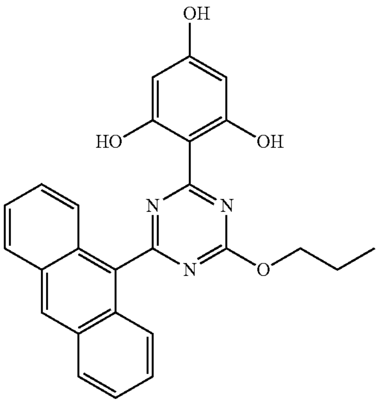
99
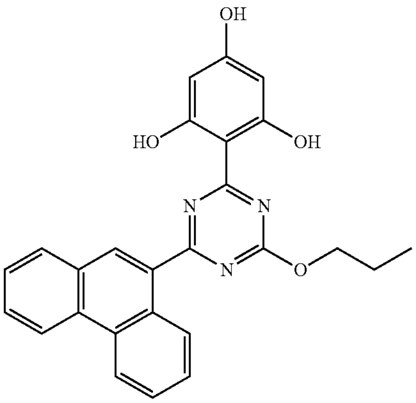
100
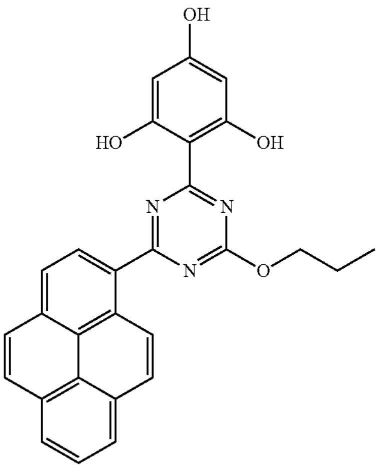

-continued
101
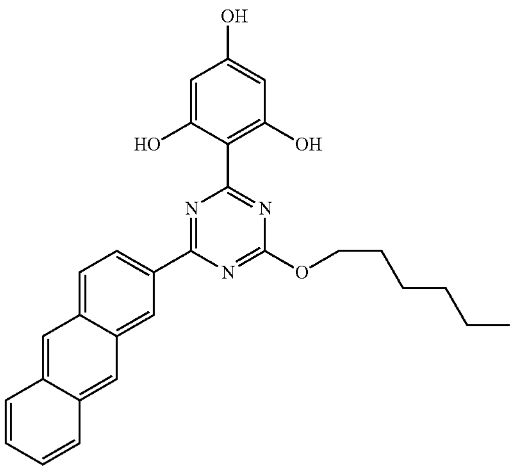
102
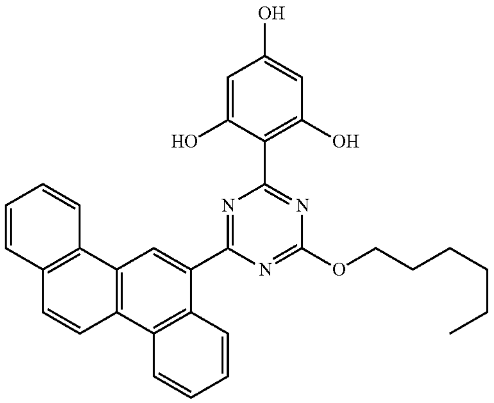
103
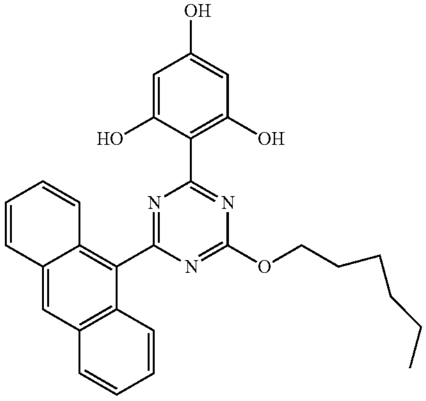
-continued
104
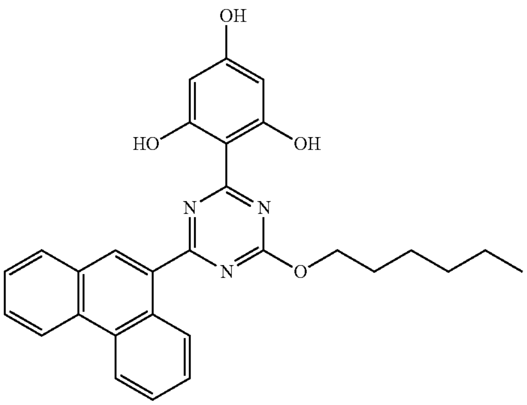
105
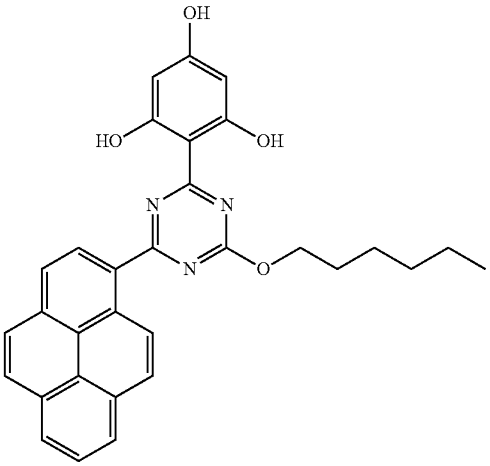
106
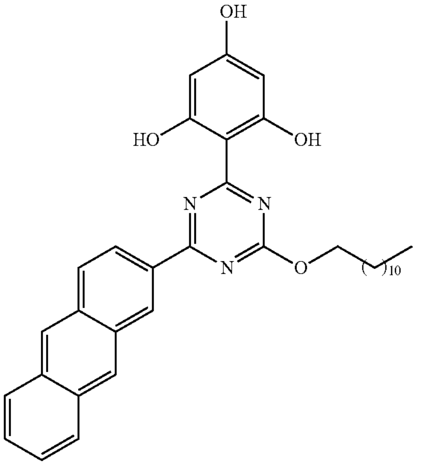

-continued
107
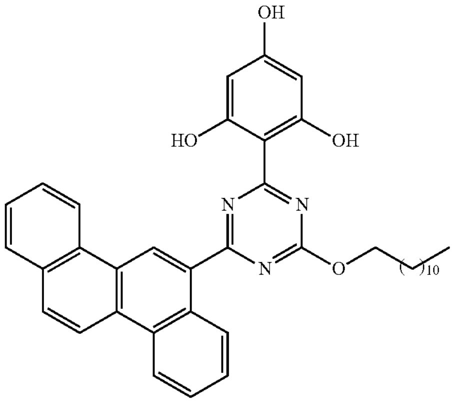
108
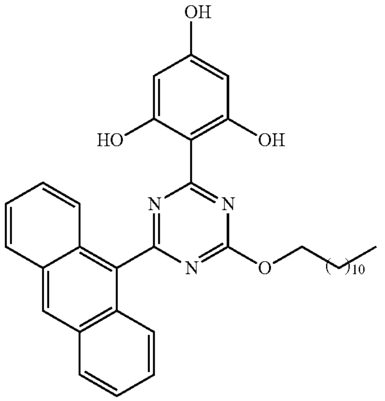
109
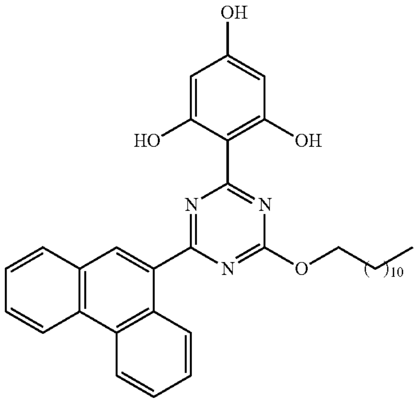
-continued
110
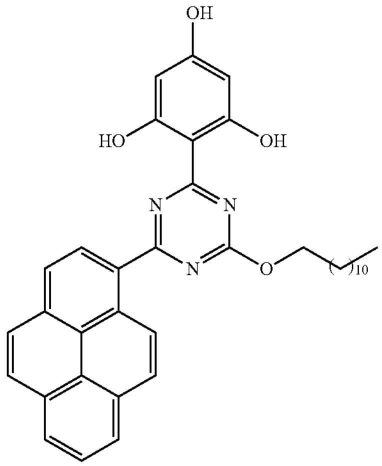
111
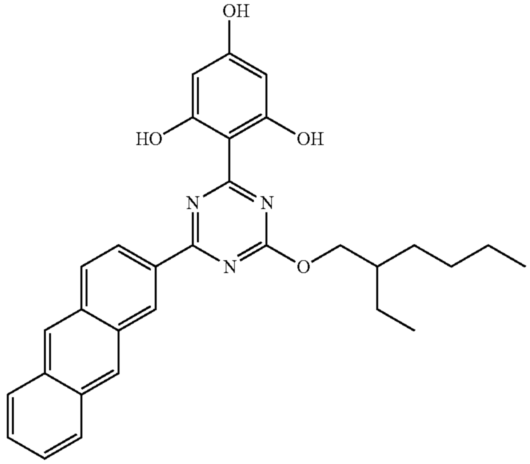
112
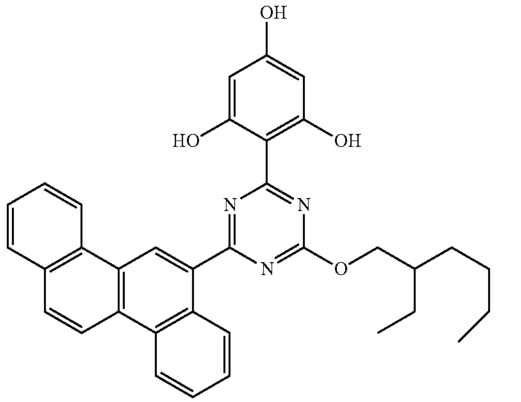

-continued
113
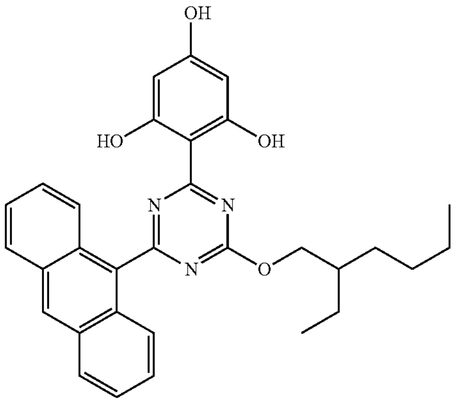
114
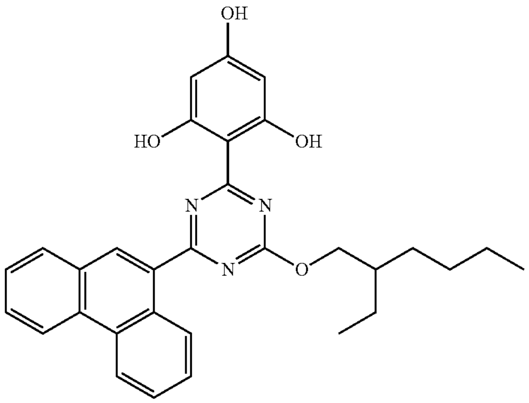
115
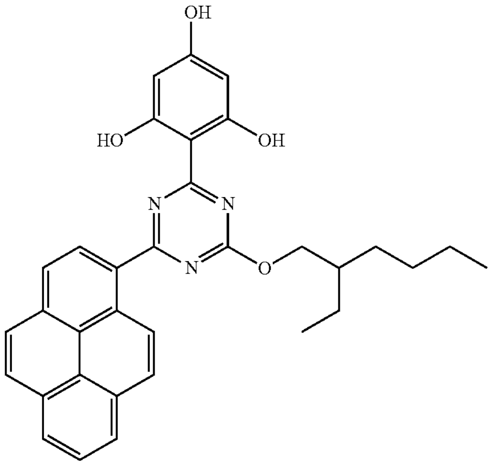
-continued
116
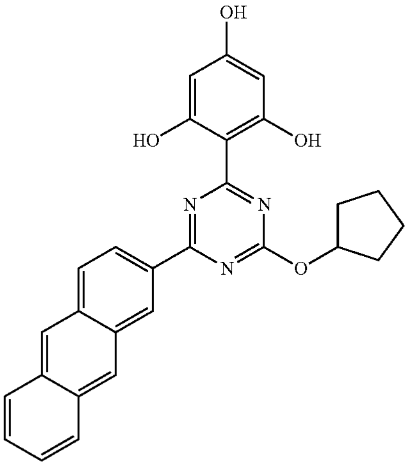
117
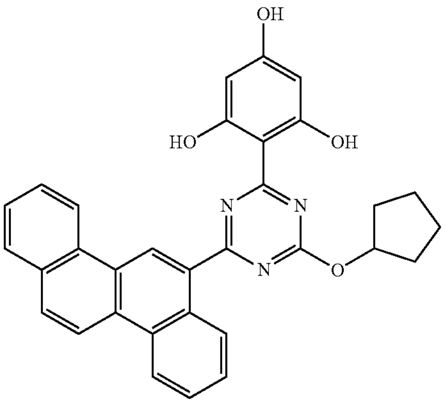
118
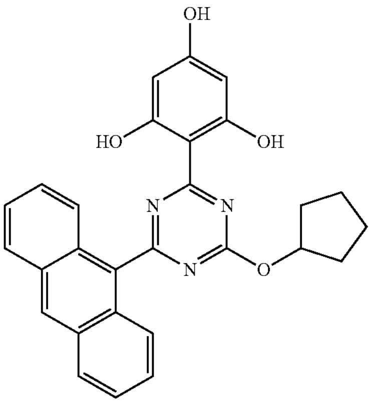

119
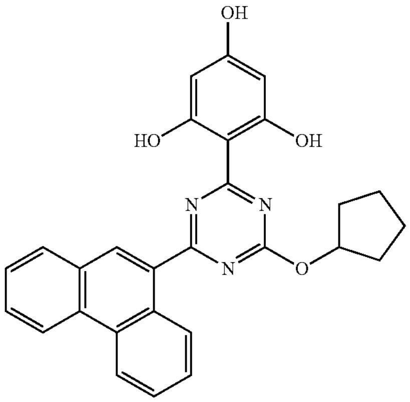
120
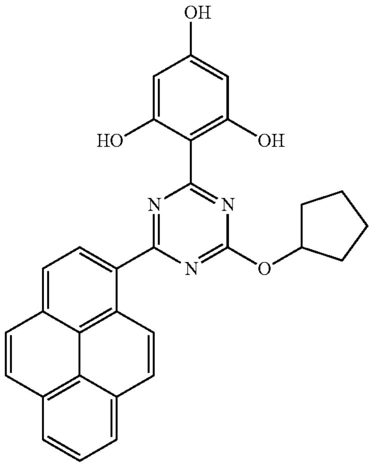
121
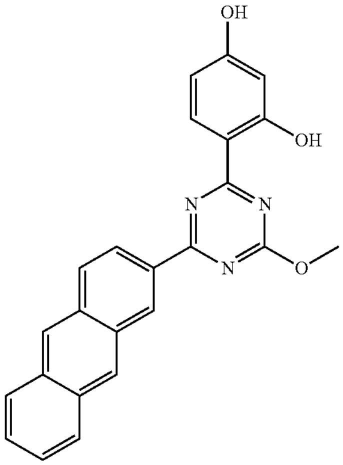
122
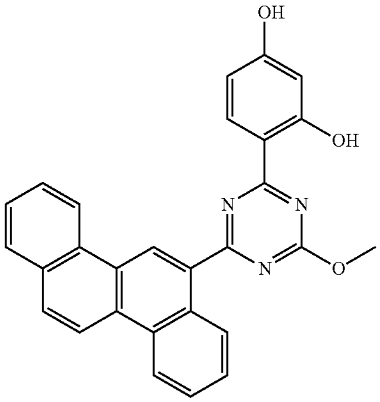
123
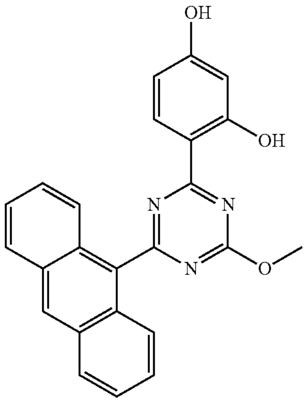
124
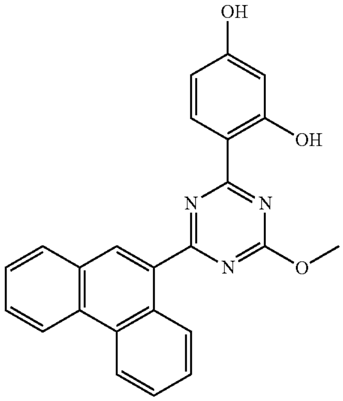

-continued
125
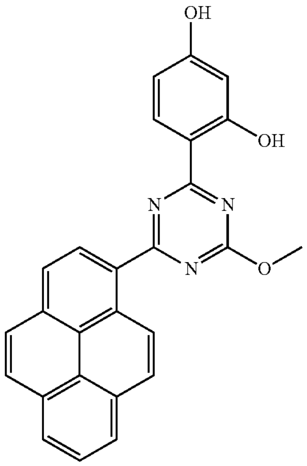
126
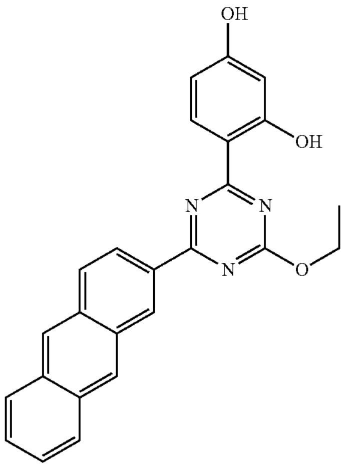
127
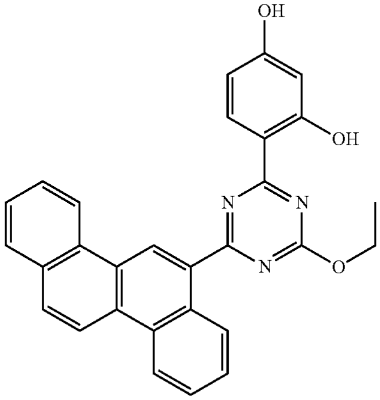
-continued
128
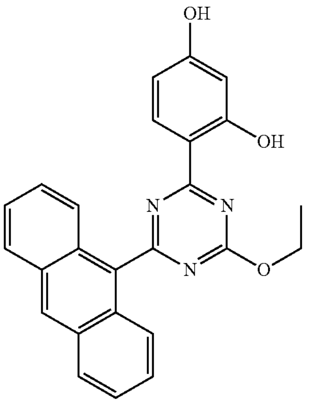
129
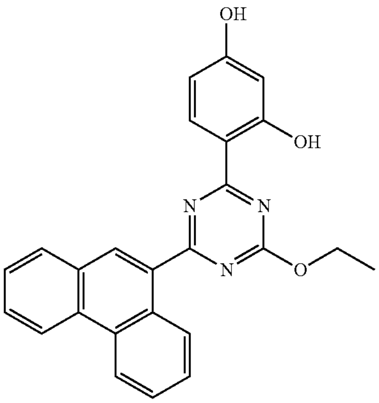
130
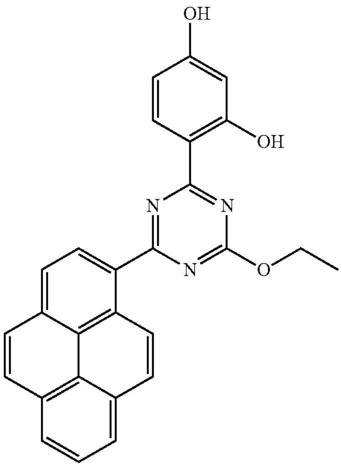

-continued
131
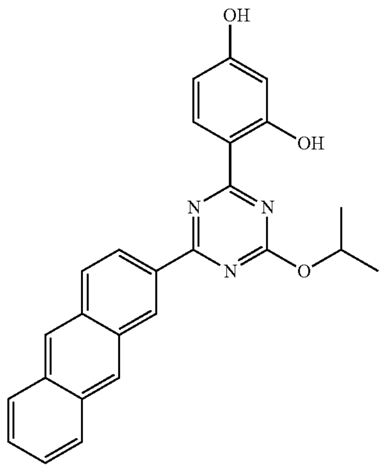
132
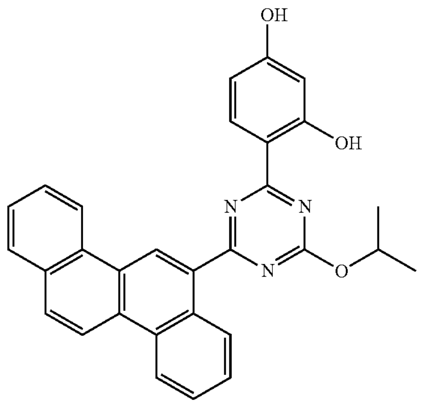
133
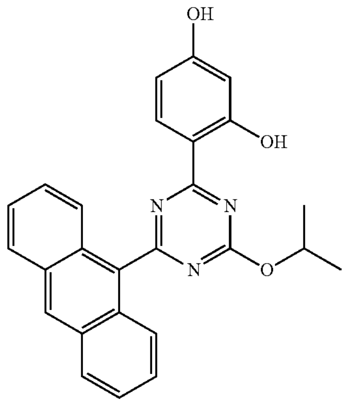
-continued
134
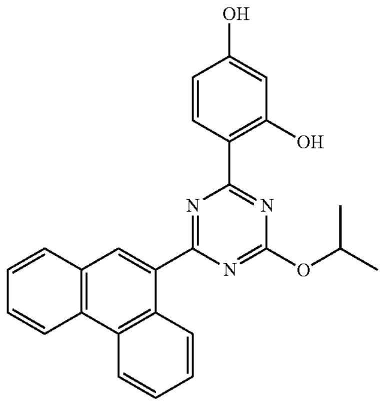
135
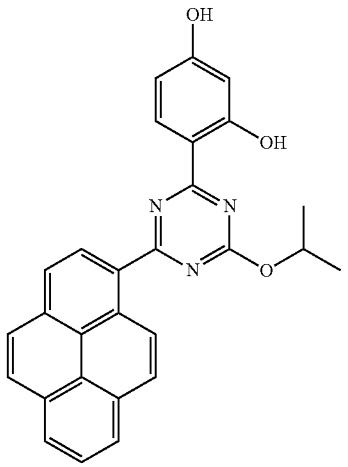
136
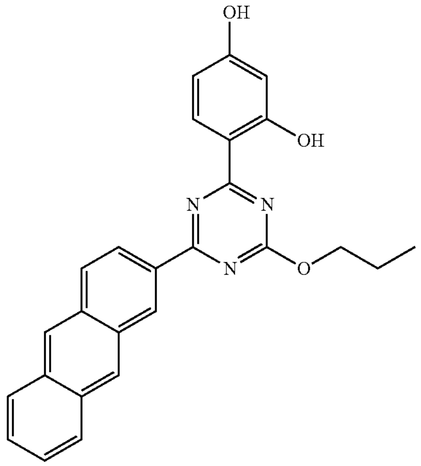

-continued
137
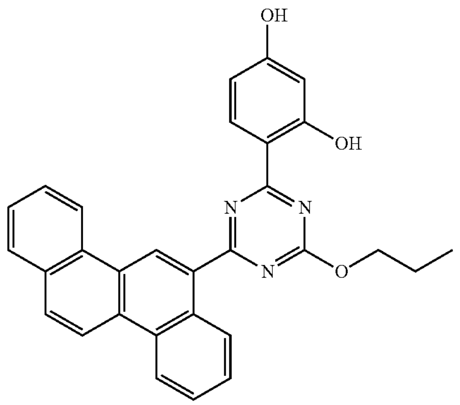
138
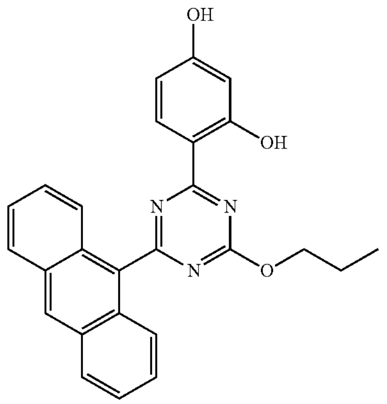
139
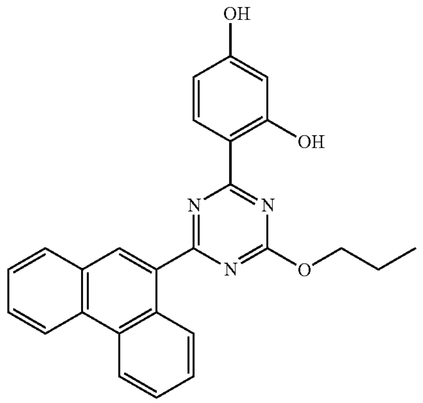
-continued
140
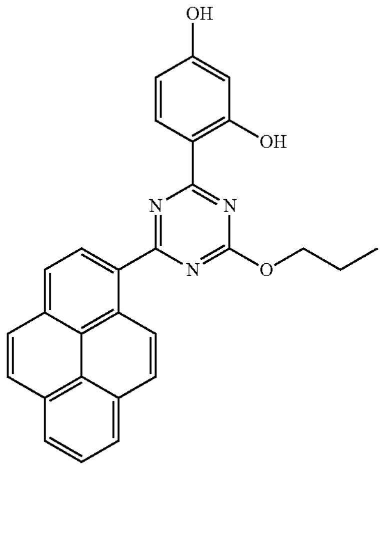
141
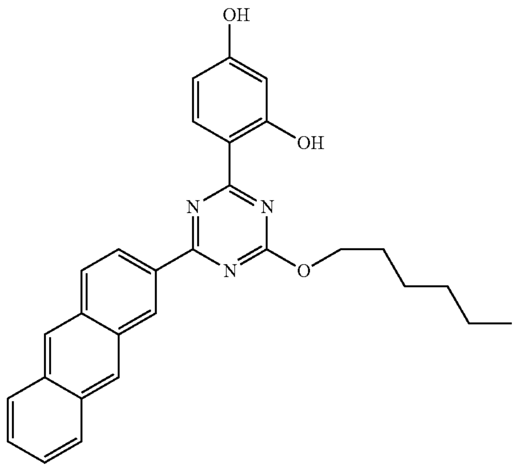
142
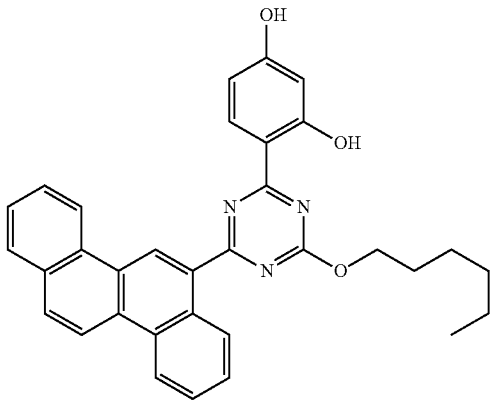

143
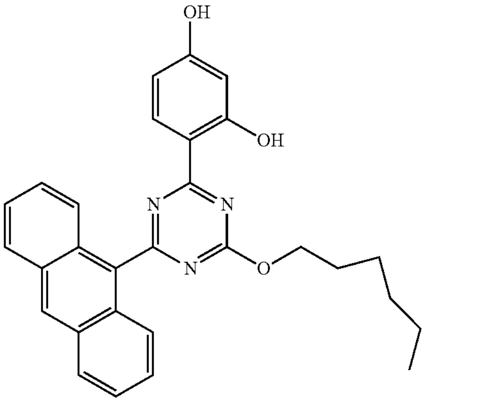
144
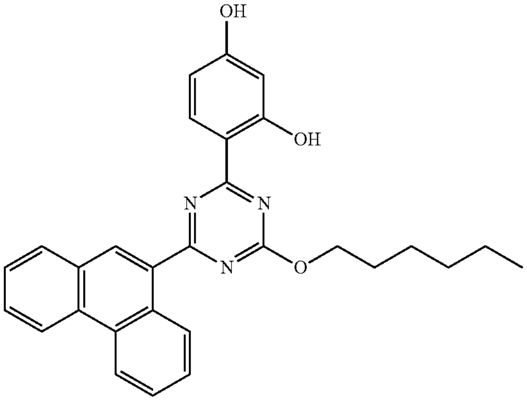
145
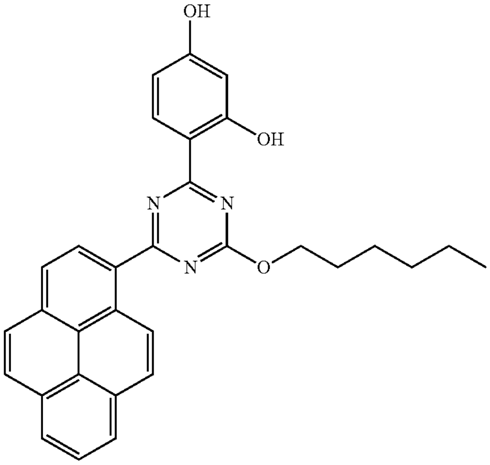
146
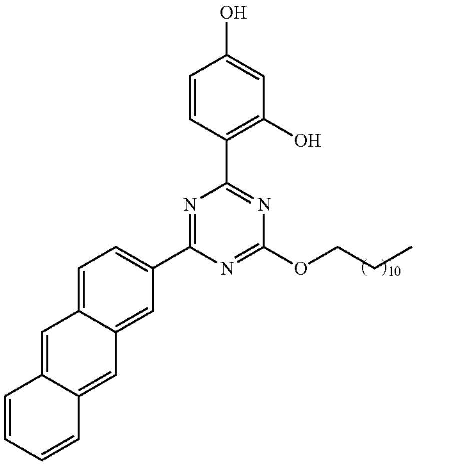
147
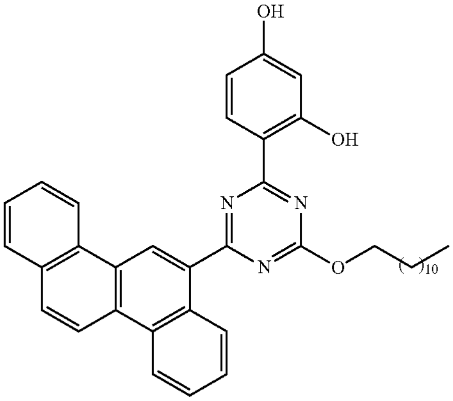
148
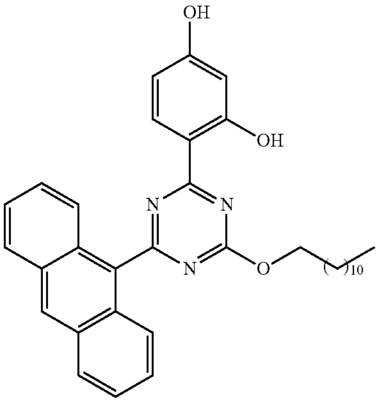

-continued
149
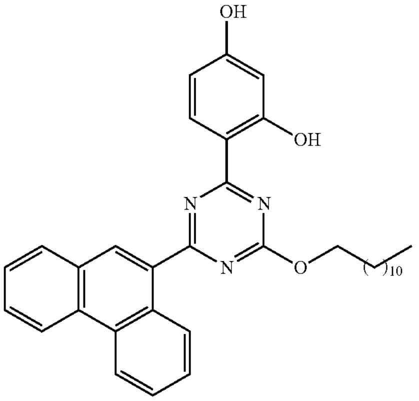
150
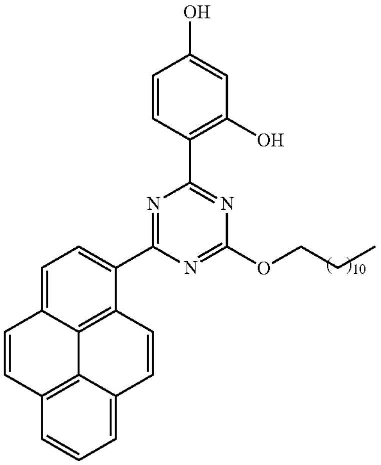
151
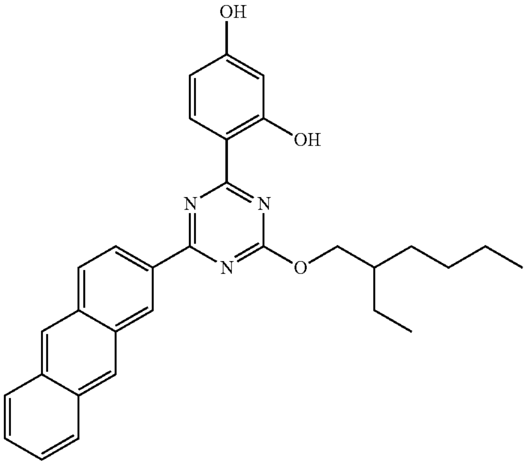
-continued
152
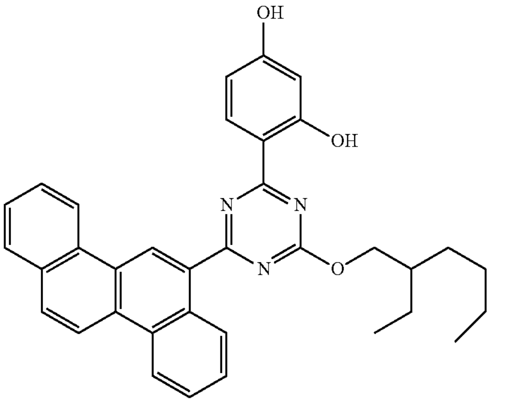
153
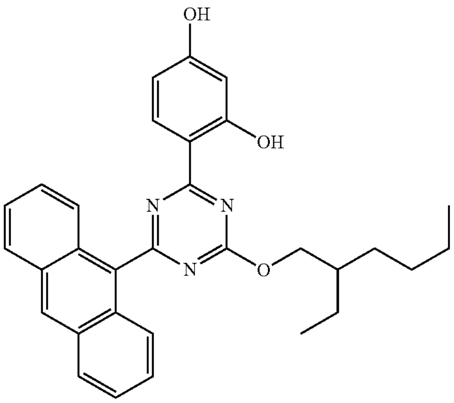
154
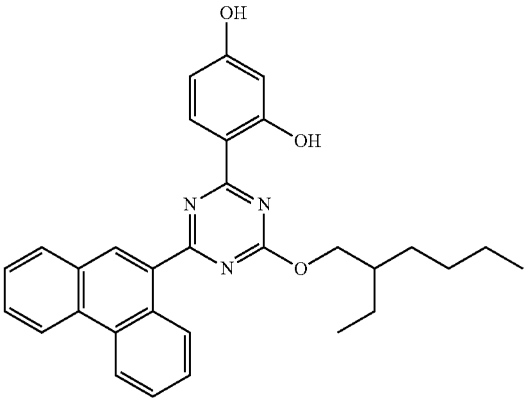

155
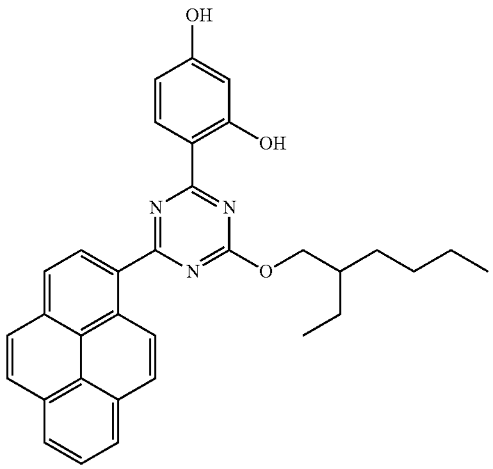
156
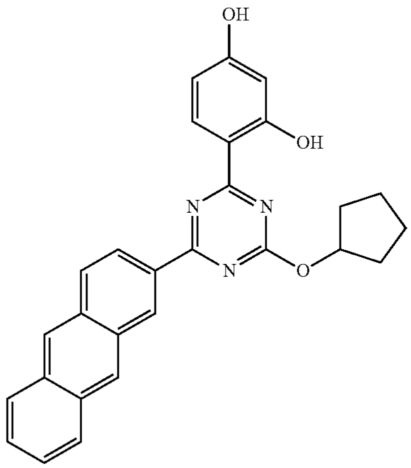
157
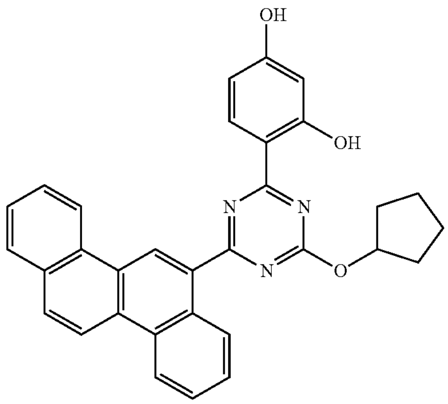
158
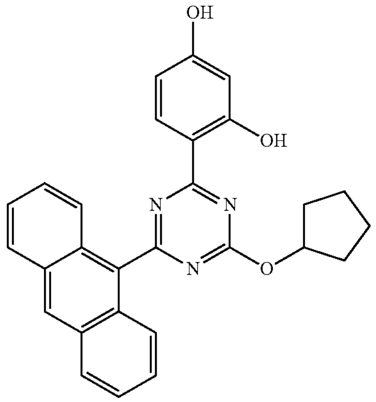
159
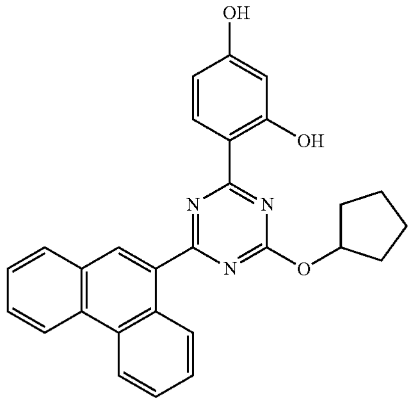
160
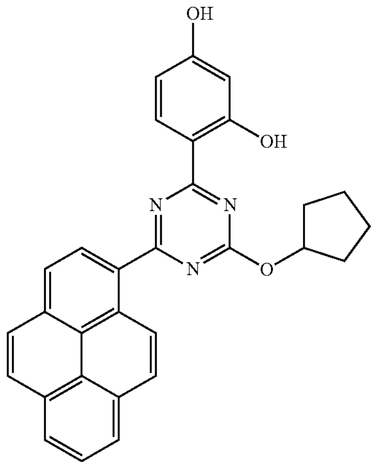

161
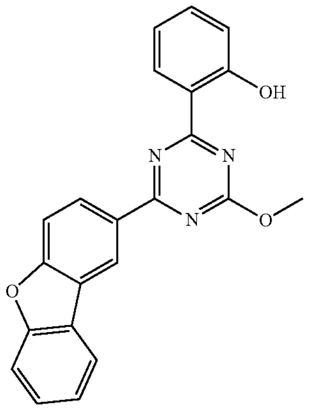
162
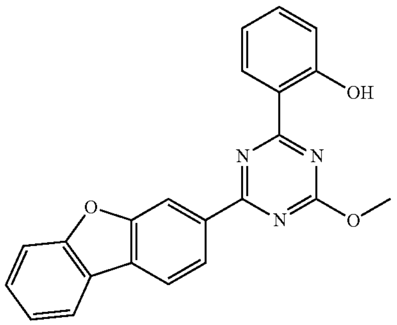
163
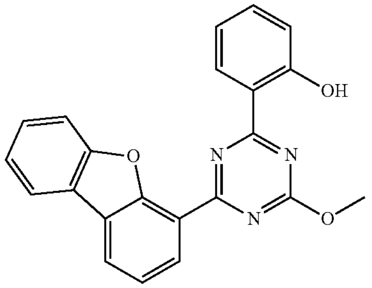
164
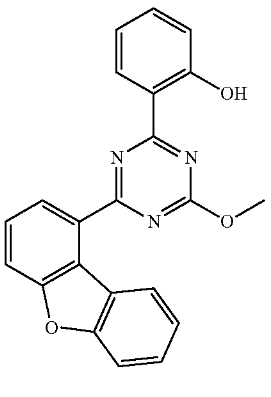
165
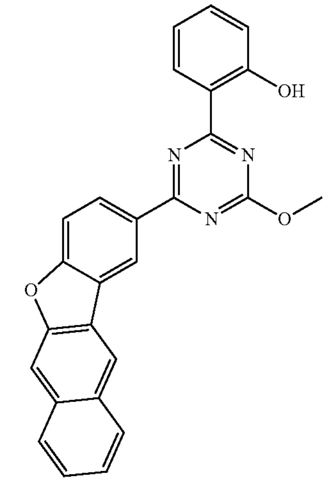
166
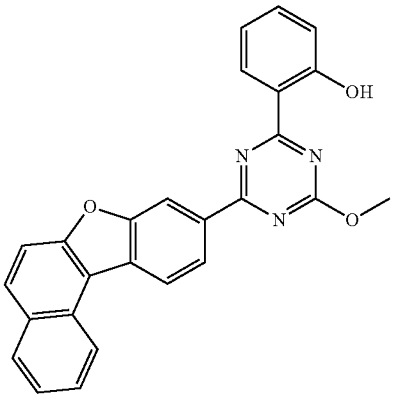
167
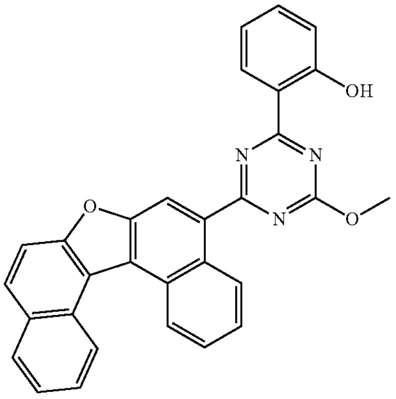
168
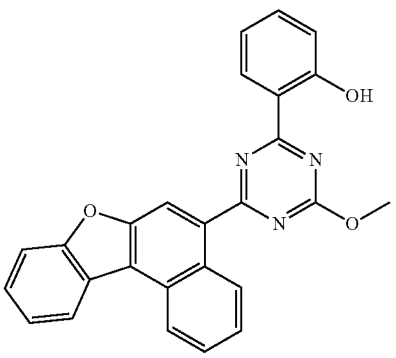

-continued
169
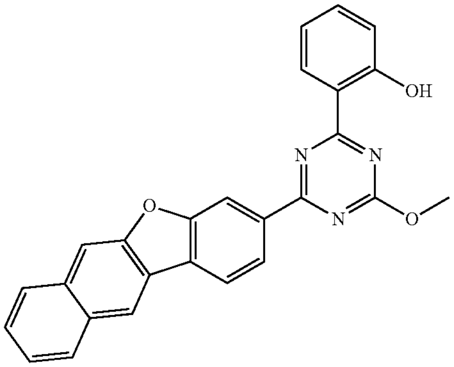
170
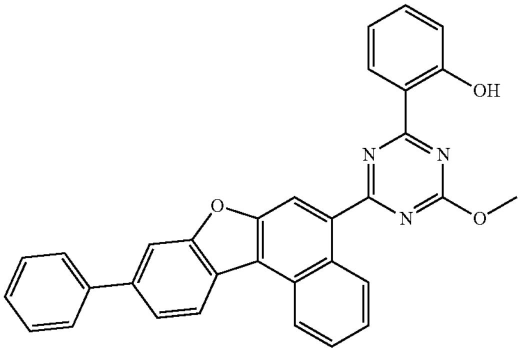
171
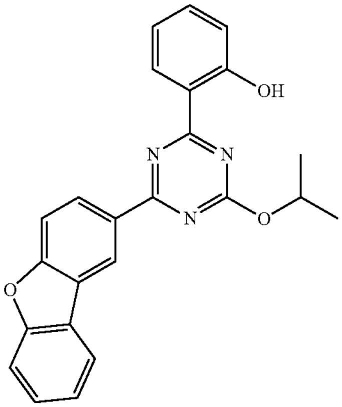
172
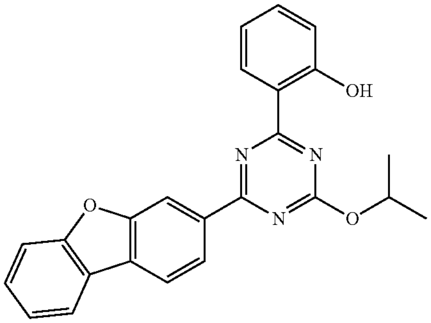
-continued
173
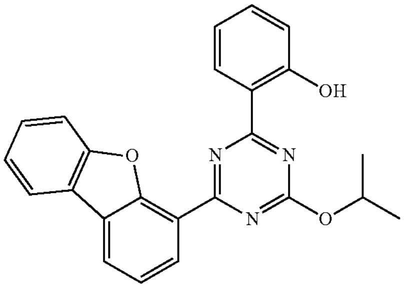
174
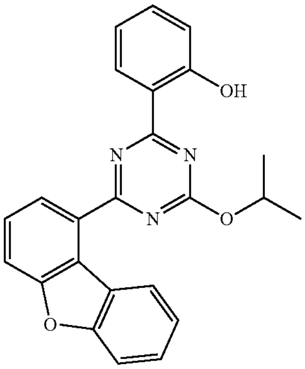
175
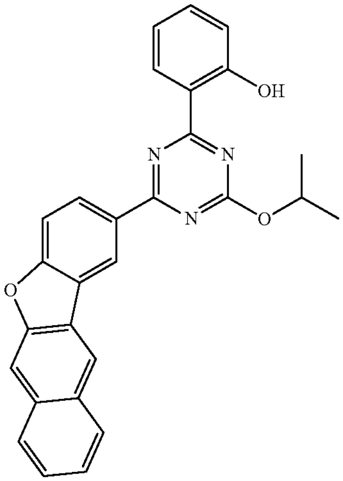
176
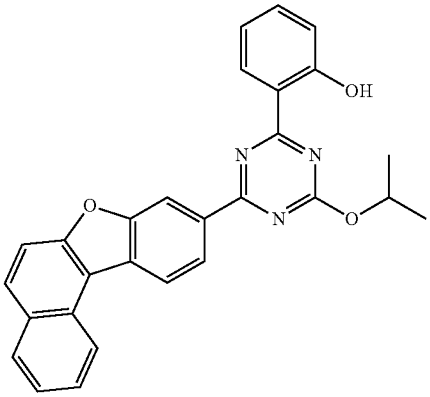

-continued
177
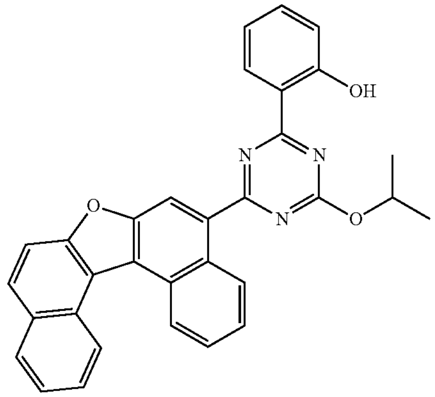
178
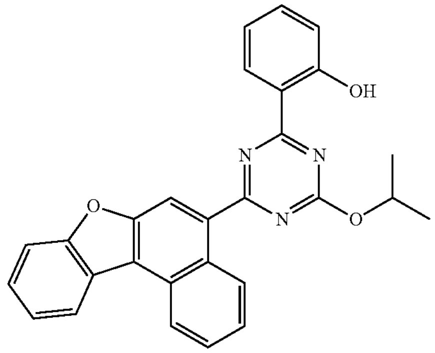
179
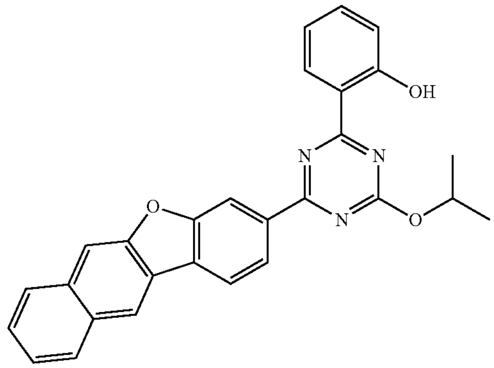
180
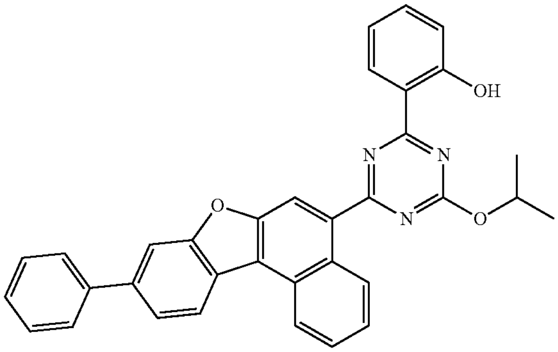
-continued
181
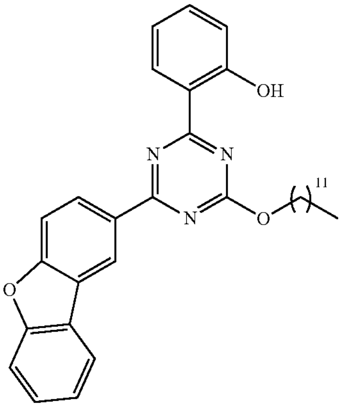
182
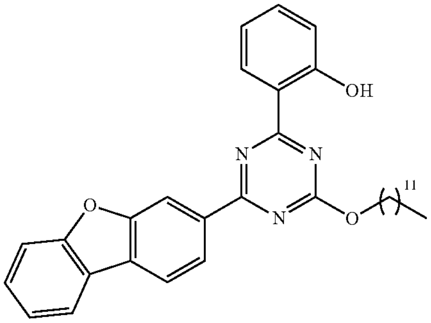
183
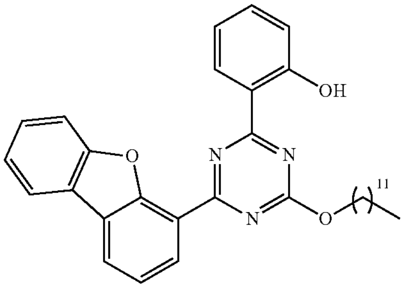
184
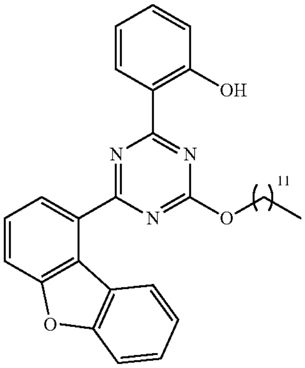

-continued
185
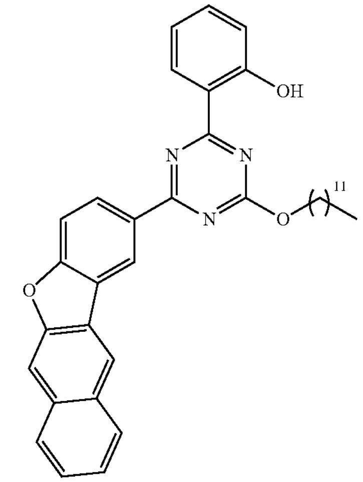
186
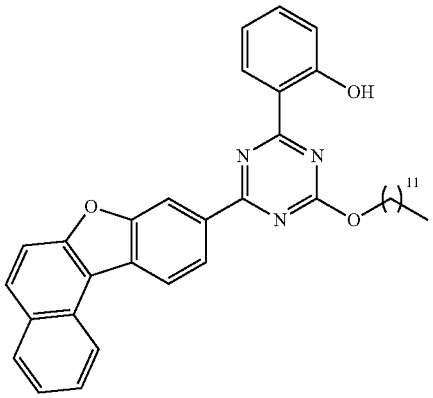
187
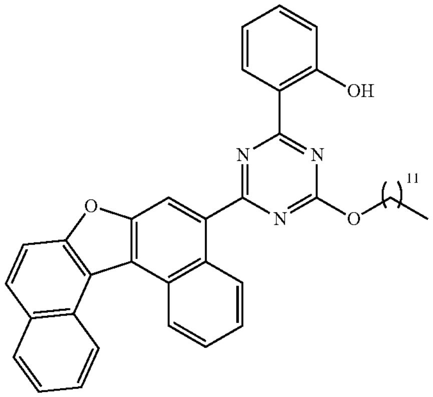
188
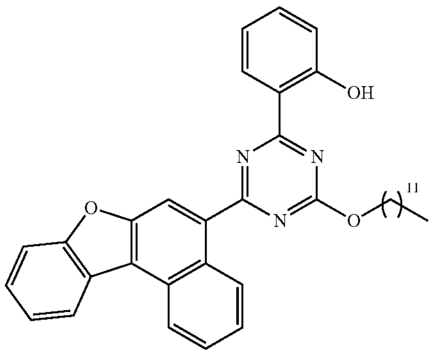
-continued
189
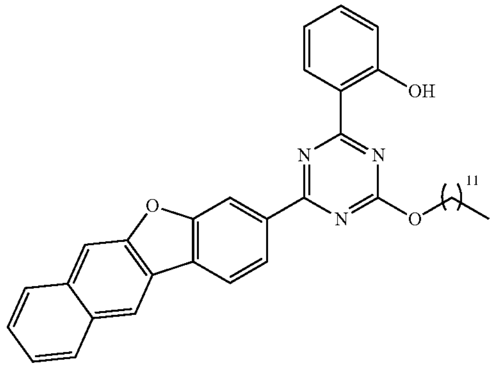
190
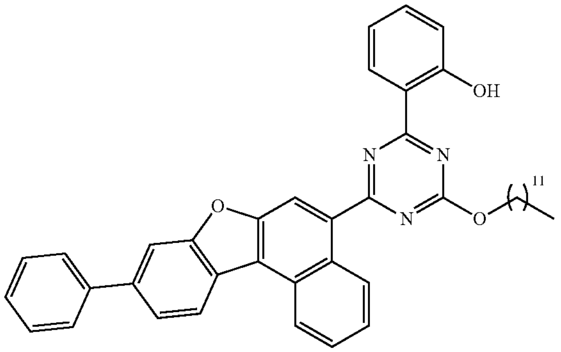
191
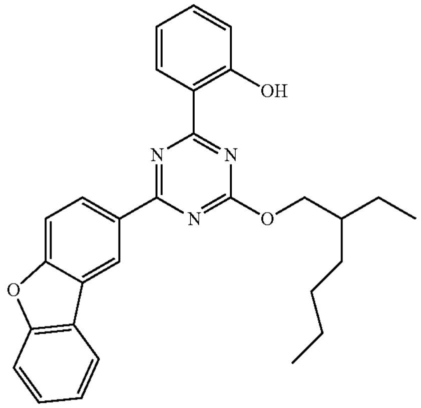
192
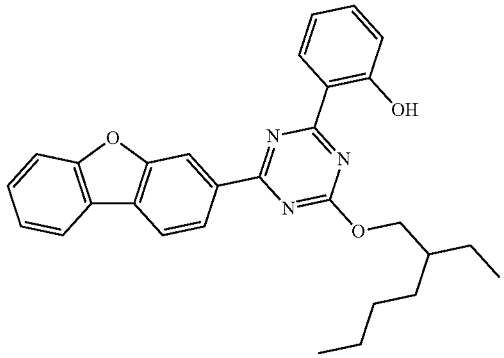

-continued
193
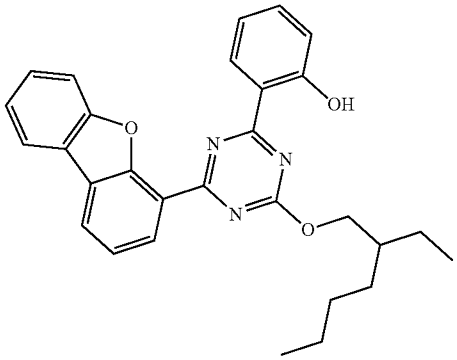
194
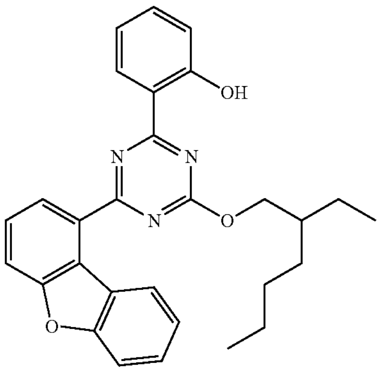
195
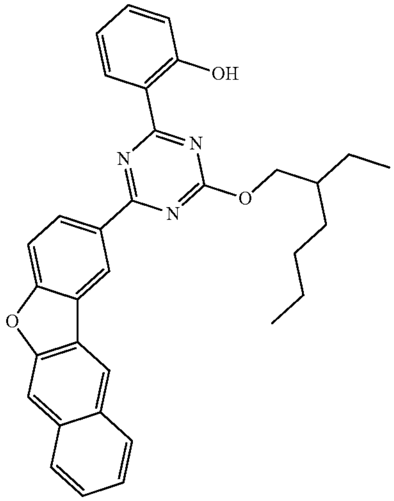
-continued
196
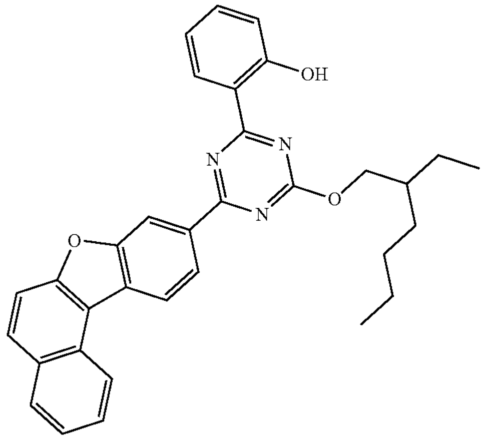
197
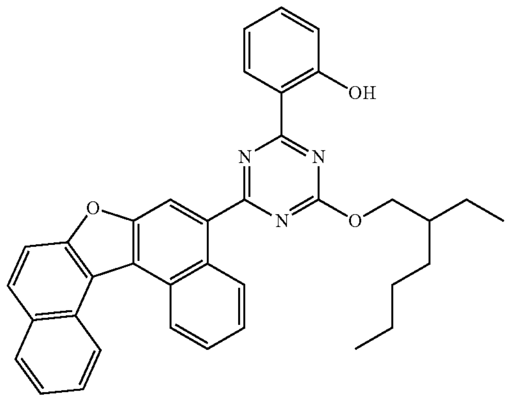
198
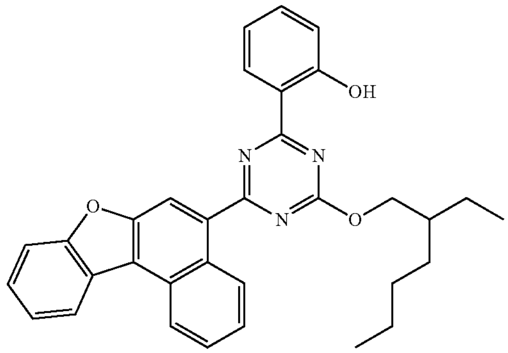

-continued
199
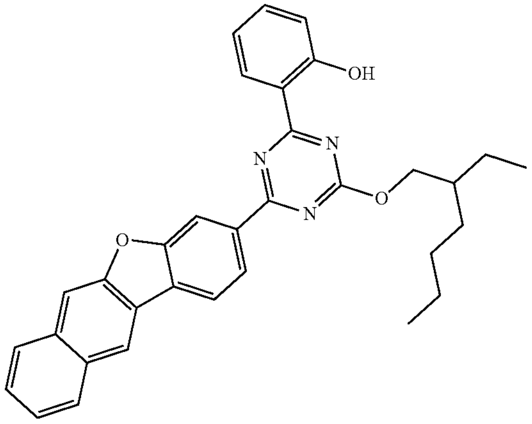
200
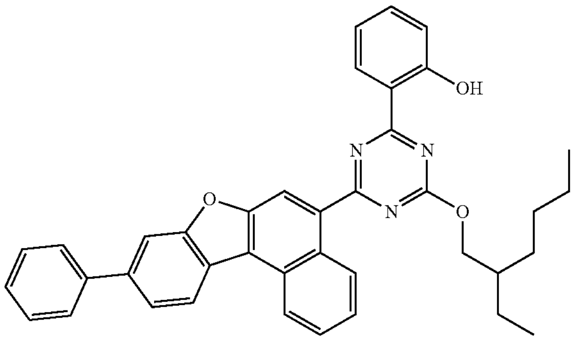
201
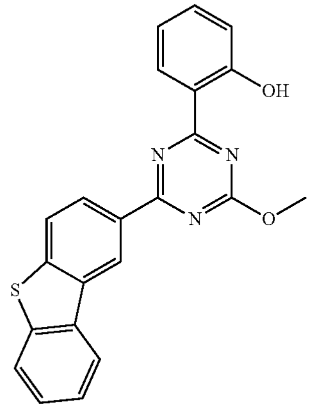
202
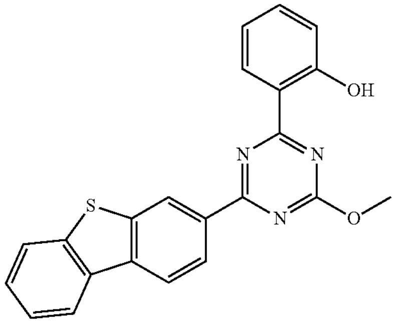
-continued
203
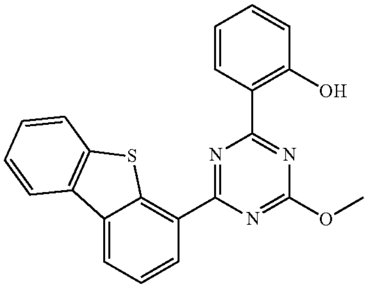
204
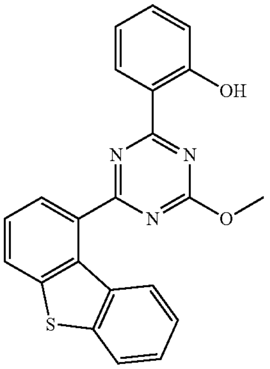
205
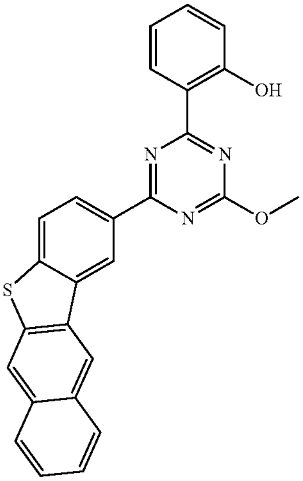
206
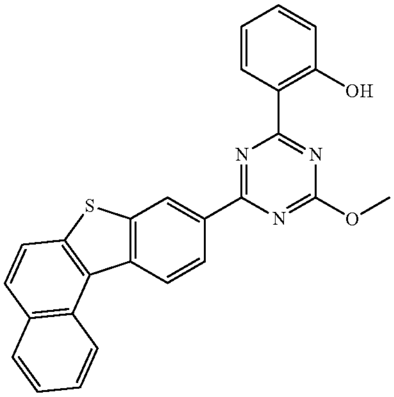

-continued
207
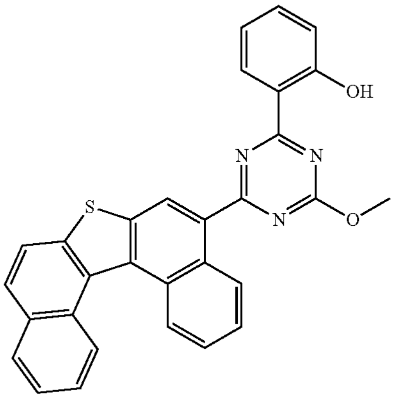
208
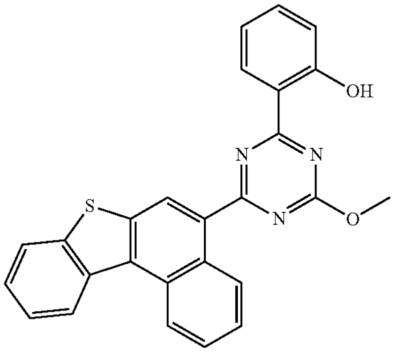
209
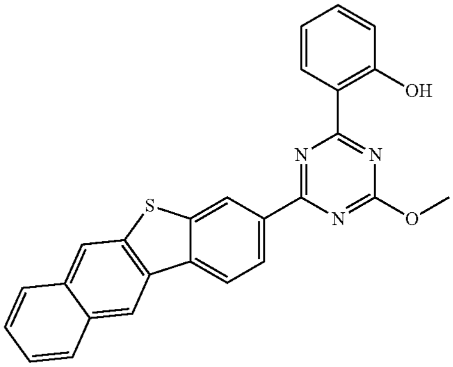
210
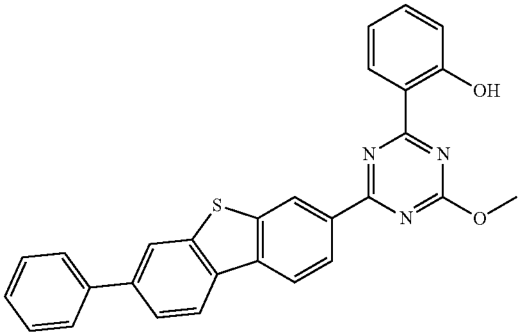
-continued
211
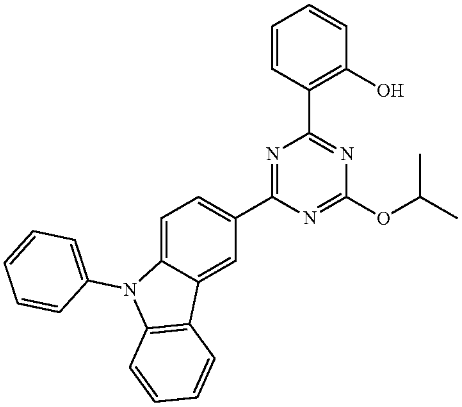
212
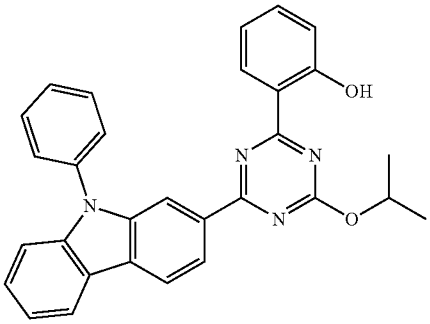
213
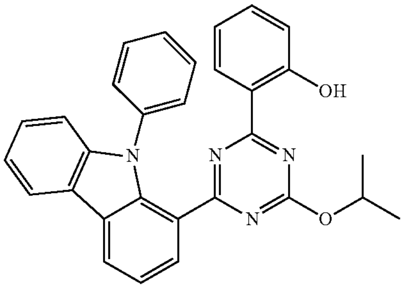
214
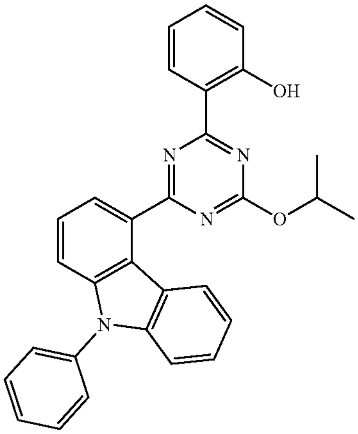

-continued
215
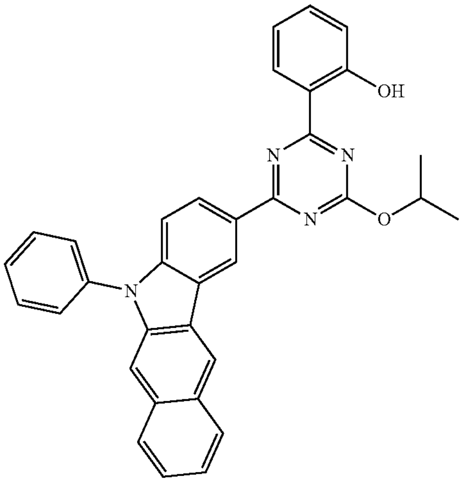
216
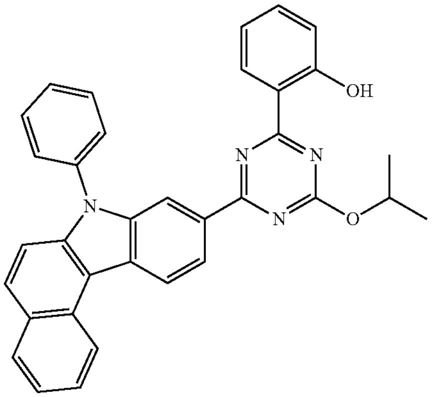
217
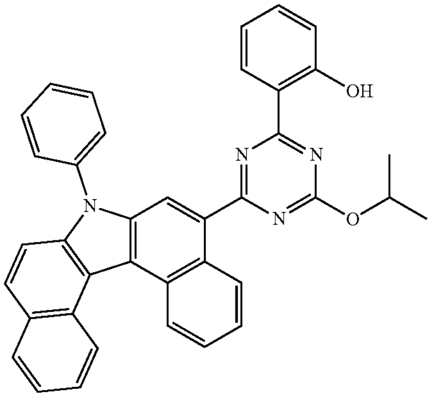
218
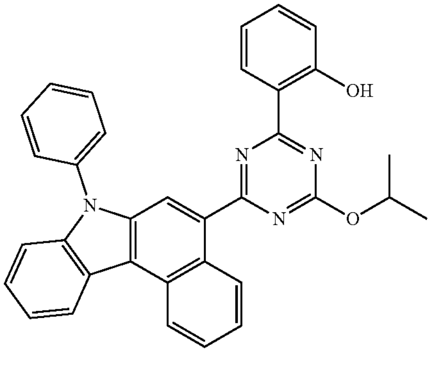
-continued
219
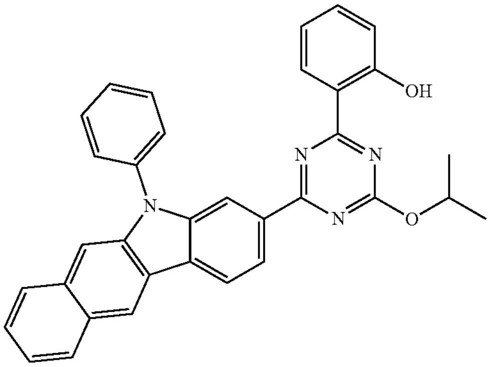
220
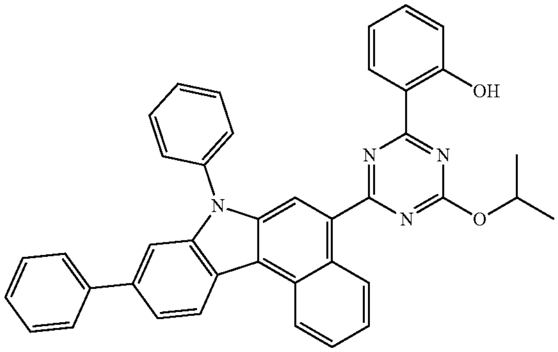
221
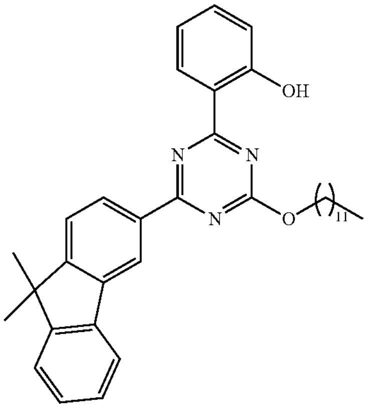
222
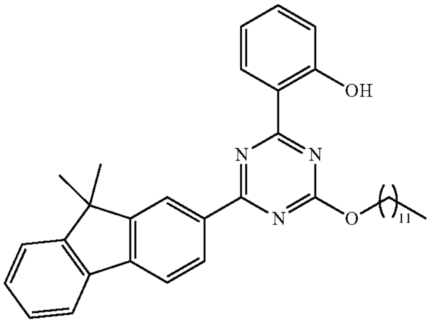

-continued
223
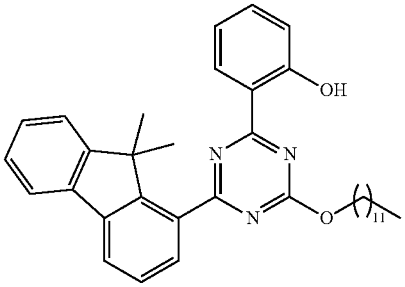
224
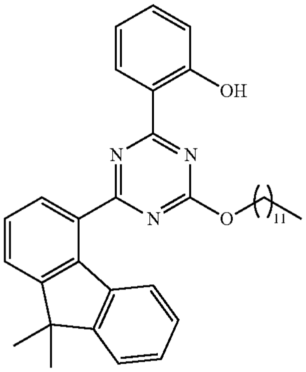
225
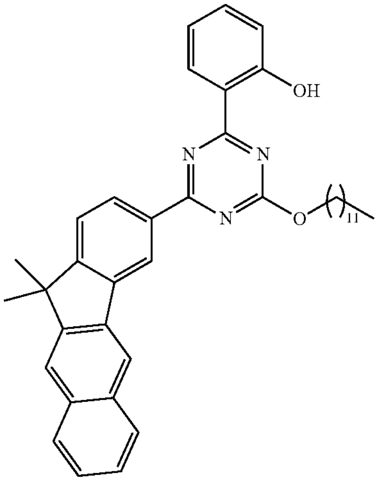
226
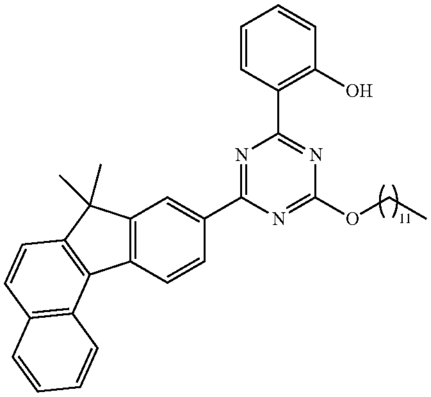
-continued
227
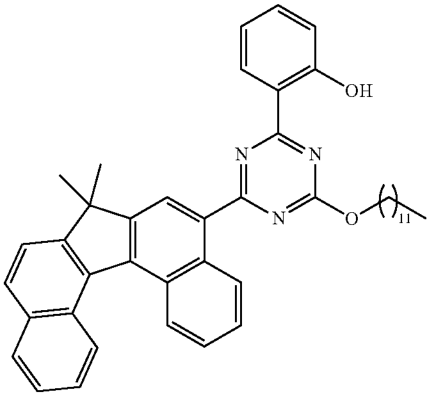
228
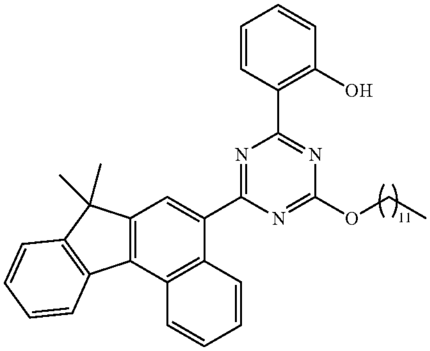
229
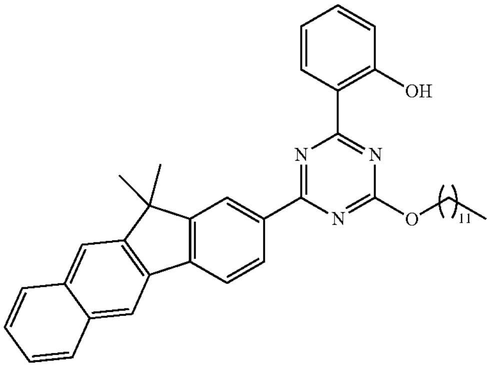
230
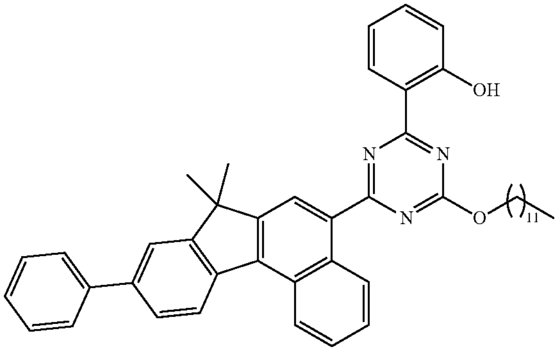

-continued
231
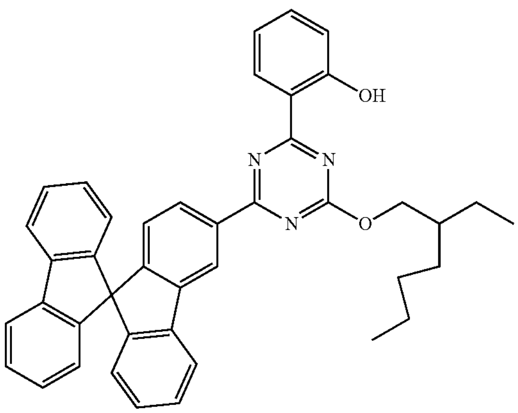
232
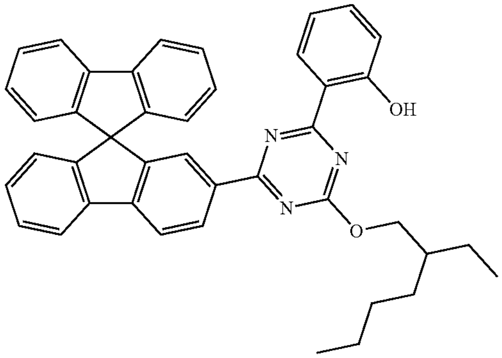
233
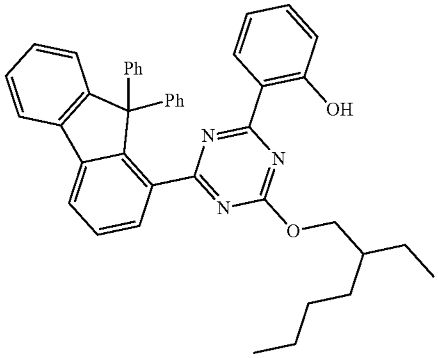
234
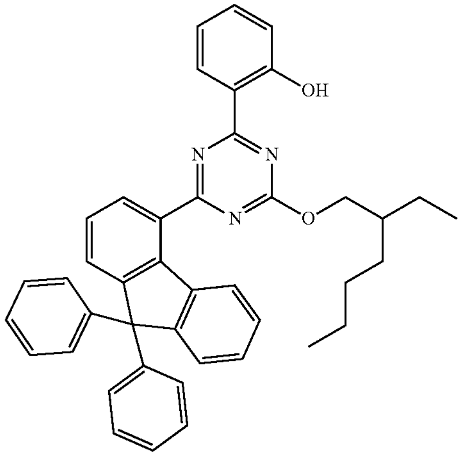
-continued
235
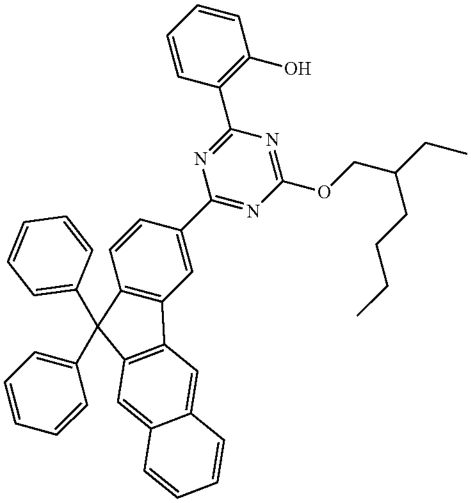
236
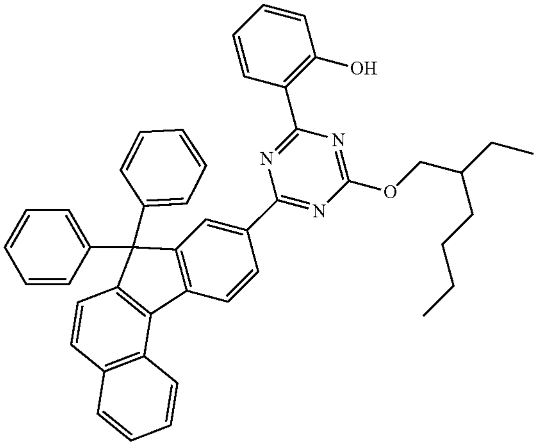
237
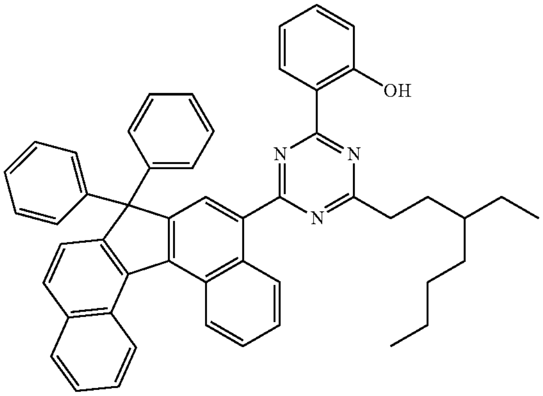

-continued
238
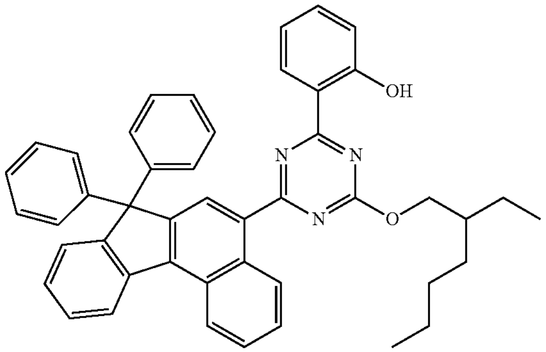
239
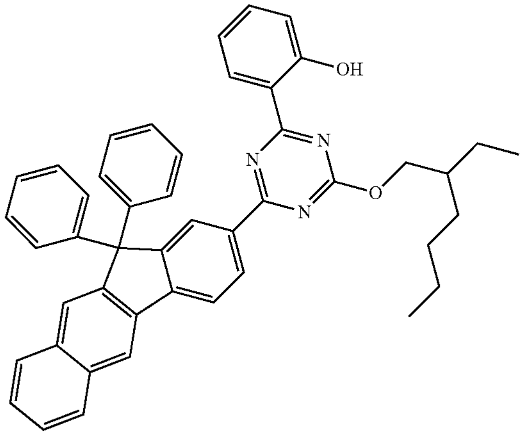
240
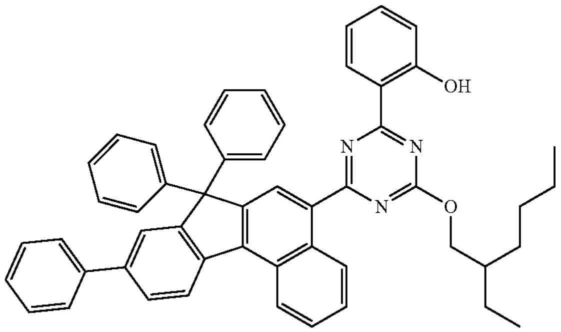
241
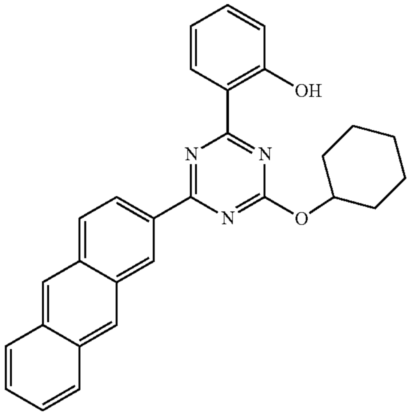
-continued
242
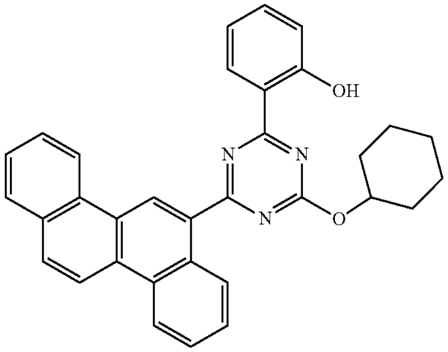
243
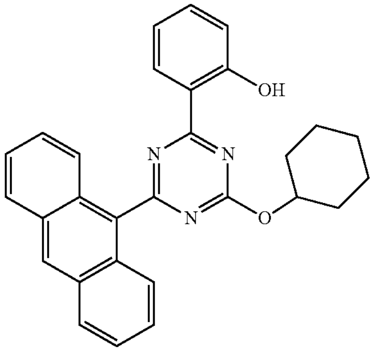
244
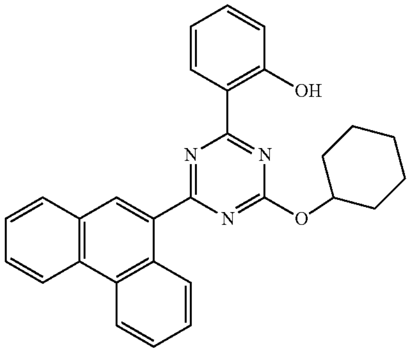
245
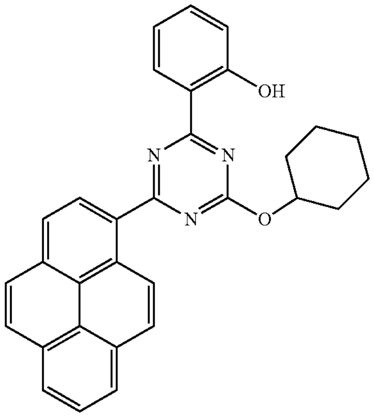

-continued
246
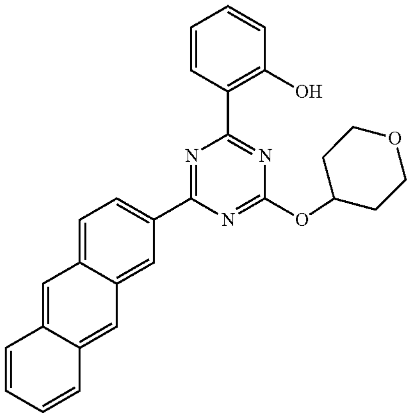
247
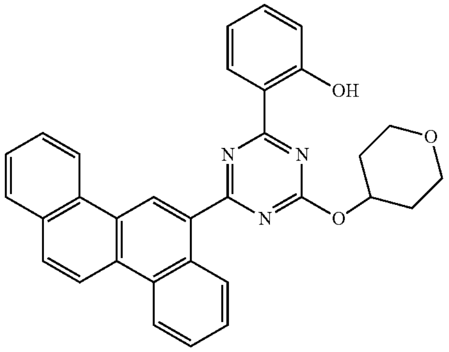
248
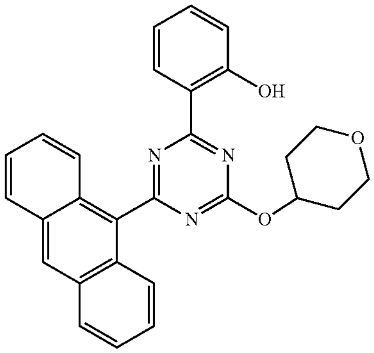
249
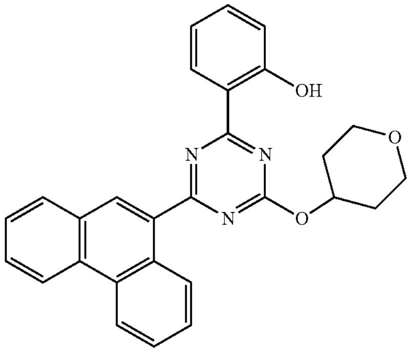
-continued
250
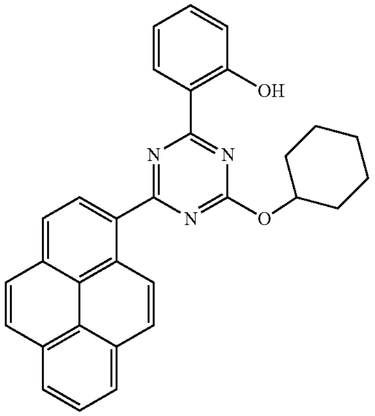
251
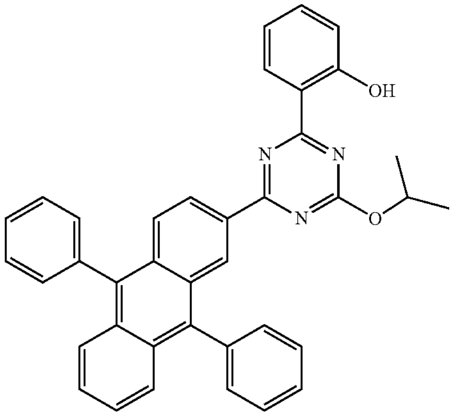
252
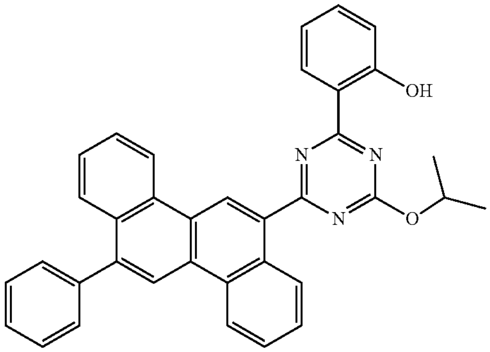
253
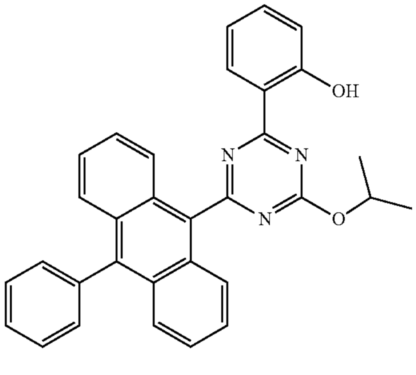

-continued
254
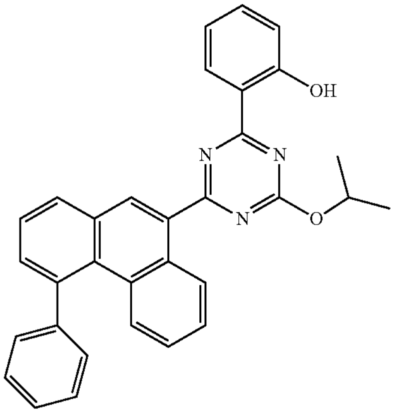
255
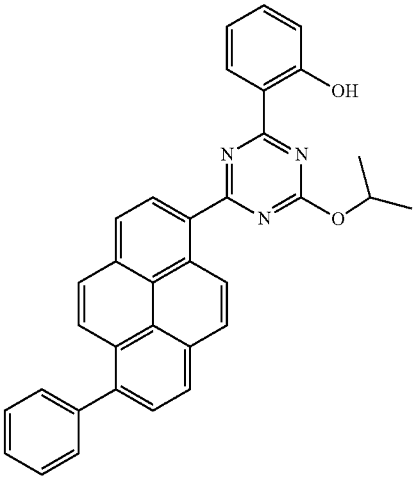
256
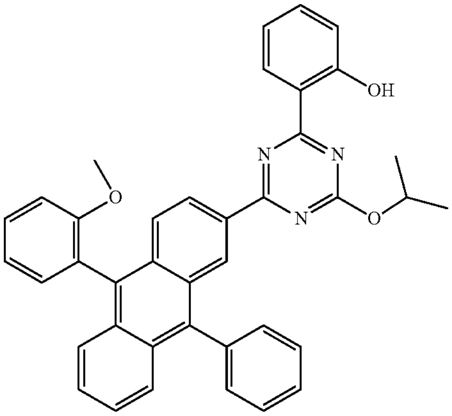
-continued
257
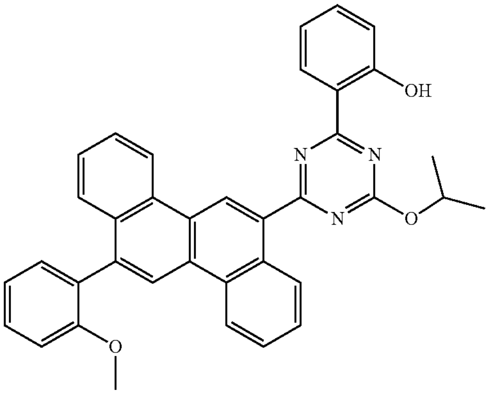
258
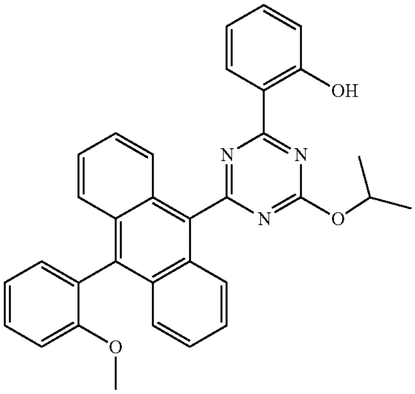
259
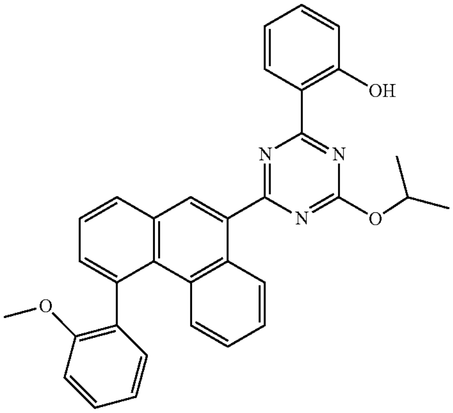

-continued
260
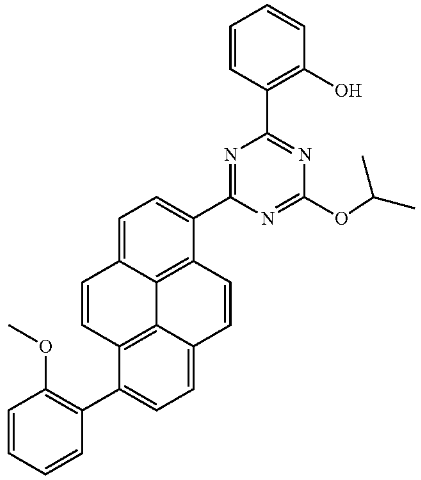
261
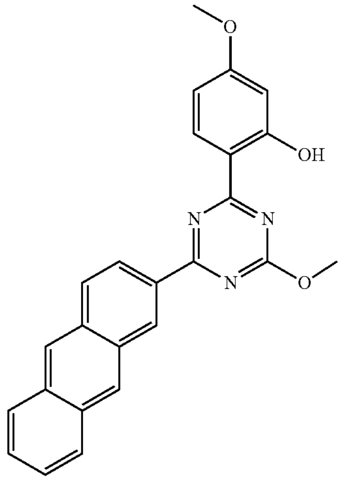
262
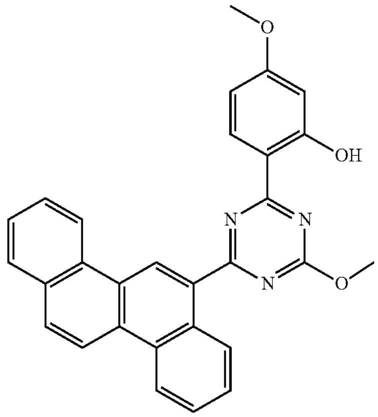
-continued
263
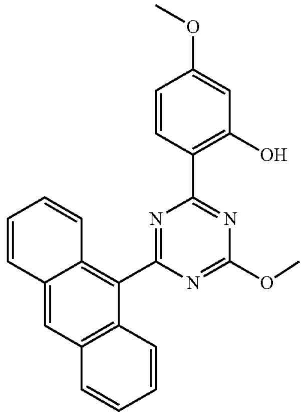
264
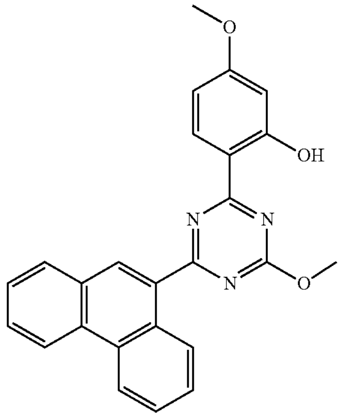
265
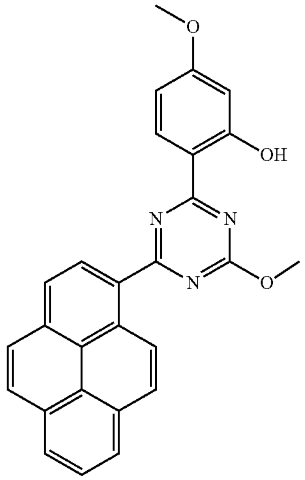

-continued
266
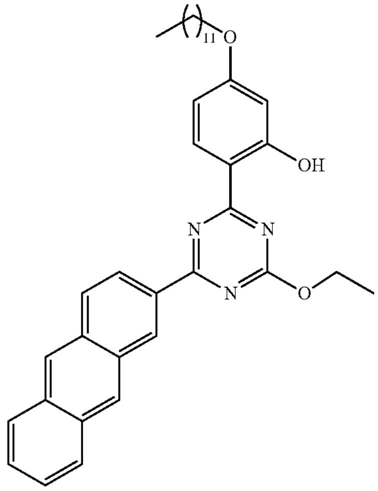
267
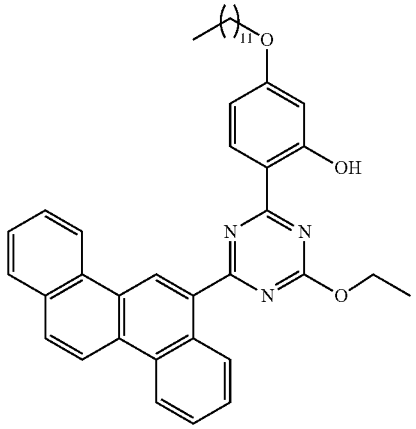
268
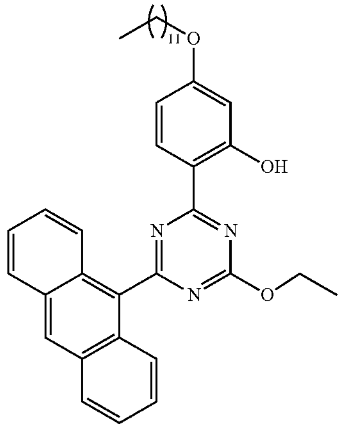
-continued
269
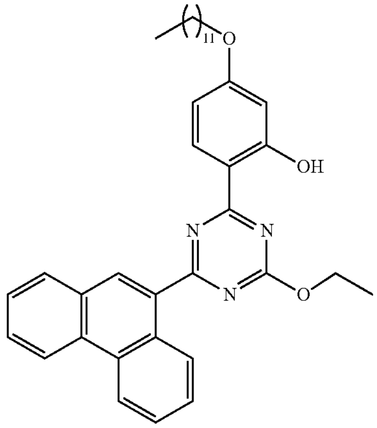
270
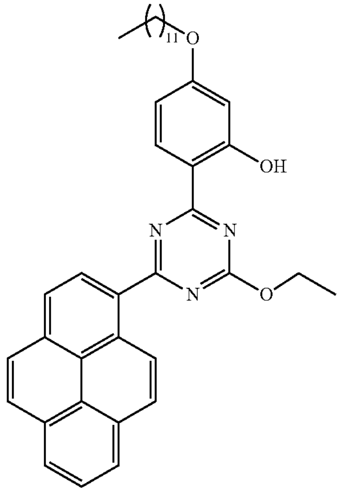
271
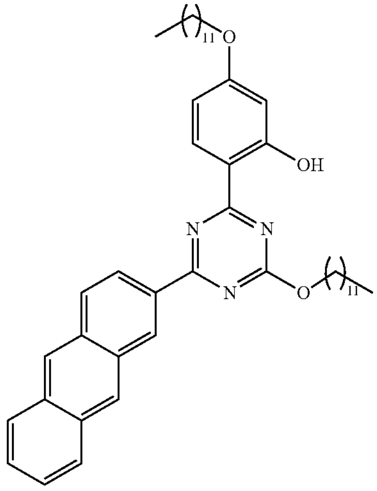

-continued
272
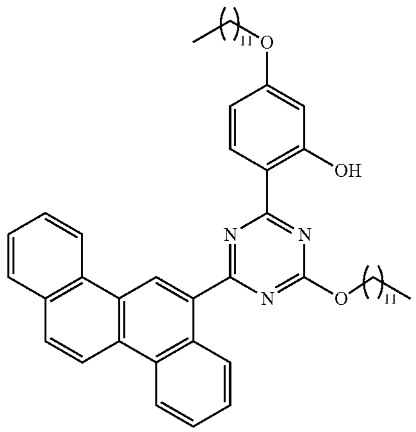
273
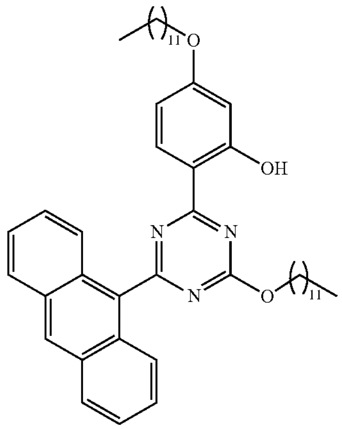
274
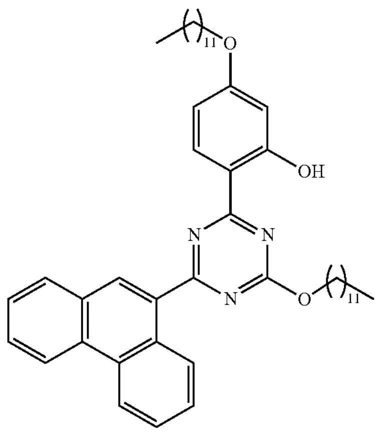
-continued
275
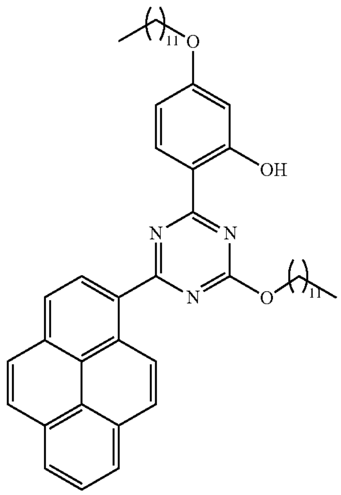
276
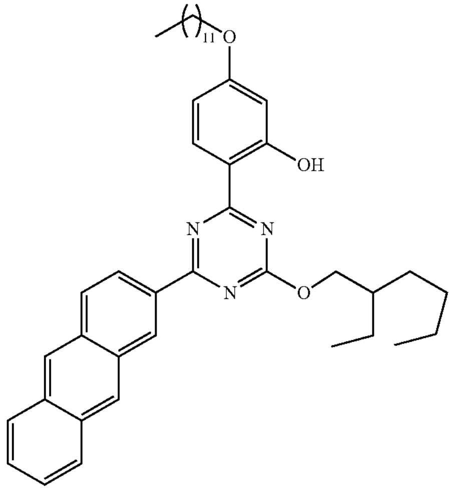
277
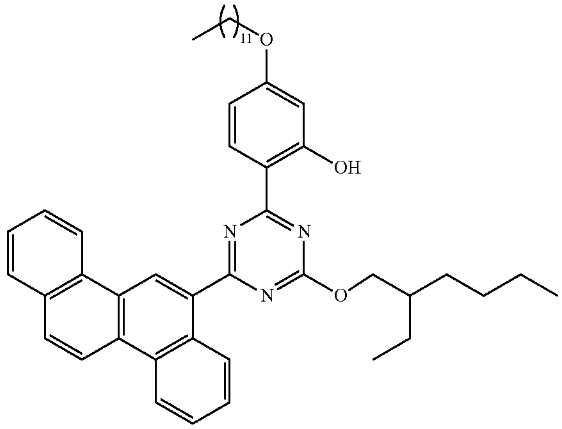

-continued
278
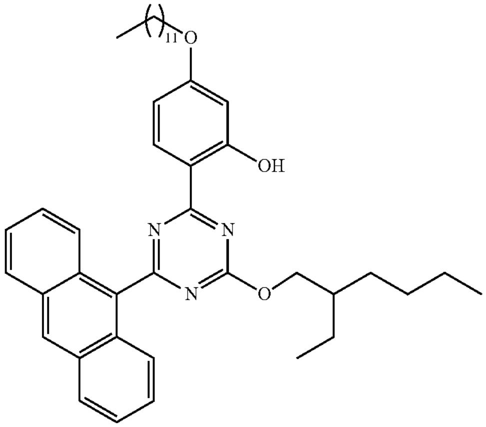
279
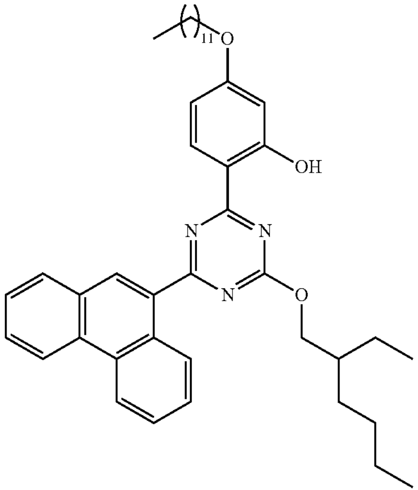
280
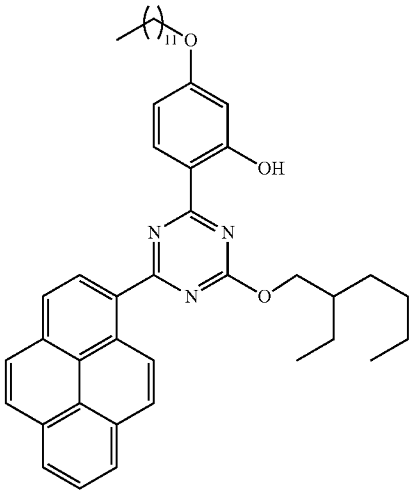
-continued
281
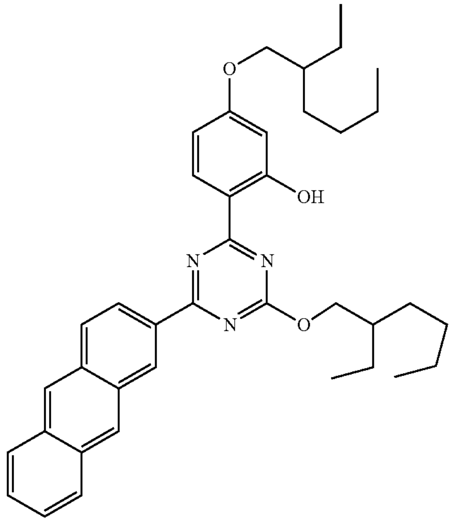
282
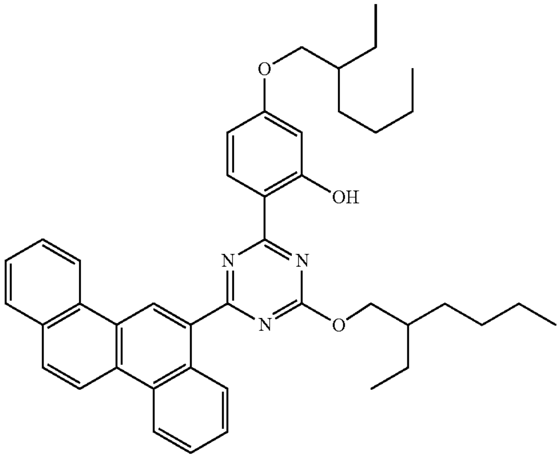
283
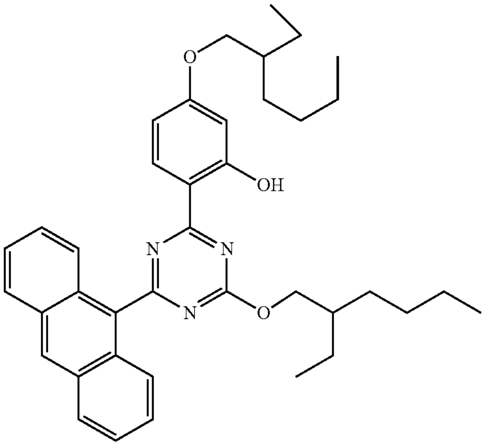

-continued
284
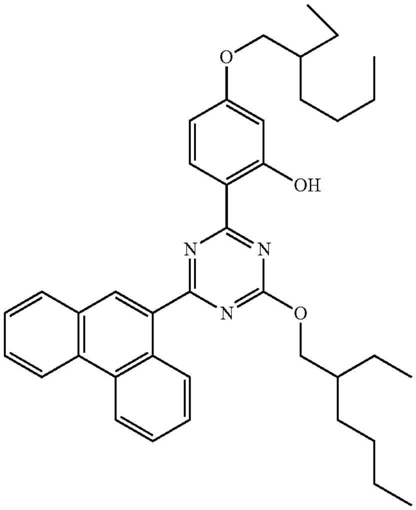
285
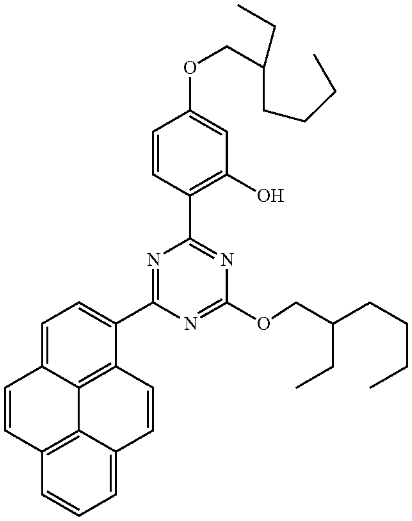
286
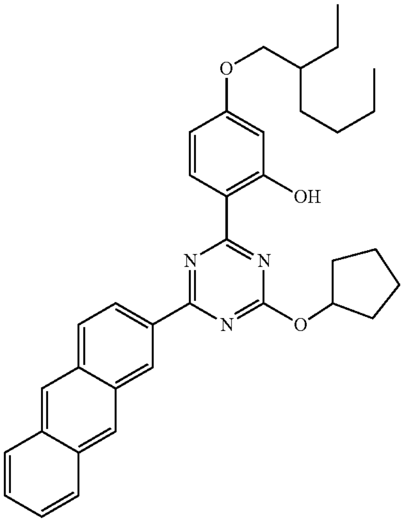
-continued
287
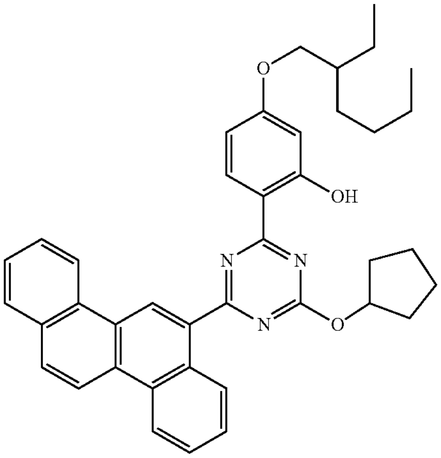
288
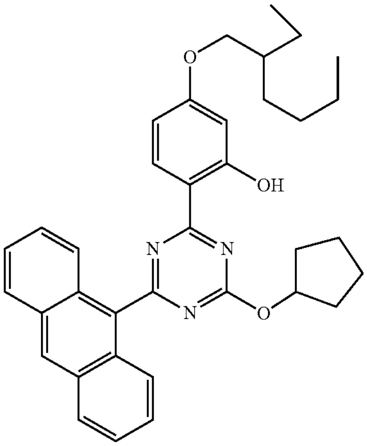
289
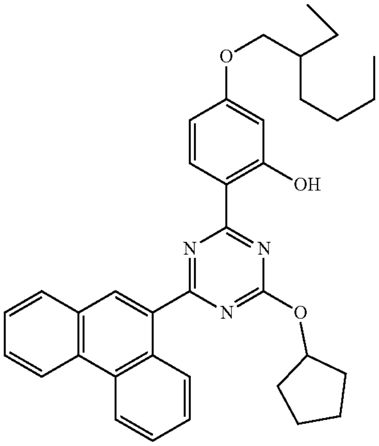

-continued
290
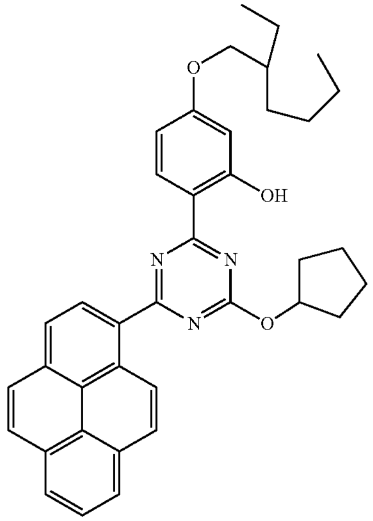
291
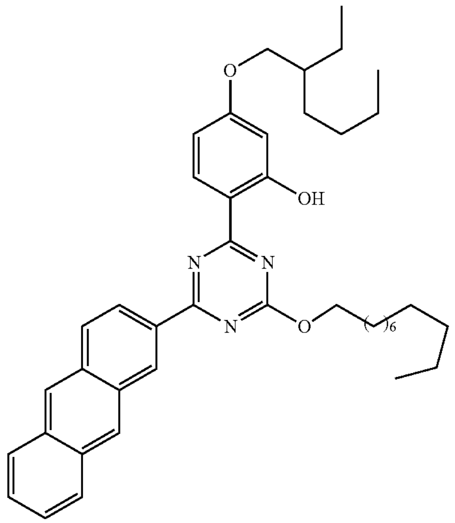
292
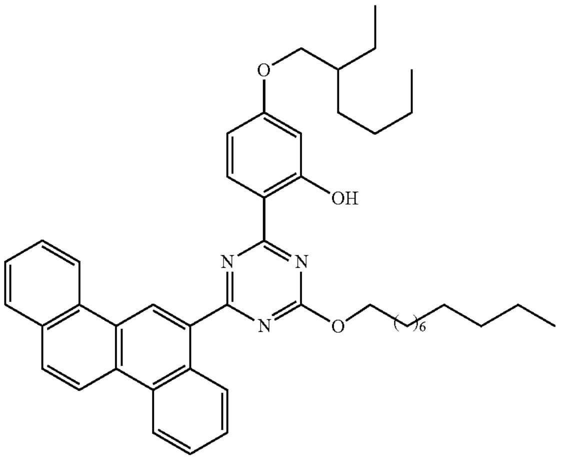
-continued
293
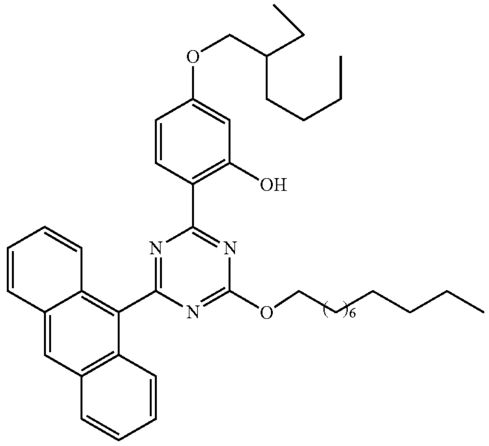
294
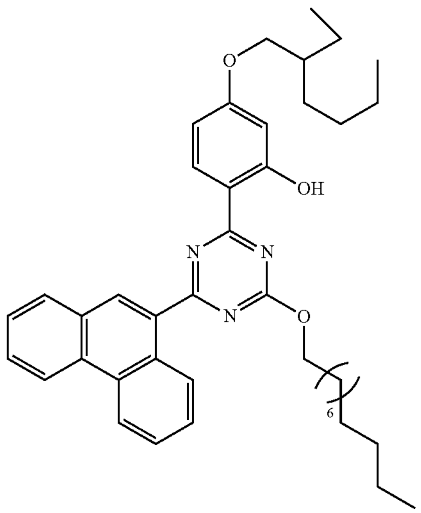
295
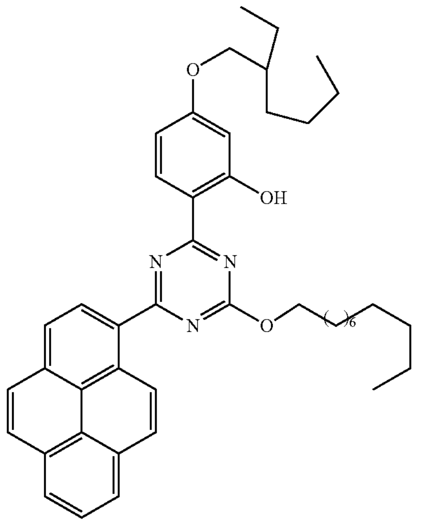

-continued
296
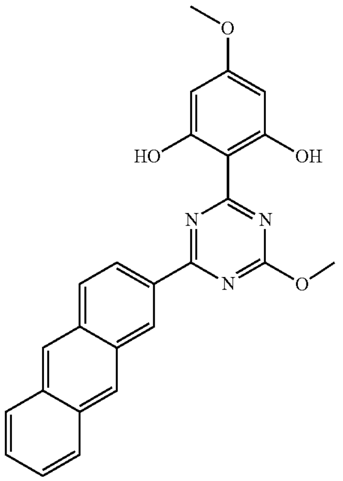
297
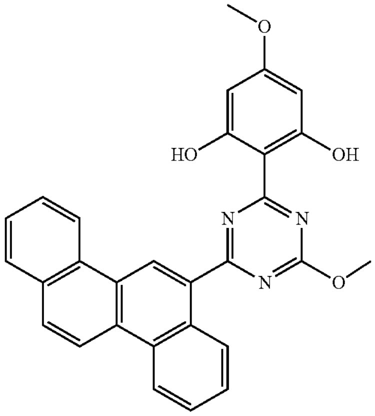
298
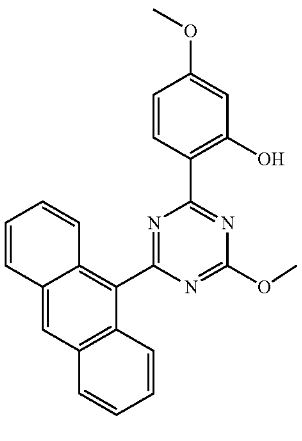
-continued
299
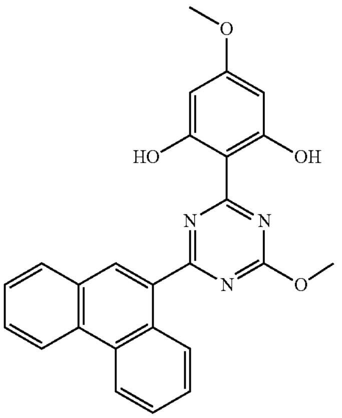
300
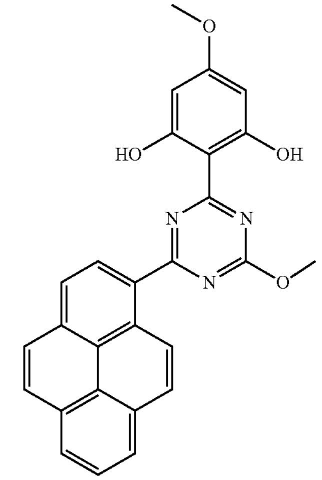
301
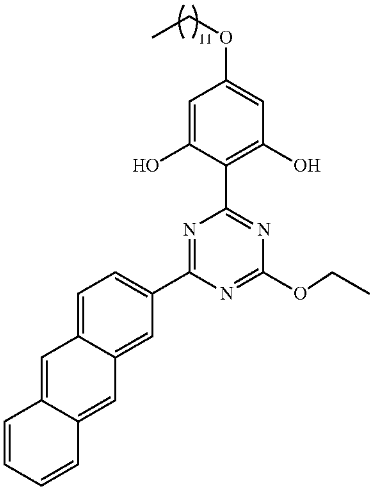

-continued
302
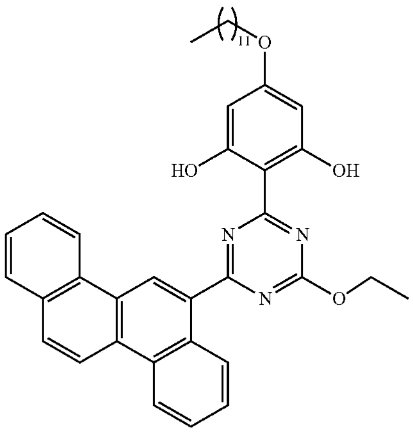
303
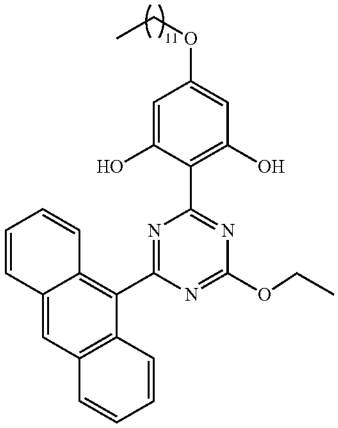
304
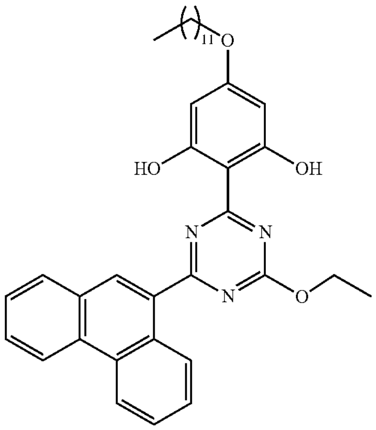
-continued
305
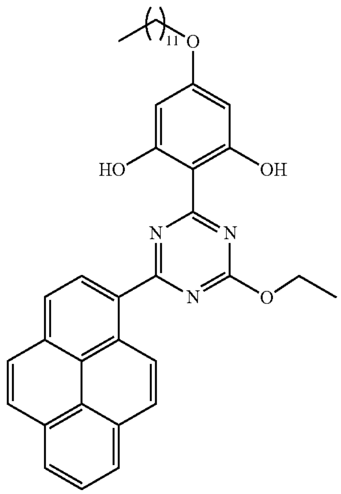
306
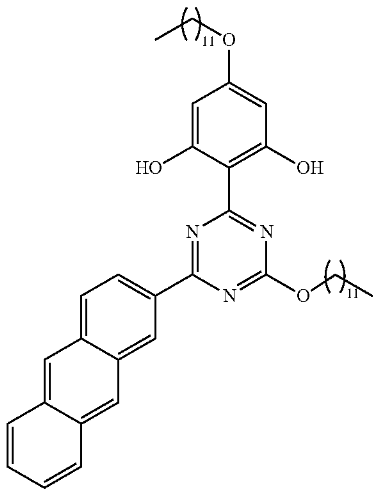
307
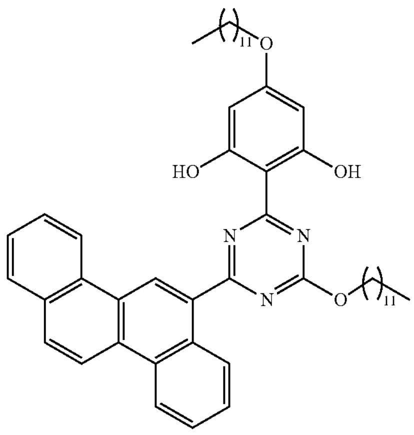

-continued
308
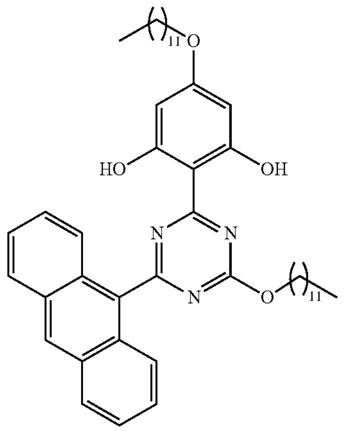
309
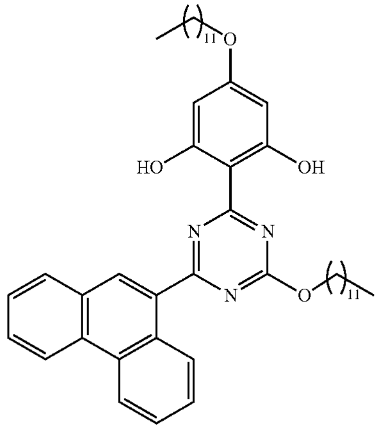
310
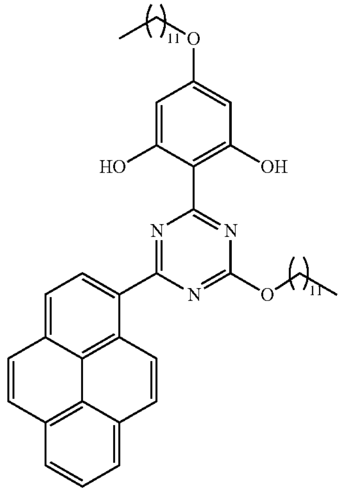
-continued
311
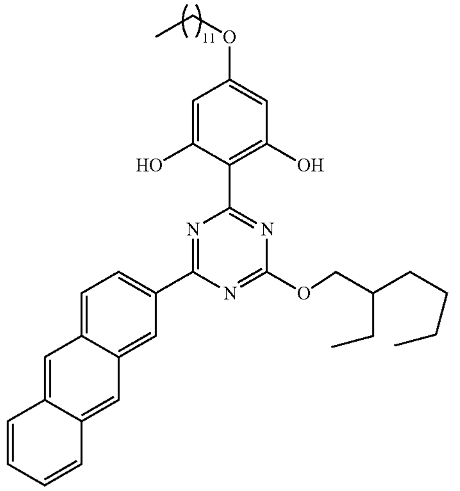
312
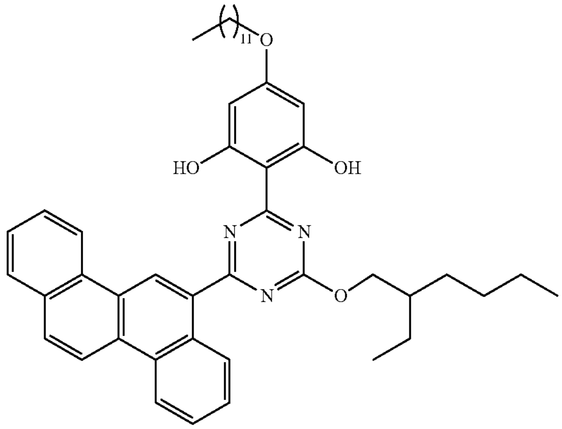
313
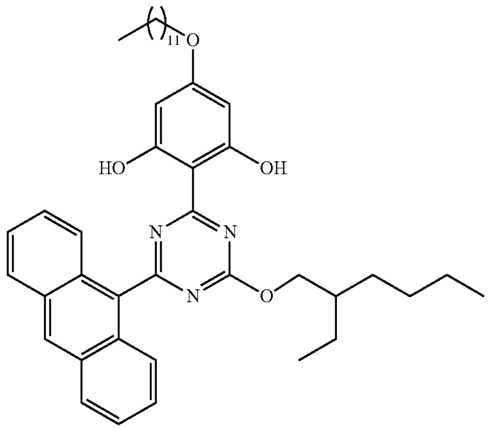

-continued
314
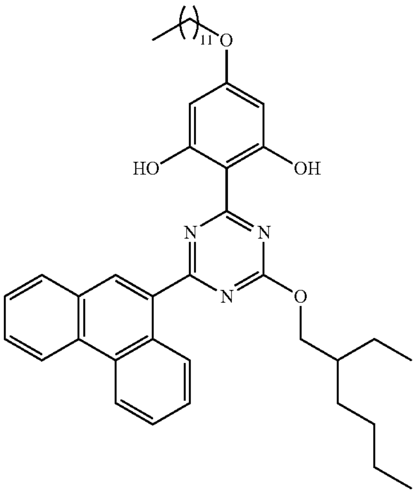
315
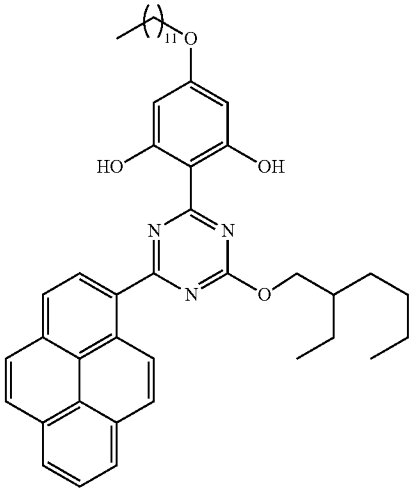
316
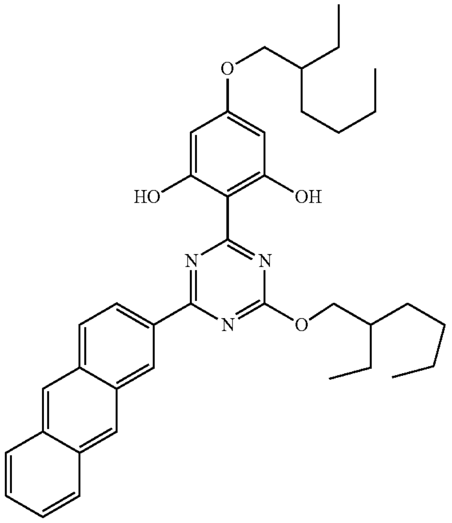
-continued
317
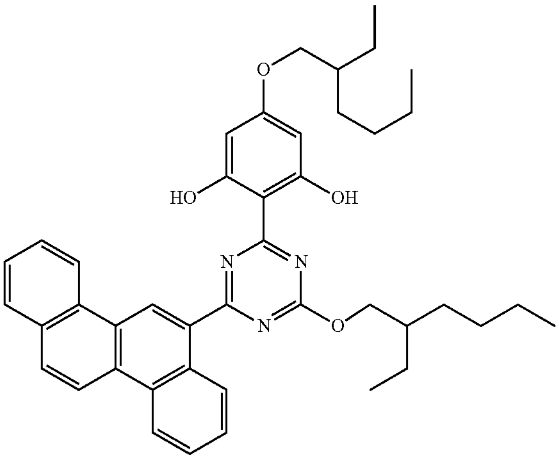
318
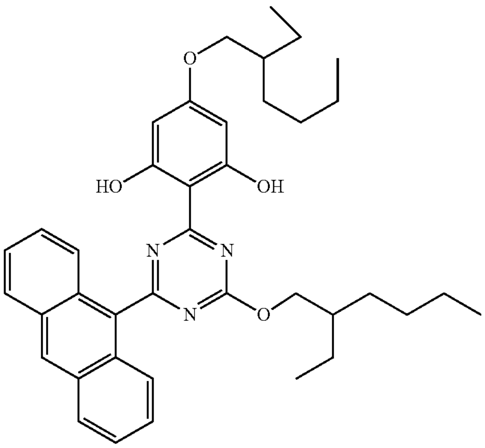
319
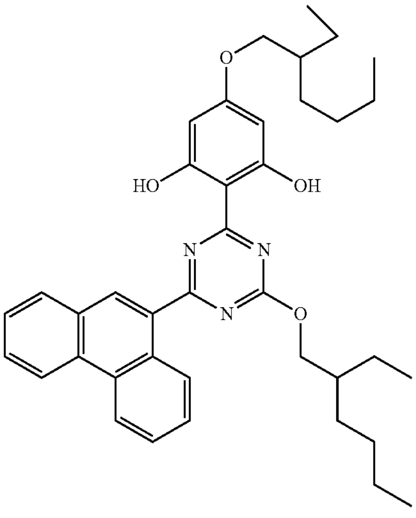

-continued
320
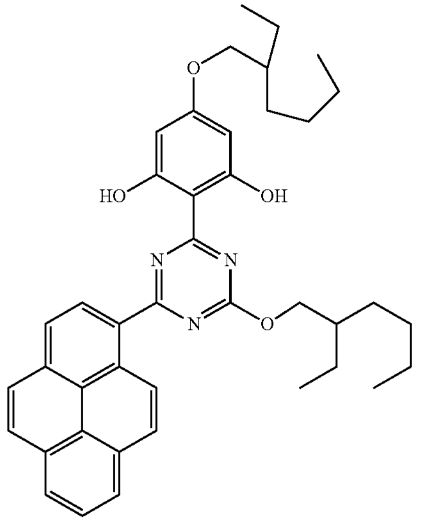
321
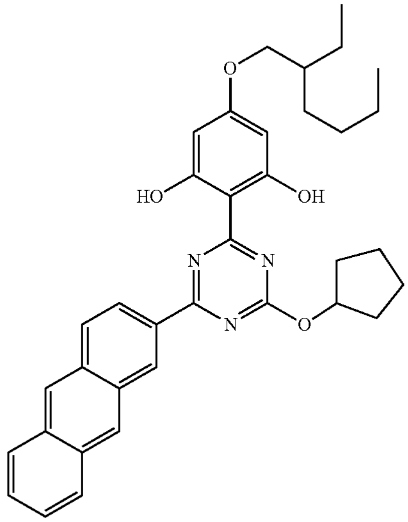
322
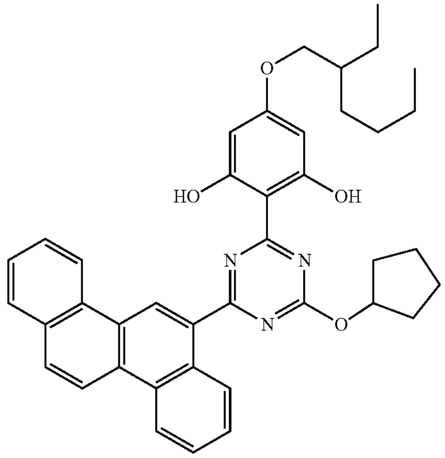
-continued
323
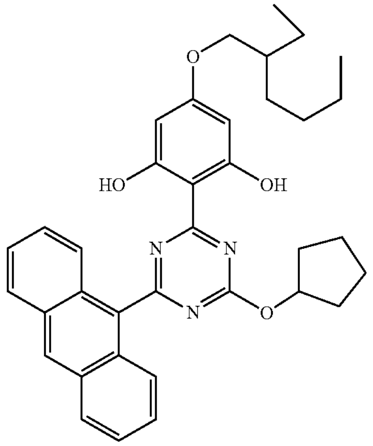
324
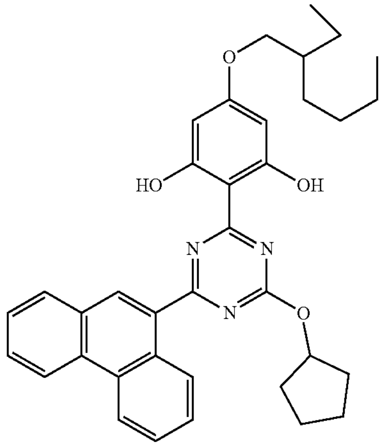
325
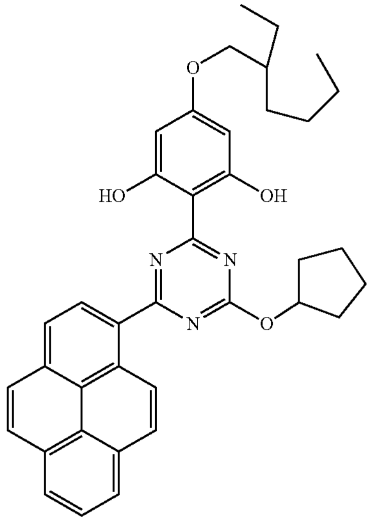

-continued
326
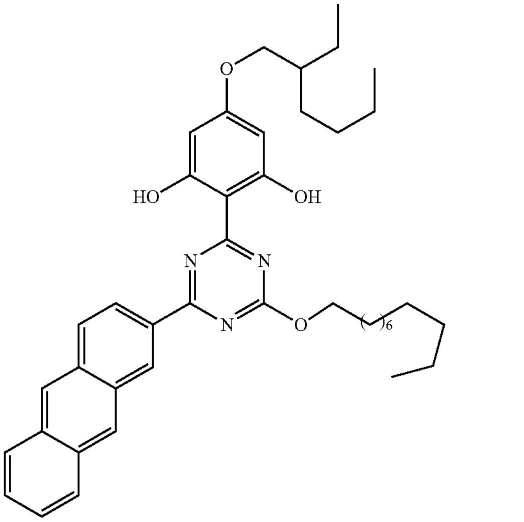
327
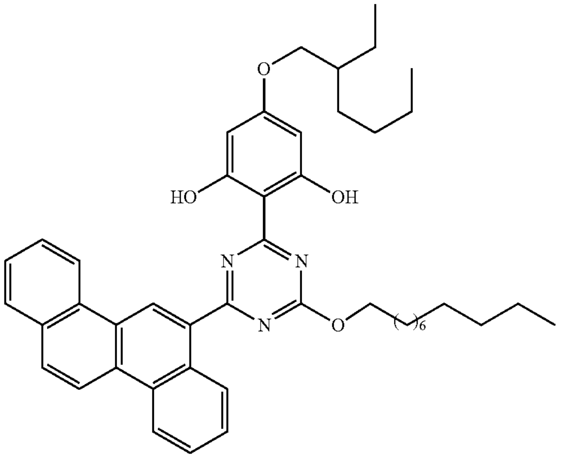
328
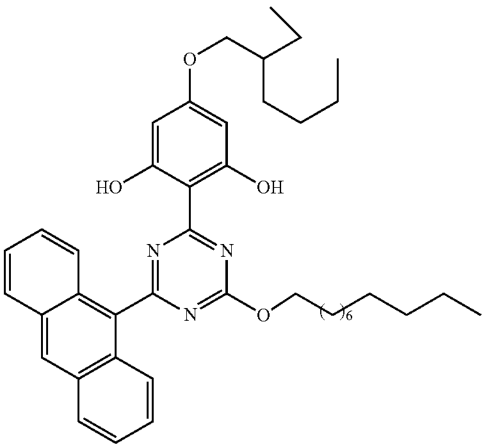
-continued
329
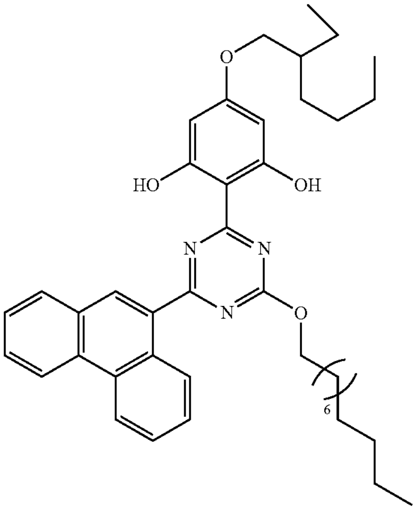
330
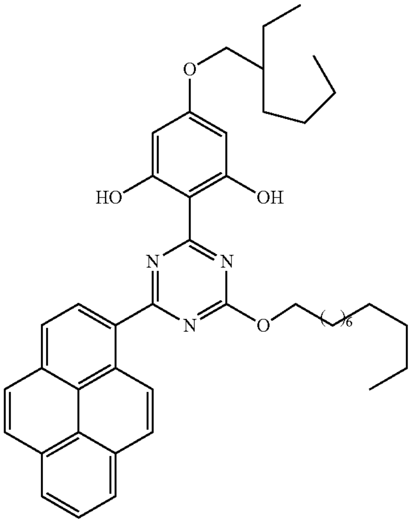
331
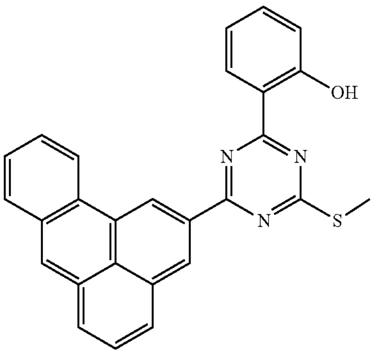

-continued
332
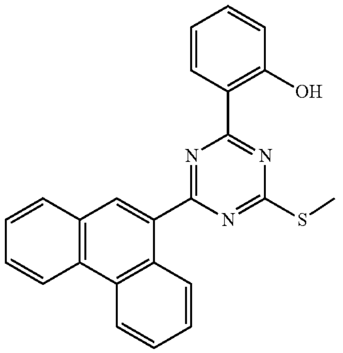
333
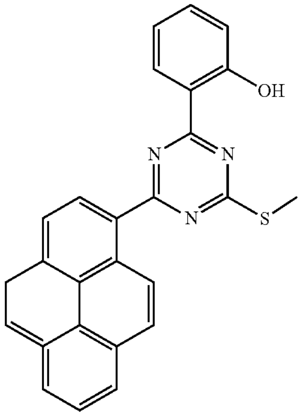
334
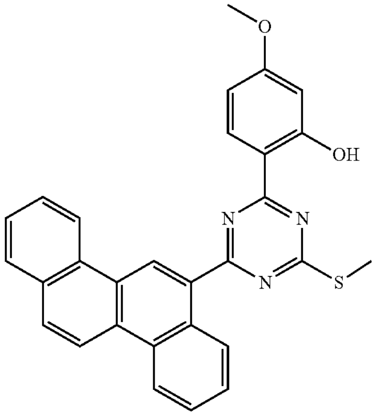
335
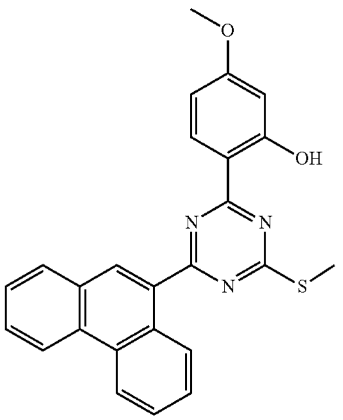
-continued
336
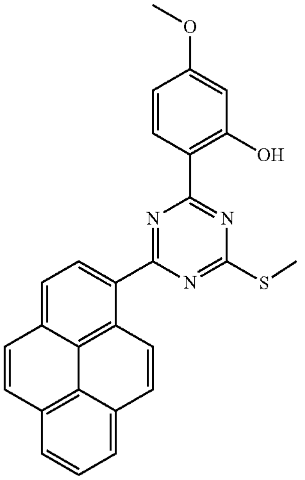
337
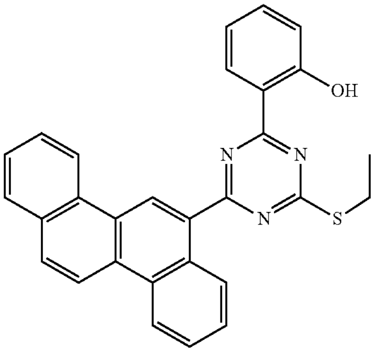
338
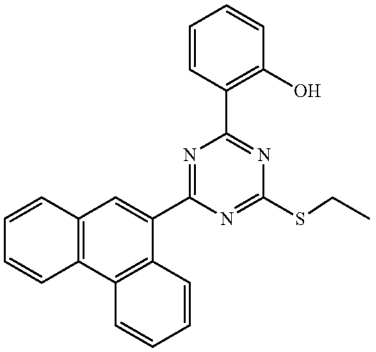
339
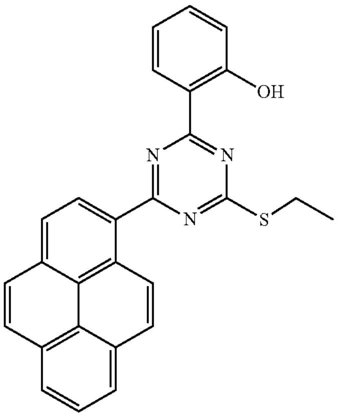

340
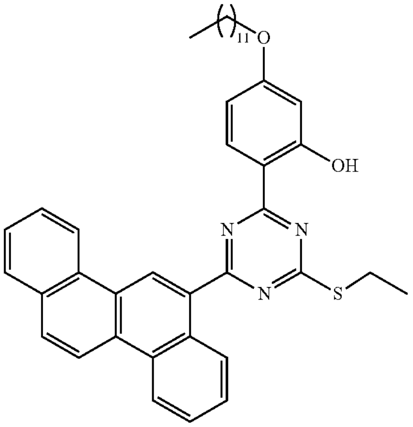
341
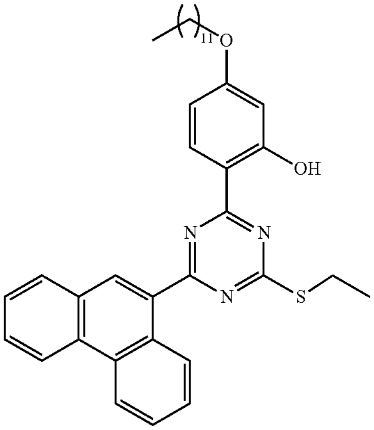
342
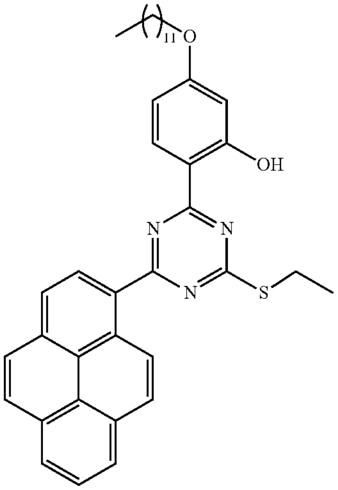
343
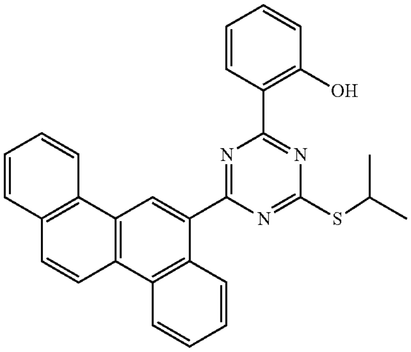
344
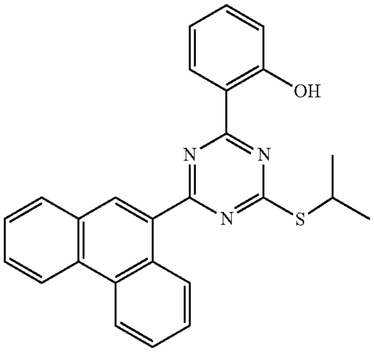
345
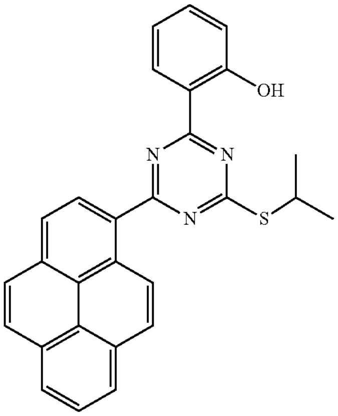
346
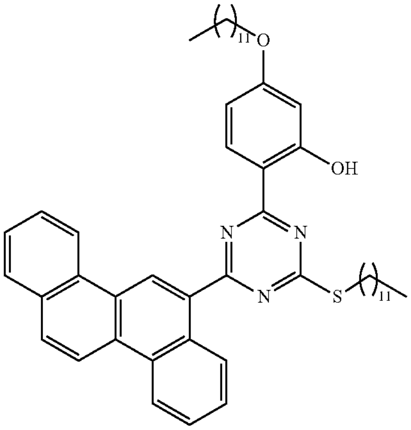

-continued
347
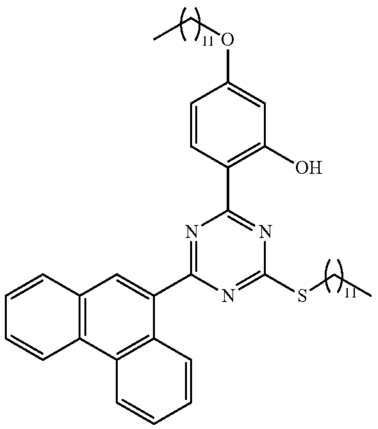
348
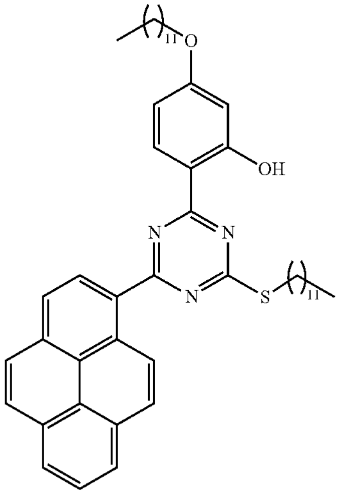
349
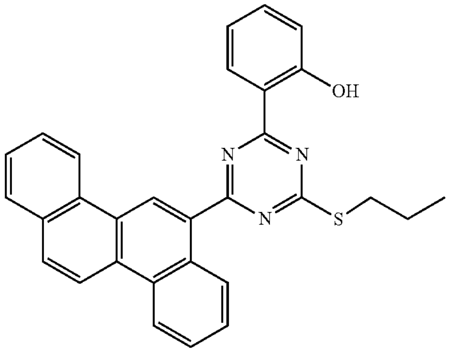
350
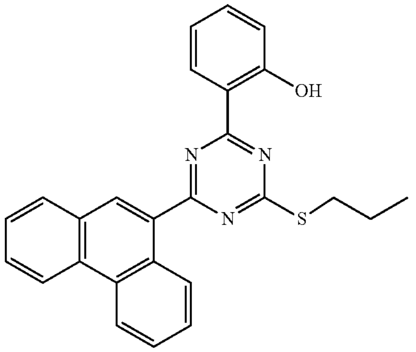
-continued
351
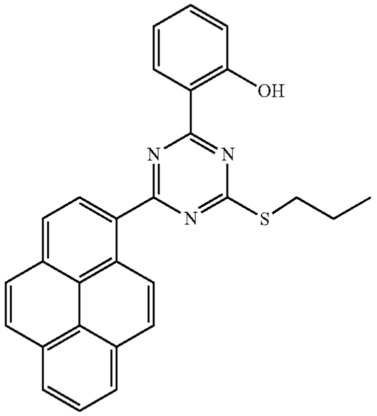
352
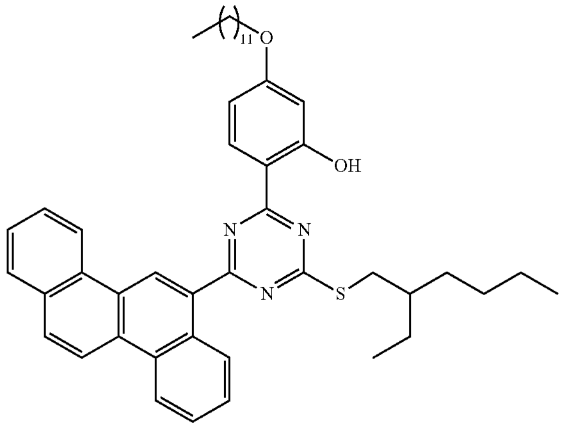
353
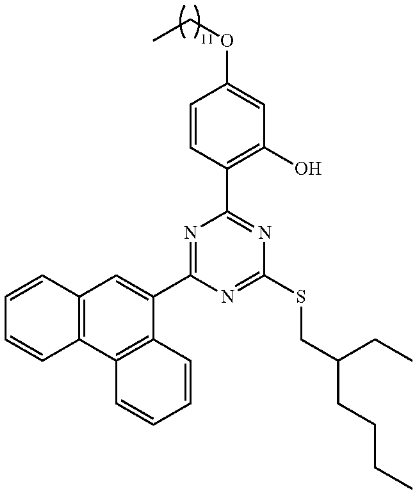

-continued
354
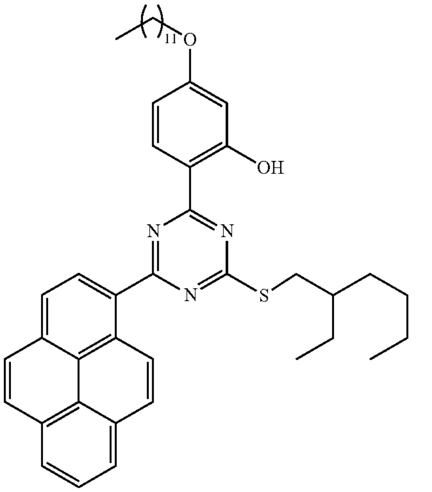
355
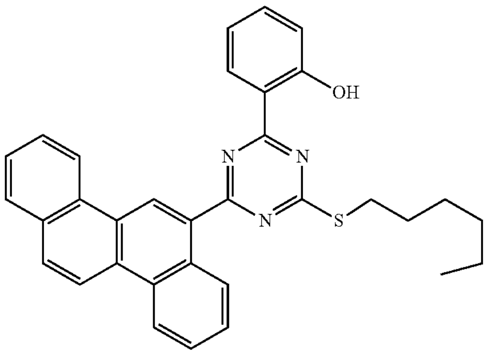
356
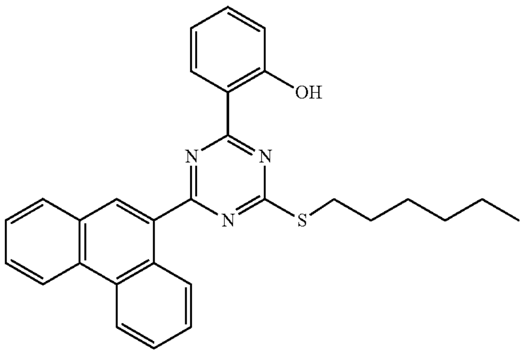
357
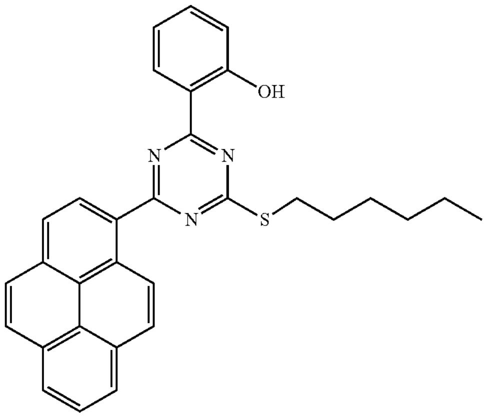
-continued
358
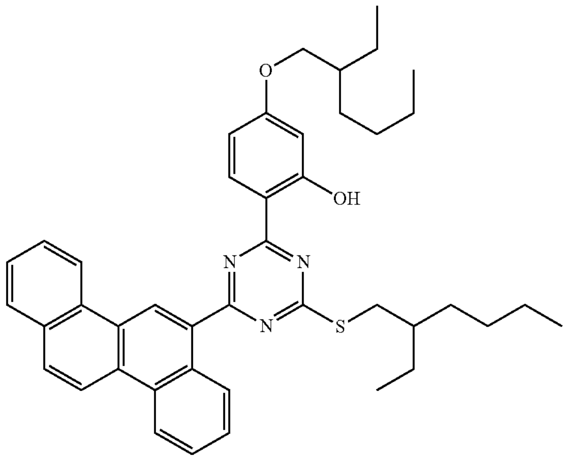
359
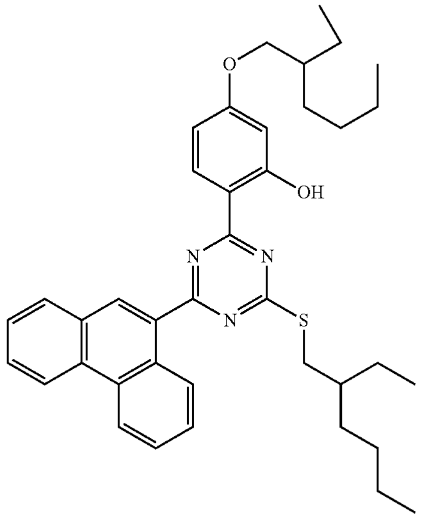
360
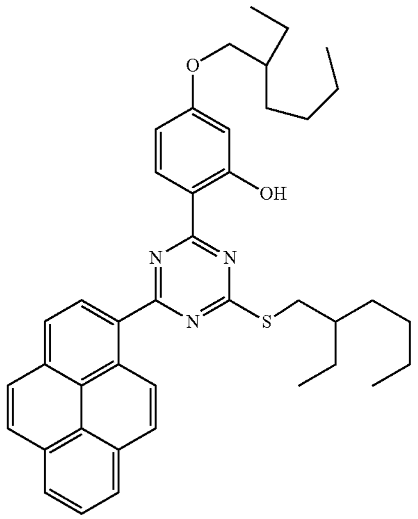

-continued
361
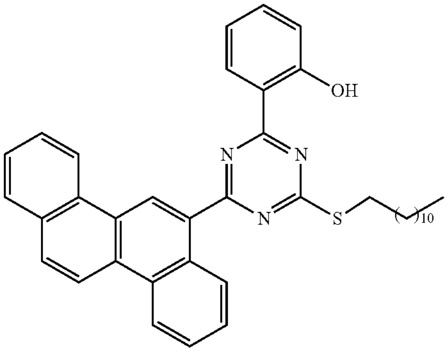
362
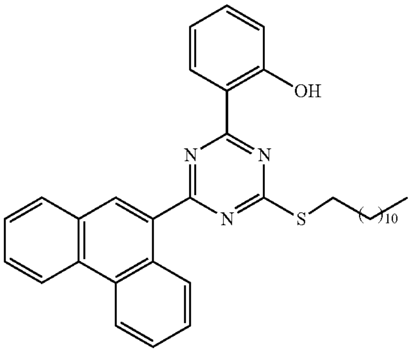
363
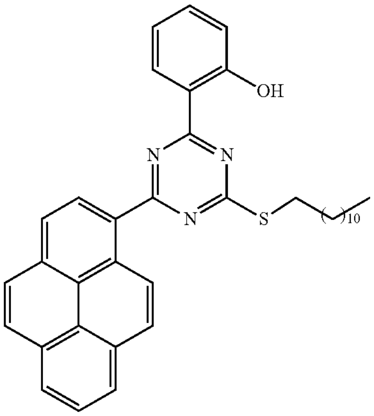
364
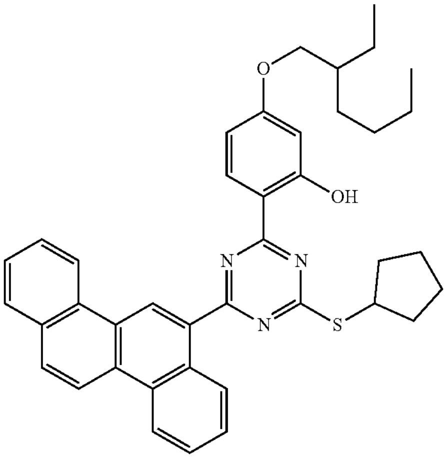
-continued
365
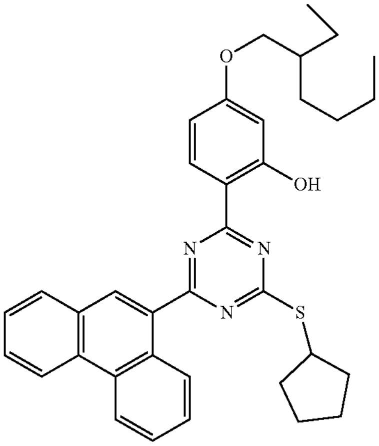
366
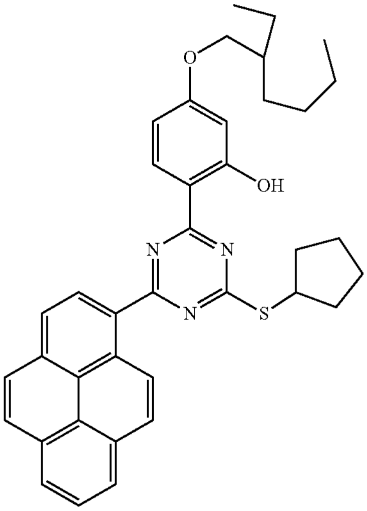
367
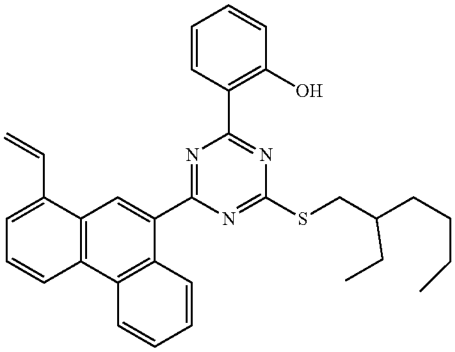

368
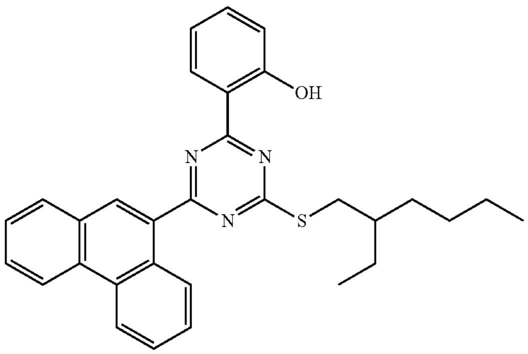
369
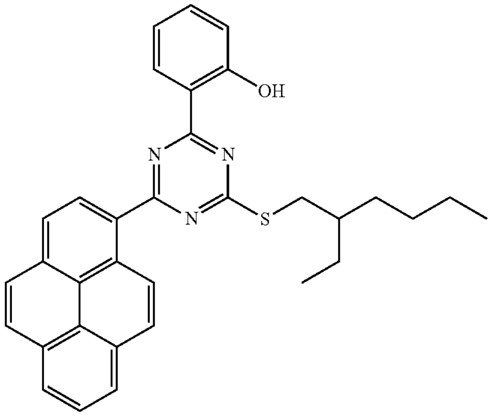
370
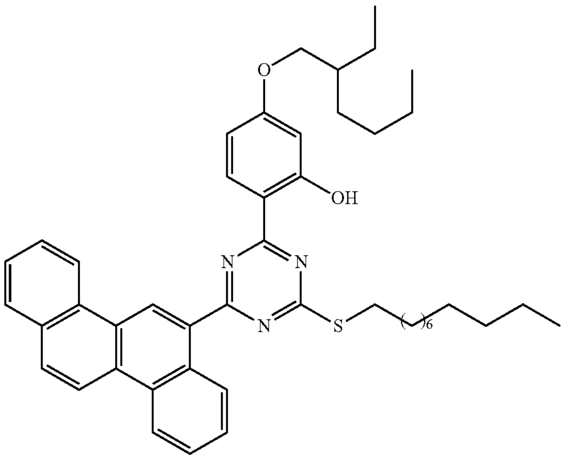
371
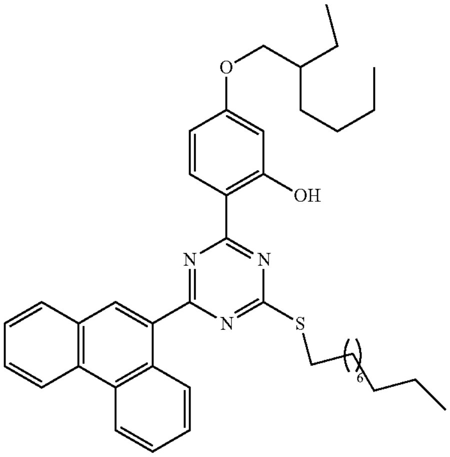
372
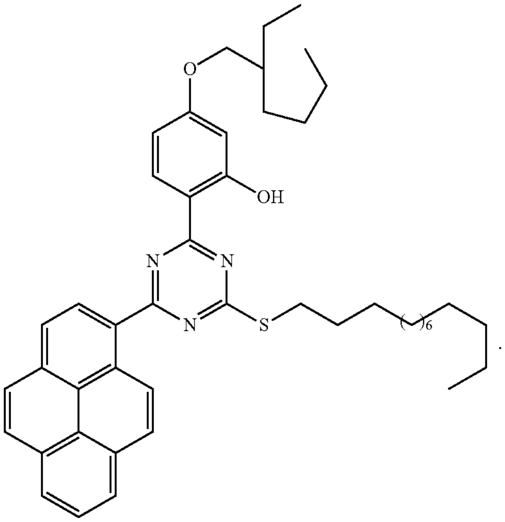
* * * * *

UNITED STATES PATENT AND TRADEMARK OFFICE

CERTIFICATE OF CORRECTION

PATENT NO. : 12,289,992 B2
APPLICATION NO. : 17/250808
DATED : April 29, 2025
INVENTOR(S) : Sanghyun Han et al.

It is certified that error appears in the above-identified patent and that said Letters Patent is hereby corrected as shown below:

In the Claims

In Column 250, Line 36, in Claim 12, above “wherein,” insert -- and --.

In Column 251, Lines 52-60, in Claim 14, Compound Ar-c, delete “ 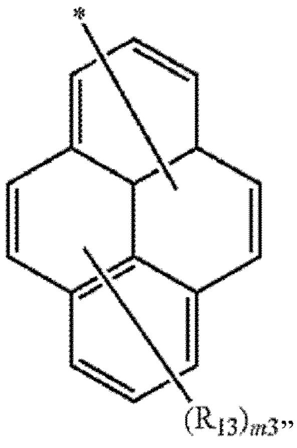 ” and insert -- 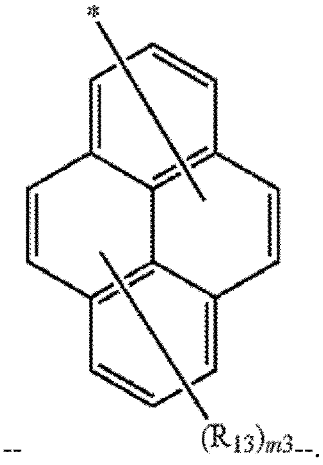 --.

Signed and Sealed this
Sixth Day of January, 2026

John A. Squires
*Director of the United States Patent and Trademark Office*

In Column 450, Lines 17-31, in Claim 23, Compound 144, delete
" 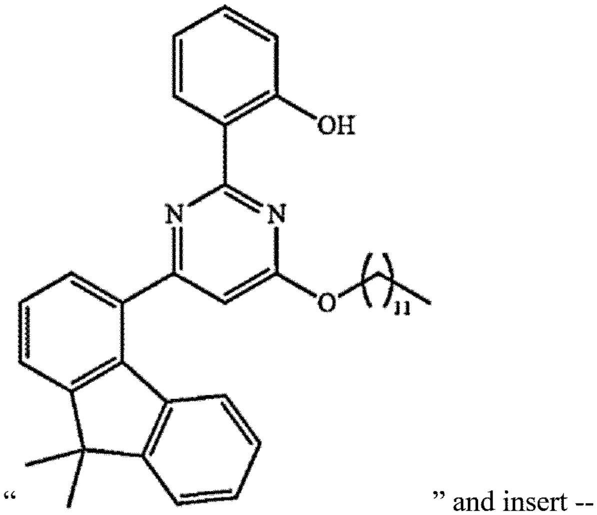 " and insert -- 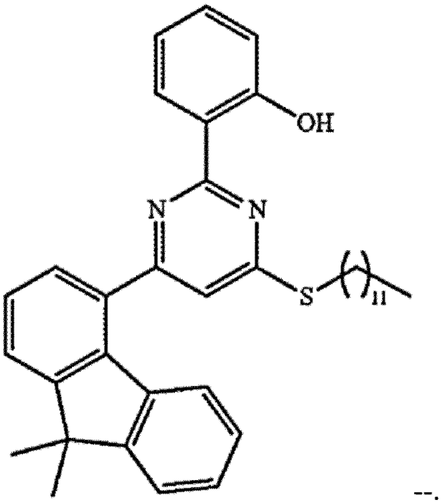 --.
In Column 453, Lines 51-65, in Claim 23, Compound 157, delete
" 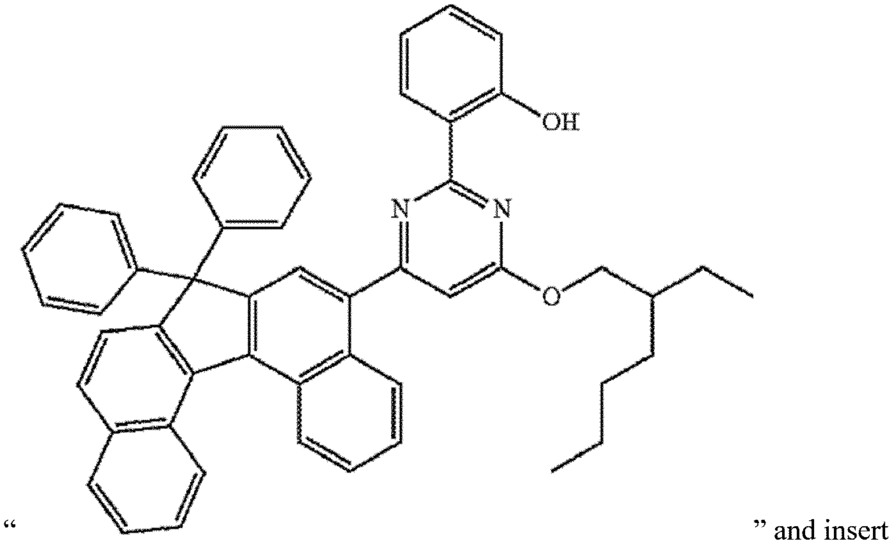 " and insert -- 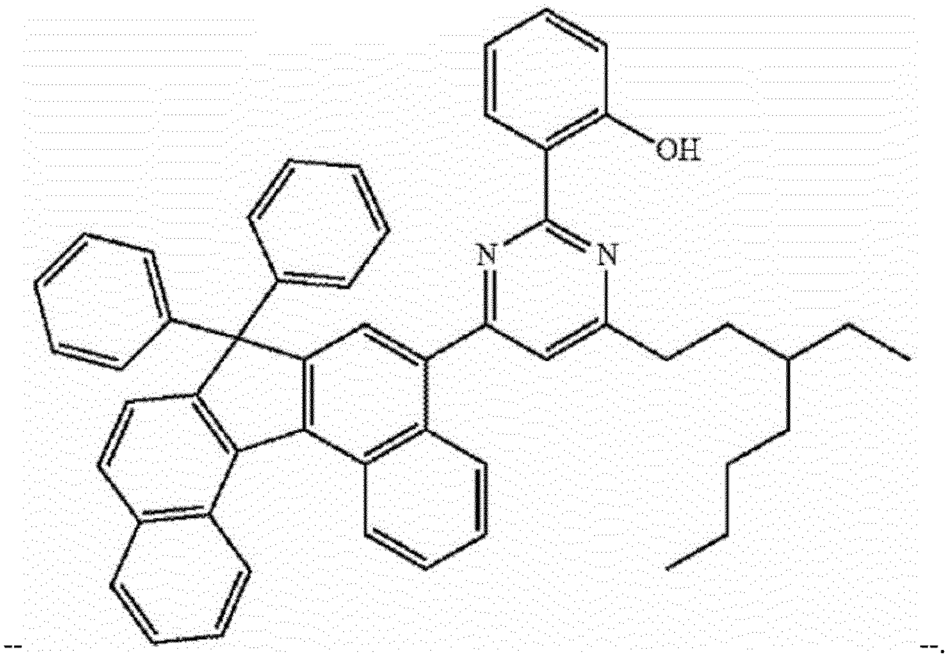 --.
In Column 464, Lines 52-65, in Claim 23, Compound 14, delete
" 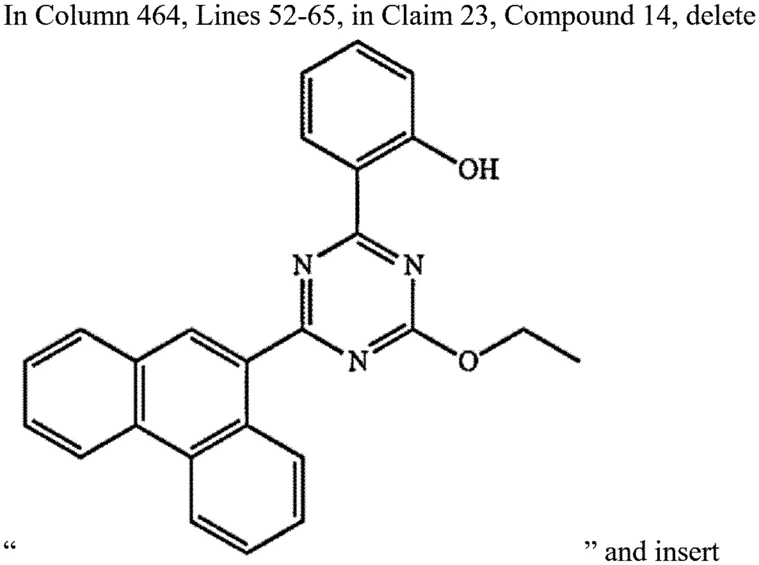 " and insert -- 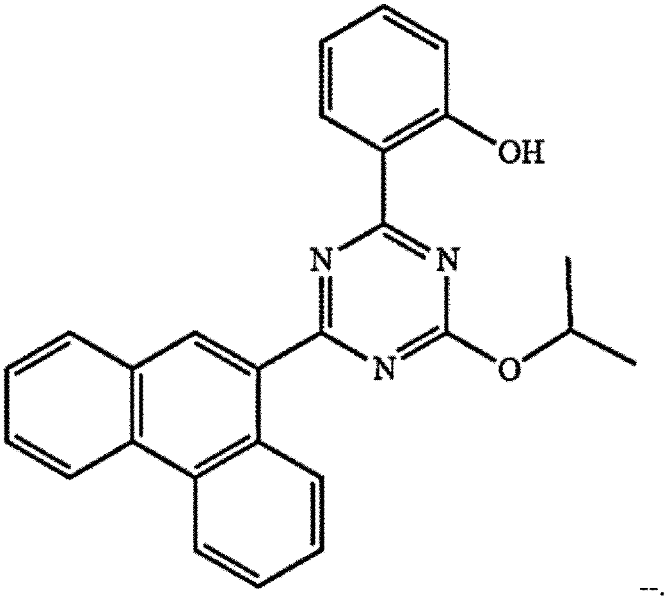 --.
In Column 465, Lines 3-18, in Claim 23, Compound 15, delete " 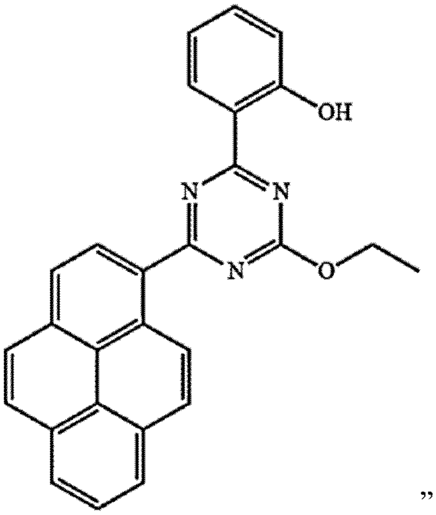 "

and insert -- 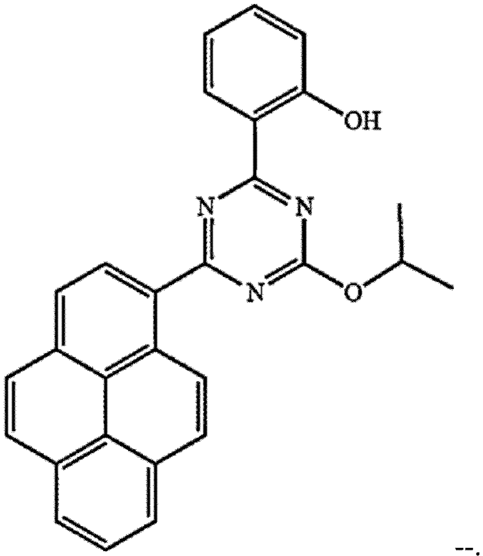 --.
In Column 530, Lines 36-51, in Claim 23, Compound 248, delete
" 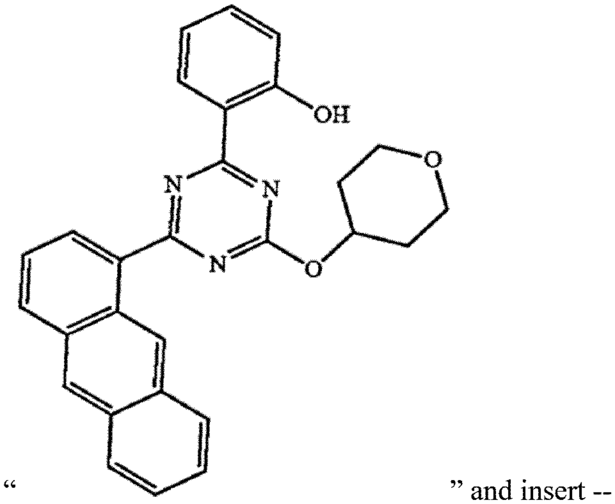 " and insert -- 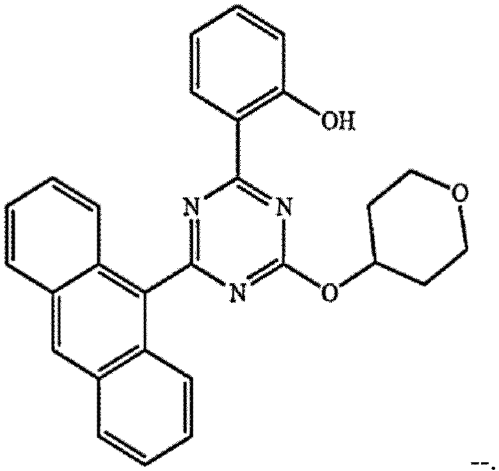 --.

In Column 541, Lines 2-21, in Claim 23, Compound 281, delete
"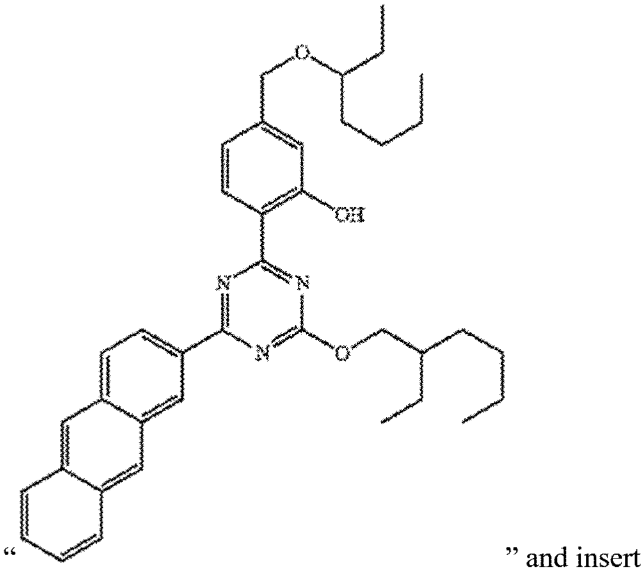" and insert
--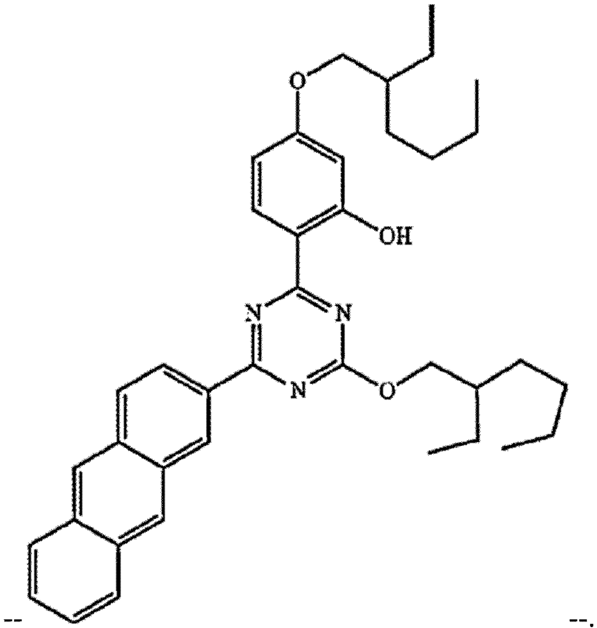--.

In Column 541, Lines 28-45, in Claim 23, Compound 282, delete
"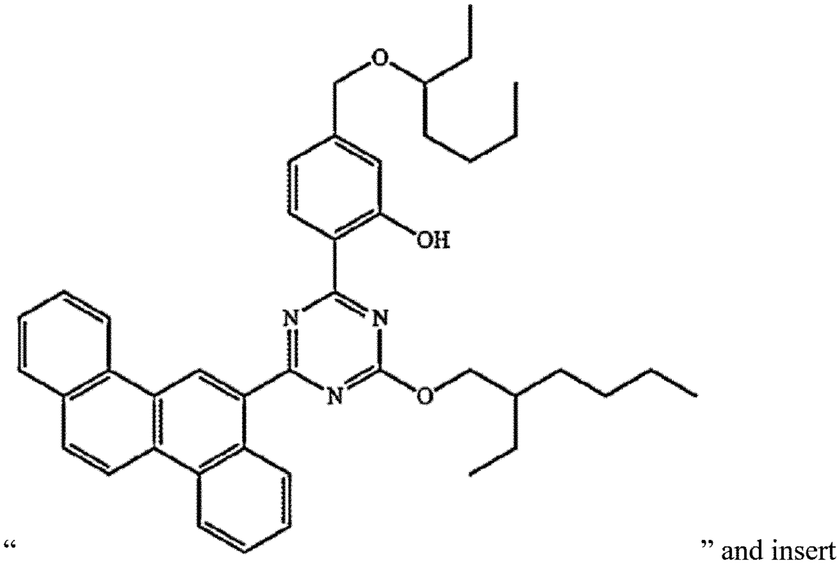" and insert
--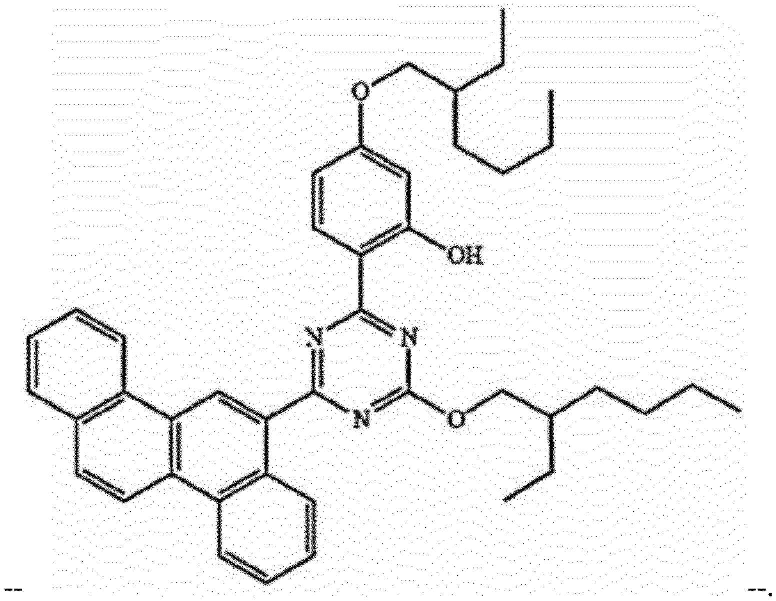--.

In Column 541, Lines 50-65, in Claim 23, Compound 283, delete
"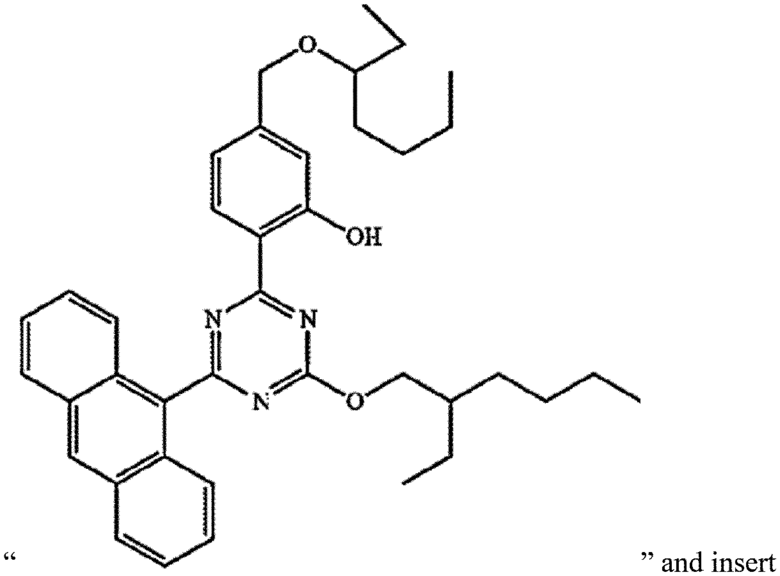" and insert
--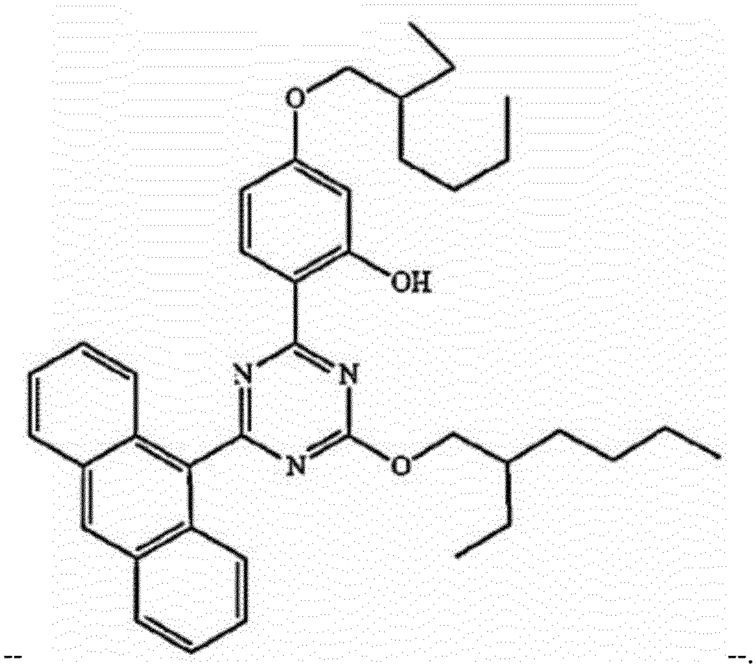--.

In Column 542, Lines 3-21, in Claim 23, Compound 284, delete
"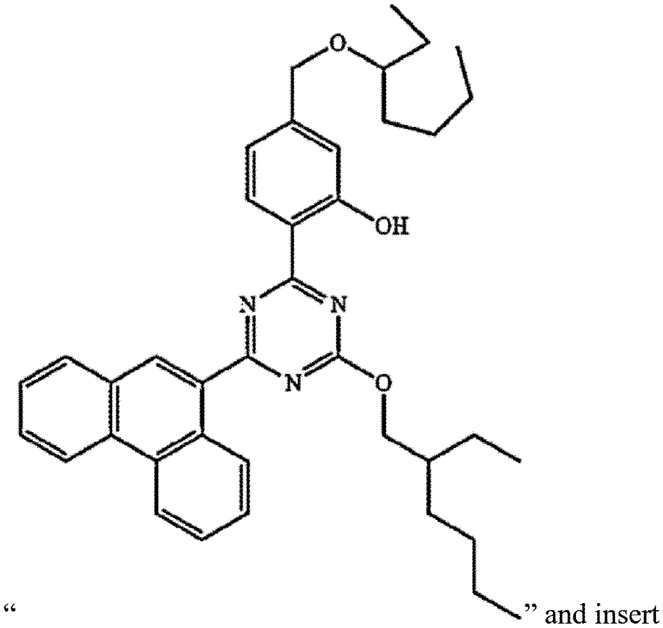" and insert
--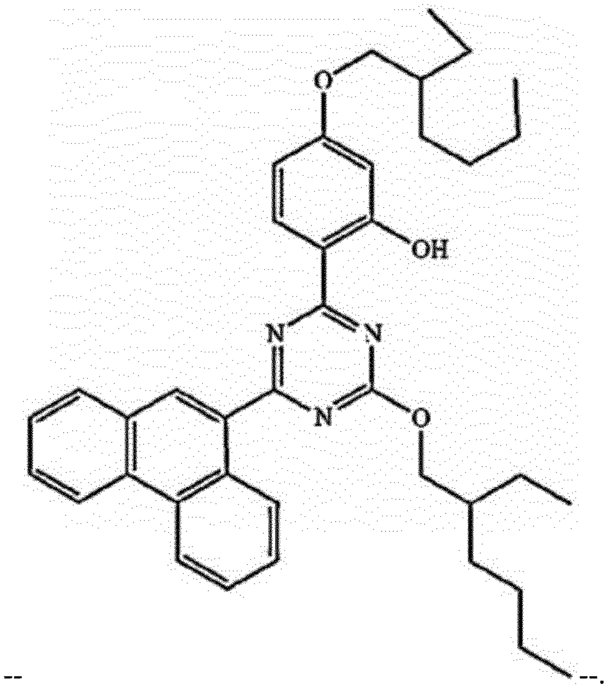--.

In Column 542, Lines 26-45, in Claim 23, Compound 285, delete
" 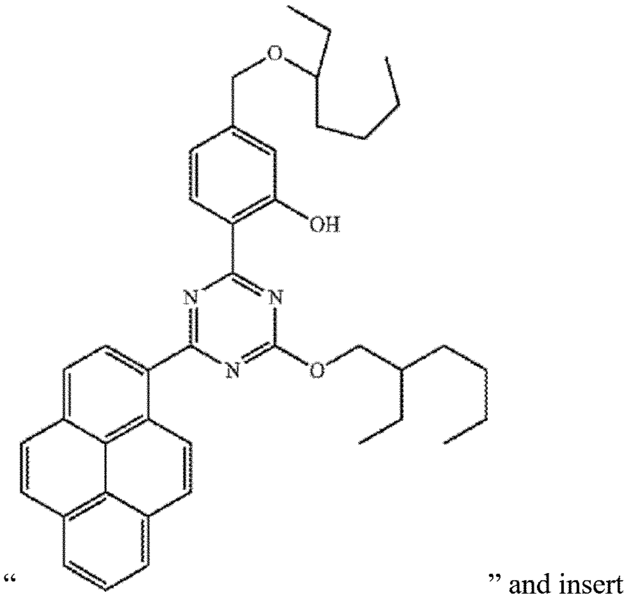 " and insert -- 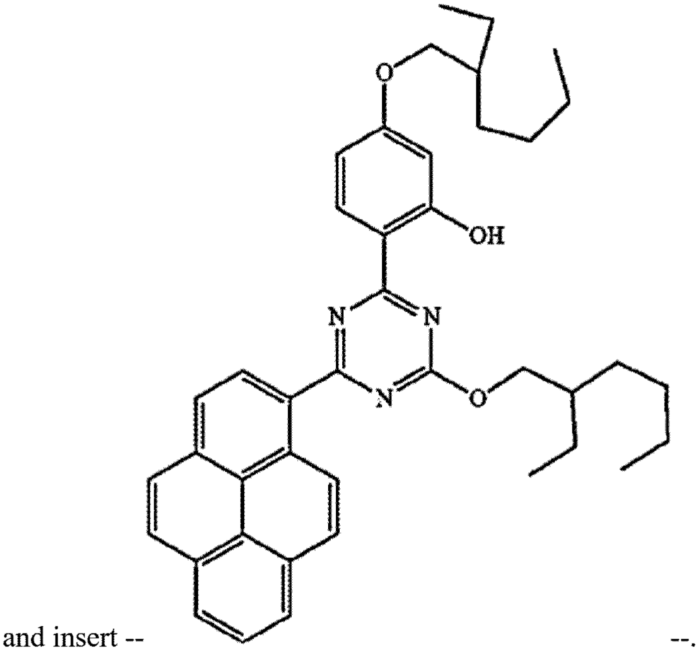 --.
In Column 542, Lines 47-66, in Claim 23, Compound 286, delete
" 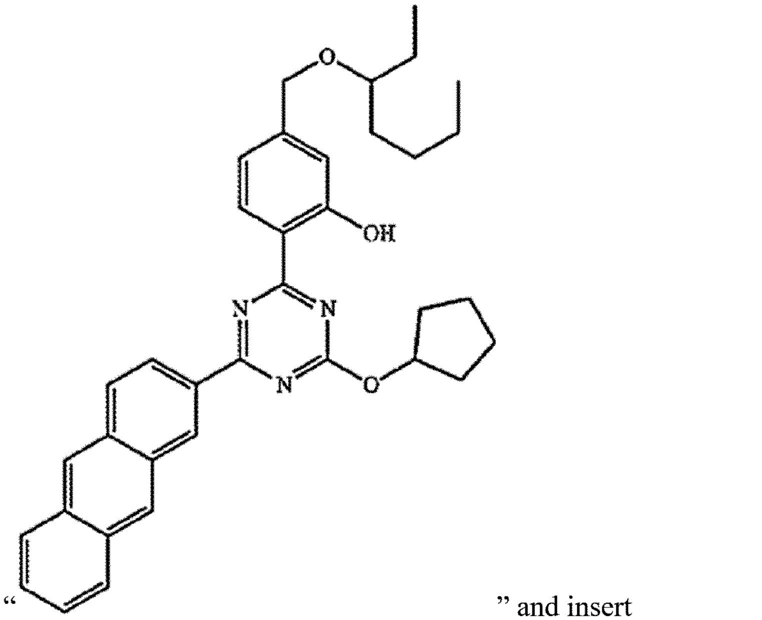 " and insert -- 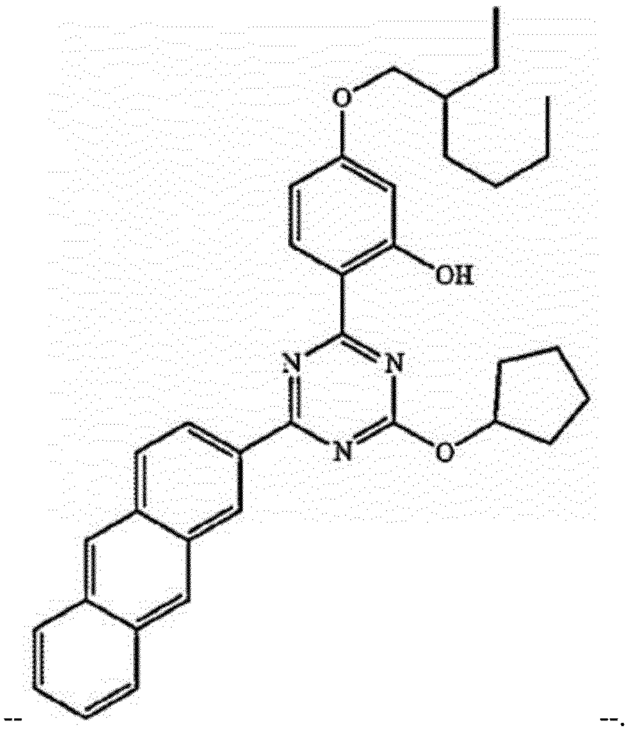 --.
In Column 543, Lines 3-20, in Claim 23, Compound 287, delete
" 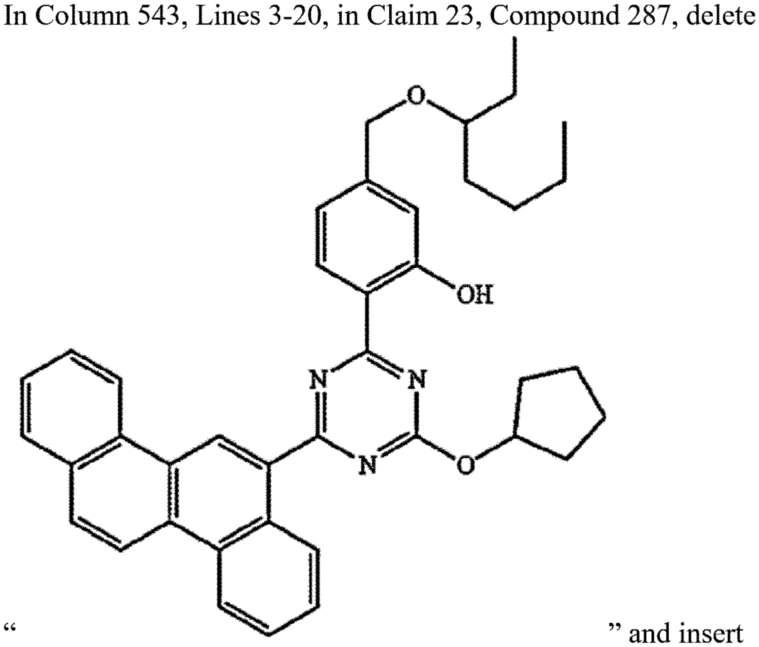 " and insert -- 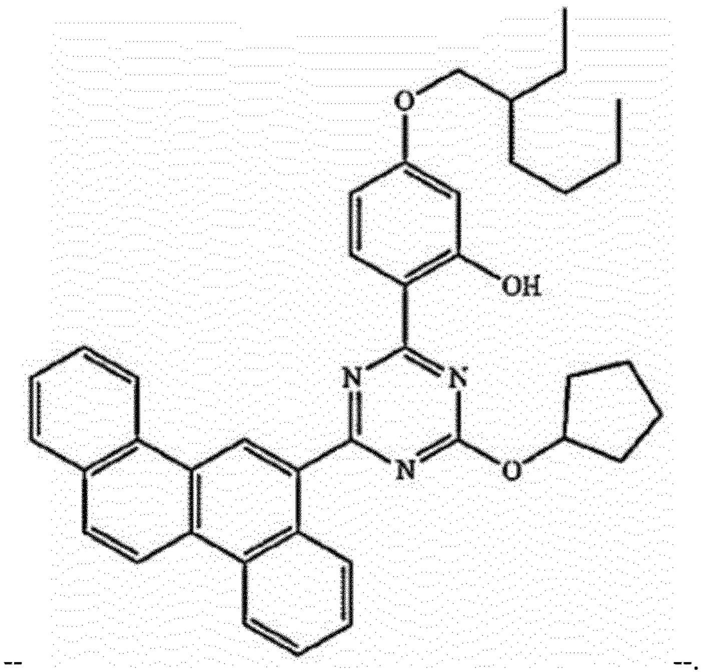 --.
In Column 543, Lines 26-43, in Claim 23, Compound 288, delete
“ 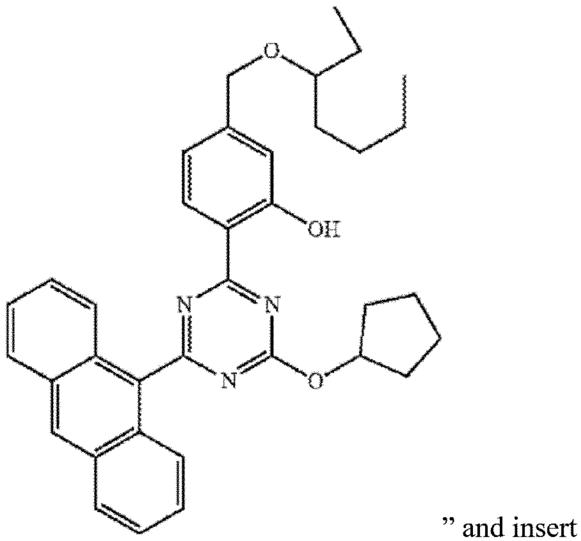 ” and insert -- 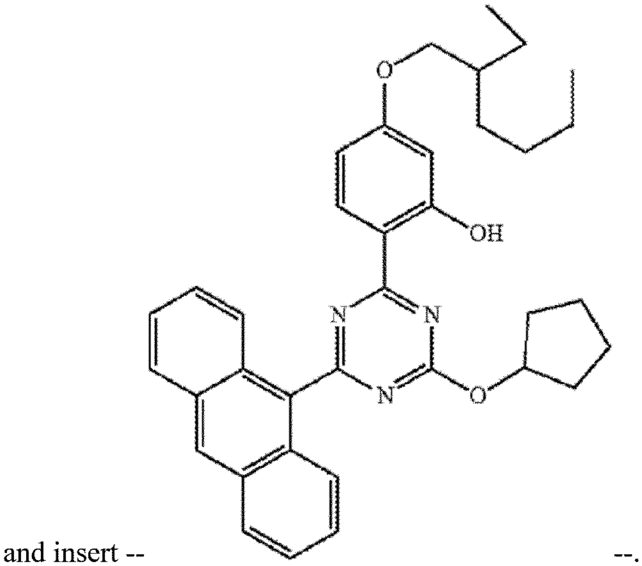 --.

In Column 543, Lines 49-65, in Claim 23, Compound 289, delete
“ 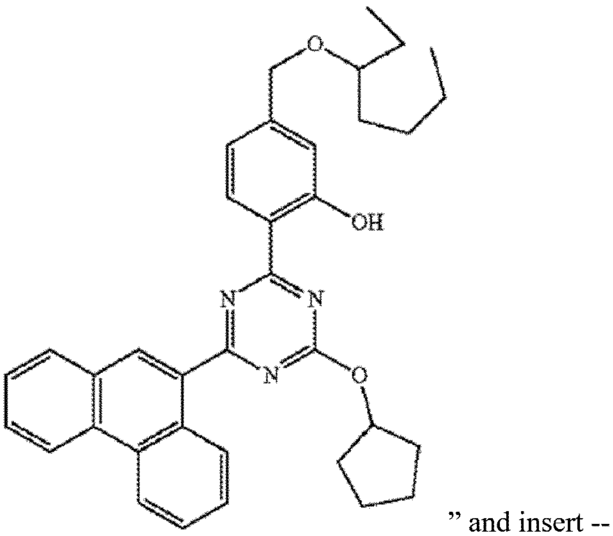 ” and insert -- 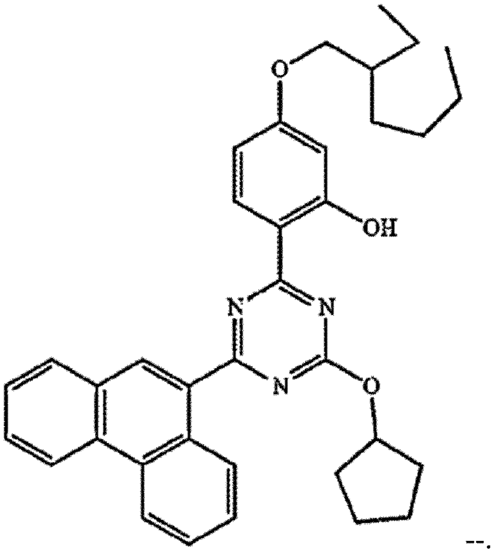 --.
In Column 544, Lines 3-22, in Claim 23, Compound 290, delete
“ 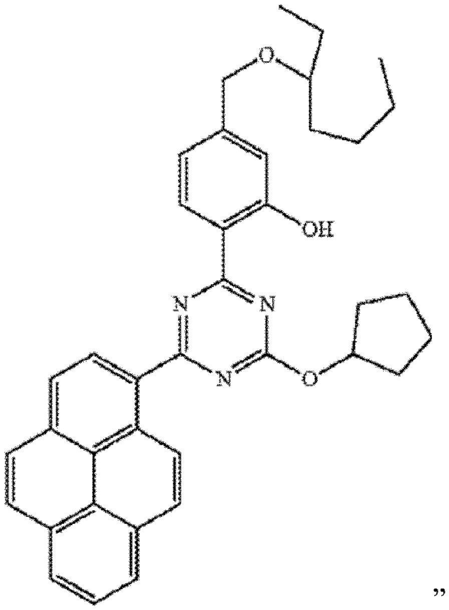 ” and insert -- 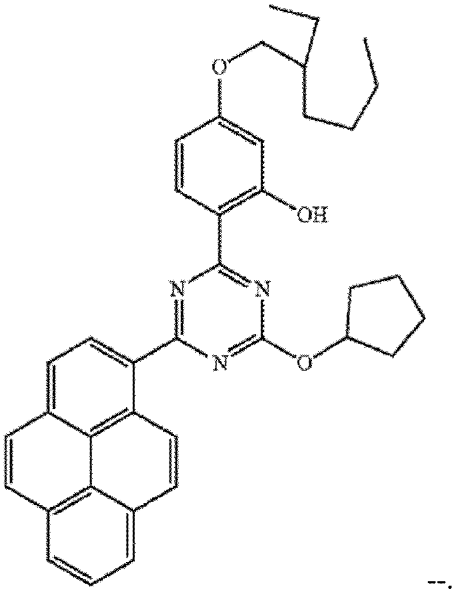 --.

In Column 544, Lines 28-48, in Claim 23, Compound 291, delete
“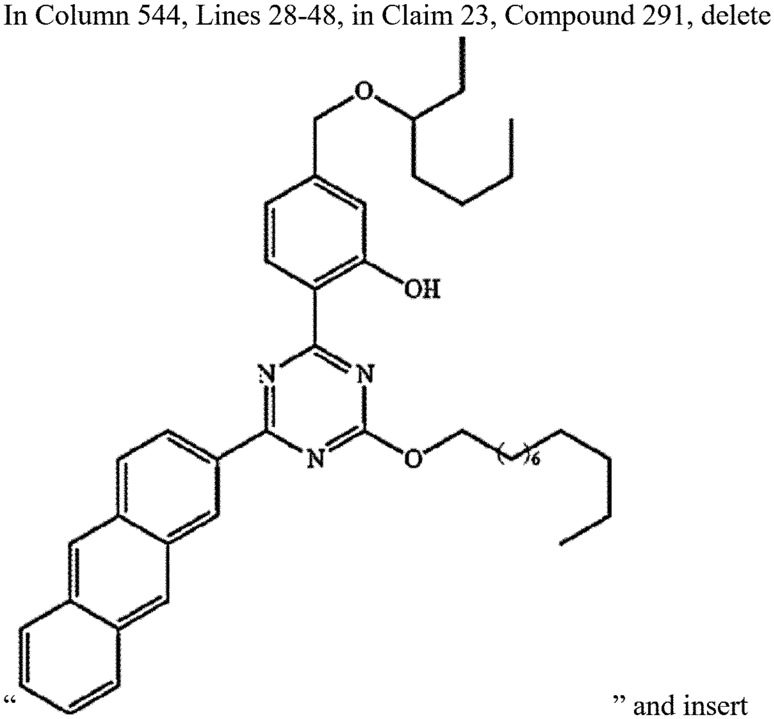” and insert
--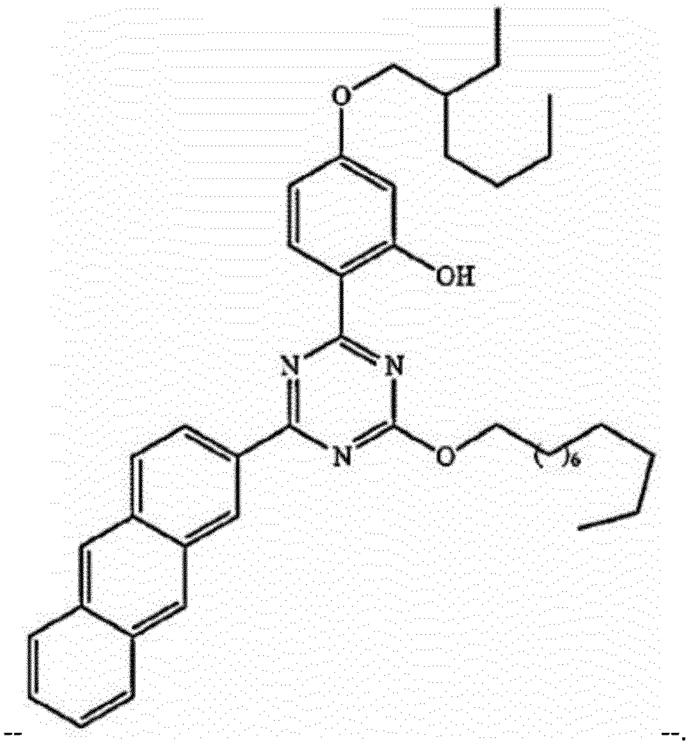--.

In Column 544, Lines 50-66, in Claim 23, Compound 292, delete
“ 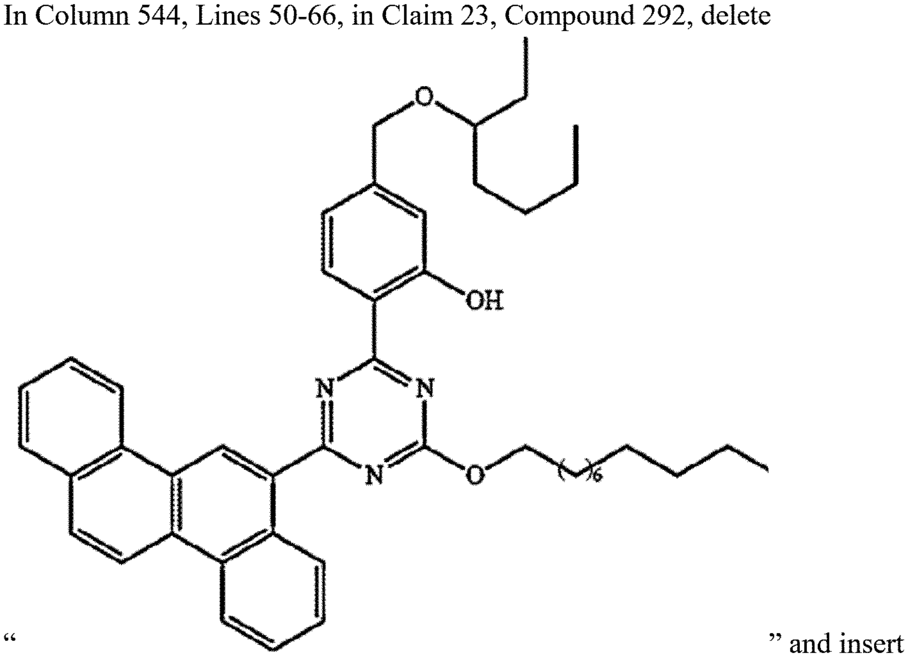 ” and insert
-- 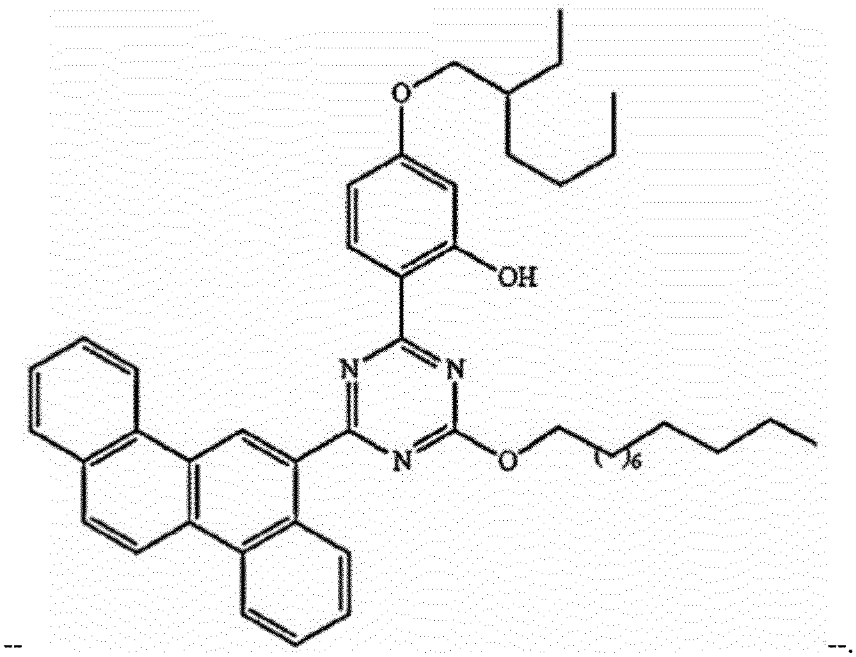 --.

In Column 545, Lines 4-20, in Claim 23, Compound 293, delete
"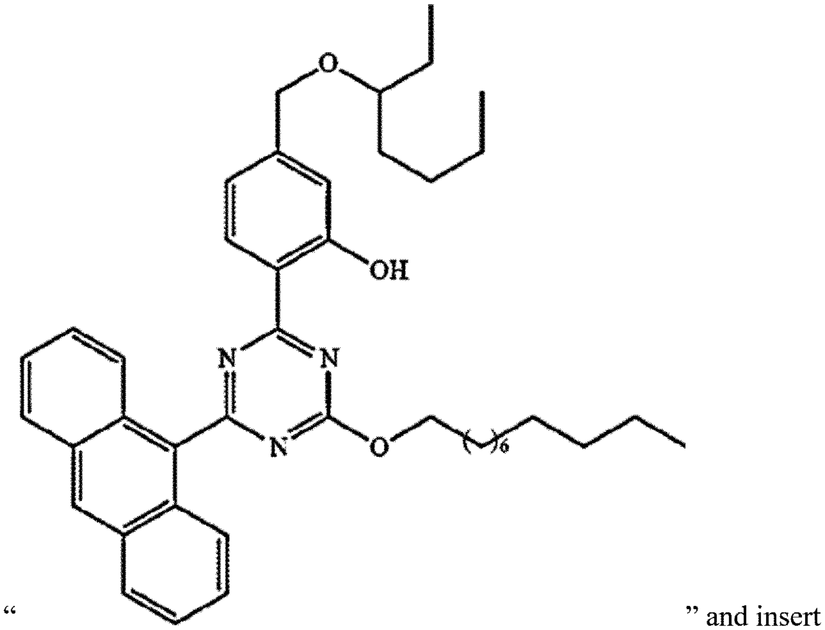" and insert
--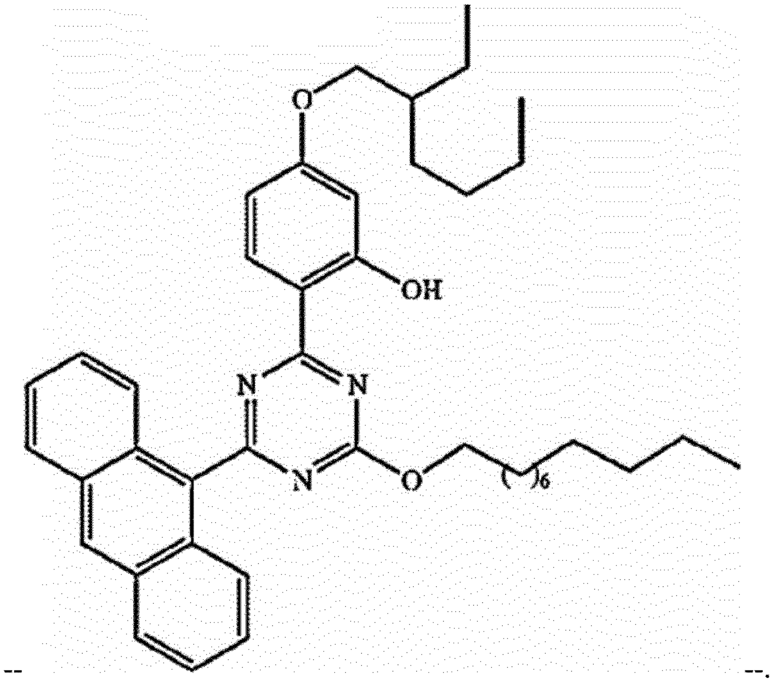--.

In Column 545, Lines 26-45, in Claim 23, Compound 294, delete
"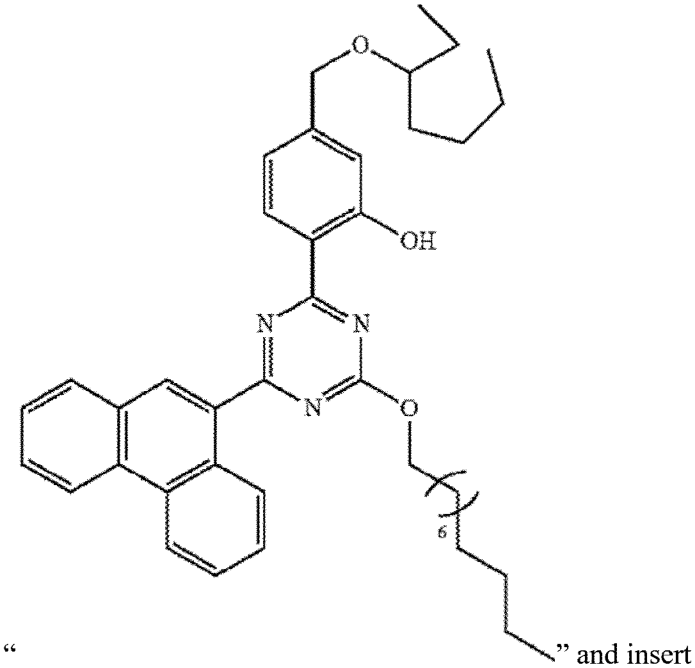" and insert
--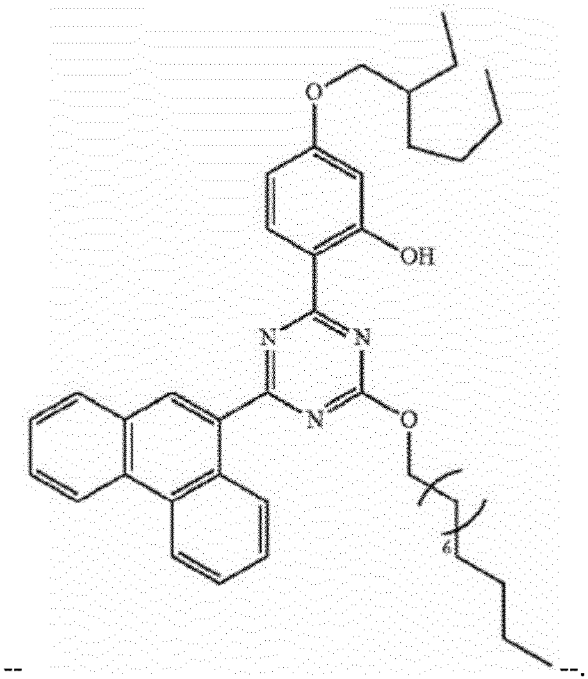--.
In Column 545, Lines 47-65, in Claim 23, Compound 295, delete “ 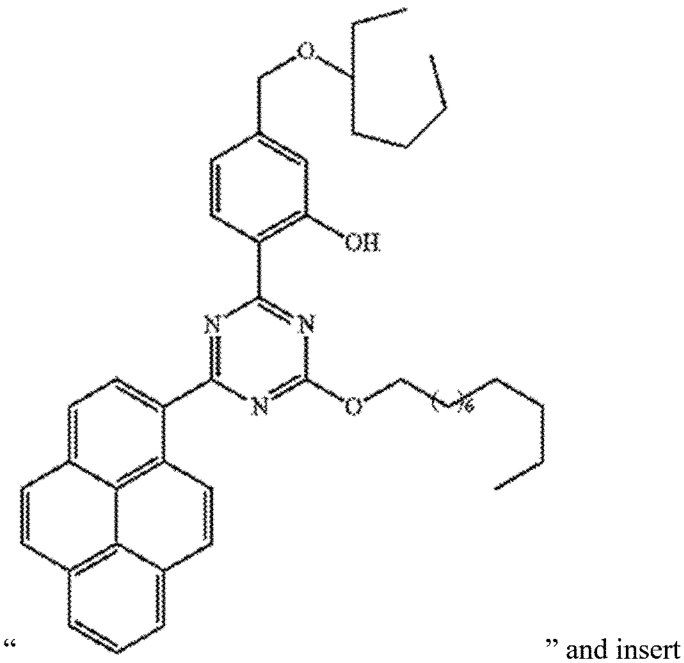 ” and insert
-- 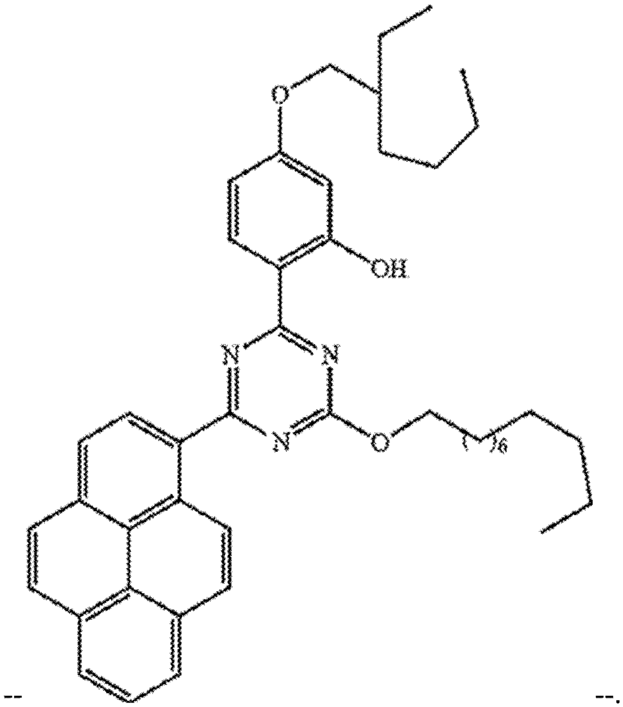 --.

In Column 554, Lines 2-21, in Claim 23, after "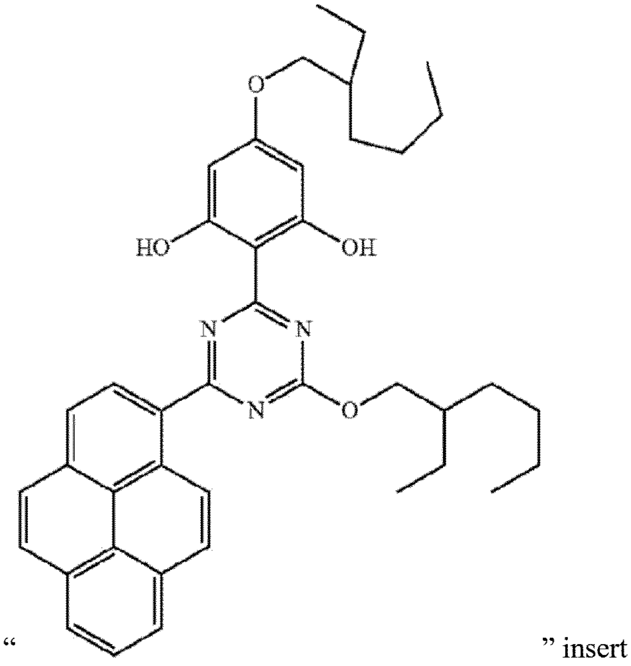" insert -- 320 --.
In Column 564, Lines 28-44, in Claim 23, Compound 355, delete
"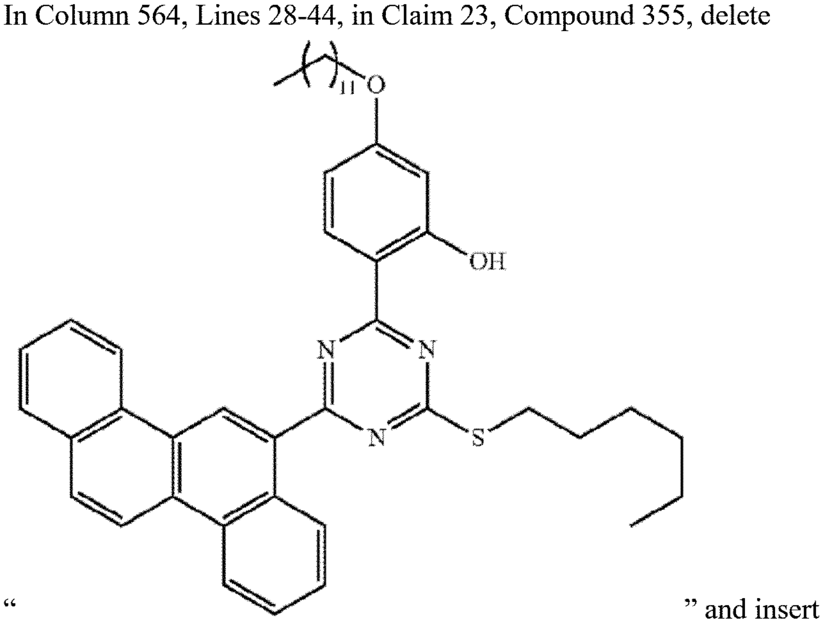" and insert -- 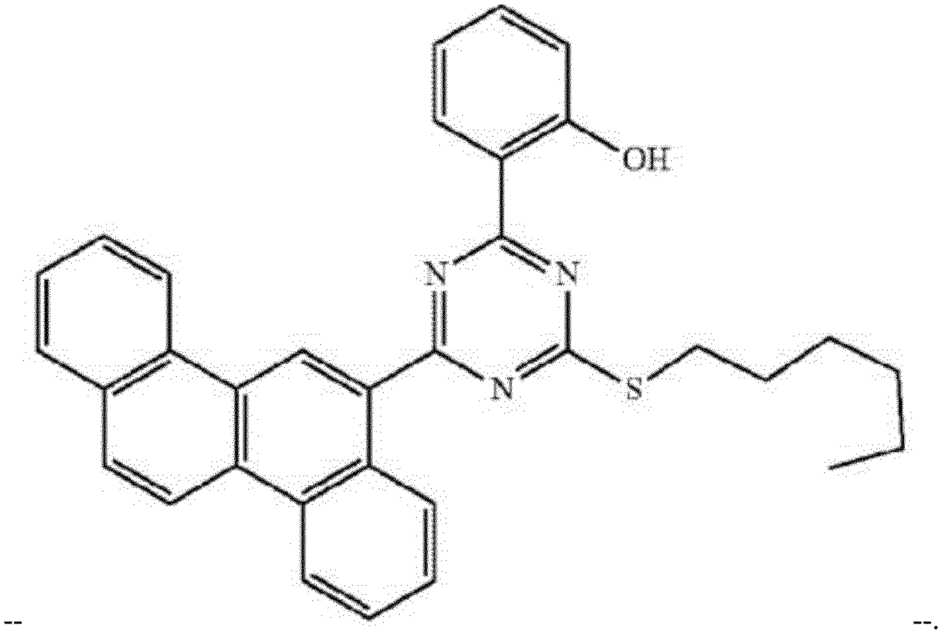 --.
In Column 574, Lines 3-12, in Claim 28, Compound Ar-c, delete
“ 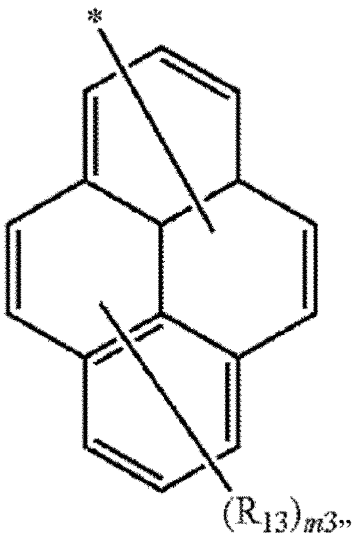 ” and insert -- 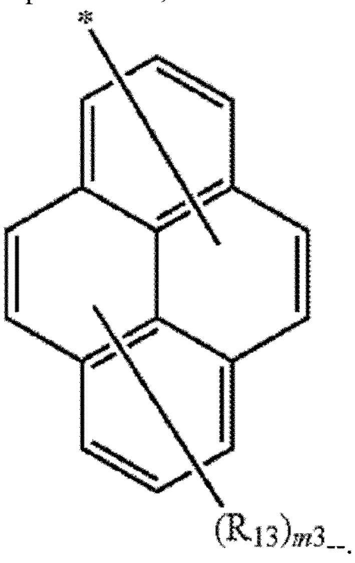 --.

In Column 613, Lines 17-30, in Claim 31, Compound 144, delete
"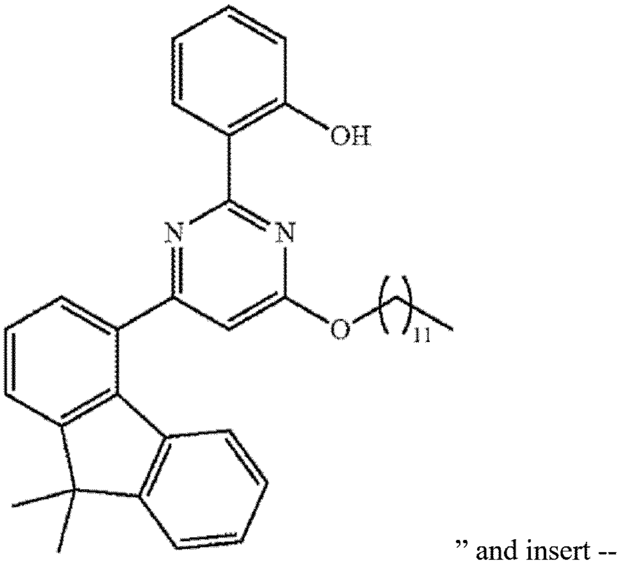" and insert --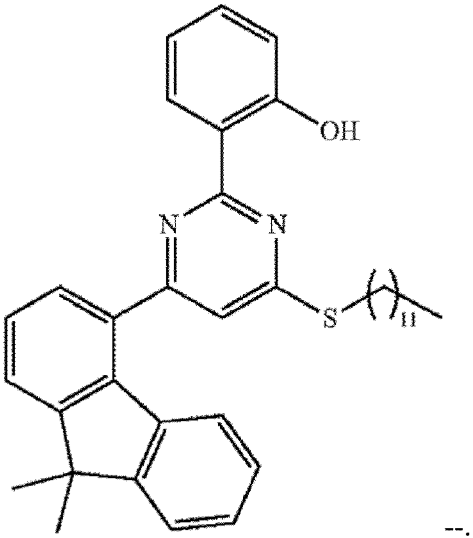--.
In Column 616, Lines 51-65, in Claim 31, Compound 157, delete
"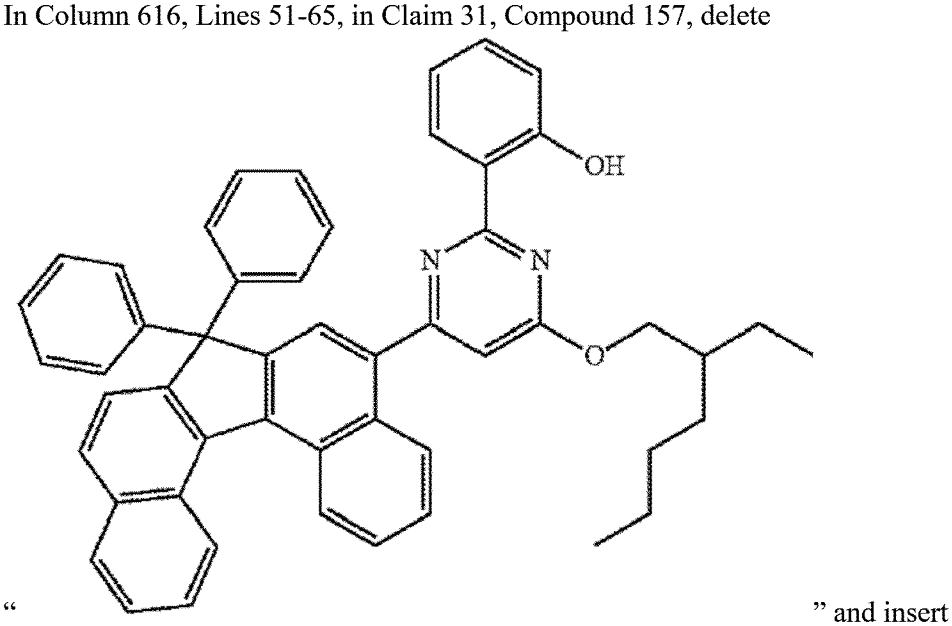" and insert -- 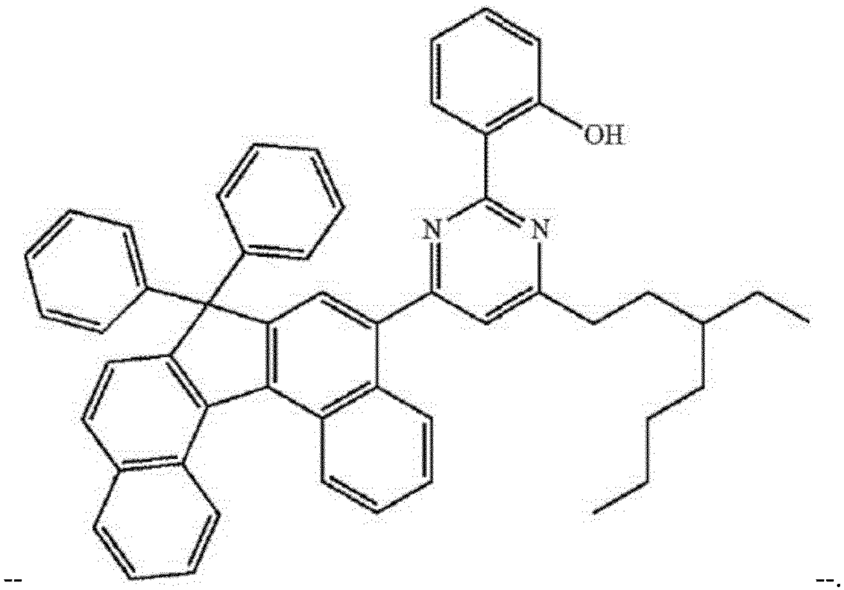 --.
In Column 618, Lines 49-66, in Claim 31, Compound 164, delete
" 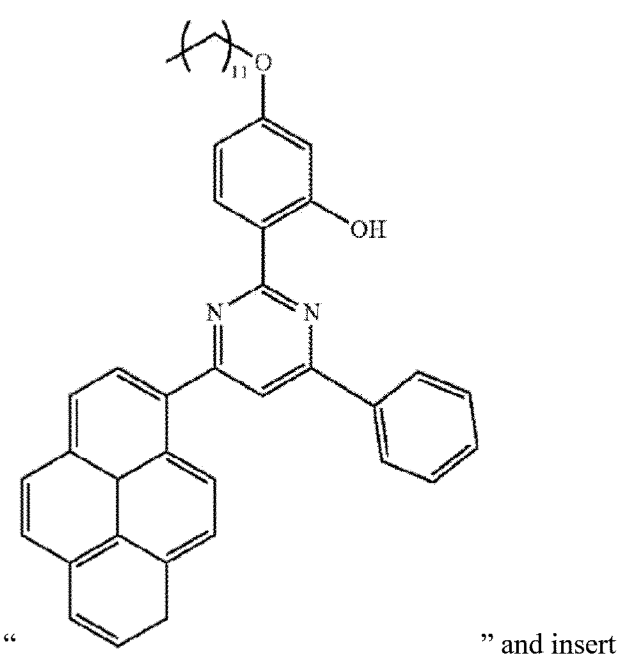 " and insert -- 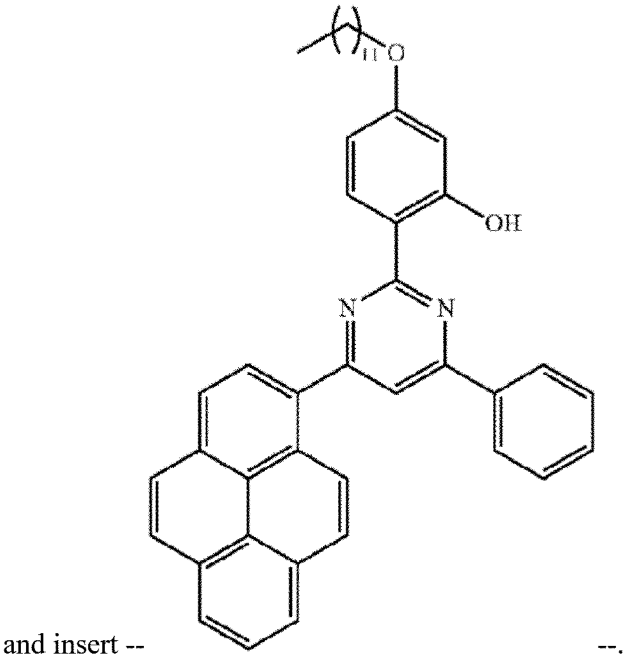 --.

In Column 619, Lines 45-65, in Claim 31, Compound 167, delete
“ 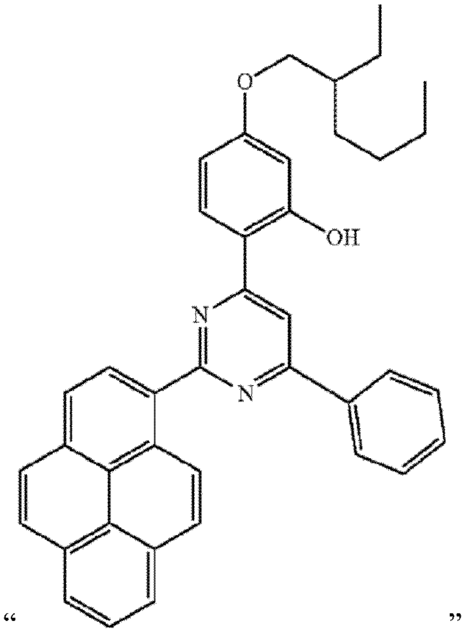 ” and insert -- 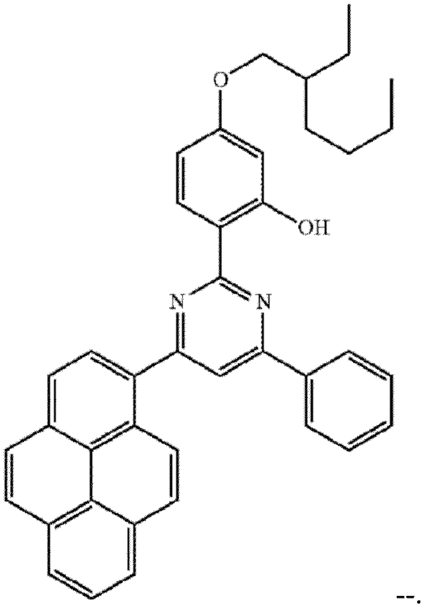 --.
In Column 676, Lines 3-19, in Claim 31, Compound 181, delete
“ 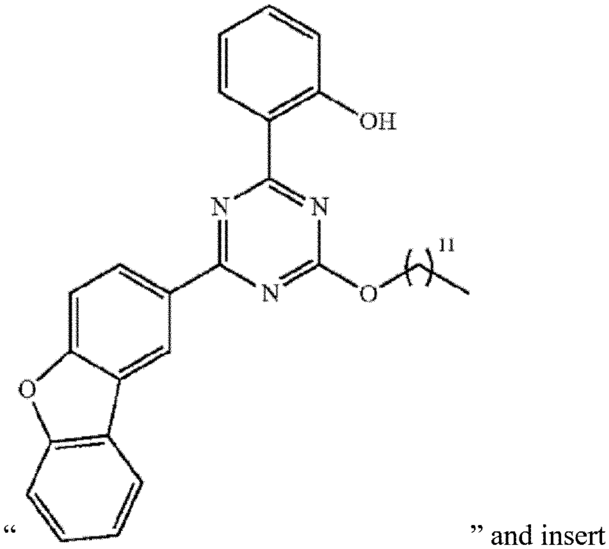 ” and insert -- 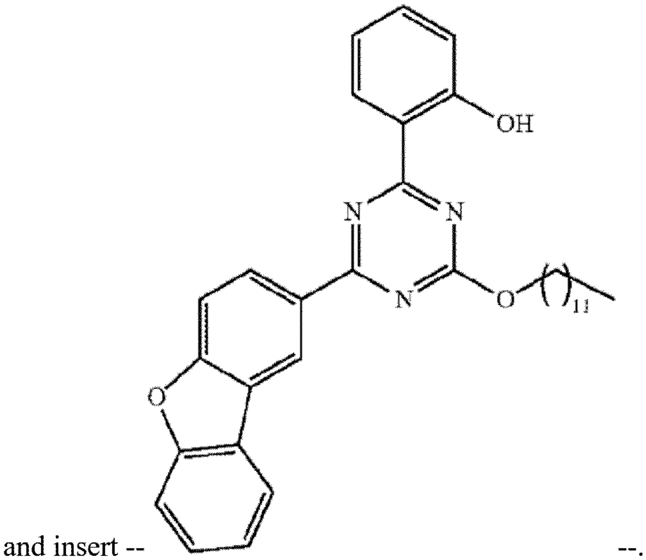 --.

In Column 676, Lines 22-34, in Claim 31, Compound 182, delete
“ 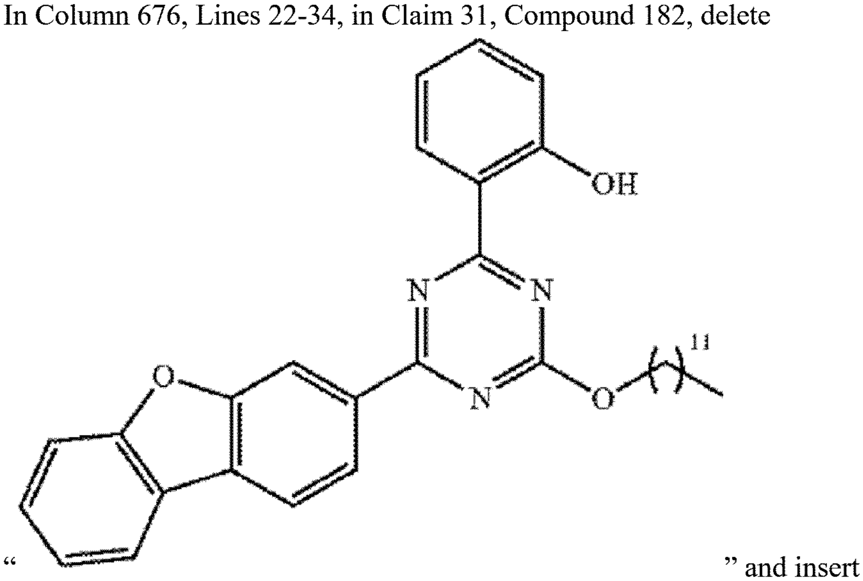 ” and insert
-- 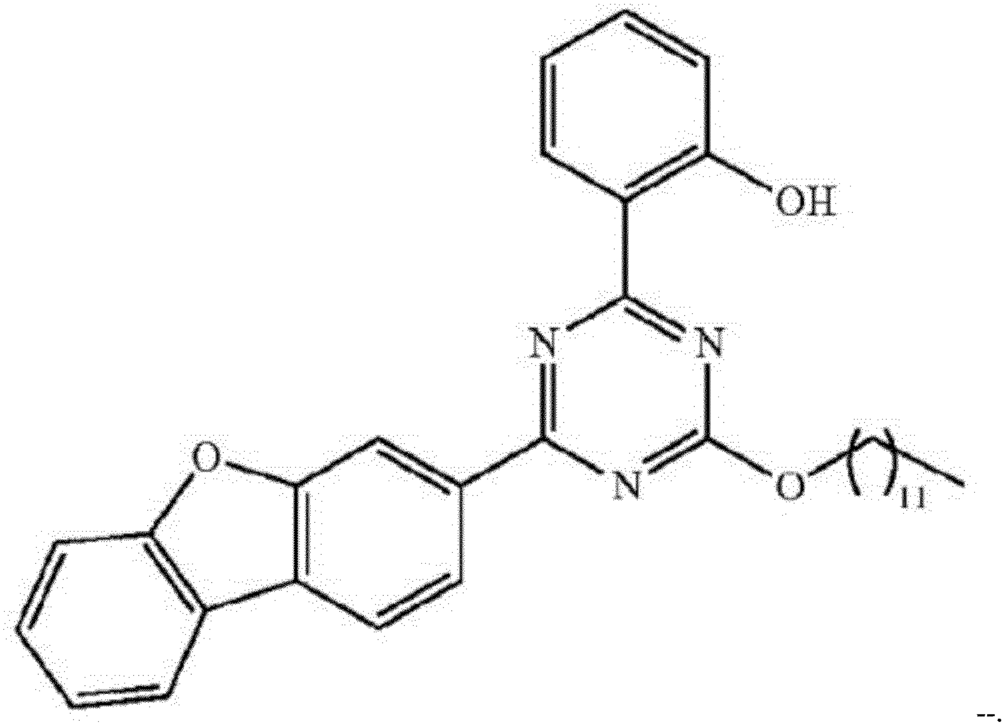 --.

In Column 676, Lines 37-48, in Claim 31, Compound 183, delete
" 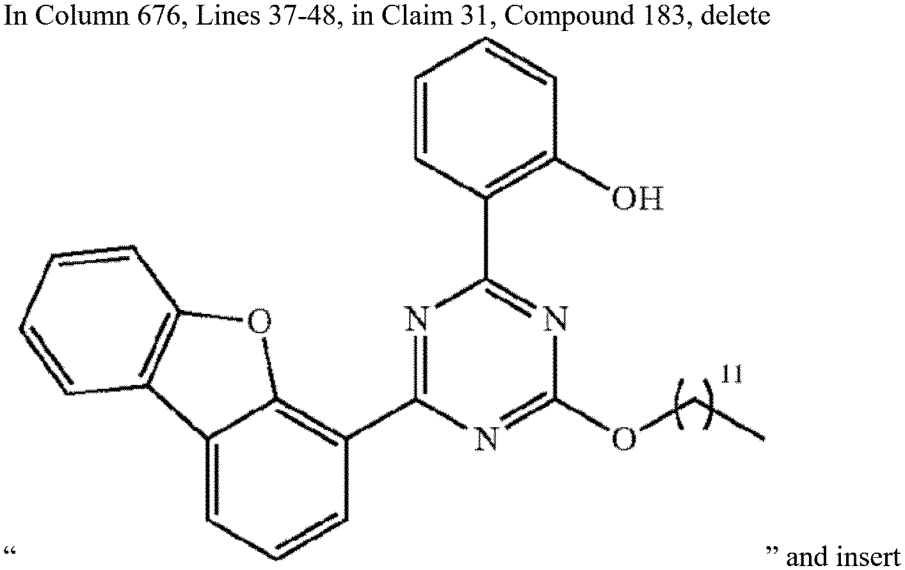 " and insert
-- 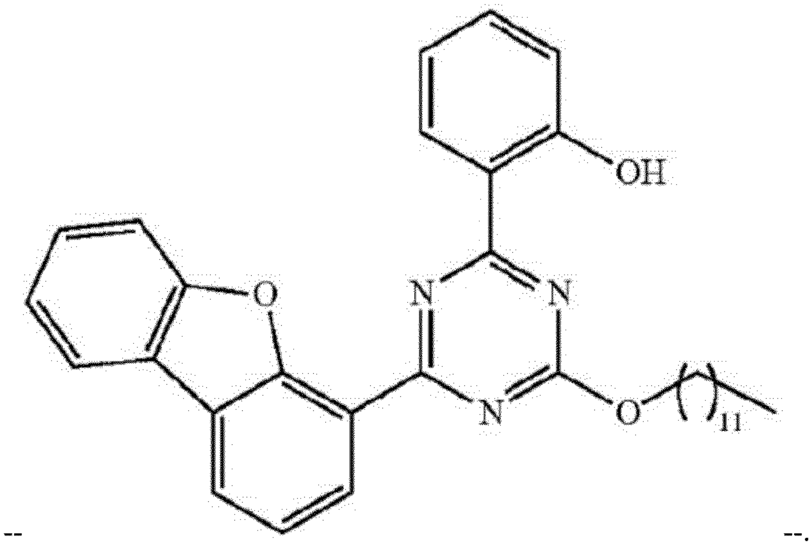 --.

In Column 676, Lines 52-65, in Claim 31, Compound 184, delete
" 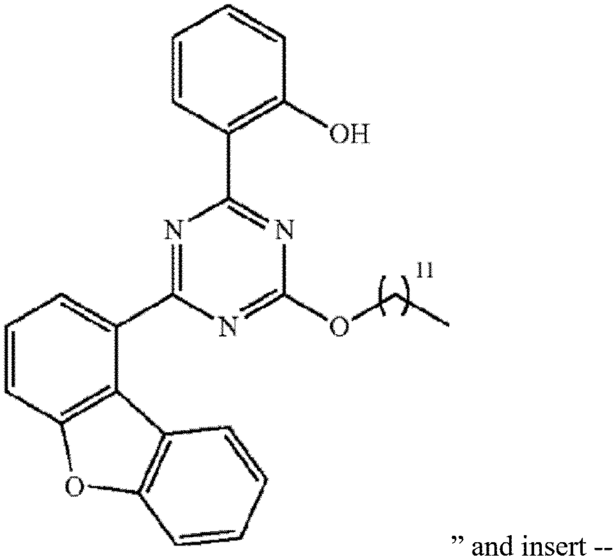 " and insert -- 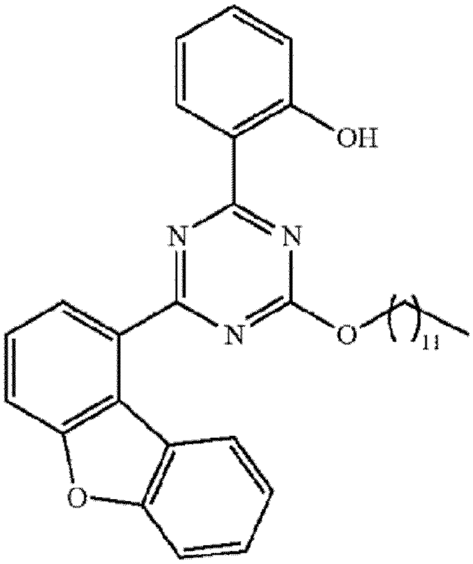 --.
In Column 677, Lines 3-20, in Claim 31, Compound 185, delete
" 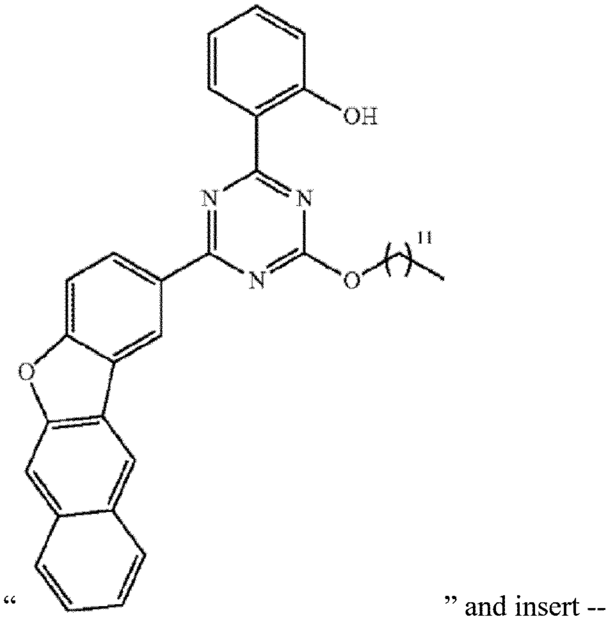 " and insert -- 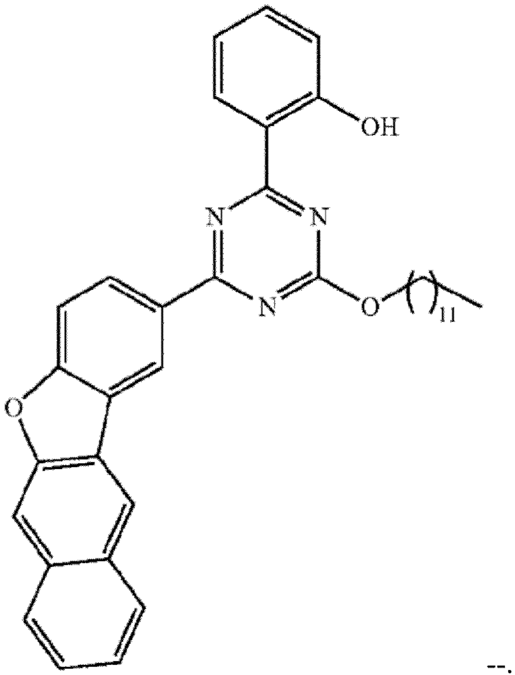 --.

In Column 677, Lines 21-36, in Claim 31, Compound 186, delete
"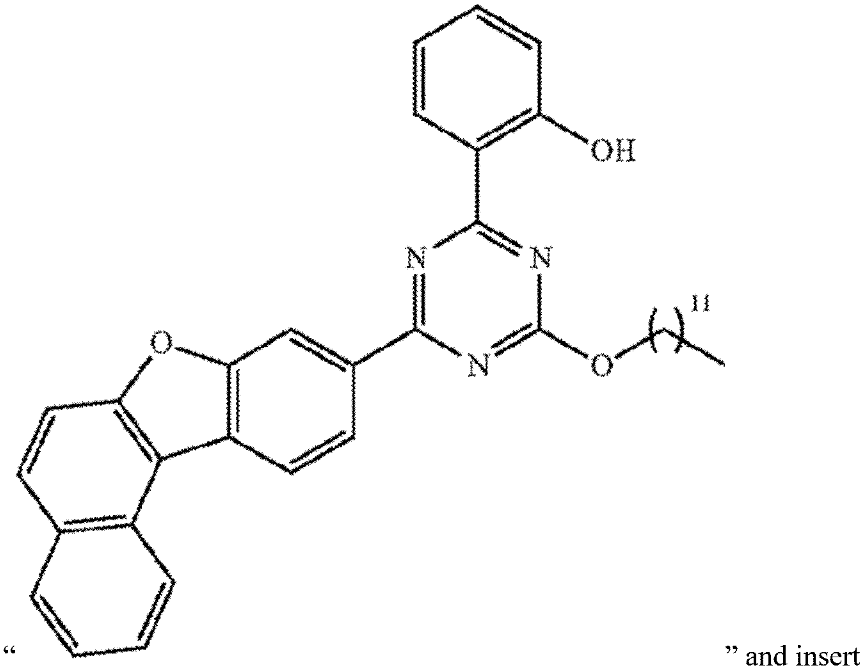" and insert
--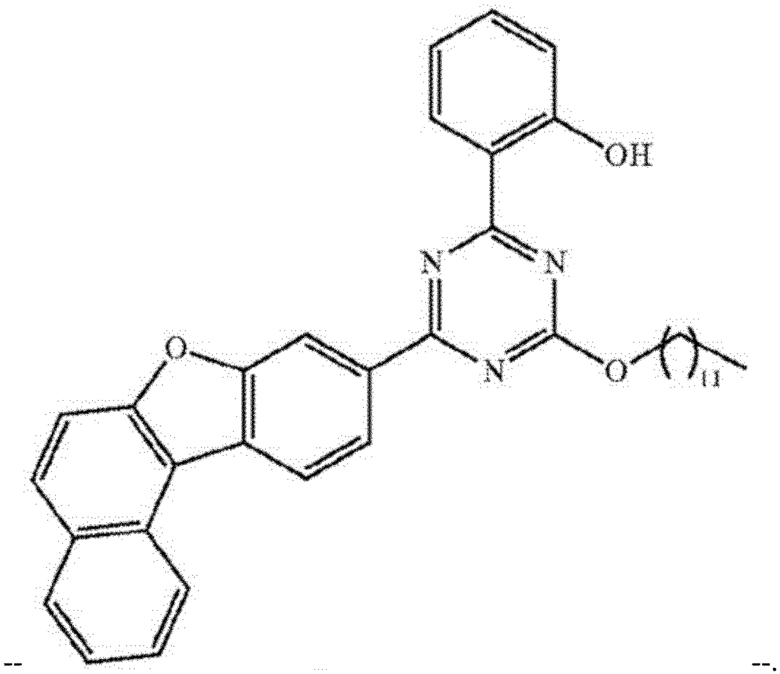--.

In Column 677, Lines 37-52, in Claim 31, Compound 187, delete
"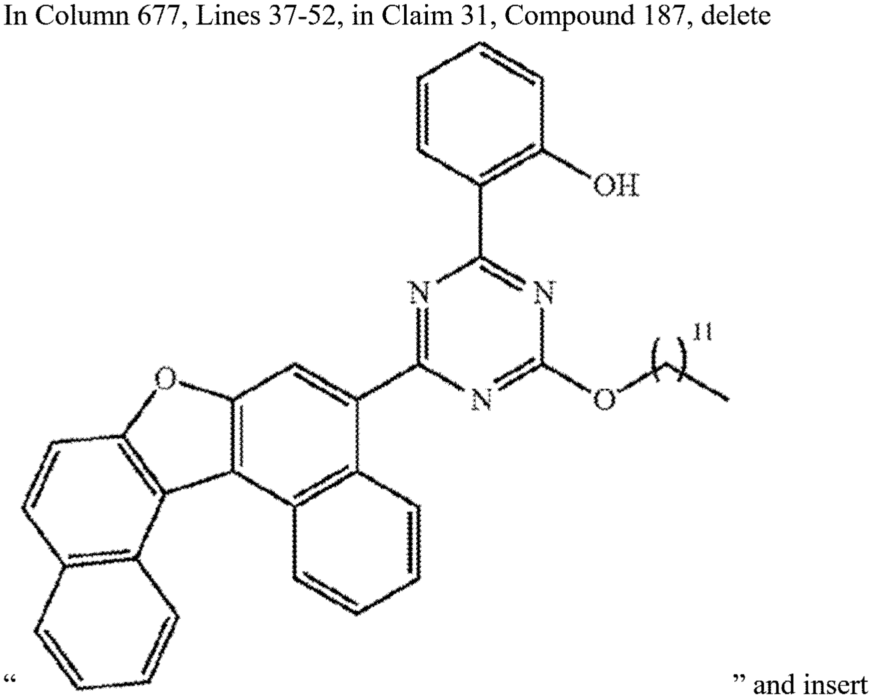" and insert
--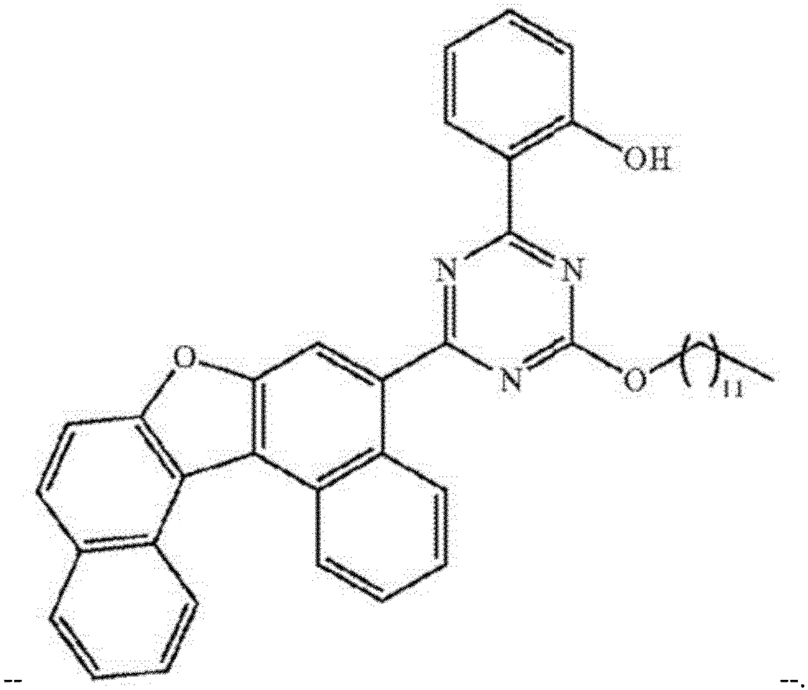--.

In Column 677, Lines 53-66, in Claim 31, Compound 188, delete
“ 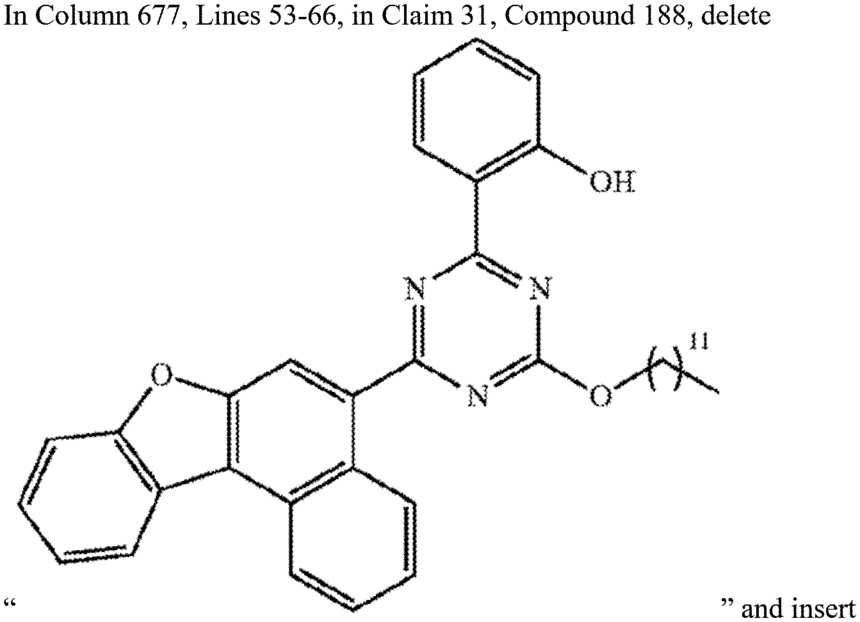 ” and insert
-- 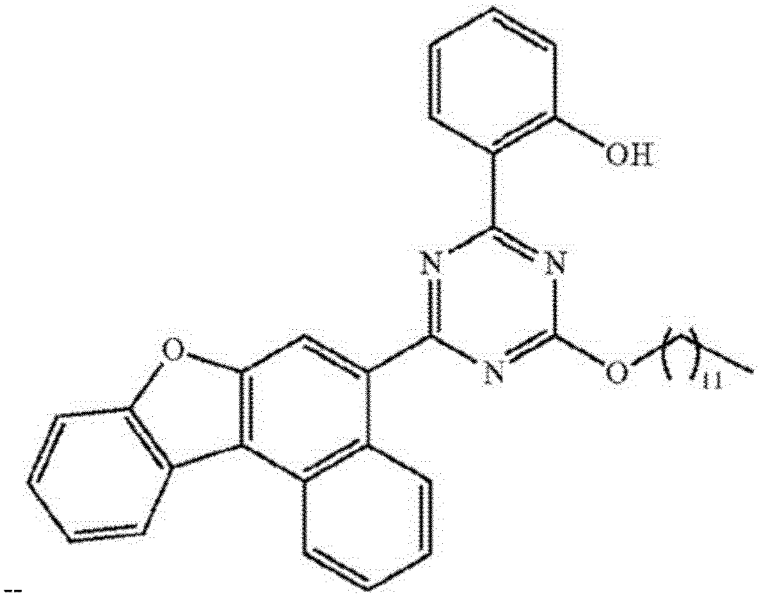 --.

In Column 678, Lines 3-17, in Claim 31, Compound 189, delete
“ 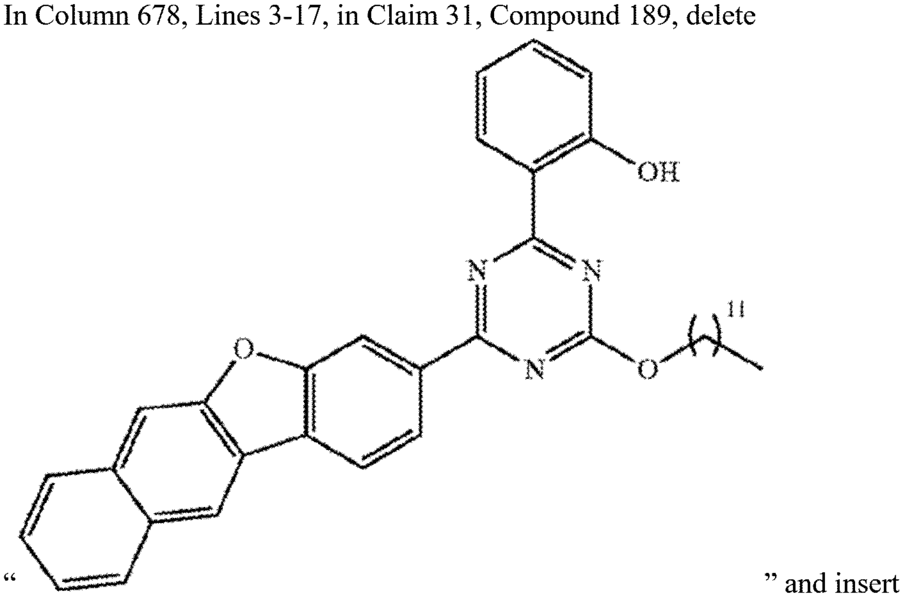 ” and insert
-- 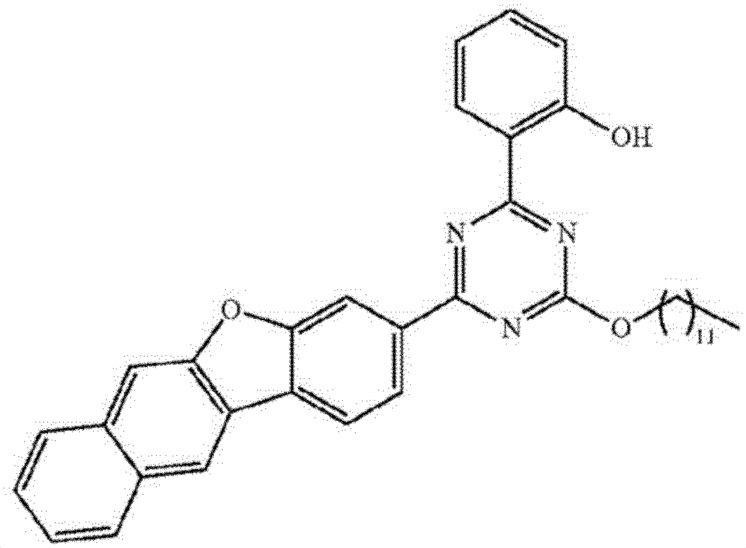 --.

In Column 678, Lines 20-32, in Claim 31, Compound 190, delete
“ 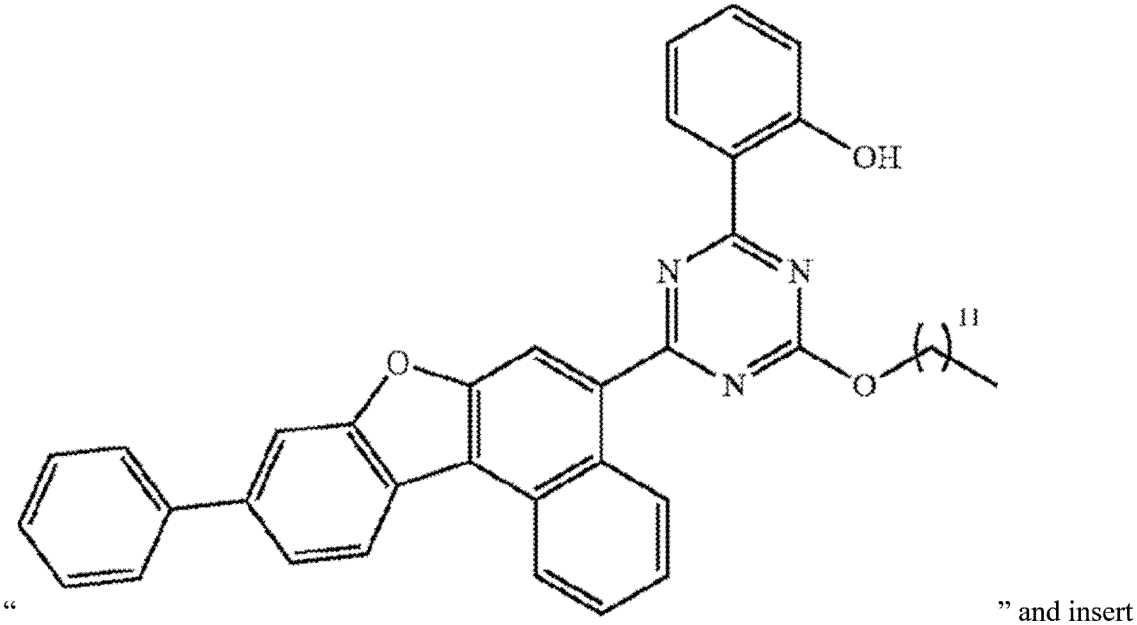 ” and insert
-- 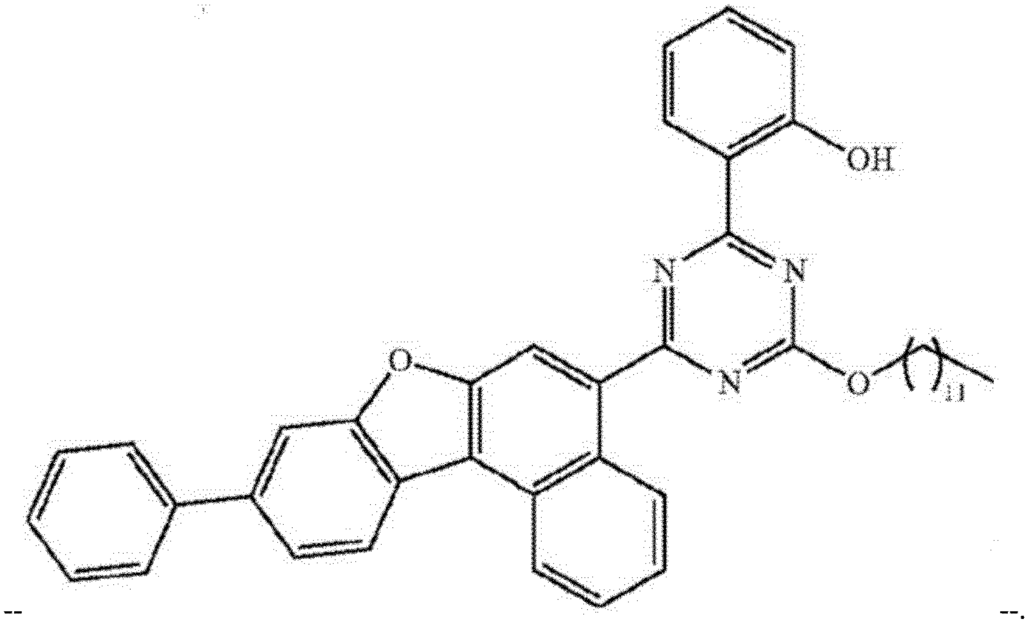 --.

In Column 683, Lines 54-65, in Claim 31, Compound 210, delete
“ 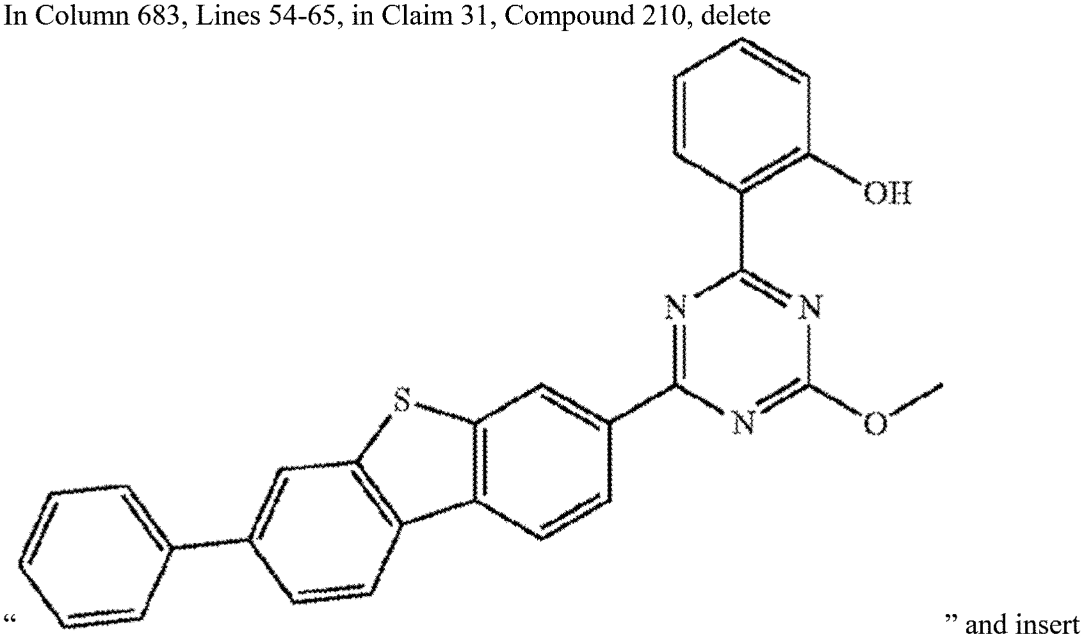 ” and insert
-- 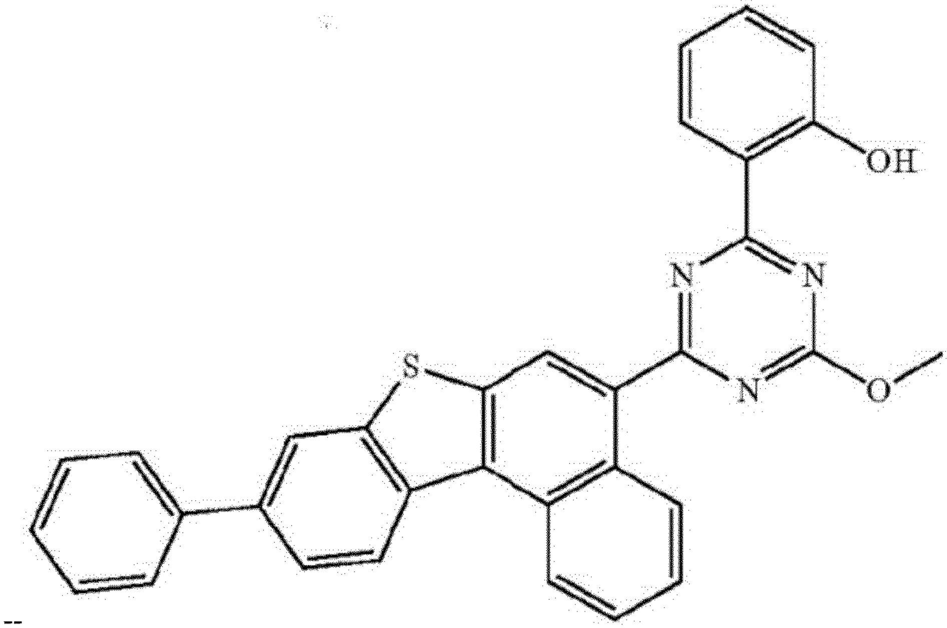 --.

In Column 690, Lines 52-66, in Claim 31, Compound 237, delete
"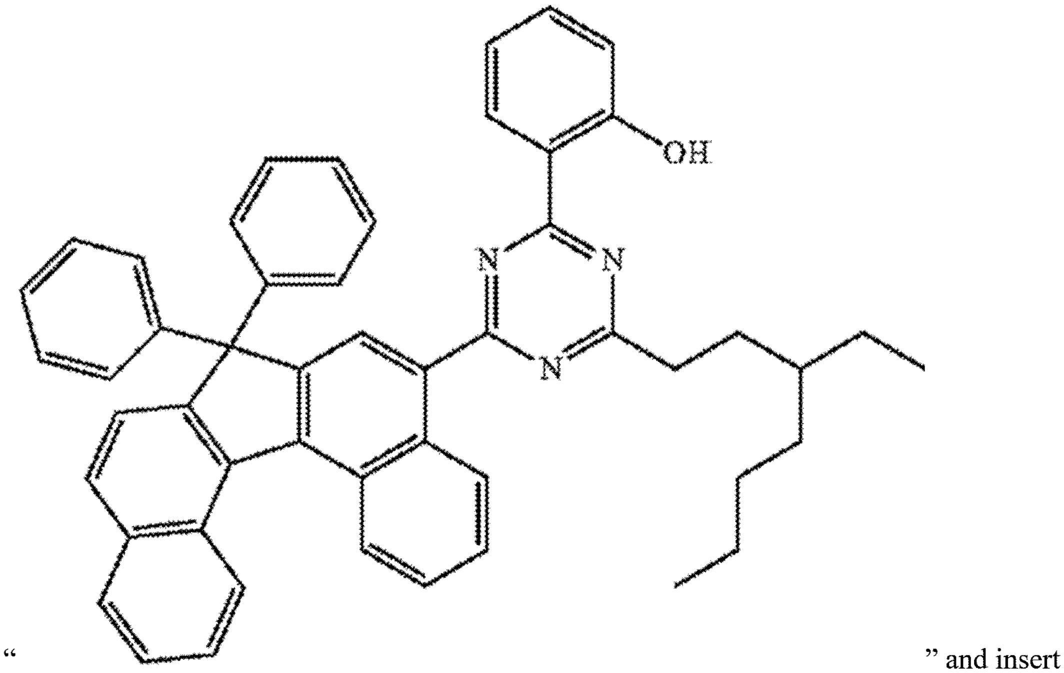" and insert
--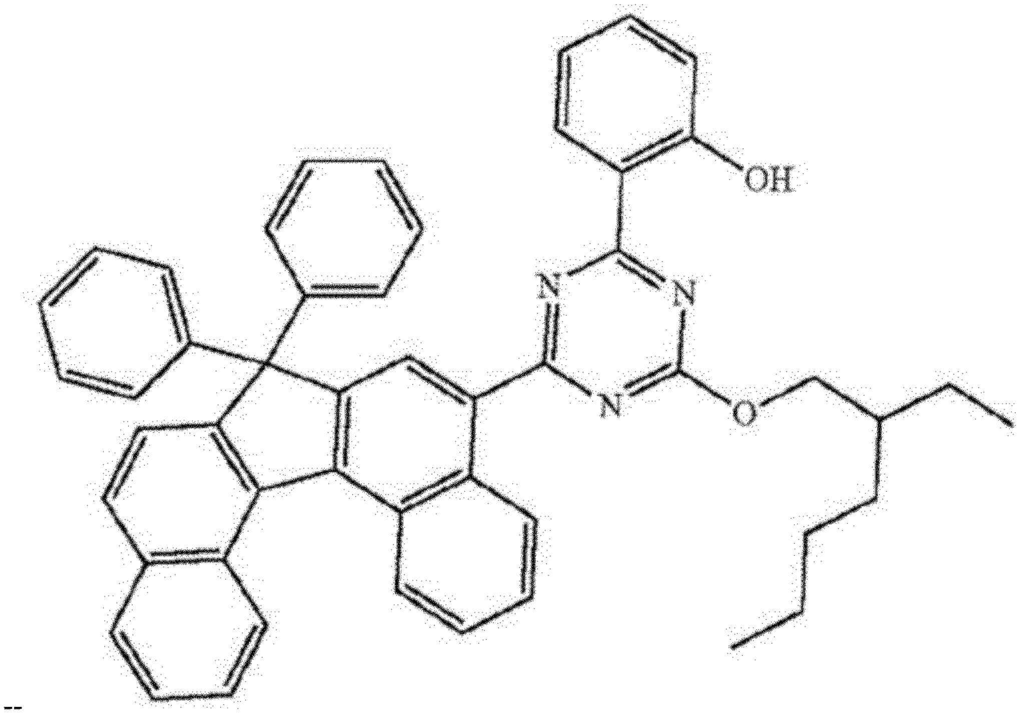--.

In Column 720, Lines 53-65, in Claim 31, Compound 331, delete
"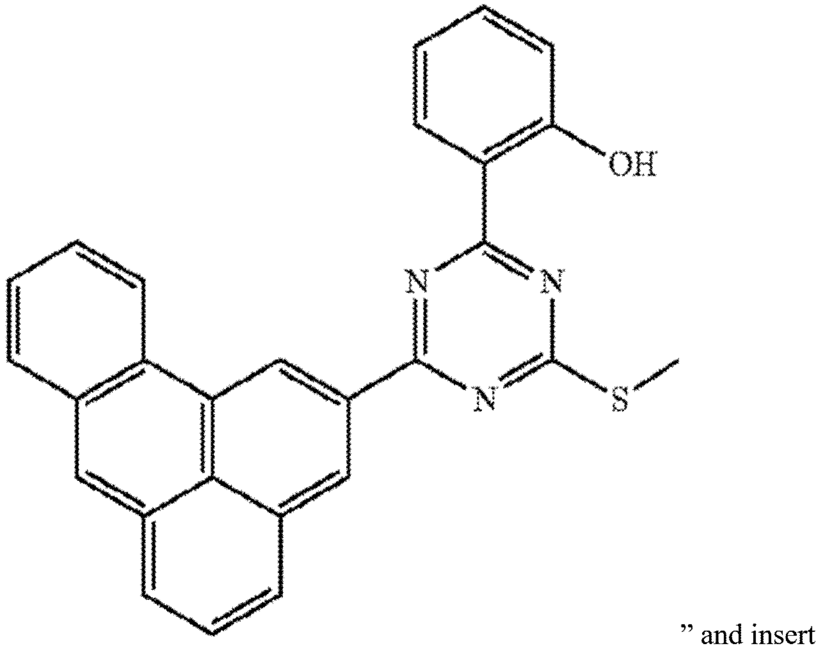" and insert
--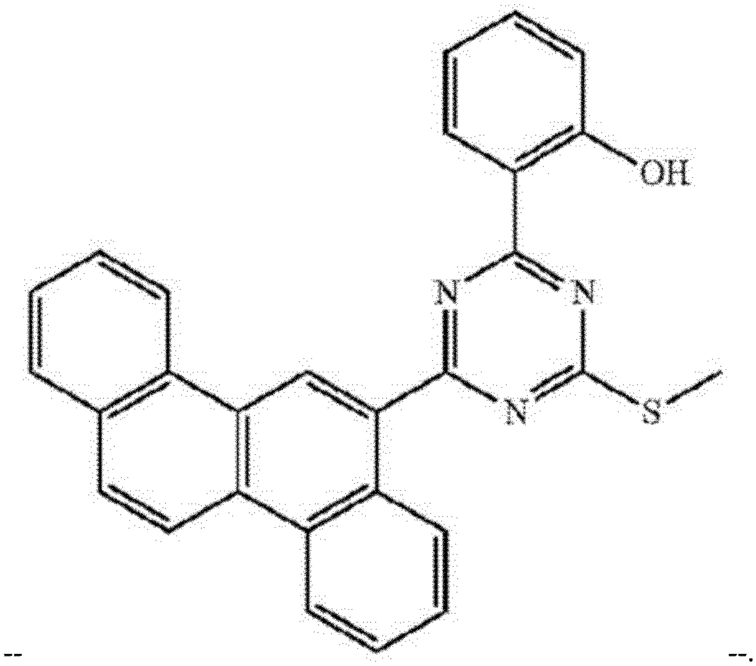--.

In Column 721, Lines 17-33, in Claim 31, Compound 333, delete
"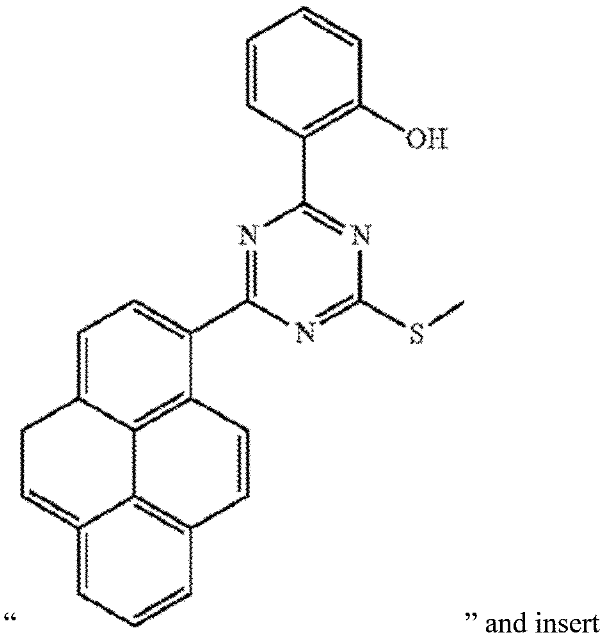" and insert
--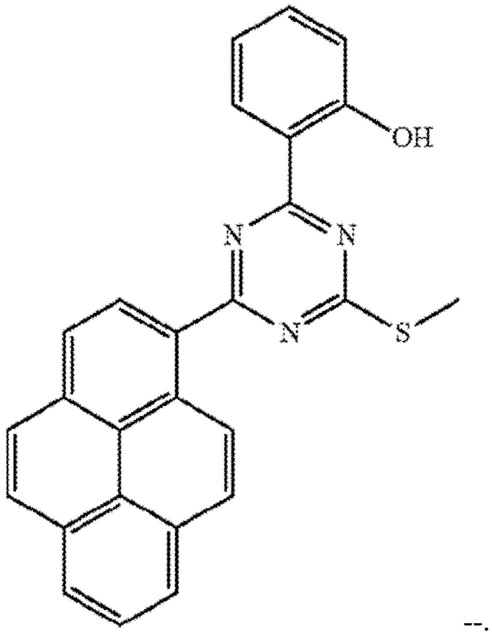--.

In Column 732, Lines 30-50, in Claim 31, Compound 372, delete
“ 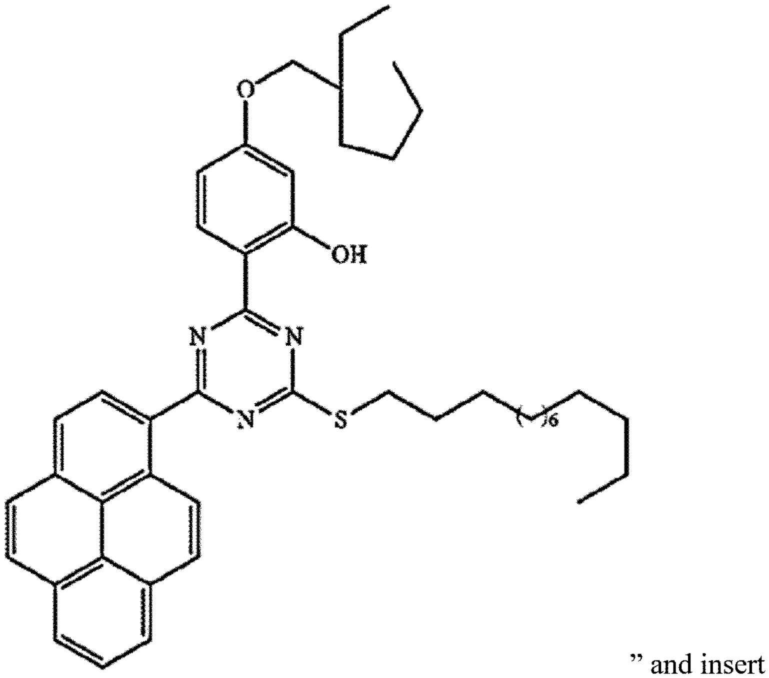 ” and insert
-- 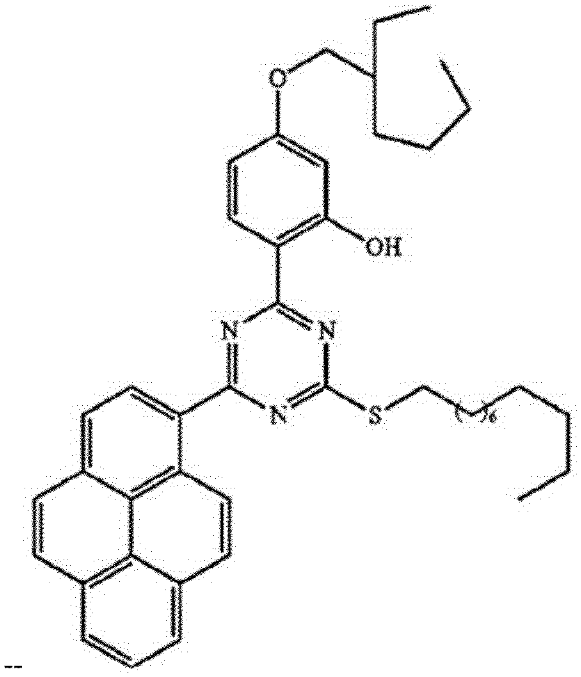 --.